US 7,008,625 B2

(12) United States Patent
Dattwyler et al.

(10) Patent No.: US 7,008,625 B2
(45) Date of Patent: Mar. 7, 2006

(54) RECOMBINANT CONSTRUCTS OF BORRELIA BURGDORFERI

(75) Inventors: Raymond J. Dattwyler, Setauket, NY (US); Maria J. C. Gomes-Solecki, New York, NY (US); Benjamin J. Luft, East Setauket, NY (US); John J. Dunn, Bellport, NY (US)

(73) Assignee: Research Foundation of the State University of New York, Stony Brook, NY (US)

( * ) Notice: Subject to any disclaimer, the term of this patent is extended or adjusted under 35 U.S.C. 154(b) by 0 days.

(21) Appl. No.: 10/369,100

(22) Filed: Feb. 18, 2003

(65) Prior Publication Data

US 2004/0033236 A1 Feb. 19, 2004

(Under 37 CFR 1.47)

Related U.S. Application Data

(63) Continuation of application No. PCT/US01/24736, filed on Aug. 7, 2001, which is a continuation-in-part of application No. 09/666,017, filed on Sep. 19, 2000, now abandoned, which is a continuation-in-part of application No. 08/235,836, filed on Apr. 29, 1994, now Pat. No. 6,248,562, which is a continuation-in-part of application No. 08/148,191, filed on Nov. 1, 1993, now abandoned.

(60) Provisional application No. 60/226,484, filed on Aug. 18, 2000.

(51) Int. Cl.
*A61K 39/00* (2006.01)
*A61K 39/02* (2006.01)
*A61K 39/38* (2006.01)
*A61K 49/00* (2006.01)

(52) U.S. Cl. ............... 424/192.1; 424/9.1; 424/9.2; 424/184.1; 424/185.1; 424/190.1; 424/234.1; 530/300; 530/350

(58) Field of Classification Search ............ 424/9.1, 424/9.2, 184.1, 185.1, 190.1, 192.1, 234.1; 530/300, 350
See application file for complete search history.

(56) References Cited

U.S. PATENT DOCUMENTS

| | | | |
|---|---|---|---|
| 5,217,872 A | 6/1993 | Dorward et al. | |
| 5,470,712 A | 11/1995 | Simpson et al. | |
| 5,523,089 A | 6/1996 | Bergstrom et al. | |
| 5,571,718 A | 11/1996 | Dunn et al. | |
| 5,620,862 A | 4/1997 | Padula | |
| 5,688,512 A | 11/1997 | Bergstrom et al. | |
| 5,747,294 A | 5/1998 | Flavell et al. | |
| 5,777,095 A | 7/1998 | Barbour et al. | |
| 5,780,041 A | 7/1998 | Simpson et al. | |
| 6,113,914 A | 9/2000 | Lobet et al. | |
| 6,197,301 B1 | 3/2001 | Flavell et al. | |
| 6,210,676 B1 | 4/2001 | Callister et al. | |
| 6,248,562 B1 | 6/2001 | Dunn et al. | |
| 2004/0023325 A1 | 2/2004 | Luft et al. | |

FOREIGN PATENT DOCUMENTS

| | | |
|---|---|---|
| EP | 0 418 827 A1 | 3/1991 |
| EP | 0 465 204 A2 | 1/1992 |
| EP | 0 492 964 A2 | 7/1992 |
| EP | 0 522 560 A2 | 1/1993 |
| EP | 0 540 457 A1 | 5/1993 |
| EP | 0 711 563 A1 | 5/1996 |
| EP | 0 643 974 B1 | 1/1999 |
| EP | 0 598 816 B1 | 6/1999 |
| EP | 1 016 416 A2 | 5/2000 |
| WO | WO 90/04411 | 5/1990 |
| WO | WO 91/09870 | 7/1991 |
| WO | WO 91/13630 | 9/1991 |
| WO | WO 93/04175 | 3/1993 |
| WO | WO 93/08286 | 4/1993 |
| WO | WO 93/08299 | 4/1993 |
| WO | WO 93/08306 | 4/1993 |
| WO | WO 93/10237 | 5/1993 |
| WO | WO 94/19697 | 9/1994 |
| WO | WO 94/20536 | 9/1994 |
| WO | WO 94/25596 | 11/1994 |
| WO | WO 95/12676 | 5/1995 |
| WO | WO 96/40290 | 12/1996 |
| WO | WO 96/40718 | 12/1996 |
| WO | WO 97/42221 | 11/1997 |
| WO | WO 92/00055 | 1/1999 |
| WO | WO 99/14345 | 3/1999 |
| WO | WO 00/06745 | 2/2000 |

OTHER PUBLICATIONS

Kumaran D., et al. "Crystal Structure of Outer Surface Protein C (OspC) From the Lyme Disease Spirochete, *Borrelia burgdorferi*," EMBO J. 20(5):971–978 (2001).

Li, H., et al., "Crystal Structure of Lyme Disease Antigen Outer Surface Protein A Complexed With An Fab," Proc. Natl. Acad. Sci. USA, 94:3584–3589 (1997).

Barbour, A.G., et al., "Lyme Disease Spirochetes and Ixodid Tick Spirochetes Share a Common Surface Antigenic Determinant Defined by a Monoclonal Antibody," Infect. Immun. 41(2):795–804 (1983).

Wallich, R. et al., "DNA Vaccines Expressing a Fusion Products of Outer Surface Proteins A and C from *Borrelia burgdorferi* Induce Protective Antibodies Suitable for Prophylaxis but Not for Resolution of Lyme Disease," Infect. Immun., 69(4):2130–2136 (2001).

(Continued)

*Primary Examiner*—Rodney P. Swartz
(74) *Attorney, Agent, or Firm*—Hamilton, Brook, Smith & Reynolds, P.C.

(57) ABSTRACT

Novel chimeric nucleic acids, encoding chimeric *Borrelia* proteins comprising OspC or an antigenic fragment thereof and OspA or an antigenic fragment thereof, are disclosed. Chimeric proteins encoded by the nucleic acid sequences are also disclosed. The chimeric proteins are useful as vaccine immunogens against Lyme borreliosis, as well as for immunodiagnostic reagents.

21 Claims, 188 Drawing Sheets

OTHER PUBLICATIONS

Kalish, R.S., et al., "Lyme Disease: Human T–cell Response to OspA and OspC Borrelia Lipoproteins Includes Both CD8+ and CD4+ T–Cells," *J. Invest. Dermatol.*, 114(4):836 Abstract 523 (2000).

Luft, B.J., et al., "A New Multi–Target OspA–OspC Vaccine for Lyme Disease," *Abstracts of the Interscience Conference on Antimicrobial Agents and Chemotherapy*, 40:248 Abstract 1932 (2000).

Gomes–Solecki, M.J.C., et al., "Recombinant Chimeric Borrelia Proteins for Diagnosis of Lyme Disease," *J. Clin. Microbiol.*, 38(7):2530–2535 (2000).

Bakken, L.L., et al., "Interlaboratory Comparison of Test Results for Detection of Lyme Disease by 516 Participants in the Wisconsin State Laboratory of Hygiene/College of American Pathologists Proficiency Testing Program," *J. Clin. Microbiol.*, 35(3):537–543 (1997).

Chang, Y–F., et al., "Expression and Secretion of Outer Surface Protein (OSP–A) of *Borrelia burgdorferi* From *Escherichia coli*," *FEMS Microbiol. Lett.* 109:297–301 (1993).

De, B.K., et al., "Purification and Characterization of *Streptococcus pneumoniae* Palmitoylated pneumococcal surface adhesin A expressed in *Escherichia coli*," *Vaccine*, 18:1811–1821 (2000).

de Silva, A.M., et al., "*Borrelia burgdorferi* OspA Is an Arthropod–Specific Transmission–Blocking Lyme Disease Vaccine," *J. Exp. Med.* 183(1):271–275 (1996).

de Silva, A.M. and E. Fikrig, "Arthopod– and Host–Specific Gene Expression by *Borrelia burgdorferi*," *J. Clin. Invest.* 99(3):377–379 (1997).

Fingerle, V., et al., "Expression of Outer Surface Proteins A and C of *Borrelia burgdorferi* in *Ixodes ricinus* Ticks Removed from Humans," *Med. Microbiol. Immunol.* 187(2):121–126 (1998).

Dykhuizen, D.E., et al., "*Borrelia burgdorferi* is Clonal: Implications for Taxonomy and Vaccine Development," *Proc. Natl. Acad. Sci. USA* 90:10163–10167 (1993).

Gilmore, R.D., Jr., et al., "Outer Surface Protein C (OspC), but Not P39, Is a Protective Immunogen Against a Tick–Transmitted *Borrelia burgdorferi* Challenge: Evidence for a Conformational Protective Epitope in OspC," *Infect. Immun.* (64)6:2234–2239 (1996).

Montgomery, R.R., et al., "Direct Demonstration of Antigenic Substitution of *Borrelia burgdorferi* Ex Vivo: Exploration of the Paradox of the Early Immune Response to Outer Surface Proteins A and C in Lyme Disease," *J. Exp. Med.* 183 (1):261–269 (1996).

Probert, W.S. and R.B. LeFebvre, "Protections of C3H/HeN Mice from Challenge with *Borrelia burgdorferi* through Active Immunization with OspA, OspB, or OspC, but Not OspD or the 83–Kilodalton Antigen," *Infect. Immun.* 62(5):1920–1926 (1994).

Probert, W.S., et al., "Immunization with Outer Surface Protein (Osp) A, but Not OspC, Provides Cross–Protection of Mice Challenged with North American Isolates of *Borrelia burgdorferi*," *J. Infect. Dis.* 175(2):400–405 (1997).

Schwan, T.G., et al., "Induction of an Outer Surface Protein on *Borrelia burgdorferi* During Tick–Feeding," *Proc. Natl. Acad. Sci. USA* 92:2909–2913 (1995).

Simon, M.M., et al., "Protective Immunization with Plasmid DNA Containing the Outer Surface Lipoprotein A Gene of *Borrelia burgdorferi* is Independent of an Eukaryotic Promoter," *Eur. J. Immunol.* 26(12):2831–2840 (1996).

Simon, M.M., et al., "Lyme Disease: Pathogenesis and Vaccine Development," *Zent.bl. Bakteriol.* 289:690–695 (1999).

Solé, M., et al., "*Borrelia burgdorferi* Escape Mutants That Survive in the Presence of Antiserum to the OspA Vaccine Are Killed When Complement Is Also Present," *Infect. Immun.* 66(6):2540–2546 (1998).

Steigbigel, R.T. and J.L. Benach, "Immunization Against Lyme Disease–An Important First Step," *N. Engl. J. Med.* 339(4):263–264 (1998).

Stover, C.K., et al., "Protective Immunity Elicited by rBCG Vaccines," *Dev. Biol. Stand.* 82:163–170 (1994).

Thanassi, W.T. and R.T. Schoen, "The Lyme Disease Vaccine: Conception, Development, and Implementation," *Ann. Intern. Med.* 132:661–668 (2000).

Wahlberg, P., "Vaccination Against Lyme borreliosis," *Ann. Med.* 31:233–235 (1999).

Wang, I–N., et al., "Genetic Diversity of ospC in a Local Population of *Borrelia burgdorferi sensu stricto*," *Genetics* 151:15–30 (1999).

Wieneke, C.A., et al., "Evaluation of Whole–Cell and OspC Enzyme–Linked Immunosorbent Assays for Discrimination of Early Lyme Borreliosis from OspA Vaccination," *J. Clin. Microbiol.*,38(1):313–317 (2000).

Wilske, B., et al., "Diversity of OspA and OspC among Cerebrospinal Fluid Ioslates of *Borrelia burgdorferi* sensu lato from Patients with Neuroborreliosis in Germany," *Med. Microbiol. Immunol.* 184:195–201 (1996).

Wilske, B., et al., "Immunological and Molecular Variability of OspA and OspC. Implications of *Borrelia* Vaccine Development," *Infection* 24(2):208–212 (1996).

Wilske, B., et al., "Immunological and Molecular Polymorphisms of OspC, an Immunodominant Major Outer Surface Protein of *Borrelia burgdorferi*," *Infect. Immun.* 61(5):2182–2191 (1993).

Zhong, W. et al., "Therapeutic Passive Vaccination Against Chronic Lyme Disease in Mice," *Proc. Natl. Acad. Sci. USA* 94:12533–12538 (1997).

Zhong, W. et al., "Resolution of Experimental and Tick––bone *Borrelia burgdorferi* Infection in Mice by Passive, But Not Active Immunization Using Recombinant OspC," *Eur. J. Immunol.* 29:946–957 (1999).

Fikrig, E., et al., "Selection of Variant *Borrelia burgdorferi* Isolates From Mice Immunized With Outer Surface Protein A or B," *Infect. Immun.*, 63(5):1658–1662 (1995).

Sellati, T.J., et al., "Outer Surface Lipoproteins of *Borrelia burgdorferi* Activate Vascular Endothelium in Vitro," *Infect. Immun.* 64(8):3180–3187 (1996).

Zhang, Y–Q., et al., "*Borrelia burgdorferi* Enzyme–Linked Immunosorbent Assay for Discrimination of OspA Vaccination from Spirochete Infection," *J. Clin. Microbiol.*, 35(1):233–238 (1997).

Bunikis, J., et al., "Access of Antibody or Trypsin to an Integral Outer Membrane Protein (P66) of *Borrelia burgdorferi* Is Hindered by Osp Lipoproteins," *Infect. Immun.*, 67(6):2874–2883 (1999).

Hughes, C.A.N., et al., "Protective Immunity Is Induced by a *Borrelia burgdorferi* Mutant That Lacks OspA and OspB," *Infect. Immun.* 61(12):5115–5122 (1993).

Wallich, R., et al., "A Recombinant Vaccine for Lyme Disease," *Behring Inst. Mitt.*, 95:106–108 (1994).

Rosa, P.A., et al., "Recombination Between Genes Encoding Major Outer Surface Proteins A and B of *Borrelia burgdorferi,*" *Mol. Microbiol.*, 6(20):3031–3040 (1992).

Stover, C.K., et al., "Protective Immunity Elicited by Recombinant Bacille Calmettte–Guerin (BCG) Expressing Outer Surface Protein A (OspA) Lipoprotein: A Candidate Lyme Disease Vaccine," *J. Exp. Med.*, 178:197–209 (1993).

Schwan, T.G., et al., "Distribution and Molecular Analysis of Lyme Disease Spirochetes, *Borrelia burgdorferi*, Isolated From Ticks Throughout California," *J. Clin. Microbiol.*, 31(12):3096–3108 (1993).

Hu, C.M., et al., "Comparison in the Immunological Properties of *Borrelia burgdorferi* Isolates from *Ixodes Ricinus* Derived From Three Endemic Areas in Switzerland," *Epidemiol. Infect.*, 112:533–542 (1994).

Schubach, W.H., et al., "Mapping Antibody–Binding Domains of the Major Outer Surface Membrane Protein (OspA) of *Borrelia burgdorferi*," *Infect. Immun.* 59(6):1911–1915 (1991).

Kitten, T., et al., "Intragenic Recombination and a Chimeric Outer Membrane Protein in the Relapsing Fever Agent *Borrelia hermsii*", *J. Bacteriol.*, 175(9):2516–2522 (1993).

McGrath, B.C., et al., "Biochemical and Biophysical Characterization of the Major Outer Surface Protein from North American and European Isolates of *Borrelia burgdorferi*", *Vaccines* 93:365–370 (1993).

France, L.L., et al., "Evidence for an α–Helical Epitope on Outer Surface Protein A From the Lyme Disease Spirochete, *Borrelia burgdorferi*: An Application of Steady–State and Time–Resolved Fluorescence Quenching Techniques," *Biochim. Biophys. Acta*, 1202:287–296 (1993).

Kantor, F.S., "Disarming Lyme Disease," *Scientific American*, pp. 34–39 (1994).

McGrath, B.C., et al., "Identification of an Immunologically Important Hypervariable Domain of Major Outer Surface Protein A of *Borrelia burgdorferi*," *Infect. Immun.*, 63(4):1356–1361 (1995).

Wilske, B., et al., "An OspA Serotyping System for *Borrelia burgdorferi* Based on Reactivity With Monoclonal Antibodies and OspA Sequence Analysis," *J. Clin. Microbiol.*, 31(2):340–350 (1993).

Marconi, R.T., et al., "Variability of osp Genes and Gene Products Among Species of Lyme Disease Spirochetes," *Infect. Immun.*, 61(6):2611–2617 (1993).

Fikrig, E., et al., "*Borrelia burgdorferi* Strain 25015: Characterization of Outer Surface Protein A and Vaccination Against Infection," *J. Immunol.* 148(7):2256–2260 (1992).

Schaible, U., et al., "Immune Sera to Individual *Borrelia burgdorferi* Isolates or Recombinant OspA Thereof Project SCID Mice Against Infection With Homologous Strains but Only Partially or Not at All Against Those of Difference OspA/OspB Genotype," *Vaccine* 11(10):1049–1054 (1993).

Masuzawa, T., et al., "Protective Activity of Antisera Against Isolates of *Borrelia burgdorferi* From Various Geographical Origins," *Microbiol. Immunol.*, 37(1):79–83 (1993).

Wallich, R., et al., "Evaluation of Genetic Divergence Among *Borrelia burgdorferi* Isolates by Use of OspA, fla, HSP60, and HSP70 Gene Probes," *Infect. Immun.*, 60(11):4856–4866 (1992).

Simon, M.M., et al., "A Mouse Model for *Borrelia burgdorferi* Infection: Approach to a Vaccine Against Lyme Disease," *Immunol. Today*, 12(1):11–16 (1991).

Schaible, U.E., et al., "Monoclonal Antibodies Specific for the Outer Surface Protein A (OspA) of *Borrelia Burgdorferi* Prevent Lyme Borreliosis in Severe Combined Immunodeficiency (*scid*) Mice," *Proc. Natl. Acad. Sci. USA*, 87:3768–3772 (1990).

Preac–Mursic, V., et al., "Active Immunization With pC Protein of *Borrelia burgdorferi* Protects Gerbils Against *B. burgdorferi* Infection," *Infection*, 20(6):342–349 (1992).

Simon, M., et al., "Spirochetes: Vaccines, Animal Models and Diagnostics," *Res. Microbiol.*, 143:641–647 (1992).

Simon, M.M., et al., "Recombinant Outer Surface Protein A from *Borrelia burgdorferi* Induces Antibodies Protective against Spirochetal Infection in Mice," *J. Infect. Dis.*, 164:123–132 (1991).

Howe, T.R., et al., "A Single Recombinant Plasmid Expressing Two Major Outer Surface Proteins of the Lyme Disease Spirochete," *Science*, 227:645–46 (1985).

Johnson, R.C., et al., "Experimental Infection of the Hamster with *Borrelia burgdorferi*," *Ann. N.Y. Acad. Sci.*, 539:258–263 (1988).

France, L.L., et al., "Structural Analysis of an Outer Surface Protein From the Lyme Disease Spirochete, *Borrelia burgdorferi*, Using Circular Dichroism and Fluorescence Spectroscopy," *Biochim. Biophys. Acta*, 1120:59–68 (1992).

Howe, T.R., et al., "Organization of Genes Encoding Two Outer Membrane Proteins of the Lyme Disease Agent *Borrelia burgdorferi* within a Single Transcriptional Unit," *Infect. Immun.*, 54(1):207–212 (1986).

Johnson, R.C., et al., "Vaccination of Hamsters Against Experimental Infection with *Borrelia burgdorferi*," *Zbl. Bakt. Hyg. A*, 263:45–48 (1986).

Johnson, R.C., et al., "Passive Immunization of Hamsters Against Experimental Infection with the Lyme Disease Spirochete," *Infect. and Immun.*, 53(3):713–714 (1986).

Johnson, R.C., et al., "Active Immunization of Hamsters Against Experimental Infection with *Borrelia burgdorferi*," *Infect. Immun.*, 54(3):897–898 (1986).

Fikrig, E., et al., "Elimination of *Borrelia burgdorferi* from Vector Ticks Feeding on OspA–Immunized Mice," *Proc. Natl. Acad. Sci. USA*, 89:5418–5421 (1992).

Fikrig, E., et al., "Long–Term Protection of Mice From Lyme Disease by Vaccination with OspA," *Infect. Immun.*, 60(3):773–777 (1992).

Fikrig, E., et al., "Protection of Mice Against the Lyme Disease Agent by Immunizing with Recombinant OspA," *Science*, 250:553–556 (1990).

Erdile, L. F. et al., "Role of Attached Lipid in Immunogenicity of *Borrelia burgdorferi* OspA," *Infect. Immun.*, 61(1):81–90 (1993).

Bockenstedt, L.K., et al., "Inability of Truncated Recombinant Osp A Proteins To Elicit Protective Immunity to *Borrelia burgdorferi* in Mice," *J. Immun.*, 151(2):900–906 (1993).

Lovrich, S.D., et al., "Seroprotective Groups Among Isolates of *Borrelia burgdorferi*," *Infect. Immun.*, 61(10):4367–4374 (1993).

Wilske, B., et al., "Molecular Analysis of the Outer Surface Protein A (OspA) of *Borrelia burgdorferi* For Conserved and Variable Antibody Binding Domains," *Med. Microbiol. Immunol.*, 181:191–207 (1992).

Sears, J.E., et al., "Molecular Mapping of Osp–A Mediated Immunity Against *Borrelia burgdorferi*, The Agent of Lyme Disease," *J. Immunol.*, 147(6):1995–2000 (1991).

Lovrich, S.D., et al., "Seroprotective Groups of Lyme Borreliosis Spirochetes from North America and Europe," *J. Inf. Dis* 170:115–121 (1994).

Gern, L., et al., "Immunization With a Polyvalent OspA Vaccine Protects Mice Against *Ixodes Ricinus* Tick Bites Infected by *Borrelia burgdorferi ss, Borrelia garinii* and *Borrelia afzelli*," *Vaccine* 15(14):1551–1557 (1997).

Golde, W.T., et al., "The Lyme Disease Vaccine Candidate Outer Surface Protein A (OspA) in a Formulation Compatible With Human Use Protects Mice Against Natural Tick Transmission of *B. Burgdorferi*," *Vaccine* 13(5):435–441 (1995).

Masuzawa, T., et al., "Negative Finding in Cross–Protective Activity of Japanese *Borrelia* Isolates Against Infection with Three Species of Lyme Disease *Borrelia* in Outbred Mice," *Microbiol. Immunol.*, 41(9):733–736 (1997).

Domain 1

|  | 34 | 35 | 36 | 37 | 38 | 39 | 40 | 41 |
|---|---|---|---|---|---|---|---|---|
| A-B31 | L | P | G | E | M | K | V | L |
| A-TRO | L | P | G | E | M | K | V | L |
| A-K48 | L | P | G | G | M | T | V | L |
| A-DK29 | L | P | G | G | M | T | V | L |
| A-P/Gau | L | P | G | E | M | K | V | L |
| A-PKo | L | P | G | E | M | K | V | L |
| A-IP3 | L | P | G | E | I | K | V | L |
| A-IP90 | L | P | G | G | M | G | V | L |
| A-25015 | L | P | G | E | M | K | V | L |

Domain 2

|  | 65 | 66 | 67 | 68 | 69 | 70 | 71 | 72 | 73 | 74 | 75 |
|---|---|---|---|---|---|---|---|---|---|---|---|
| A-B31 | G | T | S | D | K | N | N | G | S | G | V |
| A-TRO | G | T | S | D | K | S | N | G | S | G | T |
| A-K48 | G | T | S | D | K | N | N | G | S | G | T |
| A-DK29 | G | T | S | D | K | N | N | G | S | G | T |
| A-P/Gau | G | T | S | D | K | D | N | G | S | G | T |
| A-PKo | G | T | S | D | K | D | N | G | S | G | T |
| A-IP3 | G | T | S | D | K | D | N | G | S | G | V |
| A-IP90 | G | T | S | D | K | N | N | G | S | G | T |
| A-25015 | G | T | S | D | K | N | N | G | S | G | V |

Domain 3

|  | 190 | 200 | 210 | 220 |
|---|---|---|---|---|
| A-B31 | NISKSGEVSVELNDTDSSAATKKTAAWNSGT |
| A-TRO | HIPNSGEITVELNDSNSTQATKKTGKWDSNT |
| A-K48 | NILLKSGEITVALDDSDTTQATKKTGKWDSKT |
| A-DK29 | NILKSGEITAALDDSDTTRATKKTGKWDSKT |
| A-P/Gau | EIAKSGEVTVALNDTNTTQATKKTGANDSKT |
| A-PKo | EIAKSGEVTVALNDTNTTQATKKTGAWDSKT |
| A-IP3 | EIAKSGEVTVALNDTNTTQATKKTGAWDSKT |
| A-IP90 | HISNSGEITVELNDSDTTQATKKTGTWDSKT |
| A-25015 | HISKSGEVTAELNDTDSTQATKKTGKNDAGT |

Domain 4

|  | 250 | 260 | 270 |
|---|---|---|---|
| A-B31 | SNGTKLEGSAVEITKLDEIKN |
| A-TRO | SAGTNLEGNAVEIKTLDELKN |
| A-K48 | SAGTNLEGKAVEITTLKELKN |
| A-DK29 | SAGTNLEGKAVEITTLKELKN |
| A-P/Gau | SAGTNLEGTAVELKTLDELKN |
| A-PKo | SAGTNLEGTAVEIKTLDELKN |
| A-IP3 | SAGTNLEGTAVEIKTLDELKN |
| A-IP90 | SAGTNLEGKAVEITTLKELKN |
| A-25015 | SAGTNLEGTAVEIKTLDEIKN |

FIG. 2

Protein sequence of OspAs from B31, K48 and the site-directed mutants from amino acids 200-220.

↓

B31:      ELNDTDSSAATKKTAAWNSGT
K48:      ALDDSDTTQATKKTGKWDSKT

613:      ELNDSDTSAATKKTAAWNSGT
625:      ELNDTDSSAATKKTGKWNSGT
640:      ELNDTDSSAATKKTAAWDSKT
613/625:  ELNDSDTSAATKKTGKWNSGT
613/640:  ELNDSDTSAATKKTAAWDSKT

FIG. 4

```
           10              20              30              40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100             110             120             130             140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150             160             170             180             190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200             210             220             230             240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250             260             270             280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290             300             310             320             330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340             350             360             370             380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 7A.

```
       390           400           410           420           430
        *             *             *             *             *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440           450           460           470           480
        *             *             *             *             *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490           500           510           520
        *             *             *             *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530           540           550           560           570
  *             *             *             *             *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580           590           600           610           620
        *             *             *             *             *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630           640           650           660           670
        *             *             *             *             *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

680           690           700           710           720
        *             *             *             *             *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730           740           750           760
        *             *             *             *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770           780           790           800           810
  *             *             *             *             *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
  *
AAA TAA
TTT ATT
Lys ***>
```

FIG. 7B

```
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90

TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

100             110             120             130             140

GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

150             160             170             180             190

GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

200             210             220             230             240

GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

250             260             270             280

ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290            300             310             320             330

ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

340             350             360             370             380

AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

FIG. 8A

```
          390           400           410           420           430
    *       *      *       *      *       *      *       *      *       *
  AAG GCT GAA ACA TCT GAA AAA ACA ATA GTA AGA GCA AAT GGA ACC AGA
  TTC CCA CTT TGT AGA CTT TTT TGT TAT CAT TCT CGT TTA CCT TGG TCT
  Lys Gly Glu Thr Ser Glu Lys Thr Ile Val Arg Ala Asn Gly Thr Arg>

440           450           460           470           480
    *       *      *       *      *       *      *       *      *       *
  CTT GAA TAC ACA GAC ATA AAA AGC GAT GGA TCC GGA AAA GCT AAA GAA
  GAA CTT ATG TGT CTG TAT TTT TCG CTA CCT AGG CCT TTT CGA TTT CTT
  Leu Glu Tyr Thr Asp Ile Lys Ser Asp Gly Ser Gly Lys Ala Lys Glu>

490           500           510           520
        *       *      *       *      *       *      *       *      *
      GTT TTA AAA GAC TTT ACT CTT GAA GGA ACT CTA GCT GCT GAC GGC AAA
      CAA AAT TTT CTG AAA TGA GAA CTT CCT TGA GAT CGA CGA CTG CCG TTT
      Val Leu Lys Asp Phe Thr Leu Glu Gly Thr Leu Ala Ala Asp Gly Lys>

530           540           550           560           570
    *       *      *       *      *       *      *       *      *       *
  ACA ACA TTG AAA GTT ACA GAA GGC ACT GTT GTT TTA AGC AAG AAC ATT
  TGT TGT AAC TTT CAA TGT CTT CCG TGA CAA CAA AAT TCG TTC TTG TAA
  Thr Thr Leu Lys Val Thr Glu Gly Thr Val Val Leu Ser Lys Asn Ile>

580           590           600           610           620
    *       *      *       *      *       *      *       *      *       *
  TTA AAA TCC GGA GAA ATA ACA GTT GCA CTT GAT GAC TCT GAC ACT ACT
  AAT TTT AGG CCT CTT TAT TGT CAA CGT GAA CTA CTG AGA CTG TGA TGA
  Leu Lys Ser Gly Glu Ile Thr Val Ala Leu Asp Asp Ser Asp Thr Thr>

630           640           650           660           670
    *       *      *       *      *       *      *       *      *       *
  CAG GCT ACT AAA AAA ACT GGA AAA TGG GAT TCA AAA ACT TCC ACT TTA
  GTC CGA TGA TTT TTT TGA CCT TTT ACC CTA AGT TTT TGA AGG TGA AAT
  Gln Ala Thr Lys Lys Thr Gly Lys Trp Asp Ser Lys Thr Ser Thr Leu>

680           690           700           710           720
    *       *      *       *      *       *      *       *      *       *
  ACA ATT AGT GTG AAT AGC CAA AAA ACC AAA AAC CTT GTA TTC ACA AAA
  TGT TAA TCA CAC TTA TCG GTT TTT TGG TTT TTG GAA CAT AAG TGT TTT
  Thr Ile Ser Val Asn Ser Gln Lys Thr Lys Asn Leu Val Phe Thr Lys>

730           740           750           760
        *       *      *       *      *       *      *       *      *
      GAA GAC ACA ATA ACA GTA CAA AAA TAC GAC TCA GCA GGC ACC AAT CTA
      CTT CTG TGT TAT TGT CAT GTT TTT ATG CTG AGT CGT CCG TGG TTA GAT
      Glu Asp Thr Ile Thr Val Gln Lys Tyr Asp Ser Ala Gly Thr Asn Leu>
```

FIG. 8B

```
       770         780         790          800         810
        *           *           *            *           *
GAA GGC AAA GCA GTC GAA ATT ACA ACA CTT AAA GAA CTT AAA AAC GCT
CTT CCG TTT CGT CAG CTT TAA TGT TGT GAA TTT CTT GAA TTT TTG CGA
Glu Gly Lys Ala Val Glu Ile Thr Thr Leu Lys Glu Leu Lys Asn Ala>

820
     *          *
TTA AAA TAA
AAT TTT ATT
Leu Lys ***>
```

FIG. 8C

```
              10            20            30            40
         *    •    *    •    *    •-   *    •    *    •    *    •
    ATG  AAA  AAA  TAT  TTA  TTG  GGA  ATA  GGT  CTA  ATA  TTA  GCC  TTA  ATA  GCA
    TAC  TTT  TTT  ATA  AAT  AAC  CCT  TAT  CCA  GAT  TAT  AAT  CGG  AAT  TAT  CGT
    Met  Lys  Lys  Tyr  Leu  Leu  Gly  Ile  Gly  Leu  Ile  Leu  Ala  Leu  Ile  Ala>

50            60            70            80            90
         *    •    *    •    *    •    *    •    *    •    *    •
    TGC  AAG  CAA  AAT  GTT  AGC  AGC  CTT  GAT  GAA  AAA  AAC  AGC  GCT  TCA  GTA
    ACG  TTC  GTT  TTA  CAA  TCG  TCG  GAA  CTA  CTT  TTT  TTG  TCG  CGA  AGT  CAT
    Cys  Lys  Gln  Asn  Val  Ser  Ser  Leu  Asp  Glu  Lys  Asn  Ser  Ala  Ser  Val>

100           110           120           130           140
         •    •    •    •    •    •    •    •    •    •    •    •
    GAT  TTG  CCT  GGT  GAG  ATG  AAA  GTT  CTT  GTA  AGT  AAA  GAA  AAA  GAC  AAA
    CTA  AAC  GGA  CCA  CTC  TAC  TTT  CAA  GAA  CAT  TCA  TTT  CTT  TTT  CTG  TTT
    Asp  Leu  Pro  Gly  Glu  Met  Lys  Val  Leu  Val  Ser  Lys  Glu  Lys  Asp  Lys>

150           160           170           180           190
         •    •    •    •    •    •    •    •    •    •    •    •
    GAC  GGT  AAG  TAC  AGT  CTA  AAG  GCA  ACA  GTA  GAC  AAG  ATT  GAG  CTA  AAA
    CTG  CCA  TTC  ATG  TCA  GAT  TTC  CGT  TGT  CAT  CTG  TTC  TAA  CTC  GAT  TTT
    Asp  Gly  Lys  Tyr  Ser  Leu  Lys  Ala  Thr  Val  Asp  Lys  Ile  Glu  Leu  Lys>

200           210           220           230           240
         •    •    •    •    •    •    •    •    •    •    •    •
    GGA  ACT  TCT  GAT  AAA  GAC  AAT  GGT  TCT  GGA  GTG  CTT  GAA  GGT  ACA  AAA
    CCT  TGA  AGA  CTA  TTT  CTG  TTA  CCA  AGA  CCT  CAC  GAA  CTT  CCA  TGT  TTT
    Gly  Thr  Ser  Asp  Lys  Asp  Asn  Gly  Ser  Gly  Val  Leu  Glu  Gly  Thr  Lys>

250           260           270           •280
         •    •    •    •    •    •    •    •    •    •    •    •
    GAT  GAC  AAA  AGT  AAA  GCA  AAA  TTA  ACA  ATT  GCT  GAC  GAT  CTA  AGT  AAA
    CTA  CTG  TTT  TCA  TTT  CGT  TTT  AAT  TGT  TAA  CGA  CTG  CTA  GAT  TCA  TTT
    Asp  Asp  Lys  Ser  Lys  Ala  Lys  Leu  Thr  Ile  Ala  Asp  Asp  Leu  Ser  Lys>

290           300           310           320           330
         •    •    •    •    •    •    •    •    •    •    •    •
    ACC  ACA  TTC  GAA  CTT  TTA  AAA  GAA  GAT  GGC  AAA  ACA  TTA  GTG  TCA  AGA
    TGG  TGT  AAG  CTT  GAA  AAT  TTT  CTT  CTA  CCG  TTT  TGT  AAT  CAC  AGT  TCT
    Thr  Thr  Phe  Glu  Leu  Leu  Lys  Glu  Asp  Gly  Lys  Thr  Leu  Val  Ser  Arg>

340           350           360           370           380
         •    •    •    •    •    •    •    •    •    •    •    •
    AAA  GTA  AGT  TCT  AGA  GAC  AAA  ACA  TCA  ACA  GAT  GAA  ATG  TTC  AAT  GAA
    TTT  CAT  TCA  AGA  TCT  CTG  TTT  TGT  AGT  TGT  CTA  CTT  TAC  AAG  TTA  CTT
    Lys  Val  Ser  Ser  Arg  Asp  Lys  Thr  Ser  Thr  Asp  Glu  Met  Phe  Asn  Glu>
```

FIG. 9A

```
        390           400           410           420           430
    *     *       *     *     *       *     *     *     *       *
AAA GGT GAA TTG TCT GCA AAA ACC ATG ACA AGA GAA AAT GGA ACC AAA
TTT CCA CTT AAC AGA CGT TTT TGG TAC TGT TCT CTT TTA CCT TGG TTT
Lys Gly Glu Leu Ser Ala Lys Thr Met Thr Arg Glu Asn Gly Thr Lys>

440           450           460           470           480
          *     *       *     *     *     *     *     *     *     *
CTT GAA TAT ACA GAA ATG AAA AGC GAT GGA ACC GGA AAA GCT AAA GAA
GAA CTT ATA TGT CTT TAC TTT TCG CTA CCT TGG CCT TTT CGA TTT CTT
Leu Glu Tyr Thr Glu Met Lys Ser Asp Gly Thr Gly Lys Ala Lys Glu>

490           500           510           520
          *     *     *     *     *     *     *     *     *
GTT TTA AAA AAG TTT ACT CTT GAA GGA AAA GTA GCT AAT GAT AAA GTA
CAA AAT TTT TTC AAA TGA GAA CTT CCT TTT CAT CGA TTA CTA TTT CAT
Val Leu Lys Lys Phe Thr Leu Glu Gly Lys Val Ala Asn Asp Lys Val>

530           540           550           560           570
  *     *     *     *     *     *     *     *     *     *
ACA TTG GAA GTA AAA GAA GGA ACC GTT ACT TTA AGT AAG GAA ATT GCA
TGT AAC CTT CAT TTT CTT CCT TGG CAA TGA AAT TCA TTC CTT TAA CGT
Thr Leu Glu Val Lys Glu Gly Thr Val Thr Leu Ser Lys Glu Ile Ala>

580           590           600           610           620
    *     *     *     *     *     *     *     *     *     *
AAA TCT GGA GAA GTA ACA GTT GCT CTT AAT GAC ACT AAC ACT ACT CAG
TTT AGA CCT CTT CAT TGT CAA CGA GAA TTA CTG TGA TTG TGA TGA GTC
Lys Ser Gly Glu Val Thr Val Ala Leu Asn Asp Thr Asn Thr Thr Gln>

630           640           650           660           670
    *     *     *     *     *     *     *     *     *     *
GCT ACT AAA AAA ACT GGC GCA TGG GAT TCA AAA ACT TCT ACT TTA ACA
CGA TGA TTT TTT TGA CCG CGT ACC CTA AGT TTT TGA AGA TGA AAT TGT
Ala Thr Lys Lys Thr Gly Ala Trp Asp Ser Lys Thr Ser Thr Leu Thr>

680           690           700           710           720
      *     *     *     *     *     *     *     *     *     *
ATT ACT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
Ile Ser Val Asn Ser Lys Lys Thr Thr Gln Leu Val Phe Thr Lys Gln>

730           740           750           760
        *     *     *     *     *     *     *     *     *
TAC ACA ATA ACT GTA AAA CAA TAC GAC TCC GCA GGT ACC AAT TTA GAA
ATG TGT TAT TGA CAT TTT GTT ATG CTG AGG CGT CCA TGG TTA AAT CTT
Tyr Thr Ile Thr Val Lys Gln Tyr Asp Ser Ala Gly Thr Asn Leu Glu>
```

FIG. 9B

```
       770           780           790           800           810
        .             .             .             .             .
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

820
   .
AAA TAA
TTT ATT
Lys ***>
```

FIG. 9C

```
          10              20              30              40
           *               *               *               *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50           60              70              80              90
    *            *               *               *               *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100             110             120             130             140
           *               *               *               *               *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150             160             170             180             190
           *               *               *               *               *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200             210             220             230             240
           *               *               *               *               *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250             260             270             280
           *               *               *               *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290          300             310             320             330
   *            *               *               *               *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340             350             360             370             380
       *               *               *               *               *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 10A

```
        390         400         410         420         430
         *           *           *           *           *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440         450         460         470         480
         *           *           *           *           *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490         500         510         520
         *           *           *           *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530        540         550         560         570
  *          *           *           *           *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580         590         600         610         620
         *           *           *           *           *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630         640         650         660         670
         *           *           *           *           *
GCT ACT AAA AAA ACT GCA GCT TGG AAT GCA GGC ACT TCA ACT TTA ACA
CGA TGA TTT TTT TGA CGT CGA ACC TTA CGT CCG TGA AGT TGA AAT TGT
Ala Thr Lys Lys Thr Ala Ala Trp Asn Ala Gly Thr Ser Thr Leu Thr>

680         690         700         710         720
         *           *           *           *           *
ATT ACT GTA AAC AAC AAA AAA ACT AAA GCC CTT GTA TTT ACA AAA CAA
TAA TGA CAT TTG TTG TTT TTT TGA TTT CGG GAA CAT AAA TGT TTT GTT
Ile Thr Val Asn Asn Lys Lys Thr Lys Ala Leu Val Phe Thr Lys Gln>

730         740         750         760
         *           *           *           *
GAC ACA ATT ACA TCA CAA AAA TAC GAC TCA GCA GGA ACC AAC TTG GAA
CTG TGT TAA TGT AGT GTT TTT ATG CTG AGT CGT CCT TGG TTG AAC CTT
Asp Thr Ile Thr Ser Gln Lys Tyr Asp Ser Ala Gly Thr Asn Leu Glu>

OSPA 25015
770         780         790         800         810
 *           *           *           *           *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

AGA
TCT
Arg>
```

FIG. 10B

```
              10              20              30              4:
         .     *      .      *      .     .      .      .      .      *
ATG AGA TTA TTA ATA GGA TTT GCT TTA GCG TTA GCT TTA ATA GGA TGT
TAC TCT AAT AAT TAT CCT AAA CGA AAT CGC AAT CGA AAT TAT CCT ACA
Met Arg Leu Leu Ile Gly Phe Ala Leu Ala Leu Ala Leu Ile Gly Cys>

50              60              70              80              90
   *      *      *      *      *      *      *      *      *      -
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
Ala Gln Lys Gly Ala Glu Ser Ile Gly Ser Gln Lys Glu Asn Asp Leu>

100             110             120             130             140
       *     *      *      *      *      *      *      *      *      *
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
Asn Leu Glu Asp Ser Ser Lys Lys Ser His Gln Asn Ala Lys Gln Asp>

150             160             170             180             190
       *      *      *      *      *      *      *      *      *      -
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
Leu Pro Ala Val Thr Glu Asp Ser Val Ser Leu Phe Asn Gly Asn Lys>

200             210             220             230             240
           *      *      *      *      *      *      *      *      *      *
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
Ile Phe Val Ser Lys Glu Lys Asn Ser Ser Gly Lys Tyr Asp Leu Arg>

250             260             270             280
               *      *      *      *      *      *      *      *
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
Ala Thr Ile Asp Gln Val Glu Leu Lys Gly Thr Ser Asp Lys Asn Asn>

290             300             310             320             330
 *      *      *      *      *      *      *      *      *      -
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
Gly Ser Gly Thr Leu Glu Gly Ser Lys Pro Asp Lys Ser Lys Val Lys>

340             350             360             370             380
       *      *      *      *      *      *      *      *      *      *
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
Leu Thr Val Ser Ala Asp Leu Asn Thr Val Thr Leu Glu Ala Phe Asp>
          390             400             410             420             430
```

FIG. 11A

```
            .    .    .    .    .    .    .    .    .    .
            GCC  AGC  AAC  CAA  AAA  ATT  TCA  AGT  AAA  GTT  ACT  AAA  AAA  CAG  GGG  TCA
            CGG  TCG  TTG  GTT  TTT  TAA  AGT  TCA  TTT  CAA  TGA  TTT  TTT  GTC  CCC  AGT
            Ala  Ser  Asn  Gln  Lys  Ile  Ser  Ser  Lys  Val  Thr  Lys  Lys  Gln  Gly  Ser>

440         450         460         470         480
             .          .           .           .           .           .
            ATA  ACA  GAG  GAA  ACT  CTC  AAA  GCT  AAT  AAA  TTA  GAC  TCA  AAG  AAA  TTA
            TAT  TGT  CTC  CTT  TGA  GAG  TTT  CGA  TTA  TTT  AAT  CTG  AGT  TTC  TTT  AAT
            Ile  Thr  Glu  Glu  Thr  Leu  Lys  Ala  Asn  Lys  Leu  Asp  Ser  Lys  Lys  Leu>

490         500         510         520
             .          .           .           .           .            .
            ACA  AGA  TCA  AAC  GGA  ACT  ACA  CTT  GAA  TAC  TCA  CAA  ATA  ACA  GAT  GCT
            TGT  TCT  AGT  TTG  CCT  TGA  TGT  GAA  CTT  ATG  AGT  GTT  TAT  TGT  CTA  CGA
            Thr  Arg  Ser  Asn  Gly  Thr  Thr  Leu  Glu  Tyr  Ser  Gln  Ile  Thr  Asp  Ala>

530        540         550         560         570
             .          .           .           .           .           .
            GAC  AAT  GCT  ACA  AAA  GCA  GTA  GAA  ACT  CTA  AAA  AAT  AGC  ATT  AAG  CTT
            CTG  TTA  CGA  TGT  TTT  CGT  CAT  CTT  TGA  GAT  TTT  TTA  TCG  TAA  TTC  GAA
            Asp  Asn  Ala  Thr  Lys  Ala  Val  Glu  Thr  Leu  Lys  Asn  Ser  Ile  Lys  Leu>

580         590         600         610         620
             .          .           .           .           .           .
            GAA  GGA  AGT  CTT  GTA  GTC  GGA  AAA  ACA  ACA  GTG  GAA  ATT  AAA  GAA  GGT
            CTT  CCT  TCA  GAA  CAT  CAG  CCT  TTT  TGT  TGT  CAC  CTT  TAA  TTT  CTT  CCA
            Glu  Gly  Ser  Leu  Val  Val  Gly  Lys  Thr  Thr  Val  Glu  Ile  Lys  Glu  Gly>

630         640         650         660         670
             .          .           .           .           .           .
            ACT  GTT  ACT  CTA  AAA  AGA  GAA  ATT  GAA  AAA  GAT  GGA  AAA  GTA  AAA  GTC
            TGA  CAA  TGA  GAT  TTT  TCT  CTT  TAA  CTT  TTT  CTA  CCT  TTT  CAT  TTT  CAG
            Thr  Val  Thr  Leu  Lys  Arg  Glu  Ile  Glu  Lys  Asp  Gly  Lys  Val  Lys  Val>

680         690         700         710         720
             .          .           .           .           .           .
            TTT  TTG  AAT  GAC  ACT  GCA  GGT  TCT  AAC  AAA  AAA  ACA  GGT  AAA  TGG  GAA
            AAA  AAC  TTA  CTG  TGA  CGT  CCA  AGA  TTG  TTT  TTT  TGT  CCA  TTT  ACC  CTT
            Phe  Leu  Asn  Asp  Thr  Ala  Gly  Ser  Asn  Lys  Lys  Thr  Gly  Lys  Trp  Glu>

730         740         750         760
             .          .           .           .           .           .
            GAC  AGT  ACT  AGC  ACT  TTA  ACA  ATT  AGT  GCT  GAC  AGC  AAA  AAA  ACT  AAA
            CTG  TCA  TGA  TCG  TGA  AAT  TGT  TAA  TCA  CGA  CTG  TCG  TTT  TTT  TGA  TTT
            Asp  Ser  Thr  Ser  Thr  Leu  Thr  Ile  Ser  Ala  Asp  Ser  Lys  Lys  Thr  Lys>

770        780         790         800         810
             .          .           .           .           .           .
            GAT  TTG  GTG  TTC  TTA  ACA  GAT  GGT  ACA  ATT  ACA  GTA  CAA  CAA  TAC  AAC
            CTA  AAC  CAC  AAG  AAT  TGT  CTA  CCA  TGT  TAA  TGT  CAT  GTT  GTT  ATG  TTG
            Asp  Leu  Val  Phe  Leu  Thr  Asp  Gly  Thr  Ile  Thr  Val  Gln  Gln  Tyr  Asn>
```

FIG. 11B

```
         820           830           840           850           860
          .     .       .     .       .     .       . .   .       .
     ACA GCT GGA ACC AGC CTA GAA GGA TCA GCA AGT GAA ATT AAA AAT CTT
     TGT CGA CCT TGG TCG GAT CTT CCT AGT CGT TCA CTT TAA TTT TTA GAA
     Thr Ala Gly Thr Ser Leu Glu Gly Ser Ala Ser Glu Ile Lys Asn Leu>

870           880           890
      .     .       .     .       .     .
     TCA GAG CTT AAA AAC GCT TTA AAA TAA
     AGT CTC GAA TTT TTG CGA AAT TTT ATT
     Ser Glu Leu Lys Asn Ala Leu Lys ***>
```

FIG. 11C

```
          10             20             30             40
     *    *    *    *    *    *    *    *    *
ATG  AAA  AAG  AAT  ACA  TTA  AGT  GCG  ATA  TTA  ATG  ACT  TTA  TTT  TTA  TTT
TAC  TTT  TTC  TTA  TGT  AAT  TCA  CGC  TAT  AAT  TAC  TGA  AAT  AAA  AAT  AAA
Met  Lys  Lys  Asn  Thr  Leu  Ser  Ala  Ile  Leu  Met  Thr  Leu  Phe  Leu  Phe>

50             60             70             80             90
     *    *    *    *    *    *    *    *    *    *
ATA  TCT  TGT  AAT  AAT  TCA  GGG  AAA  GAT  GGG  AAT  ACA  TCT  GCA  AAT  TCT
TAT  AGA  ACA  TTA  TTA  AGT  CCC  TTT  CTA  CCC  TTA  TGT  AGA  CGT  TTA  AGA
Ile  Ser  Cys  Asn  Asn  Ser  Gly  Lys  Asp  Gly  Asn  Thr  Ser  Ala  Asn  Ser>

100            110            120            130            140
     *    *    *    *    *    *    *    *    *    *
GCT  GAT  GAG  TCT  GTT  AAA  GGG  CCT  AAT  CTT  ACA  GAA  ATA  AGT  AAA  AAA
CGA  CTA  CTC  AGA  CAA  TTT  CCC  GGA  TTA  GAA  TGT  CTT  TAT  TCA  TTT  TTT
Ala  Asp  Glu  Ser  Val  Lys  Gly  Pro  Asn  Leu  Thr  Glu  Ile  Ser  Lys  Lys>

150            160            170            180            190
     *    *    *    *    *    *    *    *    *    *
ATT  ACG  GAT  TCT  AAT  GCG  GTT  TTA  CTT  GCT  GTG  AAA  GAG  GTT  GAA  GCG
TAA  TGC  CTA  AGA  TTA  CGC  CAA  AAT  GAA  CGA  CAC  TTT  CTC  CAA  CTT  CGC
Ile  Thr  Asp  Ser  Asn  Ala  Val  Leu  Leu  Ala  Val  Lys  Glu  Val  Glu  Ala>

200            210            220            230            240
     *    *    *    *    *    *    *    *    *    *
TTG  CTG  TCA  TCT  ATA  GAT  GAA  ATT  GCT  GCT  AAA  GCT  ATT  GGT  AAA  AAA
AAC  GAC  AGT  AGA  TAT  CTA  CTT  TAA  CGA  CGA  TTT  CGA  TAA  CCA  TTT  TTT
Leu  Leu  Ser  Ser  Ile  Asp  Glu  Ile  Ala  Ala  Lys  Ala  Ile  Gly  Lys  Lys>

250            260            270            280
     *    *    *    *    *    *    *    *    *
ATA  CAC  CAA  AAT  AAT  GGT  TTG  GAT  ACC  GAA  TAT  AAT  CAC  AAT  GGA  TCA
TAT  GTG  GTT  TTA  TTA  CCA  AAC  CTA  TGG  CTT  ATA  TTA  GTG  TTA  CCT  AGT
Ile  His  Gln  Asn  Asn  Gly  Leu  Asp  Thr  Glu  Tyr  Asn  His  Asn  Gly  Ser>

290            300            310            320            330
     *    *    *    *    *    *    *    *    *    *
TTG  TTA  GCG  GGA  CGT  TAT  GCA  ATA  TCA  ACC  CTA  ATA  AAA  CAA  AAA  TTA
AAC  AAT  CGC  CCT  GCA  ATA  CGT  TAT  AGT  TGG  GAT  TAT  TTT  GTT  TTT  AAT
Leu  Leu  Ala  Gly  Arg  Tyr  Ala  Ile  Ser  Thr  Leu  Ile  Lys  Gln  Lys  Leu>

340            350            360            370            380
     *    *    *    *    *    *    *    *    *
GAT  GGA  TTG  AAA  AAT  GAA  GGA  TTA  AAG  GAA  AAA  ATT  GAT  GCG  GCT  AAG
CTA  CCT  AAC  TTT  TTA  CTT  CCT  AAT  TTC  CTT  TTT  TAA  CTA  CGC  CGA  TTC
Asp  Gly  Leu  Lys  Asn  Glu  Gly  Leu  Lys  Glu  Lys  Ile  Asp  Ala  Ala  Lys>
```

FIG. 12A

```
        390             400             410             420             430
    *       *       *       *       *       *       *       *       *       *
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
Lys Cys Ser Glu Thr Phe Thr Asn Lys Leu Lys Glu Lys His Thr Asp>

440             450             460             470             480
    *       *       *       *       *       *       *       *       *       *
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
Leu Gly Lys Glu Gly Val Thr Asp Ala Asp Ala Lys Glu Ala Ile Leu>

490             500             510             520
        *       *       *       *       *       *       *       *
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
Lys Thr Asn Gly Thr Lys Thr Lys Gly Ala Glu Glu Leu Gly Lys Leu>

530             540             550             560             570
    *       *       *       *       *       *       *       *       *
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
Phe Glu Ser Val Glu Val Leu Ser Lys Ala Ala Lys Glu Met Leu Ala>

580             590             600             610             620
    *       *       *       *       *       *       *       *       *
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
Asn Ser Val Lys Glu Leu Thr Ser Pro Val Val Ala Glu Ser Pro Lys>

630
    *       *
AAA CCT TAA
TTT GGA ATT
Lys Pro ***>
```

FIG. 12B

```
           10              20              30              40
            *               *               *               *         *
ATG AAA AAG AAT ACA TTA AGT GCG ATA TTA ATG ACT TTA TTT TTA TTT
TAC TTT TTC TTA TGT AAT TCA CGC TAT AAT TAC TGA AAT AAA AAT AAA
Met Lys Lys Asn Thr Leu Ser Ala Ile Leu Met Thr Leu Phe Leu Phe>

50              60              70              80              90
  *               *               *               *               *
ATA TCT TGT AAT AAT TCA GGT GGG GAT ACC GCA TCT ACT AAT CCT GAT
TAT AGA ACA TTA TTA AGT CCA CCC CTA TGG CGT AGA TGA TTA GGA CTA
Ile Ser Cys Asn Asn Ser Gly Gly Asp Thr Ala Ser Thr Asn Pro Asp>

100             110             120             130             140
         *               *               *               *               *
GAG TCT GCA AAA GGA CCT AAT CTT ACA GTA ATA AGC AAA AAA ATT ACA
CTC AGA CGT TTT CCT GGA TTA GAA TGT CAT TAT TCG TTT TTT TAA TGT
Glu Ser Ala Lys Gly Pro Asn Leu Thr Val Ile Ser Lys Lys Ile Thr>

150             160             170             180             190
            *               *               *               *               *
GAT TCT AAT GCA TTT GTA CTG GCT GTG AAA GAA GTT GAG GCT TTG ATC
CTA AGA TTA CGT AAA CAT GAC CGA CAC TTT CTT CAA CTC CGA AAC TAG
Asp Ser Asn Ala Phe Val Leu Ala Val Lys Glu Val Glu Ala Leu Ile>

200             210             220             230             240
            *               *               *               *               *
TCA TCT ATA GAT GAA CTT GCT AAT AAA GCT ATT GGT AAA GTA ATA CAT
AGT AGA TAT CTA CTT GAA CGA TTA TTT CGA TAA CCA TTT CAT TAT GTA
Ser Ser Ile Asp Glu Leu Ala Asn Lys Ala Ile Gly Lys Val Ile His>

250             260             270             280
            *               *               *               *         *
CAA AAT AAT GGT TTA AAT GCT AAT GCG GGT CAA AAC GGA TCA TTG TTA
GTT TTA TTA CCA AAT TTA CGA TTA CGC CCA GTT TTG CCT AGT AAC AAT
Gln Asn Asn Gly Leu Asn Ala Asn Ala Gly Gln Asn Gly Ser Leu Leu>

290             300             310             320             330
 *               *               *               *               *
GCA GGA GCC TAT GCA ATA TCA ACC CTA ATA ACA GAA AAA TTA AGT AAA
CGT CCT CGG ATA CGT TAT AGT TGG GAT TAT TGT CTT TTT AAT TCA TTT
Ala Gly Ala Tyr Ala Ile Ser Thr Leu Ile Thr Glu Lys Leu Ser Lys>

340             350             360             370             380
            *               *               *               *               *
TTG AAA AAT TCA GAA GAG TTA AAT AAA AAA ATT GAA GAG GCT AAG AAC
AAC TTT TTA AGT CTT CTC AAT TTA TTT TTT TAA CTT CTC CGA TTC TTG
Leu Lys Asn Ser Glu Glu Leu Asn Lys Lys Ile Glu Glu Ala Lys Asn>
```

FIG. 13A

```
          390              400              410              420              430
     *    *     +     *     *     *     *     *     *     *     v
     CAT  TCT  GAA  GCA  TTT  ACT  AAT  AGA  CTA  AAA  GGT  TCT  CAT  GCA  CAA  CTT
     GTA  AGA  CTT  CGT  AAA  TGA  TTA  TCT  GAT  TTT  CCA  AGA  GTA  CGT  GTT  GAA
     His  Ser  Glu  Ala  Phe  Thr  Asn  Arg  Leu  Lys  Gly  Ser  His  Ala  Gln  Leu>

440              450              460              470              480
     *    *     +     *     *     *     *     *     *     *     *     *
     GGA  GTT  GCT  GCT  GCT  ACT  GAT  GAT  CAT  GCA  AAA  GAA  GCT  ATT  TTA  AAG
     CCT  CAA  CGA  CGA  CGA  TGA  CTA  CTA  GTA  CGT  TTT  CTT  CGA  TAA  AAT  TTC
     Gly  Val  Ala  Ala  Ala  Thr  Asp  Asp  His  Ala  Lys  Glu  Ala  Ile  Leu  Lys>

490              500              510              520
          *     *     *     *     *     *     *     *     *
     TCA  AAT  CCT  ACT  AAA  GAT  AAG  GGT  GCT  AAA  GCA  CTT  AAA  GAC  TTA  TCT
     AGT  TTA  GGA  TGA  TTT  CTA  TTC  CCA  CGA  TTT  CGT  GAA  TTT  CTG  AAT  AGA
     Ser  Asn  Pro  Thr  Lys  Asp  Lys  Gly  Ala  Lys  Ala  Leu  Lys  Asp  Leu  Ser>

530            540              550              560              570
     *    *     *     *     *     *     *     *     *     *     *
     GAA  TCA  GTA  GAA  AGC  TTG  GCA  AAA  GCA  GCG  CAA  GAA  GCA  TTA  GCT  AAT
     CTT  AGT  CAT  CTT  TCG  AAC  CGT  TTT  CGT  CGC  GTT  CTT  CGT  AAT  CGA  TTA
     Glu  Ser  Val  Glu  Ser  Leu  Ala  Lys  Ala  Ala  Gln  Glu  Ala  Leu  Ala  Asn>

580              590              600              610              620
     *    *     *     *     *     *     *     *     *
     TCA  GTT  AAA  GAA  CTT  ACA  AAT  CCT  GTT  GTG  GCA  GAA  AGT  CCA  AAA  AAA
     AGT  CAA  TTT  CTT  GAA  TGT  TTA  GGA  CAA  CAC  CGT  CTT  TCA  GGT  TTT  TTT
     Ser  Val  Lys  Glu  Leu  Thr  Asn  Pro  Val  Val  Ala  Glu  Ser  Pro  Lys  Lys>

630
     *    *
     CCT  TAA
     GGA  ATT
     Pro  ***>
```

FIG. 13B

```
            10          20          30          40
         *      *      *      *      *      *      *      *
ATG AAA AAG AAT ACA TTA AGT GCG ATA TTA ATG ACT TTA TTT TTA TTT
TAC TTT TTC TTA TGT AAT TCA CGC TAT AAT TAC TGA AAT AAA AAT AAA
Met Lys Lys Asn Thr Leu Ser Ala Ile Leu Met Thr Leu Phe Leu Phe>

50          60          70          80          90
   *      *      *      *      *      *      *      *      *
ATA TCT TGT AGT AAT TCA GGG AAA GGT GGG GAT TCT GCA TCT ACT AAT
TAT AGA ACA TCA TTA AGT CCC TTT CCA CCC CTA AGA CGT AGA TGA TTA
Ile Ser Cys Ser Asn Ser Gly Lys Gly Gly Asp Ser Ala Ser Thr Asn>

100         110         120         130         140
   *      *      *      *      *      *      *      *      *
CCT GCT GAC GAG TCT GCG AAA GGG CCT AAT CTT ACA GAA ATA AGC AAA
GGA CGA CTG CTC AGA CGC TTT CCC GGA TTA GAA TGT CTT TAT TCG TTT
Pro Ala Asp Glu Ser Ala Lys Gly Pro Asn Leu Thr Glu Ile Ser Lys>

150         160         170         180         190
   *      *      *      *      *      *      *      *      *
AAA ATT ACA GAT TCT AAT GCA TTT GTA CTT GCT GTT AAA GAA GTT GAG
TTT TAA TGT CTA AGA TTA CGT AAA CAT GAA CGA CAA TTT CTT CAA CTC
Lys Ile Thr Asp Ser Asn Ala Phe Val Leu Ala Val Lys Glu Val Glu>

200         210         220         230         240
   *      *      *      *      *      *      *      *      *
ACT TTG GTT TTA TCT ATA GAT GAA CTT GCT AAG AAA GCT ATT GGT CAA
TGA AAC CAA AAT AGA TAT CTA CTT GAA CGA TTC TTT CGA TAA CCA GTT
Thr Leu Val Leu Ser Ile Asp Glu Leu Ala Lys Lys Ala Ile Gly Gln>

250         260         270         280
   *      *      *      *      *      *      *      *      *
AAA ATA GAC AAT AAT AAT GGT TTA GCT GCT TTA AAT AAT CAG AAT GGA
TTT TAT CTG TTA TTA TTA CCA AAT CGA CGA AAT TTA TTA GTC TTA CCT
Lys Ile Asp Asn Asn Asn Gly Leu Ala Ala Leu Asn Asn Gln Asn Gly>

290         300         310         320         330
   *      *      *      *      *      *      *      *      *
TCG TTG TTA GCA GGA GCC TAT GCA ATA TCA ACC CTA ATA ACA GAA AAA
AGC AAC AAT CGT CCT CGG ATA CGT TAT AGT TGG GAT TAT TGT CTT TTT
Ser Leu Leu Ala Gly Ala Tyr Ala Ile Ser Thr Leu Ile Thr Glu Lys>

340         350         360         370         380
   *      *      *      *      *      *      *      *      *
TTG AGT AAA TTG AAA AAT TTA GAA GAA TTA AAG ACA GAA ATT GCA AAG
AAC TCA TTT AAC TTT TTA AAT CTT CTT AAT TTC TGT CTT TAA CGT TTC
Leu Ser Lys Leu Lys Asn Leu Glu Glu Leu Lys Thr Glu Ile Ala Lys>
```

FIG. 14A

```
              390           400           410           420           430
         *     *      *      *      *      *      *      *      *      *
         GCT  AAG  AAA  TGT  TCC  GAA  GAA  TTT  ACT  AAT  AAA  CTA  AAA  AGT  GGT  CAT
         CGA  TTC  TTT  ACA  AGG  CTT  CTT  AAA  TGA  TTA  TTT  GAT  TTT  TCA  CCA  GTA
         Ala  Lys  Lys  Cys  Ser  Glu  Glu  Phe  Thr  Asn  Lys  Leu  Lys  Ser  Gly  His>

440           450           460           470           480
         *     *      *      *      *      *      *      *      *      *
         GCA  GAT  CTT  GGC  AAA  CAG  GAT  GCT  ACC  GAT  GAT  CAT  GCA  AAA  GCA  GCT
         CGT  CTA  GAA  CCG  TTT  GTC  CTA  CGA  TGG  CTA  CTA  GTA  CGT  TTT  CGT  CGA
         Ala  Asp  Leu  Gly  Lys  Gln  Asp  Ala  Thr  Asp  Asp  His  Ala  Lys  Ala  Ala>

490           500           510           520
         *     *      *      *      *      *      *      *
         ATT  TTA  AAA  ACA  CAT  GCA  ACT  ACC  GAT  AAA  GGT  GCT  AAA  GAA  TTT  AAA
         TAA  AAT  TTT  TGT  GTA  CGT  TGA  TGG  CTA  TTT  CCA  CGA  TTT  CTT  AAA  TTT
         Ile  Leu  Lys  Thr  His  Ala  Thr  Thr  Asp  Lys  Gly  Ala  Lys  Glu  Phe  Lys>

530           540           550           560           570
         *     *      *      *      *      *      *      *      *      *
         GAT  TTA  TTT  GAA  TCA  GTA  GAA  GGT  TTG  TTA  AAA  GCA  GCT  CAA  GTA  GCA
         CTA  AAT  AAA  CTT  AGT  CAT  CTT  CCA  AAC  AAT  TTT  CGT  CGA  GTT  CAT  CGT
         Asp  Leu  Phe  Glu  Ser  Val  Glu  Gly  Leu  Leu  Lys  Ala  Ala  Gln  Val  Ala>

580           590           600           610           620
         *     *      *      *      *      *      *      *      *      *
         CTA  ACT  AAT  TCA  GTT  AAA  GAA  CTT  ACA  AGT  CCT  GTT  GTA  GCA  GAA  AGT
         GAT  TGA  TTA  AGT  CAA  TTT  CTT  GAA  TGT  TCA  GGA  CAA  CAT  CGT  CTT  TCA
         Leu  Thr  Asn  Ser  Val  Lys  Glu  Leu  Thr  Ser  Pro  Val  Val  Ala  Glu  Ser>

630
         *     *      *
         CCA  AAA  AAA  CCT  TAA
         GGT  TTT  TTT  GGA  ATT
         Pro  Lys  Lys  Pro  ***>
```

FIG. 14B

```
              10           20           30           40
               *    *       *    *       *    *       *    *
          ATG AAA AAG AAT ACA TTA AGT GCG ATA TTA ATG ACT TTA TTT TTA TTT
          TAC TTT TTC TTA TGT AAT TCA CGC TAT AAT TAC TGA AAT AAA AAT AAA
          Met Lys Lys Asn Thr Leu Ser Ala Ile Leu Met Thr Leu Phe Leu Phe>

50           60           70           80           90
            *    *       *    *       *    *       *    *       *    *
          ATA TCT TGT AAT AAT TCA GGT GGG GAT TCT GCA TCT ACT AAT CCT GAT
          TAT AGA ACA TTA TTA AGT CCA CCC CTA AGA CGT AGA TGA TTA GGA CTA
          Ile Ser Cys Asn Asn Ser Gly Gly Asp Ser Ala Ser Thr Asn Pro Asp>

100          110          120          130          140
            *    *       *    *       *.   *       *    *       *    *
          GAG TCT GCA AAA GGA CCT AAT CTT ACC GTA ATA AGC AAA AAA ATT ACA
          CTC AGA CGT TTT CCT GGA TTA GAA TGG CAT TAT TCG TTT TTT TAA TGT
          Glu Ser Ala Lys Gly Pro Asn Leu Thr Val Ile Ser Lys Lys Ile Thr>

150          160          170          180          190
               *    *       *    *       *    *       *    *       *    *
          GAT TCT AAT GCA TTT TTA CTG GCT GTG AAA GAA GTT GAG GCT TTG CTT
          CTA AGA TTA CGT AAA AAT GAC CGA CAC TTT CTT CAA CTC CGA AAC GAA
          Asp Ser Asn Ala Phe Leu Leu Ala Val Lys Glu Val Glu Ala Leu Leu>

200          210          220          230          240
               *    *       *    *       *    *       *    *       *    *
          TCA TCT ATA GAT GAA CTT TCT AAA GCT ATT GGT AAA AAA ATA AAA AAT
          AGT AGA TAT CTA CTT GAA AGA TTT CGA TAA CCA TTT TTT TAT TTT TTA
          Ser Ser Ile Asp Glu Leu Ser Lys Ala Ile Gly Lys Lys Ile Lys Asn>

250          260          270          280
                  *    *       *    *       *    *       *    *    *
          GAT GGT ACT TTA GAT AAC GAA GCA AAT CGA AAC GAA TCA TTC ATA GCA
          CTA CCA TGA AAT CTA TTG CTT CGT TTA GCT TTG CTT AGT AAT TAT CGT
          Asp Gly Thr Leu Asp Asn Glu Ala Asn Arg Asn Glu Ser Leu Ile Ala>

290          300          310          320          330
            *    *       *    *       *    *       *    *       *    *
          GGA GCT TAT GAA ATA TCA AAA CTA ATA ACA CAA AAA TTA AGT GTA TTG
          CCT CGA ATA CTT TAT AGT TTT GAT TAT TGT GTT TTT AAT TCA CAT AAC
          Gly Ala Tyr Glu Ile Ser Lys Leu Ile Thr Gln Lys Leu Ser Val Leu>

340          350          360          370          380
            *    *       *    *       *    *       *    *       *
          AAT TCA GAA GAA TTA AAG AAA AAA ATT AAA GAG GCT AAG GAT TGT TCC
          TTA AGT CTT CTT AAT TTC TTT TTT TAA TTT CTC CGA TTC CTA ACA AGG
          Asn Ser Glu Glu Leu Lys Lys Lys Ile Lys Glu Ala Lys Asp Cys Ser>
```

FIG. 15A

```
OspC-TRO 390           400           410           420           430
   *     *      *      *      *      *      *     *      *      *
GAA AAA TTT ACT ACT AAG CTA AAA GAT AGT CAT GCA GAG CTT GGT ATA
CTT TTT AAA TGA TGA TTC GAT TTT CTA TCA GTA CGT CTC GAA CCA TAT
Glu Lys Phe Thr Thr Lys Leu Lys Asp Ser His Ala Glu Leu Gly Ile>

440           450           460           470           480
   *     *      *      *      *      *      *     *      *      *
CAA AGC GTT CAG GAT GAT AAT GCA AAA AAA GCT ATT TTA AAA ACA CAT
GTT TCG CAA GTC CTA CTA TTA CGT TTT TTT CGA TAA AAT TTT TGT GTA
Gln Ser Val Gln Asp Asp Asn Ala Lys Lys Ala Ile Leu Lys Thr His>

490           500           510           520
   *     *      *      *      *      *      *     *      *
GGA ACT AAA GAC AAG GGT GCT AAA GAA CTT GAA GAG TTA TTT AAA TCA
CCT TGA TTT CTG TTC CCA CGA TTT CTT GAA CTT CTC AAT AAA TTT AGT
Gly Thr Lys Asp Lys Gly Ala Lys Glu Leu Glu Glu Leu Phe Lys Ser>

530          540           550           560           570
   *     *      *      *      *      *      *     *      *      *
CTA GAA AGC TTG TCA AAA GCA GCG CAA GCA GCA TTA ACT AAT TCA GTT
GAT CTT TCG AAC AGT TTT CGT CGC GTT CGT CGT AAT TGA TTA AGT CAA
Leu Glu Ser Leu Ser Lys Ala Ala Gln Ala Ala Leu Thr Asn Ser Val>

580           590           600           610           620
   *     *      *      *      *      *      *     *      *      *
AAA GAG CTT ACA AAT CCT GTT GTG GCA GAA AGT CCA AAA AAA CCT TAA
TTT CTC GAA TGT TTA GGA CAA CAC CGT CTT TCA GGT TTT TTT GGA ATT
Lys Glu Leu Thr Asn Pro Val Val Ala Glu Ser Pro Lys Lys Pro ***>
```

FIG. 15B

```
          10          20          30          40
ATG AAA AAA ATG TTA CTA ATC TTT AGT TTT TTT CTT ATT TTC TTG AAT
TAC TTT TTT TAC AAT GAT TAG AAA TCA AAA AAA GAA TAA AAG AAC TTA
Met Lys Lys Met Leu Leu Ile Phe Ser Phe Phe Leu Ile Phe Leu Asn>

50          60          70          80          90
GGA TTT CCT GTT AGT GCA AGA GAA GTT GAT AGG GAA AAA TTA AAG GAC
CCT AAA GGA CAA TCA CGT TCT CTT CAA CTA TCC CTT TTT AAT TTC CTG
Gly Phe Pro Val Ser Ala Arg Glu Val Asp Arg Glu Lys Leu Lys Asp>

100         110         120         130         140
TTT GTT AAT ATG GAT CTT GAG TTT GTA AAT TAT AAA GGC CCT TAT GAT
AAA CAA TTA TAC CTA GAA CTC AAA CAT TTA ATA TTT CCG GGA ATA CTA
Phe Val Asn Met Asp Leu Glu Phe Val Asn Tyr Lys Gly Pro Tyr Asp>

150         160         170         180         190
TCT ACA AAT ACA TAT GAA CAA ATA GTG GGT ATT GGG GAG TTT TTA GCA
AGA TGT TTA TGT ATA CTT GTT TAT CAC CCA TAA CCC CTC AAA AAT CGT
Ser Thr Asn Thr Tyr Glu Gln Ile Val Gly Ile Gly Glu Phe Leu Ala>

200         210         220         230         240
AGA CCG TTG ACC AAT TCC AAT AGC AAC TCA AGT TAT TAT GGT AAA TAT
TCT GGC AAC TGG TTA AGG TTA TCG TTG AGT TCA ATA ATA CCA TTT ATA
Arg Pro Leu Thr Asn Ser Asn Ser Asn Ser Ser Tyr Tyr Gly Lys Tyr>

250         260         270         280
TTT ATT AAT AGA TTT ATT GAT GAT CAA GAT AAA AAA GCA AGC GTT GAT
AAA TAA TTA TCT AAA TAA CTA CTA GTT CTA TTT TTT CGT TCG CAA CTA
Phe Ile Asn Arg Phe Ile Asp Asp Gln Asp Lys Lys Ala Ser Val Asp>

290         300         310         320         330
GTT TTT TCT ATT GGT AGT AAG TCA GAG CTT GAC AGT ATA TTG AAT TTA
CAA AAA AGA TAA CCA TCA TTC AGT CTC GAA CTG TCA TAT AAC TTA AAT
Val Phe Ser Ile Gly Ser Lys Ser Glu Leu Asp Ser Ile Leu Asn Leu>

340         350         360         370         380
AGA AGA ATT CTT ACA GGG TAT TTA ATA AAG TCT TTC GAT TAT GAC AGG
TCT TCT TAA GAA TGT CCC ATA AAT TAT TTC AGA AAG CTA ATA CTG TCC
Arg Arg Ile Leu Thr Gly Tyr Leu Ile Lys Ser Phe Asp Tyr Asp Arg>
```

FIG. 16A

```
       390         400         410         420         430
  *      *     *    *      *    *      *    *      *    *
TCT AGT GCA GAA TTA ATT GCT AAG GTT ATT ACA ATA TAT AAT GCT GTT
AGA TCA CGT CTT AAT TAA CGA TTC CAA TAA TGT TAT ATA TTA CGA CAA
Ser Ser Ala Glu Leu Ile Ala Lys Val Ile Thr Ile Tyr Asn Ala Val>

440         450         460         470         480
  *      *     *    *      *    *      *    *      *    *
TAT AGA GGA GAT TTG GAT TAT TAT AAA GGG TTT TAT ATT GAG GCT GCT
ATA TCT CCT CTA AAC CTA ATA ATA TTT CCC AAA ATA TAA CTC CGA CGA
Tyr Arg Gly Asp Leu Asp Tyr Tyr Lys Gly Phe Tyr Ile Glu Ala Ala>

490         500         510         520
  *      *     *    *      *    *      *    *      *    *
TTA AAG TCT TTA AGT AAA GAA AAT GCA GGT CTT TCT AGG GTT TAT AGT
AAT TTC AGA AAT TCA TTT CTT TTA CGT CCA GAA AGA TCC CAA ATA TCA
Leu Lys Ser Leu Ser Lys Glu Asn Ala Gly Leu Ser Arg Val Tyr Ser>

530         540         550         560         570
  *      *     *    *      *    *      *    *      *    *
CAG TGG GCT GGA AAG ACA CAA ATA TTT ATT CCT CTT AAA AAG GAT ATT
GTC ACC CGA CCT TTC TGT GTT TAT AAA TAA GGA GAA TTT TTC CTA TAA
Gln Trp Ala Gly Lys Thr Gln Ile Phe Ile Pro Leu Lys Lys Asp Ile>

580         590         600         610         620
  *      *     *    *      *    *      *    *      *    *
TTG TCT GGA AAT ATT GAG TCT GAC ATT GAT ATT GAC AGT TTA GTT ACA
AAC AGA CCT TTA TAA CTC AGA CTG TAA CTA TAA CTG TCA AAT CAA TGT
Leu Ser Gly Asn Ile Glu Ser Asp Ile Asp Ile Asp Ser Leu Val Thr>

630         640         650         660         670
  *      *     *    *      *    *      *    *      *    *
GAT AAG GTG GTG GCA GCT CTT TTA AGT GAA AAT GAA GCA GGT GTT AAC
CTA TTC CAC CAC CGT CGA GAA AAT TCA CTT TTA CTT CGT CCA CAA TTG
Asp Lys Val Val Ala Ala Leu Leu Ser Glu Asn Glu Ala Gly Val Asn>

680         690         700         710         720
  *      *     *    *      *    *      *    *      *    *
TTT GCA AGA GAT ATT ACA GAT ATT CAA GGC GAA ACT CAT AAG GCA GAT
AAA CGT TCT CTA TAA TGT CTA TAA GTT CCG CTT TGA GTA TTC CGT CTA
Phe Ala Arg Asp Ile Thr Asp Ile Gln Gly Glu Thr His Lys Ala Asp>

730         740         750         760
  *      *     *    *      *    *      *    *      *    *
CAA GAT AAA ATT GAT ATT GAA TTA GAC AAT ATT CAT GAA AGT GAT TCC
GTT CTA TTT TAA CTA TAA CTT AAT CTG TTA TAA GTA CTT TCA CTA AGG
Gln Asp Lys Ile Asp Ile Glu Leu Asp Asn Ile His Glu Ser Asp Ser>

770         780         790         800         810
  *      *     *    *      *    *      *    *      *    *
AAT ATA ACA GAA ACT ATT GAA AAT TTA AGG GAT CAG CTT GAA AAA GCT
TTA TAT TGT CTT TGA TAA CTT TTA AAT TCC CTA GTC GAA CTT TTT CGA
Asn Ile Thr Glu Thr Ile Glu Asn Leu Arg Asp Gln Leu Glu Lys Ala>
```

FIG. 16B

```
         820           830           840           850           860
          *             *             *             *             *
ACA GAT GAA GAG CAT AAA AAA GAG ATT GAA AGT CAG GTT GAT GCT AAA
TGT CTA CTT CTC GTA TTT TTT CTC TAA CTT TCA GTC CAA CTA CGA TTT
Thr Asp Glu Glu His Lys Lys Glu Ile Glu Ser Gln Val Asp Ala Lys>

870           880           890           900           910
          *             *             *             *             *
AAG AAA CAA AAG GAA GAG CTA GAT AAA AAG GCA ATA AAT CTT GAT AAA
TTC TTT GTT TTC CTT CTC GAT CTA TTT TTC CGT TAT TTA GAA CTA TTT
Lys Lys Gln Lys Glu Glu Leu Asp Lys Lys Ala Ile Asn Leu Asp Lys>

920           930           940           950           960
          *             *             *             *             *
GCT CAG CAA AAA TTA GAT TCT GCT GAA GAT AAT TTA GAT GTT CAA AGA
CGA GTC GTT TTT AAT CTA AGA CGA CTT CTA TTA AAT CTA CAA GTT TCT
Ala Gln Gln Lys Leu Asp Ser Ala Glu Asp Asn Leu Asp Val Gln Arg>

970           980           990          1000
          *             *             *             *
AAT ACT GTT AGA GAG AAA ATT CAA GAG GAT ATT AAC GAA ATT AAC AAG
TTA TGA CAA TCT CTC TTT TAA GTT CTC CTA TAA TTG CTT TAA TTG TTC
Asn Thr Val Arg Glu Lys Ile Gln Glu Asp Ile Asn Glu Ile Asn Lys>

1010          1020          1030          1040          1050
          *             *             *             *             *
GAA AAG AAT TTA CCA AAG CCT GGT GAT GTA AGT TCT CCT AAA GTT GAT
CTT TTC TTA AAT GGT TTC GGA CCA CTA CAT TCA AGA GGA TTT CAA CTA
Glu Lys Asn Leu Pro Lys Pro Gly Asp Val Ser Ser Pro Lys Val Asp>

1060          1070          1080          1090          1100
          *             *             *             *             *
AAG CAA CTA CAA ATA AAA GAG AGC CTG GAA GAT TTG CAG GAG CAG CTT
TTC GTT GAT GTT TAT TTT CTC TCG GAC CTT CTA AAC GTC CTC GTC GAA
Lys Gln Leu Gln Ile Lys Glu Ser Leu Glu Asp Leu Gln Glu Gln Leu>

1110          1120          1130          1140          1150
          *             *             *             *             *
AAA GAA ACT GGT GAT GAA AAT CAG AAA AGA GAA ATT GAA AAG CAA ATT
TTT CTT TGA CCA CTA CTT TTA GTC TTT TCT CTT TAA CTT TTC GTT TAA
Lys Glu Thr Gly Asp Glu Asn Gln Lys Arg Glu Ile Glu Lys Gln Ile>

1160          1170          1180          1190          1200
          *             *             *             *             *
GAA ATC AAA AAA AGT GAT GAA AAG CTT TTA AAA AGT AAA GAT GAT AAA
CTT TAG TTT TTT TCA CTA CTT TTC GAA AAT TTT TCA TTT CTA CTA TTT
Glu Ile Lys Lys Ser Asp Glu Lys Leu Leu Lys Ser Lys Asp Asp Lys>

1210          1220          1230          1240
          *             *             *             *
GCA AGT AAA GAT GGT AAA GCC TTG GAT CTT GAT CGA GAA TTA AAT TCT
CGT TCA TTT CTA CCA TTT CGG AAC CTA GAA CTA GCT CTT AAT TTA AGA
Ala Ser Lys Asp Gly Lys Ala Leu Asp Leu Asp Arg Glu Leu Asn Ser>
```

FIG. 16C

```
      1250           1260          1270          1280          1290
AAA GCT TCT AGC AAA GAA AAA AGT AAA GCC AAG GAA GAA GAA ATA ACC
TTT CGA AGA TCG TTT CTT TTT TCA TTT CGG TTC CTT CTT CTT TAT TGG
Lys Ala Ser Ser Lys Glu Lys Ser Lys Ala Lys Glu Glu Glu Ile Thr>

1300           1310          1320          1330          1340
AAG GGT AAG TCA CAG AAA AGC TTA GGC GAT TTG AAT AAT GAT GAA AAT
TTC CCA TTC AGT GTC TTT TCG AAT CCG CTA AAC TTA TTA CTA CTT TTA
Lys Gly Lys Ser Gln Lys Ser Leu Gly Asp Leu Asn Asn Asp Glu Asn>

1350           1360          1370          1380          1390
CTT ATG ATG CCA GAA GAT CAA AAA TTA CCT GAG GTT AAA AAA TTA GAT
GAA TAC TAC GGT CTT CTA GTT TTT AAT GGA CTC CAA TTT TTT AAT CTA
Leu Met Met Pro Glu Asp Gln Lys Leu Pro Glu Val Lys Lys Leu Asp>

1400           1410          1420          1430          1440
AGC AAA AAA GAA TTT AAA CCT GTT TCT GAG GTT GAG AAA TTA GAT AAG
TCG TTT TTT CTT AAA TTT GGA CAA AGA CTC CAA CTC TTT AAT CTA TTC
Ser Lys Lys Glu Phe Lys Pro Val Ser Glu Val Glu Lys Leu Asp Lys>

1450           1460          1470          1480
ATT TTC AAG TCT AAT AAC AAT GTT GGA GAA TTA TCA CCG TTA GAT AAA
TAA AAG TTC AGA TTA TTG TTA CAA CCT CTT AAT AGT GGC AAT CTA TTT
Ile Phe Lys Ser Asn Asn Asn Val Gly Glu Leu Ser Pro Leu Asp Lys>

1490           1500          1510          1520          1530
TCT TCT TAT AAA GAC ATT GAT TCA AAA GAG GAG ACA GTT AAT AAA GAT
AGA AGA ATA TTT CTG TAA CTA AGT TTT CTC CTC TGT CAA TTA TTT CTA
Ser Ser Tyr Lys Asp Ile Asp Ser Lys Glu Glu Thr Val Asn Lys Asp>

1540           1550          1560          1570          1580
GTT AAT TTG CAA AAG ACT AAG CCT CAG GTT AAA GAC CAA GTT ACT TCT
CAA TTA AAC GTT TTC TGA TTC GGA GTC CAA TTT CTG GTT CAA TGA AGA
Val Asn Leu Gln Lys Thr Lys Pro Gln Val Lys Asp Gln Val Thr Ser>

1590           1600          1610          1620          1630
TTG AAT GAA GAT TTG ACT ACT ATG TCT ATA GAT TCC AGT AGT CCT GTA
AAC TTA CTT CTA AAC TGA TGA TAC AGA TAT CTA AGG TCA TCA GGA CAT
Leu Asn Glu Asp Leu Thr Thr Met Ser Ile Asp Ser Ser Ser Pro Val>

1640           1650          1660          1670          1680
TTT TTA GAG GTT ATT GAT CCA ATT ACA AAT TTA GGA ACT CTT CAA CTT
AAA AAT CTC CAA TAA CTA GGT TAA TGT TTA AAT CCT TGA GAA GTT GAA
Phe Leu Glu Val Ile Asp Pro Ile Thr Asn Leu Gly Thr Leu Gln Leu>
```

FIG. 16D

```
              1690            1700            1710            1720
               *       *       *       *       *       *       *       *       *
            ATT GAT TTA AAT ACT GGT GTT AGG CTT AAA GAA AGC ACT CAG CAA GGC
            TAA CTA AAT TTA TGA CCA CAA TCC GAA TTT CTT TCG TGA GTC GTT CCG
            Ile Asp Leu Asn Thr Gly Val Arg Leu Lys Glu Ser Thr Gln Gln Gly>

1730           1740            1750            1760            1770
      *       *       *       *       *       *       *       *       *
     ATT CAG CGG TAT GGA ATT TAT GAA CGT GAA AAA GAT TTG GTT GTT ATT
     TAA GTC GCC ATA CCT TAA ATA CTT GCA CTT TTT CTA AAC CAA CAA TAA
     Ile Gln Arg Tyr Gly Ile Tyr Glu Arg Glu Lys Asp Leu Val Val Ile>

1780            1790            1800            1810            1820
         *       *       *       *       *       *       *       *       *
        AAA ATG GAT TCA GGA AAA GCT AAG CTT CAG ATA CTT GAT AAA CTT GAA
        TTT TAC CTA AGT CCT TTT CGA TTC GAA GTC TAT GAA CTA TTT GAA CTT
        Lys Met Asp Ser Gly Lys Ala Lys Leu Gln Ile Leu Asp Lys Leu Glu>

1830            1840            1850            1860            1870
            *       *       *       *       *       *       *       *       *
           AAT TTA AAA GTG GTA TCA GAG TCT AAT TTT GAG ATT AAT AAA AAT TCA
           TTA AAT TTT CAC CAT AGT CTC AGA TTA AAA CTC TAA TTA TTT TTA AGT
           Asn Leu Lys Val Val Ser Glu Ser Asn Phe Glu Ile Asn Lys Asn Ser>

1880            1890            1900            1910            1920
               *       *       *       *       *       *       *       *       *
              TCT CTT TAT GTT GAT TCT AAA ATG ATT TTA GTA GCT GTT AGG GAT AAA
              AGA GAA ATA CAA CTA AGA TTT TAC TAA AAT CAT CGA CAA TCC CTA TTT
              Ser Leu Tyr Val Asp Ser Lys Met Ile Leu Val Ala Val Arg Asp Lys>

1930            1940            1950            1960
                  *       *       *       *       *       *       *       *
                 GAT AGT AGT AAT GAT TGG AGA TTG GCC AAA TTT TCT CCT AAA AAT TTA
                 CTA TCA TCA TTA CTA ACC TCT AAC CGG TTT AAA AGA GGA TTT TTA AAT
                 Asp Ser Ser Asn Asp Trp Arg Leu Ala Lys Phe Ser Pro Lys Asn Leu>

1970            1980            1990            2000            2010
      *       *       *       *       *       *       *       *       *
     GAT GAG TTT ATT CTT TCA GAG AAT AAA ATT ATG CCT TTT ACT AGC TTT
     CTA CTC AAA TAA GAA AGT CTC TTA TTT TAA TAC GGA AAA TGA TCG AAA
     Asp Glu Phe Ile Leu Ser Glu Asn Lys Ile Met Pro Phe Thr Ser Phe>

2020            2030            2040            2050            2060
         *       *       *       *       *       *       *       *       *
        TCT GTG AGA AAA AAT TTT ATT TAT TTG CAA GAT GAG TTT AAA AGT CTA
        AGA CAC TCT TTT TTA AAA TAA ATA AAC GTT CTA CTC AAA TTT TCA GAT
        Ser Val Arg Lys Asn Phe Ile Tyr Leu Gln Asp Glu Phe Lys Ser Leu>

2070            2080            2090            2100
            *       *       *       *       *       *       *       *
           GTT ATT TTA GAT GTA AAT ACT TTA AAA AAA GTT AAG TA
           CAA TAA AAT CTA CAT TTA TGA AAT TTT TTT CAA TTC AT
           Val Ile Leu Asp Val Asn Thr Leu Lys Lys Val Lys Xxx>
```

FIG. 16E

```
   1 ATGAAAAAAT TGTTACTAAT CTTTAGTTTT TTTCTTATTT CTTTGAATGG ATTTCCTCTT
  61 AATTCAAGGG AAGTTGATAA GGAAAAATTA AAGGATTTTG TTAATATGGA TCTTGAGTTT
 121 GTAAACTATA AAGGTCCTTA TGATTCTACA AATACATATG AACAAATAGT AGGTATTGGT
 181 GAGTTTTTAG CAAGACCATT GATTAATTCC AATAGCAACT CAATTTATTA TGGTAAATAT
 241 TTTATTAATA GATTTATTGA TGATCAAGAT AAAAAAGCAA GCGTTGATGT TTTTTCTATT
 301 GGTAGTAGGT CACAGCTTGA CAGTATATTG AATCTAAGAA GAATTCTTAC AGGGTATTTG
 361 ATAAAGTCTT TTGATTATGA AAGATCTAGT GCTGAATTAA TTGCTAAGGT TATTACAATA
 421 CATAATGCTG TTTATAGAGG GGATTTAAAT TATTATAAAG AGGTTTATAT TGAGGCTGCT
 481 TTAAAGTCTT TAACTAAAGA AAATGCAGGT CTTTCTAGAG TGTACAGTCA ATGGGCTGGA
 541 AAGACACAAA TATTTATTCC TCTTAAAAAG AATATTTTAT CTGGAAAAGT TGAGTCTGAC
 601 ATTGATATTG ACAGTTTGGT TACAGATAAG GTTGTGGCAG CTGTTTTAAG CGAGAATGAA
 661 GCAGGTGTTA ACTTTGCAAG AGATATTACA GATATTCAAG GCGAAACTCA TAAAGCAGAT
 721 CAAGATAAAA TTGATATTGA ATTAGATAAT GTTCATAAAA GTGATTCCAA TATAACAGAG
 781 ACTATTGAGA ATTTAAGAGA TCAGCTTCAA AAGGCTACAG ATGAAGAGCA TAGAAAAGAG
 841 ATTGAAAGTC AGGTTGATGC TAAAAGAAA CAAAAAGAAG AACTAGATAA AAAGGCAATC
 901 GATCTTGATA AAGCCCAACA AAAATTAGAT TCTTCTGAAG ATAATTTAGA TATTCAAAGC
 961 GATACTGTTA GAGAGAAGAT TCAAGGGGAT ATTGACGAGA TTAATAAAGA AAAGAATTTG
1021 CCAAAACCTG GTGATGTAAG TTCTCCTAAA GTTGATAAGC AGCTACAAAT AAAAGAGAGT
1081 CTAGAAGACT TGCAGGAACA GCTTAAAGAA ACTAGCGATG AAAATCAAAA AAGAGAAATT
1141 GAAAAGCAAA TTGAAATCAA AAAAAGTGAT GAAGAACTTT TAAAAAGTAA AGATCCTAAA
1201 GCATTAGATC TTAATGGAGA TTTAAATTCT AAAGTTTCTA GTAAAGAAAA AATTAAAGGC
1261 AAAGAAGGAG AAATAGTCAA AGAGGAATCA AAGGCAAGTT TAGCTGATTT GAATAATGAC
1321 GAAAATCTTA TGAGGCCGGA AGATCAAAAA TTATCTGAGG ATAAAAATT AGATAGTAAA
1381 AAAAATTTAA AACCTGTTTC TGAGATTGAG AGAGTAAATG AAATTTCGAA GTCTAACAAC
1441 AATGAGATTA GTAATCATC ACCATTATAT AAGCCTTCTT ATAGCGATAT GGATTCAAAA
1501 GAGGGTATAG ATAATAAAGA TGTTAACTTG CAAGAAACCA AGTCTCAAAC TAAAAGTCAA
1561 CCTACTTCTT TAAATCAAGA TTTGACTACT ATGTCTATAG ATTCTAGTAA TCCTGTATTT
1621 TTAGAGGTTA TTGATCCTAT TACAAATTTA GGAACGCTTC AACTTATTGA TTTGAATACC
1681 GGTGTTAGAC TTAAAGAAAG TACTCAGCAA GGCATTCAGC GGTATGGAAT TTATGAACGT
1741 GAAAAAGATT TAGTTGTTAT TAAATGGAT TCAGGAAAAG CCAAGCTTCA AATACTTAAT
1801 AAACTTGAGA ATTTAAAAGT GATATCGGAG TCTAATTTTG AGATTAATAA AAATTCATCT
1861 CTTTATGTTG ACTCTAAAAT GATTTTAGTA GTTGTGAGAG ATAGTGGTAA TGTTTGGAGA
1921 TTGGCTAAAT TTTCTCCTAA AAATTTAAAT GAGTTTATTC TTTCAGAGAA TAAAATTTTG
1981 CCTTTTACTA GCTTTTCTGT GAGAAAGAAT TTTATTTATT TGCAGGATGA GTTAAAAAGT
2041 CTTATTACTT TAGATGTAAA TACTTTAAAA AAAGTTAAGT A
```

FIG. 17

```
   1 ATGAAAAAAA TGTTACTAAT CTTTAGTTTT TTTCTTGTTT TTTTAAATGG ATTTCCTCTT
  61 AATGCAAGGG AAGTTGATAA GGAAAAATTA AAGGACTTTG TTAATATGGA TCTTGAATTT
 121 GTTAATTACA AGGGTCCTTA TGATTCTACA GATACATATG AACAAATAGT AGGTATTGGG
 181 GAGTTTTTAG CAAGGCCGTT GAACAATTCC AATAGTAATT CAAGTTATTA TGGTAAATAT
 241 TTTGTTAATA GATTTATTGA CCATCAAGAT AAAAAAGCAA GTGTTGATAT TTTTTCTATT
 301 GGTAGTAAGT CAGAGCTTGA TAGTATATTA AATCTAAGAA GAATTCTTAC AGGGTATTTA
 361 ATGAAGTCTT TTGATTATGA GAGGTCTAGT GCGGAATTAA TTGCTAAAGC TATTACAATA
 421 TATAATGCTG TTTATAGAGG AGATTTAGAT TATTACAAAG AGTTTTATAT TGAGGCTTCT
 481 TTGAAGTCTT TGACTAAACA AAATGCAGGT CTTTCTAGGG TGTACAGTCA ATGGGCTGGG
 541 AAGACACAAA TATTTATTCC TCTTAAAAAG AATATTTTAT CTGGAAATGT TGAGTCTGAC
 601 ATTGATATTG ATAGTTTGGT TACAGATAAG GTGGTGGCAG CTCTTTTAAG TGAGAATGAA
 661 TCAGGTGTTA ACTTTGCAAG AGATATTACA GACATTCAAG GCGAAACTCA TAAAGCAGAT
 721 CAAGATAAAA TTGATATTGA ATTAGATAAT TTTCATGAAA GTGATTCCAA TATAACAGAA
 781 ACTATTGAGA ATTTAAGGGA TCAGCTTGAA AAAGCTACAG ATGAAGAGCA TAAAAAGAG
 841 ATTGAAAGTC AGGTTGATGC TAAAAAGAAA CAAAAGGAAG AATTAGATAA AAAGGCAATT
 901 GATCTTGATA AAGCTCAACA AAAATTAGAT TTTGCTGAAG ATAATCTAGA TATTCAAAGG
 961 GATACTGTTA GAGAGAAGCT TCAAGAAAAT ATTAACGAGA CTAATAAGGA AAAGAATTTA
1021 CCAAAGCCTG GTGATGTAAG TTCTCCTAAG GTTGATAAGC AGTTGCAGAT AAAAGAGAGT
1081 CTAGAAGATT TGCAAGAGCA GCTTAAAGAA GCTAGTGATG AAAATCAAAA AAGAGAAATA
1141 GAAAAGCAAA TTGAAATCAA AAAAAATGAT GAAGAACTTT TTAAAAATAA AGATCATAAA
1201 GCATTAGATC TTAAGCAAGA ATTAAATTCT AAAGCTTCTA GTAAAGAAAA AATTGAAGGC
1261 GAAGAAGAGG ATAAAGAATT AGATAGTAAA AAAAATTTAG AGCCTGTTTC TGAGGCTGAT
1321 AAAGTAGATA AAATTTCCAA GTCTAACAAC AATGAGGTTA GTAAATTATC CCCGTTAGAT
1381 GAGCCTTCTT ATAGCGACAT TGATTCGAAA GAGGGTGTAG ATAACAAAGA TGTTGATTTG
1441 CAAAAAACTA AACCCCAAGT TGAAAGTCAA CCTACTTCGT TAAATGAAGA TTTGATTGAT
1501 GTGTCTATAG ATTCCAGTAA TCCTGTCTTT TTAGAGGTTA TCGATCCGAT TACAAATTTA
1561 GGAACGCTTC AACTTATTGA TTTGAATACC GGTGTTAGAC TTAAAGAAAG TGCTCAACAA
1621 GGTATTCAGC GATATGGAAT TTATGAACGT GAAAAAGATT TGGTTGTTAT TAAAATAGAT
1681 TCAGGAAAAG CTAAGCTTCA GATACTTGAT AAACTCGAGA ATTTAAAAGT GATATCAGAG
1741 TCTAATTTTG AGATTAATAA AAATTCATCT CTTTATGTTG ACTCTAGAAT GATTTTAGTA
1801 GTTGTTAAGG ACGATAGTAA TGCTTGGAGA TTGGCTAAAT TTTCTCCTAA AAATTTAGAT
1861 GAATTTATTC TGTCAGAAAA TAAAATTTTG CCTTTTACTA GCTTTGCTGT GAGAAAGAAT
1921 TTTATTTATT TGCAAGATGA ACTTAAAAGC TTAGTTACTT TAGATGTAAA TACTTTAAAA
1981 AAAGTTAAGT A
```

FIG. 18

```
   1 ATGAAAAAAA TGTTACTAAT CTTTAGTTTT TTTCTTATTT CTTTGAATGG ATTTCCCCTT
  61 AATGCAAGGG AAGTTGATAA GGAAAAATTA AAGGACTTTG TTAATATGGA TCTTGAGTTT
 121 GTAAACTATA AAGGTCCTTA TGATTCTACA AATACATATG AACAAATAGT AGGTATTGGT
 181 GAGTTTTTAG CAAGACCATT GATTAATTTC AATAGCAACT CAAGTTATTA TGGTAAATAT
 241 TTTATTAATA GATTTATTGA CGATCAAGAT AAAAAAGCAA GCGTTGATGT TTTTTCTATT
 301 AGTAGTAAGT CACAGCTTGA CAGTATATTG AATTTAAGAA GAATTCTTAC AGGGTATTTG
 361 ATAAAGTCTT TTGATTATGA AAGATCTAGT GCTGAATTAA TTGCCAAGGT TATTACAATA
 421 CATAATGCTG TTTATAGAGG TGATTTAAAT TATTATAAAG AGTTTTATAT TGAGTCTGCT
 481 TTAAAGTCTT TAACTAAAGA AAATGCAGGT CTTTCTAGAG TGTACAGTCA ATGGGCTGGA
 541 AAGACACAAA TATTTATTCC TCTTAAAAAG AATATTTTAT CTGGAAAAAT TGAGTCTGAC
 601 ATTGATATTG ATAGTTTGGT TACAGATAAG GTTGTGGCAG CTGTTTAAG CGAAAATGAA
 661 GCAGGTGTTA ACTTTGCAAG GGATATTACA GATATTCAAG GAGAAACTCA TAAAGCAGAT
 721 CAAGATAAAA TTGATATTGA ATTAGATAAT GTTCATGAAA GTGATTCCAA TATAACAGAA
 781 ACTATTGAGA ATTTAAGAGA TCAGCTTGAA AAGGCTACAG ATAAGAGCA TAGAAAGAG
 841 ATTGAAAGTC AAGTTGATGC TAAAAAGAAA CAAAAAGAAG AACTAGATAA AAAGGCAATC
 901 GATCTTGATA AAGCCCAACA AAAATTAGAT TTTTCTGAAG ATAATTTAGA TATTCAAAGG
 961 CATACTGTTA GAGAGAAGAT TCAAGAGGAT ATTAACGAGA TTAATAAGGA AAAGAATTTA
1021 CCAAAACCTG GTGATGTAAG TTCTCCTAAA GTTGATAAGC AGCTACAAAT AAAAGAGAGT
1081 CTAGAAGACT TGCAGCAGCA GCTTAAAGAA ACTAGCGATG AAAATCAAAA AAGAGAAATT
1141 GAAAAGCAAA TTGAAATCAA AAAAAGTGAT GAAGAACTTT TAAAAAGCAA AGATCCTAAA
1201 GCATTAGATC TTAATCGAGA TTTAAATTCT AAAGCTTCTA GTAAAGAAAA AATTAAAGGC
1261 AAAGAAAAAG AAATAGTCAA AGAGAAATCA AAGGTAAGTT TAGGTCATTT CGATAATGAC
1321 GAAACCCTTA TGACGCCGGA AGATCAAAAA TTATCTGAGG ATAAAAAATT AGATAGTAAA
1381 AAAAATTTAA AACCTGTTTC TGAGATTGAG AGAGTAAATG AAATTTCAAA GTCTAACAAC
1441 AATGAGGTTA GCAAATCATC ACCATTAGAT AAGCCTTCTT ATAGTGATAT CGATTCAAAA
1501 GAGGTTGTAG ATAATAAAGA TGTTAATTTG CAAGAAACCA AGCCTCAAGC TAAAAGTCAA
1561 TCTACTTCTT TAAATCAAGA TTTGATTACT ATGTCTATAG ATTCTAGTAA TCCTGTATTT
1621 TTAGAGGTTA TTGATCCTAT TACAAATTTA GGAATGCTTC AACTTATTGA TTTAAATACT
1681 GGTGTTAGAC TTAAAGAAAG CACTCAGCAA GGCATTCAGC GTTATGGAAT TTATGAACGT
1741 GAAAAAGATT TAGTTGTTAT TAAAATGGAT TCAGGAAAAG CTAAGCTTCA AATACTTAAT
1801 AAACTTGAGA ATTTAAAAGT GATATCAGAG TCTAATTTTG AGATTAATAA AAATTCATCT
1861 CTTTATGTTG ACTCTAAAAT GATTTTAGTA GCTGTGAAAG ATAGTGGTAA TGTTTGGAGA
1921 TTGGCTAAAT TTTCTCCTAA AAATTTAGAT GAGTTTATTC TTTCAGAGAA TAAAATTTTG
1981 CCTTTTACTA GCTTTTCTGT GAGAAAGAAT TTTATTTATT TGCAAGATGA GTTTAAAAGT
2041 CTTATTACTT TAGATGTAAA TACTTTAAAA AAAGTTAAGT A
```

FIG. 19

```
   1 ATGAAAAAAA TGTTACTAAT CTTTAGTTTT TTTCTTGTTT TTTTAAATGG ATTTCCTCTT
  61 AATGCAAGGG AAGTTGATAA GGAAAAATTA AAGGACTTTG TTAATATGGA TCTTGAATTT
 121 GTTAATTACA AGGGTCCTTA TGATTCTACA AATACATATG AACAAATAGT AGGTATTGGG
 181 GAGTTTTTAG CAAGGCCGTT GATCAATTCC AATAGTAATT CAAGTTATTA TGGTAAATAT
 241 TTTGTTAATA GATTTATTGA CGATCAAGAT AAAAAAGCAA GTGTTGATAT TTTTTCTATT
 301 GGTAGTAAGT CAGAGCTTGA TAGTATATTA AATCTAAGAA GAATTCTTAC AGGGTATTTA
 361 ATGAAGTCTT TTGATTATGA GAGGTCTAGT GCGGAATTAA TTGCTAAAGC TATTACAATA
 421 TATAATGCTG TTTATAGAGG AGATTTAGAT TATTACAAAG AGTTTTATAT TGAGGCTTCT
 481 TTGAAGTCTT TGACTAAAGA AAATGCAGGT CTTTCTAGGG TGTACAGTCA ATGGGCTGGG
 541 AAGACACAAA TATTTATTCC TCTTAAAAAG AATATTTTAT CTGGAAATGT TGAGTCTGAC
 601 ATTGATATTG ATAGTTTGGT TACAGATAAG GTGGTGGCAG CTCTTTTAAG TGAGAATGAA
 661 TCAGGTGTTA ACTTTGCAAG AGATATTACA GACATTCAAG GCGAAACTCA TAAAGCAGAT
 721 CAAGATAAAA TTGATATTGA ATTAGATAAT ATTCATGAAA GTGATTCCAA TATAACAGAA
 781 ACTATTGAGA ATTTAAGGGA TCAGCTTGAA AAAGCTACAG ATGAAGAGCA TAAAAAAGAG
 841 ATTGAAAGTC AGGTTGATGC TAAAAAGAAA CAAAAGGAAG AATTAGATAA AAAGGCAATT
 901 GATCTTGATA AAGCTCAACA AAAATTAGAT TTTGCTGAAG ATAATCTAGA TATTCAAAGG
 961 GATACTGTTA GAGAGAAGCT TCAAGAGAAT ATTAACGAGA CTAATAAGGA AAAGAATTTA
1021 CCAAAGCCTG GTGATGTAAG TTCTCCTAAA GTTGATAAGC AACTACAAAT AAAAGAGAGC
1081 CTGGAAGATT TGCAGGAGCA GCTTAAAGAA ACTGGTGATG AAATCAGAA AAGAGAAATT
1141 GAAAAGCAAA TTGAAATCAA AAAAAGTGAT GAAAAGCTTT TAAAAAGTAA AGATGATAAA
1201 GCAAGTAAAG ATGGTAAAGC CTTGGATCTT GATCGAGAAT TAAATTCTAA AGCTTCTAGC
1261 AAAGAAAAAA GTAAAGCCAA GGAAGAAGAA ATAACCAAGG GTAAGTCACA GAAAAGCTTA
1321 GGCGATTTGA ATAATGATGA AAATCTTATG ATGCCAGAAG ATCAAAAATT ACCTGAGGTT
1381 AAAAAATTAG ATAGCAAAAA AGAATTTAAA CCTGTTTCTG AGGTTGAGAA ATTAGATAAG
1441 ATTTTCAAGT CTAATAACAA TGTTGGAGAA TTATCACCGT TAGATAAATC TTCTTATAAA
1501 GACATTGATT CAAAAGAGGA GACAGTTAAT AAAGATGTTA ATTTGCAAAA GACTAAGCCT
1561 CAGGTTAAAG ACCAAGTTAC TTCTTTGAAT GAAGATTTGA CTACTATGTC TATAGATTCC
1621 AGTAGTCCTG TATTTTTAGA GGTTATTGAT CCAATTACAA ATTTAGGAAC TCTTCAACTT
1681 ATTGATTTAA ATACTGGTGT TAGGCTTAAA GAAAGCACTC AGCAAGGCAT TCAGCGGTAT
1741 GGAATTTATG AACGTGAAAA AGATTTGGTT GTTATTAAAA TGGATTCAGG AAAAGCTAAG
1801 CTTCAGATAC TTGATAAACT TGAAAATTTA AAAGTGGTAT CAGAGTCTAA TTTTGAGATT
1861 AATAAAAATT CATCTCTTTA TGTTGATTCT AAAATGATTT TAGTAGCTGT TACGGATAAA
1921 GATAGTAGTA ATGATTGGAG ATTGGCCAAA TTTTCTCCTA AAAATTTAGA TGAGTTTATT
1981 CTTTCAGAGA ATAAAATTAT GCCTTTTACT AGCTTTTCTG TGAGAAAAAA TTTTATTTAT
2041 TTGCAAGATG AGTTTAAAAG TCTAGTTATT TTAGATGTAA ATACTTTAAA AAAAGTTAAG
2101 TAAAGCC
```

FIG. 20

```
   1 ATGAAAAAAA TGTTACTAAT CTTTAGTTTT TTTCTTGTTT TTTTAAATGG ATTTCCTCTT
  61 AATGCAAGGG AAGTTGATAA GGAAAAATTA AAGGACTTTG TTAATATGGA TCTTGAATTT
 121 GTTAATTACA AGGGTCCTTA TGATTCTACA AATACATATG AACAAATAGT AGGTATTGGG
 181 GAGTTTTTAG CAAGGCCGTT GATCAATTCC AATAGTAATT CAAGTTATTA TGGTAAATAT
 241 TTTGTTAATA GATTTATTGA CGATCAAGAT AAAAAAGCAA GTGTTGATAT TTTTTCTATT
 301 GGTAGTAAGT CAGAGCTTGA TAGTATATTA AATCTAAGAA GAATTCTTAC AGGGTATTTA
 361 ATGAAGTCTT TTGATTATGA GAGGTCTAGT GCGGAATTAA TTGCTAAAGC TATTACAATA
 421 TATAATGCTG TTTATAGAGG AGATTTAGAT TATTACAAAG AGTTTTATAT TGAGGCTTCT
 481 TTGAAGTCTT TGACTAAAGA AAATGCAGGT CTTTCTAGGG TGTACAGTCA ATGGGCTGGG
 541 AAGACACAAA TATTTATTCC TCTTAAAAAG AATATTTTAT CTGGAAATGT TGAGTCTGAC
 601 ATTGATATTG ATAGTTTGGT TACAGATAAG GTGGTGGCAG CTCTTTTAAG TGAGAATGAA
 651 TCAGGTGTTA ACTTTGCAAG AGATATTACA GACATTCAAG GCGAAACTCA TAAAGCAGAT
 721 CAAGATAAAA TTGATATTGA ATTAGATAAT TTTCATGAAA GTGATTCCAA TATAACAGAA
 781 ACTATTGAGA ATTTAAGGGA TCAGCTTGAA AAAGCTACAG ATGAAGAGCA TAAAAAAGAG
 841 ATTGAAAGTC AGGTTGATGC TAAAAAGAAA CAAAAGGAAG AATTAGATAA AAAGGCAATT
 901 GATCTTGATA AAGCTCAACA AAAATTAGAT TTTGCTGAAG ATAATCTAGA TATTCAAAGG
 961 GATACTGTTA GAGAGAAGCT TCAAGAAAAT ATTAACGAGA CTAATAAGGA AAAGAATTTA
1021 CCAAGCCTG GTGATGTAAG TTCTCCTAAG GTTGATAAGC AGTTGCAGAT AAAAGAGAGT
1081 CTAGAAGATT TGCAAGAGCA GCTTAAAGAA GCTAGTGATG AAAATCAAAA AAGAGAAATA
1141 GAAAAGCAAA TTGAAATCAA AAAAAATGAT GAAGAACTTT TTAAAAATAA AGATCATAAA
1201 GCATTAGATC TTAAGCAAGA ATTAAATTCT AAAGCTTCTA GTAAAGAAAA AATTGAAGGC
1261 GAAGAAGAGG ATAAAGAATT AGATAGTAAA AAAAATTTAG AGCCTGTTTC TGAGGCTGAT
1321 AAAGTAGATA AAATTCCAA GTCAACAAC AATGAGGTTA GTAAATTATC CCCGTTAGAT
1381 GAGCCTTCTT ATAGTGACAT TGATTCGAAA GAGGGTGTAG ATAACAAAGA TGTTGATTTG
1441 CAAAAAACTA AACCCCAAGT TGAAAGTCAA CCTACTTCGT TAAATGAAGA CTTGATTGAT
1501 GTGTCTATAG ATTCCAGTAA TCCTGTCTTT TTAGAGGTTA TCGATCCGAT TACAAATTTA
1561 GGAACGCTTC AACTTATTGA TTTGAATACC GGTGTTAGAC TTAAAGAAAG TGCTCAACAA
1621 GGTATTCAGC GATATGGAAT TTATGAACGT CAAAAGATT TGGTTGTTAT TAAAATAGAT
1681 TCAGGAAAAG CTAAGCTTCA GATACTTGAT AAACTCGAGA ATTTAAAGT GATATCAGAG
1741 TCTAATTTTG AGATTAATAA AAATTCATCT CTTTATGTTG ACTCTAGAAT GATTTTAGTA
1801 GTTGTTAAGG ACGATAGTAA TGCTTGGAGA TTGGCTAAAT TTCTTCCTAA AAATTTAGAT
1861 GAATTTATTC TGTCAGAAAA TAAAATTTTG CCTTTTACTA GCTTTGCTGT GAGAAAGAAT
1921 TTTATTTATT TGCAAGATGA ACTTAAAAGC TTAGTTACTT TAGATGTAAA TACTTTAAAA
1981 AAAGTTAAGT A
```

FIG. 21

```
   1 ATGAAAAAAA TGTTACTAAT CTTTAGTTTT TTTCTTATTT TTTTGAATGG ATTTCCTCTT
  61 AATGCAAGGA AAGTTGATAA GGAAAAATTA AAGGATTTTG TTAATATGGA TCTTGAGTTT
 121 GTAAATTATA AAGGTCCTTA TGATTCTACA AATACGTATG AACAAATAGT GGGTATTGGG
 181 GAGTTTTTAG CAAGACCGCT GACCAATTCC AATAGCAACT CAAGTTATTA TGGCAAATAT
 241 TTTATTAATA GATTTATTGA TGATCAAGAT AAAAAAGCAA GTGTTGATGT TTTTTCTATA
 301 AGCAGCAAAT CAGAGCTTGA CAGTATATTG AATTTAAGAA GAATTCTTAC AGGGTATATA
 361 ATAAAGTCTT TCGATTATGA CAGGTCTAGT GCAGAATTAA TTGCTAAGGT TATTACAATA
 421 TATAATGCTG TTTATAGAGG AGATTTGGAT TATTATAAAG GGTTTTATAT TGAGCCTGCT
 481 TTGAAGTCTT TAACTAAAGA AAACGCAGGT CTTTCTAGGG TTTACAGTCA GTGGGCTGGA
 541 AAGACTCAAA TATTTATTCC TCTTAAAAAG GATATTTTGT CTGGAAATAT TGAATCTGAC
 601 ATTGATATTG ACAGTTTGGT TACAGATAAG GTGATAGCAG CTCTTTTAAG CGAAAATGAA
 661 GCAGGCGTTA ACTTTGCAAG AGATATTACA GATATTCAAG GCGAAACTCA TAAGGCAGAT
 721 CAAGATAAGA TTGATACTGA ATTAGACAAT ATCCATGAAA GCGATTCTAA TATAACAGAA
 781 ACTATTGAAA ATTTAAGGGA TCAGCTTGAA AAAGCTACAG ATGAAGAGCA TAAAAAAGAG
 841 ATTGAAAGTC AGGTTGATGC TAAAAAGAAA GAAAAGGAAG AGCTAGATAA AAAGGCAATC
 901 AATCTTGATA AAGCTCAGCA AAAATTAGAC TCTGCTGAAG ATAATTTAGA TGTTCAAAGA
 961 GATACTGTTA GAGAGAAAAT TCAAGAGGAT ATTAATGAGA TTAATAAGGA AAAGAATTTG
1021 CCAAAACCTG GTGATGTAAG TTCTCCTAAA GTTGATAAGC AACTGCAAAT AAAAGAGAGT
1081 CTAGAAGATT TGCAGGAGCA GCTTAAAGAA GCTGGTGATG AAAATCAGAA AAGACAAATT
1141 GAGAAGCAAA TTGAAATCAA AAAAAGGGAC GAAGAACTTT TAAAAAGTAA AGATGGCAAA
1201 GTAAGTAAAG ATTATGAAGC ATTAGATCTT GATCGAGAAT TATCCAAAGC TTCTAGTAAA
1261 GAAAAAAGTA AGGTCAAGGA AGAAGAAATA ACTAAAGGTA AATCACGGGC AAGCTTAGGC
1321 GATTTGAATA ATGATAAAAA CCTTATGTTG CCAGAAGATC AAAAATTACC TGAAGATAAA
1381 AAATTGGATA GTAAATTAGA TGGTAAAAAA GAATTTAAAC CAGTTTCTGA GGTTGAAAAA
1441 TTAGATAAGA TTTCCAAGTC TAATAACAAT GAGGTTGGCA AGTTATCACC ATTAGATAAG
1501 CCTTCTTATG ATGATATTGA TTCAAAAGAG GAGGTAGATA ATAAAGCTAT TAATTTGCAA
1561 AAGATCGACC CTAAAGTTAA AGACCAAACT ACTTCTTTGA ATGAAGATTT GGATAAAGAT
1621 TTGACTACTA TGTCTATAGA TTCCAGCAGT CCTGTATTTC TAGAGGTTAT TGATCCTATT
1681 ACAAATTTAG GAACCCTGCA GCTTATTGAT TTAAATACTG GGGTTAGGCT TAAGGAAAGC
1741 ACTCAGCAAG GCATTCAGCG GTATGGAATT TATGAACGTG AAAAACATTT GGTTGTTATT
1801 AAAATGGATT CAGGAAAGGC TAAGCTTCAA ATACTTAATA AGCTTCAAAA TTTGAAAGTG
1861 GTATCAGAGT CTAATTTTGA GATCAATAAA AATTCATCTC TTTATGTTGA CTCTAAAATG
1921 ATTTTGGCAG CTGTTAGAGA TAAGGATGAT AGCAATGCTT GGAGATTGGC TAAATTTTCT
1981 CCTAAAAATT TGGATGAGTT TATTCTTTCA GAGAATAAAA TTTTGCCTTT TACTAGCTTT
2041 TCTGTGAGAA AAAATTTTAT TTATTTGCAA GATGAGCTTA AAATCTAGT TATTTTAGAT
2101 GTAAATACTT TAAAAAAAGT TAAGTA
```

FIG. 22

```
              10             20             30             40
        *      *      *      *      *      *      *      *      *
       ATG    AAA    AAA    TAT    TTA    TTG    GGA    ATA    GGT    CTA    ATA    TTA    GCC    TTA    ATA    GCA
       TAC    TTT    TTT    ATA    AAT    AAC    CCT    TAT    CCA    GAT    TAT    AAT    CGG    AAT    TAT    CGT
       Met    Lys    Lys    Tyr    Leu    Leu    Gly    Ile    Gly    Leu    Ile    Leu    Ala    Leu    Ile    Ala>

50             60             70             80             90
        *      *      *      *      *      *      *      *      *      *
       TGT    AAG    CAA    AAT    GTT    AGC    AGC    CTT    GAT    GAA    AAA    AAT    AGC    GTT    TCA    GTA
       ACA    TTC    GTT    TTA    CAA    TCG    TCG    GAA    CTA    CTT    TTT    TTA    TCG    CAA    AGT    CAT
       Cys    Lys    Gln    Asn    Val    Ser    Ser    Leu    Asp    Glu    Lys    Asn    Ser    Val    Ser    Val>

100            110            120            130            140
        *      *      *      *      *      *      *      *      *
       GAT    TTA    CCT    GGT    GGA    ATG    ACA    GTT    CTT    GTA    AGT    AAA    GAA    AAA    GAC    AAA
       CTA    AAT    GGA    CCA    CCT    TAC    TGT    CAA    GAA    CAT    TCA    TTT    CTT    TTT    CTG    TTT
       Asp    Leu    Pro    Gly    Gly    Met    Thr    Val    Leu    Val    Ser    Lys    Glu    Lys    Asp    Lys>

150            160            170            180            190
        *      *      *      *      *      *      *      *      *      *
       GAC    GGT    AAA    TAC    AGT    CTA    GAG    GCA    ACA    GTA    GAC    AAG    CTT    GAG    CTT    AAA
       CTG    CCA    TTT    ATG    TCA    GAT    CTC    CGT    TGT    CAT    CTG    TTC    GAA    CTC    GAA    TTT
       Asp    Gly    Lys    Tyr    Ser    Leu    Glu    Ala    Thr    Val    Asp    Lys    Leu    Glu    Leu    Lys>

200            210            220            230            240
        *      *      *      *      *      *      *      *      *      *
       GGA    ACT    TCT    GAT    AAA    AAC    AAC    GGT    TCT    GGA    ACA    CTT    GAA    GGT    GAA    AAA
       CCT    TGA    AGA    CTA    TTT    TTG    TTG    CCA    AGA    CCT    TGT    GAA    CTT    CCA    CTT    TTT
       Gly    Thr    Ser    Asp    Lys    Asn    Asn    Gly    Ser    Gly    Thr    Leu    Glu    Gly    Glu    Lys>

250            260            270            280
        *      *      *      *      *      *      *      *      *
       ACT    GAC    AAA    AGT    AAA    GTA    AAA    TTA    ACA    ATT    GCT    GAT    GAC    CTA    AGT    CAA
       TGA    CTG    TTT    TCA    TTT    CAT    TTT    AAT    TGT    TAA    CGA    CTA    CTG    GAT    TCA    GTT
       Thr    Asp    Lys    Ser    Lys    Val    Lys    Leu    Thr    Ile    Ala    Asp    Asp    Leu    Ser    Gln>

290            300            310            320            330
        *      *      *      *      *      *      *      *      *      *
       ACT    AAA    TTT    GAA    ATT    TTC    AAA    GAA    GAT    GCC    AAA    ACA    TTA    GTA    TCA    AAA
       TGA    TTT    AAA    CTT    TAA    AAG    TTT    CTT    CTA    CGG    TTT    TGT    AAT    CAT    AGT    TTT
       Thr    Lys    Phe    Glu    Ile    Phe    Lys    Glu    Asp    Ala    Lys    Thr    Leu    Val    Ser    Lys>

340            350            360            370            380
        *      *      *      *      *      *      *      *      *
       AAA    GTA    ACC    CTT    AAA    GAC    AAG    TCA    TCA    ACA    GAA    GAA    AAA    TTC    AAC    GAA
       TTT    CAT    TGG    GAA    TTT    CTG    TTC    AGT    AGT    TGT    CTT    CTT    TTT    AAG    TTG    CTT
       Lys    Val    Thr    Leu    Lys    Asp    Lys    Ser    Ser    Thr    Glu    Glu    Lys    Phe    Asn    Glu>
```

FIG. 23A

```
              390           400           410           420           430
      *       *      *       *      *      *      *      *      *       *
     AAG GCT GAA ACA TCT GAA AAA ACA ATA GTA AGA GCA AAT GGA ACC AGA
     TTC CCA CTT TGT AGA CTT TTT TGT TAT CAT TCT CGT TTA CCT TGG TCT
     Lys Gly Glu Thr Ser Glu Lys Thr Ile Val Arg Ala Asn Gly Thr Arg>

440           450           460           470           480
      *       *      *       *      *      *      *      *      *       *
     CTT GAA TAC ACA GAC ATA AAA AGC GAT GGA TCC GGA AAA GCT AAA GAA
     GAA CTT ATG TGT CTG TAT TTT TCG CTA CCT AGG CCT TTT CGA TTT CTT
     Leu Glu Tyr Thr Asp Ile Lys Ser Asp Gly Ser Gly Lys Ala Lys Glu>

490           500           510           520
      *       *      *       *      *      *      *      *      *
     GTT TTA AAA GAC TTT ACT CTT GAA GGA ACT CTA GCT GCT GAC GGC AAA
     CAA AAT TTT CTG AAA TGA GAA CTT CCT TGA GAT CGA CGA CTG CCG TTT
     Val Leu Lys Asp Phe Thr Leu Glu Gly Thr Leu Ala Ala Asp Gly Lys>

530           540           550           560           570
      *      *      *       *      *      *      *      *      *       *
     ACA ACA TTG AAA GTT ACA GAA GGC ACT GTT GTT TTA AGC AAG AAC ATT
     TGT TGT AAC TTT CAA TGT CTT CCG TGA CAA CAA AAT TCG TTC TTG TAA
     Thr Thr Leu Lys Val Thr Glu Gly Thr Val Val Leu Ser Lys Asn Ile>

580           590           600           610           620
      *       *      *       *      *      *      *      *      *
     TTA AAA TCC GGA GAA ATA ACA GTT GCA CTT GAT GAC TCT GAC ACT ACT
     AAT TTT AGG CCT CTT TAT TGT CAA CGT GAA CTA CTG AGA CTG TGA TGA
     Leu Lys Ser Gly Glu Ile Thr Val Ala Leu Asp Asp Ser Asp Thr Thr>

630           640           650           660           670
      *       *      *       *      *      *      *      *      *      *
     CAG GCT ACT AAA AAA ACT GGA AAA TGG GAT TCA AAA ACT TCT ACT TTA
     GTC CGA TGA TTT TTT TGA CCT TTT ACC CTA AGT TTT TGA AGA TGA AAT
     Gln Ala Thr Lys Lys Thr Gly Lys Trp Asp Ser Lys Thr Ser Thr Leu>

680           690           700           710           720
      *       *      *       *      *      *      *      *      *       *
     ACA ATT AGT GTT AAC AGC AAA AAA ACT ACA CAA CTT GTG TTT ACT AAA
     TGT TAA TCA CAA TTG TCG TTT TTT TGA TGT GTT GAA CAC AAA TGA TTT
     Thr Ile Ser Val Asn Ser Lys Lys Thr Thr Gln Leu Val Phe Thr Lys>

730           740           750           760
      *       *      *       *      *      *      *      *      *
     CAA TAC ACA ATA ACT GTA AAA CAA TAC GAC TCC GCA GGT ACC AAT TTA
     GTT ATG TGT TAT TGA CAT TTT GTT ATG CTG AGG CGT CCA TGG TTA AAT
     Gln Tyr Thr Ile Thr Val Lys Gln Tyr Asp Ser Ala Gly Thr Asn Leu>
```

FIG. 23B

```
     770          780          790          800          810
      *     *      *     *      *     .      *     .      *     *
    GAA GGC ACA GCA GTC GAA ATT AAA ACA CTT GAT GAA CTT AAA AAC GCT
    CTT CCG TGT CGT CAG CTT TAA TTT TGT GAA CTA CTT GAA TTT TTG CGA
    Glu Gly Thr Ala Val Glu Ile Lys Thr Leu Asp Glu Leu Lys Asn Ala>

820
      *     *
    TTA AAA TAA
    AAT TTT ATT
    Leu Lys ***>
```

FIG. 23C

```
          10          20          30          40
           .           .           .           .
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
  .           .           .           .           .
TGC AAG CAA AAT GTT AGC AGC CTT GAT GAA AAA AAC AGC GCT TCA GTA
ACG TTC GTT TTA CAA TCG TCG GAA CTA CTT TTT TTG TCG CGA AGT CAT
Cys Lys Gln Asn Val Ser Ser Leu Asp Glu Lys Asn Ser Ala Ser Val>

100         110         120         130         140
       .           .           .           .           .
GAT TTG CCT GGT GAG ATG AAA GTT CTT GTA AGT AAA GAA AAA GAC AAA
CTA AAC GGA CCA CTC TAC TTT CAA GAA CAT TCA TTT CTT TTT CTG TTT
Asp Leu Pro Gly Glu Met Lys Val Leu Val Ser Lys Glu Lys Asp Lys>

150         160         170         180         190
           .           .           .           .           .
GAC GGT AAG TAC AGT CTA AAG GCA ACA GTA GAC AAG ATT GAG CTA AAA
CTG CCA TTC ATG TCA GAT TTC CGT TGT CAT CTG TTC TAA CTC GAT TTT
Asp Gly Lys Tyr Ser Leu Lys Ala Thr Val Asp Lys Ile Glu Leu Lys>

200         210         220         230         240
           .           .           .           .           .
GGA ACT TCT GAT AAA GAC AAT GGT TCT GGA GTG CTT GAA GGT ACA AAA
CCT TGA AGA CTA TTT CTG TTA CCA AGA CCT CAC GAA CTT CCA TGT TTT
Gly Thr Ser Asp Lys Asp Asn Gly Ser Gly Val Leu Glu Gly Thr Lys>

250         260         270         280
           .           .           .           .
GAT GAC AAA AGT AAA GCA AAA TTA ACA ATT GCT GAC GAT CTA AGT AAA
CTA CTG TTT TCA TTT CGT TTT AAT TGT TAA CGA CTG CTA GAT TCA TTT
Asp Asp Lys Ser Lys Ala Lys Leu Thr Ile Ala Asp Asp Leu Ser Lys>

290         300         310         320         330
  .           .           .           .           .
ACC ACA TTC GAA CTT TTA AAA GAA GAT GGC AAA ACA TTA GTG TCA AGA
TGG TGT AAG CTT GAA AAT TTT CTT CTA CCG TTT TGT AAT CAC AGT TCT
Thr Thr Phe Glu Leu Leu Lys Glu Asp Gly Lys Thr Leu Val Ser Arg>

340         350         360         370         380
       .           .           .           .           .
AAA GTA AGT TCT AGA GAC AAA ACA TCA ACA GAT GAA ATG TTC AAT GAA
TTT CAT TCA AGA TCT CTG TTT TGT AGT TGT CTA CTT TAC AAG TTA CTT
Lys Val Ser Ser Arg Asp Lys Thr Ser Thr Asp Glu Met Phe Asn Glu>
```

FIG. 24A

```
          390           400           410           420           430
      .     .       .     .       .     .       .     .       .     .
     AAA GGT GAA TTG TCT GCA AAA ACC ATG ACA AGA GAA AAT GGA ACC AAA
     TTT CCA CTT AAC AGA CGT TTT TGG TAC TGT TCT CTT TTA CCT TGG TTT
     Lys Gly Glu Leu Ser Ala Lys Thr Met Thr Arg Glu Asn Gly Thr Lys>

440           450           460           470           480
          .     .       .     .       .     .       .     .       .     .
     CTT GAA TAT ACA GAA ATG AAA AGC GAT GGA ACC GGA AAA GCT AAA GAA
     GAA CTT ATA TGT CTT TAC TTT TCG CTA CCT TGG CCT TTT CGA TTT CTT
     Leu Glu Tyr Thr Glu Met Lys Ser Asp Gly Thr Gly Lys Ala Lys Glu>

490           500           510           520
          .     .       .     .       .     .       .     .
     GTT TTA AAA AAG TTT ACT CTT GAA GGA AAA GTA GCT AAT GAT AAA GTA
     CAA AAT TTT TTC AAA TGA GAA CTT CCT TTT CAT CGA TTA CTA TTT CAT
     Val Leu Lys Lys Phe Thr Leu Glu Gly Lys Val Ala Asn Asp Lys Val>

530           540           550           560           570
       .     .       .     .       .     .       .     .       .     .
     ACA TTG GAA GTA AAA GAA GGA ACC GTT ACT TTA AGT AAG GAA ATT GCA
     TGT AAC CTT CAT TTT CTT CCT TGG CAA TGA AAT TCA TTC CTT TAA CGT
     Thr Leu Glu Val Lys Glu Gly Thr Val Thr Leu Ser Lys Glu Ile Ala>

580           590           600           610           620
         .     .       .     .       .     .       .     .       .     .
     AAA TCT GGA GAA GTA ACA GTT GCT CTT AAT GAC ACT AAC ACT ACT CAG
     TTT AGA CCT CTT CAT TGT CAA CGA GAA TTA CTG TGA TTG TGA TGA GTC
     Lys Ser Gly Glu Val Thr Val Ala Leu Asn Asp Thr Asn Thr Thr Gln>

630           640           650           660           670
          .     .       .     .       .     .       .     .       .     .
     GCT ACT AAA AAA ACT GGC GCA TGG GAT TCA AAA ACT TCT ACT TTA ACA
     CGA TGA TTT TTT TGA CCG CGT ACC CTA AGT TTT TGA AGA TGA AAT TGT
     Ala Thr Lys Lys Thr Gly Ala Trp Asp Ser Lys Thr Ser Thr Leu Thr>

680           690           700           710           720
          .     .       .     .       .     .       .     .       .     .
     ATT AGT GTT AAC AGC AAA AAA ACT ACA CAA CTT GTG TTT ACT AAA CAA
     TAA TCA CAA TTG TCG TTT TTT TGA TGT GTT GAA CAC AAA TGA TTT GTT
     Ile Ser Val Asn Ser Lys Lys Thr Thr Gln Leu Val Phe Thr Lys Gln>

730           740           750           760
             .     .       .     .       .     .       .     .
     TAC ACA ATA ACT GTA AAA CAA TAC GAC TCC GCA GGT ACC AAT TTA GAA
     ATG TGT TAT TGA CAT TTT GTT ATG CTG AGG CGT CCA TGG TTA AAT CTT
     Tyr Thr Ile Thr Val Lys Gln Tyr Asp Ser Ala Gly Thr Asn Leu Glu>
```

FIG. 24B

```
       770         780         790         800         810
        *           *           *           *           *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

820
        *
AAA TAA
TTT ATT
Lys ***>
```

FIG. 24C

```
          10          20          30          40
           *           *           *           *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
      *           *           *           *           *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100         110         120         130         140
      *           *           *           *           *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150         160         170         180         190
      *           *           *           *           *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200         210         220         230         240
      *           *           *           *           *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250         260         270         280
      *           *           *           *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
 *           *           *           *           *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340         350         360         370         380
      *           *           *           *           *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>

390         400         410         420         430
      *           *           *           *           *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>
```

FIG. 25A

```
          440              450              460              470              480
           *                *                *                *                *
     *         *        *        *        *        *        *        *        *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490              500              510              520
              *                *                *                *
        *         *        *        *        *        *        *        *        *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530              540              550              560              570
 *                *                *                *                *
     *        *        *        *        *        *        *        *        *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580              590              600              610              620
           *                *                *                *                *
     *        *        *        *        *        *        *        *        *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630              640              650              660              670
             *                *                *                *                *
     *        *        *        *        *        *        *        *        *
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

680              690              700              710              720
              *                *                *                *                *
     *        *        *        *        *        *        *        *        *
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

730              740              750              760
               *                *                *                *
     *        *        *        *        *        *        *        *        *
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>

770              780              790              800              810
 *                *                *                *                *
     *        *        *        *        *        *        *        *        *
GGC AAA GCA GTC GAA ATT ACA ACA CTT AAA GAA CTT AAA AAC GCT TTA
CCG TTT CGT CAG CTT TAA TGT TGT GAA TTT CTT GAA TTT TTG CGA AAT
Gly Lys Ala Val Glu Ile Thr Thr Leu Lys Glu Leu Lys Asn Ala Leu>

820
  *
AAA TAA
TTT ATT
Lys ***>
```

FIG. 25B

```
                10              20              30              40
                 *               *               *               *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90
     *               *               *               *               *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100             110             120             130             140
        *               *               *               *               *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150             160             170             180             190
          *               *               *               *               *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200             210             220             230             240
          *               *               *               *               *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250             260             270             280
          *               *               *               *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290             300             310             320             330
    *               *               *               *               *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340             350             360             370             380
       *               *               *               *               *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 26A

```
     390           400           410           420           430
      *             *             *             *             *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440           450           460           470           480
          *             *             *             *             *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490           500           510           520
             *             *             *             *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530           540           550           560           570
  *             *             *             *             *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580           590           600           610           620
     *             *             *             *             *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630           640           650           660           670
        *             *             *             *             *
GCT ACT AAA AAA ACT GCA GCT TGG AAT GCA GGC ACT TCA ACT TTA ACA
CGA TGA TTT TTT TGA CGT CGA ACC TTA CGT CCG TGA AGT TGA AAT TGT
Ala Thr Lys Lys Thr Ala Ala Trp Asn Ala Gly Thr Ser Thr Leu Thr>

680           690           700           710           720
           *             *             *             *             *
ATT ACT GTA AAC AAC AAA AAA ACT AAA GCC CTT GTA TTT ACA AAA CAA
TAA TGA CAT TTG TTG TTT TTT TGA TTT CGG GAA CAT AAA TGT TTT GTT
Ile Thr Val Asn Asn Lys Lys Thr Lys Ala Leu Val Phe Thr Lys Gln>

730           740           750           760
              *             *             *             *
GAC ACA ATT ACA TCA CAA AAA TAC GAC TCA GCA GGA ACC AAC TTG GAA
CTG TGT TAA TGT AGT GTT TTT ATG CTG AGT CGT CCT TGG TTG AAC CTT
Asp Thr Ile Thr Ser Gln Lys Tyr Asp Ser Ala Gly Thr Asn Leu Glu>
```

FIG. 26B

```
      770         780         790         800         810
       .     .     .     .     .     .     .     .     .     .
      GGC ACA GCA GTC GAA ATT AAA ACA CTT GAT GAA CTT AAA AAC GCT TTA
      CCG TGT CGT CAG CTT TAA TTT TGT GAA CTA CTT GAA TTT TTG CGA AAT
      Gly Thr Ala Val Glu Ile Lys Thr Leu Asp Glu Leu Lys Asn Ala Leu>

AGA
      TCT
      Arg>
```

FIG. 26C

```
         10           20           30           40
     *    .    *    .    *    .    *    .    *    .
    ATG  AAA  AAA  TAT  TTA  TTG  GGA  ATA  GGT  CTA  ATA  TTA  GCC  TTA  ATA  GCA
    TAC  TTT  TTT  ATA  AAT  AAC  CCT  TAT  CCA  GAT  TAT  AAT  CGG  AAT  TAT  CGT
    Met  Lys  Lys  Tyr  Leu  Leu  Gly  Ile  Gly  Leu  Ile  Leu  Ala  Leu  Ile  Ala>

50           60           70           80           90
     *    .    *    .    *    .    *    .    *    .
    TGT  AAG  CAA  AAT  GTT  AGC  AGC  CTT  GAT  GAA  AAA  AAT  AGC  GTT  TCA  GTA
    ACA  TTC  GTT  TTA  CAA  TCG  TCG  GAA  CTA  CTT  TTT  TTA  TCG  CAA  AGT  CAT
    Cys  Lys  Gln  Asn  Val  Ser  Ser  Leu  Asp  Glu  Lys  Asn  Ser  Val  Ser  Val>

100          110          120          130          140
     *    .    *    .    *    .    *    .    *    .
    GAT  TTA  CCT  GGT  GGA  ATG  ACA  GTT  CTT  GTA  AGT  AAA  GAA  AAA  GAC  AAA
    CTA  AAT  GGA  CCA  CCT  TAC  TGT  CAA  GAA  CAT  TCA  TTT  CTT  TTT  CTG  TTT
    Asp  Leu  Pro  Gly  Gly  Met  Thr  Val  Leu  Val  Ser  Lys  Glu  Lys  Asp  Lys>

150          160          170          180          190
     *    .    *    .    *    .    *    .    *    .
    GAC  GGT  AAA  TAC  AGT  CTA  GAG  GCA  ACA  GTA  GAC  AAG  CTT  GAG  CTT  AAA
    CTG  CCA  TTT  ATG  TCA  GAT  CTC  CGT  TGT  CAT  CTG  TTC  GAA  CTC  GAA  TTT
    Asp  Gly  Lys  Tyr  Ser  Leu  Glu  Ala  Thr  Val  Asp  Lys  Leu  Glu  Leu  Lys>

200          210          220          230          240
     *    .    *    .    *    .    *    .    *    .
    GGA  ACT  TCT  GAT  AAA  AAC  AAC  GGT  TCT  GGA  ACA  CTT  GAA  GGT  GAA  AAA
    CCT  TGA  AGA  CTA  TTT  TTG  TTG  CCA  AGA  CCT  TGT  GAA  CTT  CCA  CTT  TTT
    Gly  Thr  Ser  Asp  Lys  Asn  Asn  Gly  Ser  Gly  Thr  Leu  Glu  Gly  Glu  Lys>

250          260          270          280
     *    .    *    .    *    .    *    .    *    .
    ACT  GAC  AAA  AGT  AAA  GTA  AAA  TTA  ACA  ATT  GCT  GAT  GAC  CTA  AGT  CAA
    TGA  CTG  TTT  TCA  TTT  CAT  TTT  AAT  TGT  TAA  CGA  CTA  CTG  GAT  TCA  GTT
    Thr  Asp  Lys  Ser  Lys  Val  Lys  Leu  Thr  Ile  Ala  Asp  Asp  Leu  Ser  Gln>

290          300          310          320          330
     *    .    *    .    *    .    *    .    *    .
    ACT  AAA  TTT  GAA  ATT  TTC  AAA  GAA  GAT  GCC  AAA  ACA  TTA  GTA  TCA  AAA
    TGA  TTT  AAA  CTT  TAA  AAG  TTT  CTT  CTA  CGG  TTT  TGT  AAT  CAT  AGT  TTT
    Thr  Lys  Phe  Glu  Ile  Phe  Lys  Glu  Asp  Ala  Lys  Thr  Leu  Val  Ser  Lys>

340          350          360          370          380
     *    .    *    .    *    .    *    .    *    .
    AAA  GTA  ACC  CTT  AAA  GAC  AAG  TCA  TCA  ACA  GAA  GAA  AAA  TTC  AAC  GAA
    TTT  CAT  TGG  GAA  TTT  CTG  TTC  AGT  AGT  TGT  CTT  CTT  TTT  AAG  TTG  CTT
    Lys  Val  Thr  Leu  Lys  Asp  Lys  Ser  Ser  Thr  Glu  Glu  Lys  Phe  Asn  Glu>
```

FIG. 27A

```
      390           400           410           420           430
       *             *             *             *             *
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

440           450           460           470           480
          *             *             *             *             *
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

490           500           510           520
             *             *             *             *             *
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530           540           550           560           570
   *             *             *             *             *
ACA ACA TTG AAA GTT ACA GAA GGC ACT GTT GTT TTA AGC AAG ATT TCA
TGT TGT AAC TTT CAA TGT CTT CCG TGA CAA CAA AAT TCG TTC TAA AGT
Thr Thr Leu Lys Val Thr Glu Gly Thr Val Val Leu Ser Lys Ile Ser>

580           590           600           610           620
      *             *             *             *             *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630           640           650           660           670
         *             *             *             *             *
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

680           690           700           710           720
            *             *             *             *             *
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

730           740           750           760
               *             *             *             *             *
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>
```

FIG. 27B

```
         770           780           790           800           810
          .   .   .     .   .   .     .   .   .     .   .   .     .   .   .
         GGC AAA GCA GTC GAA ATT ACA ACA CTT AAA GAA CTT AAA AAC GCT TTA
         CCG TTT CGT CAG CTT TAA TGT TGT GAA TTT CTT GAA TTT TTG CGA AAT
         Gly Lys Ala Val Glu Ile Thr Thr Leu Lys Glu Leu Lys Asn Ala Leu>

820
          .
         AAA TAA
         TTT ATT
         Lys ***>
```

FIG. 27C

```
              10           20           30           40
               *            *            *            *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50           60           70           80           90
      *            *            *            *            *
TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

100          110          120          130          140
           *            *            *            *            *
GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

150          160          170          180          190
           *            *            *            *            *
GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

200          210          220          230          240
           *            *            *            *            *
GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

250          260          270          280
           *            *            *            *
ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290          300          310          320          330
   *            *            *            *            *
ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

340          350          360          370          380
       *            *            *            *            *
AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

FIG. 28A

```
        390           400           410           420           430
     *    *        *    *        *    *        *    *        *    *
    AAG  GGT  GAA  ACA  TCT  GAA  AAA  ACA  ATA  GTA  AGA  GCA  AAT  GGA  ACC  AGA
    TTC  CCA  CTT  TGT  AGA  CTT  TTT  TGT  TAT  CAT  TCT  CGT  TTA  CCT  TGG  TCT
    Lys  Gly  Glu  Thr  Ser  Glu  Lys  Thr  Ile  Val  Arg  Ala  Asn  Gly  Thr  Arg>

440           450           460           470           480
         *   *        *    *        *    *        *    *        *    *
    CTT  GAA  TAC  ACA  GAC  ATA  AAA  AGC  GAT  GGA  TCC  GGA  AAA  GCT  AAA  GAA
    GAA  CTT  ATG  TGT  CTG  TAT  TTT  TCG  CTA  CCT  AGG  CCT  TTT  CGA  TTT  CTT
    Leu  Glu  Tyr  Thr  Asp  Ile  Lys  Ser  Asp  Gly  Ser  Gly  Lys  Ala  Lys  Glu>

490           500           510           520
           *    *       *    *        *    *        *    *      *
    GTT  TTA  AAA  GAC  TTT  ACT  CTT  GAA  GGA  ACT  CTA  GCT  GCT  GAC  GGC  AAA
    CAA  AAT  TTT  CTG  AAA  TGA  GAA  CTT  CCT  TGA  GAT  CGA  CGA  CTG  CCG  TTT
    Val  Leu  Lys  Asp  Phe  Thr  Leu  Glu  Gly  Thr  Leu  Ala  Ala  Asp  Gly  Lys>

530           540           550           560           570
     *    *        *    *        *    *        *    *        *    *
    ACA  ACA  TTG  AAA  GTT  ACA  GAA  GGC  ACT  GTT  GTT  TTA  AGC  AAG  ATT  TCA
    TGT  TGT  AAC  TTT  CAA  TGT  CTT  CCG  TGA  CAA  CAA  AAT  TCG  TTC  TAA  AGT
    Thr  Thr  Leu  Lys  Val  Thr  Glu  Gly  Thr  Val  Val  Leu  Ser  Lys  Ile  Ser>

580           590           600           610           620
         *   *        *    *        *    *        *    *        *    *
    AAA  TCT  GGG  GAA  GTT  TCA  GTT  GAA  CTT  AAT  GAC  ACT  GAC  AGT  AGT  GCT
    TTT  AGA  CCC  CTT  CAA  AGT  CAA  CTT  GAA  TTA  CTG  TGA  CTG  TCA  TCA  CGA
    Lys  Ser  Gly  Glu  Val  Ser  Val  Glu  Leu  Asn  Asp  Thr  Asp  Ser  Ser  Ala>

630           640           650           660           670
         *    *       *    *        *    *        *    *        *    *
    GCT  ACT  AAA  AAA  ACT  GCA  GCT  TGG  AAT  TCA  AAA  ACT  TCC  ACT  TTA  ACA
    CGA  TGA  TTT  TTT  TGA  CGT  CGA  ACC  TTA  AGT  TTT  TGA  AGG  TGA  AAT  TGT
    Ala  Thr  Lys  Lys  Thr  Ala  Ala  Trp  Asn  Ser  Lys  Thr  Ser  Thr  Leu  Thr>

680           690           700           710           720
         *   *        *    *        *    *        *    *        *    *
    ATT  AGT  GTG  AAT  AGC  CAA  AAA  ACC  AAA  AAC  CTT  GTA  TTC  ACA  AAA  GAA
    TAA  TCA  CAC  TTA  TCG  GTT  TTT  TGG  TTT  TTG  GAA  CAT  AAG  TGT  TTT  CTT
    Ile  Ser  Val  Asn  Ser  Gln  Lys  Thr  Lys  Asn  Leu  Val  Phe  Thr  Lys  Glu>

730           740           750           760
         *    *        *    *        *    *        *    *      *
    GAC  ACA  ATA  ACA  GTA  CAA  AAA  TAC  GAC  TCA  GCA  GGC  ACC  AAT  CTA  GAA
    CTG  TGT  TAT  TGT  CAT  GTT  TTT  ATG  CTG  AGT  CGT  CCG  TGG  TTA  GAT  CTT
    Asp  Thr  Ile  Thr  Val  Gln  Lys  Tyr  Asp  Ser  Ala  Gly  Thr  Asn  Leu  Glu>
```

FIG. 28B

```
        770         780         790         800         810
GGC AAA GCA GTG GAA ATT ACA ACA CTT AAA GAA CTT AAA AAC GCT TTA
CCG TTT CGT CAG CTT TAA TGT TGT GAA TTT CTT GAA TTT TTG CGA AAT
Gly Lys Ala Val Glu Ile Thr Thr Leu Lys Glu Leu Lys Asn Ala Leu>

820
AAA TAA
TTT ATT
Lys ***>
```

FIG. 28C

```
            10             20            30             40
     •   •    •    •    •   •    •    •    •   •    •    •
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50            60            70            80            90
     •   •    •    •    •   •    •    •    •   •    •    •
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100           110           120           130          140
     •   •    •    •    •   •    •    •    •   •    •    •
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150           160           170           180          190
     •   •    •    •    •   •    •    •    •   •    •    •
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200           210           220           230          240
     •   •    •    •    •   •    •    •    •   •    •    •
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250           260           270           280
     •   •    •    •    •   •    •    •    •
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290           300           310           320          330
     •   •    •    •    •   •    •    •    •   •    •    •
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340           350           360           370          380
     •   •    •    •    •   •    •    •    •   •    •    •
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 29A

```
            390         400         410         420         430
             *           *           *           *           *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440         450         460         470         480
         *           *           *           *           *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490         500         510         520
         *           *           *           *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
  *           *           *           *           *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580         590         600         610         620
     *           *           *           *           *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630         640         650         660         670
         *           *           *           *           *
GCT ACT AAA AAA ACT GCA GCT TGG AAT GAC AGT ACT AGC ACT TTA ACA
CGA TGA TTT TTT TGA CGT CGA ACC TTA CTG TCA TGA TCG TGA AAT TGT
Ala Thr Lys Lys Thr Ala Ala Trp Asn Asp Ser Thr Ser Thr Leu Thr>

680         690         700         710         720
         *           *           *           *           *
ATT AGT GCT GAC AGC AAA AAA ACT AAA GAT TTG GTG TTC TTA ACA GAT
TAA TCA CGA CTG TCG TTT TTT TGA TTT CTA AAC CAC AAG AAT TGT CTA
Ile Ser Ala Asp Ser Lys Lys Thr Lys Asp Leu Val Phe Leu Thr Asp>

730         740         750         760
         *           *           *           *
GGT ACA ATT ACA GTA CAA CAA TAC AAC ACA GCT GGA ACC AGC CTA GAA
CCA TGT TAA TGT CAT GTT GTT ATG TTG TGT CGA CCT TGG TCG GAT CTT
Gly Thr Ile Thr Val Gln Gln Tyr Asn Thr Ala Gly Thr Ser Leu Glu>
```

FIG. 29B

```
       770           780           790           800           810
        *             *             *             *             *
  GGA TCA GCA AGT GAA ATT AAA AAT CTT TCA GAG CTT AAA AAC GCT TTA
  CCT AGT CGT TCA CTT TAA TTT TTA GAA AGT CTC GAA TTT TTG CGA AAT
  Gly Ser Ala Ser Glu Ile Lys Asn Leu Ser Glu Leu Lys Asn Ala Leu>

820
        *
  AAA TAA
  TTT ATT
  Lys ***>
```

FIG. 29C

```
              10           20           30           40
               *            *            *            *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50           60           70           80           90
      *            *            *            *            *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100          110          120          130          140
         *            *            *            *            *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150         160          170          180          190
            *           *            *            *            *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200          210          220          230          240
               *            *            *            *            *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250          260          270          280
               *            *            *            *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290          300          310          320          330
 *            *            *            *            *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340          350          360          370          380
   *            *            *            *            *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 30A

```
        390            400            410           420           430
         .    *    .    *    .    *    .    *    .    *    .    *    .
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440            450            460           470           480
         .    *    .    *    .    *    .    *    .    *    .    *    .
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490            500            510           520
         .    *    .    *    .    *    .    *    .    *    .
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530            540            550           560           570
  .    *    .    *    .    *    .    *    .    *    .    *    .
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580            590            600           610           620
         .    *    .    *    .    *    .    *    .    *    .    *    .
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630            640            650           660           670
         .    *    .    *    .    *    .    *    .    *    .    *    .
GCT ACT AAA AAA ACT GCA GCT TGG AAT GAC AGT ACT AGC ACT TTA ACA
CGA TGA TTT TTT TGA CGT CGA ACC TTA CTG TCA TGA TCG TGA AAT TGT
Ala Thr Lys Lys Thr Ala Ala Trp Asn Asp Ser Thr Ser Thr Leu Thr>

680            690            700           710           720
         .    *    .    *    .    *    .    *    .    *    .    *    .
ATT AGT GCT GAC AGC AAA AAA ACT AAA GAT TTG GTG TTC TTA ACA GAT
TAA TCA CGA CTG TCG TTT TTT TGA TTT CTA AAC CAC AAG AAT TGT CTA
Ile Ser Ala Asp Ser Lys Lys Thr Lys Asp Leu Val Phe Leu Thr Asp>

730            740            750           760
         .    *    .    *    .    *    .    *    .    *    .
GGT ACA ATT ACA GTA CAA CAA TAC AAC ACA GCT GGA ACC AGC CTA GAA
CCA TGT TAA TGT CAT GTT GTT ATG TTG TGT CGA CCT TGG TCG GAT CTT
Gly Thr Ile Thr Val Gln Gln Tyr Asn Thr Ala Gly Thr Ser Leu Glu>
```

FIG. 30B

```
      770           780           790           800           810
       .             .             .             .             .
   .   .   .   .   .   .   .   .   .   .   .   .   .   .   .
GGA TCA GCA AGT GAA ATT AAA AAT CTT TCA GAG CTT AAA AAC GCT TTA
CCT AGT CGT TCA CTT TAA TTT TTA GAA AGT CTC GAA TTT TTG CGA AAT
Gly Ser Ala Ser Glu Ile Lys Asn Leu Ser Glu Leu Lys Asn Ala Leu>

820           830           840           850           860
       .             .             .             .             .
   .   .   .   .   .   .   .   .   .   .   .   .   .   .   .
AAA ATG GCT AAT AAT TCA GGG AAA GAT GGG AAT ACA TCT GCA AAT TCT
TTT TAC CGA TTA TTA AGT CCC TTT CTA CCC TTA TGT AGA CGT TTA AGA
Lys Met Ala Asn Asn Ser Gly Lys Asp Gly Asn Thr Ser Ala Asn Ser>

870           880           890           900           910
       .             .             .             .             .
   .   .   .   .   .   .   .   .   .   .   .   .   .   .   .
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
Ala Asp Glu Ser Val Lys Gly Pro Asn Leu Thr Glu Ile Ser Lys Lys>

920           930           940           950           960
           .             .             .             .             .
       .   .   .   .   .   .   .   .   .   .   .   .   .   .   .
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
Ile Thr Asp Ser Asn Ala Val Leu Leu Ala Val Lys Glu Val Glu Ala>

970           980           990          1000
               .             .             .             .
           .   .   .   .   .   .   .   .   .   .   .   .
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
Leu Leu Ser Ser Ile Asp Glu Ile Ala Ala Lys Ala Ile Gly Lys Lys>

1010          1020          1030          1040          1050
       .             .             .             .             .
   .   .   .   .   .   .   .   .   .   .   .   .   .   .   .
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
Ile His Gln Asn Asn Gly Leu Asp Thr Glu Tyr Asn His Asn Gly Ser>

1060          1070          1080          1090          1100
       .             .             .             .             .
   .   .   .   .   .   .   .   .   .   .   .   .   .   .   .
TTG TTA GCG GGA CGT TAT GCA ATA TCA ACC CTA ATA AAA CAA AAA TTA
AAC AAT CGC CCT GCA ATA CGT TAT AGT TGG GAT TAT TTT GTT TTT AAT
Leu Leu Ala Gly Arg Tyr Ala Ile Ser Thr Leu Ile Lys Gln Lys Leu>

1110          1120          1130          1140          1150
       .             .             .             .             .
   .   .   .   .   .   .   .   .   .   .   .   .   .   .   .
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
Asp Gly Leu Lys Asn Glu Gly Leu Lys Glu Lys Ile Asp Ala Ala Lys>
```

FIG. 30C

```
          1160           1170           1180           1190           1200
      *      •       *      •       *      •       •      •       *      *
   AAA TGT TCT GAA ACA TTT ACT AAT AAA TTA AAA GCA AAA CAC ACA GAT
   TTT ACA AGA CTT TGT AAA TGA TTA TTT AAT TTT CGT TTT GTG TGT CTA
   Lys Cys Ser Glu Thr Phe Thr Asn Lys Leu Lys Ala Lys His Thr Asp>

1210           1220           1230           1240
      *      •       •      *       *      *       *      •       •
   CTT GGT AAA GAA GGT GTT ACT GAT GCT GAT GCA AAA GAA GCC ATT TTA
   GAA CCA TTT CTT CCA CAA TGA CTA CGA CTA CGT TTT CTT CGG TAA AAT
   Leu Gly Lys Glu Gly Val Thr Asp Ala Asp Ala Lys Glu Ala Ile Leu>

1250           1260           1270           1280           1290
   .      •       *      •       •      *       *      •       *      *
   AAA ACA AAT GGT ACT AAA ACT AAA GGT GCT GAA GAA CTT GGA AAA TTA
   TTT TGT TTA CCA TGA TTT TGA TTT CCA CGA CTT CTT GAA CCT TTT AAT
   Lys Thr Asn Gly Thr Lys Thr Lys Gly Ala Glu Glu Leu Gly Lys Leu>

1300           1310           1320           1330           1340
      *      -       *      •       *      •       *      *       *      •
   TTT GAA TCA GTA GAG GTC TTG TCA AAA GCA GCT AAA GAG ATG CTT GCT
   AAA CTT AGT CAT CTC CAG AAC AGT TTT CGT CGA TTT CTC TAC GAA CGA
   Phe Glu Ser Val Glu Val Leu Ser Lys Ala Ala Lys Glu Met Leu Ala>

1350           1360           1370           1380           1390
      •      •       •      •       •      *       *      •       *      •
   AAT TCA GTT AAA GAG CTT ACA AGC CCT GTT GTG GCA GAA AGT CCA AAA
   TTA AGT CAA TTT CTC GAA TGT TCG GGA CAA CAC CGT CTT TCA GGT TTT
   Asn Ser Val Lys Glu Leu Thr Ser Pro Val Val Ala Glu Ser Pro Lys>

1400
      *      *
   AAA CCT TAA
   TTT GGA ATT
   Lys Pro ***>
```

FIG. 30D

```
            10              20              30              40
             *       *       *       *       *       *       *       *
        ATG AAA AAG AAT ACA TTA AGT GCG ATA TTA ATG ACT TTA TTT TTA TTT
        TAC TTT TTC TTA TGT AAT TCA CGC TAT AAT TAC TGA AAT AAA AAT AAA
        Met Lys Lys Asn Thr Leu Ser Ala Ile Leu Met Thr Leu Phe Leu Phe>

50              60              70              80              90
           *       *       *       *       *       *       *       *       *
        ATA TCT TGT AAT AAT TCA GGG AAA GAT GGG AAT ACA TCT GCA AAT TCT
        TAT AGA ACA TTA TTA AGT CCC TTT CTA CCC TTA TGT AGA CGT TTA AGA
        Ile Ser Cys Asn Asn Ser Gly Lys Asp Gly Asn Thr Ser Ala Asn Ser>

100             110             120             130             140
             *       *       *       *       *       *       *       *
        GCT GAT GAG TCT GTT AAA GGG CCT AAT CTT ACA GAA ATA AGT AAA AAA
        CGA CTA CTC AGA CAA TTT CCC GGA TTA GAA TGT CTT TAT TCA TTT TTT
        Ala Asp Glu Ser Val Lys Gly Pro Asn Leu Thr Glu Ile Ser Lys Lys>

150             160             170             180             190
             *       *       *       *       *       *       *       *
        ATT ACG GAT TCT AAT GCG GTT TTA CTT GCT GTG AAA GAG GTT GAA GCG
        TAA TGC CTA AGA TTA CGC CAA AAT GAA CGA CAC TTT CTC CAA CTT CGC
        Ile Thr Asp Ser Asn Ala Val Leu Leu Ala Val Lys Glu Val Glu Ala>

200             210             220             230             240
             *       *       *       *       *       *       *       *
        TTG CTG TCA TCT ATA GAT GAA ATT GCT GCT AAA GCT ATT GGT AAA AAA
        AAC GAC AGT AGA TAT CTA CTT TAA CGA CGA TTT CGA TAA CCA TTT TTT
        Leu Leu Ser Ser Ile Asp Glu Ile Ala Ala Lys Ala Ile Gly Lys Lys>

250             260             270             280
             *       *       *       *       *       *       *
        ATA CAC CAA AAT AAT GGT TTG GAT ACC GAA TAT AAT CAC AAT GGA TCA
        TAT GTG GTT TTA TTA CCA AAC CTA TGG CTT ATA TTA GTG TTA CCT AGT
        Ile His Gln Asn Asn Gly Leu Asp Thr Glu Tyr Asn His Asn Gly Ser>

290             300             310             320             330
          *       *       *       *       *       *       *       *       *
        TTG TTA GCG GGA CGT TAT GCA ATA TCA ACC CTA ATA AAA CAA AAA TTA
        AAC AAT CGC CCT GCA ATA CGT TAT AGT TGG GAT TAT TTT GTT TTT AAT
        Leu Leu Ala Gly Arg Tyr Ala Ile Ser Thr Leu Ile Lys Gln Lys Leu>

340             350             360             370             380
             *       *       *       *       *       *       *       *
        GAT GGA TTG AAA AAT GAA GGA TTA AAG GAA AAA ATT GAT GCG GCT AAG
        CTA CCT AAC TTT TTA CTT CCT AAT TTC CTT TTT TAA CTA CGC CGA TTC
        Asp Gly Leu Lys Asn Glu Gly Leu Lys Glu Lys Ile Asp Ala Ala Lys>
```

FIG. 31A

```
          390           400           410           420           430
           *             *             *             *             *
AAA TGT TCT GAA ACA TTT ACT AAT AAA TTA AAA GCA AAA CAC ACA GAT
TTT ACA AGA CTT TGT AAA TGA TTA TTT AAT TTT CGT TTT GTG TGT CTA
Lys Cys Ser Glu Thr Phe Thr Asn Lys Leu Lys Ala Lys His Thr Asp>

440           450           460           470           480
           *             *             *             *             *
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
Leu Gly Lys Glu Gly Val Thr Asp Ala Asp Ala Lys Glu Ala Ile Leu>

490           500           510           520
           *             *             *             *
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
Lys Thr Asn Gly Thr Lys Thr Lys Gly Ala Glu Glu Leu Gly Lys Leu>

530           540           550           560           570
   *             *             *             *             *
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
Phe Glu Ser Val Glu Val Leu Ser Lys Ala Ala Lys Glu Met Leu Ala>

580           590           600           610           620
   *             *             *             *             *
AAT TCA GTT AAA GAG CTT ACA AGC CCT GTT GTG GCA GAA AGT CCA AAA
TTA AGT CAA TTT CTC GAA TGT TCG GGA CAC CGT CTT TCA GGT TTT
Asn Ser Val Lys Glu Leu Thr Ser Pro Val Val Ala Glu Ser Pro Lys>

630           640           650           660           670
   *             *             *             *             *
AAA CCT AAG CAA AAT GTT AGC AGC CTT GAC GAG AAA AAC AGC GTT TCA
TTT GGA TTC GTT TTA CAA TCG TCG GAA CTG CTC TTT TTG TCG CAA AGT
Lys Pro Lys Gln Asn Val Ser Ser Leu Asp Glu Lys Asn Ser Val Ser>

680           690           700           710           720
           *             *             *             *             *
GTA GAT TTG CCT GGT GAA ATG AAA GTT CTT GTA AGC AAA GAA AAA AAC
CAT CTA AAC GGA CCA CTT TAC TTT CAA GAA CAT TCG TTT CTT TTT TTG
Val Asp Leu Pro Gly Glu Met Lys Val Leu Val Ser Lys Glu Lys Asn>

730           740           750           760
           *             *             *             *
AAA GAC GGC AAG TAC GAT CTA ATT GCA ACA GTA GAC AAG CTT GAG CTT
TTT CTG CCG TTC ATG CTA GAT TAA CGT TGT CAT CTG TTC GAA CTC GAA
Lys Asp Gly Lys Tyr Asp Leu Ile Ala Thr Val Asp Lys Leu Glu Leu>
```

FIG. 31B

```
        770           780           790           800           810
          .             .             .             .             .
     .   .   .     .   .   .     .   .   .     .   .   .     .   .   .
    AAA GGA ACT TCT GAT AAA AAC AAT GGA TCT GGA GTA CTT GAA GGC GTA
    TTT CCT TGA AGA CTA TTT TTG TTA CCT AGA CCT CAT GAA CTT CCG CAT
    Lys Gly Thr Ser Asp Lys Asn Asn Gly Ser Gly Val Leu Glu Gly Val>

820           830           840           850           860
          .             .             .             .             .
     .   .   .     .   .   .     .   .   .     .   .   .     .   .   .
    AAA GCT GAC AAA AGT AAA GTA AAA TTA ACA ATT TCT GAC GAT CTA GGT
    TTT CGA CTG TTT TCA TTT CAT TTT AAT TGT TAA AGA CTG CTA GAT CCA
    Lys Ala Asp Lys Ser Lys Val Lys Leu Thr Ile Ser Asp Asp Leu Gly>

870           880           890           900           910
          .             .             .             .             .
     .   .   .     .   .   .     .   .   .     .   .   .     .   .   .
    CAA ACC ACA CTT GAA GTT TTC AAA GAA GAT GGC AAA ACA CTA GTA TCA
    GTT TGG TGT GAA CTT CAA AAG TTT CTT CTA CCG TTT TGT GAT CAT AGT
    Gln Thr Thr Leu Glu Val Phe Lys Glu Asp Gly Lys Thr Leu Val Ser>

920           930           940           950           960
          .             .             .             .             .
     .   .   .     .   .   .     .   .   .     .   .   .     .   .   .
    AAA AAA GTA ACT TCC AAA GAC AAG TCA TCA ACA GAA GAA AAA TTC AAT
    TTT TTT CAT TGA AGG TTT CTG TTC AGT AGT TGT CTT CTT TTT AAG TTA
    Lys Lys Val Thr Ser Lys Asp Lys Ser Ser Thr Glu Glu Lys Phe Asn>

970           980           990          1000
          .             .             .             .
     .   .   .     .   .   .     .   .   .     .   .   .     .   .   .
    GAA AAA GGT GAA GTA TCT GAA AAA ATA ATA ACA AGA GCA GAC GGA ACC
    CTT TTT CCA CTT CAT AGA CTT TTT TAT TAT TGT TCT CGT CTG CCT TGG
    Glu Lys Gly Glu Val Ser Glu Lys Ile Ile Thr Arg Ala Asp Gly Thr>

1010          1020          1030          1040          1050
     .             .             .             .             .
     .   .   .     .   .   .     .   .   .     .   .   .     .   .   .
    AGA CTT GAA TAC ACA GGA ATT AAA AGC GAT GGA TCT GGA AAA GCT AAA
    TCT GAA CTT ATG TGT CCT TAA TTT TCG CTA CCT AGA CCT TTT CGA TTT
    Arg Leu Glu Tyr Thr Gly Ile Lys Ser Asp Gly Ser Gly Lys Ala Lys>

1060          1070          1080          1090          1100
          .             .             .             .             .
     .   .   .     .   .   .     .   .   .     .   .   .     .   .   .
    GAG GTT TTA AAA GGC TAT GTT CTT GAA GGA ACT CTA ACT GCT GAA AAA
    CTC CAA AAT TTT CCG ATA CAA GAA CTT CCT TGA GAT TGA CGA CTT TTT
    Glu Val Leu Lys Gly Tyr Val Leu Glu Gly Thr Leu Thr Ala Glu Lys>

1110          1120          1130          1140          1150
          .             .             .             .             .
     .   .   .     .   .   .     .   .   .     .   .   .     .   .   .
    ACA ACA TTG GTG GTT AAA GAA GGA ACT GTT ACT TTA AGC AAA AAT ATT
    TGT TGT AAC CAC CAA TTT CTT CCT TGA CAA TGA AAT TCG TTT TTA TAA
    Thr Thr Leu Val Val Lys Glu Gly Thr Val Thr Leu Ser Lys Asn Ile>
```

FIG. 31C

```
            1160          1170          1180          1190          1200
             *     *       *     *       *     *       *     *       *     *
        TCA AAA TCT GGG GAA GTT TCA GTT GAA CTT AAT GAC ACT GAC AGT AGT
        AGT TTT AGA CCC CTT CAA AGT CAA CTT GAA TTA CTG TGA CTG TCA TCA
        Ser Lys Ser Gly Glu Val Ser Val Glu Leu Asn Asp Thr Asp Ser Ser>

1210          1220          1230          1240
             *     *       *     *       *     *       *     *
        GCT GCT ACT AAA AAA ACT GCA GCT TGG AAT GAC AGT ACT AGC ACT TTA
        CGA CGA TGA TTT TTT TGA CGT CGA ACC TTA CTG TCA TGA TCG TGA AAT
        Ala Ala Thr Lys Lys Thr Ala Ala Trp Asn Asp Ser Thr Ser Thr Leu>

1250          1260          1270          1280          1290
     *     *       *     *       *     *       *     *       *     *
    ACA ATT AGT GCT GAC AGC AAA AAA ACT AAA GAT TTG GTG TTC TTA ACA
    TGT TAA TCA CGA CTG TCG TTT TTT TGA TTT CTA AAC CAC AAG AAT TGT
    Thr Ile Ser Ala Asp Ser Lys Lys Thr Lys Asp Leu Val Phe Leu Thr>

1300          1310          1320          1330          1340
             *     *       *     *       *     *       *     *       *     *
        GAT GGT ACA ATT ACA GTA CAA CAA TAC AAC ACA GCT GGA ACC AGC CTA
        CTA CCA TGT TAA TGT CAT GTT GTT ATG TTG TGT CGA CCT TGG TCG GAT
        Asp Gly Thr Ile Thr Val Gln Gln Tyr Asn Thr Ala Gly Thr Ser Leu>

1350          1360          1370          1380          1390
             *     *       *     *       *     *       *     *       *     *
        GAA GGA TCA GCA AGT GAA ATT AAA AAT CTT TCA GAG CTT AAA AAC GCT
        CTT CCT AGT CGT TCA CTT TAA TTT TTA GAA AGT CTC GAA TTT TTG CGA
        Glu Gly Ser Ala Ser Glu Ile Lys Asn Leu Ser Glu Leu Lys Asn Ala>

1400
             *     *
        TTA AAA TAA
        AAT TTT ATT
        Leu Lys ***>
```

FIG. 31D

```
           10              20              30              40
            *               *               *               *
AAG CAA AAT GTT AGC AGC CTT GAC GAG AAA AAC AGC GTT TCA GTA GAT
TTC GTT TTA CAA TCG TCG GAA CTG CTC TTT TTG TCG CAA AGT CAT CTA
 K   Q   N   V   S   S   L   D   E   K   N   S   V   S   V   D>

50              60              70              80              90
       *               *               *               *               *
TTG CCT GGT GAA ATG AAA GTT CTT GTA AGC AAA GAA AAA AAC AAA GAC
AAC GGA CCA CTT TAC TTT CAA GAA CAT TCG TTT CTT TTT TTG TTT CTG
 L   P   G   E   M   K   V   L   V   S   K   E   K   N   K   D>

100             110             120             130             140
       *               *               *               *               *
GGC AAG TAC GAT CTA ATT GCA ACA GTA GAC AAG CTT GAG CTT AAA GGA
CCG TTC ATG CTA GAT TAA CGT TGT CAT CTG TTC GAA CTC GAA TTT CCT
 G   K   Y   D   L   I   A   T   V   D   K   L   E   L   K   G>

150             160             170             180             190
       *               *               *               *               *
ACT TCT GAT AAA AAC AAT GGA TCT GGA GTA CTT GAA GGC GTA AAA GCT
TGA AGA CTA TTT TTG TTA CCT AGA CCT CAT GAA CTT CCG CAT TTT CGA
 T   S   D   K   N   N   G   S   G   V   L   E   G   V   K   A>

200             210             220             230             240
       *               *               *               *               *
GAC AAA AGT AAA GTA AAA TTA ACA ATT TCT GAC GAT CTA GGT CAA ACC
CTG TTT TCA TTT CAT TTT AAT TGT TAA AGA CTG CTA GAT CCA GTT TGG
 D   K   S   K   V   K   L   T   I   S   D   D   L   G   Q   T>

250             260             270             280
       *               *               *               *
ACA CTT GAA GTT TTC AAA GAA GAT GGC AAA ACA CTA GTA TCA AAA AAA
TGT GAA CTT CAA AAG TTT CTT CTA CCG TTT TGT GAT CAT AGT TTT TTT
 T   L   E   V   F   K   E   D   G   K   T   L   V   S   K   K>

290             300             310             320             330
   *               *               *               *               *
GTA ACT TCC AAA GAC AAG TCA TCA ACA GAA GAA AAA TTC AAT GAA AAA
CAT TGA AGG TTT CTG TTC AGT AGT TGT CTT CTT TTT AAG TTA CTT TTT
 V   T   S   K   D   K   S   S   T   E   E   K   F   N   E   K>

340             350             360             370             380
   *               *               *               *               *
GGT GAA GTA TCT GAA AAA ATA ATA ACA AGA GCA GAC GGA ACC AGA CTT
CCA CTT CAT AGA CTT TTT TAT TAT TGT TCT CGT CTG CCT TGG TCT GAA
 G   E   V   S   E   K   I   I   T   R   A   D   G   T   R   L>
```

FIG. 32A

```
         390           400           410           420           430
          *             *             *             *             *
          .             .             .             .             .
GAA  TAC  ACA  GGA  ATT  AAA  AGC  GAT  GGA  TCT  GGA  AAA  GCT  AAA  GAG  GTT
CTT  ATG  TGT  CCT  TAA  TTT  TCG  CTA  CCT  AGA  CCT  TTT  CGA  TTT  CTC  CAA
 E    Y    T    G    I    K    S    D    G    S    G    K    A    K    E    V>

440           450           460           470           480
                *             *             *             *             *
                .             .             .             .             .
TTA  AAA  GGC  TAT  GTT  CTT  GAA  GGA  ACT  CTA  ACT  GCT  GAA  AAA  ACA  ACA
AAT  TTT  CCG  ATA  CAA  GAA  CTT  CCT  TGA  GAT  TGA  CGA  CTT  TTT  TGT  TGT
 L    K    G    Y    V    L    E    G    T    L    T    A    E    K    T    T>

490           500           510           520
                     *             *             *             *
                     .             .             .             .
TTG  GTG  GTT  AAA  GAA  GGA  ACT  GTT  ACT  TTA  AGC  AAA  AAT  ATT  TCA  AAA
AAC  CAC  CAA  TTT  CTT  CCT  TGA  CAA  TGA  AAT  TCG  TTT  TTA  TAA  AGT  TTT
 L    V    V    K    E    G    T    V    T    L    S    K    N    I    S    K>

530           540           550           560           570
  *             *             *             *             *
  .             .             .             .             .
TCT  GGG  GAA  GTT  TCA  GTT  GAA  CTT  AAT  GAC  ACT  GAC  AGT  AGT  GCT  GCT
AGA  CCC  CTT  CAA  AGT  CAA  CTT  GAA  TTA  CTG  TGA  CTG  TCA  TCA  CGA  CGA
 S    G    E    V    S    V    E    L    N    D    T    D    S    S    A    A>

580           590           600           610           620
           *             *             *             *             *
           .             .             .             .             .
ACT  AAA  AAA  ACT  GCA  GCT  TGG  AAT  TCA  GGC  ACT  TCA  ACT  TTA  ACA  ATT
TGA  TTT  TTT  TGA  CGT  CGA  ACC  TTA  AGT  CCG  TGA  AGT  TGA  AAT  TGT  TAA
 T    K    K    T    A    A    W    N    S    G    T    S    T    L    T    I>

630           640           650           660           670
                *             *             *             *             *
                .             .             .             .             .
ACT  GTA  AAC  AGT  AAA  AAA  ACT  AAA  GAC  CTT  GTG  TTT  ACA  AAA  GAA  AAC
TGA  CAT  TTG  TCA  TTT  TTT  TGA  TTT  CTG  GAA  CAC  AAA  TGT  TTT  CTT  TTG
 T    V    N    S    K    K    T    K    D    L    V    F    T    K    E    N>

680           690           700           710           720
                     *             *             *             *             *
                     .             .             .             .             .
ACA  ATT  ACA  GTA  CAA  CAA  TAC  GAC  TCA  AAT  GGC  ACC  AAA  TTA  GAG  GGG
TGT  TAA  TGT  CAT  GTT  GTT  ATG  CTG  AGT  TTA  CCG  TGG  TTT  AAT  CTC  CCC
 T    I    T    V    Q    Q    Y    D    S    N    G    T    K    L    E    G>

730           740           750           760
                          *             *             *             *
                          .             .             .             .
TCA  GCA  GTT  GAA  ATT  ACA  AAA  CTT  GAT  GAA  ATT  AAA  AAC  GCT  TTA  AAA
AGT  CGT  CAA  CTT  TAA  TGT  TTT  GAA  CTA  CTT  TAA  TTT  TTG  CGA  AAT  TTT
 S    A    V    E    I    T    K    L    D    E    I    K    N    A    L    K>
```

FIG. 32B

```
     770              780            790            800             810
 GGT CAC CCC ATG GAT GAA AAG CTT TTA AAA AGT AAA GAT GAT AAA GCA
 CCA GTG GGG TAC CTA CTT TTC GAA AAT TTT TCA TTT CTA CTA TTT CGT
  G   H   P   M   D   E   K   L   L   K   S   K   D   D   K   A>

820            830            840             850            860
 AGT AAA GAT GGT AAA GCC TTG GAT CTT GAT CGA GAA TTA AAT TCT AAA
 TCA TTT CTA CCA TTT CGG AAC CTA GAA CTA GCT CTT AAT TTA AGA TTT
  S   K   D   G   K   A   L   D   L   D   R   E   L   N   S   K>

870            880            890             900            910
 GCT TCT AGC AAA GAA AAA AGT AAA GCC AAG GAA GAA GAA ATA ACC AAG
 CGA AGA TCG TTT CTT TTT TCA TTT CGG TTC CTT CTT CTT TAT TGG TTC
  A   S   S   K   E   K   S   K   A   K   E   E   E   I   T   K>

920            930            940             950            960
 GGT AAG TCA CAG AAA AGC TTA GGC GAT TTG AAT AAT GAT GAA AAT CTT
 CCA TTC AGT GTC TTT TCG AAT CCG CTA AAC TTA TTA CTA CTT TTA GAA
  G   K   S   Q   K   S   L   G   D   L   N   N   D   E   N   L>

970           980            990           1000
 ATG ATG CCA GAA GAT CAA AAA TTA CCT GAG GTT AAA AAA TTA GAT AGC
 TAC TAC GGT CTT CTA GTT TTT AAT GGA CTC CAA TTT TTT AAT CTA TCG
  M   M   P   E   D   Q   K   L   P   E   V   K   K   L   D   S>

1010           1020           1030           1040            1050
 AAA AAA GAA TTT AAA CCT GTT TCT GAG GTT GAG AAA TTA GAT AAG ATT
 TTT TTT CTT AAA TTT GGA CAA AGA CTC CAA CTC TTT AAT CTA TTC TAA
  K   K   E   F   K   P   V   S   E   V   E   K   L   D   K   I>

1060           1070           1080           1090            1100
 TTC AAG TCT AAT AAC AAT GTT GGA GAA TTA TCA CCG TTA GAT AAA TCT
 AAG TTC AGA TTA TTG TTA CAA CCT CTT AAT AGT GGC AAT CTA TTT AGA
  F   K   S   N   N   N   V   G   E   L   S   P   L   D   K   S>

1110           1120           1130           1140            1150
 TCT TAT AAA GAC ATT GAT TCA AAA GAG GAG ACA GTT AAT AAA GAT GTT
 AGA ATA TTT CTG TAA CTA AGT TTT CTC CTC TGT CAA TTA TTT CTA CAA
  S   Y   K   D   I   D   S   K   E   E   T   V   N   K   D   V>
```

FIG. 32C

```
        1160          1170          1180          1190          1200
  .      *     .       *     .       *     .       *     .       *
AAT TTG CAA AAG ACT AAG CCT CAG GTT AAA GAC CAA GTT ACT TCT TTG
TTA AAC GTT TTC TGA TTC GGA GTC CAA TTT CTG GTT CAA TGA AGA AAC
 N   L   Q   K   T   K   P   Q   V   K   D   Q   V   T   S   L>

1210         1220          1230          1240
   .         *    .      *     .       *    .        *     .
AAT GAA GAT TTG ACT ACT ATG TCT ATA GAT TCC AGT AGT CCT GTA TTT
TTA CTT CTA AAC TGA TGA TAC AGA TAT CTA AGG TCA TCA GGA CAT AAA
 N   E   D   L   T   T   M   S   I   D   S   S   S   P   V   F>

1250        1260          1270          1280          1290
   .          *     .      *     .       *     .       *    .
TTA GAG GTT ATT GAT CCA ATT ACA AAT TTA GGA ACT CTT CAA CTT ATT
AAT CTC CAA TAA CTA GGT TAA TGT TTA AAT CCT TGA GAA GTT GAA TAA
 L   E   V   I   D   P   I   T   N   L   G   T   L   Q   L   I>

1300          1310          1320          1330          1340
   .     *     .       *     .       *     .       *     .
GAT TTA AAT ACT GGT GTT AGG CTT AAA GAA AGC ACT CAG CAA GGC ATT
CTA AAT TTA TGA CCA CAA TCC GAA TTT CTT TCG TGA GTC GTT CCG TAA
 D   L   N   T   G   V   R   L   K   E   S   T   Q   Q   G   I>

1350          1360          1370          1380          1390
   .      *     .       *     .       *     .       *     .
CAG CGG TAT GGA ATT TAT GAA CGT GAA AAA GAT TTG GTT GTT ATT AAA
GTC GCC ATA CCT TAA ATA CTT GCA CTT TTT CTA AAC CAA CAA TAA TTT
 Q   R   Y   G   I   Y   E   R   E   K   D   L   V   V   I   K>

1400          1410          1420          1430         1440
   .       *     .       *     .       *     .       *     .
ATG GAT TCA GGA AAA GCT AAG CTT CAG ATA CTT GAT AAA CTT GAA AAT
TAC CTA AGT CCT TTT CGA TTC GAA GTC TAT GAA CTA TTT GAA CTT TTA
 M   D   S   G   K   A   K   L   Q   I   L   D   K   L   E   N>

1450          1460          1470          1480
    .       *     .      *     .       *     .       *     .
TTA AAA GTG GTA TCA GAG TCT AAT TTT GAG ATT AAT AAA AAT TCA TCT
AAT TTT CAC CAT AGT CTC AGA TTA AAA CTC TAA TTA TTT TTA AGT AGA
 L   K   V   V   S   E   S   N   F   E   I   N   K   N   S   S>

1490        1500          1510          1520         1530
   .         *    .       *    .        *    .        *     .
CTT TAT GTT GAT TCT AAA ATG ATT TTA GTA GCT GTT AGG GAT AAA GAT
GAA ATA CAA CTA AGA TTT TAC TAA AAT CAT CGA CAA TCC CTA TTT CTA
 L   Y   V   D   S   K   M   I   L   V   A   V   R   D   K   D>
```

FIG. 32D

```
         1540          1550          1560         1570          1580
           *             *             *  *          *             *
       AGT AGT AAT GAT TGG AGA TTG GCC AAA TTT TCT CCT AAA AAT TTA GAT
       TCA TCA TTA CTA ACC TCT AAC CGG TTT AAA AGA GGA TTT TTA AAT CTA
        S   S   N   D   W   R   L   A   K   F   S   P   K   N   L   D>

1590          1600          1610         1620          1630
           *   *         *             *  *         *             *   *
       GAG TTT ATT CTT TCA GAG AAT AAA ATT ATG CCT TTT ACT AGC TTT TCT
       CTC AAA TAA GAA AGT CTC TTA TTT TAA TAC GGA AAA TGA TCG AAA AGA
        E   F   I   L   S   E   N   K   I   M   P   F   T   S   F   S>

1640          1650         1660          1670          1680
             *             *            *             *             *
       GTG AGA AAA AAT TTT ATT TAT TTG CAA GAT GAG TTT AAA AGT CTA GTT
       CAC TCT TTT TTA AAA TAA ATA AAC GTT CTA CTC AAA TTT TCA GAT CAA
        V   R   K   N   F   I   Y   L   Q   D   E   F   K   S   L   V>

1690          1700         1710          1720
               *             *   *        *  *          *   *
       ATT TTA GAT GTA AAT ACT TTA AAA AAA GTT AAG GGT CAC C
       TAA AAT CTA CAT TTA TGA AAT TTT TTT CAA TTC CCA GTG G
        I   L   D   V   N   T   L   K   K   V   K   G   H   X>
```

FIG. 32E

```
         10              20              30              40
          •   •     •     •     •    •    •     •    •
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

50              60              70              80              90
      •   •     •    •     •     •    •     •    •    •     •
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

100             110             120             130             140
         •   •     •     •    •     •    •     •    •     •     •
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

150             160             170             180             190
         •   •     •    •     •     •    •     •    •     •     •
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

200             210             220             230             240
         •   •     •    •     •     •    •     •    •     •     •
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

250             260             270             280
         •   •     •    •     •     •    •     •    •
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290             300             310             320             330
 •   •     •    •     •     •    •     •    •     •     •
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

340             350             360             370             380
         •   •     •    •     •     •    •     •    •     •
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

FIG. 33A

```
       390              400              410              420              430
  .      .       .       .       .       .       .       .       .       .
ATA  ACA  GAG  GAA  ACT  CTC  AAA  GCT  AAT  AAA  TTA  GAC  TCA  AAG  AAA  TTA
TAT  TGT  CTC  CTT  TGA  GAG  TTT  CGA  TTA  TTT  AAT  CTG  AGT  TTC  TTT  AAT
 I    T    E    E    T    L    K    A    N    K    L    D    S    K    K    L>

440              450              460              470              480
    .       .       .       .       .       .       .       .       .       .
ACA  AGA  TCA  AAC  GGA  ACT  ACA  CTT  GAA  TAC  TCA  CAA  ATA  ACA  GAT  GCT
TGT  TCT  AGT  TTG  CCT  TGA  TGT  GAA  CTT  ATG  AGT  GTT  TAT  TGT  CTA  CGA
 T    R    S    N    G    T    T    L    E    Y    S    Q    I    T    D    A>

490              500              510              520
       .       .       .       .       .       .       .       .       .
GAC  AAT  GCT  ACA  AAA  GCA  GTA  GAA  ACT  CTA  AAA  AAT  AGC  ATT  AAG  CTT
CTG  TTA  CGA  TGT  TTT  CGT  CAT  CTT  TGA  GAT  TTT  TTA  TCG  TAA  TTC  GAA
 D    N    A    T    K    A    V    E    T    L    K    N    S    I    K    L>

530              540              550              560              570
  .      .       .       .       .       .       .       .       .       .
GAA  GGA  AGT  CTT  GTA  GTC  GGA  AAA  ACA  ACA  GTG  GAA  ATT  AAA  GAA  GGT
CTT  CCT  TCA  GAA  CAT  CAG  CCT  TTT  TGT  TGT  CAC  CTT  TAA  TTT  CTT  CCA
 E    G    S    L    V    V    G    K    T    T    V    E    I    K    E    G>

580              590              600              610              620
     .       .       .       .       .       .       .       .       .       .
ACT  GTT  ACT  CTA  AAA  AGA  GAA  ATT  GAA  AAA  GAT  GGA  AAA  GTA  AAA  GTC
TGA  CAA  TGA  GAT  TTT  TCT  CTT  TAA  CTT  TTT  CTA  CCT  TTT  CAT  TTT  CAG
 T    V    T    L    K    R    E    I    E    K    D    G    K    V    K    V>

630              640              650              660              670
    .       .       .       .       .       .       .       .       .       .
TTT  TTG  AAT  GAC  ACT  GCA  GGT  TCT  AAC  AAA  AAA  ACA  GGT  AAA  TGG  GAA
AAA  AAC  TTA  CTG  TGA  CGT  CCA  AGA  TTG  TTT  TTT  TGT  CCA  TTT  ACC  CTT
 F    L    N    D    T    A    G    S    N    K    K    T    G    K    W    E>

680              690              700              710              720
       .       .       .       .       .       .       .       .       .       .
GAC  AGT  ACT  AGC  ACT  TTA  ACA  ATT  AGT  GCT  GAC  AGC  AAA  AAA  ACT  AAA
CTG  TCA  TGA  TCG  TGA  AAT  TGT  TAA  TCA  CGA  CTG  TCG  TTT  TTT  TGA  TTT
 D    S    T    S    T    L    T    I    S    A    D    S    K    K    T    K>

730              740              750              760
       .       .       .       .       .       .       .       .       .
GAT  TTG  GTG  TTC  TTA  ACA  GAT  GGT  ACA  ATT  ACA  GTA  CAA  CAA  TAC  AAC
CTA  AAC  CAC  AAG  AAT  TGT  CTA  CCA  TGT  TAA  TGT  CAT  GTT  GTT  ATG  TTG
 D    L    V    F    L    T    D    G    T    I    T    V    Q    Q    Y    N>
```

FIG. 33B

```
        770         780         790         800         810
         .           .           .           .           .
         •           •           •           •           •
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
 T   A   G   T   S   L   E   G   S   A   S   E   I   K   N   L>

820         830         840         850         860
         .           .           .           .           .
         •           •           •           •           •
TCA GAG CTT AAA AAC GCT TTA AAA GGT CAC CCC ATG GCT CAA TAT AAC
AGT CTC GAA TTT TTG CGA AAT TTT CCA GTG GGG TAC CGA GTT ATA TTG
 S   E   L   K   N   A   L   K   G   H   P   M   A   Q   Y   N>

870         880         890         900         910
         .           .           .           .           .
         •           •           •           •           •
CAA ATG CAC ATG TTA TCA AAC AAA TCT GCT TCT CAA AAT GTA AGA ACA
GTT TAC GTG TAC AAT AGT TTG TTT AGA CGA AGA GTT TTA CAT TCT TGT
 Q   M   H   M   L   S   N   K   S   A   S   Q   N   V   R   T>

920         930         940         950         960
         .           .           .           .           .
         •           •           •           •           •
GCT GAA GAG CTT GGA ATG CAG CCT GCA AAA ATT AAC ACA CCA GCA TCA
CGA CTT CTC GAA CCT TAC GTC GGA CGT TTT TAA TTG TGT GGT CGT AGT
 A   E   E   L   G   M   Q   P   A   K   I   N   T   P   A   S>

970         980         990        1000
         .           .           .           .           .
         •           •           •           •           •
CTT TCA GGG CTT CAA GCG TCT TGG ACT TTA AGA GTT CAT GTT GGA GCA
GAA AGT CCC GAA GTT CGC AGA ACC TGA AAT TCT CAA GTA CAA CCT CGT
 L   S   G   L   Q   A   S   W   T   L   R   V   H   V   G   A>

1010        1020        1030        1040        1050
  .           .           .           .           .
  •           •           •           •           •
ACC CAA GAT GAA GCT ATT GCT GTA AAT ATT TAT GCA GCT AAT GTT GCA
TGG GTT CTA CTT CGA TAA CGA CAT TTA TAA ATA CGT CGA TTA CAA CGT
 T   Q   D   E   A   I   A   V   N   I   Y   A   A   N   V   A>

1060        1070        1080        1090        1100
         .           .           .           .           .
         •           •           •           •           •
AAT CTT TTC TCT GGT GAG GGA GCT CAA ACT GCT CAG GCT GCA CCG GTT
TTA GAA AAG AGA CCA CTC CCT CGA GTT TGA CGA GTC CGA CGT GGC CAA
 N   L   F   S   G   E   G   A   Q   T   A   Q   A   A   P   V>

1110        1120        1130        1140        1150
         .           .           .           .           .
         •           •           •           •           •
CAA GAG GGT GTT CAA CAG GAA GGA GCT CAA CAG CCA GCA CCT GCT ACA
GTT CTC CCA CAA GTT GTC CTT CCT CGA GTT GTC GGT CGT GGA CGA TGT
 Q   E   G   V   Q   Q   E   G   A   Q   Q   P   A   P   A   T>
```

FIG. 33C

```
            1160           1170           1180
         *    *         *    *         *    *
        GCA CCT TCT CAA GGC GGA GTT GGT CAC C
        CGT GGA AGA GTT CCG CCT CAA CCA GTG G
         A   P   S   Q   G   G   V   G   H   X>
```

FIG. 33D

```
          10              20              30              40
 *    .    *    .    *    .    *    .    *    .    *    .    *    .    *
GCA  CAA  AAA  GGT  GCT  GAG  TCA  ATT  GGT  TCT  CAA  AAA  GAA  AAT  GAT  CTA
CGT  GTT  TTT  CCA  CGA  CTC  AGT  TAA  CCA  AGA  GTT  TTT  CTT  TTA  CTA  GAT
 A    Q    K    G    A    E    S    I    G    S    Q    K    E    N    D    L>

50              60              70              80              90
 *    .    *    .    *    .    *    .    *    .    *    .    *    .    *    .
AAC  CTT  GAA  GAC  TCT  AGT  AAA  AAA  TCA  CAT  CAA  AAC  GCT  AAA  CAA  GAC
TTG  GAA  CTT  CTG  AGA  TCA  TTT  TTT  AGT  GTA  GTT  TTG  CGA  TTT  GTT  CTG
 N    L    E    D    S    S    K    K    S    H    Q    N    A    K    Q    D>

100             110             120             130             140
 *    .    *    .    *    .    *    .    *    .    *    .    *    .    *
CTT  CCT  GCG  GTG  ACA  GAA  GAC  TCA  GTG  TCT  TTG  TTT  AAT  GGT  AAT  AAA
GAA  GGA  CGC  CAC  TGT  CTT  CTG  AGT  CAC  AGA  AAC  AAA  TTA  CCA  TTA  TTT
 L    P    A    V    T    E    D    S    V    S    L    F    N    G    N    K>

150             160             170             180             190
 *    .    *    .    *    .    *    .    *    .    *    .    *    .    *
ATT  TTT  GTA  AGC  AAA  GAA  AAA  AAT  AGC  TCC  GGC  AAA  TAT  GAT  TTA  AGA
TAA  AAA  CAT  TCG  TTT  CTT  TTT  TTA  TCG  AGG  CCG  TTT  ATA  CTA  AAT  TCT
 I    F    V    S    K    E    K    N    S    S    G    K    Y    D    L    R>

200             210             220             230             240
 *    .    *    .    *    .    *    .    *    .    *    .    *    .    *    .
GCA  ACA  ATT  GAT  CAG  GTT  GAA  CTT  AAA  GGA  ACT  TCC  GAT  AAA  AAC  AAT
CGT  TGT  TAA  CTA  GTC  CAA  CTT  GAA  TTT  CCT  TGA  AGG  CTA  TTT  TTG  TTA
 A    T    I    D    Q    V    E    L    K    G    T    S    D    K    N    N>

250             260             270             280
 *    .    *    .    *    .    *    .    *    .    *    .    *    .    *
GGT  TCT  GGA  ACC  CTT  GAA  GGT  TCA  AAG  CCT  GAC  AAG  AGT  AAA  GTA  AAA
CCA  AGA  CCT  TGG  GAA  CTT  CCA  AGT  TTC  GGA  CTG  TTC  TCA  TTT  CAT  TTT
 G    S    G    T    L    E    G    S    K    P    D    K    S    K    V    K>

290             300             310             320             330
 *    .    *    .    *    .    *    .    *    .    *    .    *    .    *
TTA  ACA  GTT  TCT  GCT  GAT  TTA  AAC  ACA  GTA  ACC  TTA  GAA  GCA  TTT  GAT
AAT  TGT  CAA  AGA  CGA  CTA  AAT  TTG  TGT  CAT  TGG  AAT  CTT  CGT  AAA  CTA
 L    T    V    S    A    D    L    N    T    V    T    L    E    A    F    D>

340             350             360             370             380
 *    .    *    .    *    .    *    .    *    .    *    .    *    .    *
GCC  AGC  AAC  CAA  AAA  ATT  TCA  AGT  AAA  GTT  ACT  AAA  AAA  CAG  GGG  TCA
CGG  TCG  TTG  GTT  TTT  TAA  AGT  TCA  TTT  CAA  TGA  TTT  TTT  GTC  CCC  AGT
 A    S    N    Q    K    I    S    S    K    V    T    K    K    Q    G    S>
```

FIG. 34A

```
       390         400         410         420         430
  *     *     *     *     *     *     *     *     *     *
ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
 I   T   E   E   T   L   K   A   N   K   L   D   S   K   K   L>

440         450         460         470         480
        *     *     *     *     *     *     *     *     *     *
ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
 T   R   S   N   G   T   T   L   E   Y   S   Q   I   T   D   A>

490         500         510         520
        *     *     *     *     *     *     *     *     *
GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
 D   N   A   T   K   A   V   E   T   L   K   N   S   I   K   L>

530         540         550         560         570
  *     *     *     *     *     *     *     *     *     *
GAA GGA AGT CTT GTA GTC GGA AAA ACA ACA GTG GAA ATT AAA GAA GGT
CTT CCT TCA GAA CAT CAG CCT TTT TGT TGT CAC CTT TAA TTT CTT CCA
 E   G   S   L   V   V   G   K   T   T   V   E   I   K   E   G>

580         590         600         610         620
  *     *     *     *     *     *     *     *     *     *
ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
 T   V   T   L   K   R   E   I   E   K   D   G   K   V   K   V>

630         640         650         660         670
  *     *     *     *     *     *     *     *     *     *
TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
 F   L   N   D   T   A   G   S   N   K   K   T   G   K   W   E>

680         690         700         710         720
    *     *     *     *     *     *     *     *     *     *
GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
 D   S   T   S   T   L   T   I   S   A   D   S   K   K   T   K>

730         740         750         760
        *     *     *     *     *     *     *     *     *     *
GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
 D   L   V   F   L   T   D   G   T   I   T   V   Q   Q   Y   N>
```

FIG. 34B

```
       770         780         790         800         810
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
 T   A   G   T   S   L   E   G   S   A   S   E   I   K   N   L>

820         830         840         850         860
TCA GAG CTT AAA AAC GCT TTA AAA GGT CAC CCC ATG GCT CAA TAT AAC
AGT CTC GAA TTT TTG CGA AAT TTT CCA GTG GGG TAC CGA GTT ATA TTG
 S   E   L   K   N   A   L   K   G   H   P   M   A   Q   Y   N>

870         880         890         900         910
CAA ATG CAC ATG TTA TCA AAC AAA TCT GCT TCT CAA AAT GTA AGA ACA
GTT TAC GTG TAC AAT AGT TTG TTT AGA CGA AGA GTT TTA CAT TCT TGT
 Q   M   H   M   L   S   N   K   S   A   S   Q   N   V   R   T>

920         930         940         950         960
GCT GAA GAG CTT GGA ATG CAG CCT GCA AAA ATT AAC ACA CCA GCA TCA
CGA CTT CTC GAA CCT TAC GTC GGA CGT TTT TAA TTG TGT GGT CGT AGT
 A   E   E   L   G   M   Q   P   A   K   I   N   T   P   A   S>

970         980         990        1000
CTT TCA GGG CTT CAA GCG TCT TGG ACT TTA AGA GTT CAT GTT GGA GCA
GAA AGT CCC GAA GTT CGC AGA ACC TGA AAT TCT CAA GTA CAA CCT CGT
 L   S   G   L   Q   A   S   W   T   L   R   V   H   V   G   A>

1010        1020        1030        1040        1050
ACC CAA GAT GAA GCT ATT GCT GTA AAT ATT TAT GCA GCT AAT GTT GCA
TGG GTT CTA CTT CGA TAA CGA CAT TTA TAA ATA CGT CGA TTA CAA CGT
 T   Q   D   E   A   I   A   V   N   I   Y   A   A   N   V   A>

1060        1070        1080        1090        1100
AAT CTT TTC TCT GGT GAG GGA GCT CAA ACT GCT CAG GCT GCA CCG GTT
TTA GAA AAG AGA CCA CTC CCT CGA GTT TGA CGA GTC CGA CGT GGC CAA
 N   L   F   S   G   E   G   A   Q   T   A   Q   A   A   P   V>

1110        1120        1130        1140        1150
CAA GAG GGT GTT CAA CAG GAA GGA GCT CAA CAG CCA GCA CCT GCT ACA
GTT CTC CCA CAA GTT GTC CTT CCT CGA GTT GTC GGT CGT GGA CGA TGT
 Q   E   G   V   Q   Q   E   G   A   Q   Q   P   A   P   A   T>
```

FIG. 34C

```
        1160         1170         1180         1190         1200
    *     *     *     *     *     *     *     *     *     *
   GCA CCT TCT CAA GGC GGA GTT AAT TCT CCT GTT AAT GTT ACA ACT ACA
   CGT GGA AGA GTT CCG CCT CAA TTA AGA GGA CAA TTA CAA TGT TGA TGT
    A   P   S   Q   G   G   V   N   S   P   V   N   V   T   T   T>

1210         1220         1230         1240
      *     *     *     *     *     *     *     *     *
    GTT GAT GCT AAT ACA TCA CTT GCT AAA ATT GAA AAT GCT ATT AGA ATG
    CAA CTA CGA TTA TGT AGT GAA CGA TTT TAA CTT TTA CGA TAA TCT TAC
     V   D   A   N   T   S   L   A   K   I   E   N   A   I   R   M>

1250         1260         1270         1280         1290
    *     *     *     *     *     *     *     *     *     *
   ATA AGT GAT CAA AGG GCA AAT TTA GGT GCT TTC CAA AAT AGA CTT GAA
   TAT TCA CTA GTT TCC CGT TTA AAT CCA CGA AAG GTT TTA TCT GAA CTT
    I   S   D   Q   R   A   N   L   G   A   F   Q   N   R   L   E>

1300         1310         1320         1330         1340
      *     *     *     *     *     *     *     *     *     *
    TCT ATA AAG AAT AGT ACT GAG TAT GCA ATT GAA AAT CTA AAA GCA TCT
    AGA TAT TTC TTA TCA TGA CTC ATA CGT TAA CTT TTA GAT TTT CGT AGA
     S   I   K   N   S   T   E   Y   A   I   E   N   L   K   A   S>

1350         1360
        *     *     *     *
      TAT GCT CAA ATA GGT CAC C
      ATA CGA GTT TAT CCA GTG G
       Y   A   Q   I   G   H   X>
```

FIG. 34D

```
                10              20              30              40
                 *               *               *               *
   GCA CAA AAA GGT GCT GAG TCA ATT GGT TCT CAA AAA GAA AAT GAT CTA
   CGT GTT TTT CCA CGA CTC AGT TAA CCA AGA GTT TTT CTT TTA CTA GAT
    A   Q   K   G   A   E   S   I   G   S   Q   K   E   N   D   L>

50              60              70              80              90
     *               *               *               *               *
   AAC CTT GAA GAC TCT AGT AAA AAA TCA CAT CAA AAC GCT AAA CAA GAC
   TTG GAA CTT CTG AGA TCA TTT TTT AGT GTA GTT TTG CGA TTT GTT CTG
    N   L   E   D   S   S   K   K   S   H   Q   N   A   K   Q   D>

100             110             120             130             140
        *               *               *               *               *
   CTT CCT GCG GTG ACA GAA GAC TCA GTG TCT TTG TTT AAT GGT AAT AAA
   GAA GGA CGC CAC TGT CTT CTG AGT CAC AGA AAC AAA TTA CCA TTA TTT
    L   P   A   V   T   E   D   S   V   S   L   F   N   G   N   K>

150             160             170             180             190
        *               *               *               *               *
   ATT TTT GTA AGC AAA GAA AAA AAT AGC TCC GGC AAA TAT GAT TTA AGA
   TAA AAA CAT TCG TTT CTT TTT TTA TCG AGG CCG TTT ATA CTA AAT TCT
    I   F   V   S   K   E   K   N   S   S   G   K   Y   D   L   R>

200             210             220             230             240
        *               *               *               *               *
   GCA ACA ATT GAT CAG GTT GAA CTT AAA GGA ACT TCC GAT AAA AAC AAT
   CGT TGT TAA CTA GTC CAA CTT GAA TTT CCT TGA AGG CTA TTT TTG TTA
    A   T   I   D   Q   V   E   L   K   G   T   S   D   K   N   N>

250             260             270             280
        *               *               *               *
   GGT TCT GGA ACC CTT GAA GGT TCA AAG CCT GAC AAG AGT AAA GTA AAA
   CCA AGA CCT TGG GAA CTT CCA AGT TTC GGA CTG TTC TCA TTT CAT TTT
    G   S   G   T   L   E   G   S   K   P   D   K   S   K   V   K>

290             300             310             320             330
     *               *               *               *               *
   TTA ACA GTT TCT GCT GAT TTA AAC ACA GTA ACC TTA GAA GCA TTT GAT
   AAT TGT CAA AGA CGA CTA AAT TTG TGT CAT TGG AAT CTT CGT AAA CTA
    L   T   V   S   A   D   L   N   T   V   T   L   E   A   F   D>

340             350             360             370             380
        *               *               *               *               *
   GCC AGC AAC CAA AAA ATT TCA AGT AAA GTT ACT AAA AAA CAG GGG TCA
   CGG TCG TTG GTT TTT TAA AGT TCA TTT CAA TGA TTT TTT GTC CCC AGT
    A   S   N   Q   K   I   S   S   K   V   T   K   K   Q   G   S>
```

FIG. 35A

```
         390           400           410           420           430
          *             *             *             *             *
   *      *      *      *      *      *      *      *      *      *
ATA   ACA   GAG   GAA   ACT   CTC   AAA   GCT   AAT   AAA   TTA   GAC   TCA   AAG   AAA   TTA
TAT   TGT   CTC   CTT   TGA   GAG   TTT   CGA   TTA   TTT   AAT   CTG   AGT   TTC   TTT   AAT
 I     T     E     E     T     L     K     A     N     K     L     D     S     K     K     L>

440           450           460           470           480
                 *             *             *             *             *
   *      *      *      *      *      *      *      *      *      *      *
ACA   AGA   TCA   AAC   GGA   ACT   ACA   CTT   GAA   TAC   TCA   CAA   ATA   ACA   GAT   GCT
TGT   TCT   AGT   TTG   CCT   TGA   TGT   GAA   CTT   ATG   AGT   GTT   TAT   TGT   CTA   CGA
 T     R     S     N     G     T     T     L     E     Y     S     Q     I     T     D     A>

490           500           510           520
                       *             *             *             *
   *      *      *      *      *      *      *      *      *      *
GAC   AAT   GCT   ACA   AAA   GCA   GTA   GAA   ACT   CTA   AAA   AAT   AGC   ATT   AAG   CTT
CTG   TTA   CGA   TGT   TTT   CGT   CAT   CTT   TGA   GAT   TTT   TTA   TCG   TAA   TTC   GAA
 D     N     A     T     K     A     V     E     T     L     K     N     S     I     K     L>

530           540           550           560           570
   *             *             *             *             *
   *      *      *      *      *      *      *      *      *      *
GAA   GGA   AGT   CTT   GTA   GTC   GGA   AAA   ACA   ACA   GTG   GAA   ATT   AAA   GAA   GGT
CTT   CCT   TCA   GAA   CAT   CAG   CCT   TTT   TGT   TGT   CAC   CTT   TAA   TTT   CTT   CCA
 E     G     S     L     V     V     G     K     T     T     V     E     I     K     E     G>

580           590           600           610           620
          *             *             *             *             *
   *      *      *      *      *      *      *      *      *      *
ACT   GTT   ACT   CTA   AAA   AGA   GAA   ATT   GAA   AAA   GAT   GGA   AAA   GTA   AAA   GTC
TGA   CAA   TGA   GAT   TTT   TCT   CTT   TAA   CTT   TTT   CTA   CCT   TTT   CAT   TTT   CAG
 T     V     T     L     K     R     E     I     E     K     D     G     K     V     K     V>

630           640           650           660           670
                 *             *             *             *             *
   *      *      *      *      *      *      *      *      *      *      *
TTT   TTG   AAT   GAC   ACT   GCA   GGT   TCT   AAC   AAA   AAA   ACA   GGT   AAA   TGG   GAA
AAA   AAC   TTA   CTG   TGA   CGT   CCA   AGA   TTG   TTT   TTT   TGT   CCA   TTT   ACC   CTT
 F     L     N     D     T     A     G     S     N     K     K     T     G     K     W     E>

680           690           700           710           720
                       *             *             *             *             *
   *      *      *      *      *      *      *      *      *      *      *
GAC   AGT   ACT   AGC   ACT   TTA   ACA   ATT   AGT   GCT   GAC   AGC   AAA   AAA   ACT   AAA
CTG   TCA   TGA   TCG   TGA   AAT   TGT   TAA   TCA   CGA   CTG   TCG   TTT   TTT   TGA   TTT
 D     S     T     S     T     L     T     I     S     A     D     S     K     K     T     K>

730           740           750           760
                             *             *             *             *
   *      *      *      *      *      *      *      *      *      *      *
GAT   TTG   GTG   TTC   TTA   ACA   GAT   GGT   ACA   ATT   ACA   GTA   CAA   CAA   TAC   AAC
CTA   AAC   CAC   AAG   AAT   TGT   CTA   CCA   TGT   TAA   TGT   CAT   GTT   GTT   ATG   TTG
 D     L     V     F     L     T     D     G     T     I     T     V     Q     Q     Y     N>
```

FIG. 35B

```
      770           780           790           800           810
   .     *      .      *      .      *      .      *      .      *
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
 T   A   G   T   S   L   E   G   S   A   S   E   I   K   N   L>

820           830           840           850           860
   .     *      .      *      .      *      .      *      .      *
TCA GAG CTT AAA AAC GCT TTA AAA GGT CAC CCC ATG GCT TCT CAA AAT
AGT CTC GAA TTT TTG CGA AAT TTT CCA GTG GGG TAC CGA AGA GTT TTA
 S   E   L   K   N   A   L   K   G   H   P   M   A   S   Q   N>

870           880           890           900           910
   .     *      .      *      .      *      .      *      .      *
GTA AGA ACA GCT GAA GAG CTT GGA ATG CAG CCT GCA AAA ATT AAC ACA
CAT TCT TGT CGA CTT CTC GAA CCT TAC GTC GGA CGT TTT TAA TTG TGT
 V   R   T   A   E   E   L   G   M   Q   P   A   K   I   N   T>

920           930           940           950           960
   .     *      .      *      .      *      .      *      .      *
CCA GCA TCA CTT TCA GGG CTT CAA GCG TCT TGG ACT TTA AGA GTT CAT
GGT CGT AGT GAA AGT CCC GAA GTT CGC AGA ACC TGA AAT TCT CAA GTA
 P   A   S   L   S   G   L   Q   A   S   W   T   L   R   V   H>

970           980           990           1000
   .     *      .      *      .      *      .      *      .      *
GTT GGA GCA ACC CAA GAT GAA GCT ATT GCT GTA AAT ATT TAT GCA GCT
CAA CCT CGT TGG GTT CTA CTT CGA TAA CGA CAT TTA TAA ATA CGT CGA
 V   G   A   T   Q   D   E   A   I   A   V   N   I   Y   A   A>

1010          1020          1030          1040          1050
   .     *      .      *      .      *      .      *      .      *
AAT GTT GCA AAT CTT TTC TCT GGT GAG GGA GCT CAA ACT GCT CAG GCT
TTA CAA CGT TTA GAA AAG AGA CCA CTC CCT CGA GTT TGA CGA GTC CGA
 N   V   A   N   L   F   S   G   E   G   A   Q   T   A   Q   A>

1060          1070          1080          1090          1100
   .     *      .      *      .      *      .      *      .      *
GCA CCG GTT CAA GAG GGT GTT CAA CAG GAA GGA GCT CAA CAG CCA GCA
CGT GGC CAA GTT CTC CCA CAA GTT GTC CTT CCT CGA GTT GTC GGT CGT
 A   P   V   Q   E   G   V   Q   Q   E   G   A   Q   Q   P   A>

1110          1120          1130          1140
   .     *      .      *      .      *      .      *
CCT GCT ACA GCA CCT TCT CAA GGC GGA GTT GGT CAC C
GGA CGA TGT CGT GGA AGA GTT CCG CCT CAA CCA GTG G
 P   A   T   A   P   S   Q   G   G   V   G   H   X>
```

FIG. 35C

```
          10              20              30              40
     *    .    *     .    *    .     *    .    *    .
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

50             60              70              80              90
     *    .    *    .     *    .    *    .    *    .    *    .
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

100             110             120             130             140
     *    .    *    .     *    .    *    .    *    .    *    .
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

150             160             170             180             190
     *    .    *    .     *    .    *    .    *    .    *    .
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

200             210             220             230             240
     *    .    *    .     *    .    *    .    *    .    *    .
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

250             260             270             280
     *    .    *    .     *    .    *    .    *    .    *    .
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290             300             310             320             330
     *    .    *    .     *    .    *    .    *    .    *    .
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

340             350             360             370             380
     *    .    *    .     *    .    *    .    *    .    *    .
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

FIG. 36A

```
       390             400           410            420           430
  .     *        .      *      .      *       .      *       .      *
ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
 I   T   E   E   T   L   K   A   N   K   L   D   S   K   K   L>

440          450           460           470          480
       .      *      .     *     .      *       .     *      .     *
ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
 T   R   S   N   G   T   T   L   E   Y   S   Q   I   T   D   A>

490          500           510           520
       .      *      .     *     .      *       .     *       .    *
GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
 D   N   A   T   K   A   V   E   T   L   K   N   S   I   K   L>

530          540          550           560           570
  .    *       .    *       .    *        .     *      .     *
GAA GGA AGT CTT GTA GTC GGA AAA ACA ACA GTG GAA ATT AAA GAA GGT
CTT CCT TCA GAA CAT CAG CCT TTT TGT TGT CAC CTT TAA TTT CTT CCA
 E   G   S   L   V   V   G   K   T   T   V   E   I   K   E   G>

580          590          600           610           620
  .     *      .     *      .     *     .      *      .      *
ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
 T   V   T   L   K   R   E   I   E   K   D   G   K   V   K   V>

630          640          650           660          670
  .     *       .    *      .     *      .     *       .    *
TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
 F   L   N   D   T   A   G   S   N   K   K   T   G   K   W   E>

680          690          700           710          720
  .     *      .     *      .    *      .     *       .     *
GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
 D   S   T   S   T   L   T   I   S   A   D   S   K   K   T   K>

730          740          750           760
  .     *      .     *      .     *      .     *      .     *
GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
 D   L   V   F   L   T   D   G   T   I   T   V   Q   Q   Y   N>
```

FIG. 36B

```
      770         780         790         800         810
       *           *           *           *           *
  ACA GCT GGA ACC AGC CTA GAA GGA TCA GCA AGT GAA ATT AAA AAT CTT
  TGT CGA CCT TGG TCG GAT CTT CCT AGT CGT TCA CTT TAA TTT TTA GAA
   T   A   G   T   S   L   E   G   S   A   S   E   I   K   N   L>

820         830         840         850         860
       *           *           *           *           *
  TCA GAG CTT AAA AAC GCT TTA AAA GGT CAC CCC ATG GCT TCT CAA AAT
  AGT CTC GAA TTT TTG CGA AAT TTT CCA GTG GGG TAC CGA AGA GTT TTA
   S   E   L   K   N   A   L   K   G   H   P   M   A   S   Q   N>

870         880         890         900         910
       *           *           *           *           *
  GTA AGA ACA GCT GAA GAG CTT GGA ATG CAG CCT GCA AAA ATT AAC ACA
  CAT TCT TGT CGA CTT CTC GAA CCT TAC GTC GGA CGT TTT TAA TTG TGT
   V   R   T   A   E   E   L   G   M   Q   P   A   K   I   N   T>

920         930         940         950         960
       *           *           *           *           *
  CCA GCA TCA CTT TCA GGG CTT CAA GCG TCT TGG ACT TTA AGA GTT CAT
  GGT CGT AGT GAA AGT CCC GAA GTT CGC AGA ACC TGA AAT TCT CAA GTA
   P   A   S   L   S   G   L   Q   A   S   W   T   L   R   V   H>

970         980         990        1000
       *           *           *           *
  GTT GGA GCA ACC CAA GAT GAA GCT ATT GCT GTA AAT ATT TAT GCA GCT
  CAA CCT CGT TGG GTT CTA CTT CGA TAA CGA CAT TTA TAA ATA CGT CGA
   V   G   A   T   Q   D   E   A   I   A   V   N   I   Y   A   A>

1010        1020        1030        1040        1050
       *           *           *           *           *
  AAT GTT GCA AAT CTT TTC TCT GGT GAG GGA GCT CAA ACT GCT CAG GCT
  TTA CAA CGT TTA GAA AAG AGA CCA CTC CCT CGA GTT TGA CGA GTC CGA
   N   V   A   N   L   F   S   G   E   G   A   Q   T   A   Q   A>

1060        1070        1080        1090        1100
       *           *           *           *           *
  GCA CCG GTT CAA GAG GGT GTT CAA CAG GAA GGA GCT CAA CAG CCA GCA
  CGT GGC CAA GTT CTC CCA CAA GTT GTC CTT CCT CGA GTT GTC GGT CGT
   A   P   V   Q   E   G   V   Q   Q   E   G   A   Q   Q   P   A>

1110        1120        1130        1140        1150
       *           *           *           *           *
  CCT GCT ACA GCA CCT TCT CAA GGC GGA GTT AAT TCT CCT GTT AAT GTT
  GGA CGA TGT CGT GGA AGA GTT CCG CCT CAA TTA AGA GGA CAA TTA CAA
   P   A   T   A   P   S   Q   G   G   V   N   S   P   V   N   V>
```

FIG. 36C

```
         1160           1170           1180           1190           1200
           *              *              *              *              *
      ACA ACT ACA GTT GAT GCT AAT ACA TCA CTT GCT AAA ATT GAA AAT GCT
      TGT TGA TGT CAA CTA CGA TTA TGT AGT GAA CGA TTT TAA CTT TTA CGA
       T   T   T   V   D   A   N   T   S   L   A   K   I   E   N   A>

1210           1220           1230           1240
              *              *              *              *
      ATT AGA ATG ATA AGT GAT CAA AGG GCA AAT TTA GGT GCT TTC CAA AAT
      TAA TCT TAC TAT TCA CTA GTT TCC CGT TTA AAT CCA CGA AAG GTT TTA
       I   R   M   I   S   D   Q   R   A   N   L   G   A   F   Q   N>

1250           1260           1270           1280           1290
    *              *              *              *              *
  AGA CTT GAA TCT ATA AAG AAT AGT ACT GAG TAT GCA ATT GAA AAT CTA
  TCT GAA CTT AGA TAT TTC TTA TCA TGA CTC ATA CGT TAA CTT TTA GAT
   R   L   E   S   I   K   N   S   T   E   Y   A   I   E   N   L>

1300           1310           1320
        *              *              *
      AAA GCA TCT TAT GCT CAA ATA GGT CAC C
      TTT CGT AGA ATA CGA GTT TAT CCA GTG G
       K   A   S   Y   A   Q   I   G   H   X>
```

FIG. 36D

```
              10              20              30              40
               *               *               *               *
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

50              60              70              80              90
        *               *               *               *               *
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

100             110             120             130             140
        *               *               *               *               *
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

150             160             170             180             190
        *               *               *               *               *
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

200             210             220             230             240
        *               *               *               *               *
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

250             260             270             285
        *               *               *               *
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290             300             310             320             330
        *               *               *               *               *
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

340             350             360             370             380
        *               *               *               *               *
GCC AGC AAC CAA AAA ATT TCA AGT AAA GTT ACT AAA AAG CAG GGG TCA
CGG TCG TTG GTT TTT TAA AGT TCA TTT CAA TGA TTT TTC GTC CCC AGT
 A   S   N   Q   K   I   S   S   K   V   T   K   K   Q   G   S>
```

FIG. 37A

```
        390             400             410             420             430
 *       *       *       *       *       *       *       *       *       *
ATA     ACA     GAG     GAA     ACT     CTC     AAA     GCT     AAT     AAA     TTA     GAC     TCA     AAG     AAA     TTA
TAT     TGT     CTC     CTT     TGA     GAG     TTT     CGA     TTA     TTT     AAT     CTG     AGT     TTC     TTT     AAT
 I       T       E       E       T       L       K       A       N       K       L       D       S       K       K       L>

440             450             460             470             480
 *       *       *       *       *       *       *       *       *       *
ACA     AGA     TCA     AAC     GGA     ACT     ACA     CTT     GAA     TAC     TCA     CAA     ATA     ACA     GAT     GCT
TGT     TCT     AGT     TTG     CCT     TGA     TGT     GAA     CTT     ATG     AGT     GTT     TAT     TGT     CTA     CGA
 T       R       S       N       G       T       T       L       E       Y       S       Q       I       T       D       A>

490             500             510             520
 *       *       *       *       *       *       *       *
GAC     AAT     GCT     ACA     AAA     GCA     GTA     GAA     ACT     CTA     AAA     AAT     AGC     ATT     AAG     CTT
CTG     TTA     CGA     TGT     TTT     CGT     CAT     CTT     TGA     GAT     TTT     TTA     TCG     TAA     TTC     GAA
 D       N       A       T       K       A       V       E       T       L       K       N       S       I       K       L>

530             540             550             560             570
 *       *       *       *       *       *       *       *       *       *
GAA     GGA     AGT     CTT     GTA     GTC     GGA     AAA     ACA     ACA     GTG     GAA     ATT     AAA     GAA     GGT
CTT     CCT     TCA     GAA     CAT     CAG     CCT     TTT     TGT     TGT     CAC     CTT     TAA     TTT     CTT     CCA
 E       G       S       L       V       V       G       K       T       T       V       E       I       K       E       G>

580             590             600             610             620
 *       *       *       *       *       *       *       *       *       *
ACT     GTT     ACT     CTA     AAA     AGA     GAA     ATT     GAA     AAA     GAT     GGA     AAA     GTA     AAA     GTC
TGA     CAA     TGA     GAT     TTT     TCT     CTT     TAA     CTT     TTT     CTA     CCT     TTT     CAT     TTT     CAG
 T       V       T       L       K       R       E       I       E       K       D       G       K       V       K       V>

630             640             650             660             670
 *       *       *       *       *       *       *       *       *       *
TTT     TTG     AAT     GAC     ACT     GCA     GGT     TCT     AAC     AAA     AAA     ACA     GGT     AAA     TGG     GAA
AAA     AAC     TTA     CTG     TGA     CGT     CCA     AGA     TTG     TTT     TTT     TGT     CCA     TTT     ACC     CTT
 F       L       N       D       T       A       G       S       N       K       K       T       G       K       W       E>

680             690             700             710             720
 *       *       *       *       *       *       *       *       *       *
GAC     AGT     ACT     AGC     ACT     TTA     ACA     ATT     AGT     GCT     GAC     AGC     AAA     AAA     ACT     AAA
CTG     TCA     TGA     TCG     TGA     AAT     TGT     TAA     TCA     CGA     CTG     TCG     TTT     TTT     TGA     TTT
 D       S       T       S       T       L       T       I       S       A       D       S       K       K       T       K>

730             740             750             760
 *       *       *       *       *       *       *       *       *
GAT     TTG     GTG     TTC     TTA     ACA     GAT     GGT     ACA     ATT     ACA     GTA     CAA     CAA     TAC     AAC
CTA     AAC     CAC     AAG     AAT     TGT     CTA     CCA     TGT     TAA     TGT     CAT     GTT     GTT     ATG     TTG
 D       L       V       F       L       T       D       G       T       I       T       V       Q       Q       Y       N>
```

FIG. 37B

```
       770         780         790         800         810
        •           •           •           •           •
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
 T   A   G   T   S   L   E   G   S   A   S   E   I   K   N   L>

820         830         840         850         860
        •           •           •           •           •
TCA GAG CTT AAA AAC GCT TTA AAA GGT CAC CCC ATG GGA AAT AAT TCA
AGT CTC GAA TTT TTG CGA AAT TTT CCA GTG GGG TAC CCT TTA TTA AGT
 S   E   L   K   N   A   L   K   G   H   P   M   G   N   N   S>

870         880         890         900         910
        •           •           •           •           •
GGG AAA GAT GGG AAT ACA TCT GCA AAT TCT GCT GAT GAG TCT GTT AAA
CCC TTT CTA CCC TTA TGT AGA CGT TTA AGA CGA CTA CTC AGA CAA TTT
 G   K   D   G   N   T   S   A   N   S   A   D   E   S   V   K>

920         930         940         950         960
        •           •           •           •           •
GGG CCT AAT CTT ACA GAA ATA AGT AAA AAA ATT ACG GAT TCT AAT GCG
CCC GGA TTA GAA TGT CTT TAT TCA TTT TTT TAA TGC CTA AGA TTA CGC
 G   P   N   L   T   E   I   S   K   K   I   T   D   S   N   A>

970         980         990         1000
        •           •           •           •
GTT TTA CTT GCT GTG AAA GAG GTT GAA GCG TTG CTG TCA TCT ATA GAT
CAA AAT GAA CGA CAC TTT CTC CAA CTT CGC AAC GAC AGT AGA TAT CTA
 V   L   L   A   V   K   E   V   E   A   L   L   S   S   I   D>

1010        1020        1030        1040        1050
 •           •           •           •           •
GAA ATT GCT GCT AAA GCT ATT GGT AAA AAA ATA CAC CAA AAT AAT GGT
CTT TAA CGA CGA TTT CGA TAA CCA TTT TTT TAT GTG GTT TTA TTA CCA
 E   I   A   A   K   A   I   G   K   K   I   H   Q   N   N   G>

1060        1070        1080        1090        1100
        •           •           •           •           •
TTG GAT ACC GAA TAT AAT CAC AAT GGA TCA TTG TTA GCG GGA CGT TAT
AAC CTA TGG CTT ATA TTA GTG TTA CCT AGT AAC AAT CGC CCT GCA ATA
 L   D   T   E   Y   N   H   N   G   S   L   L   A   G   R   Y>

1110        1120        1130        1140        1150
        •           •           •           •           •
GCA ATA TCA ACC CTA ATA AAA CAA AAA TTA GAT GGA TTG AAA AAT GAA
CGT TAT AGT TGG GAT TAT TTT GTT TTT AAT CTA CCT AAC TTT TTA CTT
 A   I   S   T   L   I   K   Q   K   L   D   G   L   K   N   E>
```

FIG. 37C

```
         1160            1170            1180            1190            1200
    *      *      *      *      *      *      *      *      *      *      *
   GGA    TTA    AAG    GAA    AAA    ATT    GAT    GCG    GCT    AAG    AAA    TGT    TCT    GAA    ACA    TTT
   CCT    AAT    TTC    CTT    TTT    TAA    CTA    CGC    CGA    TTC    TTT    ACA    AGA    CTT    TGT    AAA
    G      L      K      E      K      I      D      A      A      K      K      C      S      E      T      F>

1210            1220            1230            1240
     *      *      *      *      *      *      *      *      *
    ACT    AAT    AAA    TTA    AAA    GAA    AAA    CAC    ACA    GAT    CTT    GGT    AAA    GAA    GGT    GTT
    TGA    TTA    TTT    AAT    TTT    CTT    TTT    GTG    TGT    CTA    GAA    CCA    TTT    CTT    CCA    CAA
     T      N      K      L      E      K      H      T      D      L      G      K      E      G      V>

1250            1260            1270            1280            1290
    *      *      *      *      *      *      *      *      *      *      *
   ACT    GAT    GCT    GAT    GCA    AAA    GAA    GCC    ATT    TTA    AAA    ACA    AAT    GGT    ACT    AAA
   TGA    CTA    CGA    CTA    CGT    TTT    CTT    CGG    TAA    AAT    TTT    TGT    TTA    CCA    TGA    TTT
    T      D      A      D      A      K      E      A      I      L      K      T      N      G      T      K>

1300            1310            1320            1330            1340
    *      *      *      *      *      *      *      *      *      *      *
   ACT    AAA    GGT    GCT    GAA    GAA    CTT    GGA    AAA    TTA    TTT    GAA    TCA    GTA    GAG    GTC
   TGA    TTT    CCA    CGA    CTT    CTT    GAA    CCT    TTT    AAT    AAA    CTT    AGT    CAT    CTC    CAG
    T      K      G      A      E      E      L      G      K      L      F      E      S      V      E      V>

1350            1360            1370            1380            1390
     *      *      *      *      *      *      *      *      *      *      *
    TTG    TCA    AAA    GCA    GCT    AAA    GAG    ATG    CTT    GCT    AAT    TCA    GTT    AAA    GAG    CTT
    AAC    AGT    TTT    CGT    CGA    TTT    CTC    TAC    GAA    CGA    TTA    AGT    CAA    TTT    CTC    GAA
     L      S      K      A      A      K      E      M      L      A      N      S      V      K      E      L>

1400            1410            1420            1430            1440
     *      *      *      *      *      *      *      *      *      *      *
    ACA    AGC    CCT    GTT    GTG    GCA    GAA    AGT    CCA    AAA    AAA    CCT    GGT    ACC    ATG    GCT
    TGT    TCG    GGA    CAA    CAC    CGT    CTT    TCA    GGT    TTT    TTT    GGA    CCA    TGG    TAC    CGA
     T      S      P      V      V      A      E      S      P      K      K      P      G      T      M      A>

1450            1460            1470            1480
     *      *      *      *      *      *      *      *      *
    CAA    TAT    AAC    CAA    ATG    CAC    ATG    TTA    TCA    AAC    AAA    TCT    GCT    TCT    CAA    AAT
    GTT    ATA    TTG    GTT    TAC    GTG    TAC    AAT    AGT    TTG    TTT    AGA    CGA    AGA    GTT    TTA
     Q      Y      N      Q      M      H      M      L      S      N      K      S      A      S      Q      N>

1490            1500            1510            1520            1530
    *      *      *      *      *      *      *      *      *      *      *
   GTA    AGA    ACA    GCT    GAA    GAG    CTT    GGA    ATG    CAG    CCT    GCA    AAA    ATT    AAC    ACA
   CAT    TCT    TGT    CGA    CTT    CTC    GAA    CCT    TAC    GTC    GGA    CGT    TTT    TAA    TTG    TGT
    V      R      T      A      E      E      L      G      M      Q      P      A      K      I      N      T>
```

FIG. 37D

```
             1540          1550          1560          1570          1580
               *      *      *      *      *      *      *      *      *
             CCA GCA TCA CTT TCA GGG CTT CAA GCG TCT TGG ACT TTA AGA GTT CAT
             GGT CGT AGT GAA AGT CCC GAA GTT CGC AGA ACC TGA AAT TCT CAA GTA
              P   A   S   L   S   G   L   Q   A   S   W   T   L   R   V   H>

1590          1600          1610          1620          1630
               *      *      *      *      *      *      *      *      *      *
             GTT GGA GCA ACC CAA GAT GAA GCT ATT GCT GTA AAT ATT TAT GCA GCT
             CAA CCT CGT TGG GTT CTA CTT CGA TAA CGA CAT TTA TAA ATA CGT CGA
              V   G   A   T   Q   D   E   A   I   A   V   N   I   Y   A   A>

1640          1650          1660          1670          1680
               *      *      *      *      *      *      *      *      *      *
             AAT GTT GCA AAT CTT TTC TCT GGT GAG GGA GCT CAA ACT GCT CAG GCT
             TTA CAA CGT TTA GAA AAG AGA CCA CTC CCT CGA GTT TGA CGA GTC CGA
              N   V   A   N   L   F   S   G   E   G   A   Q   T   A   Q   A>

1690          1700          1710          1720
               *      *      *      *      *      *      *      *      *
             GCA CCG GTT CAA GAG GGT GTT CAA CAG GAA GGA GCT CAA CAG CCA GCA
             CGT GGC CAA GTT CTC CCA CAA GTT GTC CTT CCT CGA GTT GTC GGT CGT
              A   P   V   Q   E   G   V   Q   Q   E   G   A   Q   Q   P   A>

1730          1740          1750          1760
         *      *      *      *      *      *      *      *
       CCT GCT ACA GCA CCT TCT CAA GGC GGA GTT GGT CAC C
       GGA CGA TGT CGT GGA AGA GTT CCG CCT CAA CCA GTG G
        P   A   T   A   P   S   Q   G   G   V   G   H   X>
```

FIG. 37E

```
               10          20          30          40
                *     *    *      *    *     *    *     *
OspC-B31    ATG AAA AAG AAT ACA TTA AGT GCG ATA TTA ATG ACT TTA TTT TTA TTT
            TAC TTT TTC TTA TGT AAT TCA CGC TAT AAT TAC TGA AAT AAA AAT AAA

1. OspC-PK            10          20          30          40
 [ 1832 ]   ... ... ... ... ... ... ... ... ... ... ... ... ... ... ... ...>

2. OspC-TR            10          20          30          40
 [ 1786 ]   ... ... ... ... ... ... ... ... ... ... ... ... ... ... ... ...>

3. OspC-K4            10          20          30          40
 [ 1774 ]   ... ... ... ... ... ... ... ... ... ... ... ... ... ... ... ...>

50          60          70          80          90
                *     *    *      *    *     *    *     *    *     *
OspC-B31    ATA TCT TGT AAT AAT TCA GGG AAA GAT GGG AAT ACA TCT GCA AAT TCT
            TAT AGA ACA TTA TTA AGT CCC TTT CTA CCC TTA TGT AGA CGT TTA AGA
                                                      tgc
                                                       |
 1. OspC-PK50          60          70          80  |   90
 [ 1832 ]   ... ... ... ... .g. ... ... ... .g. ... g.. t.. ... a.t ... c..>

2. OspC-TR50          60          70          80          90
 [ 1786 ]   ... ... ... ... ... ... ..t ggg ... --- td. g.. ... a.t ..- ..->

3. OspC-K450          60          70          80          90
 [ 1774 ]   ... ... ... ... ... ... ..t ggg ... --- .cc g.. ... a.t ..- ..->

100         110         120         130         140
                *     *    *      *    *     *    *     *    *
OspC-B31    GCT GAT GAG TCT GTT AAA GGG CCT AAT CTT ACA GAA ATA AGT AAA AAA
            CGA CTA CTC AGA CAA TTT CCC GGA TTA GAA TGT CTT TAT TCA TTT TTT

1. OspC-100           110         120         130         140
 [ 1832 ]   ... ..c ... ... .cg ... ... ... ... ... ... ... ..c ... ...>

2. OspC-TR            100         110         120         130
 [ 1786 ]   -.. ... ... ... .ca ... ..a ... ... ... ..c .t. ... ..c ... ...>

3. OspC-K4            100         110         120         130
 [ 1774 ]   -.. ... ... ... .ca ... ..a ... ... ... .t. ... ..c ... ...>
```

FIG. 38A

```
                    150         160         170         180         190
                *    *       *    *       *    *       *    *       *    *
OspC-B31     ATT ACG GAT TCT AAT GCG GTT TTA CTT GCT GTG AAA GAG GTT GAA GCG
             TAA TGC CTA AGA TTA CGC CAA AAT GAA CGA CAC TTT CTC CAA CTT CGC

1. OspC-PK 150         160         170         180         190
  [ 1832 ]      ..a ... ... ... ..a t.. g.. ... ... ..t ... ..a ... ..g a.t>

2. OspC-T 140         150         160         170         180
  [ 1786 ]      ..a ... ... ... ..a t.. ... ..g ... ... ... ..a ... ..g ..t>

3. OspC-K 140         150         160         170         180
  [ 1774 ]      ..a ... ... ... ..a t.. g.. ..g ... ... ... ..a ... ..g ..t>

200         210         220         230         240
                *    *       *    *       *    *       *    *       *    *
OspC-B31     TTG CTG TCA TCT ATA GAT GAA ATT GCT GCT AAA GCT ATT GGT AAA AAA
             AAC GAC AGT AGA TAT CTA CTT TAA CGA CGA TTT CGA TAA CCA TTT TTT

1. OspC-PK 200         210         220         230         240
  [ 1832 ]      g.t .t. ... ... ... ... c.. ... aag ... ... ... ... c.. ...>

2. OspC-TR 190         200         210         220         230
  [ 1786 ]      ... ..t ... ... ... ... c.. --. -.. ... ... ... ... ... ...>

3. OspC-K4 190         200         210         220         230
  [ 1774 ]      a.c ... ... ... ... ... c.. ... aa. ... ... ... ... ... gt.>

250         260         270         280
                *    *       *    *       *    *       *    *       *
OspC-B31     ATA CAC CAA AAT AAT GGT TTG GAT ACC GAA TAT AAT CAC AAT GGA TCA
             TAT GTG GTT TTA TTA CCA AAC CTA TGG CTT ATA TTA GTG TTA CCT AGT

1. OspC-PK 250         260         270         280         290
  [ 1832 ]      g.. a.t ... ... ... ..a .c. g.t tt. a.. ... ..g ... ... ..g> tac
                           |
  2. OspC-TR 240         |250         260         270
  [ 1786 ]      ... -.- -.. ... g.. ... ... a ... .a. ... gca ... .ga ..c .a. ...>

3. OspC-K4 240         250         260         270         280
  [ 1774 ]      ... ..t ... ... ... ... ..a a.. g.t a.t gcg gg. ..a ..c ... ...>

290         300         310         320         330
                *    *       *    *       *    *       *    *       *    *
OspC-B31     TTG TTA GCG GGA CGT TAT GCA ATA TCA ACC CTA ATA AAA CAA AAA TTA
             AAC AAT CGC CCT GCA ATA CGT TAT AGT TGG GAT TAT TTT GTT TTT AAT

1. OspC-PK 300         310         320         330
  [ 1832 ]      ... ... ..a ... gcc ... ... ... ... ... ... ... .c. g.. ... ..g>

2. OspC-280 290         300         310         320
  [ 1786 ]      ... a.. ..a ... gc. ... .a. ... ... .aa ... ... .c. ... ... ...>
```

FIG. 38B

```
3. OspC-K4        290         300         310         320         330
[ 1774 ]         ... ... ..a ... gcc ... ... ... ... ... ... .c. g.. ... ...>

340           350           360           370           380
               *             *             *             *             *
OspC-B31    GAT GGA TTG AAA AAT GAA GGA TTA AAG GAA AAA ATT GAT GCG GCT AAG
            CTA CCT AAC TTT TTA CTT CCT AAT TTC CTT TTT TAA CTA CGC CGA TTC ttt
                        |
1. OspC-340       350   | 360          370           380           390
[ 1832 ]     ag. aa. ... ... ..a ... .a. ... ... ac. g.. ... .ca aa. ... ...>

2. OspC-TR330         340           350           360           370
[ 1786 ]     ag. .t. ... ..t tca ... .a. ... ... a.. ... ... a.a .a. ... ...> ttc
                        |
3. OspC-K4        340   | 350          360           370           380
[ 1774 ]     ag. aa. ... ... ..a ... .ag ... ..t a.. ... ... ..a .a. ... ...>

390           400           410           420           430
               *             *             *             *             *
OspC-B31    AAA TGT TCT GAA ACA TTT ACT AAT AAA TTA AAA GAA AAA CAC ACA GAT
            TTT ACA AGA CTT TGT AAA TGA TTA TTT AAT TTT CTT TTT GTG TGT CTA

1. OspC-PK        400           410           420           430
[ 1832 ]    ... ... ..c ... ga. ... ... ... ... c.. ... agt ggt ..t g.. ...>

2. OspC-TR    380           390           400           410           420
[ 1786 ]    g.t ... ..c ... .a. ... ... .c. ...g c.. ... ..t .gt ..t g.. ..g>

3. OspC-K4        390           400           410           420
[ 1774 ]    ..c ca. ... ... g.. ... ... ... .g. c.. ... .gt tct ..t g.. c.a>

440           450           460           470           480
                   *             *             *             *             *
OspC-B31        CTT GGT AAA GAA GGT GTT ACT GAT GCT GAT GCA AAA GAA GCC ATT TTA
                GAA CCA TTT CTT CCA CAA TGA CTA CGA CTA CGT TTT CTT CGG TAA AAT

1. OspC-P440          450           460           470           480
[ 1832 ]        ... ..c ... c.g .a. .c. ..c ... .a. c.. ... ... .c. ..t ... ...>

2. OspC-TR        430           440           450           460           470
[ 1786 ]        ... ... .t. c.. a.c ... cag ... .a. a.. ... ... a.. ..t ... ...>

3. OspC-430           440           450           460           470
[ 1774 ]        ... ..a gtt .ct .c. .c. ... ... .a. c.. ... ... ... ..t ... ...>
```

FIG. 38C

```
                  490         500         510         520
                   *           *           *           *
OspC-B31    AAA ACA AAT GGT ACT AAA ACT AAA GGT GCT GAA GAA CTT GGA AAA TTA
            TTT TGT TTA CCA TGA TTT TGA TTT CCA CGA CTT CTT GAA CCT TTT AAT

1. OspC-PK   490         500         510         520         530
 [ 1832 ]    ... ... c.. .ca ... .cc ga. ... ... ... a.. ... t.. aa. g.t ...>

2. OspC-TR       480         490         500         510
 [ 1786 ]    ... ... c.. ..a ... ... gac ..g ... ... a.. ... ... .a. g.g ...>

3. OspC-K4 480         490         500         510         520
 [ 1774 ]    ..g t.. ... cc. ... ... ga. ..g ... ... a.. .c. ... aa. g.c ...>

530         540         550         560         570
             *           *           *           *           *
OspC-B31    TTT GAA TCA GTA GAG GTC TTG TCA AAA GCA GCT AAA GAG ATG CTT GCT
            AAA CTT AGT CAT CTC CAG AAC AGT TTT CGT CGA TTT CTC TAC GAA CGA

1. OspC-PK   540         550         560         570         580
 [ 1832 ]    ... ... ... ... ..a .gt ... .t. ... ... ... c.. .ta gca ..a a..>

2. OspC-520       530         540         550         560
 [ 1786 ]    ... a.. ... c.. ..a ag. ... ... ... ... ..g c.. .ca gca t.a a..>

3. OspC-K4 530         540         550         560         570
 [ 1774 ]    .c. ... ... ... ..a ag. ... g.. ... ... ..g c.. ..a gca t.a ...>

580         590         600         610         620
             *           *           *           *           *
OspC-B31    AAT TCA GTT AAA GAG CTT ACA AGC CCT GTT GTG GCA GAA AGT CCA AAA
            TTA AGT CAA TTT CTC GAA TGT TCG GGA CAA CAC CGT CTT TCA GGT TTT

1. OspC-PK       590         600         610         620         630
 [ 1832 ]    ... ... ... ... ..a ... ... ..t ... ... ..a ... ... ... ... ...>

2. OspC-TR 570       580         590         600         610
 [ 1786 ]    ... ... ... ... ... ... ... .at ... ... ... ... ... ... ... ...>

3. OspC-K4       580         590         600         610         620
 [ 1774 ]    ... ... ... ... ..a ... ... .at ... ... ... ... ... ... ... ...>

630
             *
OspC-B31    AAA CCT TAA
            TTT GGA ATT

1. OspC-PK
 [ 1832 ]    ... ... ...>

2. OspC-TR  520
 [ 1786 ]    ... ... ...>

3. OspC-K4       630
 [ 1774 ]    ... ... ...>
```

FIG. 38D

```
                        10          20          30          40
                    *        *        *        *        *        *
BO ospD     CTA CTG TTA AGT TTA TTT TTA TTG CTC TCA ATA TCT TGT TCT TTA GAT
            GAT GAC AAT TCA AAT AAA AAT AAC GAG AGT TAT AGA ACA AGA AAT CTA 1. P-Gau o         10          20          30          40
  [ 2804 ]   ... ... ... ... ... ... ... ... ... ... ... ... .a. ... ...>

2. DK29 os         10          20          30          40
  [ 2786 ]   ... ...c.. ... ... ... ... ... ... ... ... .g.. ... ... ...>

3. K48 osp         10          20          30          40
  [ 2786 ]   ... ... ... ... ... ... ... ... ... ... ... ... ... ... ...>

50          60          70          80          90
            *        *        *        *        *        *        *
BO ospD     AAT GAA GGT GTA AAC TCA AAA GAT TAC GAG TCA AAA AAA CAG AGT ATA
            TTA CTT CCA CAT TTG AGT TTT CTA ATG CTC AGT TTT TTT GTC TCA TAT 1. P-Gau o50         60          70          80          90
  [ 2804 ]   ... ... ... ... ... ... ... ... ... ... ... ... ... ... ...>

2. DK29 os50        60          70          80          90
  [ 2786 ]   ... ... ... ... ... ... ... ... ... ... ... ... ... ... ...>

3. K48 osp50        60          70          80          90
  [ 2786 ]   ... ... ... ... .g.. ... ... ... ... ... ... ... ... ... ...>

100         110         120         130         140
            *        *        *        *        *        *        *
BO ospD     CTA GGT GAA TTA AAT CAG CTA TTG GGG CAA ACT ACA AAT TCA CTA AAA
            GAT CCA CTT AAT TTA GTC GAT AAC CCC GTT TGA TGT TTA AGT GAT TTT 1. P-Gau o 100       110         120         130         140
  [ 2804 ]   ... ... ... ... ... ... ... ... ... ... ... ... ... ... ...>

2. DK29 os 100       110         120         130         140
  [ 2786 ]   ... ... ... ... ... ... ... ... ... ... ... ... ... ... ...>

3. K48 csp 100       110         120         130         140
  [ 2786 ]   ... ... ... ... ... ... ... ... ... ... ... ... ... ... ...>

```
                    *       *       *       *       *       *       *       *       *       *
BO ospD         GAA GCA AAA AAT ACA ACA GAT AAT TTA AAT GCA TCA AAT GAG GCA AAT
                CTT CGT TTT TTA TGT TGT CTA TTA AAT TTA CGT AGT TTA CTC CGT TTA 1. P-Gau o       150             160             170             180             190
    [ 2804 ]      ... ... ... ... ... ... ... ... ... ... ... ... ... ... ... ...>

2. DK29 os       150             160             170             180             190
    [ 2786 ]      ... ... ... ... ... ... ... ... ... ... ... ... ... ... ... ...>

3. K48 osp       150             160             170             180             190
    [ 2786 ]      ... ... ... ... ... ... ... ... ... ... ... ... ... ... ... ...>

200             210             220             230             240
                    *       *       *       *       *       *       *       *       *       *
BO ospD         AAA GTT GTA GAA GCA GTT ATA AGT GTG GTT AAT TTA ATT TCA TCT GCT
                TTT CAA CAT CTT CGT CAA TAT TCA CAC CAA TTA AAT TAA AGT AGA CGA 1. P-Gau o       200             210             220             230             240
    [ 2804 ]      ... ... ... ... ... ... ... ... ... ... ... ... ... ... ... ...>

2

```
              340         350         360         370         380
               *     *     *     *     *     *     *     *     *
BO ospD    TAG TTG CGG CTA ATG TTG CGA AAG AAG CAT ATA ACC TTA CTA AAG CAG
           ATC AAC GCC GAT TAC AAC GCT TTC TTC GTA TAT TGG AAT GAT TTC GTC 1. P-Gau o  340        350         360         370         380
  [ 2804 ]   ... ... ... ... ... ... ... ... ... ... ... ... ... ... ... ...>

2. DK29 os  340        350         360         370         380
  [ 2786 ]   ... ... ... ... ... ... ... ... ... ... ... ... ... ... ... ...>

3. K48 osp  340        350         360         370         380
  [ 2786 ]   ... ... ... ... ... ... ... ... ... ... ... ... ... ... ... ...>

390         400         410         420         430
               *     *     *     *     *     *     *     *     *
BO ospD    TAG AAC AAA ATA TGC AAA AAC TGT ACA AAG AGC AAG AAG AGC AAC TAA
           ATC TTG TTT TAT ACG TTT TTG ACA TGT TTC TCG TTC TTC TCG TTG ATT 1. P-Gau o  390        400         410         420         430
  [ 2804 ]   ... ... ... ... ... ... ... ... ... ... ... ... ... ... ... ...>

2. DK29 os  390        400         410         420         430
  [ 2786 ]   ... ... ... ... ... ... ... ... ... ... ... ... ... ... ... ...>

3. K48 osp  390        400         410         420         430
  [ 2786 ]   ... ... ... ... ... ... ... ... ... ... ... ... ... ... ... ...>

440         450         460         470         480
               *     *     *     *     *     *     *     *     *
BO ospD    AAC ACT ATC TGA TTC TGA TGA AAC AGA ACG AGT TTC TGA TGA AAT AAA
           TTG TGA TAG ACT AAG ACT ACT TTG TCT TGC TCA AAG ACT ACT TTA TTT 1. P-Gau o  440        450         460         470         480
  [ 2804 ]   ... ... ... ... ... ... ... ... ... ... ... ... ... ... ... ...>

2. DK29 os  440        450         460         470         480
  [ 2786 ]   ... ... ... ... .g. ... ... ... ... ... ... ... ... ... ... ...>

3. K48 osp  440        450         460         470         480
  [ 2786 ]   ... ... ... ... .g. ... ... ... ... ... ... ... ... ... ... ...>

490         500         510         520
               *     *     *     *     *     *     *     *     *
BO ospD    ACA AGC TAA AGA GGC TGT AGA AAT AGC TTG GAA AGC CAC AGT AAA AGT
           TGT TCG ATT TCT CCG ACA TCT TTA TCG AAC CTT TCG GTG TCA TTT TCA 1. P-Gau o  490        500         510         520
  [ 2804 ]   ... ... ... ... ... ... ... ... ... ... ... ... ... ... ... ...>

2. DK29 os  490        500         510         520
  [ 2786 ]   ... ... ... ... ... ... ... ... ... ... ... ... ... ... ... ...>

3. K48 osp  490        500         510         520
```

FIG. 39C

```
              530         540         550         560         570
               *           *           *           *           *
BO ospD   AAA AGA TGA GTT AAT TGA TGT AGA AAA TGC AGT CAA AGA GGC ATT GGA
          TTT TCT ACT CAA TTA ACT ACA TCT TTT ACG TCA GTT TCT CCG TAA CCT 1. P-Gau 530         540         550         560         570
  [ 2804 ]  ... ... ... ... ... ... ... ... ... ... ... ... ... ... ...>

2. DK29 o530         540         550         560         570
  [ 2786 ]  ... ... ... ... ... ... ... ... ... ... ... ... ... ... ...>

3. K48 os 530        540         550         560         570
  [ 2786 ]  ... ... ... ... ... ... ... ... ... ... ... ... ... ... ...>

580         590         600         610         620
               *           *           *           *           *
BO ospD   TAA AAT AAA GAC AGA AAC CGC GAA CAA TAC AAA ACT TAC AGA TAT AGA
          ATT TTA TTT CTG TCT TTG GCG CTT GTT ATG TTT TGA ATG TCT ATA TCT 1. P-Gau o 580       590         600         610         620
  [ 2804 ]  ... ... ... ... ... ... ... ... ... ... ... ... ... ... ...>

2. DK29 os 580       590         600         610         620
  [ 2786 ]  ... ... ... ... ... ... ... ... ... ... ... ... ... ... ...>

3. K48 osp 580       590         600         610         620
  [ 2786 ]  ... ... ... ... ..g ... ... ... ... ... ... ... ... ... ...>

630         640         650         660         670
               *           *           *           *           *
BO ospD   AGA AGT AGC AGA GTT AGT ATT ACA GAT AGC CAA AAA TGT AGC GGA AAT
          TCT TCA TCG TCT CAA TCA TAA TGT CTA TCG GTT TTT ACA TCG CCT TTA 1. P-Gau o 630       640         650         660         670
  [ 2804 ]  ... ... ... ... ... ... ... ... a.. ... ... ... ... ... ...>

2. DK29 os 630       640         650         660         670
  [ 2786 ]  ... ... ... ... ... ... ... ... a.. ... ... ... - ... ...>

3. K48 osp 630       640         650         660         670
  [ 2786 ]  ... ... ... ... ... ... ... ... a.. ... ... ... - ... ...>

680         690         700
               *           *           *
BO ospD   AGC GCA AGA AGT TGT GGC CTT GTT AAA TAC TT
          TCG CGT TCT TCA ACA CCG GAA CAA TTT ATG AA 1. P-Gau o 680       690         700
  [ 2804 ]  ... ... ... ... ... ... ... ... ... ..>

2. DK29 os 680       690         700
  [ 2786 ]  ... ... ... ... ... ... ... ... ... ..>

3. K48 osp 680       690         700
  [ 2786 ]  ... ... ... ... ... ... ... ... ... ..>
```

FIG. 39D

```
         10            20           30           40
         •             •            •            •
ATG ATT ATC AAT CAT AAT ACA TCA GCT ATT AAT GCT TCA AGA AAT AAT
TAC TAA TAG TTA GTA TTA TGT AGT CGA TAA TTA CGA AGT TCT TTA TTA
Met Ile Ile Asn His Asn Thr Ser Ala Ile Asn Ala Ser Arg Asn Asn>

50            60           70           80           90
    •             •            •            •            •
GGC ATT AAC GCT GCT AAT CTT AGT AAA ACT CAA GAA AAG CTT TCT AGT
CCG TAA TTG CGA CGA TTA GAA TCA TTT TGA GTT CTT TTC GAA AGA TCA
Gly Ile Asn Ala Ala Asn Leu Ser Lys Thr Gln Glu Lys Leu Ser Ser>

100           110          120          130          140
       •             •            •            •            •
GGC TAC AGA ATT AAT CGA GCT TCT GAT GAT GCT GCT GGC ATG GGA GTT
CCG ATG TCT TAA TTA GCT CGA AGA CTA CTA CGA CGA CCG TAC CCT CAA
Gly Tyr Arg Ile Asn Arg Ala Ser Asp Asp Ala Ala Gly Met Gly Val>

150           160          170          180          190
         •             •            •            •            •
TCT GGT AAG ATT AAT GCT CAA ATA AGA GGT TTG TCA CAA GCT TCT AGA
AGA CCA TTC TAA TTA CGA GTT TAT TCT CCA AAC AGT GTT CGA AGA TCT
Ser Gly Lys Ile Asn Ala Gln Ile Arg Gly Leu Ser Gln Ala Ser Arg>

200           210          220          230          240
         •             •            •            •            •
AAT ACT TCA AAG GCT ATT AAT TTT ATT CAG ACA ACA GAA GGG AAT TTA
TTA TGA AGT TTC CGA TAA TTA AAA TAA GTC TGT TGT CTT CCC TTA AAT
Asn Thr Ser Lys Ala Ile Asn Phe Ile Gln Thr Thr Glu Gly Asn Leu>

250           260          270          280
         •             •            •            •
AAT GAA GTA GAA AAA GTC TTA GTA AGA ATG AAG GAA TTG GCA GTT CAA
TTA CTT CAT CTT TTT CAG AAT CAT TCT TAC TTC CTT AAC CGT CAA GTT
Asn Glu Val Glu Lys Val Leu Val Arg Met Lys Glu Leu Ala Val Gln>

290        300          310          320          330
    •          •            •            •            •
TCA GGT AAC GGC ACA TAT TCA GAT GCA GAC AGA GGT TCT ATA CAA ATT
AGT CCA TTG CCG TGT ATA AGT CTA CGT CTG TCT CCA AGA TAT GTT TAA
Ser Gly Asn Gly Thr Tyr Ser Asp Ala Asp Arg Gly Ser Ile Gln Ile>

340           350          360          370          380
       •             •            •            •            •
GAA ATA GAG CAA CTT ACA GAC GAA ATT AAT AGA ATT GCT GAT CAA GCT
CTT TAT CTC GTT GAA TGT CTG CTT TAA TTA TCT TAA CGA CTA GTT CGA
Glu Ile Glu Gln Leu Thr Asp Glu Ile Asn Arg Ile Ala Asp Gln Ala>
```

FIG. 40A

```
        390           400           410           420           430
         *             *             *             *             *
   *     •       *     •       *     •       *     •       *     •
CAA TAT AAC CAA ATG CAC ATG TTA TCA AAC AAA TCT GCT TCT CAA AAT
GTT ATA TTG GTT TAC GTG TAC AAT AGT TTG TTT AGA CGA AGA GTT TTA
Gln Tyr Asn Gln Met His Met Leu Ser Asn Lys Ser Ala Ser Gln Asn>

440           450           460           470           480
         *             *             *             *             *
   *     •       *     •       *     •       *     •       *     •
GTA AGA ACA GCT GAA GAG CTT GGA ATG CAG CCT GCA AAA ATT AAC ACA
CAT TCT TGT CGA CTT CTC GAA CCT TAC GTC GGA CGT TTT TAA TTG TGT
Val Arg Thr Ala Glu Glu Leu Gly Met Gln Pro Ala Lys Ile Asn Thr>

490           500           510           520
         *             *             *             *
   *     •       *     •       *     •       *     •       *     •
CCA GCA TCA CTT TCA GGG CTT CAA GCG TCT TGG ACT TTA AGA GTT CAT
GGT CGT AGT GAA AGT CCC GAA GTT CGC AGA ACC TGA AAT TCT CAA GTA
Pro Ala Ser Leu Ser Gly Leu Gln Ala Ser Trp Thr Leu Arg Val His>

530           540           550           560           570
  *             *             *             *             *
  •      *      •      *      •      *      •      *      •      *
GTT GGA GCA ACC CAA GAT GAA GCT ATT GCT GTA AAT ATT TAT GCA GCT
CAA CCT CGT TGG GTT CTA CTT CGA TAA CGA CAT TTA TAA ATA CGT CGA
Val Gly Ala Thr Gln Asp Glu Ala Ile Ala Val Asn Ile Tyr Ala Ala>

580           590           600           610           620
         *             *             *             *             *
   •     *       •     *       •     *       •     *       •
AAT GTT GCA AAT CTT TTC TCT GGT GAG GGA GCT CAA ACT GCT CAG GCT
TTA CAA CGT TTA GAA AAG AGA CCA CTC CCT CGA GTT TGA CGA GTC CGA
Asn Val Ala Asn Leu Phe Ser Gly Glu Gly Ala Gln Thr Ala Gln Ala>

630           640           650           660           670
         *             *             *             *             *
   *     •       *     •       *     •       *     •       *     •
GCA CCG GTT CAA GAG GGT GTT CAA CAG GAA GGA GCT CAA CAG CCA GCA
CGT GGC CAA GTT CTC CCA CAA GTT GTC CTT CCT CGA GTT GTC GGT CGT
Ala Pro Val Gln Glu Gly Val Gln Gln Glu Gly Ala Gln Gln Pro Ala>

680           690           700           710           720
         *             *             *             *             *
   •     *       •     *       •     *       •     *       •     *
CCT GCT ACA GCA CCT TCT CAA GGC GGA GTT AAT TCT CCT GTT AAT GTT
GGA CGA TGT CGT GGA AGA GTT CCG CCT CAA TTA AGA GGA CAA TTA CAA
Pro Ala Thr Ala Pro Ser Gln Gly Gly Val Asn Ser Pro Val Asn Val>

730           740           750           760
         *             *             *             *
   *     •       *     •       *     •       *     •       *
ACA ACT ACA GTT GAT GCT AAT ACA TCA CTT GCT AAA ATT GAA AAT GCT
TGT TGA TGT CAA CTA CGA TTA TGT AGT GAA CGA TTT TAA CTT TTA CGA
Thr Thr Thr Val Asp Ala Asn Thr Ser Leu Ala Lys Ile Glu Asn Ala>

770           780           790           800           810
  *             *             *             *             *
  •      *      •      *      •      *      •      *      •
ATT AGA ATG ATA AGT GAT CAA AGG GCA AAT TTA GGT GCT TTC CAA AAT
TAA TCT TAC TAT TCA CTA GTT TCC CGT TTA AAT CCA CGA AAG GTT TTA
Ile Arg Met Ile Ser Asp Gln Arg Ala Asn Leu Gly Ala Phe Gln Asn>
```

FIG. 40B

```
        820         830         840         850         860
         *           *           *           *           *
AGA CTT GAA TCT ATA AAG AAT AGT ACT GAG TAT GCA ATT GAA AAT CTA
TCT GAA CTT AGA TAT TTC TTA TCA TGA CTC ATA CGT TAA CTT TTA GAT
Arg Leu Glu Ser Ile Lys Asn Ser Thr Glu Tyr Ala Ile Glu Asn Leu>

870         880         890         900         910
         *           *           *           *           *
AAA GCA TCT TAT GCT CAA ATA AAA GAT GCT ACA ATG ACA GAT GAG GTT
TTT CGT AGA ATA CGA GTT TAT TTT CTA CGA TGT TAC TGT CTA CTC CAA
Lys Ala Ser Tyr Ala Gln Ile Lys Asp Ala Thr Met Thr Asp Glu Val>

920         930         940         950         960
         *           *           *           *           *
GTA GCA GCA ACA ACT AAT ATG ATT TTA ACA CAA TCT GCA ATG GCA ATG
CAT CGT CGT TGT TGA TTA TAC TAA AAT TGT GTT AGA CGT TAC CGT TAC
Val Ala Ala Thr Thr Asn Met Ile Leu Thr Gln Ser Ala Met Ala Met>

970         980         990        1000
         *           *           *           *
ATT GCG CAG GCT AAT CAA GTT CCC CAA TAT GTT TTG TCA TTG CTT AGA
TAA CGC GTC CGA TTA GTT CAA GGG GTT ATA CAA AAC AGT AAC GAA TCT
Ile Ala Gln Ala Asn Gln Val Pro Gln Tyr Val Leu Ser Leu Leu Arg>

1010
  *
TAA
ATT
***>
```

FIG. 40C

```
                      10          20          30          40
                       *           *           *           *
   B31-41kD  ATG ATT ATC AAT CAT AAT ACA TCA GCT ATT AAT GCT TCA AGA AAT AAT
             TAC TAA TAG TTA GTA TTA TGT AGT CGA TAA TTA CGA AGT TCT TTA TTA

1. KA-41kD         10          20          30          40
    [ 3996 ]    ... ... ... ... ... ... ... ... ... ... ... ... ... ... ...>

2. P-Gau-4         10          20          30          40
    [ 3696 ]    ... ... ... ... ... ... ... ... ... ... ... ... ... ... ...>

3. BO-41kD         10          20          30          40
    [ 3684 ]    ... ... ... ... ... ... ... ... ... ... ... ... ... ... ...>

4. DK29-41         10          20          30          40
    [ 3672 ]    ... ... ... ... ... ... ... ... ... ... ... ... ... ... ...>

5. PKO-41k         10          20          30          40
    [ 3672 ]    ... ... ... ... ... ... ... ... ... ... ... ... ... ... ...>

50          60          70          80          90
                  *           *           *           *           *
   B31-41kD  GGC ATT AAC GCT GCT AAT CTT AGT AAA ACT CAA GAA AAG CTT TCT AGT
             CCG TAA TTG CGA CGA TTA GAA TCA TTT TGA GTT CTT TTC GAA AGA TCA

1. KA-41kD50        60          70          80          90
    [ 3996 ]    ... ... ... ... ... ... ... ... ... ... ... ... ... ... ...>

2. P-Gau-450        60          70          80          90
    [ 3696 ]    .c. ... ..t ... ... ... ... ... ... ... ..c ... ..g ... ...>

3. BO-41kD50        60          70          80          90
    [ 3684 ]    .c. ... ..t ... ... ... ... ... ... ... ..c ... ..g ... ...>

4. DK29-4150        60          70          80          90
    [ 2672 ]    ..t ... ..t ... ... ... ... ... ... ... ... ... ..g ... ...>

5. PKO-41k50        60          70          80          90
    [ 3672 ]    .c. ... ..t ... ... ... ... ... ... ... ..c ... ..g ... .c.>

100         110         120         130         140
                  *           *           *           *           *
   B31-41kD  GGC TAC AGA ATT AAT CGA GCT TCT GAT GAT GCT GCT GGC ATG GGA GTT
             CCG ATG TCT TAA TTA GCT CGA AGA CTA CTA CGA CGA CCG TAC CCT CAA
```

2. P-Gau-4  100          110          120          130          140
[ 3696 ]     ..t ... ... ... ... ... ... ... ... ... ... ..t ... ..g ...>

3. BO-41kD  100          110          120          130          140
[ 3684 ]     ..t ... ... ... ... ... ... ... ... ... ... ..t ... ..g ...>

4. DK29-41  100          110          120          130          140
[ 3672 ]     ..t ... ... ... ... a.. ... ... ... ... ... ..t ... ..g ...>

5. PKO-41k  100          110          120          130          140
[ 3672 ]     ..t ... ... ... ... ... ... ... ... ... ... ..t ... ..g ...>

150          160          170          180          190
                *  *        *   *        *   *        *   *        *   *
B31-41kD      TCT GGT AAG ATT AAT GCT CAA ATA AGA GGT TTG TCA CAA GCT TCT AGA
              AGA CCA TTC TAA TTA CGA GTT TAT TCT CCA AAC AGT GTT CGA AGA TCT

1. KA-41kD   150          160          170          180          190
[ 3996 ]     ... ... ... ... ... ... ... ... ... ... ... ... ... ... ...>

2. P-Gau-4  150          160          170          180          190
[ 3696 ]     ... ..c ... ... ... ... ... ... ... .c. ..c ..a ... ... ...>

3. BO-41kD  150          160          170          180          190
[ 3684 ]     ... ..c ... ... ... ... ... ... ... ..c ..a ... ... ... ...>

4. DK29-41  150          160          170          180          190
[ 3672 ]     ... ..g ... ... ... ... ... ... ... ... ..a ... ... ... ...>

5. PKO-41k  150          160          170          180          190
[ 3672 ]     ... ..c ... ... ... ... ... ... ... ..c ..a ... ... ... ...>

200          210          220          230          240
                *  *        *   *        *   *        *   *        *   *
B31-41kD      AAT ACT TCA AAG GCT ATT AAT TTT ATT CAG ACA ACA GAA GGG AAT TTA
              TTA TGA AGT TTC CGA TAA TTA AAA TAA GTC TGT TGT CTT CCC TTA AAT

1. KA-41kD   200          210          220          230          240
[ 3996 ]     ... ... ... ... ... ... ... ... ... ... ... ... ... ... ...>

2. P-Gau-4  200          210          220          230          240
[ 3696 ]     ..c ... ... ..a ... ..c ... ... ... ... ... ... ..a ... ...>

3. BO-41kD  200          210          220          230          240
[ 3684 ]     ..c ... ... ..a ... ..c ... ... ... ... ... ... ..a ... ...>

4. DK29-41  200          210          220          230          240
[ 3672 ]     ..c ... ... ..a ... ..c ... ... ... ... ... ... ..a ... ..g>

5. PKO-41k  200          210          220          230          240
[ 3672 ]     ..c ... ... ..a ... ..c ... ... ... ... ... ... ..a ... ...>
```

FIG. 41B

```
                          250         260         270         280
                           *           *           *           *
B31-41kD    AAT GAA GTA CAA AAA GTC TTA GTA AGA ATG AAG GAA TTG GCA GTT CAA
            TTA CTT CAT CTT TTT CAG AAT CAT TCT TAC TTC CTT AAC CGT CAA GTT

1. KA-41kD           250         260         270         280
  [ 3996 ]      ... ... ... ... ... ... ... ... ... ... ... ... ... ... ...>

2. P-Gau-4           250         260         270         280
  [ 3696 ]      ... ... ... ... ... ..t ... ... ... ..a ... ..a ... ... ...>

3. BO-41kD           250         260         270         280
  [ 3684 ]      ... ... ... ... ... ..t ... ... ... ..a ... ..a ... ... ...>

4. DK29-41           250         260         270         280
  [ 3672 ]      ... ... ... ... ... ..t ... ... ... ..a ... ..a ... ... ...>

5. PKO-41k           250         260         270         280
  [ 3672 ]      ... ... ... ... ... ..t ... ... ... ..a ... ..a ... ... ...>

290         300         310         320         330
                  *           *           *           *           *
B31-41kD    TCA GGT AAC GGC ACA TAT TCA GAT GCA GAC AGA GGT TCT ATA CAA ATT
            AGT CCA TTG CCG TGT ATA AGT CTA CGT CTG TCT CCA AGA TAT GTT TAA

1. KA-41k290         300         310         320         330
  [ 3996 ]      ... ... ... ... ... ... ... ... ... ... ... ... ... ... ...>

2. P-Gau-290         300         310         320         330
  [ 3696 ]      ... ... ... ..a ..g ... ... ..c ... ... ... ... ... ..g ...>

3. BO-41k290         300         310         320         330
  [ 3684 ]      ... ... ... ..a ..g ... ... ..c t.. ... ... ... ... ..g ...>

4. DK29-4290         300         310         320         330
  [ 3672 ]      ... ... ... ..t ... ... ... ..c ... ... ... ... ... ... ...>

5. PKO-41290         300         310         320         330
  [ 3672 ]      ... ... ... ..a ..g ... ... ..c t.. ... ... ... ... ..g ...>

340         350         360         370         380
                  *           *           *           *           *
B31-41kD    GAA ATA GAG CAA CTT ACA GAC GAA ATT AAT AGA ATT GCT GAT CAA GCT
            CTT TAT CTC GTT GAA TGT CTG CTT TAA TTA TCT TAA CGA CTA GTT CGA

1. KA-41kD 340         350         360         370         380
  [ 3996 ]      ... ... ... ... ... ... ... ... ... ... ... ... ... ... ...>

2. P-Gau-4 340         350         360         370         380
  [ 3696 ]      ... ... ... ... ... ... ... ... ... ... ... ... ... ..g ...>

```
        5. PKO-41k   340         350         360         370         380
        [ 3672 ]     ... ... ... ... ... ... ... ... ... ... ... ... ..g ...>

390         400         410         420         430
                     *    *      *    *      *    *      *    *      *    *
        B31-41kD     CAA TAT AAC CAA ATG CAC ATG TTA TCA AAC AAA TCT GCT TCT CAA AAT
                     GTT ATA TTG GTT TAC GTG TAC AAT AGT TTG TTT AGA CGA AGA GTT TTA

1. KA-41kD   390         400         410         420         430
        [ 3996 ]     ... ... ... ... ... ... ... ... ... ... ... ... ... ... ...>

2. P-Gau-4   390         400         410         420         430
        [ 3696 ]     ... ... ... ... ... ... ..g ... ... ... ... ..c ... ...>

3. BO-41kD   390         400         410         420         430
        [ 3684 ]     ... ... ... ... ... ... ..g ... ... ... ... ..c ... ...>

4. DK29-41   390         400         410         420         430
        [ 3672 ]     ... ... ... ... ... ... ..g ... ... ... ... ..c ... ...>

5. PKO-41k   390         400         410         420         430
        [ 3672 ]     ... ... ... ... ... ... ..g ... ... ... ... ..c ... ...>

440         450         460         470         480
                     *    *      *    *      *    *      *    *      *    *
        B31-41kD     GTA AGA ACA GCT GAA GAG CTT GGA ATG CAG CCT GCA AAA ATT AAC ACA
                     CAT TCT TGT CGA CTT CTC GAA CCT TAC GTC GGA CGT TTT TAA TTG TGT

1. KA-41kD   440         450         460         470         480
        [ 3996 ]     ... ... ... ... ... ... ... ... ... ... ... ... ... ...>

2. P-Gau-4   440         450         460         470         480
        [ 3696 ]     ... .a. ... ... ... ... ... ... ... ... ... ... ... ...>

3. BO-41kD   440         450         460         470         480
        [ 3684 ]     ... .a. ... ... ... ... ... ... ... ... ... ... ... ...>

4. DK29-41   440         450         460         470         480
        [ 3672 ]     ... ... ... ... ... ..a ... ... ... ..a ... ... ..c ... ...>

5. PKO-41k   440         450         460         470         480
        [ 3672 ]     ... .a. ... ... ... ... ... ... ... ... ... ... ... ...>

490         500         510         520
                     *    *      *    *      *    *      *    *      *
        B31-41kD     CCA GCA TCA CTT TCA GGG CTT CAA GCG TCT TGG ACT TTA AGA GTT CAT
                     GGT CGT AGT GAA AGT CCC GAA GTT CGC AGA ACC TGA AAT TCT CAA GTA

1. KA-41kD   490         500         510         520
        [ 3996 ]     ... ... ... ... ... ... tc. ... ... ... ... ... ... ...>

2. P-Gau-4   490         500         510         520
        [ 3696 ]     ... ... ... ... ... ..a tc. ... ..t ... ... ... ... ...>
```

5. PKO-41k        490         500         510         520
[ 3672 ]    ... ... ... ... ... ..a tc. ... ..t ... ... ... ... ... ... ...>

530         540         550         560         570
               *     *     *     *     *     *     *     *     *     *
B31-41kD   GTT GGA GCA ACC CAA GAT GAA GCT ATT GCT GTA AAT ATT TAT GCA GCT
           CAA CCT CGT TGG GTT CTA CTT CGA TAA CGA CAT TTA TAA ATA CGT CGA

1. KA-41k530       540         550         560         570
[ 3996 ]    ... ... ... .a. ... ... ... ... ... ... ... ... ... ... ... ...>

2. P-Gau-530       540         550         560         570
[ 3695 ]    ..g ... ... .at ... ... ... ..a ... ... ... ... ... t.. ...>

3. BO-41k530       540         550         560         570
[ 3684 ]    ..g ... ... .at ... ... ... ..a ... ... ... ... ... t.. ...>

4. DK29-4530       540         550         560         570
[ 3672 ]    ..g ... ... .at ... ... ... ..g ... ... ... ... - ..t ...>

5. PKO-41530       540         550         560         570
[ 3672 ]    ..g ... ... .at ... ... ... ..a ... ... ... ... - t.. ...>

580         590         600         610         620
               *     *     *     *     *     *     *     *     *     *
B31-41kD   AAT GTT GCA AAT CTT TTC TCT GGT GAG GCA GCT CAA ACT GCT CAG GCT
           TTA CAA CGT TTA GAA AAG AGA CCA CTC CCT CGA GTT TGA CGA GTC CGA

1. KA-41kD 580     590         600         610         620
[ 3996 ]    ... ... ... ... ... ... ... ... ... ... ... ... - ... ...>

2. P-Gau-4 580     590         600         610         620
[ 3696 ]    ... ... ... ... ... ..t g.. ... ... ... ... g.. ... - ... ...>

3. BO-41kD 580     590         600         610         620
[ 3684 ]    ... ... ... ... ... ..t g.. ... ... ... ... g.. ... - ... ...>

4. DK29-41 580     590         600         610         620
[ 3672 ]    ... ... ... ... ..a ... ... ... ..a ... ... ..g g.. ... - ... a..>

5. PKO-41k 580     590         600         610         620
[ 3672 ]    ... ... ... ... ... ..t g.. ... ... ... ... g.. ... - ... ...>

630         640         650         660         670
               *     *     *     *     *     *     *     *     *     *
B31-41kD   GCA CCG GTT CAA GAG GGT GTT CAA CAG GAA GGA GCT CAA CAG CCA GCA
           CGT GGC CAA GTT CTC CCA CAA GTT GTC CTT CCT CGA GTT GTC GGT CGT
```

2. P-Gau-4   630         640         650         660         670
[ 3696 ]        ... ..t ... ... ... ... .c. ... g.a ... ... ... ..g ..a ... a..>

3. BO-41kD   630         640         650         660         670
[ 3684 ]        ... ..t ... ... ... ... .c. ... g.a ... ... ... ..g ..a ... a..>

4. DK29-41   630         640         650         660         670
[ 3672 ]        ... ..t ... ... ...a ... .c. ... ..a ... ... ... ... ..a ... ...>

5. PKO-41k   630         640         650         660         670
[ 3672 ]        ... ..t ... ... ... ... .c. ... g.a ... ... ... ..g ..a ... a..>

680         690         700         710         720
                  *           *           *           *     *     *           *    *
B31-41kD    CCT GCT ACA GCA CCT TCT CAA GGC GGA GTT AAT TCT CCT GTT AAT GTT
            GGA CGA TGT CGT GGA AGA GTT CCG CCT CAA TTA AGA GGA CAA TTA CAA

1. KA-41kD    680         690         700         710         720
[ 3996 ]        ... ... ... ... ... ... ... ... ... ... ... ... ... ... ...>

2. P-Gau-4   680         690         700         710         720
[ 3696 ]        ... ... ... ... ... a.. ... ... ..t ... ... ... ... ... ...>

3. BO-41kD   680         690         700         710         720
[ 3684 ]        ... ... ... ... ... a.. ... ... ..t ... ... ... ... ... ...>

4. DK29-41   680         690         700         710         720
[ 3672 ]        ... ... ... ... ..g ... ... ..g ..t ... ... ... ... ... ...>

5. PKO-41k   680         690         700         710         720
[ 3672 ]        ... ... ... ... ... a.. ... ... ..t ... ... ... ... ... ...>

730         740         750         760
                  *           *           *           *           *
B31-41kD    ACA ACT ACA GTT GAT GCT AAT ACA TCA CTT GCT AAA ATT CAA AAT GCT
            TGT TGA TGT CAA CTA CGA TTA TGT AGT GAA CGA TTT TAA CTT TTA CGA

1. KA-41kD    730         740         750         760
[ 3996 ]        ... ... ... ... ... ... ... ... ... ... ... ... ... ... ...>

2. P-Gau-4   730         740         750         760
[ 3696 ]        ... ..c ... ... ... ... ... ... ... ... ... ... ..a ... ...>

3. BO-41kD   730         740         750         760
[ 3684 ]        ... ..c ... ... ... ... ... ... ... ... ... ... ..a ... ...>

4. DK29-41   730         740         750         760
[ 3672 ]        ... ... ... ... ..c ... ... ... ..t ... ... ... ..a ... ...>

5. PKO-41k   730         740         750         760
[ 3672 ]        ... ..c ... ... ... ... ... ... ... ... ... ... ..a ... ...>
```

FIG. 41F

```
              770         780         790         800         810
               *           *           *           *           *
B31-41kD  ATT AGA ATG ATA AGT GAT CAA AGG GCA AAT TTA GGT GCT TTC CAA AAT
          TAA TCT TAC TAT TCA CTA GTT TCC CGT TTA AAT CCA CGA AAG GTT TTA

1. KA-41k770        780         790         800         810
  [ 3996 ]    ... ... ... ... ... ... ... ... ... ... ... ... ... ... ... ...>

2. P-Gau-770        780         790         800         810
  [ 3696 ]    ... ... ... ... ... ... ...a... ... ... ... ... ... ... ... ...>

3. BO-41k770        780         790         800         810
  [ 3684 ]    ... ... ... ... ... ... ...a... ... ... ... ... ... ... ... ...>

4. DK29-4770        780         790         800         810
  [ 3672 ]    ... ... ... ... ... ... ...a... ... ... ... ... ... ... ... ...>

5. PKO-41770        780         790         800         810
  [ 3672 ]    ... ... ... ... ... ... ...a... ... ... ... ... ... ... ... ...>

820         830         840         850         860
               *           *           *           *           *
B31-41kD  AGA CTT GAA TCT ATA AAG AAT AGT ACT GAG TAT GCA ATT GAA AAT CTA
          TCT GAA CTT AGA TAT TTC TTA TCA TGA CTC ATA CGT TAA CTT TTA GAT

1. KA-41kD  820         830         840         850         860
  [ 3996 ]    ... ... ... ... ... ... ... ... ... ... ... ... ... ... ... ...>

2. P-Gau-4  820         830         840         850         860
  [ 3696 ]    ... ... ... ... ... ... ...c... ... ... ...t... ... ... ... ...>

3. BO-41kD  820         830         840         850         860
  [ 3684 ]    ... ... ... ... ... ... ...c... ... ... ...t... ... ... ... ...>

4. DK29-41  820         830         840         850         860
  [ 3672 ]    ... ...g... ... ...g... ... ... ... ...t... ... ... ..c ...>

5. PKO-41k  820         830         840         850         860
  [ 3672 ]    ... ... ... ... ... ... ...c... ... ... ...t... ... ... ... ...>

870         880         890         900         910
               *           *           *           *           *
B31-41kD  AAA GCA TCT TAT GCT CAA ATA AAA GAT GCT ACA ATG ACA GAT GAG GTT
          TTT CGT AGA ATA CGA GTT TAT TTT CTA CGA TGT TAC TGT CTA CTC CAA

1. KA-41kD  870         880         890         900         910
  [ 3996 ]    ... ... ... ... ... ... ... ... ... ... ... ... ... ... ... ...>

2. P-Gau-4  870         880         890         900         910
  [ 3696 ]    ... ... ... ... ... ... ... ... ... ... ... ... ... ... ... ...>

```
5. PKO-41k    870         880         890         900         910
[ 3672 ]      ... ... ... ... ... ... ... ... ... ... ... ... ... ... ...>

920         930         940         950         960
              *   *       *   *       *   *       *   *       *   *
B31-41kD      GTA GCA GCA ACA ACT AAT ATG ATT TTA ACA CAA TCT GCA ATG GCA ATG
              CAT CGT CGT TGT TGA TTA TAC TAA AAT TGT GTT AGA CGT TAC CGT TAC

1. KA-41kD      920         930         940         950         960
[ 3996 ]      ... ... ... ... ... ... .gt ... ... ... ... ... ... ... ... ...>

2. P-Gau-4     920         930         940         950         960
[ 3696 ]      ... ... ..t ... ... ... .gt ... ... ..t ... ... ... ... ... ...>

3. BO-41kD     920         930         940         950         960
[ 3684 ]      ... ... ..t ... ... ... .gt ... ... ..t ... ... ... ... ... ...>

4. DK29-41    920         930         940         950         960
[ 3672 ]      ... ... ..t ... ... ... .gt ... ... ... ... .g. ... ... ... ...>

5. PKO-41k    920         930         940         950         960
[ 3672 ]      ... ... ..t ... ... ..a .gt ... ... ..t ... ... ... ... ... ...>

970         980         990         1000
              *   *       *   *       *   *       *   *       *
B31-41kD      ATT GCG CAG GCT AAT CAA GTT CCC CAA TAT GTT TTG TCA TTG CTT AGA
              TAA CGC GTC CGA TTA GTT CAA GGG GTT ATA CAA AAC AGT AAC GAA TCT

1. KA-41kD      970         980         990         1000
[ 3996 ]      ... ... ... ... ... ... ... ... ... ... ... ... ... ... ... ...>

2. P-Gau-4     970         980         990         1000
[ 3696 ]      ... ..a ... ... ... ... ... ..t ... ... ... ... ... ... ... ...>

3. BO-41kD     970         980         990         1000
[ 3684 ]      ... ..a ... ... ... ... ... ..t ... ... ... ... ... ... ... ...>

4. DK29-41    970         980         990         1000
[ 3672 ]      ... ... ..a ... ... ... ... ..t ... ... ... ... ... ... ... ...>

5. PKO-41k    970         980         990         1000
[ 3672 ]      ... ..a ... ... ... ... ... ..t ... ... ... ... ... ... ... ...>

1010
              *
B31-41kD      TAA
              ATT

2. P-Gau1010
[ 3696 ]      ...>
```

FIG. 41H

Sequence Range: 1 to 822

```
                        10              20              30              40
                         *               *               *               *
OspA-B31        ATG AAA AAA TAT TTA TTG GGA ATA GGT CTA ATA TTA GCC TTA ATA GCA
                TAC TTT TTT ATA AAT AAC CCT TAT CCA GAT TAT AAT CGG AAT TAT CGT

OspA-B31                10              20              30              40
[ 3288 ]        ... ... ... ... ... ... ... ... ... ... ... ... ... ... ... ...>

OspA-KA                 10              20              30              40
[ 3288 ]        ... ... ... ... ... ... ... ... ... ... ... ... ... ... ... ...>

OspA-N40                10              20              30              40
[ 3276 ]        ... ... ... ... ... ... ... ... ... ... ... ... ... ... ... ...>

OspA-ZS7                10              20              30              40
[ 3264 ]        ... ... ... ... ... ... ... ... ... ... ... ... ... ... ... ...>

OspA-25015              10              20              30              40
[ 2802 ]        ... ... ... ... ... ... ... ... ... ... ... ...t ... ... ... ...>

OspA-TRO                10              20              30              40
[ 2648 ]        ... ... ... ... ... ... ... ... ... ... ... ... ... ... ... ...>

OspA-K48                10              20              30              40
[ 2534 ]        ... ... ... ... ... ... ... ... ... ... ... ... ... ... ... ...>

OspA-HE 11              10              20              30              40
[ 2580 ]        ... ... ... ... ... ... ... ... ... ... ... ... ... ... ... ...>

OspA-DK29               10              20              30              40
[ 2566 ]        ... ... ... ... ... ... ... ... ... ... ... ... ... ... ... ...>

OspA-Ip90               10              20              30              40
[ 2562 ]        ... ... ... ... ... ... ... ... ... ... ... ..a ... ... ... ...>

OspA-BO                 10              20              30              40
[ 2558 ]        ... ... ... ... ... ... ... ... ... ... ... ... ... ... ... ...>

OSPA-IP3                10              20              30              40
[ 2558 ]        ... ... ... ... ... ... ... ... ... ... ... ... ... ... ... ...>

OspA-PKO                10              20              30              40
[ 2558 ]        ... ... ... ... ... ... ... ... ... ... ... ... ... ... ... ...>

OspA-ACAI               10              20              30              40
[ 2556 ]        ... ... ... ... ... ... ... ... ... ... ... ... ... ... ... ...>

OspA-P-GAU              10              20              30              40
[ 2544 ]        ... ... ... ... ... ... ... ... ... ... ... ... ... ... ... ...>

50              60              70              80              90
                 *               *               *               *               *
OspA-B31        TGT AAG CAA AAT GTT AGC AGC CTT GAC GAG AAA AAC AGC GTT TCA GTA
                ACA TTC GTT TTA CAA TCG TCG GAA CTG CTC TTT TTG TCG CAA AGT CAT
```

FIG. 42A

```
OspA-B31      50            60            70            80            90
[ 3288 ]      ... ... ... ... ... ... ... ... ... ... ... ... ... ... ... ...>

OspA-KA       50            60            70            80            90
[ 3288 ]      ... ... ... ... ... ... ... ... ... ... ... ... ... ... ... ...>

OspA-N40      50            60            70            80            90
[ 3276 ]      ... ... ... ... ... ... ... ... ... ... ... ... ... ... ... ...>

OspA-ZS7      50            60            70            80            90
[ 3264 ]      ... ... ... ... ... ... ... ... ... ... ... ... ... ... ... ...>

OspA-25015    50            60            70            80            90
[ 2802 ]      ... ... ... ... ... ... ... ... ... ... ... ... ... ... ... ...>

OspA-TRO      50            60            70            80            90
[ 2648 ]      ... ... ... ... ... ... ... ..t ... ... ... ... ... ... ... ...>

OspA-K48      50            60            70            80            90
[ 2584 ]      ... ... ... ... ... ... ... ..t ..a ... ..t ... ... ... ... ...>

OspA-HE11     50            60            70            80            90
[ 2580 ]      ... ... ... ... ... ... ... ..t ..a ... ..t ... ... ... ... ...>

OspA-DK29     50            60            70            80            90
[ 2556 ]      ... ... ... ... ... ... ... ..t ..a ... ..t ... ... ... ... ...>

OspA-Ip90     50            60            70            80            90
[ 2562 ]      ... ... ... ... ... ... ... ..t ..a ... ..t ... ... ... ... ...>

OspA-BO       50            60            70            80            90
[ 2558 ]      ..c ... ... ... ... ... ... ..t ..a ... ... ... .c. ... ... ...>

OSPA-IP3      50            60            70            80            90
[ 2558 ]      ..c ... ... ... ... ... ... ..t ..a ... ... ... .c. ... ... ...>

OspA-PKO      50            60            70            80            90
[ 2558 ]      ..c ... ... ... ... ... ... ..t ..a ... ... ... .c. ... ... ...>

OspA-ACAI     50            60            70            80            90
[ 2556 ]      ..c ... ... ... ... ... ... ..t ..a ... ... ... .c. ... ... ...> ospA-P-GAU    50            60            70            80            90
[ 2544 ]      ..c ... ... ... ... ... ... ..t ..a ... ... ... .c. ... ... ...>

100           110           120           130           140
OspA-B31      GAT TTG CCT GGT GAA ATG AAA GTT CTT GTA AGC AAA GAA AAA AAC AAA
              CTA AAC GCA CCA CTT TAC TTT CAA GAA CAT TCG TTT CTT TTT TTG TTT

OspA-B31      100           110           120           130           140
[ 3288 ]      ... ... ... ... ... ... ... ... ... ... ... ... ... ... ... ...>

OspA-KA       100           110           120           130           140
[ 3288 ]      ... ... ... ... ... ... ... ... ... ... ... ... ... ... ... ...>

OspA-N40      100           110           120           130           140
```

OspA-Z57         100        110        120        130        140
[ 3264 ]         ...  ...  ...  ...  ...  ..c ...  ...  ...  ...  ...  ...  ...  ...  ...>

OspA-25015       100        110        120        130        140
[ 2802 ]         ...  ...  ...  ...  ...  ...  ...  ...  ...  ...  ...  ...  g.. ...>

OspA-TRO         100        110        120        130        140
[ 2648 ]         ...  ..a ...  ...  ...  ...  ...  ...  ...  ...  ...  ...  g.. ...>

OspA-K48         100        110        120        130        140
[ 2594 ]         ...  ..a ...  ...  .g.  ...  .c.  ...  ...  ...  ..t ...  ...  ...  g.. ...>

OspA-HE 11       100        110        120        130        140
[ 2580 ]         ...  ..a ...  ...  .g.  ...  ...  ...  ...  ..t ...  ...  ...  g.. ...>

OspA-DK29        100        110        120        130        140
[ 2566 ]         ...  ..a ...  ...  .g.  ...  .c.  ...  ...  ...  ..t ...  ...  ...  .g.. ...>

OspA-Ip90        100        110        120        130        140
[ 2562 ]         ...  ..a ...  ...  .g.  ...  c..  ...  ...  ...  ..t ...  ...  ...  g.. ...>

OspA-PO          100        110        120        130        140
[ 2558 ]         ...  ...  ...  ...  ..g  ...  ...  ...  ...  ...  ..t ...  ...  ...  g.. ...>

OSPA-IP3         100        110        120        130        140
[ 2558 ]         ...  ...  ...  ...  ..g  ...t ...  ...  ...  ..t ...  ...  ...  g.. ...>

OspA-PKO         100        110        120        130        140
[ 2558 ]         ...  ...  ...  ...  ..g  ...  ...  ...  ...  ..t ...  ...  ...  g.. ...>

OspA-ACAI        100        110        120        130        140
[ 2556 ]         ...  ...  ...  ...  ..g  ...  ...  ...  ...  ..t ...  ...  ...  g.. ...>

OspA-P-GAU       100        110        120        130        140
[ 2544 ]         ...  ...  ...  ...  ..g  ...  ...  ...  ...  ..t ...  ...  ...  g.. ...>

150        160        170        180        190
                           *          *          *          *          *
OspA-B31         GAC  GGC  AAG  TAC  GAT  CTA  ATT  GCA  ACA  GTA  GAC  AAG  CTT  GAG  CTT  AAA
                 CTG  CCG  TTC  ATG  CTA  GAT  TAA  CGT  TGT  CAT  CTG  TTC  GAA  CTC  GAA  TTT

OspA-B31         150        160        170        180        190
[ 3288 ]         ...  ...  ...  ...  ...  ...  ...  ...  ...  ...  ...  ...  ...  ...  ...>

OspA-KA          150        160        170        180        190
[ 3288 ]         ...  ...  ...  ...  ...  ...  ...  ...  ...  ...  ...  ...  ...  ...  ...>

OspA-N40         150        160        170        180        190
[ 3276 ]         ...  ...  ...  ...  ...  ...  ...  ...  ...  ...  ...  ...  ...  ...  ...>

OspA-Z57         150        160        170        180        190
[ 3264 ]         ...  ...  ...  ...  ...  ...  ...  ...  ...  ...  ...  ...  ...  ...  ...>

OspA-25015       150        160        170        180        190
[ 2802 ]         ...  ...  ...  ...  ag.  ...  ..g  ...  ...  ...  ...  ...  ...  ...  ...>
```

FIG. 42C

```
OspA-TRO        150         160         170         180         190
[ 2648 ]    ..t ..t ..a ... ag. ... ..g ... ... ... ... ... ..a ... ... ...>

OspA-K48        150         160         170         180         190
[ 2584 ]    ... ..t ..a ... ag. ... gag ... ... ... ... ... ... ... ... ...>

OspA-HE 11      150         160         170         180         190
[ 2580 ]    ..t ..t ..a ... ag. ... ..g ... ... ... ... ... ..a ... ... ...>

OspA-DK29       150         160         170         180         190
[ 2566 ]    ... ..t ..a ... ag. ... gag ... ... ... ... ... ... ... ... ...>

OspA-Ip90       150         160         170         180         190
[ 2562 ]    ..t ..t ..a ... ag. ... ..g ... ... ... ... ... ... ... ... ...>

OspA-BO         150         160         170         180         190
[ 2558 ]    ... ..t ... ... ag. ... .ag ... ... ... ... ... a.. ... ..a ...>

OSPA-IP3        150         160         170         180         190
[ 2558 ]    ... ..t ... ... ag. ... .ag ... ... ... ... ... a.. ... ..a ...>

OspA-PKO        150         160         170         180         190
[ 2553 ]    ... ..t ... ... ag. ... .ag ... ... ... ... ... a.. ... ..a ...>

OspA-ACAI       150         160         170         180         190
[ 2556 ]    ... ..t ... ... ag. ... .ag ... ... ... ... ... a.. ... ..a ...>

OspA-P-GAU      150         160         170         180         190
[ 2544 ]    ... ..t ... ... ag. ... .ag ... ... ... ... ... a.. ... ..a ...>

200         210         220         230         240
                    *           *           *           *           *
OspA-B31        GGA ACT TCT GAT AAA AAC AAT GGA TCT GGA GTA CTT GAA GGC GTA AAA
                CCT TGA AGA CTA TTT TTG TTA CCT AGA CCT CAT GAA CTT CCG CAT TTT

OspA-B31        200         210         220         230         240
[ 3288 ]    ... ... ... ... ... ... ... ... ... ... ... ... ... ... ... ...>

OspA-YA         200         210         220         230         240
[ 3288 ]    ... ... ... ... ... ... ... ... ... ... ... ... ... ... ... ...>

OspA-N40        200         210         220         230         240
[ 3276 ]    ... ... ... ... ... ... ... ... ... ... ... ... ... ... ... ...>

OspA-ZS7        200         210         220         230         240
[ 3264 ]    ... ... ... ... ... ... ... ... ... ... ... ... ... ... ... ...>

OspA-25015      200         210         220         230         240
[ 2802 ]    ... ..a ... ... ... ... ... ... ... ... ..g ...g ... ... ... ...>

OspA-TRO        200         210         220         230         240
[ 2648 ]    ... ... ... ... ... .g. ..c ..t ... ... ac. ... ... ..t .a. ...>

OspA-K48        200         210         220         230         240
[ 2584 ]    ... ... ... ... ... ... ..c ..t ... ... ac. ... ... ..t .a. ...>
```

FIG. 42D

```
OspA-HB 11        200         210         220         230         240
[ 2580 ]          ... ... ... ... ... ..c ..t ... ... ac. ... ... ..t .a. ...>

OspA-DK29         200         210         220         230         240
[ 2566 ]          ... ... ... ... ... ..c ..t ... ... ac. ... ... ..t .a. ...>

OspA-Ip90         200         210         220         230         240
[ 2562 ]          ... ... ... ... ... ..c ..t ... ... ac. ... ... ..t .a. ...>

OspA-BO           200         210         220         230         240
[ 2558 ]          ... ... ... ... ... g.. ... ..t ... ..g ..g ... ... ..t ac. ...>

OSPA-IP3          200         210         220         230         240
[ 2558 ]          ... ... ... ... ... g.. ... ..t ... ... ..g ... ... ..t ac. ...>

OspA-PKO          200         210         220         230         240
[ 2558 ]          ... ... ... ... ... g.. ... ..t ... ..g ..g ... ... ..t ac. ...>

OspA-ACAI         200         210         220         230         240
[ 2556 ]          ... ... ... ... ... g.. ... ..t ... ... ..g ... ... ..t ac. ...>

OspA-P-GAU        200         210         220         230         240
[ 2544 ]          ... ... ... ... ... g.. ... ..t ... ... ..g ... ... ..t ac. ...>

250         260         270         280
                   *     *     *     *     *     *     *     *     *
OspA-B31           GCT GAC AAA AGT AAA GTA AAA TTA ACA ATT TCT GAC GAT CTA GGT CAA
                   CGA CTG TTT TCA TTT CAT TTT AAT TGT TAA AGA CTG CTA GAT CCA GTT

OspA-B21               250         260         270         280
[ 3288 ]          ... ... ... ... ... ... ... ... ... ... ... ... ... ... ...>

OspA-KA                250         260         270         280
[ 3288 ]          ... ... ... ... ... ... ... ... ... ... ... ... ... ... ...>

OspA-N40               250         260         270         280
[ 3276 ]          ... ... ... ... ... ... ... ... ... ... ... ... ... ... ...>

OspA-ZS7               250         260         270         280
[ 3264 ]          ... ... ... ... ... ... ... ... ... ... ... ... ... ... ...>

OspA-Z5015             250         260         270         280
[ 2802 ]          ... ... ... ..c ... ... ... ... ... g.. ... ... ... a..c ac.>

OspA-TRO               250         260         270         280
[ 2648 ]          t.. ... ... ... .c. ... ... ... ... ..a ... ... a.. a..>

OspA-K48               250         260         270         280
[ 2584 ]          a.. ... ... ... ... ... ... ... ... g.. ..t ..c ... a.. ...>

OspA-HB 11             250         260         270         280
[ 2580 ]          a.. ... ... ... ... ... ... ... ... g.. ..g ... ... a.. a..>

OspA-DK29              250         260         270         280
[ 2566 ]          a.. ... ... ... ..c ... ... .c. ... g.. ..t ..c ... a.. ...>

OspA-Ip90              250         260         270         280
```

FIG. 42E

```
[ 2562 ]      a.. ... ... ... ...  .c. ... ... ... ...  g.. ..g ... ...  a.. a..>
OspA-BO           250         260         270         280
[ 2558 ]      .a. ... ... ... ...  .c. ... ... ... ...  g.. ... ... ...  ... a..>
OSPA-IP3          250         260         270         280
[ 2558 ]      .a. ... ... ... ...  .c. ... ... ... ...  g.. ... ...  ... a.. a..>
OspA-PKO          250         260         270         280
[ 2558 ]      .a. ... ... ... ...  .c. ... ... ... ...  g.. ... ... ...  ... a..>
OspA-ACAI         250         260         270         280
[ 2556 ]      .a. ... ... ... ...  .c. ... ... ... ...  g.. ... ... ...  a.. a..>
OspA-P-GAU        250         260         270         280
[ 2544 ]      .a. ... ... ... ...  .c. ... ... ... ...  g.. ... ... ...  a.. a..>

290         300         310         320         330
               *           *           *           *           *
OspA-B31     ACC ACA CTT GAA GTT TTC AAA GAA GAT GGC AAA ACA CTA GTA TCA AAA
             TGG TGT GAA CTT CAA AAG TTT CTT CTA CCG TTT TGT GAT CAT AGT TTT

OspA-B31     290         300         310         320         330
[ 3288 ]     ... ... ... ... ... ... ... ... ... ... ... ... ... ... ... ...>

OspA-KA      290         300         310         320         330
[ 3288 ]     ... ... ... ... ... ... ... ... ... ... ... ... ... ... ... ...>

OspA-N40     290         300         310         320         330
[ 3276 ]     ... ... ... ... ... ... ... ... ... ... ... ... ... ... ... ...>

OspA-ZS7     290         300         310         320         330
[ 3264 ]     ... ... ... ... ... ... ... ... ... ... ... ... ... ... ... ...>

OspA-25015   290         300         310         320         330
[ 2802 ]     ... ... ... ... ..a ... ... ... ... ... ... t.. ..g ... ...>

OspA-TRO     290         300         310         320         330
[ 2648 ]     ... ... t.. ... a.. ... ... ... ... ... ... t.. ... ... ...>

OspA-K48     290         300         310         320         330
[ 2584 ]     ..t .a. t.. ... a.. ... ... ... .c. ... ... t.. ... ... ...>

OspA-HE 11   290         300         310         320         330
[ 2580 ]     ... ... t.. ... a.c ... ... ... ... ... ... t.. ... -.g ...>

OspA-DK29    290         300         310         320         330
[ 2566 ]     ..t .a. t.. ... a.. ... ... ... ... ... ... t.. ... -.. ...>

OspA-Ip90    290         300         310         320         330
[ 2562 ]     ... ... t.. ... a.c ... ... ... ... ... ... t.. ... -.. ...>

OspA-BO      290         300         310         320         330
[ 2558 ]     ... ... t.c ... c.. ... ... ... ... ... ... t.. ..g -.. .g.>

OSPA-IP3     290         300         310         320         330
[ 2558 ]     ... ... t.c ... c.. ... ... ... ... ... ... t.. ..g - .. .g.>
```

FIG. 42F

```
OspA-PKO    290         300         310         320         330
[ 2558 ]    ... ... t.c ... c.. ... ... ... ... ... ... t.. ..g ... .g.>

OspA-ACAI   290         300         310         320         330
[ 2556 ]    ... ... t.c ... c.. ... ... ... ... ... ... t.. ..g ... .g.>

OspA-P-GAU  290         300         310         320         330
[ 2544 ]    ... ... t.c ... c.. ..a ... ... ... ... ... t.. ..g ... .g.>

340         350         360         370         380
                 *           *           *           *           *
OspA-B31    AAA GTA ACT TCC AAA GAC AAG TCA TCA ACA GAA GAA AAA TTC AAT GAA
            TTT CAT TGA AGG TTT CTG TTC AGT AGT TGT CTT CTT TTT AAG TTA CTT

OspA-B31    340         350         360         370         380
[ 3288 ]    ... ... ... ... ... ... ... ... ... ... ... ... ... ... ...>

OspA-KA     340         350         360         370         380
[ 3288 ]    ... ... ... ... ... ... ... ... ... ... ... ... ... ... ...>

OspA-N40    340         350         360         370         380
[ 3276 ]    ... ... ... ... ... ... ... ... ... ... ... ... ... ... ...>

OspA-ZS7    340         350         360         370         380
[ 3264 ]    ... ... ... ... ... ... ... ... ... ... ... ... ... ... ...>

OspA-25015  340         350         360         370         380
[ 2802 ]    ... ag. ... ..t ... ..t ... ... ... ... ... ..g ... ... ...>

OspA-TRO    340         350         360         370         380
[ 2648 ]    ... ... .a. ..t ... ..t ... ... .t. ... ... ... ... ..c .c.>

OspA-K48    340         350         360         370         380
[ 2584 ]    ... ... ..c ctt ... ... ... ... ... ... ... ... ... ..c ...>

OspA-HE11   340         350         360         370         380
[ 2580 ]    ... ... ..c ctt ... ... ... ... ... ... ... ... ... ..c ...>

OspA-DK29   340         350         360         370         380
[ 2566 ]    ... ... ..c ctt ... ... ... ... ... ... ... ... ... ..c .g.>

OspA-Ip90   340         350         360         370         380
[ 2562 ]    ... ... ..c ctt ... ... ... ... ... ... ... ... ... ..c .c.>

OspA-BO     340         350         360         370         380
[ 2558 ]    ... ... .g. ..t ... ... ..a a.. ... ... ..t ... .tg ... ...>

OSPA-IP3    340         350         360         370         380
[ 2558 ]    ... ... .g. ..t ... ... ..a a.. ... ... ..t ... .tg ... ...>

OspA-PKO    340         350         360         370         380
[ 2558 ]    ... ... .g. ..t ... ... ..a a.. ... ... ..t ... .tg ... ...>

OspA-ACAI   340         350         360         370         380
[ 2556 ]    ... ... .g. ..t ... ... ..a a.. ... ... ..t ... .tg ... ...>
```

FIG. 42G

```
OspA-P-GAU    340         350         360         370         380
[ 2544 ]      ... ... .g. ...t .g. ... ..a a.. ... ... ..t ... .tg ... ... ...>

390         400         410         420         430
               *           *           *           *           *
OspA-B31      AAA GGT GAA GTA TCT GAA AAA ATA ATA ACA AGA GCA GAC GGA ACC AGA
              TTT CCA CTT CAT AGA CTT TTT TAT TAT TGT TCT CGT CTG CCT TGG TCT

OspA-B31      390         400         410         420         430
[ 3288 ]      ... ... ... ... ... ... ... ... ... ... ... ... ... ... ... ...>

OspA-KA       390         400         410         420         430
[ 3288 ]      ... ... ... ... ... ... ... ... ... ... ... ... ... ... ... ...>

OspA-N40      390         400         410         420         430
[ 3276 ]      ... ... ... ... ... ... ... ... ... ... ... ... ... ... ... ...>

OspA-ZS7      390         400         410         420         430
[ 3264 ]      ... ... ... ... ... ... ... ... ... ... ... ... ... ... ... ...>

OspA-25015    390         400         410         420         430
[ 2802 ]      ... ..c ... t.. gt. ... ... ..g g.. ... ... a.. ... ... .t.>

OspA-TRO      390         400         410         420         430
[ 2648 ]      ... ... ... t.. ... ... ... .c. ... ct. ... ... a.. ... ... ..g>

OspA-K48      390         400         410         420         430
[ 2584 ]      ..g ... ... ac. ... ... ... .c. ... gt. ... ... a.t ... ... ...>

OspA-HE 11    390         400         410         420         430
[ 2580 ]      ..g ... ... a.. ... ... ... .c. ... gt. ... ... a.t ... ... ...>

OspA-DK29     390         400         410         420         430
[ 2566 ]      ..g ... ... ac. ... ... ... .c. ... gt. ... ... a.t ... ... ...>

OspA-Ip90     390         400         410         420         430
[ 2562 ]      ..g ... ... .c. ... ... ... .c. ... gt. ... ... a.t ... ... ...>

OspA-30       390         400         410         420         430
[ 2558 ]      ... ... ... t.g ... .c. ... .cc ..g ... ... .a. a.t ... ... .a.>

OSPA-IP3      390         400         410         420         430
[ 2558 ]      ... ... ... t.g ... .c. ... .cc ..g ... ... .a. a.t ... ... .a.>

OspA-PKO      390         400         410         420         430
[ 2558 ]      ... ... ... t.g ... .c. ... .cc ..g ... ... .a. a.t ... ... .a.>

OspA-ACAI     390         400         410         420         430
[ 2556 ]      ... ... ... t.g ... .c. ... .cc ..g ... ... .a. a.t ... ... .a.>

OspA-P-GAU    390         400         410         420         430
[ 2544 ]      ... ... ... t.g ... .c. ... .cc ..g ... ... .a. a.t ... ... .a.>

440         450         460         470         480
               *           *           *           *           *
OspA-B31      CTT GAA TAC ACA GGA ATT AAA AGC GAT GGA TCT GGA AAA GCT AAA GAG
```

FIG. 42H

```
                    GAA CTT ATG TGT CCT TAA TTT TCG CTA CCT AGA CCT TTT CGA TTT CTC
OspA-B31              440         450         460         470         480
[ 3288 ]            ... ... ... ... ... ... ... ... ... ... ... ... ... ... ...>

OspA-KA               440         450         460         470         480
[ 3288 ]            ... ... ... ... ... ... ... ... ... ... ... ... ... ... ...>

OspA-N40              440         450         460         470         480
[ 3276 ]            ... ... ... ... .a. ... ... ... ... ... ... ... ... ... ...>

OspA-ZS7              440         450         460         470         480
[ 3264 ]            ... ... ... ... .a. ... ... ... ... ... ... ... ... ... ...>

OspA-25015            440         450         460         470         480
[ 2802 ]            ... ... ... ... ... ... ... ... ... ..c ... ... ... ... ..a>

OspA-TRO              440         450         460         470         480
[ 2648 ]            ... ... ... ... .a. ..a ... ... ... a.c ... ... ... ... ..a>

OspA-K48              440         450         460         470         480
[ 2584 ]            ... ... ... ... .ac ..a ... ... ... ..c ... ... ... ... ..a>

OspA-HE 11            440         450         460         470         480
[ 2580 ]            ... ... ... ... .ac ..a ... ... ... aa. a.c ... ... ... ..a>

OspA-DK29             440         450         460         470         480
[ 2565 ]            ... ... ... ... .ac ..a ... ... ... ..c ... ... ... ... ..a>

OspA-Ip90             440         450         460         470         480
[ 2562 ]            ... ... ... ... .ac ..a ... ... ... aa. a.c ... ... ... ..a>

OspA-BO               440         450         460         470         480
[ 2558 ]            ... ... ..t ... .a. ..g ... ... ... ... a.c ... ... ... ..a>

OSPA-IP3              440         450         460         470         480
[ 2558 ]            ... ... ..t ... .a. ..g ... ... ... ... a.c ... ... ... ..a>

OspA-PKO              440         450         460         470         480
[ 2558 ]            ... ... ..t ... .a. ..g ... ... ... ... a.c ... ... ... ..a>

OspA-ACAI             440         450         460         470         480
[ 2556 ]            ... ... ..t ... .a. ..g ... ... ... ... a.c ... ... ... ..a>

OspA-P-GAU            440         450         460         470         480
[ 2544 ]            ... ... ..t ... .a. ..g ... ... ... ... a.c ... ... ... ..a>

490         500         510         520
OspA-B31            GTT TTA AAA GGC TAT GTT CTT GAA GGA ACT CTA ACT GCT GAA AAA ACA
                    CAA AAT TTT CCG ATA CAA GAA CTT CCT TGA GAT TGA CGA CTT TTT TGT

OspA-B31                    490         500         510         520
[ 3288 ]            ... ... ... ... ... ... ... ... ... ... ... ... ... ... ...>

OspA-KA                     490         500         510         520
[ 3288 ]            ... ... ... ... ... ... ... ... ... ... ... ... ... ... ...>
```

FIG. 42I

```
OspA-N40          490         500         510         520
[ 3276 ]       ... ... ... ... ... ... ... ... ... ... ... ... ... ...>

OspA-ZS7          490         500         510         520
[ 3264 ]       ... ... ... a.. ... ... ... ... ... ... t.. ... ... ... ... ...>

OspA-25015        490         500         510         520
[ 2802 ]       ac. ... ... .aa ... ... ... ... ... ... ... ... ... ... g.. .>

OspA-TRO.         490         500         510         520
[ 2648 ]       .c. .:. ... .a. .t. .c. ... ... ... ... g.. ...c ...c ... ...> cgg
                                                           |
OspA-K48          490         500         510         520|   530
[ 2584 ]       ... ... ... .a. .t. ac. ... ... ... ... g.. ... ..c ... ...> cgg
                                                           |
OspA-HE 11        490         500         510         520|   530
[ 2580 ]       ... ... ... .a. .t. ac. ... ... ... ... g.. ... ..c ... ...> cgg
                                                           |
OspA-DK29         490         500         510         520|   530
[ 2566 ]       ... ... ... .a. .t. ac. ... ... ... ... g.. ... ..c ... ...> cgg
                                                           |
OspA-Ip90         490         500         510         520|   530
[ 2562 ]       ... ... ... .a. .t. .c. ... ... ... ... g.. ... ..c ... ...>

OspA-BO           490         500         510         520
[ 2558 ]       ... ... ... aa. .t. ac. ... ... ... .aa g.. g.. aa. ...t ... gt.>

OSPA-IP3          490         500         510         520
[ 2558 ]       ... ... ... aa. .t. ac. ... ... ... .aa g.. g.. aa. ...t ... gt.>

OspA-PKO          490         500         510         520
[ 2558 ]       ... ... ... aa. .t. ac. ... ... ... .aa g.. g.. aa. ...t ... gt.>

OspA-ACAI         490         500         510         520
[ 2556 ]       ... ... ... aa. .t. ac. ... ... ... .aa g.. g.. aa. ...t ... gt.>

OspA-P-GAU        490         500         510         520
[ 2544 ]       ... ... ... aag .t. ac. ... ... ... .aa g.. g.. aa. ...t ... gt.>

530         540         550         560         570
               *           *           *           *           *
OspA-B31      ACA TTG GTG GTT AAA GAA GGA ACT GTT ACT TTA AGC AAA AAT ATT TCA
              TGT AAC CAC CAA TTT CTT CCT TGA CAA TGA AAT TCG TTT TTA TAA AGT

OspA-B31      530         540         550         560         570
[ 3288 ]      ... ... ... ... ... ... ... ... ... ... ... ... ... . .. ...>

OspA-KA       530         540         550         560         570
```

FIG. 42J

```
[ 3288 ]      ...  ...  ...  ...  ...  ...  ...  ...  ...  ...  ...  ...  ...  ...  ...  ...>
OspA-N40      530         540         550         560         570
[ 3276 ]      ...  ...  ...  ...  ...  ...  ...  ...  ...  ...  ...  ...  ...  ...  ...  ...>
OspA-ZS7      530         540         550         560         570
[ 3264 ]      ...  ...  ...  ...  ...  ...  ...  ...  ...  ...  ...  ...  ...  ...  ...  ...>
OspA-25015    530         540         550         560         570
[ 2802 ]      ...  ...  ...  ...  ...  ...  ...  ...  ...  ...  ..t  ..g  c.c  ...  ...  ...>
OspA-TRO      530         540         550         560         570
[ 2648 ]      ...  ...  aaa  ...  .c.  ...  ..c  ...  ...  gt.  ...  ...  ...  c.c  ...  c..>
OspA-K43                  540         550         560-        570
[ 2534 ]      ...  ...  aaa  ...  .c.  ...  ..c  ...  ...  gt.  ...  ...  ..g  ..c  ...  .t.>
OspA-HE II                540         550         560         570
[ 2580 ]      ...  ...  aaa  ...  .c.  ..g  ..c  ...  ...  ...  ...  ...  ..g  ..c  ...  ...>
OspA-DK29                 540         550         560         570
[ 2566 ]      ...  ...  aaa  ...  .c.  ...  ..c  ...  ...  gt.  ...  ...  ..g  ..c  ...  .t.>
OspA-Ip90                 540         550         560         570
[ 2562 ]      ...  ..a  aaa  ...  .c.  ...  ..c  ...  ...  gt.  ...  ...  ...  c.c  ...  ...>
OspA-BO       530         540         550         560         570
[ 2558 ]      ...  ...  .aa  ...a ...  ...  ...  ..c  ...  ...  ...  ..t  ..g  g.a  ...  g..>
OSPA-IP3      530         540         550         560         570
[ 2558 ]      ...  .:.  .aa  ...a ...  ...  ...  ..c  ...  ...  ...  ..t  ..g  g.a  ...  g..>
OspA-PKO      530         540         550         560         570
[ 2558 ]      ...  ...  .aa  ..a  ...  ...  ...  ..c  ...  ...  ...  ..t  ..g  g.a  ...  g..>
OspA-ACAI     530         540         550         560         570
[ 2556 ]      ...  ...  .aa  ..a  ...  ...  ...  ..c  ...  ...  ...  ..t  ..g  g.a  ...  g..>
OspA-P-GAU    530         540         550         560         570
[ 2544 ]      ...  ...  .aa  ..a  ...  ...  ...  ..c  ...  ...  ...  ..t  ..g  g.a  ...  g..>

580         590         600         610         620
OspA-B31      AAA TCT GGG GAA GTT TCA GTT GAA CTT AAT GAC ACT GAC AGT AGT GCT
              TTT AGA CCC CTT CAA AGT CAA CTT GAA TTA CTG TGA CTG TCA TCA CGA

OspA-B31      580         590         600         610         620
[ 3288 ]      ...  ...  ...  ...  ...  ...  ...  ...  ...  ...  ...  ...  ...  ...  ...>
OspA-KA       580         590         600         610         620
[ 3288 ]      ...  ...  ...  ...  ...  ...  ...  ...  ...  ...  ...  ...  ...  ...  ...>
OspA-N40      580         590         600         610         620
[ 3276 ]      ...  ...  ...  ...  ...  ...  ...  ...  ...  ...  ...  ...  ...  ...  ...>
OspA-ZS7      580         590         600         610         620
[ 3264 ]      ...  ...  ...  ...  ...  ...  ...  ...  ...  ...  ...  ...  ...  ...  ...>
```

FIG. 42K

```
OspA-25015     580          590          600          610          620
[ 2802 ]      ... ... ..a ... ..a a.. .c. ... ... ... ... ... ... .c. caa>

OspA-TRO       580          590          600          610          620
[ 2648 ]      ..c ... ..a ... a.a a.. ... ..g ... ... ... t.. a.. tc. .c. cag>

OspA-K48       580          590·         ·600         610          620
[ 2584 ]      ... ..c ..a ... a.a a.. ... .c. ... g.. ... t.. ... .c. .c. cag>

OspA-HE       11580         590    ·     600          610          620
[ 2580 ]      ... ..c ..a ... a.a a.. ... .c. ... g.. ... ... ... tc. .-- ..g>

OspA-DK29      580          590          600          610          620
[ 2566 ]      ... ..c ..a ... a.a a.. ic. .c. ... g.. ... .t.. ... .c. .c. cgg>

OspA-Ip90      580          590          600          610          620
[ 2562 ]      ..c ... ..a ... a.a a.. ... ..g ... ... ... t.. ... .c. .c. cag>

OspA-BO        580          590          600          610          620
[ 2558 ]      ... ... ..a ... ..a a.. ... .ct ... ... ... ... a.. .c. .c. cag>

OSPA-IP3       580          590          600          610          620
[ 2558 ]      ... ... ..a ... ..a a.. ... .ct ... ... ... ... a.. .c. .c. cag>

OspA-PKO       580          590          600          610          620
[ 2558 ]      ... ... ..a ... ..a a.. ... .ct ... ... ... ... a.. .c. .c. cag>

OspA-ACAI      580          590          600          610          620
[ 2556 ]      ... ... ..a ... ..a a.. ... .ct ... ... ... ... a.. .c. .c. cag>

OspA-P-GAU     580          590          600          610          620
[ 2544 ]      ... ... ..a ... ..a a.. ... .ct ... ... ... ... a.. .c. .c. cag>

630          640          650          660          670
                *     *      *     *      *     *      *     *      *     *
OspA-B31      GCT ACT AAA AAA ACT GCA GCT TGG AAT TCA GGC ACT TCA ACT TTA ACA
              CGA TGA TTT TTT TGA CGT CGA ACC TTA AGT CCG TGA AGT TGA AAT TGT

OspA-B31          630          640          650          660          670
[ 3288 ]      ... ... ... ... ... ... ... ... ... ... ... ... ... .- . ...>

OspA-KA           630          640          650          660          670
[ 3288 ]      ... ... ... ... ... ... ... ... ... ... ... ... ... .- . ...>

OspA-N40          630          640          650          660          670
[ 3276 ]      ... ... ... ... ... ... ... ... ... ... ... ... ... .- . ...>

OspA-Z57          630          640          650          660          670
[ 3264 ]      ... ... ... ... ... ... ... ... ... ... ... ... ... .- . ...>

OspA-25015        630          640          650          660          670
[ 2802 ]      ... ... ... ... ... .gg aaa ... g.. g.. ... ... ... .- . ...>

OspA-TRO          630          640          650          660          670
[ 2648 ]      ... ... ... ... ... .g. aaa ... g.. ... aat ... ..c ... .- . ...>
```

FIG. 42L

```
OspA-K48      630        640        650        660        670
[ 2584 ]      ... ... ... ... ... .g. aaa ... g.. ... aaa ... ..c ... ... ...>

OspA-HE 11    630        640        650        660        670
[ 2580 ]      ..- .a. ... ... t.c .g. a.a ... g.. ... ..t ... ..t ... ... ...>

OspA-DK29     630        640        650        660        670
[ 2556 ]      ... ... ... ... ... .g. aaa ... g.. ... aag ... ..c ... ... ...>

OspA-Ip90     630        640        650        660        670
[ 2562 ]      ... ... ... ... ... .g. a.a ... g.. ... aag ... ..c ... ... ...>

OspA-BÖ       630        640        650        660        670
[ 2558 ]      ... ... ... ... ... .gc ..a ... g.. ... aaa ... ..t ... ... ...>

OSPA-IP3      630        640        650        660        670
[ 2558 ]      ... ... ... ... ... .gc ..a ... g.. ... aaa ... ..t ... ... ...>

OspA-PKO      630        640        650        660        670
[ 2558 ]      ... ... ... ... ... .gc ..a ... g.. ... aaa ... ..t ... ... ...>

OspA-ACAI     630        640        650        660        670
[ 2556 ]      ... ... ... ... ... .gc ..a ... g.. ... aaa ... ..t ... ... ...>

OspA-P-GAU    630        640        650        660        670
[ 2544 ]      ... ... ... ... ... .gc ..a ... g.. ... aaa ... ..t ... ... ...>

680        690        700        710        720
               *    *     *    *     *    *     *    *     *    *
OspA-B31      ATT ACT GTA AAC AGT AAA AAA ACT AAA GAC CTT GTG TTT ACA AAA GAA
              TAA TGA CAT TTG TCA TTT TTT TGA TTT CTG GAA CAC AAA TGT TTT CTT

OspA-B31      680        690        700        710        720
[ 3288 ]      ... ... ... ... ... ... ... ... ... ... ... ... ... ... ... ...>

OspA-KA       680        690        700        710        720
[ 3288 ]      ... ... ... ... ... ... ... ... ... ... ... ... ... ... ... ...>

OspA-N40      680        690        700        710        720
[ 3276 ]      ... ... ... ... ... ... ... ... ... ... ... ... ... ... ... ...>

OspA-ZS7      680        690        700        710        720
[ 3264 ]      ... ... ... ... ... ... ... ... ... ... ... ... ... ... ... ...>

OspA-25015    680        690        700        710        720
[ 2802 ]      ... ... ... ... .ac ... ... ... .c. ... ...a ... ... ... ..c..>

OspA-TRO      680        690        700        710        720
[ 2648 ]      ... .g. ...g ..t ..c ... ... ... ... a.. a.. ..a ... ... . ...>

OspA-K48      680        690        700        710        720
[ 2584 ]      ... .g. ...g ..t ..c c.. ... ..c ... a.. ... ..a ..c ... .. ...>

OspA-HE 11    680        690        700        710        720
[ 2580 ]      ... .g. aa. ... ..a c.. ... ... c.a ... ..a ..c ... .. - ...>

OspA-DK29     680        690        700        710        720
```

FIG. 42M

```
[ 2566 ]       . .... .g. ...g ..t ..c c..  ...  ..c  ... a..  ...  ..a ..c  ...  ... ...>
OspA-Ip90          680          690          700          710          720
[ 2562 ]       ... .g. ...g ..t ..c cg.  ...  ..c  ... a..  ...  ..a ..c  ...  ... ...>
OspA-BO            680          690          700          710          720
[ 2558 ]       ... .g. ...t ...  ..c  ...  ...  ...  .c. c.a ...  ...  ...  ..t  ... c..>
OSPA-IP3           680          690          700          710          720
[ 2558 ]       ... .g. ...t ...  ...  ...  ...  ...  .c. c.a ...  ...  ...  ..t  ... c..>
OspA-PKO           680          690          700          710          720
[ 2558 ]       ... .g. ...t ...  ..c  ...  ...  ...  .c. c.a ...  ...  ...  ..t  ... c..>
OspA-ACAI          680          690          700          710          720
[ 2556 ]       ... .g. ...t ...  ..c  ...  ...  ...  .c. c.a ...  ...  ...  ..t  ... c..>
ospA-P-GAU         680          690          700          710          720
[ 2544 ]       ... .g. ...t ...  ..c  ...  ...  ...  .c. c.a ...  ...  ...  ..t  ... c..>

730          740          750          760
OspA-B31       AAC ACA ATT ACA GTA CAA CAA TAC GAC TCA AAT GGC ACC AAA TTA GAG
               TTG TGT TAA TGT CAT GTT GTT ATG CTG AGT TTA CCG TGG TTT AAT CTC

OspA-B31              730          740          750          760
[ 3288 ]       ... ... ... ... ... ... ... ... ... ... ... ... ... ... ... ...>
OspA-KA               730          740          750          760
[ 3288 ]       ... ... ... ... ... ... ... ... ... ... ... ... ... ... ... ...>
OspA-N40              730          740          750          760
[ 3276 ]       ... ... ... ... ... ... ... ... ... ... ... ... ... ... ... ...>
OspA-ZS7              730          740          750          760
[ 3264 ]       ... ... ... ... ... ... ... ... ... ... ... ... ... ... ... ...>
OspA-25015            730          740          750          760
[ 2802 ]       g.. ... ... ... tc. ... a.. ... ... ... gca ..a ... ..c ..g ..a>
OspA-TRO              730          740          750          760
[ 2648 ]       g.. ... ..a ... ... ... a.. ... ... ... gca ... ... ..t c.. ..a>
OspA-K48              730          740          750          760          770
[ 2584 ]       g.. ... ..a ... ... ... a.. ... ... ... gca ... ... ..t c.. ..a>
OspA-HE 11            730          740          750          760
[ 2580 ]       g.. ... ..a ... ... ... a.c ... ... ... gca ... ... ..t c.. ..a>
OspA-DK29             730          740          750          760          770
[ 2566 ]       g.. ... ..a ... ... ... ag. ... ... ... gca ... ... ..t c.. ..a>
OspA-Ip90             730          .740         750          760          770
[ 2562 ]       g.. ... ..a ... ... ... a... ... ... ... gca ... ... ..t c.. ..a>
OspA-BO               730          740          750          760
[ 2558 ]       g.. ... ..a ..t ... ... a.. ... ... ..c gca ..t ... ..t ... ..a>
```

FIG. 42N

```
OSPA-IP3            730             740             750             760
[ 2558 ]    g.. ... ..a ..t ... ... a.. ... ... ..c gca ..t ... ..t ... ..a>

OspA-PKO            730             740             750             760
[ 2558 ]    g.. ... ..a ..t ... ... a.. ... ... ..c gca ..t ......t ... ..a>

OspA-ACAI           730             740             750             760
[ 2556 ]    g.. ... ..a ..t ... ... a.. ... ... ..c gca ..t ... ..t ... ..a> ospA-P-GAU          730             740             750             760
[ 2544 ]    t.. ... ..a ..t ... a.. ... ... ... ..c gca ..t ... ..t ... ..a>

770         780         790         800         810
             *           *           *           *           *
OspA-B31    GGG TCA GCA GTT GAA ATT ACA AAA CTT GAT GAA ATT AAA AAC GCT TTA
            CCC AGT CGT CAA CTT TAA TGT TTT GAA CTA CTT TAA TTT TTG CGA AAT

OspA-B31    770         780         790         800         810
[ 3288 ]    ... ... ... ... ... ... ... ... ... ... ... ... ... ... ...>

OspA-KA     770         780         790         800         810
[ 3288 ]    ... ... ... ... ... ... ... ... ... ... ... ... ... ... ...>

OspA-N40    770         780         790         800         810
[ 3276 ]    ... ... ... ... ... ... ... ... ... ... ... ... ... ... ...>

OspA-ZS7    770         780         790         800         810
[ 3264 ]    ... ... ... ... ... ... ... ... ... ... ... ... ... ... ...>

OspA-25015  770         780         790         800         810
[ 2802 ]    ..c a.. ... ..c ... ... .a. .c. ... ... ... c.. ... ... ...>

OspA-TRO    770         780         790         800         810
[ 2648 ]    ..c aac ... ..c ... ... .a. .c. ... ... ... c.. ... ... ...>

OspA-K48                780         790         800         810
[ 2584 ]    ..c aa. ... ..c ... ... .c. ... a.a ... c.. ... ... ... ...>

OspA-HE 11  770         780         790         800         810
[ 2580 ]    ..c aa. ... ..c ... ... .c. ... a.a ... c.. ... ... ... ...>

OspA-DK29               780         790         800         810
[ 2566 ]    ..c aa. ... ..c ... ... .c. ... a.a ... c.. ... ... ... ...>

OspA-Ip90               780         790         800         810
[ 2562 ]    ..c aa. ... ..c ... ... .cg ... a.a ... c.. ... g.t ... ...>

OspA-BO     770         780         790         800         810
[ 2558 ]    ..c a.. ... ..c ... ... .a. .c. ... ... ... c.. ... ... ...>

OSPA-IP3    770         780         790         800         810
[ 2558 ]    ..c a.. ... ..c ... ... .a. .c. ... ... ... c.. ... ... ...>

OspA-PKO    770         780         790         800         810
[ 2558 ]    ..c a.. ... ..c ... ... .a. .c. ... ... ... c.. ... ... ...>
```

FIG. 42O

```
OspA-ACAI  770          780          790          800          810
[ 2556 ]   ..c a.. ... ..c ... ... .a. .c. ... ... ... c.. ... ... ... ..g> ospA-P-GAU 770          780          790          800          810
[ 2544 ]   ..c a.. ... ..c ... ... .a. .c. ... ... ... c.. ... ... ... ...>

820
                 *
OspA-B31       AAA TAA
               TTT ATT

OspA-B31        820
[ 3288 ]       ... ...>

OspA-KA         820
[ 3288 ]       ... ...>

OspA-N40        820
[ 3276 ]       ... ...>

OspA-ZS7        820
[ 3264 ]       ... ...>

OspA-25015
[ 2802 ]       .g.>

OspA-TRO        820
[ 2648 ]       ... ..>

OspA-K48   820
[ 2584 ]       ... ...>

OspA-HE 11      820
[ 2580 ]       ... ..>

OspA-DK29 820
[ 2566 ]       ... ...>

OspA-Ip90 820
[ 2562 ]       ... ..>

OspA-BO         820
[ 2558 ]       ... ..>

OSPA-IP3        820
[ 2558 ]       ... ..>

OspA-PKO        820
[ 2558 ]       ... ..>

OspA-ACAI       820
[ 2556 ]       ... ...> ospA-P-GAU      820
[ 2544 ]       ... ...>
```

FIG. 42P

```
              10              20              30              40
         *    *     *    *     *    *     *    *     *    *     *
       ATG AAA AAA TAT TTA TTG GGA ATA GGT CTA ATA TTA GCC TTA ATA
       TAC TTT TTT ATA AAT AAC CCT TAT CCA GAT TAT AAT CGG AAT TAT 50              60              70              80              90
         *    *     *    *     *    *     *    *     *    *     *
       GCA TGT AAG CAA AAT GTT AGC AGC CTT GAT GAA AAA AAT AGC GTT
       CGT ACA TTC GTT TTA CAA TCG TCG GAA CTA CTT TTT TTA TCG CAA 100             110             120             130
         *    *     *    *     *    *     *    *     *    *     *
       TCA GTA GAT TTA CCT GGT GGA ATG ACA GTT CTT GTA AGT AAA GAA
       AGT CAT CTA AAT GGA CCA CCT TAC TGT CAA GAA CAT TCA TTT CTT 140             150             160             170             180
         *    *     *    *     *    *     *    *     *    *     *
       AAA GAC AAA CAC GGT AAA TAC AGT CTA GAG GCA ACA GTA GAC AAG
       TTT CTG TTT CTG CCA TTT ATG TCA GAT CTC CGT TGT CAT CTG TTC 190             200             210             220
         *    *     *    *     *    *     *    *     *    *     *
       CTT GAG CTT AAA GGA ACT TCT GAT AAA AAC AAC GGT TCT GGA ACA
       GAA CTC GAA TTT CCT TGA AGA CTA TTT TTG TTG CCA AGA CCT TGT 230             240             250             260             270
         *    *     *    *     *    *     *    *     *    *     *
       CTT GAA GGT GAA AAA ACT GAC AAA AGT AAA GTA AAA TTA ACA ATT
       GAA CTT CCA CTT TTT TGA CTG TTT TCA TTT CAT TTT AAT TGT TAA 280             290             300             310
         *    *     *    *     *    *     *    *     *    *     *
       GCT GAT GAC CTA AGT CAA ACT AAA TTT GAA ATT TTC AAA GAA GAT
       CGA CTA CTG GAT TCA GTT TGA TTT AAA CTT TAA AAG TTT CTT CTA 320             330             340             350             360
         *    *     *    *     *    *     *    *     *    *     *
       GCC AAA ACA TTA GTA TCA AAA AAA GTA ACC CTT AAA GAC AAG TCA
       CGG TTT TGT AAT CAT AGT TTT TTT CAT TGG GAA TTT CTG TTC AGT 370             380             390             400
         *    *     *    *     *    *     *    *     *    *     *
       TCA ACA GAA GAA AAA TTC AAC GAA AAG GGT GAA ACA TCT GAA AAA
       AGT TGT CTT CTT TTT AAG TTG CTT TTC CCA CTT TGT AGA CTT TTT 410             420             430             440             450
         *    *     *    *     *    *     *    *     *    *     *
       ACA ATA GTA AGA GCA AAT GGA ACC AGA CTT GAA TAC ACA GAC ATA
       TGT TAT CAT TCT CGT TTA CCT TGG TCT GAA CTT ATG TGT CTG TAT 460             470             480             490
         *    *     *    *     *    *     *    *     *    *     *
       AAA AGC GAT GGA TCC GGA AAA GCT AAA GAA GTT TTA AAA GAC TTT
       TTT TCG CTA CCT AGG CCT TTT CGA TTT CTT CAA AAT TTT CTG AAA 500             510             520             530             540
         *    *     *    *     *    *     *    *     *    *     *
       ACT CTT GAA GGA ACT CTA GCT GCT GAC GGC AAA ACA ACA TTG AAA
       TGA GAA CTT CCT TGA GAT CGA CGA CTG CCG TTT TGT TGT AAC TTT 550             560             570             580
         *    *     *    *     *    *     *    *     *    *     *
       GTT ACA GAA GGC ACT GTT GTT TTA ACC AAG AAC ATT TTA AAA TCC
```

FIG. 43A

```
        CAA TGT CTT CCG TGA CAA CAA AAT TCG TTC TTG TAA AAT TTT AGG 590         600         610         620         630
             *           *           *           *     *     *     *     *
        GGA GAA ATA ACA GTT GCA CTT GAT GAC TCT GAC ACT ACT CAG GCT
        CCT CTT TAT TGT CAA CGT GAA CTA CTG AGA CTG TGA TGA GTC CGA 640         650         660         670
             *     *     *     *     *     *     *     *     *
        ACT AAA AAA ACT GGA AAA TGG GAT TCA AAT ACT TCC ACT TTA ACA
        TGA TTT TTT TGA CCT TTT ACC CTA AGT TTA TGA AGG TGA AAT TGT 680         690         700         710         720
             *     *     *     *     *     *     *     *     *     *
        ATT AGT GTG AAT AGC AAA AAA ACT AAA AAC ATT GTA TTT ACA AAA
        TAA TCA CAC TTA TCG TTT TTT TGA TTT TTG TAA CAT AAA TGT TTT 730         740         750         760
             *     *     *     *     *     *     *     *     *
        GAA GAC ACA ATA ACA GTA CAA AAA TAC GAC TCA GCA GGC ACC AAT
        CTT CTG TGT TAT TGT CAT GTT TTT ATG CTG AGT CGT CCG TGG TTA 770         780         790         800         810
             *     *     *     *     *     *     *     *     *     *
        CTA GAA GGC AAC GCA GTC GAA ATT AAA ACA CTT GAT GAA CTT AAA
        GAT CTT CCG TTG CGT CAG CTT TAA TTT TGT GAA CTA CTT GAA TTT

820
             *     *     *
        AAC GCT TTA AAA TAG
        TTG CGA AAT TTT ATC
```

FIG. 43B

```
            10          20          30          40
             *           *           *           *          *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT 50          60          70          80          90
        *           *           *           *           *
GCA TGC AAG CAA AAT GTT AGC AGC CTT GAT GAA AAA AAC AGC GCT
CGT ACG TTC GTT TTA CAA TCG TCG GAA CTA CTT TTT TTG TCG CGA 100         110         120          130
             *           *           *           *           *
TCA GTA GAT TTG CCT GGT GAG ATG AAA GTT CTT GTA AGT AAA GAA
AGT CAT CTA AAC GGA CCA CTC TAC TTT CAA GAA CAT TCA TTT CTT 140         150         160         170         180
         *           *           *           *           *
AAA GAC AAA GAC GGT AAG TAC AGT CTA AAG GCA ACA GTA GAC AAG
TTT CTG TTT CTG CCA TTC ATG TCA GAT TTC CGT TGT CAT CTG TTC 190         200         210         220
             *           *           *           *           *
ATT GAG CTA AAA GGA ACT TCT GAT AAA GAC AAT GGT TCT GGA GTG
TAA CTC GAT TTT CCT TGA AGA CTA TTT CTG TTA CCA AGA CCT CAC 230         240         250         260         270
         *           *           *           *           *
CTT GAA GGT ACA AAA GAT GAC AAA AGT AAA GCA AAA TTA ACA ATT
GAA CTT CCA TGT TTT CTA CTG TTT TCA TTT CGT TTT AAT TGT TAA 280         290         300         310
             *           *           *           *           *
GCT GAC GAT CTA AGT AAA ACC ACA TTC GAA CTT TTA AAA GAA GAT
CGA CTG CTA GAT TCA TTT TGG TGT AAG CTT GAA AAT TTT CTT CTA 320         330         340         350         360
         *           *           *           *           *
GGC AAA ACA TTA GTG TCA AGA AAA GTA AGT TCT AGA GAC AAA ACA
CCG TTT TGT AAT CAC AGT TCT TTT CAT TCA AGA TCT CTG TTT TGT 370         380         390         400
             *           *           *           *           *
TCA ACA CAT GAA ATG TTC AAT GAA AAA GGT GAA TTG TCT GCA AAA
AGT TGT CTA CTT TAC AAG TTA CTT TTT CCA CTT AAC AGA CGT TTT 410         420         430         440         450
         *           *           *           *           *
ACC ATG ACA AGA GAA AAT GGA ACC AAA CTT GAA TAT ACA GAA ATG
TGG TAC TGT TCT CTT TTA CCT TGG TTT GAA CTT ATA TGT CTT TAC 450         470         480         490
             *           *           *           *           *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA 500         510         520         530         540
         *           *           *           *           *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT 550         560         570         580
             *           *           *           *           *
AAA GAA GGA ACC GTT ACT TTA AGT AAG GAA ATT GCA AAA TCT GCA
```

FIG. 44A

```
              TTT CTT CCT TGG CAA TGA AAT TCA TTC CTT TAA CGT TTT AGA CCT, 590         600         610         620         630
         *           *           *           *           *
        GAA GTA ACA GTT GCT CTT AAT GAC ACT AAC ACT ACT CAG GCT ACT
        CTT CAT TGT CAA CGA GAA TTA CTG TGA TTG TGA TGA GTC CGA TGA 640         650         660         670
               *           *           *           *
        AAA AAA ACT GGC GCA TGG GAT TCA AAA ACT TCT ACT TTA ACA ATT
        TTT TTT TGA CCG CGT ACC CTA AGT TTT TGA AGA TGA AAT TGT TAA 680         690         700         710         720
         *           *           *           *           *
        AGT GTT AAC AGC AAA AAA ACT ACA CAA CTT GTG TTT ACT AAA CAA
        TCA CAA TTG TCG TTT TTT TGA TGT GTT GAA CAC AAA TGA TTT GTT 730         740         750         760
               *           *           *           *
        GAC ACA ATA ACT GTA CAA AAA TAC GAC TCC GCA GGT ACC AAT TTA
        CTG TGT TAT TGA CAT GTT TTT ATG CTG AGG CGT CCA TGG TTA AAT 770         780         790         800         810
         *           *           *           *           *
        GAA GGC ACA GCA GTC GAA ATT AAA ACA CTT GAT GAA CTT AAA AAC
        CTT CCG TGT CGT CAG CTT TAA TTT TGT GAA CTA CTT GAA TTT TTG

820
               *
        GCT TTA AAA TAG
        CGA AAT TTT ATC
```

FIG. 44B

```
              10          20          30          40
       *   *    *    *    *    *    *    *    *    *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT 50          60          70          80          90
       *    *    *    *    *    *    *    *    *    *
GCA TGT AAG CAA AAT GTT AGC AGC CTT GAC GAG AAA AAC AGC GTT
CGT ACA TTC GTT TTA CAA TCG TCG GAA CTG CTC TTT TTG TCG CAA 100         110         120         130
       *    *    *    *    *    *    *    *    *    *
TCA GTA GAT TTG CCT GGT GAA ATG AAA GTT CTT GTA AGC AAA GAA
AGT CAT CTA AAC GGA CCA CTT TAC TTT CAA GAA CAT TCG TTT CTT 140         150         160         170         180
       *    *    *    *    *    *    *    *    *    *
AAA AAC AAA GAC GGC AAG TAC GAT CTA ATT GCA ACA GTA GAC AAG
TTT TTG TTT CTG CCG TTC ATG CTA GAT TAA CGT TGT CAT CTG TTC 190         200         210         220
       *    *    *    *    *    *    *    *    *    *
CTT GAG CTT AAA GGA ACT TCT GAT AAA AAC AAT GGA TCT GGA GTA
GAA CTC GAA TTT CCT TGA AGA CTA TTT TTG TTA CCT AGA CCT CAT 230         240         250         260         270
       *    *    *    *    *    *    *    *    *    *
CTT GAA GGC GTA AAA GCT GAC AAA AGT AAA GTA AAA TTA ACA ATT
GAA CTT CCG CAT TTT CGA CTG TTT TCA TTT CAT TTT AAT TGT TAA 280         290         300         310
       *    *    *    *    *    *    *    *    *    *
TCT GAC GAT CTA GGT CAA ACC ACA CTT GAA GTT TTC AAA GAA GAT
AGA CTG CTA GAT CCA GTT TGG TGT GAA CTT CAA AAG TTT CTT CTA 320         330         340         350         360
       *    *    *    *    *    *    *    *    *    *
GGC AAA ACA CTA GTA TCA AAA AAA GTA ACT TCC AAA GAC AAG TCA
CCG TTT TGT GAT CAT AGT TTT TTT CAT TGA AGG TTT CTG TTC AGT 370         380         390         400
       *    *    *    *    *    *    *    *    *    *
TCA ACA GAA GAA AAA TTC AAT GAA AAA GGT GAA GTA TCT GAA AAA
AGT TGT CTT CTT TTT AAG TTA CTT TTT CCA CTT CAT AGA CTT TTT 410         420         430         440         450
       *    *    *    *    *    *    *    *    *    *
ATA ATA ACA AGA GCA AAT GGA ACC AAA CTT GAA TAT ACA GAA ATG
TAT TAT TGT TCT CGT TTA CCT TGG TTT GAA CTT ATA TGT CTT TAC 460         470         480         490
       *    *    *    *    *    *    *    *    *    *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA 500         510         520         530         540
       *    *    *    *    *    *    *    *    *    *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT 550         560         570         580
       *    *    *    *    *    *    *    *    *    *
AAA GAA GGA ACC GTT ACT TTA AGT AAG GAA ATT TCA AAA TCT GGG
```

FIG. 45A

```
          TTT CTT CCT TGG CAA TGA AAT TCA TTC CTT TAA AGT TTT AGA CCC 590         600         610         620         630
          *     *     *     *     *     *     *     *     *
         GAA GTT TCA GTT GAA CTT AAT GAC ACT GAC AGT AGT GCT GCT ACT
         CTT CAA AGT CAA CTT GAA TTA CTG TGA CTG TCA TCA CGA CGA TGA 640         650         660         670
                *     *     *     *     *     *     *     *     *
         AAA AAA ACT GCA GCT TGG AAT TCA AAA ACT TCC ACT TTA ACA ATT
         TTT TTT TGA CGT CGA ACC TTA AGT TTT TGA AGG TGA AAT TGT TAA 680         690         700         710         720
          *     *     *     *     *     *     *     *     *
         AGT GTG AAT AGC CAA AAA ACC AAA AAC CTT GTA TTC ACA AAA GAA
         TCA CAC TTA TCG GTT TTT TGG TTT TTG GAA CAT AAG TGT TTT CTT 730         740         750         760
                *     *     *     *     *     *     *     *     *
         GAC ACA ATA ACA GTA CAA AAA TAC GAC TCA GCA GGC ACC AAT CTA
         CTG TGT TAT TGT CAT GTT TTT ATG CTG AGT CGT CCG TGG TTA GAT 770         780         790         800         810
          *     *     *     *     *     *     *     *     *
         GAA GGC AAA GCA GTC GAA ATT ACA ACA CTT AAA GAA CTT AAA AAC
         CTT CCG TTT CGT CAG CTT TAA TGT TGT GAA TTT CTT GAA TTT TTG

820
                *     *
         GCT TTA AAA TAA
         CGA AAT TTT ATT
```

FIG. 45B

```
              10             20             30              40
              *              *              *               *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT 50             60             70             80             90
       *              *              *              *              *
GCA TGC AAG CAA AAT GTT AGC AGC CTT GAT GAA AAA AAC AGC GCT
CGT ACG TTC GTT TTA CAA TCG TCG GAA CTA CTT TTT TTG TCG CGA 100            110            120            130
              *              *              *              *
TCA GTA GAT TTG CCT GGT GAG ATG AAA GTT CTT GTA AGT AAA GAA
AGT CAT CTA AAC GGA CCA CTC TAC TTT CAA GAA CAT TCA TTT CTT 140            150            160            170            180
       *              *              *              *              *
AAA GAC AAA GAC GGT AAG TAC AGT CTA AAG GCA ACA GTA GAC AAG
TTT CTG TTT CTG CCA TTC ATG TCA GAT TTC CGT TGT CAT CTG TTC 190            200            210            220
              *              *              *              *
ATT GAG CTA AAA GGA ACT TCT GAT AAA GAC AAT GGT TCT GGA GTG
TAA CTC GAT TTT CCT TGA AGA CTA TTT CTG TTA CCA AGA CCT CAC 230            240            250            260            270
       *              *              *              *              *
CTT GAA GGT ACA AAA GAT GAC AAA AGT AAA GCA AAA TTA ACA ATT
GAA CTT CCA TGT TTT CTA CTG TTT TCA TTT CGT TTT AAT TGT TAA 280            290            300            310
              *              *              *              *
GCT GAC GAT CTA AGT AAA ACC ACA TTC GAA CTT TTA AAA GAA GAT
CGA CTG CTA GAT TCA TTT TGG TGT AAG CTT GAA AAT TTT CTT CTA 320            330            340            350            360
       *              *              *              *              *
GGC AAA ACA TTA GTG TCA AGA AAA GTA AGT TCT AGA GAC AAA ACA
CCG TTT TGT AAT CAC AGT TCT TTT CAT TCA AGA TCT CTG TTT TGT 370            380            390            400
              *              *              *              *
TCA ACA GAT GAA ATG TTC AAT GAA AAA GGT GAA TTG TCT GCA AAA
AGT TGT CTA CTT TAC AAG TTA CTT TTT CCA CTT AAC AGA CGT TTT 410            420            430            440            450
       *              *              *              *              *
ACC ATG ACA AGA GAA AAT GGA ACC AAA CTT GAA TAT ACA GAA ATG
TGG TAC TGT TCT CTT TTA CCT TGG TTT GAA CTT ATA TGT CTT TAC 460            470            480            490
              *              *              *              *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA 500            510            520            530            540
       *              *              *              *              *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT 550            560            570            580
              *              *              *              *
AAA GAA GGA ACC GTT ACT TTA AGT AAG GAA ATT TCA AAA TCT GGG
```

FIG. 46A

```
          TTT CTT CCT TGG CAA TGA AAT TCA TTC CTT TAA AGT TTT AGA CCC
           590         600         610         620          630
            *       *    *      *     *     *      *      *     *
          GAA GTT TCA GTT GAA CTT AAT GAC ACT GAC AGT AGT GCT GCT ACT
          CTT CAA AGT CAA CTT GAA TTA CTG TGA CTG TCA TCA CGA CGA TGA 640         650         660         670
              *       *    *      *     *     *      *      *     *
          AAA AAA ACT GCA GCT TGG AAT TCA AAA ACT TCC ACT TTA ACA ATT
          TTT TTT TGA CGT CGA ACC TTA AGT TTT TGA AGG TGA AAT TGT TAA 680         690         700         710         720
            *       *    *      *     *     *      *      *     *
          AGT GTG AAT AGC CAA AAA ACC AAA AAC CTT GTA TTC ACA AAA GAA
          TCA CAC TTA TCG GTT TTT TGG TTT TTG GAA CAT AAG TGT TTT CTT 730         740         750         760
              *       *    *      *     *     *      *      *     *
          GAC ACA ATA ACA GTA CAA AAA TAC GAC TCA GCA GGC ACC AAT CTA
          CTG TGT TAT TGT CAT GTT TTT ATG CTG AGT CGT CCG TGG TTA GAT 770         780         790         800         810
            *       *    *      *     *     *      *      *     *
          GAA GGC AAA GCA GTC GAA ATT ACA ACA CTT AAA GAA CTT AAA AAC
          CTT CCG TTT CGT CAG CTT TAA TGT TGT GAA TTT CTT GAA TTT TTG

820
              *       *
          GCT TTA AAA TAA
          CGA AAT TTT ATT
```

FIG. 46B

```
        10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200             210             220             230             240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250             260             270             280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290             300             310             320             330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340             350             360             370             380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390             400             410             420             430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440             450             460             470             480
AAA GCA AAT GGT ACT AAA ACT AAA GCT GCT GAA GAA CTT GGA AAA TTA
TTT CGT TTA CCA TGA TTT TGA TTT CGA CGA CTT CTT GAA CCT TTT AAT
 K   A   N   G   T   K   T   K   G   A   E   E   L   G   K   L>

490             500             510             520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 55A

```
     530           540           550           560           570
  AAT TCA GTT AAA GAG CTT ACA AGC CCT GTT GTG GCA GAA AGT CCA AAA
  TTA AGT CAA TTT CTC GAA TGT TCG GGA CAA CAC CGT CTT TCA GGT TTT
   N   S   V   K   E   L   T   S   P   V   V   A   E   S   P   K>

580           590           600           610           620
  AAA CCT TCC ATG GCC AAG CAA AAT GTT AGC AGC CTT GAC GAG AAA AAC
  TTT GGA AGG TAC CGG TTC GTT TTA CAA TCG TCG GAA CTG CTC TTT TTG
   K   P   S   M   A   K   Q   N   V   S   S   L   D   E   K   N>

630           640           650           660           670
  AGC GTT TCA GTA GAT TTG CCT GGT GAA ATG AAA GTT CTT GTA AGC AAA
  TCG CAA AGT CAT CTA AAC GGA CCA CTT TAC TTT CAA GAA CAT TCG TTT
   S   V   S   V   D   L   P   G   E   M   K   V   L   V   S   K>

680           690           700           710           720
  GAA AAA AAC AAA GAC GGC AAG TAC GAT CTA ATT GCA ACA GTA GAC AAG
  CTT TTT TTG TTT CTG CCG TTC ATG CTA GAT TAA CGT TGT CAT CTG TTC
   E   K   N   K   D   G   K   Y   D   L   I   A   T   V   D   K>

730           740           750           760
  CTT GAG CTT AAA GGA ACT TCT GAT AAA AAC AAT GGA TCT GGA GTA CTT
  GAA CTC GAA TTT CCT TGA AGA CTA TTT TTG TTA CCT AGA CCT CAT GAA
   L   E   L   K   G   T   S   D   K   N   N   G   S   G   V   L>

770           780           790           800           810
  GAA GGC GTA AAA GCT GAC AAA AGT AAA GTA AAA TTA ACA ATT TCT GAC
  CTT CCG CAT TTT CGA CTG TTT TCA TTT CAT TTT AAT TGT TAA AGA CTG
   E   G   V   K   A   D   K   S   K   V   K   L   T   I   S   D>

820           830           840           850           860
  GAT CTA GGT CAA ACC ACA CTT GAA GTT TTC AAA GAA GAT GGC AAA ACA
  CTA GAT CCA GTT TGG TGT GAA CTT CAA AAG TTT CTT CTA CCG TTT TGT
   D   L   G   Q   T   T   L   E   V   F   K   E   D   G   K   T>

870           880           890           900           910
  CTA GTA TCA AAA AAA GTA ACT TCC AAA GAC AAG TCA TCA ACA GAA GAA
  GAT CAT AGT TTT TTT CAT TGA AGG TTT CTG TTC AGT AGT TGT CTT CTT
   L   V   S   K   K   V   T   S   K   D   K   S   S   T   E   E>

920           930           940           950           960
  AAA TTC AAT GAA AAA GGT GAA GTA TCT GAA AAA ATA ATA ACA AGA GCA
  TTT AAG TTA CTT TTT CCA CTT CAT AGA CTT TTT TAT TAT TGT TCT CGT
   K   F   N   E   K   G   E   V   S   E   K   I   I   T   R   A>

970           980           990          1000
  GAC GGA ACC AGA CTT GAA TAC ACA GGA ATT AAA AGC GAT GGA TCT GGA
  CTG CCT TGG TCT GAA CTT ATG TGT CCT TAA TTT TCG CTA CCT AGA CCT
   D   G   T   R   L   E   Y   T   G   I   K   S   D   G   S   G>

1010          1020          1030          1040          1050
  AAA GCT AAA GAG GTT TTA AAA GGC TAT GTT CTT GAA GGA ACT CTA ACT
  TTT CGA TTT CTC CAA AAT TTT CCG ATA CAA GAA CTT CCT TGA GAT TGA
   K   A   K   E   V   L   K   G   Y   V   L   E   G   T   L   T>

1060          1070          1080          1090          1100
  GCT GAA AAA ACA ACA TTG GTG GTT AAA GAA GGA ACT GTT ACT TTA AGC
```

FIG. 55B

```
CGA CTT TTT TGT TGT AAC CAC CAA TTT CTT CCT TGA CAA TGA AAT TCG
 A   L   F   C   C   N   H   Q   F   L   P   *   Q   *   N   S>

1110        1120        1130        1140        1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
 K   N   I   S   K   S   G   E   V   S   V   E   L   N   D   T>

1160        1170        1180        1190        1200
GAC AGT AGT GCT GCT ACT AAA AAA ACT GCA GCT TGG AAT TCA GGC ACT
CTG TCA TCA CGA CGA TGA TTT TTT TGA CGT CGA ACC TTA AGT CCG TGA
 D   S   S   A   A   T   K   K   T   A   A   W   N   S   G   T>

1210        1220        1230        1240
TCA ACT TTA ACA ATT ACT GTA AAC AGT AAA AAA ACT AAA GAC CTT GTG
AGT TGA AAT TGT TAA TGA CAT TTG TCA TTT TTT TGA TTT CTG GAA CAC
 S   T   L   T   I   T   V   N   S   K   K   T   K   D   L   V>

1250     1260        1270        1280        1290
    TTT ACA AAA GAA AAC ACA ATT ACA GTA CAA CAA TAC GAC TCA AAT GGC
    AAA TGT TTT CTT TTG TGT TAA TGT CAT GTT GTT ATG CTG AGT TTA CCG
     F   T   K   E   N   T   I   T   V   Q   Q   Y   D   S   N   G>

1300        1310        1320        1330        1340
ACC AAA TTA GAG GGG TCA GCA GTT GAA ATT ACA AAA CTT GAT GAA ATT
TGG TTT AAT CTC CCC AGT CGT CAA CTT TAA TGT TTT GAA CTA CTT TAA
 T   K   L   E   G   S   A   V   E   I   T   K   L   D   E   I>

1350        1360
AAA AAC GCT TTA AAA TAA
TTT TTG CGA AAT TTT ATT
 K   N   A   L   K   *>
```

FIG. 55C

```
              10              20              30              40
  ATG GCT TGT AAT AAT TCA GGG AAA GAT GGG AAT ACA TCT GCA AAT TCT
  TAC CGA ACA TTA TTA AGT CCC TTT CTA CCC TTA TGT AGA CGT TTA AGA
   M   A   C   N   N   S   G   K   D   G   N   T   S   A   N   S>

50              60              70              80              90
  GCT GAT GAG TCT GTT AAA GGG CCT AAT CTT ACA GAA ATA AAT AAA AAA
  CGA CTA CTC AGA CAA TTT CCC GGA TTA GAA TGT CTT TAT TTA TTT TTT
   A   D   E   S   V   K   G   P   N   L   T   E   I   N   K   K>

100             110             120             130             140
  ATT ACG GAT TCT AAT GCG GTT TTA CTT GCT GTG AAA GAG GTT GAA GCG
  TAA TGC CTA AGA TTA CGC CAA AAT GAA CGA CAC TTT CTC CAA CTT CGC
   I   T   D   S   N   A   V   L   L   A   V   K   E   V   E   A>

150             160             170             180             190
  TTG CTG TCA TCT ATA GAT GAA ATT GCT GCT AAA GCT ATT GGT AAA AAA
  AAC GAC AGT AGA TAT CTA CTT TAA CGA CGA TTT CGA TAA CCA TTT TTT
   L   L   S   S   I   D   E   I   A   A   K   A   I   G   K   K>

200             210             220             230             240
  ATA CAC CAA AAT AAT GGT TTG GAT ACC GAA AAT AAT CAC AAT GGA TCA
  TAT GTG GTT TTA TTA CCA AAC CTA TGG CTT TTA TTA GTG TTA CCT AGT
   I   H   Q   N   N   G   L   D   T   E   N   N   H   N   G   S>

250             260             270             280
  TTG TTA GCG GGA GCT TAT GCA ATA TCA ACC CTA ATA AAA CAA AAA TTA
  AAC AAT CGC CCT CGA ATA CGT TAT AGT TGG GAT TAT TTT GTT TTT AAT
   L   L   A   G   A   Y   A   I   S   T   L   I   K   Q   K   L>

290             300             310             320             330
  GAT GGA TTG AAA AAT GAA GGA TTA AAG GAA AAA ATT GAT GCG GCT AAG
  CTA CCT AAC TTT TTA CTT CCT AAT TTC CTT TTT TAA CTA CGC CGA TTC
   D   G   L   K   N   E   G   L   K   E   K   I   D   A   A   K>

340             350             360             370             380
  AAA TGT TCT GAA ACA TTT ACT AAT AAA TTA AAA GAA AAA CAC ACA GAT
  TTT ACA AGA CTT TGT AAA TGA TTA TTT AAT TTT CTT TTT GTG TGT CTA
   K   C   S   E   T   F   T   N   K   L   K   E   K   H   T   D>

390             400             410             420             430
  CTT GGT AAA GAA GGT GTT ACT GAT GCT GAT GCA AAA GAA GCC ATT TTA
  GAA CCA TTT CTT CCA CAA TGA CTA CGA CTA CGT TTT CTT CGG TAA AAT
   L   G   K   E   G   V   T   D   A   D   A   K   E   A   I   L>

440             450             460             470             480
  AAA GCA AAT GGT ACT AAA ACT AAA GGT GCT GAA GAA CTT GGA AAA TTA
  TTT CGT TTA CCA TGA TTT TGA TTT CCA CGA CTT CTT GAA CCT TTT AAT
   K   A   N   G   T   K   T   K   G   A   E   E   L   G   K   L>

490             500             510             520
  TTT GAA TCA GTA GAG GTC TTG TCA AAA GCA GCT AAA GAG ATG CTT GCT
  AAA CTT AGT CAT CTC CAG AAC AGT TTT CGT CGA TTT CTC TAC GAA CGA
   F   E   S   V   E   V   L   S   K   A   A   K   E   M   L   A>
```

FIG. 56A

```
     530           540           550           560           570
 AAT TCA GTT AAA GAG CTT ACA AGC CCT GTT GTG GCA GAA AGT CCA GCC
 TTA AGT CAA TTT CTC GAA TGT TCG GGA CAA CAC CGT CTT TCA GGT CGG
  N   S   V   K   E   L   T   S   P   V   V   A   E   S   P   A>

580           590           600           610           620
 ATG GCC AAG CAA AAT GTT AGC AGC CTT GAC GAG AAA AAC AGC GTT TCA
 TAC CGG TTC GTT TTA CAA TCG TCG GAA CTG CTC TTT TTG TCG CAA AGT
  M   A   K   Q   N   V   S   S   L   D   E   K   N   S   V   S>

630           640           650           660           670
 GTA GAT TTG CCT GGT GAA ATG AAA GTT CTT GTA AGC AAA GAA AAA AAC
 CAT CTA AAC GGA CCA CTT TAC TTT CAA GAA CAT TCG TTT CTT TTT TTG
  V   D   L   P   G   E   M   K   V   L   V   S   K   E   K   N>

680           690           700           710           720
 AAA GAC GGC AAG TAC GAT CTA ATT GCA ACA GTA GAC AAG CTT GAG CTT
 TTT CTG CCG TTC ATG CTA GAT TAA CGT TGT CAT CTG TTC GAA CTC GAA
  K   D   G   K   Y   D   L   I   A   T   V   D   K   L   E   L>

730           740           750           760
 AAA GGA ACT TCT GAT AAA AAC AAT GGA TCT GGA GTA CTT GAA GGC GTA
 TTT CCT TGA AGA CTA TTT TTG TTA CCT AGA CCT CAT GAA CTT CCG CAT
  K   G   T   S   D   K   N   N   G   S   G   V   L   E   G   V>

770           780           790           800           810
 AAA GCT GAC AAA AGT AAA GTA AAA TTA ACA ATT TCT GAC GAT CTA GGT
 TTT CGA CTG TTT TCA TTT CAT TTT AAT TGT TAA AGA CTG CTA GAT CCA
  K   A   D   K   S   K   V   K   L   T   I   S   D   D   L   G>

820           830           840           850           860
 CAA ACC ACA CTT GAA GTT TTC AAA GAA GAT GGC AAA ACA CTA GTA TCA
 GTT TGG TGT GAA CTT CAA AAG TTT CTT CTA CCG TTT TGT GAT CAT AGT
  Q   T   T   L   E   V   F   K   E   D   G   K   T   L   V   S>

870           880           890           900           910
 AAA AAA GTA ACT TCC AAA GAC AAG TCA TCA ACA GAA GAA AAA TTC AAT
 TTT TTT CAT TGA AGG TTT CTG TTC AGT AGT TGT CTT CTT TTT AAG TTA
  K   K   V   T   S   K   D   K   S   S   T   E   E   K   F   N>

920           930           940           950           960
 GAA AAA GGT GAA GTA TCT GAA AAA ATA ATA ACA AGA GCA GAC GGA ACC
 CTT TTT CCA CTT CAT AGA CTT TTT TAT TAT TGT TCT CGT CTG CCT TGG
  E   K   G   E   V   S   E   K   I   I   T   R   A   D   G   T>

970           980           990          1000
 AGA CTT GAA TAC ACA GGA ATT AAA AGC GAT GGA TCT GGA AAA GCT AAA
 TCT GAA CTT ATG TGT CCT TAA TTT TCG CTA CCT AGA CCT TTT CGA TTT
  R   L   E   Y   T   G   I   K   S   D   G   S   G   K   A   K>

1010          1020          1030          1040          1050
 GAG GTT TTA AAA GGC TAT GTT CTT GAA GGA ACT CTA ACT GCT GAA AAA
 CTC CAA AAT TTT CCG ATA CAA GAA CTT CCT TGA GAT TGA CGA CTT TTT
  E   V   L   K   G   Y   V   L   E   G   T   L   T   A   E   K>

1060          1070          1080          1090          1100
 ACA ACA TTG GTG GTT AAA GAA GGA ACT GTT ACT TTA AGC AAA AAT ATT
```

FIG. 56B

```
          TGT TGT AAC CAC CAA TTT CTT CCT TGA CAA TGA AAT TCG TTT TTA TAA
           T   T   L   V   V   K   E   G   T   V   T   L   S   K   N   I>

1110        1120        1130        1140        1150
          TCA AAA TCT GGG GAA GTT TCA GTT GAA CTT AAT GAC ACT GAC AGT AGT
          AGT TTT AGA CCC CTT CAA AGT CAA CTT GAA TTA CTG TGA CTG TCA TCA
           S   K   S   G   E   V   S   V   E   L   N   D   T   D   S   S>

1160        1170        1180        1190        1200
          GCT GCT ACT AAA AAA ACT GCA GCT TGG AAT TCA GGC ACT TCA ACT TTA
          CGA CGA TGA TTT TTT TGA CGT CGA ACC TTA AGT CCG TGA AGT TGA AAT
           A   A   T   K   K   T   A   A   W   N   S   G   T   S   T   L>

1210        1220        1230        1240
          ACA ATT ACT GTA AAC AGT AAA AAA ACT AAA GAC CTT GTG TTT ACA AAA
          TGT TAA TGA CAT TTG TCA TTT TTT TGA TTT CTG GAA CAC AAA TGT TTT
           T   I   T   V   N   S   K   K   T   K   D   L   V   F   T   K>

1250        1260        1270        1280        1290
          GAA AAC ACA ATT ACA GTA CAA CAA TAC GAC TCA AAT GGC ACC AAA TTA
          CTT TTG TGT TAA TGT CAT GTT GTT ATG CTG AGT TTA CCG TGG TTT AAT
           E   N   T   I   T   V   Q   Q   Y   D   S   N   G   T   K   L>

1300        1310        1320        1330        1340
          GAG GGG TCA GCA GTT GAA ATT ACA AAA CTT GAT GAA ATT AAA AAC GCT
          CTC CCC AGT CGT CAA CTT TAA TGT TTT GAA CTA CTT TAA TTT TTG CGA
           E   G   S   A   V   E   I   T   K   L   D   E   I   K   N   A>

1350
          TTA AAA TAA
          AAT TTT ATT
           L   K   *>
```

FIG. 56C

```
         10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
 L   L   S   S   I   D   E   L   A   K   A   I   G   K   K   I>

200             210             220             230             240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
 K   N   D   G   S   L   D   N   E   A   N   R   N   E   S   L>

250             260             270             280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
 L   A   G   A   Y   T   I   S   T   L   I   T   Q   K   L   S>

290             300             310             320             330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
 K   L   N   G   S   E   G   L   K   E   K   I   A   A   A   K>

340             350             360             370             380
AAA TGC TCT GAA GAG TTT AGT ACT AAA CTA AAA GAT AAT CAT GCA CAG
TTT ACG AGA CTT CTC AAA TCA TGA TTT GAT TTA CTA TTA GTA CGT GTC
 K   C   S   E   E   F   S   T   K   L   K   D   N   H   A   Q>

390             400             410             420             430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
 L   G   I   Q   G   V   T   D   E   N   A   K   K   A   I   L>

440             450             460             470             480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
 K   A   N   A   A   G   K   D   K   G   V   E   E   L   E   K>

490             500             510             520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
 L   S   G   S   L   E   S   L   S   K   A   A   K   E   M   L>
```

FIG. 57A

```
      530         540         550         560         570
      GCT AAT TCA GTT AAA GAG CTT ACA AGC CCT GTT GTC CAT GGC AAG CAA
      CGA TTA AGT CAA TTT CTC GAA TGT TCG GGA CAA CAG GTA CCG TTC GTT
       A   N   S   V   K   E   L   T   S   P   V   V   H   G   K   Q>

580         590         600         610          620
      AAT GTT AGC AGC CTT GAC GAG AAA AAC AGC GTT TCA GTA GAT TTG CCT
      TTA CAA TCG TCG GAA CTG CTC TTT TTG TCG CAA AGT CAT CTA AAC GGA
       N   V   S   S   L   D   E   K   N   S   V   S   V   D   L   P>

630         640         650          660          670
      GGT GAA ATG AAA GTT CTT GTA AGC AAA GAA AAA AAC AAA GAC GGC AAG
      CCA CTT TAC TTT CAA GAA CAT TCG TTT CTT TTT TTG TTT CTG CCG TTC
       G   E   M   K   V   L   V   S   K   E   K   N   K   D   G   K>

680         690          700          710·        720
      TAC GAT CTA ATT GCA ACA GTA GAC AAG CTT GAG CTT AAA GGA ACT TCT
      ATG CTA GAT TAA CGT TGT CAT CTG TTC GAA CTC GAA TTT CCT TGA AGA
       Y   D   L   I   A   T   V   D   K   L   E   L   K   G   T   S>

730         740          750          760
      GAT AAA AAC AAT GGA TCT GGA GTA CTT GAA GGC GTA AAA GCT GAC AAA
      CTA TTT TTG TTA CCT AGA CCT CAT GAA CTT CCG CAT TTT CGA CTG TTT
       D   K   N   N   G   S   G   V   L   E   G   V   K   A   D   K>

770         780         790          800          810
      AGT AAA GTA AAA TTA ACA ATT TCT GAC GAT CTA GGT CAA ACC ACA CTT
      TCA TTT CAT TTT AAT TGT TAA AGA CTG CTA GAT CCA GTT TGG TGT GAA
       S   K   V   K   L   T   I   S   D   D   L   G   Q   T   T   L>

820         830          840          850         860
      GAA GTT TTC AAA GAA GAT GGC AAA ACA CTA GTA TCA AAA AAA GTA ACT
      CTT CAA AAG TTT CTT CTA CCG TTT TGT GAT CAT AGT TTT TTT CAT TGA
       E   V   F   K   E   D   G   K   T   L   V   S   K   K   V   T>

870         880          890          900         910
      TCC AAA GAC AAG TCA TCA ACA GAA GAA AAA TTC AAT GAA AAA GGT GAA
      AGG TTT CTG TTC AGT AGT TGT CTT CTT TTT AAG TTA CTT TTT CCA CTT
       S   K   D   K   S   S   T   E   E   K   F   N   E   K   G   E>

920         930         940          950         960
      GTA TCT GAA AAA ATA ATA ACA AGA GCA GAC GGA ACC AGA CTT GAA TAC
      CAT AGA CTT TTT TAT TAT TGT TCT CGT CTG CCT TGG TCT GAA CTT ATG
       V   S   E   K   I   I   T   R   A   D   G   T   R   L   E   Y>

970         980         990          1000
      ACA GGA ATT AAA AGC GAT GGA TCT GGA AAA GCT AAA GAG GTT TTA AAA
      TGT CCT TAA TTT TCG CTA CCT AGA CCT TTT CGA TTT CTC CAA AAT TTT
       T   G   I   K   S   D   G   S   G   K   A   K   E   V   L   K>

1010         1020         1030         1040         1050
      GGC TAT GTT CTT GAA GGA ACT CTA ACT GCT GAA AAA ACA ACA TTG GTG
      CCG ATA CAA GAA CTT CCT TGA GAT TGA CGA CTT TTT TGT TGT AAC CAC
       G   Y   V   L   E   G   T   L   T   A   E   K   T   T   L   V>

1060         1070         1080         1090         1100
      GTT AAA GAA GGA ACT GTT ACT TTA AGC AAA AAT ATT TCA AAA TCT GGG
```

FIG. 57B

```
CAA TTT CTT CCT TGA CAA TGA AAT TCG TTT TTA TAA AGT TTT AGA CCC
 V   K   E   G   T   V   T   L   S   K   N   I   S   K   S   G>

1110            1120            1130            1140            1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
 E   V   S   V   E   L   N   D   T   D   S   S   A   A   T   K>

1160            1170            1180            1190            1200
AAA ACT GCA GCT TGG AAT TCA GGC ACT TCA ACT TTA ACA ATT ACT GTA
TTT TGA CGT CGA ACC TTA AGT CCG TGA AGT TGA AAT TGT TAA TGA CAT
 K   T   A   A   W   N   S   G   T   S   T   L   T   I   T   V>

1210            1220            1230            1240
AAC AGT AAA AAA ACT AAA GAC CTT GTG TTT ACA AAA GAA AAC ACA ATT
TTG TCA TTT TTT TGA TTT CTG GAA CAC AAA TGT TTT CTT TTG TGT TAA
 N   S   K   K   T   K   D   L   V   F   T   K   E   N   T   I>

1250         1260            1270            1280            1290
ACA GTA CAA CAA TAC GAC TCA AAT GGC ACC AAA TTA GAG GGG TCA GCA
TGT CAT GTT GTT ATG CTG AGT TTA CCG TGG TTT AAT CTC CCC AGT CGT
 T   V   Q   Q   Y   D   S   N   G   T   K   L   E   G   S   A>

1300            1310            1320            1330            1340
GTT GAA ATT ACA AAA CTT GAT GAA ATT AAA AAC GCT TTA AAA TAA
CAA CTT TAA TGT TTT GAA CTA CTT TAA TTT TTG CGA AAT TTT ATT
 V   E   I   T   K   L   D   E   I   K   N   A   L   K   *>
```

FIG. 57C

```
        10          20          30          40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50          60          70          80          90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100         110         120         130         140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150         160         170         180         190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200         210         220         230         240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250         260         270         280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290         300         310         320         330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340         350         360         370         380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390         400         410         420         430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440         450         460         470         480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490         500         510         520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 58A

```
        530           540           550           560           570
     AAT TCA GTT AAA GAG CTT ACA AGC CCT GTT GTG GCA GAA AGT CCA AAA
     TTA AGT CAA TTT CTC GAA TGT TCG GGA CAA CAC CGT CTT TCA GGT TTT
      N   S   V   K   E   L   T   S   P   V   V   A   E   S   P   K>

580           590           600           610           620
     AAA CCT TCC ATG GCC AAG CAA AAT GTT AGC AGC CTT GAC GAG AAA AAC
     TTT GGA AGG TAC CGG TTC GTT TTA CAA TCG TCG GAA CTG CTC TTT TTG
      K   P   S   M   A   K   Q   N   V   S   S   L   D   E   K   N>

630           640           650           660           670
     AGC GTT TCA GTA GAT TTG CCT GGT GAA ATG AAA GTT CTT GTA AGC AAA
     TCG CAA AGT CAT CTA AAC GGA CCA CTT TAC TTT CAA GAA CAT TCG TTT
      S   V   S   V   D   L   P   G   E   M   K   V   L   V   S   K>

680           690           700           710          720
     GAA AAA AAC AAA GAC GGC AAG TAC GAT CTA ATT GCA ACA GTA GAC AAG
     CTT TTT TTG TTT CTG CCG TTC ATG CTA GAT TAA CGT TGT CAT CTG TTC
      E   K   N   K   D   G   K   Y   D   L   I   A   T   V   D   K>

730           740           750           760
     CTT GAG CTT AAA GGA ACT TCT GAT AAA AAC AAT GGA TCT GGA GTA CTT
     GAA CTC GAA TTT CCT TGA AGA CTA TTT TTG TTA CCT AGA CCT CAT GAA
      L   E   L   K   G   T   S   D   K   N   N   G   S   G   V   L>

770           780           790           800           810
     GAA GGC GTA AAA GCT GAC AAA AGT AAA GTA AAA TTA ACA ATT TCT GAC
     CTT CCG CAT TTT CGA CTG TTT TCA TTT CAT TTT AAT TGT TAA AGA CTG
      E   G   V   K   A   D   K   S   K   V   K   L   T   I   S   D>

820           830           840           850           860
     GAT CTA GGT CAA ACC ACA CTT GAA GTT TTC AAA GAA GAT GGC AAA ACA
     CTA GAT CCA GTT TGG TGT GAA CTT CAA AAG TTT CTT CTA CCG TTT TGT
      D   L   G   Q   T   T   L   E   V   F   K   E   D   G   K   T>

870           880           890           900           910
     CTA GTA TCA AAA AAA GTA ACT TCC AAA GAC AAG TCA TCA ACA GAA GAA
     GAT CAT AGT TTT TTT CAT TGA AGG TTT CTG TTC AGT AGT TGT CTT CTT
      L   V   S   K   K   V   T   S   K   D   K   S   S   T   E   E>

920           930           940           950           960
     AAA TTC AAT GAA AAA GGT GAA GTA TCT GAA AAA ATA ATA ACA AGA GCA
     TTT AAG TTA CTT TTT CCA CTT CAT AGA CTT TTT TAT TAT TGT TCT CGT
      K   F   N   E   K   G   E   V   S   E   K   I   I   T   R   A>

970           980           990           1000
     GAC GGA ACC AGA CTT GAA TAC ACA GGA ATT AAA AGC GAT GGA TCT GGA
     CTG CCT TGG TCT GAA CTT ATG TGT CCT TAA TTT TCG CTA CCT AGA CCT
      D   G   T   R   L   E   Y   T   G   I   K   S   D   G   S   G>

1010          1020          1030          1040          1050
     AAA GCT AAA GAG GTT TTA AAA GGC TAT GTT CTT GAA GGA ACT CTA ACT
     TTT CGA TTT CTC CAA AAT TTT CCG ATA CAA GAA CTT CCT TGA GAT TGA
      K   A   K   E   V   L   K   G   Y   V   L   E   G   T   L   T>

1060          1070          1080          1090          1100
     GCT GAA AAA ACA ACA TTG GTG GTT AAA GAA GGA ACT GTT ACT TTA AGC
```

FIG. 58B

```
                                                                1100
CGA CTT TTT TGT TGT AAC CAC CAA TTT CTT CCT TGA CAA TGA AAT TCG
 A   E   K   T   T   L   V   V   K   E   G   T   V   T   L   S>

1110        1120        1130        1140        1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
 K   N   I   S   K   S   G   E   V   S   V   E   L   N   D   T>

1160        1170        1180        1190        1200
GAC AGT AGT GCT GCT ACT AAA AAA ACT GCA GCT TGG AAT TCA AAA ACT
CTG TCA TCA CGA CGA TGA TTT TTT TGA CGT CGA ACC TTA AGT TTT TGA
 D   S   S   A   A   T   K   K   T   A   A   W   N   S   K   T>

1210        1220        1230        1240
TCC ACT TTA ACA ATT AGT GTG AAT AGC CAA AAA ACC AAA AAC CTT GTA
AGG TGA AAT TGT TAA TCA CAC TTA TCG GTT TTT TGG TTT TTG GAA CAT
 S   T   L   T   I   S   V   N   S   Q   K   T   K   N   L   V>

1250        1260        1270        1280        1290
TTC ACA AAA GAA GAC ACA ATA ACA GTA CAA AAA TAC GAC TCA GCA GGC
AAG TGT TTT CTT CTG TGT TAT TGT CAT GTT TTT ATG CTG AGT CGT CCG
 F   T   K   E   D   T   I   T   V   Q   K   Y   D   S   A   G>

1300        1310        1320        1330        1340
ACC AAT CTA GAA GGC AAA GCA GTC GAA ATT ACA ACA CTT AAA GAA CTT
TGG TTA GAT CTT CCG TTT CGT CAG CTT TAA TGT TGT GAA TTT CTT GAA
 T   N   L   E   G   K   A   V   E   I   T   T   L   K   E   L>

1350        1360
AAA AAC GCT TTA AAA TAA
TTT TTG CGA AAT TTT ATT
 K   N   A   L   K   *>
```

```
       530             540             550             560             570
    GCT AAT TCA GTT AAA GAG CTT ACA AGC CCT GTT GTC CAT GGC AAG CAA
    CGA TTA AGT CAA TTT CTC GAA TGT TCG GGA CAA CAG GTA CCG TTC GTT
     A   N   S   V   K   E   L   T   S   P   V   V   H   G   K   Q>

580             590             600             610             620
    AAT GTT AGC AGC CTT GAC GAG AAA AAC AGC GTT TCA GTA GAT TTG CCT
    TTA CAA TCG TCG GAA CTG CTC TTT TTG TCG CAA AGT CAT CTA AAC GGA
     N   V   S   S   L   D   E   K   N   S   V   S   V   D   L   P>

630             640             650             660             670
    GGT GAA ATG AAA GTT CTT GTA AGC AAA GAA AAA AAC AAA GAC GGC AAG
    CCA CTT TAC TTT CAA GAA CAT TCG TTT CTT TTT TTG TTT CTG CCG TTC
     G   E   M   K   V   L   V   S   K   E   K   N   K   D   G   K>

680             690             700             710             720
    TAC GAT CTA ATT GCA ACA GTA GAC AAG CTT GAG CTT AAA GGA ACT TCT
    ATG CTA GAT TAA CGT TGT CAT CTG TTC GAA CTC GAA TTT CCT TGA AGA
     Y   D   L   I   A   T   V   D   K   L   E   L   K   G   T   S>

730             740             750             760
    GAT AAA AAC AAT GGA TCT GGA GTA CTT GAA GGC GTA AAA GCT GAC AAA
    CTA TTT TTG TTA CCT AGA CCT CAT GAA CTT CCG CAT TTT CGA CTG TTT
     D   K   N   N   G   S   G   V   L   E   G   V   K   A   D   K>

770           780             790             800             810
    AGT AAA GTA AAA TTA ACA ATT TCT GAC GAT CTA GGT CAA ACC ACA CTT
    TCA TTT CAT TTT AAT TGT TAA AGA CTG CTA GAT CCA GTT TGG TGT GAA
     S   K   V   K   L   T   I   S   D   D   L   G   Q   T   T   L>

820             830             840             850             860
    GAA GTT TTC AAA GAA GAT GGC AAA ACA CTA GTA TCA AAA AAA GTA ACT
    CTT CAA AAG TTT CTT CTA CCG TTT TGT GAT CAT AGT TTT TTT CAT TGA
     E   V   F   K   E   D   G   K   T   L   V   S   K   K   V   T>

870             880             890             900             910
    TCC AAA GAC AAG TCA TCA ACA GAA GAA AAA TTC AAT GAA AAA GGT GAA
    AGG TTT CTG TTC AGT AGT TGT CTT CTT TTT AAG TTA CTT TTT CCA CTT
     S   K   D   K   S   S   T   E   E   K   F   N   E   K   G   E>

920             930             940             950             960
    GTA TCT GAA AAA ATA ATA ACA AGA GCA GAC GGA ACC AGA CTT GAA TAC
    CAT AGA CTT TTT TAT TAT TGT TCT CGT CTG CCT TGG TCT GAA CTT ATG
     V   S   E   K   I   I   T   R   A   D   G   T   R   L   E   Y>

970             980             990             1000
    ACA GGA ATT AAA AGC GAT GGA TCT GGA AAA GCT AAA GAG GTT TTA AAA
    TGT CCT TAA TTT TCG CTA CCT AGA CCT TTT CGA TTT CTC CAA AAT TTT
     T   G   I   K   S   D   G   S   G   K   A   K   E   V   L   K>

1010          1020            1030            1040            1050
    GGC TAT GTT CTT GAA GGA ACT CTA ACT GCT GAA AAA ACA ACA TTG GTG
    CCG ATA CAA GAA CTT CCT TGA GAT TGA CGA CTT TTT TGT TGT AAC CAC
     G   Y   V   L   E   G   T   L   T   A   E   K   T   T   L   V>

1060            1070            1080            1090            1100
    GTT AAA GAA GGA ACT GTT ACT TTA AGC AAA AAT ATT TCA AAA TCT GGG
```

FIG. 59B

```
CAA TTT CTT CCT TGA CAA TGA AAT TCG TTT TTA TAA AGT TTT AGA CCC
 V   K   E   G   T   V   T   L   S   K   N   I   S   K   S   G>

1110            1120            1130            1140            1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
 E   V   S   V   E   L   N   D   T   D   S   S   A   A   T   K>

1160            1170            1180            1190            1200
AAA ACT GCA GCT TGG AAT TCA AAA ACT TCC ACT TTA ACA ATT AGT GTG
TTT TGA CGT CGA ACC TTA AGT TTT TGA AGG TGA AAT TGT TAA TCA CAC
 K   T   A   A   W   N   S   K   T   S   T   L   T   I   S   V>

1210            1220            1230            1240
AAT AGC CAA AAA ACC AAA AAC CTT GTA TTC ACA AAA GAA GAC ACA ATA
TTA TCG GTT TTT TGG TTT TTG GAA CAT AAG TGT TTT CTT CTG TGT TAT
 N   S   Q   K   T   K   N   L   V   F   T   K   E   D   T   I>

1250            1260            1270            1280            1290
    ACA GTA CAA AAA TAC GAC TCA GCA GGC ACC AAT CTA GAA GGC AAA GCA
    TGT CAT GTT TTT ATG CTG AGT CGT CCG TGG TTA GAT CTT CCG TTT CGT
     T   V   Q   K   Y   D   S   A   G   T   N   L   E   G   K   A>

1300            1310            1320            1330            1340
GTC GAA ATT ACA ACA CTT AAA GAA CTT AAA AAC GCT TTA AAA TAA
CAG CTT TAA TGT TGT GAA TTT CTT GAA TTT TTG CGA AAT TTT ATT
 V   E   I   T   T   L   K   E   L   K   N   A   L   K   *>
```

FIG. 59C

```
           10            20             30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50            60             70              80             90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100           110            120             130            140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150           160            170            180            190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200           210            220            230            240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250           260            270            280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290           300            310             320            330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340           350            360             370            380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390           400            410            420            430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440           450            460            470            480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490           500            510            520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 60A

```
      530         540         550         560         570
      AAT TCA GTT AAA GAG CTT ACA AGC CCT GTT GTG GCA GAA AGT CCA AAA
      TTA AGT CAA TTT CTC GAA TGT TCG GGA CAA CAC CGT CTT TCA GGT TTT
       N   S   V   K   E   L   T   S   P   V   V   A   E   S   P   K>

580         590         600         610         620
      AAA CCT TCC ATG GCC AAG CAA AAT GTT AGC AGC CTT GAC GAG AAA AAC
      TTT GGA AGG TAC CGG TTC GTT TTA CAA TCG TCG GAA CTG CTC TTT TTG
       K   P   S   M   A   K   Q   N   V   S   S   L   D   E   K   N>

630         640         650         660         670
      AGC GTT TCA GTA GAT TTG CCT GGT GAA ATG AAA GTT CTT GTA AGC AAA
      TCG CAA AGT CAT CTA AAC GGA CCA CTT TAC TTT CAA GAA CAT TCG TTT
       S   V   S   V   D   L   P   G   E   M   K   V   L   V   S   K>

680         690         700         710         720
      GAA AAA AAC AAA GAC GGC AAG TAC GAT CTA ATT GCA ACA GTA GAC AAG
      CTT TTT TTG TTT CTG CCG TTC ATG CTA GAT TAA CGT TGT CAT CTG TTC
       E   K   N   K   D   G   K   Y   D   L   I   A   T   V   D   K>

730         740         750         760
      CTT GAG CTT AAA GGA ACT TCT GAT AAA AAC AAT GGA TCT GGA GTA CTT
      GAA CTC GAA TTT CCT TGA AGA CTA TTT TTG TTA CCT AGA CCT CAT GAA
       L   E   L   K   G   T   S   D   K   N   N   G   S   G   V   L>

770         780         790         800         810
      GAA GGC GTA AAA GCT GAC AAA AGT AAA GTA AAA TTA ACA ATT TCT GAC
      CTT CCG CAT TTT CGA CTG TTT TCA TTT CAT TTT AAT TGT TAA AGA CTG
       E   G   V   K   A   D   K   S   K   V   K   L   T   I   S   D>

820         830         840         850         860
      GAT CTA GGT CAA ACC ACA CTT GAA GTT TTC AAA GAA GAT GGC AAA ACA
      CTA GAT CCA GTT TGG TGT GAA CTT CAA AAG TTT CTT CTA CCG TTT TGT
       D   L   G   Q   T   T   L   E   V   F   K   E   D   G   K   T>

870         880         890         900         910
      CTA GTA TCA AAA AAA GTA ACT TCC AAA GAC AAG TCA TCA ACA GAA GAA
      GAT CAT AGT TTT TTT CAT TGA AGG TTT CTG TTC AGT AGT TGT CTT CTT
       L   V   S   K   K   V   T   S   K   D   K   S   S   T   E   E>

920         930         940         950         960
      AAA TTC AAT GAA AAA GGT GAA GTA TCT GAA AAA ATA ATA ACA AGA GCA
      TTT AAG TTA CTT TTT CCA CTT CAT AGA CTT TTT TAT TAT TGT TCT CGT
       K   F   N   E   K   G   E   V   S   E   K   I   I   T   R   A>

970         980         990        1000
      GAC GGA ACC AGA CTT GAA TAC ACA GGA ATT AAA AGC GAT GGA TCT GGA
      CTG CCT TGG TCT GAA CTT ATG TGT CCT TAA TTT TCG CTA CCT AGA CCT
       D   G   T   R   L   E   Y   T   G   I   K   S   D   G   S   G>

1010        1020        1030        1040        1050
      AAA GCT AAA GAG GTT TTA AAA GGC TAT GTT CTT GAA GGA ACT CTA ACT
      TTT CGA TTT CTC CAA AAT TTT CCG ATA CAA GAA CTT CCT TGA GAT TGA
       K   A   K   E   V   L   K   G   Y   V   L   E   G   T   L   T>

1060        1070        1080        1090        1100
      GCT GAA AAA ACA ACA TTG GTG GTT AAA GAA GGA ACT GTT ACT TTA AGC
```

FIG. 60B

```
CGA CTT TTT TGT TGT AAC CAC CAA TTT CTT CCT TGA CAA TGA AAT TCG
 A   E   K   T   T   L   V   V   K   E   G   T   V   T   L  S>

1110            1120            1130            1140            1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
 K   N   I   S   K   S   G   E   V   S   V   E   L   N   D   T>

1160            1170            1180            1190            1200
GAC AGT AGT GCT GCT ACT AAA AAA ACT GCA GCT TGG AAT TCA AAA ACT
CTG TCA TCA CGA CGA TGA TTT TTT TGA CGT CGA ACC TTA AGT TTT TGA
 D   S   S   A   A   T   K   K   T   A   A   W   N   S   K   T>

1210            1220            1230            1240
TCT ACT TTA ACA ATT AGT GTT AAC AGC AAA AAA ACT ACA CAA CTT GTG
AGA TGA AAT TGT TAA TCA CAA TTG TCG TTT TTT TGA TGT GTT GAA CAC
 S   T   L   T   I   S   V   N   S   K   K   T   T   Q   L   V>

1250        1260            1270            1280            1290
TTT ACT AAA CAA GAC ACA ATA ACT GTA CAA AAA TAC GAC TCC GCA GGT
AAA TGA TTT GTT CTG TGT TAT TGA CAT GTT TTT ATG CTG AGG CGT CCA
 F   T   K   Q   D   T   I   T   V   Q   K   Y   D   S   A   G>

1300            1310            1320            1330            1340
ACC AAT TTA GAA GGC ACA GCA GTC GAA ATT AAA ACA CTT GAT GAA CTT
TGG TTA AAT CTT CCG TGT CGT CAG CTT TAA TTT TGT GAA CTA CTT GAA
 T   N   L   E   G   T   A   V   E   I   K   T   L   D   E   L>

1350            1360
AAA AAC GCT TTA AAA TAA
TTT TTG CGA AAT TTT ATT
 K   N   A   L   K   *>
```

FIG. 60C

```
            10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
 L   L   S   S   I   D   E   L   A   K   A   I   G   K   K   I>

200             210             220             230             240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
 K   N   D   G   S   L   D   N   E   A   N   R   N   E   S   L>

250             260             270             280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
 L   A   G   A   Y   T   I   S   T   L   I   T   Q   K   L   S>

290             300             310             320             330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
 K   L   N   G   S   E   G   L   K   E   K   I   A   A   A   K>

340             350             360             370             380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
 K   C   S   E   E   F   S   T   K   L   K   D   N   H   A   Q>

390             400             410             420             430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
 L   G   I   Q   G   V   T   D   E   N   A   K   K   A   I   L>

440             450             460             470             480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
 K   A   N   A   A   G   K   D   K   G   V   E   E   L   E   K>

490             500             510             520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
 L   S   G   S   L   E   S   L   S   K   A   A   K   E   M   L>
```

FIG. 61A

```
       530            540           550           560          570
    GCT AAT TCA GTT AAA GAG CTT ACA AGC CCT GTT GTC CAT GGC AAG CAA
    CGA TTA AGT CAA TTT CTC GAA TGT TCG GGA CAA CAG GTA CCG TTC GTT
     A   N   S   V   K   E   L   T   S   P   V   V   H   G   K   Q>

580            590           600           610          620
    AAT GTT AGC AGC CTT GAC GAG AAA AAC AGC GTT TCA GTA GAT TTG CCT
    TTA CAA TCG TCG GAA CTG CTC TTT TTG TCG CAA AGT CAT CTA AAC GGA
     N   V   S   S   L   D   E   K   N   S   V   S   V   D   L   P>

630            640           650           660          670
    GGT GAA ATG AAA GTT CTT GTA AGC AAA GAA AAA AAC AAA GAC GGC AAG
    CCA CTT TAC TTT CAA GAA CAT TCG TTT CTT TTT TTG TTT CTG CCG TTC
     G   E   M   K   V   L   V   S   K   E   K   N   K   D   G   K>

680            690           700           710          720
    TAC GAT CTA ATT GCA ACA GTA GAC AAG CTT GAG CTT AAA GGA ACT TCT
    ATG CTA GAT TAA CGT TGT CAT CTG TTC GAA CTC GAA TTT CCT TGA AGA
     Y   D   L   I   A   T   V   D   K   L   E   L   K   G   T   S>

730            740           750           760
    GAT AAA AAC AAT GGA TCT GGA GTA CTT GAA GGC GTA AAA GCT GAC AAA
    CTA TTT TTG TTA CCT AGA CCT CAT GAA CTT CCG CAT TTT CGA CTG TTT
     D   K   N   N   G   S   G   V   L   E   G   V   K   A   D   K>

770            780           790           800          810
    AGT AAA GTA AAA TTA ACA ATT TCT GAC GAT CTA GGT CAA ACC ACA CTT
    TCA TTT CAT TTT AAT TGT TAA AGA CTG CTA GAT CCA GTT TGG TGT GAA
     S   K   V   K   L   T   I   S   D   D   L   G   Q   T   T   L>

820            830           840           850          860
    GAA GTT TTC AAA GAA GAT GGC AAA ACA CTA GTA TCA AAA AAA GTA ACT
    CTT CAA AAG TTT CTT CTA CCG TTT TGT GAT CAT AGT TTT TTT CAT TGA
     E   V   F   K   E   D   G   K   T   L   V   S   K   K   V   T>

870            880           890           900          910
    TCC AAA GAC AAG TCA TCA ACA GAA GAA AAA TTC AAT GAA AAA GGT GAA
    AGG TTT CTG TTC AGT AGT TGT CTT CTT TTT AAG TTA CTT TTT CCA CTT
     S   K   D   K   S   S   T   E   E   K   F   N   E   K   G   E>

920            930           940           950          960
    GTA TCT GAA AAA ATA ATA ACA AGA GCA GAC GGA ACC AGA CTT GAA TAC
    CAT AGA CTT TTT TAT TAT TGT TCT CGT CTG CCT TGG TCT GAA CTT ATG
     V   S   E   K   I   I   T   R   A   D   G   T   R   L   E   Y>

970            980           990           1000
    ACA GGA ATT AAA AGC GAT GGA TCT GGA AAA GCT AAA GAG GTT TTA AAA
    TGT CCT TAA TTT TCG CTA CCT AGA CCT TTT CGA TTT CTC CAA AAT TTT
     T   G   I   K   S   D   G   S   G   K   A   K   E   V   L   K>

1010           1020          1030          1040         1050
    GGC TAT GTT CTT GAA GGA ACT CTA ACT GCT GAA AAA ACA ACA TTG GTG
    CCG ATA CAA GAA CTT CCT TGA GAT TGA CGA CTT TTT TGT TGT AAC CAC
     G   Y   V   L   E   G   T   L   T   A   E   K   T   T   L   V>

1060           1070          1080          1090         1100
    GTT AAA GAA GGA ACT GTT ACT TTA AGC AAA AAT ATT TCA AAA TCT GGG
```

FIG. 61B

```
CAA TTT CTT CCT TGA CAA TGA AAT TCG TTT TTA TAA AGT TTT AGA CCC
 V   K   E   G   T   V   T   L   S   K   N   I   S   K   S   G>

1110          1120          1130          1140          1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
 E   V   S   V   E   L   N   D   T   D   S   S   A   A   T   K>

1160          1170          1180          1190          1200
AAA ACT GCA GCT TGG AAT TCA AAA ACT TCT ACT TTA ACA ATT AGT GTT
TTT TGA CGT CGA ACC TTA AGT TTT TGA AGA TGA AAT TGT TAA TCA CAA
 K   T   A   A   W   N   S   K   T   S   T   L   T   I   S   V>

1210          1220          1230          1240
AAC AGC AAA AAA ACT ACA CAA CTT GTG TTT ACT AAA CAA TAC ACA ATA
TTG TCG TTT TTT TGA TGT GTT GAA CAC AAA TGA TTT GTT ATG TGT TAT
 N   S   K   K   T   T   Q   L   V   F   T   K   Q   Y   T   I>

1250       1260          1270          1280          1290
ACT GTA AAA CAA TAC GAC TCC GCA GGT ACC AAT TTA GAA GGC ACA GCA
TGA CAT TTT GTT ATG CTG AGG CGT CCA TGG TTA AAT CTT CCG TGT CGT
 T   V   K   Q   Y   D   S   A   G   T   N   L   E   G   T   A>

1300          1310          1320          1330          1340
GTC GAA ATT AAA ACA CTT GAT GAA CTT AAA AAC GCT TTA AAA TAA
CAG CTT TAA TTT TGT GAA CTA CTT GAA TTT TTG CGA AAT TTT ATT
 V   E   I   K   T   L   D   E   L   K   N   A   L   K   *>
```

FIG. 61C

```
              10          20          30          40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50          60          70          80          90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100         110         120         130         140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150         160         170         180         190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200         210         220         230         240
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
 I   H   Q   N   N   G   L   D   T   E   Y   N   H   N   G   S>

250         260         270         280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290         300         310         320         330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340         350         360         370         380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390         400         410         420         430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440         450         460         470         480
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
 K   T   N   G   T   K   T   K   G   A   E   E   L   G   K   L>

490         500         510         520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

```
CGA CTG CCG TTT TGT TGT AAC TTT CAA TGT CTT CCG TGA CAA CAA AAT
 A   D   G   K   T   T   L   K   V   T   E   G   T   V   V  L>

1110         1120         1130         1140         1150
AGC AAG AAC ATT TTA AAA TCC GGA GAA ATA ACA GTT GCA CTT GAT GAC
TCG TTC TTG TAA AAT TTT AGG CCT CTT TAT TGT CAA CGT GAA CTA CTG
 S   K   N   I   L   K   S   G   E   I   T   V   A   L   D  D>

1160         1170         1180         1190         1200
TCT GAC ACT ACT CAG GCT ACT AAA AAA ACT GGA AAA TGG GAT TCA AAT
AGA CTG TGA TGA GTC CGA TGA TTT TTT TGA CCT TTT ACC CTA AGT TTA
 S   D   T   T   Q   A   T   K   K   T   G   K   W   D   S  N>

1210         1220         1230         1240
ACT TCC ACT TTA ACA ATT AGT GTG AAT AGC AAA AAA ATT AAA AAC ATT
TGA AGG TGA AAT TGT TAA TCA CAC TTA TCG TTT TTT TAA TTT TTG TAA
 T   S   T   L   T   I   S   V   N   S   K   K   I   K   N  I>

1250         1260         1270         1280         1290
 GTA TTT ACA AAA GAA GAC ACA ATA ACA GTA CAA AAA TAC GAC TCA GCA
 CAT AAA TGT TTT CTT CTG TGT TAT TGT CAT GTT TTT ATG CTG AGT CGT
  V   F   T   K   E   D   T   I   T   V   Q   K   Y   D   S  A>

1300         1310         1320         1330         1340
GGC ACC AAT CTA GAA GGC AAC GCA GTC GAA ATT AAA ACA CTT GAT GAA
CCG TGG TTA GAT CTT CCG TTG CGT CAG CTT TAA TTT TGT GAA CTA CTT
 G   T   N   L   E   G   N   A   V   E   I   K   T   L   D  E>

1350         1360
CTT AAA AAC GCT TTA AAA TAG
GAA TTT TTG CGA AAT TTT ATC
 L   K   N   A   L   K   *>
```

FIG. 62C

```
              10                  20                  30                  40
     ATG GCT TGT AAT AAT TCA GGG AAA GAT GGG AAT ACA TCT GCA AAT TCT
     TAC CGA ACA TTA TTA AGT CCC TTT CTA CCC TTA TGT AGA CGT TTA AGA
      M   A   C   N   N   S   G   K   D   G   N   T   S   A   N   S>

50                  60                  70                  80                  90
     GCT GAT GAG TCT GTT AAA GGG CCT AAT CTT ACA GAA ATA AGT AAA AAA
     CGA CTA CTC AGA CAA TTT CCC GGA TTA GAA TGT CTT TAT TCA TTT TTT
      A   D   E   S   V   K   G   P   N   L   T   E   I   S   K   K>

100                 110                 120                 130                 140
     ATT ACG GAT TCT AAT GCG GTT TTA CTT GCT GTG AAA GAG GTT GAA GCG
     TAA TGC CTA AGA TTA CGC CAA AAT GAA CGA CAC TTT CTC CAA CTT CGC
      I   T   D   S   N   A   V   L   L   A   V   K   E   V   E   A>

150                 160                 170                 180                 190
     TTG CTG TCA TCT ATA GAT GAG CTT GCT AAA GCT ATT GGT AAA AAA ATA
     AAC GAC AGT AGA TAT CTA CTC GAA CGA TTT CGA TAA CCA TTT TTT TAT
      L   L   S   S   I   D   E   L   A   K   A   I   G   K   K   I>

200                 210                 220                 230                 240
     AAA AAC GAT GGT AGT TTA GAT AAT GAA GCA AAT CGC AAC GAG TCA TTG
     TTT TTG CTA CCA TCA AAT CTA TTA CTT CGT TTA GCG TTG CTC AGT AAC
      K   N   D   G   S   L   D   N   E   A   N   R   N   E   S   L>

250                 260                 270                 280
     TTA GCA GGA GCT TAT ACA ATA TCA ACC TTA ATA ACA CAA AAA TTA AGT
     AAT CGT CCT CGA ATA TGT TAT AGT TGG AAT TAT TGT GTT TTT AAT TCA
      L   A   G   A   Y   T   I   S   T   L   I   T   Q   K   L   S>

290                 300                 310                 320                 330
     AAA TTA AAC GGA TCA GAA GGT TTA AAG GAA AAG ATT GCC GCA GCT AAG
     TTT AAT TTG CCT AGT CTT CCA AAT TTC CTT TTC TAA CGG CGT CGA TTC
      K   L   N   G   S   E   G   L   K   E   K   I   A   A   A   K>

340                 350                 360                 370                 380
     AAA TGC TCT GAA GAG TTT AGT ACT AAA CTA AAA GAT AAT CAT GCA CAG
     TTT ACG AGA CTT CTC AAA TCA TGA TTT GAT TTT CTA TTA GTA CGT GTC
      K   C   S   E   E   F   S   T   K   L   K   D   N   H   A   Q>

390                 400                 410                 420                 430
     CTT GGT ATA CAG GGC GTT ACT GAT GAA AAT GCA AAA AAA GCT ATT TTA
     GAA CCA TAT GTC CCG CAA TGA CTA CTT TTA CGT TTT TTT CGA TAA AAT
      L   G   I   Q   G   V   T   D   E   N   A   K   K   A   I   L>

440                 450                 460                 470                 480
     AAA GCA AAT GCA GCG GGT AAA GAT AAG GGC GTT GAA GAA CTT GAA AAG
     TTT CGT TTA CGT CGC CCA TTT CTA TTC CCG CAA CTT CTT GAA CTT TTC
      K   A   N   A   A   G   K   D   K   G   V   E   E   L   E   K>

490                 500                 510                 520
     TTG TCC GGA TCA TTA GAA AGC TTA TCA AAA GCA GCT AAA GAG ATG CTT
     AAC AGG CCT AGT AAT CTT TCG AAT AGT TTT CGT CGA TTT CTC TAC GAA
      L   S   G   S   L   E   S   L   S   K   A   A   K   E   M   L>
```

FIG. 63A

```
     530           540           550           560           570
  GCT AAT TCA GTT AAA GAG CTT ACA AGC CCT GTT GTC CAT GGC AAG CAA
  CGA TTA AGT CAA TTT CTC GAA TGT TCG GGA CAA CAG GTA CCG TTC GTT
   A   N   S   V   K   E   L   T   S   P   V   V   H   G   K   Q>

580           590           600           610           620
  AAT GTT AGC AGC CTT GAT GAA AAA AAT AGC GTT TCA GTA GAT TTA CCT
  TTA CAA TCG TCG GAA CTA CTT TTT TTA TCG CAA AGT CAT CTA AAT GGA
   N   V   S   S   L   D   E   K   N   S   V   S   V   D   L   P>

630           640           650           660           670
  GGT GCA ATG ACA GTT CTT GTA AGT AAA GAA AAA GAC AAA GAC GGT AAA
  CCA CGT TAC TGT CAA GAA CAT TCA TTT CTT TTT CTG TTT CTG CCA TTT
   G   G   M   T   V   L   V   S   K   E   K   D   K   D   G   K>

680           690           700           710           720
  TAC AGT CTA GAG GCA ACA GTA GAC AAG CTT GAG CTT AAA GGA ACT TCT
  ATG TCA GAT CTC CGT TGT CAT CTG TTC GAA CTC GAA TTT CCT TGA AGA
   Y   S   L   E   A   T   V   D   K   L   E   L   K   G   T   S>

730           740           750           760
  GAT AAA AAC AAC GGT TCT GGA ACA CTT GAA GGT GAA AAA ACT GAC AAA
  CTA TTT TTG TTG CCA AGA CCT TGT GAA CTT CCA CTT TTT TGA CTG TTT
   D   K   N   N   G   S   G   T   L   E   G   E   K   T   D   K>

770           780           790           800           810
  AGT AAA GTA AAA TTA ACA ATT GCT GAT GAC CTA AGT CAA ACT AAA TTT
  TCA TTT CAT TTT AAT TGT TAA CGA CTA CTG GAT TCA GTT TGA TTT AAA
   S   K   V   K   L   T   I   A   D   D   L   S   Q   T   K   F>

820           830           840           850           860
  GAA ATT TTC AAA GAA GAT GCC AAA ACA TTA GTA TCA AAA AAA GTA ACC
  CTT TAA AAG TTT CTT CTA CGG TTT TGT AAT CAT AGT TTT TTT CAT TGG
   E   I   F   K   E   D   A   K   T   L   V   S   K   K   V   T>

870           880           890           900           910
  CTT AAA GAC AAG TCA TCA ACA GAA GAA AAA TTC AAC GAA AAG GGT GAA
  GAA TTT CTG TTC AGT AGT TGT CTT CTT TTT AAG TTG CTT TTC CCA CTT
   L   K   D   K   S   S   T   E   E   K   F   N   E   K   G   E>

920           930           940           950           960
  ACA TCT GAA AAA ACA ATA CTA AGA GCA AAT GGA ACC AGA CTT GAA TAC
  TGT AGA CTT TTT TGT TAT CAT TCT CGT TTA CCT TGG TCT GAA CTT ATG
   T   S   E   K   T   I   V   R   A   N   G   T   R   L   E   Y>

970           980           990          1000
  ACA GAC ATA AAA AGC GAT GGA TCC GGA AAA GCT AAA GAA GTT TTA AAA
  TGT CTG TAT TTT TCG CTA CCT AGG CCT TTT CGA TTT CTT CAA AAT TTT
   T   D   I   K   S   D   G   S   G   K   A   K   E   V   L   K>

1010          1020          1030          1040          1050
     GAC TTT ACT CTT GAA GGA ACT CTA GCT GCT GAC GGC AAA ACA ACA TTG
     CTG AAA TGA GAA CTT CCT TGA GAT CGA CGA CTG CCG TTT TGT TGT AAC
      D   F   T   L   E   G   T   L   A   A   D   G   K   T   T   L>

1060          1070          1080          1090          1100
     AAA GTT ACA GAA GGC ACT GTT GTT TTA AGC AAG AAC ATT TTA AAA TCC
```

FIG. 63B

```
        TTT CAA TGT CTT CCG TGA CAA CAA AAT TCG TTC TTG TAA AAT TTT AGG
         K   V   T   E   G   T   V   V   L   S   K   N   I   L   K   S>

1110        1120        1130        1140        1150
        GGA GAA ATA ACA GTT GCA CTT GAT GAC TCT GAC ACT ACT CAG GCT ACT
        CCT CTT TAT TGT CAA CGT GAA CTA CTG AGA CTG TGA TGA GTC CGA TGA
         G   E   I   T   V   A   L   D   D   S   D   T   T   Q   A   T>

1160        1170        1180        1190        1200
        AAA AAA ACT GGA AAA TGG GAT TCA AAT ACT TCC ACT TTA ACA ATT AGT
        TTT TTT TGA CCT TTT ACC CTA AGT TTA TGA AGG TGA AAT TGT TAA TCA
         K   K   T   G   K   W   D   S   N   T   S   T   L   T   I   S>

1210        1220        1230        1240
        GTG AAT AGC AAA AAA ACT AAA AAC ATT GTA TTT ACA AAA GAA GAC ACA
        CAC TTA TCG TTT TTT TGA TTT TTG TAA CAT AAA TGT TTT CTT CTG TGT
         V   N   S   K   K   T   K   N   I   V   F   T   K   E   D   T>

1250        1260        1270        1280        1290
    ATA ACA GTA CAA AAA TAC GAC TCA GCA GGC ACC AAT CTA GAA GGC AAC
    TAT TGT CAT GTT TTT ATG CTG AGT CGT CCG TGG TTA GAT CTT CCG TTG
     I   T   V   Q   K   Y   D   S   A   G   T   N   L   E   G   N>

1300        1310        1320        1330        1340
    GCA GTC GAA ATT AAA ACA CTT GAT GAA CTT AAA AAC GCT TTA AAA TAG
    CGT CAG CTT TAA TTT TGT GAA CTA CTT GAA TTT TTG CGA AAT TTT ATC
     A   V   E   I   K   T   L   D   E   L   K   N   A   L   K   *>
```

FIG. 63C

```
              10            20            30            40
ATG GCT TGT AAT AAT TCA GGA AAA GAT GGG AAT ACA TCT GCA AAT TCT
TAC CGA ACA TTA TTA AGT CCT TTT CTA CCC TTA TGT AGA CGT TTA AGA
 M   A   C   N   N   S   G   K   D   G   N   T   S   A   N   S>

50            60            70            80            90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100           110           120           130           140
ATT ACA GAA TCT AAC GCA GTT GTT CTG GCT GTG AAA GAA ATT GAA ACT
TAA TGT CTT AGA TTG CGT CAA CAA GAC CGA CAC TTT CTT TAA CTT TGA
 I   T   E   S   N   A   V   V   L   A   V   K   E   I   E   T>

150           160           170           180           190
TTG CTT GCA TCT ATA GAT GAA CTT GCT ACT AAA GCT ATT GGT AAA AAA
AAC GAA CGT AGA TAT CTA CTT GAA CGA TGA TTT CGA TAA CCA TTT TTT
 L   L   A   S   I   D   E   L   A   T   K   A   I   G   K   K>

200           210           220           230           240
ATA CAA CAA AAT GGT GGT TTA GCT GTC GAA GCG GGG CAT AAT GGA ACA
TAT GTT GTT TTA CCA CCA AAT CGA CAG CTT CGC CCC GTA TTA CCT TGT
 I   Q   Q   N   G   G   L   A   V   E   A   G   H   N   G   T>

250           260           270           280
TTG TTA GCA GGT GCT TAT ACA ATA TCA AAA CTA ATA ACA CAA AAA TTA
AAC AAT CGT CCA CGA ATA TGT TAT AGT TTT GAT TAT TGT GTT TTT AAT
 L   L   A   G   A   Y   T   I   S   K   L   I   T   Q   K   L>

290           300           310           320           330
GAT GGA TTG AAA AAT TCA GAA AAA TTA AAG GAA AAA ATT GAA AAT GCT
CTA CCT AAC TTT TTA AGT CTT TTT AAT TTC CTT TTT TAA CTT TTA CGA
 D   G   L   K   N   S   E   K   L   K   E   K   I   E   N   A>

340           350           360           370           380
AAG AAA TGT TCT GAA GAT TTT ACT AAA AAA CTA GAA GGA GAA CAT GCG
TTC TTT ACA AGA CTT CTA AAA TGA TTT TTT GAT CTT CCT CTT GTA CGC
 K   K   C   S   E   D   F   T   K   K   L   E   G   E   H   A>

390           400           410           420           430
CAA CTT GGA ATT GAA AAT GTT ACT GAT GAG AAT GCA AAA AAA GCT ATT
GTT GAA CCT TAA CTT TTA CAA TGA CTA CTC TTA CGT TTT TTT CGA TAA
 Q   L   G   I   E   N   V   T   D   E   N   A   K   K   A   I>

440           450           460           470           480
TTA ATA ACA GAT GCA GCT AAA GAT AAG GGC GCT GCA GAG CTT GAA AAG
AAT TAT TGT CTA CGT CGA TTT CTA TTC CCG CGA CGT CTC GAA CTT TTC
 L   I   T   D   A   A   K   D   K   G   A   A   E   L   E   K>

490           500           510           520
CTA TTT AAA GCA GTA GAA AAC TTG GCA AAA GCA GCT AAA GAG ATG CTT
GAT AAA TTT CGT CAT CTT TTG AAC CGT TTT CGT CGA TTT CTC TAC GAA
 L   F   K   A   V   E   N   L   A   K   A   A   K   E   M   L>
```

FIG. 64A

```
      530             540             550             560             570
  GCT AAT TCA GTT AAA GAG CTT ACA AGT CCT ATT GTG CAT GGC GTT TCA
  CGA TTA AGT CAA TTT CTC GAA TGT TCA GGA TAA CAC GTA CCG CAA AGT
   A   N   S   V   K   E   L   T   S   P   I   V   H   G   V   S>

580             590             600             610             620
  GTA GAT TTG CCT GGT GAA ATG AAA GTT CTT GTA AGC AAA GAA AAA AAC
  CAT CTA AAC GGA CCA CTT TAC TTT CAA GAA CAT TCG TTT CTT TTT TTG
   V   D   L   P   G   E   M   K   V   L   V   S   K   E   K   N>

630             640             650             660             670
  AAA GAC GGC AAG TAC GAT CTA ATT GCA ACA GTA GAC AAG CTT GAG CTT
  TTT CTG CCG TTC ATG CTA GAT TAA CGT TGT CAT CTG TTC GAA CTC GAA
   K   D   G   K   Y   D   L   I   A   T   V   D   K   L   E   L>

680             690             700             710             720
  AAA GGA ACT TCT GAT AAA AAC AAT GGA TCT GGA GTA CTT GAA GGC GTA
  TTT CCT TGA AGA CTA TTT TTG TTA CCT AGA CCT CAT GAA CTT CCG CAT
   K   G   T   S   D   K   N   N   G   S   G   V   L   E   G   V>

730             740             750             760
  AAA GCT GAC AAA AGT AAA GTA AAA TTA ACA ATT TCT GAC GAT CTA GGT
  TTT CGA CTG TTT TCA TTT CAT TTT AAT TGT TAA AGA CTG CTA GAT CCA
   K   A   D   K   S   K   V   K   L   T   I   S   D   D   L   G>

770.         780             790             800             810
  CAA ACC ACA CTT GAA GTT TTC AAA GAA GAT GGC AAA ACA CTA GTA TCA
  GTT TGG TGT GAA CTT CAA AAG TTT CTT CTA CCG TTT TGT GAT CAT AGT
   Q   T   T   L   E   V   F   K   E   D   G   K   T   L   V   S>

820             830             840             850             860
  AAA AAA GTA ACT TCC AAA GAC AAG TCA TCA ACA GAA GAA AAA TTC AAT
  TTT TTT CAT TGA AGG TTT CTG TTC AGT AGT TGT CTT CTT TTT AAG TTA
   K   K   V   T   S   K   D   K   S   S   T   E   E   K   F   N>

870             880             890             900             910
  GAA AAA GGT GAA GTA TCT GAA AAA ATA ATA ACA AGA GCA GAC GGA ACC
  CTT TTT CCA CTT CAT AGA CTT TTT TAT TAT TGT TCT CGT CTG CCT TGG
   E   K   G   E   V   S   E   K   I   I   T   R   A   D   G   T>

920             930             940             950             960
  AGA CTT GAA TAC ACA GGA ATT AAA AGC GAT GGA TCT GGA AAA GCT AAA
  TCT GAA CTT ATG TGT CCT TAA TTT TCG CTA CCT AGA CCT TTT CGA TTT
   R   L   E   Y   T   G   I   K   S   D   G   S   G   K   A   K>

970             980             990             1000
  GAG GTT TTA AAA AAA TTT ACT CTT GAA GGA AAA GTA GCT AAT GAT AAA
  CTC CAA AAT TTT TTT AAA TGA GAA CTT CCT TTT CAT CGA TTA CTA TTT
   E   V   L   K   K   F   T   L   E   G   K   V   A   N   D   K>

1010         1020            1030            1040            1050
  GTA ACA TTG GAA GTA AAA GAA GGA ACC GTT ACT TTA AGT AAG AAC ATT
  CAT TGT AAC CTT CAT TTT CTT CCT TGG CAA TGA AAT TCA TTC TTG TAA
   V   T   L   E   V   K   E   G   T   V   T   L   S   K   N   I>

1060            1070            1080            1090            1100
  TCA AAA TCT GGG GAA GTT TCA GTT GAA CTT AAT GAC ACT GAC AGT AGT
```

FIG. 64B

```
              AGT TTT AGA CCC CTT CAA AGT CAA CTT GAA TTA CTG TGA CTG TCA TCA
              S   K   S   G   E   V   S   V   E   L   N   D   T   D   S   S>

1110            1120            1130            1140            1150
     GCT GCT ACT AAA AAA ACT GCA GCT TGG AAT TCA GGC ACT TCA ACT TTA
     CGA CGA TGA TTT TTT TGA CGT CGA ACC TTA AGT CCG TGA AGT TGA AAT
     A   A   T   K   K   T   A   A   W   N   S   G   T   S   T   L>

1160            1170            1180            1190            1200
     ACA ATT ACT GTA AAC AGT AAA AAA ACT AAA GAC CTT GTG TTT ACA AAA
     TGT TAA TGA CAT TTG TCA TTT TTT TGA TTT CTG GAA CAC AAA TGT TTT
     T   I   T   V   N   S   K   K   T   K   D   L   V   F   T   K>

1210            1220            1230            1240
     GAA AAC ACA ATT ACA GTA CAA CAA TAC GAC TCA AAT GGC ACC AAA TTA
     CTT TTG TGT TAA TGT CAT GTT GTT ATG CTG AGT TTA CCG TGG TTT AAT
     E   N   T   I   T   V   Q   Q   Y   D   S   N   G   T   K   L>

1250            1260            1270            1280            1290
     GAG GGG TCA GCA GTT GAA ATT ACA AAA CTT GAT GAA ATT AAA AAC GCT
     CTC CCC AGT CGT CAA CTT TAA TGT TTT GAA CTA CTT TAA TTT TTG CGA
     E   G   S   A   V   E   I   T   K   L   D   E   I   K   N   A>

1300
TTA AAA TAA
AAT TTT ATT
L   K   *>
```

FIG. 64C

```
          10              20              30              40
ATG GCT TGT ACT AAT TCA GGG AAA GGT GGG GAT TCT GCA TCT ACT AAT
TAC CGA ACA TGA TTA AGT CCC TTT CCA CCC CTA AGA CGT AGA TGA TTA
 M   A   C   S   N   S   G   K   G   G   D   S   A   S   T   N>

50              60              70              80              90
CCT GCT GAC GAG TCT GCG AAA GGG CCT AAT CTT ACA GAA ATA AGC AAA
GGA CGA CTG CTC AGA CGC TTT CCC GGA TTA GAA TGT CTT TAT TCG TTT
 P   A   D   E   S   A   K   G   P   N   L   T   E   I   S   K>

100             110             120             130             140
AAA ATT ACA GAT TCT AAT GCA TTT GTA CTT GCT GTT AAA GAA GTT GAG
TTT TAA TGT CTA AGA TTA CGT AAA CAT GAA CGA CAA TTT CTT CAA CTC
 K   I   T   D   S   N   A   F   V   L   A   V   K   E   V   E>

150             160             170             180             190
ACT TTG GTT TTA TCT ATA GAT GAA CTT GCT AAG AAA GCT ATT GGT CAA
TGA AAC CAA AAT AGA TAT CTA CTT GAA CGA TTC TTT CGA TAA CCA GTT
 T   L   V   L   S   I   D   E   L   A   K   K   A   I   G   Q>

200             210             220             230             240
AAA ATA GAC AAT AAT AAT GGT TTA GCT GCT TTA AAT AAT CAG AAT GGA
TTT TAT CTG TTA TTA TTA CCA AAT CGA CGA AAT TTA TTA GTC TTA CCT
 K   I   D   N   N   N   G   L   A   A   L   N   N   Q   N   G>

250             260             270             280
TCG TTG TTA GCA GGA GCC TAT GCA ATA TCA ACC CTA ATA ACA GAA AAA
AGC AAC AAT CGT CCT CGG ATA CGT TAT AGT TGG GAT TAT TGT CTT TTT
 S   L   L   A   G   A   Y   A   I   S   T   L   I   T   E   K>

290             300             310             320             330
TTG AGT AAA TTG AAA AAT TTA GAA GAA TTA AAG ACA GAA ATT GCA AAG
AAC TCA TTT AAC TTT TTA AAT CTT CTT AAT TTC TGT CTT TAA CGT TTC
 L   S   K   L   K   N   L   E   E   L   K   T   E   I   A   K>

340             350             360             370             380
GCT AAG AAA TGT TCC GAA GAA TTT ACT AAT AAA CTA AAA AGT GGT CAT
CGA TTC TTT ACA AGG CTT CTT AAA TGA TTA TTT GAT TTT TCA CCA GTA
 A   K   K   C   S   E   E   F   T   N   K   L   K   S   G   H>

390             400             410             420             430
GCA GAT CTT GGC AAA CAG GAT GCT ACC GAT GAT CAT GCA AAA GCA GCT
CGT CTA GAA CCG TTT GTC CTA CGA TGG CTA CTA GTA CGT TTT CGT CGA
 A   D   L   G   K   Q   D   A   T   D   D   H   A   K   A   A>

440             450             460             470             480
ATT TTA AAA ACA CAT GCA ACT ACC GAT AAA GGT GCT AAA GAA TTT AAA
TAA AAT TTT TGT GTA CGT TGA TGG CTA TTT CCA CGA TTT CTT AAA TTT
 I   L   K   T   H   A   T   T   D   K   G   A   K   E   F   K>

490             500             510             520
GAT TTA TTT GAA TCA GTA GAA GGT TTG TTA AAA GCA GCT CAA GTA GCA
CTA AAT AAA CTT AGT CAT CTT CCA AAC AAT TTT CGT CGA GTT CAT CGT
 D   L   F   E   S   V   E   G   L   L   K   A   A   Q   V   A>
```

FIG. 65A

```
      530            540           550            560            570
   CTA ACT AAT TCA GTT AAA GAA CTT ACA AGT CCT GTT GTA GCA GAA AGT
   GAT TGA TTA AGT CAA TTT CTT GAA TGT TCA GGA CAA CAT CGT CTT TCA
    L   T   N   S   V   K   E   L   T   S   P   V   V   A   E   S>

580           590            600            610           620
   CCA AAA AAA CCT TCC ATG GCC GTT TCA GTA GAT TTG CCT GGT GAA ATG
   GGT TTT TTT GGA AGG TAC CGG CAA AGT CAT CTA AAC GGA CCA CTT TAC
    P   K   K   P   S   M   A   V   S   V   D   L   P   G   E   M>

630            640            650            660           670
   AAA GTT CTT GTA AGC AAA GAA AAA AAC AAA GAC GGC AAG TAC GAT CTA
   TTT CAA GAA CAT TCG TTT CTT TTT TTG TTT CTG CCG TTC ATG CTA GAT
    K   V   L   V   S   K   E   K   N   K   D   G   K   Y   D   L>

680            690            700            710           720
   ATT GCA ACA GTA GAC AAG CTT GAG AAA GGA ACT TCT GAT AAA AAC
   TAA CGT TGT CAT CTG TTC GAA CTC TTT CCT TGA AGA CTA TTT TTG
    I   A   T   V   D   K   L   E   L   K   G   T   S   D   K   N>

730            740            750           760
   AAT GGA TCT GGA GTA CTT GAA GGC GTA AAA GCT GAC AAA AGT AAA GTA
   TTA CCT AGA CCT CAT GAA CTT CCG CAT TTT CGA CTG TTT TCA TTT CAT
    N   G   S   G   V   L   E   G   V   K   A   D   K   S   K   V>

770           780            790            800           810
   AAA TTA ACA ATT TCT GAC GAT CTA GGT CAA ACC ACA CTT GAA GTT TTC
   TTT AAT TGT TAA AGA CTG CTA GAT CCA GTT TGG TGT GAA CTT CAA AAG
    K   L   T   I   S   D   D   L   G   Q   T   T   L   E   V   F>

820            830           840            850            860
   AAA GAA GAT GGC AAA ACA CTA GTA TCA AAA AAA GTA ACT TCC AAA GAC
   TTT CTT CTA CCG TTT TGT GAT CAT AGT TTT TTT CAT TGA AGG TTT CTG
    K   E   D   G   K   T   L   V   S   K   K   V   T   S   K   D>

870            880            890            900            910
   AAG TCA TCA ACA GAA GAA AAA TTC AAT GAA AAA GGT GAA GTA TCT GAA
   TTC AGT AGT TGT CTT CTT TTT AAG TTA CTT TTT CCA CTT CAT AGA CTT
    K   S   S   T   E   E   K   F   N   E   K   G   E   V   S   E>

920            930            940            950            960
   AAA ATA ATA ACA AGA GCA GAC GGA ACC AGA CTT GAA TAC ACA GGA ATT
   TTT TAT TAT TGT TCT CGT CTG CCT TGG TCT GAA CTT ATG TGT CCT TAA
    K   I   I   T   R   A   D   G   T   R   L   E   Y   T   G   I>

970           980            990            1000
   AAA AGC GAT GGA TCT GGA AAA GCT AAA GAG GTT TTA AAA AAA TTT ACT
   TTT TCG CTA CCT AGA CCT TTT CGA TTT CTC CAA AAT TTT TTT AAA TGA
    K   S   D   G   S   G   K   A   K   E   V   L   K   K   F   T>

1010           1020          1030           1040          1050
   CTT GAA GGA AAA GTA GCT AAT GAT AAA GTA ACA TTG GAA GTA AAA GAA
   GAA CTT CCT TTT CAT CGA TTA CTA TTT CAT TGT AAC CTT CAT TTT CTT
    L   E   G   K   V   A   N   D   K   V   T   L   E   V   K   E>

1060           1070          1080           1090           1100
   GGA ACC GTT ACT TTA AGT AAG AAT ATT TCA AAA TCT GGG GAA GTT TCA
```

FIG. 65B

```
                CCT TGG CAA TGA AAT TCA TTC TTA TAA AGT TTT AGA CCC CTT CAA AGT
                 G   T   V   T   L   S   K   N   I   S   K   S   G   E   V   S>

1110        1120        1130        1140        1150
GTT GAA CTT AAT GAC ACT GAC AGT AGT GCT GCT ACT AAA AAA ACT GCA
CAA CTT GAA TTA CTG TGA CTG TCA TCA CGA CGA TGA TTT TTT TGA CGT
 V   E   L   N   D   T   D   S   S   A   A   T   K   K   T   A>

1160        1170        1180        1190        1200
GCT TGG AAT TCA AAA ACT TCC ACT TTA ACA ATT AGT GTG AAT AGC CAA
CGA ACC TTA AGT TTT TGA AGG TGA AAT TGT TAA TCA CAC TTA TCG GTT
 A   W   N   S   K   T   S   T   L   T   I   S   V   N   S   Q>

1210        1220        1230        1240
AAA ACC AAA AAC CTT GTA TTC ACA AAA GAA GAC ACA ATA ACA GTA CAA
TTT TGG TTT TTG GAA CAT AAG TGT TTT CTT CTG TGT TAT TGT CAT GTT
 K   T   K   N   L   V   F   T   K   E   D   T   I   T   V   Q>

1250        1260        1270        1280        1290
AAA TAC GAC TCA GCA GGC ACC AAT CTA GAA GGC AAA GCA GTC GAA ATT
TTT ATG CTG AGT CGT CCG TGG TTA GAT CTT CCG TTT CGT CAG CTT TAA
 K   Y   D   S   A   G   T   N   L   E   G   K   A   V   E   I>

1300        1310        1320        1330
ACA ACA CTT AAA GAA CTT AAA AAC GCT TTA AAA TAA
TGT TGT GAA TTT CTT GAA TTT TTG CGA AAT TTT ATT
 T   T   L   K   E   L   K   N   A   L   K   *>
```

FIG. 65C

```
              10              20              30              40
    ATG GCT TGT AAT AAT TCA GGT GGG GAT TCT GCA TCT ACT AAT CCT GAT
    TAC CGA ACA TTA TTA AGT CCA CCC CTA AGA CGT AGA TGA TTA GGA CTA
     M   A   C   N   N   S   G   G   D   S   A   S   T   N   P   D>

50              60              70              80              90
    GAG TCT GCA AAA GGA CCT AAT CTT ACC GTA ATA AGC AAA AAA ATT ACA
    CTC AGA CGT TTT CCT GGA TTA GAA TGG CAT TAT TCG TTT TTT TAA TGT
     E   S   A   K   G   P   N   L   T   V   I   S   K   K   I   T>

100             110             120             130             140
    GAT TCT AAT GCA TTT TTA CTG GCT GTG AAA GAA GTT GAG GCT TTG CTT
    CTA AGA TTA CGT AAA AAT GAC CGA CAC TTT CTT CAA CTC CGA AAC GAA
     D   S   N   A   F   L   L   A   V   K   E   V   E   A   L   L>

150             160             170             180             190
    TCA TCT ATA GAT GAA CTT TCT AAA GCT ATT GGT AAA AAA ATA AAA AAT
    AGT AGA TAT CTA CTT GAA AGA TTT CGA TAA CCA TTT TTT TAT TTT TTA
     S   S   I   D   E   L   S   K   A   I   G   K   K   I   K   N>

200             210             220             230             240
    GAT GGT ACT TTA GAT AAC GAA GCA AAT CGA AAC GAA TCA TTG ATA GCA
    CTA CCA TGA AAT CTA TTG CTT CGT TTA GCT TTG CTT AGT AAC TAT CGT
     D   G   T   L   D   N   E   A   N   R   N   E   S   L   I   A>

250             260             270             280
    GGA GCT TAT GAA ATA TCA AAA CTA ATA ACA CAA AAA TTA AGT GTA TTG
    CCT CGA ATA CTT TAT AGT TTT GAT TAT TGT GTT TTT AAT TCA CAT AAC
     G   A   Y   E   I   S   K   L   I   T   Q   K   L   S   V   L>

290             300             310             320             330
    AAT TCA GAA GAA TTA AAG GAA AAA ATT AAA GAG GCT AAG GAT TGT TCC
    TTA AGT CTT CTT AAT TTC CTT TTT TAA TTT CTC CGA TTC CTA ACA AGG
     N   S   E   E   L   K   E   K   I   K   E   A   K   D   C   S>

340             350             360             370             380
    GAA AAA TTT ACT ACT AAG CTA AAA GAT AGT CAT GCA GAG CTT GGT ATA
    CTT TTT AAA TGA TGA TTC GAT TTT CTA TCA GTA CGT CTC GAA CCA TAT
     E   K   F   T   T   K   L   K   D   S   H   A   E   L   G   I>

390             400             410             420             430
    CAA AGC GTT CAG GAT GAT AAT GCA AAA AAA GCT ATT TTA AAA ACA CAT
    GTT TCG CAA GTC CTA CTA TTA CGT TTT TTT CGA TAA AAT TTT TGT GTA
     Q   S   V   Q   D   D   N   A   K   K   A   I   L   K   T   H>

440             450             460             470             480
    GGA ACT AAA GAC AAG GGT GCT AAA GAA CTT GAA GAG TTA TTT AAA TCA
    CCT TGA TTT CTG TTC CCA CGA TTT CTT GAA CTT CTC AAT AAA TTT AGT
     G   T   K   D   K   G   A   K   E   L   E   E   L   F   K   S>

490             500             510             520
    CTA GAA AGC TTG TCA AAA GCA GCG CAA GCA GCA TTA ACT AAT TCA GTT
    GAT CTT TCG AAC AGT TTT CGT CGC GTT CGT CGT AAT TGA TTA AGT CAA
     L   E   S   L   S   K   A   A   Q   A   A   L   T   N   S   V>
```

FIG. 66A

```
      530           540           550           560           570
   AAA GAG CTT ACA AAT CCT GTT GTG GCA GAA AGT CCA AAA AAA CCT TCC
   TTT CTC GAA TGT TTA GGA CAA CAC CGT CTT TCA GGT TTT TTT GGA AGG
    K   E   L   T   N   P   V   V   A   E   S   P   K   K   P   S>

580           590           600           610           620
   ATG GCC GTT TCA GTA GAT TTG CCT GGT GAA ATG AAA GTT CTT GTA AGC
   TAC CGG CAA AGT CAT CTA AAC GGA CCA CTT TAC TTT CAA GAA CAT TCG
    M   A   V   S   V   D   L   P   G   E   M   K   V   L   V.  S>

630           640           650           660           670
   AAA GAA AAA AAC AAA GAC GGC AAG TAC GAT CTA ATT GCA ACA GTA GAC
   TTT CTT TTT TTG TTT CTG CCG TTC ATG CTA GAT TAA CGT TGT CAT CTG
    K   E   K   N   K   D   G   K   Y.  D   L   I   A   T   V   D>

680           690           700           710           720
   AAG CTT GAG CTT AAA GGA ACT TCT GAT AAA AAC AAT GGA TCT GGA GTA
   TTC GAA CTC GAA TTT CCT TGA AGA CTA TTT TTG TTA CCT AGA CCT CAT
    K   L   E   L   K   G   T   S   D   K   N   N   G   S   G   V>

730           740           750           760
   CTT GAA GGC GTA AAA GCT GAC AAA AGT AAA GTA AAA TTA ACA ATT TCT
   GAA CTT CCG CAT TTT CGA CTG TTT TCA TTT CAT TTT AAT TGT TAA AGA
    L   E   G   V   K   A   D   K   S   K   V   K   L   T   I   S>

770          780           790           800           810
   GAC GAT CTA GGT CAA ACC ACA CTT GAA GTT TTC AAA GAA GAT GGC AAA
   CTG CTA GAT CCA GTT TGG TGT GAA CTT CAA AAG TTT CTT CTA CCG TTT
    D   D   L   G   Q   T   T   L   E   V   F   K   E   D   G   K>

820           830           840           850           860
   ACA CTA GTA TCA AAA AAA GTA ACT TCC AAA GAC AAG TCA TCA ACA GAA
   TGT GAT CAT AGT TTT TTT CAT TGA AGG TTT CTG TTC AGT AGT TGT CTT
    T   L   V   S   K   K   V   T   S   K   D   K   S   S   T   E>

870           880           890           900           910
   GAA AAA TTC AAT GAA AAA GGT GAA GTA TCT GAA AAA ATA ATA ACA AGA
   CTT TTT AAG TTA CTT TTT CCA CTT CAT AGA CTT TTT TAT TAT TGT TCT
    E   K   F   N   E   K   G   E   V   S   E   K   I   I   T   R>

920           930           940           950           960
   GCA GAC GGA ACC AGA CTT GAA TAC ACA GGA ATT AAA AGC GAT GGA TCT
   CGT CTG CCT TGG TCT GAA CTT ATG TGT CCT TAA TTT TCG CTA CCT AGA
    A   D   G   T   R   L   E   Y   T   G   I   K   S   D   G   S>

970           980           990          1000
   GGA AAA GCT AAA GAG GTT TTA AAA AAA TTT ACT CTT GAA GGA AAA GTA
   CCT TTT CGA TTT CTC CAA AAT TTT TTT AAA TGA GAA CTT CCT TTT CAT
    G   K   A   K   E   V   L   K   K   F   T   L   E   G   K   V>

1010         1020          1030          1040          1050
   GCT AAT GAT AAA GTA ACA TTG GAA GTA AAA GAA GGA ACC GTT ACT TTA
   CGA TTA CTA TTT CAT TGT AAC CTT CAT TTT CTT CCT TGG CAA TGA AAT
    A   N   D   K   V   T   L   E   V   K   E   G   T   V   T   L>

1060         1070.         1080          1090          1100
   AGT AAG AAC ATT TCA AAA TCT GGG GAA GTT TCA GTT GAA CTT AAT GAC
```

FIG. 66B

```
            TCA TTC TTG TAA AGT TTT AGA CCC CTT CAA AGT CAA CTT GAA TTA CTG
             S   K   N   I   S   K   S   G   E   V   S   V   E   L   N   D>

1110        1120        1130        1140        1150
            ACT GAC AGT AGT GCT GCT ACT AAA AAA ACT GCA GCT TGG AAT TCA AAA
            TGA CTG TCA TCA CGA CGA TGA TTT TTT TGA CGT CGA ACC TTA AGT TTT
             T   D   S   S   A   A   T   K   K   T   A   A   W   N   S   K>

1160        1170        1180        1190        1200
            ACT TCT ACT TTA ACA ATT AGT GTT AAC AGC AAA AAA ACT ACA CAA CTT
            TGA AGA TGA AAT TGT TAA TCA CAA TTG TCG TTT TTT TGA TGT GTT GAA
             T   S   T   L   T   I   S   V   N   S   K   K   T   T   Q   L>

1210        1220        1230        1240
            GTG TTT ACT AAA CAA GAC ACA ATA ACT GTA CAA AAA TAC GAC TCC GCA
            CAC AAA TGA TTT GTT CTG TGT TAT TGA CAT GTT TTT ATG CTG AGG CGT
             V   F   T   K   Q   D   T   I   T   V   Q   K   Y   D   S   A>

1250        1260        1270        1280        1290
       GGT ACC AAT TTA GAA GGC ACA GCA GTC GAA ATT AAA ACA CTT GAT GAA
       CCA TGG TTA AAT CTT CCG TGT CGT CAG CTT TAA TTT TGT GAA CTA CTT
        G   T   N   L   E   G   T   A   V   E   I   K   T   L   D   E>

1300        1310
       CTT AAA AAC GCT TTA AAA TAA
       GAA TTT TTG CGA AAT TTT ATT
        L   K   N   A   L   K   *>
```

FIG. 66C

```
                10                  20                  30                  40
      ATG GCT TGT AAT AAT TCA GGG AAA GAT GGG AAT ACA TCT GCA AAT TCT
      TAC CGA ACA TTA TTA AGT CCC TTT CTA CCC TTA TGT AGA CGT TTA AGA
       M   A   C   N   N   S   G   K   D   G   N   T   S   A   N   S>

50                  60                  70                  80                  90
      GCT GAT GAG TCT GTT AAA GGG CCT AAT CTT ACA GAA ATA AAT AAA AAA
      CGA CTA CTC AGA CAA TTT CCC GGA TTA GAA TGT CTT TAT TTA TTT TTT
       A   D   E   S   V   K   G   P   N   L   T   E   I   N   K   K>

100                 110                 120                 130                 140
      ATT ACG GAT TCT AAT GCG GTT TTA CTT GCT GTG AAA GAG GTT GAA GCG
      TAA TGC CTA AGA TTA CGC CAA AAT GAA CGA CAC TTT CTC CAA CTT CGC
       I   T   D   S   N   A   V   L   L   A   V   K   E   V   E   A>

150                 160                 170                 180                 190
      TTG CTG TCA TCT ATA GAT GAA ATT GCT GCT AAA GCT ATT GCT AAA AAA
      AAC GAC AGT AGA TAT CTA CTT TAA CGA CGA TTT CGA TAA CGA TTT TTT
       L   L   S   S   I   D   E   I   A   A   K   A   I   G   K   K>

200                 210                 220                 230                 240
      ATA CAC CAA AAT AAT GGT TTG GAT ACC GAA AAT AAT CAC AAT GGA TCA
      TAT GTG GTT TTA TTA CCA AAC CTA TGG CTT TTA TTA GTG TTA CCT AGT
       I   H   Q   N   N   G   L   D   T   E   N   N   H   N   G   S>

250                 260                 270                 280
      TTG TTA GCG GGA GCT TAT GCA ATA TCA ACC CTA ATA AAA CAA AAA TTA
      AAC AAT CGC CCT CGA ATA CGT TAT AGT TGG GAT TAT TTT GTT TTT AAT
       L   L   A   G   A   Y   A   I   S   T   L   I   K   Q   K   L>

290                 300                 310                 320                 330
      GAT GGA TTG AAA AAT GAA GGA TTA AAG GAA AAA ATT GAT GCG GCT AAG
      CTA CCT AAC TTT TTA CTT CCT AAT TTC CTT TTT TAA CTA CGC CGA TTC
       D   G   L   K   N   E   G   L   K   E   K   I   D   A   A   K>

340                 350                 360                 370                 380
      AAA TGT TCT GAA ACA TTT ACT AAT AAA TTA AAA GAA AAA CAC ACA GAT
      TTT ACA AGA CTT TGT AAA TGA TTA TTT AAT TTT CTT TTT GTG TGT CTA
       K   C   S   E   T   F   T   N   K   L   K   E   K   H   T   D>

390                 400                 410                 420                 430
      CTT GGT AAA GAA GGT GTT ACT GAT GCT GAT GCA AAA GAA GCC ATT TTA
      GAA CCA TTT CTT CCA CAA TGA CTA CGA CTA CGT TTT CTT CGG TAA AAT
       L   G   K   E   G   V   T   D   A   D   A   K   E   A   I   L>

440                 450                 460                 470                 480
      AAA GCA AAT GGT ACT AAA ACT AAA GGT GCT GAA GAA CTT GGA AAA TTA
      TTT CGT TTA CCA TGA TTT TGA TTT CCA CGA CTT CTT GAA CCT TTT AAT
       K   A   N   G   T   K   T   K   G   A   E   E   L   G   K   L>

490                 500                 510                 520
      TTT GAA TCA GTA GAG GTC TTG TCA AAA GCA GCT AAA GAG ATG CTT GCT
      AAA CTT AGT CAT CTC CAG AAC AGT TTT CGT CGA TTT CTC TAC GAA CGA
       F   E   S   V   E   V   L   S   K   A   A   K   E   M   L   A>
```

FIG. 67A

```
       530           540           550           560           570
    AAT TCA GTT AAA GAG CTT ACA AGC CCT GTT GTG GCA GAA AGT CCA AAA
    TTA AGT CAA TTT CTC GAA TGT TCG GGA CAA CAC CGT CTT TCA GGT TTT
     N   S   V   K   E   L   T   S   P   V   V   A   E   S   P   K>

580           590           600           610           620
    AAA CCT TCC ATG GCC AAG CAA AAT GTT TCT GAA AAA ATA ATA ACA AGA
    TTT GGA AGG TAC CGG TTC GTT TTA CAA AGA CTT TTT TAT TAT TGT TCT
     K   P   S   M   A   K   Q   N   V   S   E   K   I   I   T   R>

630           640           650           660           670
    GCA GAC GGA ACC AGA CTT GAA TAC ACA GGA ATT AAA AGC GAT GGA TCT
    CGT CTG CCT TGG TCT GAA CTT ATG TGT CCT TAA TTT TCG CTA CCT AGA
     A   D   G   T   R   L   E   Y   T   G   I   K   S   D   G   S>

680           690           700           710           720
    GGA AAA GCT AAA GAG GTT TTA AAA GGC TAT GTT CTT GAA GGA ACT CTA
    CCT TTT CGA TTT CTC CAA AAT TTT CCG ATA CAA GAA CTT CCT TGA GAT
     G   K   A   K   E   V   L   K   G   Y   V   L   E   G   T   L>

730           740           750           760
    ACT GCT GAA AAA ACA ACA TTG GTG GTT AAA GAA GGA ACT GTT ACT TTA
    TGA CGA CTT TTT TGT TGT AAC CAC CAA TTT CTT CCT TGA CAA TGA AAT
     T   A   E   K   T   T   L   V   V   K   E   G   T   V   T   L>

770           780           790           800           810
    AGC AAA AAT ATT TCA AAA TCT GCG GAA GTT TCA GTT CAA CTT AAT GAC
    TCG TTT TTA TAA AGT TTT AGA CGC CTT CAA AGT CAA GTT GAA TTA CTG
     S   K   N   I   S   K   S   G   E   V   S   V   E   L   N   D>

820           830           840           850           860
    ACT GAC AGT AGT GCT GCT ACT AAA AAA ACT GCA GCT TGG AAT TCA GGC
    TGA CTG TCA TCA CGA CGA TGA TTT TTT TGA CGT CGA ACC TTA AGT CCG
     T   D   S   S   A   A   T   K   K   T   A   A   W   N   S   G>

870           880           890           900           910
    ACT TCA ACT TTA ACA ATT ACT GTA AAC AGT AAA AAA ACT AAA GAC CTT
    TGA AGT TGA AAT TGT TAA TGA CAT TTG TCA TTT TTT TGA TTT CTG GAA
     T   S   T   L   T   I   T   V   N   S   K   K   T   K   D   L>

920           930           940           950           960
    GTG TTT ACA AAA GAA AAC ACA ATT ACA GTA CAA CAA TAC GAC TCA AAT
    CAC AAA TGT TTT CTT TTG TGT TAA TGT CAT GTT GTT ATG CTG AGT TTA
     V   F   T   K   E   N   T   I   T   V   Q   Q   Y   D   S   N>

970           980           990          1000
    GGC ACC AAA TTA GAG GGG TCA GCA GTT GAA ATT ACA AAA CTT GAT GAA
    CCG TGG TTT AAT CTC CCC AGT CGT CAA CTT TAA TGT TTT GAA CTA CTT
     G   T   K   L   E   G   S   A   V   E   I   T   K   L   D   E>

1010          1020
    ATT AAA AAC GCT TTA AAA TAA
    TAA TTT TTG CGA AAT TTT ATT
     I   K   N   A   L   K   *>
```

FIG. 673

```
            10           20            30           40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50          60            70           80           90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
 A   D   E   S   V   K   G   P   N   L   T   E   I   N   K   K>

100         110           120          130          140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150          160          170          180          190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200          210          220          230          240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
 I   H   Q   N   N   G   L   D   T   E   N   N   H   N   G   S>

250          260          270          280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K-  L>

290         300          310          320          330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340          350          360          370          380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390          400          410          420          430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440          450          460          470          480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
 K   A   N   G   T   K   T   K   G   A   E   E   L   G   K   L>

490          500          510          520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 68A

```
      530              540              550              560              570
   AAT TCA GTT AAA GAG CTT ACA AGC CCT GTT GTG GCA GAA AGT CCA AAA
   TTA AGT CAA TTT CTC GAA TGT TCG GGA CAA CAC CGT CTT TCA GGT TTT
    N   S   V   K   E   L   T   S   P   V   V   A   E   S   P   K>

580              590              600              610              620
   AAA CCT TCC ATG GCC AAG CAA AAT GTA TCT GAA AAA ATA ATA ACA AGA
   TTT GGA AGG TAC CGG TTC GTT TTA CAT AGA CTT TTT TAT TAT TGT TCT
    K   P   S   M   A   K   Q   N   V   S   E   K   I   I   T   R>

630              640              650              660              670
   GCA GAC GGA ACC AGA CTT GAA TAC ACA GGA ATT AAA AGC GAT GGA TCT
   CGT CTG CCT TGG TCT GAA CTT ATG TGT CCT TAA TTT TCG CTA CCT AGA
    A   D   G   T   R   L   E   Y   T   G   I   K   S   D   G   S>

680              690              700              710              720
   GGA AAA GCT AAA GAG GTT TTA AAA GGC TAT GTT CTT GAA GGA ACT CTA
   CCT TTT CGA TTT CTC CAA AAT TTT CCG ATA CAA GAA CTT CCT TGA GAT
    G   K   A   K   E   V   L   K   G   Y   V   L   E   G   T   L>

730              740              750              760
   ACT GCT GAA AAA ACA ACA TTG GTG CTT AAA GAA GGA ACT GTT ACT TTA
   TGA CGA CTT TTT TGT TGT AAC CAC GAA TTT CTT CCT TGA CAA TGA AAT
    T   A   E   K   T   T   L   V   V   K   E   G   T   V   T   L>

770              780              790              800              810
   AGC AAA AAT ATT TCA AAA TCT GGG GAA GTT TCA GTT GAA CTT AAT GAC
   TCG TTT TTA TAA AGT TTT AGA CCC CTT CAA AGT CAA CTT GAA TTA CTG
    S   K   N   I   S   K   S   G   E   V   S   V   E   L   N   D>

820              830              840              850              860
   ACT GAC AGT AGT GCT GCT ACT AAA AAA ACT GCA GCT TGG AAT TCA AAA
   TGA CTG TCA TCA CGA CGA TGA TTT TTT TGA CGT CGA ACC TTA AGT TTT
    T   D   S   S   A   A   T   K   K   T   A   A   W   N   S   K>

870              880              890              900              910
   ACT TCC ACT TTA ACA ATT AGT GTG AAT AGC CAA AAA ACC AAA AAC CTT
   TGA AGG TGA AAT TGT TAA TCA CAC TTA TCG GTT TTT TGG TTT TTG GAA
    T   S   T   L   T   I   S   V   N   S   Q   K   T   K   N   L>

920              930              940              950              960
   GTA TTC ACA AAA GAA GAC ACA ATA ACA GTA CAA AAA TAC GAC TCA GCA
   CAT AAG TGT TTT CTT CTG TGT TAT TGT CAT GTT TTT ATG CTG AGT CGT
    V   F   T   K   E   D   T   I   T   V   Q   K   Y   D   S   A>

970              980              990              1000
   GGC ACC AAT CTA GAA GGC AAA GCA GTC GAA ATT ACA ACA CTT AAA GAA
   CCG TGG TTA GAT CTT CCG TTT CGT CAG CTT TAA TGT TGT GAA TTT CTT
    G   T   N   L   E   G   K   A   V   E   I   T   T   L   K   E>

1010             1020
   CTT AAA AAC GCT TTA AAA TAA
   GAA TTT TTG CGA AAT TTT ATT
    L   K   N   A   L   K   *>
```

FIG. 68B

```
              10             20             30             40
     ATG GCT TGT AAT AAT TCA GGG AAA GAT GGG AAT ACA TCT GCA AAT TCT
     TAC CGA ACA TTA TTA AGT CCC TTT CTA CCC TTA TGT AGA CGT TTA AGA
      M   A   C   N   N   S   G   K   D   G   N   T   S   A   N   S>

50             60             70             80             90
     GCT GAT GAG TCT GTT AAA GGG CCT AAT CTT ACA GAA ATA AAT AAA AAA
     CGA CTA CTC AGA CAA TTT CCC GGA TTA GAA TGT CTT TAT TTA TTT TTT
      A   D   E   S   V   K   G   P   N   L   T   E   I   N   K   K>

100            110            120            130            140
     ATT ACG GAT TCT AAT GCG GTT TTA CTT GCT GTG AAA GAG GTT GAA GCG
     TAA TGC CTA AGA TTA CGC CAA AAT GAA CGA CAC TTT CTC CAA CTT CGC
      I   T   D   S   N   A   V   L   L   A   V   K   E   V   E   A>

150            160            170            180            190
     TTG CTG TCA TCT ATA GAT GAA ATT GCT GCT AAA GCT ATT GGT AAA AAA
     AAC GAC AGT AGA TAT CTA CTT TAA CGA CGA TTT CGA TAA CCA TTT TTT
      L   L   S   S   I   D   E   I   A   A   K   A   I   G   K   K>

200            210            220            230            240
     ATA CAC CAA AAT AAT GGT TTG GAT ACC GAA AAT AAT CAC AAT GGA TCA
     TAT GTG GTT TTA TTA CCA AAC CTA TGG CTT TTA TTA GTG TTA CCT AGT
      I   H   Q   N   N   G   L   D   T   E   N   N   H   N   G   S>

250            260            270            280
     TTG TTA GCG GGA GCT TAT GCA ATA TCA ACC CTA ATA AAA CAA AAA TTA
     AAC AAT CGC CCT CGA ATA CGT TAT AGT TGG GAT TAT TTT GTT TTT AAT
      L   L   A   G   A   Y   A   I   S   T   L   I   K   Q   K   L>

290            300            310            320            330
     GAT GGA TTG AAA AAT GAA GGA TTA AAG GAA AAA ATT GAT GCG GCT AAG
     CTA CCT AAC TTT TTA CTT CCT AAT TTC CTT TTT TAA CTA CGC CGA TTC
      D   G   L   K   N   E   G   L   K   E   K   I   D   A   A   K>

340            350            360            370            380
     AAA TGT TCT GAA ACA TTT ACT AAT AAA TTA AAA GAA AAA CAC ACA GAT
     TTT ACA AGA CTT TGT AAA TGA TTA TTT AAT TTT CTT TTT GTG TGT CTA
      K   C   S   E   T   F   T   N   K   L   K   E   K   H   T   D>

390            400            410            420            430
     CTT GGT AAA GAA GGT GTT ACT GAT GCT GAT GCA AAA GAA GCC ATT TTA
     GAA CCA TTT CTT CCA CAA TGA CTA CGA CTA CGT TTT CTT CGG TAA AAT
      L   G   K   E   G   V   T   D   A   D   A   K   E   A   I   L>

440            450            460            470            480
     AAA GCA AAT GGT ACT AAA ACT AAA GGT GCT GAA GAA CTT GGA AAA TTA
     TTT CGT TTA CCA TGA TTT TGA TTT CCA CGA CTT CTT GAA CCT TTT AAT
      K   A   N   G   T   K   T   K   G   A   E   E   L   G   K   L>

490            500            510            520
     TTT GAA TCA GTA GAG GTC TTG TCA AAA GCA GCT AAA GAG ATG CTT GCT
     AAA CTT AGT CAT CTC CAG AAC AGT TTT CGT CGA TTT CTC TAC GAA CGA
      F   E   S   V   E   V   L   S   K   A   A   K   E   M   L   A>
```

FIG. 69A

```
       530            540            550            560            570
  AAT TCA GTT AAA CAG CTT ACA AGC CCT GTT GTG GCA GAA AGT CCA AAA
  TTA AGT CAA TTT GTC GAA TGT TCG GGA CAA CAC CGT CTT TCA GGT TTT
   N   S   V   K   E   L   T   S   P   V   V   A   E   S   P   K>

580            590            600            610            620
  AAA CCT TCC ATG GCC AAG CAA AAT GTA TCT GAA AAA ATA ATA ACA AGA
  TTT GGA AGG TAC CGG TTC GTT TTA CAT AGA CTT TTT TAT TAT TGT TCT
   K   P   S   M   A   K   Q   N   V   S   E   K   I   I   T   R>

630            640            650            660            670
  GCA GAC GGA ACC AGA CTT GAA TAC ACA GGA ATT AAA AGC GAT GGA TCT
  CGT CTG CCT TGG TCT GAA CTT ATG TGT CCT TAA TTT TCG CTA CCT AGA
   A   D   G   T   R   L   E   Y   T   G   I   K   S   D   G   S>

680            690            700            710            720
  GGA AAA GCT AAA GAG GTT TTA AAA GGC TAT GTT CTT GAA GGA ACT CTA
  CCT TTT CGA TTT CTC CAA AAT TTT CCG ATA CAA GAA CTT CCT TGA GAT
   G   K   A   K   E   V   L   K   G   Y   V   L   E   G   T   L>

730            740            750            760
  ACT GCT GAA AAA ACA ACA TTG GTG GTT AAA GAA GGA ACT GTT ACT TTA
  TGA CGA CTT TTT TGT TGT AAC CAC CAA TTT CTT CCT TGA CAA TGA AAT
   T   A   E   K   T   T   L   V   V   K   E   G   T   V   T   L>

770            780            790            800            810
  AGC AAA AAT ATT TCA AAA TCT GGG GAA GTT TCA GTT GAA CTT AAT GAC
  TCG TTT TTA TAA AGT TTT AGA CCC CTT CAA AGT CAA CTT GAA TTA CTG
   S   K   N   I   S   K   S   G   E   V   S   V   E   L   N   D>

820            830            840            850            860
  ACT GAC AGT AGT GCT GCT ACT AAA AAA ACT GCA GCT TGG AAT TCA AAA
  TGA CTG TCA TCA CGA CGA TGA TTT TTT TGA CGT CGA ACC TTA AGT TTT
   T   D   S   S   A   A   T   K   K   T   A   A   W   N   S   K>

870            880            890            900            910
  ACT TCT ACT TTA ACA ATT AGT GTT AAC AGC AAA AAA ACT ACA CAA CTT
  TGA AGA TGA AAT TGT TAA TCA CAA TTG TCG TTT TTT TGA TGT GTT GAA
   T   S   T   L   T   I   S   V   N   S   K   K   T   T   Q   L>

920            930            940            950            960
  GTG TTT ACT AAA CAA GAC ACA ATA ACT GTA CAA AAA TAC GAC TCC GCA
  CAC AAA TGA TTT GTT CTG TGT TAT TGA CAT GTT TTT ATG CTG AGG CGT
   V   F   T   K   Q   D   T   I   T   V   Q   K   Y   D   S   A>

970            980            990            1000
  GGT ACC AAT TTA GAA GGC ACA GCA GTC GAA ATT AAA ACA CTT GAT GAA
  CCA TGG TTA AAT CTT CCG TGT CGT CAG CTT TAA TTT TGT GAA CTA CTT
   G   T   N   L   E   G   T   A   V   E   I   K   T   L   D   E>

1010           1020
  CTT AAA AAC GCT TTA AAA TAA
  GAA TTT TTG CGA AAT TTT ATT
   L   K   N   A   L   K   *>
```

FIG. 69B

```
              10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

200             210             220             230             240
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
 I   H   Q   N   N   G   L   D   T   E   Y   N   H   N   G   S>

250             260             270             280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290             300             310             320             330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

340             350             360             370             380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

390             400             410             420             430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

440             450             460             470             480
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
 K   T   N   G   T   K   T   K   G   A   E   E   L   G   K   L>

490             500             510             520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 70A

```
      530           540           550           560           570
    AAT TCA GTT AAA GAG CTT ACA AGC CCT GTT GTG GCA GAA AGT CCA AAA
    TTA AGT CAA TTT CTC GAA TGT TCG GGA CAA CAC CGT CTT TCA GGT TTT
     N   S   V   K   E   L   T   S   P   V   V   A   E   S   P   K>

580           590           600           610           620
    AAA CCT TCC ATG GCC AAG CAA AAT GTT ACA TCT GAA AAA ACA ATA GTA
    TTT GGA AGG TAC CGG TTC GTT TTA CAA TGT AGA CTT TTT TGT TAT CAT
     K   P   S   M   A   K   Q   N   V   T   S   E   K   T   I   V>

630           640           650           660           670
    AGA GCA AAT GGA ACC AGA CTT GAA TAC ACA GAC ATA AAA AGC GAT GGA
    TCT CGT TTA CCT TGG TCT CAA CTT ATG TGT CTG TAT TTT TCG CTA CCT
     R   A   N   G   T   R   L   E   Y   T   D   I   K   S   D   G>

680           690           700           710           720
    TCC GGA AAA GCT AAA GAA GTT TTA AAA GAC TTT ACT CTT GAA GGA ACT
    AGG CCT TTT CGA TTT CTT CAA AAT TTT CTG AAA TGA GAA CTT CCT TGA
     S   G   K   A   K   E   V   L   K   D   F   T   L   E   G   T>

730           740           750           760
        CTA GCT GCT GAC GGC AAA ACA ACA TTG AAA GTT ACA GAA GGC ACT GTT
        GAT CGA CGA CTG CCG TTT TGT TGT AAC TTT CAA TGT CTT CCG TGA CAA
         L   A   A   D   G   K   T   T   L   K   V   T   E   G   T   V>

770           780           790           800           810
    GTT TTA AGC AAG AAC ATT TTA AAA TCC GGA GAA ATA ACA GTT GCA CTT
    CAA AAT TCG TTC TTG TAA AAT TTT AGG CCT CTT TAT TGT CAA CGT GAA
     V   L   S   K   N   I   L   K   S   G   E   I   T   V   A   L>

820           830           840           850           860
    GAT GAC TCT GAC ACT ACT CAG GCT ACT AAA AAA ACT GGA AAA TGG GAT
    CTA CTG AGA CTG TGA TGA GTC CGA TGA TTT TTT TGA CCT TTT ACC CTA
     D   D   S   D   T   T   Q   A   T   K   K   T   G   K   W   D>

870           880           890           900           910
    TCA AAT ACT TCC ACT TTA ACA ATT AGT GTG AAT AGC AAA AAA ACT AAA
    AGT TTA TGA AGG TGA AAT TGT TAA TCA CAC TTA TCG TTT TTT TGA TTT
     S   N   T   S   T   L   T   I   S   V   N   S   K   K   T   K>

920           930           940           950           960
    AAC ATT GTA TTT ACA AAA GAA GAC ACA ATA ACA GTA CAA AAA TAC GAC
    TTG TAA CAT AAA TGT TTT CTT CTG TGT TAT TGT CAT GTT TTT ATG CTG
     N   I   V   F   T   K   E   D   T   I   T   V   Q   K   Y   D>

970           980           990          1000
    TCA GCA GGC ACC AAT CTA GAA GGC AAC GCA GTC GAA ATT AAA ACA CTT
    AGT CGT CCG TGG TTA GAT CTT CCG TTG CGT CAG CTT TAA TTT TGT GAA
     S   A   G   T   N   L   E   G   N   A   V   E   I   K   T   L>

1010          1020          1030
    GAT GAA CTT AAA AAC GCT TTA AAA TAG
    CTA CTT GAA TTT TTG CGA AAT TTT ATC
     D   E   L   K   N   A   L   K   *>
```

FIG. 70B

```
             10              20              30              40
    ATG GCT TGT AAT AAT TCA GGG AAA GAT GGG AAT ACA TCT GCA AAT TCT
    TAC CGA ACA TTA TTA AGT CCC TTT CTA CCC TTA TGT AGA CGT TTA AGA
     M   A   C   N   N   S   G   K   D   G   N   T   S   A   N   S>

50              60              70              80              90
    GCT GAT GAG TCT GTT AAA GGG CCT AAT CTT ACA GAA ATA AAT AAA AAA
    CGA CTA CTC AGA CAA TTT CCC GGA TTA GAA TGT CTT TAT TTA TTT TTT
     A   D   E   S   V   K   G   P   N   L   T   E   I   N   K   K>

100             110             120             130             140
    ATT ACG GAT TCT AAT GCG GTT TTA CTT GCT GTG AAA GAG GTT GAA GCG
    TAA TGC CTA AGA TTA CGC CAA AAT GAA CGA CAC TTT CTC CAA CTT CGC
     I   T   D   S   N   A   V   L   L   A   V   K   E   V   E   A>

150             160             170             180             190
    TTG CTG TCA TCT ATA GAT GAA ATT GCT GCT AAA GCT ATT GGT AAA AAA
    AAC GAC AGT AGA TAT CTA CTT TAA CGA CGA TTT CGA TAA CCA TTT TTT
     L   L   S   S   I   D   E   I   A   A   K   A   I   G   K   K>

200             210             220             230             240
    ATA CAC CAA AAT AAT GGT TTG GAT ACC GAA AAT AAT CAC AAT GGA TCA
    TAT GTG GTT TTA TTA CCA AAC CTA TGG CTT TTA TTA GTG TTA CCT AGT
     I   H   Q   N   N   G   L   D   T   E   N   N   H   N   G   S>

250             260             270             280
    TTG TTA GCG GGA GCT TAT GCA ATA TCA ACC CTA ATA AAA CAA AAA TTA
    AAC AAT CGC CCT CGA ATA CGT TAT AGT TGG GAT TAT TTT GTT TTT AAT
     L   L   A   G   A   Y   A   I   S   T   L   I   K   Q   K   L>

290             300             310             320             330
    GAT GGA TTG AAA AAT GAA GGA TTA AAG GAA AAA ATT GAT GCG GCT AAG
    CTA CCT AAC TTT TTA CTT CCT AAT TTC CTT TTT TAA CTA CGC CGA TTC
     D   G   L   K   N   E   G   L   K   E   K   I   D   A   A   K>

340             350             360             370             380
    AAA TGT TCT GAA ACA TTT ACT AAT AAA TTA AAA GAA AAA CAC ACA GAT
    TTT ACA AGA CTT TGT AAA TGA TTA TTT AAT TTT CTT TTT GTG TGT CTA
     K   C   S   E   T   F   T   N   K   L   K   E   K   H   T   D>

390             400             410             420             430
    CTT GGT AAA GAA GGT GTT ACT GAT GCT GAT GCA AAA GAA GCC ATT TTA
    GAA CCA TTT CTT CCA CAA TGA CTA CGA CTA CGT TTT CTT CGG TAA AAT
     L   G   K   E   G   V   T   D   A   D   A   K   E   A   I   L>

440             450             460             470             480
    AAA GCA AAT GGT ACT AAA ACT AAA GGT GCT GAA GAA CTT GGA AAA TTA
    TTT CGT TTA CCA TGA TTT TGA TTT CCA CGA CTT CTT GAA CCT TTT AAT
     K   A   N   G   T   K   T   K   G   A   E   E   L   G   K   L>

490             500             510             520
    TTT GAA TCA GTA GAG GTC TTG TCA AAA GCA GCT AAA GAG ATG CTT GCT
    AAA CTT AGT CAT CTC CAG AAC AGT TTT CGT CGA TTT CTC TAC GAA CGA
     F   E   S   V   E   V   L   S   K   A   A   K   E   M   L   A>
```

FIG. 71A

```
     530             540             550             560             570
  AAT TCA GTT AAA GAG CTT ACA AGC CCT GTT GTG GCA GAA AGT CCA AAA
  TTA AGT CAA TTT CTC GAA TGT TCG GGA CAA CAC CGT CTT TCA GGT TTT
   N   S   V   K   E   L   T   S   P   V   V   A   E   S   P   K>

580             590             600             610             620
  AAA CCT TCC ATG GCC GTT TCA GTA GAT TTG CCT GGT GAA ATG AAA GTT
  TTT GGA AGG TAC CGG CAA AGT CAT CTA AAC GGA CCA CTT TAC TTT CAA
   K   P   S   M   A   V   S   V   D   L   P   G   E   M   K   V>

630             640             650             660             670
  CTT GTA AGC AAA GAA AAA AAC AAA GAC GGC AAG TAC GAT CTA ATT GCA
  GAA CAT TCG TTT CTT TTT TTG TTT CTG CCG TTC ATG CTA GAT TAA CGT
   L   V   S   K   E   K   N   K   D   G   K   Y   D   L   I   A>

680             690             700             710             720
  ACA GTA GAC AAG CTT GAG CTT AAA GGA ACT TCT GAT AAA AAC AAT GGA
  TGT CAT CTG TTC GAA CTC GAA TTT CCT TGA AGA CTA TTT TTG TTA CCT
   T   V   D   K   L   E   L   K   G   T   S   D   K   N   N   G>

730             740             750             760
  TCT GGA GTA CTT GAA GGC GTA AAA GCT GAC AAA AGT AAA GTA AAA TTA
  AGA CCT CAT GAA CTT CCG CAT TTT CGA CTG TTT TCA TTT CAT TTT AAT
   S   G   V   L   E   G   V   K   A   D   K   S   K   V   K   L>

770         780             790             800             810
  ACA ATT TCT GAC GAT CTA GGT CAA ACC ACA CTT GAA GTT TTC AAA GAA
  TGT TAA AGA CTG CTA GAT CCA GTT TGG TGT GAA CTT CAA AAG TTT CTT
   T   I   S   D   D   L   G   Q   T   T   L   E   V   F   K   E>

820             830             840             850             860
  GAT GGC AAA ACA CTA GTA TCA AAA AAA GTA ACT TCC AAA GAC AAG TCA
  CTA CCG TTT TGT GAT CAT AGT TTT TTT CAT TGA AGG TTT CTG TTC AGT
   D   G   K   T   L   V   S   K   K   V   T   S   K   D   K   S>

870             880             890             900             910
  TCA ACA GAA GAA AAA TTC AAT GAA AAA GGT GAA GTA TCT GAA AAA ATA
  AGT TGT CTT CTT TTT AAG TTA CTT TTT CCA CTT CAT AGA CTT TTT TAT
   S   T   E   E   K   F   N   E   K   G   E   V   S   E   K   I>

920             930             940             950             960
  ATA ACA ACA GCA GAC GGA ACC AGA CTT GAA TAC ACA GGA ATT AAA AGC
  TAT TGT TGT CGT CTG CCT TGG TCT GAA CTT ATG TGT CCT TAA TTT TCG
   I   T   R   A   D   G   T   R   L   E   Y   T   G   I   K   S>

970             980             990             1000
  GAT GGA TCT GGA AAA GCT AAA GAG GTT TTA AAA GGC TTT ACT CTT GAA
  CTA CCT AGA CCT TTT CGA TTT CTC CAA AAT TTT CCG AAA TGA GAA CTT
   D   G   S   G   K   A   K   E   V   L   K   G   F   T   L   E>

1010        1020            1030            1040            1050
  GGA AAA GTA GCT AAT GAT AAA GTA ACA TTG GAA GTA AAA GAA GGA ACC
  CCT TTT CAT CGA TTA CTA TTT CAT TGT AAC CTT CAT TTT CTT CCT TGG
   G   K   V   A   N   D   K   V   T   L   E   V   K   E   G   T>

1060            1070            1080            1090            1100
  GTT ACT TTA AGT AAG ATT TCA AAA TCT GGG GAA GTT TCA GTT GAA CTT
```

FIG. 71B

```
                                                    CAA TGA AAT TCA TTC TAA AGT TTT AGA CCC CTT CAA AGT CAA CTT GAA
                                                     V   T   L   S   K   I   S   K   S   G   E   V   S   V   E   L>

1110             1120            1130            1140            1150
        AAT GAC ACT GAC AGT AGT GCT GCT ACT AAA AAA ACT GCA GCT TGG AAT
        TTA CTG TGA CTG TCA TCA CGA CGA TGA TTT TTT TGA CGT CGA ACC TTA
         N   D   T   D   S   S   A   A   T   K   K   T   A   A   W   N>

1160            1170            1180            1190           1200
        TCA AAA ACT TCT ACT TTA ACA ATT AGT GTT AAC AGC AAA AAA ACT ACA
        AGT TTT TGA AGA TGA AAT TGT TAA TCA CAA TTG TCG TTT TTT TGA TGT
         S   K   T   S   T   L   T   I   S   V   N   S   K   K   T   T>

1210            1220            1230            1240
        CAA CTT GTG TTT ACT AAA CAA GAC ACA ATA ACT GTA CAA AAA TAC GAC
        GTT GAA CAC AAA TGA TTT GTT CTG TGT TAT TGA CAT GTT TTT ATG CTG
         Q   L   V   F   T   K   Q   D   T   I   T   V   Q   K   Y   D>

1250            1260            1270            1280            1290
    TCC GCA GGT ACC AAT TTA GAA GGC ACA GCA GTC GAA ATT AAA ACA CTT
    AGG CGT CCA TGG TTA AAT CTT CCG TGT CGT CAG CTT TAA TTT TGT GAA
     S   A   G   T   N   L   E   G   T   A   V   E   I   K   T   L>

1300            1310            1320
    GAT GAA CTT AAA AAC GCT TTA AAA TAA
    CTA CTT GAA TTT TTG CGA AAT TTT ATT
     D   E   L   K   N   A   L   K   *>
```

FIG. 71C

```
          10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50              60              70              80              90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

150             160             170             180             190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
 L   L   S   S   I   D   E   L   A   K   A   I   G   K   K   I>

200             210             220             230             240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
 K   N   D   G   S   L   D   N   E   A   N   R   N   E   S   L>

250             260             270             280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
 L   A   G   A   Y   T   I   S   T   L   I   T   Q   K   L   S>

290             300             310             320             330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
 K   L   N   G   S   E   G   L   K   E   K   I   A   A   A   K>

340             350             360             370             380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
 K   C   S   E   E   F   S   T   K   L   K   D   N   H   A   Q>

390             400             410             420             430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
 L   G   I   Q   G   V   T   D   E   N   A   K   K   A   I   L>

440             450             460             470             480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
 K   A   N   A   A   G   K   D   K   G   V   E   E   L   E   K>

490             500             510             520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
 L   S   G   S   L   E   S   L   S   K   A   A   K   E   M   L>
```

FIG. 72A

```
         530             540             550             560             570
       GCT AAT TCA GTT AAA GAG CTT ACA AGC CCT GTT GTC CAT GGC GTT TCA
       CGA TTA AGT CAA TTT CTC GAA TGT TCG GGA CAA CAG GTA CCG CAA AGT
        A   N   S   V   K   E   L   T   S   P   V   V   H   G   V   S>

580             590             600             610             620
       GTA GAT TTG CCT GGT GAA ATG AAA GTT CTT GTA AGC AAA GAA AAA AAC
       CAT CTA AAC GGA CCA CTT TAC TTT CAA GAA CAT TCG TTT CTT TTT TTG
        V   D   L   P   G   E   M   K   V   L   V   S   K   E   K   N>

630             640             650             660             670
       AAA GAC GGC AAG TAC GAT CTA ATT GCA ACA GTA GAC AAG CTT GAG CTT
       TTT CTG CCG TTC ATG CTA GAT TAA CGT TGT CAT CTG TTC GAA CTC GAA
        K   D   G   K   Y   D   L   I   A   T   V   D   K   L   E   L>

680             690             700             710             720
       AAA GGA ACT TCT GAT AAA AAC AAT GGA TCT GGA GTA CTT GAA GGC GTA
       TTT CCT TGA AGA CTA TTT TTG TTA CCT AGA CCT CAT GAA CTT CCG CAT
        K   G   T   S   D   K   N   N   G   S   G   V   L   E   G   V>

730             740             750             760
       AAA GCT GAC AAA AGT AAA GTA AAA TTA ACA ATT TCT GAC GAT CTA GGT
       TTT CGA CTG TTT TCA TTT CAT TTT AAT TGT TAA AGA CTG CTA GAT CCA
        K   A   D   K   S   K   V   K   L   T   I   S   D   D   L   G>

770            780             790             800             810
       CAA ACC ACA CTT GAA GTT TTC AAA GAA GAT GGC AAA ACA CTA GTA TCA
       GTT TGG TGT GAA CTT CAA AAG TTT CTT CTA CCG TTT TGT GAT CAT AGT
        Q   T   T   L   E   V   F   K   E   D   G   K   T   L   V   S>

820             830             840             850             860
       AAA AAA GTA ACT TCC AAA GAC AAG TCA TCA ACA GAA GAA AAA TTC AAT
       TTT TTT CAT TGA AGG TTT CTG TTC AGT AGT TGT CTT CTT TTT AAG TTA
        K   K   V   T   S   K   D   K   S   S   T   E   E   K   F   N>

870             880             890             900             910
       GAA AAA GGT GAA GTA TCT GAA AAA ATA ATA ACA AGA GCA GAC GGA ACC
       CTT TTT CCA CTT CAT ACA CTT TTT TAT TAT TGT TCT CGT CTG CCT TGG
        E   K   G   E   V   S   E   K   I   I   T   R   A   D   G   T>

920             930             940             950             960
       AGA CTT GAA TAC ACA GGA ATT AAA AGC GAT GGA TCT GGA AAA GCT AAA
       TCT GAA CTT ATG TGT CCT TAA TTT TCG CTA CCT AGA CCT TTT CGA TTT
        R   L   E   Y   T   G   I   K   S   D   G   S   G   K   A   K>

970             980             990            1000
       GAG GTT TTA AAA GGC TTT ACT CTT GAA GGA AAA GTA GCT AAT GAT AAA
       CTC CAA AAT TTT CCG AAA TGA GAA CTT CCT TTT CAT CGA TTA CTA TTT
        E   V   L   K   G   F   T   L   E   G   K   V   A   N   D   K>

1010            1020            1030            1040            1050
       GTA ACA TTG GAA GTA AAA GAA GGA ACC GTT ACT TTA AGT AAG ATT TCA
       CAT TGT AAC CTT CAT TTT CTT CCT TGG CAA TGA AAT TCA TTC TAA AGT
        V   T   L   E   V   K   E   G   T   V   T   L   S   K   I   S>

1060            1070            1080            1090            1100
        AAA TCT GGG GAA GTT TCA GTT GAA CTT AAT GAC ACT GAC AGT AGT     GCT
```

FIG. 72B

```
TTT AGA CCC CTT CAA AGT CAA CTT GAA TTA CTG TGA CTG TCA TCA CGA
 K   S   G   E   V   S   V   E   L   N   D   T   D   S   S   A>

1110          1120          1130          1140         1150
GCT ACT AAA AAA ACT GCA GCT TGG AAT TCA AAA ACT TCT ACT TTA ACA
CGA TGA TTT TTT TGA CGT CGA ACC TTA AGT TTT TGA AGA TGA AAT TGT
 A   T   K   K   T   A   A   W   N   S   K   T   S   T   L   T>

1160          1170          1180          1190          1200
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
 I   S   V   N   S   K   K   T   T   Q   L   V   F   T   K   Q>

1210          1220          1230          1240
GAC ACA ATA ACT GTA CAA AAA TAC GAC TCC GCA GGT ACC AAT TTA GAA
CTG TGT TAT TGA CAT GTT TTT ATG CTG AGG CGT CCA TGG TTA AAT CTT
 D   T   I   T   V   Q   K   Y   D   S   A   G   T   N   L   E>

1250          1260          1270          1280          1290
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
 G   T   A   V   E   I   K   T   L   D   E   L   K   N   A   L>

1300
AAA TAA
TTT ATT
```

FIG. 72C

SEQUENCE LISTING

<160> NUMBER OF SEQ ID NOS: 213

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 1
cttaatgact ctgacactag tgc                                    23

<210> SEQ ID NO 2
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 2
gctactaaaa aaaccgggaa atggaattca                             30

<210> SEQ ID NO 3
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 3
gcagcttggg attcaaaaac atccacttta aca       33

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 4
ggagaatata ttatgaaa       18

<210> SEQ ID NO 5
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 5
ctccttattt taaagcg       17

<210> SEQ ID NO 6
<211> LENGTH: 822
<212> TYPE: DNA
<213> ORGANISM: Borrelia burgdorferi
<220> FEATURE:
<221> NAME/KEY: CDS
<222> LOCATION: (1)...(822)

<400> SEQUENCE: 6

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
 1               5                  10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
                20                  25                  30 gat ttg cct ggt gaa atg aaa gtt ctt gta agc aaa gaa aaa aac aaa     144
Asp Leu Pro Gly Glu Met Lys Val Leu Val Ser Lys Glu Lys Asn Lys
            35                  40                  45 gac ggc aag tac gat cta att gca aca gta gac aag ctt gag ctt aaa     192
Asp Gly Lys Tyr Asp Leu Ile Ala Thr Val Asp Lys Leu Glu Leu Lys
        50                  55                  60 gga act tct gat aaa aac aat gga tct gga gta ctt gaa ggc gta aaa     240
Gly Thr Ser Asp Lys Asn Asn Gly Ser Gly Val Leu Glu Gly Val Lys
 65                  70                  75                  80 gct gac aaa agt aaa gta aaa tta aca att tct gac gat cta ggt caa     288
Ala Asp Lys Ser Lys Val Lys Leu Thr Ile Ser Asp Asp Leu Gly Gln
                85                  90                  95 acc aca ctt gaa gtt ttc aaa gaa gat ggc aaa aca cta gta tca aaa     336
Thr Thr Leu Glu Val Phe Lys Glu Asp Gly Lys Thr Leu Val Ser Lys
                100                 105                 110 aaa gta act tcc aaa gac aag tca tca aca gaa gaa aaa ttc aat gaa     384
Lys Val Thr Ser Lys Asp Lys Ser Ser Thr Glu Glu Lys Phe Asn Glu
            115                 120                 125
```

```
aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140 ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160 gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175 aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205 gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220 att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240 aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255 ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270 aaa taa                                                              822
Lys *

<210> SEQ ID NO 7
<211> LENGTH: 273
<212> TYPE: PRT
<213> ORGANISM: Borrelia burgdorferi

<400> SEQUENCE: 7

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
```

-continued

```
                    165                 170                 175
Thr Leu Val Val Lys Glu Gly Thr Val Thr Leu Ser Lys Asn Ile Ser
            180                 185                 190
Lys Ser Gly Glu Val Ser Val Glu Leu Asn Asp Thr Asp Ser Ser Ala
        195                 200                 205
Ala Thr Lys Lys Thr Ala Ala Trp Asn Ser Gly Thr Ser Thr Leu Thr
    210                 215                 220
Ile Thr Val Asn Ser Lys Lys Thr Lys Asp Leu Val Phe Thr Lys Glu
225                 230                 235                 240
Asn Thr Ile Thr Val Gln Gln Tyr Asp Ser Asn Gly Thr Lys Leu Glu
            245                 250                 255
Gly Ser Ala Val Glu Ile Thr Lys Leu Asp Glu Ile Lys Asn Ala Leu
        260                 265                 270
Lys

<210> SEQ ID NO 8
<211> LENGTH: 825
<212> TYPE: DNA
<213> ORGANISM: Borrelia burgdorferi
<220> FEATURE:
<221> NA

```
                      180                 185                 190
tta aaa tcc gga gaa ata aca gtt gca ctt gat gac tct gac act act      624
Leu Lys Ser Gly Glu Ile Thr Val Ala Leu Asp Asp Ser Asp Thr Thr
            195                 200                 205 cag gct act aaa aaa act gga aaa tgg gat tca aaa act tcc act tta      672
Gln Ala Thr Lys Lys Thr Gly Lys Trp Asp Ser Lys Thr Ser Thr Leu
    210                 215                 220 aca att agt gtg aat agc caa aaa acc aaa aac ctt gta ttc aca aaa      720
Thr Ile Ser Val Asn Ser Gln Lys Thr Lys Asn Leu Val Phe Thr Lys
225                 230                 235                 240 gaa gac aca ata aca gta caa aaa tac gac tca gca ggc acc aat cta      768
Glu Asp Thr Ile Thr Val Gln Lys Tyr Asp Ser Ala Gly Thr Asn Leu
                245                 250                 255 gaa ggc aaa gca gtc gaa att aca aca ctt aaa gaa ctt aaa aac gct      816
Glu Gly Lys Ala Val Glu Ile Thr Thr Leu Lys Glu Leu Lys Asn Ala
            260                 265                 270 tta aaa taa                                                          825
Leu Lys *

<210> SEQ ID NO 9
<211> LENGTH: 274
<212> TYPE: PRT
<213> ORGANISM: Borrelia burgdorferi

<400> SEQUENCE: 9

Met Lys Lys Tyr Leu Leu Gly Ile Gly Le 245                 250                 255
Glu Gly Lys Ala Val Glu Ile Thr Thr Leu Lys Glu Leu Lys Asn Ala
        260                 265                 270

Leu Lys

<210> SEQ ID NO 10
<211> LENGTH: 822
<212> TYPE: DNA
<213> ORGANISM: Borrelia burgdorferi
<220> FEATURE:
<221> NAME/KEY: CDS
<222> LOCATION: (1)...(822)

<400> SEQUENCE: 10

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
 1               5                  10                  15 tgc aag caa aat gtt agc agc ctt gat gaa aaa aac agc gct tca gta      96
Cys Lys Gln Asn Val Ser Ser Leu Asp Glu Lys Asn Ser Ala Ser Val
                 20                  25                  30 gat ttg cct ggt gag atg aaa gtt ctt gta agt aaa gaa aaa gac aaa     144
Asp Leu Pro Gly Glu Met Lys Val Leu Val Ser Lys Glu Lys Asp Lys
             35                  40                  45 gac ggt aag tac agt cta aag gca aca gta gac aag att gag cta aaa     192
Asp Gly Lys Tyr Ser Leu Lys Ala Thr Val Asp Lys Ile Glu Leu Lys
         50                  55                  60 gga act tct gat aaa gac aat ggt tct gga gtg ctt gaa ggt aca aaa     240
Gly Thr Ser Asp Lys Asp Asn Gly Ser Gly Val Leu Glu Gly Thr Lys
 65                  70                  75                  80 gat gac aaa agt aaa gca aaa tta aca att gct gac gat cta agt aaa     288
Asp Asp Lys Ser Lys Ala Lys Leu Thr Ile Ala Asp Asp Leu Ser Lys
                 85                  90                  95 acc aca ttc gaa ctt tta aaa gaa gat ggc aaa aca tta gtg tca aga     336
Thr Thr Phe Glu Leu Leu Lys Glu Asp Gly Lys Thr Leu Val Ser Arg
                100                 105                 110 aaa gta agt tct aga gac aaa aca tca aca gat gaa atg ttc aat gaa     384
Lys Val Ser Ser Arg Asp Lys Thr Ser Thr Asp Glu Met Phe Asn Glu
            115                 120                 125 aaa ggt gaa ttg tct gca aaa acc atg aca aga gaa aat gga acc aaa     432
Lys Gly Glu Leu Ser Ala Lys Thr Met Thr Arg Glu Asn Gly Thr Lys
        130                 135                 140 ctt gaa tat aca gaa atg aaa agc gat gga acc gga aaa gct aaa gaa     480
Leu Glu Tyr Thr Glu Met Lys Ser Asp Gly Thr Gly Lys Ala Lys Glu
145                 150                 155                 160 gtt tta aaa aag ttt act ctt gaa gga aaa gta gct aat gat aaa gta     528
Val Leu Lys Lys Phe Thr Leu Glu Gly Lys Val Ala Asn Asp Lys Val
                165                 170                 175 aca ttg gaa gta aaa gaa gga acc gtt act tta agt aag gaa att gca     576
Thr Leu Glu Val Lys Glu Gly Thr Val Thr Leu Ser Lys Glu Ile Ala
            180                 185                 190 aaa tct gga gaa gta aca gtt gct ctt aat gac act aac act act cag     624
Lys Ser Gly Glu Val Thr Val Ala Leu Asn Asp Thr Asn Thr Thr Gln
        195                 200                 205 gct act aaa aaa act ggc gca tgg gat tca aaa act tct act tta aca     672
Ala Thr Lys Lys Thr Gly Ala Trp Asp Ser Lys Thr Ser Thr Leu Thr
    210                 215                 220 att agt gtt aac agc aaa aaa act aca caa ctt gtg ttt act aaa caa     720
Ile Ser Val Asn Ser Lys Lys Thr Thr Gln Leu Val Phe Thr Lys Gln
225                 230                 235                 240 tac aca ata act gta aaa caa tac gac tcc gca ggt acc aat tta gaa     768
```

```
                                                        -continued

Tyr Thr Ile Thr Val Lys Gln Tyr Asp Ser Ala Gly Thr Asn Leu Glu
                245                 250                 255 ggc aca gca gtc gaa att aaa aca ctt gat gaa ctt aaa aac gct tta        816
Gly Thr Ala Val Glu Ile Lys Thr Leu Asp Glu Leu Lys Asn Ala Leu
            260                 265                 270 aaa taa                                                                822
Lys  *

<210> SEQ ID NO 11
<211> LENGTH: 273
<212> TYPE: PRT
<213> ORGANISM: Borrelia burgdorferi

<400> SEQUENCE: 11

Met Lys Lys Tyr Leu Leu Gly Ile Gly Leu Ile Leu Ala Leu Ile Ala
  1               5                  10                  15

Cys Lys Gln Asn Val Ser Ser Leu Asp Glu Lys Asn Ser Ala Ser Val
                 20                  25                  30

Asp Leu Pro Gly Glu Met Lys Val Leu Val Ser Lys Glu Lys Asp Lys
             35                  40                  45

Asp Gly Lys Tyr Ser Leu Lys Ala Thr Val Asp Lys Ile Glu Leu Lys
         50                  55                  60

Gly Thr Ser Asp Lys Asp Asn Gly Ser Gly Val Leu Glu Gly Thr Lys
 65                  70                  75                  80

Asp Asp Lys Ser Lys Ala Lys Leu Thr Ile Ala Asp Asp Leu Ser Lys
                 85                  90                  95

Thr Thr Phe Glu Leu Leu Lys Glu Asp Gly Lys Thr Leu Val Ser Arg
                100                 105                 110

Lys Val Ser Ser Arg Asp Lys Thr Ser Thr Asp Glu Met Phe Asn Glu
            115                 120                 125

Lys Gly Glu Leu Ser Ala Lys Thr Met Thr Arg Glu Asn Gly Thr Lys
        130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Gln Leu Val Phe Thr Lys Gln
225                 230                 235                 240

Tyr Thr Ile Thr Val Lys Gln Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys

<210> SEQ ID NO 12
<211> LENGTH: 819
<212> TYPE: DNA
<213> ORGANISM: Borrelia burgdorferi
<220> FEATURE:
<221> NAME/KEY: CDS
<222> LOCATION: (1)...(819)
```

<400> SEQUENCE: 12

```
atg aaa aaa tat tta ttg gga ata ggt cta ata tta gct tta ata gca      48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
                20                  25                  30 gat ttg cct ggt gaa atg aaa gtt ctt gta agc aaa gaa aaa gac aaa      144
Asp Leu Pro Gly Glu Met Lys Val Leu Val Ser Lys Glu Lys Asp Lys
            35                  40                  45 gac ggc aag tac agt cta atg gca aca gta gac aag ctt gag ctt aaa      192
Asp Gly Lys Tyr Ser Leu Met Ala Thr Val Asp Lys Leu Glu Leu Lys
        50                  55                  60 gga aca tct gat aaa aac aat gga tct ggg gtg ctt gaa ggc gta aaa      240
Gly Thr Ser Asp Lys Asn Asn Gly Ser Gly Val Leu Glu Gly Val Lys
65                  70                  75                  80 gct gac aaa agc aaa gta aaa tta aca gtt tct gac gat cta agc aca      288
Ala Asp Lys Ser Lys Val Lys Leu Thr Val Ser Asp Asp Leu Ser Thr
                85                  90                  95 acc aca ctt gaa gtt tta aaa gaa gat ggc aaa aca tta gtg tca aaa      336
Thr Thr Leu Glu Val Leu Lys Glu Asp Gly Lys Thr Leu Val Ser Lys
                100                 105                 110 aaa aga act tct aaa gat aag tca tca aca gaa gaa aag ttc aat gaa      384
Lys Arg Thr Ser Lys Asp Lys Ser Ser Thr Glu Glu Lys Phe Asn Glu
            115                 120                 125 aaa ggc gaa tta gtt gaa aaa ata atg gca aga gca aac gga acc ata      432
Lys Gly Glu Leu Val Glu Lys Ile Met Ala Arg Ala Asn Gly Thr Ile
        130                 135                 140 ctt gaa tac aca gga att aaa agc gat gga tcc gga aaa gct aaa gaa      480
Leu Glu Tyr Thr Gly Ile Lys Ser Asp Gly Ser Gly Lys Ala Lys Glu
145                 150                 155                 160 act tta aaa gaa tat gtt ctt gaa gga act cta act gct gaa aaa gca      528
Thr Leu Lys Glu Tyr Val Leu Glu Gly Thr Leu Thr Ala Glu Lys Ala
                165                 170                 175 aca ttg gtg gtt aaa gaa gga act gtt act tta agt aag cac att tca      576
Thr Leu Val Val Lys Glu Gly Thr Val Thr Leu Ser Lys His Ile Ser
                180                 185                 190 aaa tct gga gaa gta aca gct gaa ctt aat gac act gac agt act caa      624
Lys Ser Gly Glu Val Thr Ala Glu Leu Asn Asp Thr Asp Ser Thr Gln
            195                 200                 205 gct act aaa aaa act ggg aaa tgg gat gca ggc act tca act tta aca      672
Ala Thr Lys Lys Thr Gly Lys Trp Asp Ala Gly Thr Ser Thr Leu Thr
        210                 215                 220 att act gta aac aac aaa aaa act aaa gcc ctt gta ttt aca aaa caa      720
Ile Thr Val Asn Asn Lys Lys Thr Lys Ala Leu Val Phe Thr Lys Gln
225                 230                 235                 240 gac aca att aca tca caa aaa tac gac tca gca gga acc aac ttg gaa      768
Asp Thr Ile Thr Ser Gln Lys Tyr Asp Ser Ala Gly Thr Asn Leu Glu
                245                 250                 255 ggc aca gca gtc gaa att aaa aca ctt gat gaa ctt aaa aac gct tta      816
Gly Thr Ala Val Glu Ile Lys Thr Leu Asp Glu Leu Lys Asn Ala Leu
                260                 265                 270 aga                                                                   819
Arg
```

<210> SEQ ID NO 13
<211> LENGTH: 273
<212> TYPE: PRT
<213> ORGANISM: Borrelia burgdorferi

```
<400> SEQUENCE: 13

Met Lys Lys Tyr Leu Leu Gly Ile Gly Leu Ile Leu Ala Leu Ile Ala
 1               5                  10                  15
Cys Lys Gln Asn Val Ser Ser Leu Asp Glu Lys Asn Ser Val Ser Val
            20                  25                  30
Asp Leu Pro Gly Glu Met Lys Val Leu Val Ser Lys Glu Lys Asp Lys
        35                  40                  45
Asp Gly Lys Tyr Ser Leu Met Ala Thr Val Asp Lys Leu Glu Leu Lys
    50                  55                  60
Gly Thr Ser Asp Lys Asn Asn Gly Ser Gly Val Leu Glu Gly Val Lys
65                  70                  75                  80
Ala Asp Lys Ser Lys Val Lys Leu Thr Val Ser Asp Asp Leu Ser Thr
                85                  90                  95
Thr Thr Leu Glu Val Leu Lys Glu Asp Gly Lys Thr Leu Val Ser Lys
            100                 105                 110
Lys Arg Thr Ser Lys Asp Lys Ser Ser Thr Glu Glu Lys Phe Asn Glu
        115                 120                 125
Lys Gly Glu Leu Val Glu Lys Ile Met Ala Arg Ala Asn Gly Thr Ile
    130                 135                 140
Leu Glu Tyr Thr Gly Ile Lys Ser Asp Gly Ser Gly Lys Ala Lys Glu
145                 150                 155                 160
Thr Leu Lys Glu Tyr Val Leu Glu Gly Thr Leu Thr Ala Glu Lys Ala
                165                 170                 175
Thr Leu Val Val Lys Glu Gly Thr Val Thr Leu Ser Lys His Ile Ser
            180                 185                 190
Lys Ser Gly Glu Val Thr Ala Glu Leu Asn Asp Thr Asp Ser Thr Gln
        195                 200                 205
Ala Thr Lys Lys Thr Gly Lys Trp Asp Ala Gly Thr Ser Thr Leu Thr
    210                 215                 220
Ile Thr Val Asn Asn Lys Lys Thr Lys Ala Leu Val Phe Thr Lys Gln
225                 230                 235                 240
Asp Thr Ile Thr Ser Gln Lys Tyr Asp Ser Ala Gly Thr Asn Leu Glu
                245                 250                 255
Gly Thr Ala Val Glu Ile Lys Thr Leu Asp Glu Leu Lys Asn Ala Leu
            260                 265                 270
Arg

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 14
gtctgcaaaa accatgacaa g                                        21

<210> SEQ ID NO 15
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 15
gtcatcaaca gaagaaaaat tc                                       22
```

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 16
ccggatccat atgaaaaaat atttattggg                              30

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 17
ccgggatcca tatggctaag caaaatgtta gc                           32

<210> SEQ ID NO 18
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 18
gcgttcaagt actccaga                                           18

<210> SEQ ID NO 19
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 19
gatatctaga tcttatttta aagcgtt                                 27

<210> SEQ ID NO 20
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 20
ggatccggtg accttttaaa gcgttttaa t                             31

<210> SEQ ID NO 21
<211> LENGTH: 891
<212> TYPE: DNA
<213> ORGANISM: Borrelia burgdorferi
<220> FEATURE:
<221> NAME/KEY: CDS
<222> LOCATION: (1)...(891)

<400> SEQUENCE: 21

```
atg aga tta tta ata gga ttt gct tta gcg tta gct tta ata gga tgt       48
Met Arg Leu Leu Ile Gly Phe Ala Leu Ala Leu Ala Leu Ile Gly Cys
 1               5                  10                  15 gca caa aaa ggt gct gag tca att ggt tct caa aaa gaa aat gat cta       96
Ala Gln Lys Gly Ala Glu Ser Ile Gly Ser Gln Lys Glu Asn Asp Leu
             20                  25                  30
```

```
aac ctt gaa gac tct agt aaa aaa tca cat caa aac gct aaa caa gac        144
Asn Leu Glu Asp Ser Ser Lys Lys Ser His Gln Asn Ala Lys Gln Asp
            35                  40                  45 ctt cct gcg gtg aca gaa gac tca gtg tct ttg ttt aat ggt aat aaa        192
Leu Pro Ala Val Thr Glu Asp Ser Val Ser Leu Phe Asn Gly Asn Lys
 50                  55                  60 att ttt gta agc aaa gaa aaa aat agc tcc ggc aaa tat gat tta aga        240
Ile Phe Val Ser Lys Glu Lys Asn Ser Ser Gly Lys Tyr Asp Leu Arg
 65                  70                  75                  80 gca aca att gat cag gtt gaa ctt aaa gga act tcc gat aaa aac aat        288
Ala Thr Ile Asp Gln Val Glu Leu Lys Gly Thr Ser Asp Lys Asn Asn
            85                  90                  95 ggt tct gga acc ctt gaa ggt tca aag cct gac aag agt aaa gta aaa        336
Gly Ser Gly Thr Leu Glu Gly Ser Lys Pro Asp Lys Ser Lys Val Lys
            100                 105                 110 tta aca gtt tct gct gat tta aac aca gta acc tta gaa gca ttt gat        384
Leu Thr Val Ser Ala Asp Leu Asn Thr Val Thr Leu Glu Ala Phe Asp
            115                 120                 125 gcc agc aac caa aaa att tca agt aaa gtt act aaa aaa cag ggg tca        432
Ala Ser Asn Gln Lys Ile Ser Ser Lys Val Thr Lys Lys Gln Gly Ser
130                 135                 140 ata aca gag gaa act ctc aaa gct aat aaa tta gac tca aag aaa tta        480
Ile Thr Glu Glu Thr Leu Lys Ala Asn Lys Leu Asp Ser Lys Lys Leu
145                 150                 155                 160 aca aga tca aac gga act aca ctt gaa tac tca caa ata aca gat gct        528
Thr Arg Ser Asn Gly Thr Thr Leu Glu Tyr Ser Gln Ile Thr Asp Ala
            165                 170                 175 gac aat gct aca aaa gca gta gaa act cta aaa aat agc att aag ctt        576
Asp Asn Ala Thr Lys Ala Val Glu Thr Leu Lys Asn Ser Ile Lys Leu
            180                 185                 190 gaa gga agt ctt gta gtc gga aaa aca aca gtg gaa att aaa gaa ggt        624
Glu Gly Ser Leu Val Val Gly Lys Thr Thr Val Glu Ile Lys Glu Gly
            195                 200                 205 act gtt act cta aaa aga gaa att gaa aaa gat gga aaa gta aaa gtc        672
Thr Val Thr Leu Lys Arg Glu Ile Glu Lys Asp Gly Lys Val Lys Val
210                 215                 220 ttt ttg aat gac act gca ggt tct aac aaa aaa aca ggt aaa tgg gaa        720
Phe Leu Asn Asp Thr Ala Gly Ser Asn Lys Lys Thr Gly Lys Trp Glu
225                 230                 235                 240 gac agt act agc act tta aca att agt gct gac agc aaa aaa act aaa        768
Asp Ser Thr Ser Thr Leu Thr Ile Ser Ala Asp Ser Lys Lys Thr Lys
            245                 250                 255 gat ttg gtg ttc tta aca gat ggt aca att aca gta caa caa tac aac        816
Asp Leu Val Phe Leu Thr Asp Gly Thr Ile Thr Val Gln Gln Tyr Asn
            260                 265                 270 aca gct gga acc agc cta gaa gga tca gca agt gaa att aaa aat ctt        864
Thr Ala Gly Thr Ser Leu Glu Gly Ser Ala Ser Glu Ile Lys Asn Leu
            275                 280                 285 tca gag ctt aaa aac gct tta aaa taa                                     891
Ser Glu Leu Lys Asn Ala Leu Lys *
            290                 295
```

<210> SEQ ID NO 22
<211> LENGTH: 296
<212> TYPE: PRT
<213> ORGANISM: Borrelia burgdorferi

<400> SEQUENCE: 22

```
Met Arg Leu Leu Ile Gly Phe Ala Leu Ala Leu Ala Leu Ile Gly Cys
 1               5                  10                  15
```

Ala Gln Lys Gly Ala Glu Ser Ile Gly Ser Gln Lys Glu Asn Asp Leu
         20                  25                  30

Asn Leu Glu Asp Ser Ser Lys Lys Ser His Gln Asn Ala Lys Gln Asp
             35                  40                  45

Leu Pro Ala Val Thr Glu Asp Ser Val Ser Leu Phe Asn Gly Asn Lys
         50                  55                  60

Ile Phe Val Ser Lys Glu Lys Asn Ser Ser Gly Lys Tyr Asp Leu Arg
 65                  70                  75                  80

Ala Thr Ile Asp Gln Val Glu Leu Lys Gly Thr Ser Asp Lys Asn Asn
                 85                  90                  95

Gly Ser Gly Thr Leu Glu Gly Ser Lys Pro Asp Lys Ser Lys Val Lys
             100                 105                 110

Leu Thr Val Ser Ala Asp Leu Asn Thr Val Thr Leu Glu Ala Phe Asp
         115                 120                 125

Ala Ser Asn Gln Lys Ile Ser Ser Lys Val Thr Lys Lys Gln Gly Ser
    130                 135                 140

Ile Thr Glu Glu Thr Leu Lys Ala Asn Lys Leu Asp Ser Lys Lys Leu
145                 150                 155                 160

Thr Arg Ser Asn Gly Thr Thr Leu Glu Tyr Ser Gln Ile Thr Asp Ala
                165                 170                 175

Asp Asn Ala Thr Lys Ala Val Glu Thr Leu Lys Asn Ser Ile Lys Leu
            180                 185                 190

Glu Gly Ser Leu Val Val Gly Lys Thr Thr Val Glu Ile Lys Glu Gly
        195                 200                 205

Thr Val Thr Leu Lys Arg Glu Ile Glu Lys Asp Gly Lys Val Lys Val
    210                 215                 220

Phe Leu Asn Asp Thr Ala Gly Ser Asn Lys Lys Thr Gly Lys Trp Glu
225                 230                 235                 240

Asp Ser Thr Ser Thr Leu Thr Ile Ser Ala Asp Ser Lys Lys Thr Lys
                245                 250                 255

Asp Leu Val Phe Leu Thr Asp Gly Thr Ile Thr Val Gln Gln Tyr Asn
            260                 265                 270

Thr Ala Gly Thr Ser Leu Glu Gly Ser Ala Ser Glu Ile Lys Asn Leu
        275                 280                 285

Ser Glu Leu Lys Asn Ala Leu Lys
    290                 295

<210> SEQ ID NO 23
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 23
ggtacaatta cagtacaa                                         18

<210> SEQ ID NO 24
<211> LENGTH: 42
<212> TYPE: DNA
<213> ORGANISM: Artificial Sequence
<220> FEATURE:
<223> OTHER INFORMATION: Oligonucleotide Primer

<400> SEQUENCE: 24
ccgagaatct catatggcac aaaaaggtgc tgagtcaatt gg               42

-continued

<210> SEQ ID NO 25
<211> LENGTH: 35
<212> TYPE: DNA
<213> ORGANISM: Artificial Sequence
<220> FEATURE:
<223> OTHER INFORMATION: Oligonucleotide Primer

<400> SEQUENCE: 25
ccgatatcgg atcctatttt aaagcgtttt taagc                           35

<210> SEQ ID NO 26
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 26
ggatccggtg accttttaaa gcgtttttaa g                               31

<210> SEQ ID NO 27
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 27
gtgcgcgacc atatgaaaaa gaatacatta agtgcg                          36

<210> SEQ ID NO 28
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 28
gtcggcggat ccttaaggtt tttttggact ttctgc                          36

<210> SEQ ID NO 29
<211> LENGTH: 633
<212> TYPE: DNA
<213> ORGANISM: Borrelia burgdorferi
<220> FEATURE:
<221

```
ata cac caa aat aat ggt ttg gat acc gaa tat aat cac aat gga tca         288
Ile His Gln Asn Asn Gly Leu Asp Thr Glu Tyr Asn His Asn Gly Ser
             85                  90                  95 ttg tta gcg gga cgt tat gca ata tca acc cta ata aaa caa aaa tta         336
Leu Leu Ala Gly Arg Tyr Ala Ile Ser Thr Leu Ile Lys Gln Lys Leu
        100                 105                 110 gat gga ttg aaa aat gaa gga tta aag gaa aaa att gat gcg gct aag         384
Asp Gly Leu Lys Asn Glu Gly Leu Lys Glu Lys Ile Asp Ala Ala Lys
        115                 120                 125 aaa tgt tct gaa aca ttt act aat aaa tta aaa gaa aaa cac aca gat         432
Lys Cys Ser Glu Thr Phe Thr Asn Lys Leu Lys Glu Lys His Thr Asp
    130                 135                 140 ctt ggt aaa gaa ggt gtt act gat gct gat gca aaa gaa gcc att tta         480
Leu Gly Lys Glu Gly Val Thr Asp Ala Asp Ala Lys Glu Ala Ile Leu
145                 150                 155                 160 aaa aca aat ggt act aaa act aaa ggt gct gaa gaa ctt gga aaa tta         528
Lys Thr Asn Gly Thr Lys Thr Lys Gly Ala Glu Glu Leu Gly Lys Leu
            165                 170                 175 ttt gaa tca gta gag gtc ttg tca aaa gca gct aaa gag atg ctt gct         576
Phe Glu Ser Val Glu Val Leu Ser Lys Ala Ala Lys Glu Met Leu Ala
        180                 185                 190 aat tca gtt aaa gag ctt aca agc cct gtt gtg gca gaa agt cca aaa         624
Asn Ser Val Lys Glu Leu Thr Ser Pro Val Val Ala Glu Ser Pro Lys
        195                 200                 205 aaa cct taa                                                             633
Lys Pro  *
    210

<210> SEQ ID NO 30
<211> LENGTH: 210
<212> TYPE: PRT
<213> ORGANISM: Borrelia burgdorferi

<400> SEQUENCE: 30

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Tyr Asn His Asn Gly Ser
            85                  90                  95

Leu Leu Ala Gly Arg Tyr Ala Ile Ser Thr Leu Ile Lys Gln Lys Leu
        100                 105                 110

Asp Gly Leu Lys Asn Glu Gly Leu Lys Glu Lys Ile Asp Ala Ala Lys
    115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
            165                 170                 175

Phe Glu Ser Val Glu Val Leu Ser Lys Ala Ala Lys Glu Met Leu Ala
        180                 185                 190
```

```
Asn Ser Val Lys Glu Leu Thr Ser Pro Val Val Ala Glu Ser Pro Lys
        195                 200                 205

Lys Pro
    210

<210> SEQ ID NO 31
<211> LENGTH: 630
<212> TYPE: DNA
<213> ORGANISM: Borrelia burgdorferi
<220> FEATURE:
<221> NAME/KEY: CDS
<222> LOCATION: (1)...(630)

<400> SEQUENCE: 31 atg aaa aag aat aca tta agt gcg ata tta atg act tta ttt tta ttt     48
Met Lys Lys Asn Thr Leu Ser Ala Ile Leu Met Thr Leu Phe Leu Phe
 1               5                  10                  15 ata tct tgt aat aat tca ggt ggg gat acc gca tct act aat cct gat     96
Ile Ser Cys Asn Asn Ser Gly Gly Asp Thr Ala Ser Thr Asn Pro Asp
            20                  25                  30 gag tct gca aaa gga cct aat ctt aca gta ata agc aaa aaa att aca    144
Glu Ser Ala Lys Gly Pro Asn Leu Thr Val Ile Ser Lys Lys Ile Thr
        35                  40                  45 gat tct aat gca ttt gta ctg gct gtg aaa gaa gtt gag gct ttg atc    192
Asp Ser Asn Ala Phe Val Leu Ala Val Lys Glu Val Glu Ala Leu Ile
 50                  55                  60 tca tct ata gat gaa ctt gct aat aaa gct att ggt aaa gta ata cat    240
Ser Ser Ile Asp Glu Leu Ala Asn Lys Ala Ile Gly Lys Val Ile His
 65                  70                  75                  80 caa aat aat ggt tta aat gct aat gcg ggt caa aac gga tca ttg tta    288
Gln Asn Asn Gly Leu Asn Ala Asn Ala Gly Gln Asn Gly Ser Leu Leu
                85                  90                  95 gca gga gcc tat gca ata tca acc cta ata aca gaa aaa tta agt aaa    336
Ala Gly Ala Tyr Ala Ile Ser Thr Leu Ile Thr Glu Lys Leu Ser Lys
            100                 105                 110 ttg aaa aat tca gaa gag tta aat aaa aaa att gaa gag gct aag aac    384
Leu Lys Asn Ser Glu Glu Leu Asn Lys Lys Ile Glu Glu Ala Lys Asn
        115                 120                 125 cat tct gaa gca ttt act aat aga cta aaa ggt tct cat gca caa ctt    432
His Ser Glu Ala Phe Thr Asn Arg Leu Lys Gly Ser His Ala Gln Leu
130                 135                 140 gga gtt gct gct gct act gat gat cat gca aaa gaa gct att tta aag    480
Gly Val Ala Ala Ala Thr Asp Asp His Ala Lys Glu Ala Ile Leu Lys
145                 150                 155                 160 tca aat cct act aaa gat aag ggt gct aaa gca ctt aaa gac tta tct    528
Ser Asn Pro Thr Lys Asp Lys Gly Ala Lys Ala Leu Lys Asp Leu Ser
                165                 170                 175 gaa tca gta gaa agc ttg gca aaa gca gcg caa gaa gca tta gct aat    576
Glu Ser Val Glu Ser Leu Ala Lys Ala Ala Gln Glu Ala Leu Ala Asn
            180                 185                 190 tca gtt aaa gaa ctt aca aat cct gtt gtg gca gaa agt cca aaa aaa    624
Ser Val Lys Glu Leu Thr Asn Pro Val Val Ala Glu Ser Pro Lys Lys
        195                 200                 205 cct taa                                                            630
Pro *

<210> SEQ ID NO 32
<211> LENGTH: 209
<212> TYPE: PRT
<213> ORGANISM: Borrelia burgdorferi
```

```
<400> SEQUENCE: 32

Met Lys Lys Asn Thr Leu Ser Ala Ile Leu Met Thr Leu Phe Leu Phe
  1               5                  10                  15

Ile Ser Cys Asn Asn Ser Gly Gly Asp Thr Ala Ser Thr Asn Pro Asp
             20                  25                  30

Glu Ser Ala Lys Gly Pro Asn Leu Thr Val Ile Ser Lys Lys Ile Thr
         35                  40                  45

Asp Ser Asn Ala Phe Val Leu Ala Val Lys Glu Val Glu Ala Leu Ile
     50                  55                  60

Ser Ser Ile Asp Glu Leu Ala Asn Lys Ala Ile Gly Lys Val Ile His
 65                  70                  75                  80

Gln Asn Asn Gly Leu Asn Ala Asn Ala Gly Gln Asn Gly Ser Leu Leu
                 85                  90                  95

Ala Gly Ala Tyr Ala Ile Ser Thr Leu Ile Thr Glu Lys Leu Ser Lys
             100                 105                 110

Leu Lys Asn Ser Glu Glu Leu Asn Lys Lys Ile Glu Glu Ala Lys Asn
             115                 120                 125

His Ser Glu Ala Phe Thr Asn Arg Leu Lys Gly Ser His Ala Gln Leu
130                 135                 140

Gly Val Ala Ala Thr Asp Asp His Ala Lys Glu Ala Ile Leu Lys
145                 150                 155                 160

Ser Asn Pro Thr Lys Asp Lys Gly Ala Lys Ala Leu Lys Asp Leu Ser
                165                 170                 175

Glu Ser Val Glu Ser Leu Ala Lys Ala Ala Gln Glu Ala Leu Ala Asn
            180                 185                 190

Ser Val Lys Glu Leu Thr Asn Pro Val Val Ala Glu Ser Pro Lys Lys
        195                 200                 205

Pro

<210> SEQ ID NO 33
<211> LENGTH: 639
<212> TYPE: DNA
<213> ORGANISM: Borrelia burgdorferi
<220> FEATURE:
<221> NAME/KEY: CDS
<222> LOCATION: (1)...(639)

<400> SEQUENCE: 33 atg aaa aag aat aca tta agt g

-continued

```
                Ser Leu Leu Ala Gly Ala Tyr Ala Ile Ser Thr Leu Ile Thr Glu Lys
                            100                 105                 110 ttg agt aaa ttg aaa aat tta gaa gaa tta aag aca gaa att gca aag        384
Leu Ser Lys Leu Lys Asn Leu Glu Glu Leu Lys Thr Glu Ile Ala Lys
            115                 120                 125 gct aag aaa tgt tcc gaa gaa ttt act aat aaa cta aaa agt ggt cat        432
Ala Lys Lys Cys Ser Glu Glu Phe Thr Asn Lys Leu Lys Ser Gly His
    130                 135                 140 gca gat ctt ggc aaa cag gat gct acc gat gat cat gca aaa gca gct        480
Ala Asp Leu Gly Lys Gln Asp Ala Thr Asp Asp His Ala Lys Ala Ala
145                 150                 155                 160 att tta aaa aca cat gca act acc gat aaa ggt gct aaa gaa ttt aaa        528
Ile Leu Lys Thr His Ala Thr Thr Asp Lys Gly Ala Lys Glu Phe Lys
                165                 170                 175 gat tta ttt gaa tca gta gaa ggt ttg tta aaa gca gct caa gta gca        576
Asp Leu Phe Glu Ser Val Glu Gly Leu Leu Lys Ala Ala Gln Val Ala
                180                 185                 190 cta act aat tca gtt aaa gaa ctt aca agt cct gtt gta gca gaa agt        624
Leu Thr Asn Ser Val Lys Glu Leu Thr Ser Pro Val Val Ala Glu Ser
            195                 200                 205 cca aaa aaa cct taa                                                    639
Pro Lys Lys Pro *
    210
```

<210> SEQ ID NO 34
<211> LENGTH: 212
<212> TYPE: PRT
<213> ORGANISM: Borrelia burgdorferi

<400> SEQUENCE: 34

```
Met Lys Lys Asn Thr Leu Ser Ala Ile Leu Met Thr Leu Phe Leu Phe
  1               5                  10                  15

Ile Ser Cys Ser Asn Ser Gly Lys Gly Gly Asp Ser Ala Ser Thr Asn
            20                  25                  30

Pro Ala Asp Glu Ser Ala Lys Gly Pro Asn Leu Thr Glu Ile Ser Lys
        35                  40                  45

Lys Ile Thr Asp Ser Asn Ala Phe Val Leu Ala Val Lys Glu Val Glu
    50                  55                  60

Thr Leu Val Leu Ser Ile Asp Glu Leu Ala Lys Lys Ala Ile Gly Gln
65                  70                  75                  80

Lys Ile Asp Asn Asn Asn Gly Leu Ala Ala Leu Asn Asn Gln Asn Gly
                85                  90                  95

Ser Leu Leu Ala Gly Ala Tyr Ala Ile Ser Thr Leu Ile Thr Glu Lys
            100                 105                 110

Leu Ser Lys Leu Lys Asn Leu Glu Glu Leu Lys Thr Glu Ile Ala Lys
        115                 120                 125

Ala Lys Lys Cys Ser Glu Glu Phe Thr Asn Lys Leu Lys Ser Gly His
    130                 135                 140

Ala Asp Leu Gly Lys Gln Asp Ala Thr Asp Asp His Ala Lys Ala Ala
145                 150                 155                 160

Ile Leu Lys Thr His Ala Thr Thr Asp Lys Gly Ala Lys Glu Phe Lys
                165                 170                 175

Asp Leu Phe Glu Ser Val Glu Gly Leu Leu Lys Ala Ala Gln Val Ala
            180                 185                 190

Leu Thr Asn Ser Val Lys Glu Leu Thr Ser Pro Val Val Ala Glu Ser
        195                 200                 205

Pro Lys Lys Pro
```

-continued

<210> SEQ ID NO 35
<211> LENGTH: 624
<212> TYPE: DNA
<213> ORGANISM: Borrelia burgdorferi
<220> FEATURE:
<221> NAME/KEY: CDS
<222> LOCATION: (1)...(624)

<400> SEQUENCE: 35

| | | | | | | | | | | | | | | | | |
|---|---|---|---|---|---|---|---|---|---|---|---|---|---|---|---|---|
| atg | aaa | aag | aat | aca | tta | agt | gcg | ata | tta | atg | act | tta | ttt | tta | ttt | 48 |
| Met | Lys | Lys | Asn | Thr | Leu | Ser | Ala | Ile | Leu | Met | Thr | Leu | Phe | Leu | Phe | |
| 1 | | | | 5 | | | | | 10 | | | | | 15 | | |
| ata | tct | tgt | aat | aat | tca | ggt | ggg | gat | tct | gca | tct | act | aat | cct | gat | 96 |
| Ile | Ser | Cys | Asn | Asn | Ser | Gly | Gly | Asp | Ser | Ala | Ser | Thr | Asn | Pro | Asp | |
| | | | | 20 | | | | | 25 | | | | | 30 | | |
| gag | tct | gca | aaa | gga | cct | aat | ctt | acc | gta | ata | agc | aaa | aaa | att | aca | 144 |
| Glu | Ser | Ala | Lys | Gly | Pro | Asn | Leu | Thr | Val | Ile | Ser | Lys | Lys | Ile | Thr | |
| | | | 35 | | | | | 40 | | | | | 45 | | | |
| gat | tct | aat | gca | ttt | tta | ctg | gct | gtg | aaa | gaa | gtt | gag | gct | ttg | ctt | 192 |
| Asp | Ser | Asn | Ala | Phe | Leu | Leu | Ala | Val | Lys | Glu | Val | Glu | Ala | Leu | Leu | |
| 50 | | | | | 55 | | | | | 60 | | | | | | |
| tca | tct | ata | gat | gaa | ctt | tct | aaa | gct | att | ggt | aaa | aaa | ata | aaa | aat | 240 |
| Ser | Ser | Ile | Asp | Glu | Leu | Ser | Lys | Ala | Ile | Gly | Lys | Lys | Ile | Lys | Asn | |
| 65 | | | | | 70 | | | | | 75 | | | | | 80 | |
| gat | ggt | act | tta | gat | aac | gaa | gca | aat | cga | aac | gaa | tca | ttg | ata | gca | 288 |
| Asp | Gly | Thr | Leu | Asp | Asn | Glu | Ala | Asn | Arg | Asn | Glu | Ser | Leu | Ile | Ala | |
| | | | | 85 | | | | | 90 | | | | | 95 | | |
| gga | gct | tat | gaa | ata | tca | aaa | cta | ata | aca | caa | aaa | tta | agt | gta | ttg | 336 |
| Gly | Ala | Tyr | Glu | Ile | Ser | Lys | Leu | Ile | Thr | Gln | Lys | Leu | Ser | Val | Leu | |
| | | | 100 | | | | | 105 | | | | | 110 | | | |
| aat | tca | gaa | gaa | tta | aag | aaa | aaa | att | aaa | gag | gct | aag | gat | tgt | tcc | 384 |
| Asn | Ser | Glu | Glu | Leu | Lys | Lys | Lys | Ile | Lys | Glu | Ala | Lys | Asp | Cys | Ser | |
| | | | 115 | | | | | 120 | | | | | 125 | | | |
| gaa | aaa | ttt | act | act | aag | cta | aaa | gat | agt | cat | gca | gag | ctt | ggt | ata | 432 |
| Glu | Lys | Phe | Thr | Thr | Lys | Leu | Lys | Asp | Ser | His | Ala | Glu | Leu | Gly | Ile | |
| | 130 | | | | | 135 | | | | | 140 | | | | | |
| caa | agc | gtt | cag | gat | gat | aat | gca | aaa | aaa | gct | att | tta | aaa | aca | cat | 480 |
| Gln | Ser | Val | Gln | Asp | Asp | Asn | Ala | Lys | Lys | Ala | Ile | Leu | Lys | Thr | His | |
| 145 | | | | | 150 | | | | | 155 | | | | | 160 | |
| gga | act | aaa | gac | aag | ggt | gct | aaa | gaa | ctt | gaa | gag | tta | ttt | aaa | tca | 528 |
| Gly | Thr | Lys | Asp | Lys | Gly | Ala | Lys | Glu | Leu | Glu | Glu | Leu | Phe | Lys | Ser | |
| | | | | 165 | | | | | 170 | | | | | 175 | | |
| cta | gaa | agc | ttg | tca | aaa | gca | gcg | caa | gca | gca | tta | act | aat | tca | gtt | 576 |
| Leu | Glu | Ser | Leu | Ser | Lys | Ala | Ala | Gln | Ala | Ala | Leu | Thr | Asn | Ser | Val | |
| | | | | 180 | | | | | 185 | | | | | 190 | | |
| aaa | gag | ctt | aca | aat | cct | gtt | gtg | gca | gaa | agt | cca | aaa | aaa | cct | taa | 624 |
| Lys | Glu | Leu | Thr | Asn | Pro | Val | Val | Ala | Glu | Ser | Pro | Lys | Lys | Pro | * | |
| | | | 195 | | | | | 200 | | | | | 205 | | | |

<210> SEQ ID NO 36
<211> LENGTH: 207
<212> TYPE: PRT
<213> ORGANISM: Borrelia burgdorferi

<400> SEQUENCE: 36

Met Lys Lys Asn Thr Leu Ser Ala Ile Leu Met Thr Leu Phe Leu Phe
1               5                   10                  15

Ile Ser Cys Asn Asn Ser Gly Gly Asp Ser Ala Ser Thr Asn Pro Asp
                20                  25                  30

```
Glu Ser Ala Lys Gly Pro Asn Leu Thr Val Ile Ser Lys Lys Ile Thr
         35                  40                  45

Asp Ser Asn Ala Phe Leu Leu Ala Val Lys Glu Val Glu Ala Leu Leu
     50                  55                  60

Ser Ser Ile Asp Glu Leu Ser Lys Ala Ile Gly Lys Lys Ile Lys Asn
 65                  70                  75                  80

Asp Gly Thr Leu Asp Asn Glu Ala Asn Arg Asn Glu Ser Leu Ile Ala
                 85                  90                  95

Gly Ala Tyr Glu Ile Ser Lys Leu Ile Thr Gln Lys Leu Ser Val Leu
            100                 105                 110

Asn Ser Glu Glu Leu Lys Lys Ile Lys Glu Ala Lys Asp Cys Ser
        115                 120                 125

Glu Lys Phe Thr Thr Lys Leu Lys Asp Ser His Ala Glu Leu Gly Ile
    130                 135                 140

Gln Ser Val Gln Asp Asp Asn Ala Lys Lys Ala Ile Leu Lys Thr His
145                 150                 155                 160

Gly Thr Lys Asp Lys Gly Ala Lys Glu Leu Glu Leu Phe Lys Ser
                165                 170                 175

Leu Glu Ser Leu Ser Lys Ala Ala Gln Ala Ala Leu Thr Asn Ser Val
            180                 185                 190

Lys Glu Leu Thr Asn Pro Val Val Ala Glu Ser Pro Lys Lys Pro
        195                 200                 205

<210> SEQ ID NO 37
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 37
gtgcgcgacc atatggctaa taattcaggg aaagat                          36

<210> SEQ ID NO 38
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 38
gtgcgcgacc atatggctag taattcaggg aaaggt                          36

<210> SEQ ID NO 39
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 39
gtgcgcgacc atatggctaa taattcaggt ggggat                          36

<210> SEQ ID NO 40
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 40
```

-continued

```
cttggaaaat tatttgaa                                          18

<210> SEQ ID NO 41
<211> LENGTH: 35
<212> TYPE: DNA
<213> ORGANISM: Artificial Sequence
<220> FEATURE:
<223> OTHER INFORMATION: Oligonucleotide Primer

<400> SEQUENCE: 41
cacggtcacc ccatgggaaa taattcaggg aaagg                       35

<210> SEQ ID NO 42
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 42
tatagatgac agcaacgc                                          18

<210> SEQ ID NO 43
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 43
ccggtgaccc catggtacca ggttttttttg gactttctgc                 40

<210> SEQ ID NO 44
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 44
ccggatccat atggttaaaa aataatatt tatttc                       36

<210> SEQ ID NO 45
<211> LENGTH: 37
<212> TYPE: DNA
<213> ORGANISM: Artificial Sequence
<220> FEATURE:
<223> OTHER INFORMATION: Oligonucleotide Primer

<400> SEQUENCE: 45
gatatctaga tctttaattg ctctgctcac tctcttc                     37

<210> SEQ ID NO 46
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 46
ccgggatcca tatggctagt gcaattggtc gtgg                        34

<210> SEQ ID NO 47
<211> LENGTH: 18
<212> TYPE: DNA
<213> ORGANISM: Artificial Sequence
```

-continued

<220> FEATURE:
<223> OTHER INFORMATION: Oligonucleotide Primer

<400> SEQUENCE: 47
atgattatca atcataat 18

<210> SEQ ID NO 48
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 48
tctgaacaat gacaaaac 18

<210> SEQ ID NO 49
<211> LENGTH: 825
<212> TYPE: DNA
<213> ORGANISM: Borrelia burgdorferi

<400> SEQUENCE: 49
atgaaaaaat atttattggg aataggtcta atattagcct taatagcatg taagcaaaat 60
gttagcagcc ttgatgaaaa aaatagcgtt tcagtagatt tacctggtgg aatgacagtt 120
cttgtaagta aagaaaaaga caaagacggt aaatacagtc tagaggcaac agtagacaag 180
cttgagctta aaggaacttc tgataaaaac aacggttctg gaacacttga aggtgaaaaa 240
actgacaaaa gtaaagtaaa atcaacaatt gctgatgacc taagtcaaac taaatttgaa 300
attttcaaag aagatggcaa aacattagta tcaaaaaaag taacccttaa agacaagtca 360
tcaacagaag aaaaattcaa cggaaagggt gaaacatctg aaaaaacaat agtaagagca 420
aatggaacca gacttgaata cacagacata aaaagcgatg gatccggaaa agctaaagaa 480
gttttaaaag actttactct tgaaggaact ctagctgctg acggcaaaac aacattgaaa 540
gttacagaag gcactgttgt tttaagcaag aacattttaa aatccggaga aataacagct 600
gcacttgatg actctgacac tactcgggct actaaaaaaa ctggaaaatg ggattcaaag 660
acttccactt taacaattag tgtgaatagc caaaaaacca aaaaccttgt attcacaaaa 720
gaagacacaa taacagtaca aagatacgac tcagcaggca ccaatctaga aggcaaagca 780
gtcgaaatta caacacttaa agaacttaaa aacgctttaa aataa 825

<210> SEQ ID NO 50
<211> LENGTH: 824
<212> TYPE: DNA
<213> ORGANISM: Borrelia burgdorferi

<400> SEQUENCE: 50
atgaaaaaat atttattggg aataggtcta atattagcat taatagcatg taagcaaaat 60
gttagcagcc ttgatgaaaa aaatagcgtt tcagtagatt tacctggtgg aatgcaagtt 120
cttgtaagta aagaaaaaga caaagatggt aaatacagtc taatggcaac agtagacaag 180
cttgagctta aaggaacttc tgataaaaac aacggttctg gaacacttga aggtgaaaaa 240
actgacaaaa gtaaagcaaa attaacaatt gctgaggatc taagtaaaac cacatttgaa 300
atcttcaaag aagatggcaa aacattagta tcaaaaaaag taacccttaa agacaagtca 360
tcaacagaag aaaaattcaa cgcaaagggt gaagcatctg aaaaaacaat agtaagagca 420
aatggaacca gacttgaata cacagacata aaaagcgata aaaccggaaa agctaaagaa 480
gttttaaaag actttgctct tgaaggaact ctagctgctg acggcaaaac aacattaaaa 540
gttacagaag gcactgttgt tttaagcaaa cacatttcaa actctggaga aataacagtt 600
gagcttaatg actctgacac tactcaggct actaaaaaaa ctggaacatg ggattcaaag 660
acttccactt taacaattag tgtgaatagc cgaaaaacca aaaaccttgt attcacaaaa 720
gaagacacaa taacagtaca aaaatacgac tcagcaggca ccaatctaga aggcaaagca 780
gtcgaaatta caacgcttaa agaacttaaa gatgctttaa aata 824

-continued

```
<210> SEQ ID NO 51
<211> LENGTH: 1011
<212> TYPE: DNA
<213> ORGANISM: Borrelia burgdorferi
<220> FEATURE:
<221> NAME/KEY: CDS
<222> LOCATION: (1)...(1011)

<400> SEQUENCE: 51 atg att atc aat cat aat aca tca gct att aat gct tca aga aat aat      48
Met Ile Ile Asn His Asn Thr Ser Ala Ile Asn Ala Ser Arg Asn Asn
 1               5                  10                  15 gcc att aat gct gct aat ctt agt aaa acc caa gag aag ctt tct agt      96
Ala Ile Asn Ala Ala Asn Leu Ser Lys Thr Gln Glu Lys Leu Ser Ser
             20                  25                  30 ggt tac aga att aat cga gct tct gat gat gct gct ggt atg ggg gtt    144
Gly Tyr Arg Ile Asn Arg Ala Ser Asp Asp Ala Ala Gly Met Gly Val
         35                  40                  45 tct ggc aag att aat gct caa ata aca ggc tta tca caa gct tct aga    192
Ser Gly Lys Ile Asn Ala Gln Ile Thr Gly Leu Ser Gln Ala Ser Arg
 50                  55                  60 aac act tca aaa gct atc aat ttt att cag aca aca gaa gga aat tta    240
Asn Thr Ser Lys Ala Ile Asn Phe Ile Gln Thr Thr Glu Gly Asn Leu
 65                  70                  75                  80 aat gaa gta gaa aaa gtt tta gta aga atg aaa gaa tta gca gtt caa    288
Asn Glu Val Glu Lys Val Leu Val Arg Met Lys Glu Leu Ala Val Gln
                 85                  90                  95 tca ggt aac gga acg tat tca gac gca gac aga ggt tct ata cag att    336
Ser Gly Asn Gly Thr Tyr Ser Asp Ala Asp Arg Gly Ser Ile Gln Ile
            100                 105                 110 gaa ata gag caa ctt aca gac gaa att aat aga att gct gat cag gct    384
Glu Ile Glu Gln Leu Thr Asp Glu Ile Asn Arg Ile Ala Asp Gln Ala
        115                 120                 125 caa tat aac caa atg cac atg ttg tca aac aaa tct gct tcc caa aat    432
Gln Tyr Asn Gln Met His Met Leu Ser Asn Lys Ser Ala Ser Gln Asn
130                 135                 140 gta aaa aca gct gaa gag ctt gga atg cag cct gca aaa att aac aca    480
Val Lys Thr Ala Glu Glu Leu Gly Met Gln Pro Ala Lys Ile Asn Thr
145                 150                 155                 160 cca gca tca ctt tca gga tct caa gct tct tgg act tta aga gtt cat    528
Pro Ala Ser Leu Ser Gly Ser Gln Ala Ser Trp Thr Leu Arg Val His
                165                 170                 175 gtg gga gca aat caa gat gaa gca att gct gta aat att tat tca gct    576
Val Gly Ala Asn Gln Asp Glu Ala Ile Ala Val Asn Ile Tyr Ser Ala
            180                 185                 190 aat gtt gca aat ctt ttt gct ggt gag gga gct caa gct gct cag gct    624
Asn Val Ala Asn Leu Phe Ala Gly Glu Gly Ala Gln Ala Ala Gln Ala
        195                 200                 205 gca cct gtt caa gag ggt gct caa gaa gaa gga gct cag caa cca aca    672
Ala Pro Val Gln Glu Gly Ala Gln Glu Glu Gly Ala Gln Gln Pro Thr
    210                 215                 220 cct gct aca gca cct act caa ggt gga gtt aat tct cct gtt aat gtt    720
Pro Ala Thr Ala Pro Thr Gln Gly Gly Val Asn Ser Pro Val Asn Val
225                 230                 235                 240 aca acc aca gtt gat gct aat aca tca ctt gct aaa ata gaa aat gct    768
Thr Thr Thr Val Asp Ala Asn Thr Ser Leu Ala Lys Ile Glu Asn Ala
                245                 250                 255 att aga atg ata agt gat caa aga gca aat tta ggt gct ttc caa aat    816
Ile Arg Met Ile Ser Asp Gln Arg Ala Asn Leu Gly Ala Phe Gln Asn
            260                 265                 270 aga ctt gaa tct ata aag aat agc act gag tat gct att gaa aat cta    864
```

-continued

```
Arg Leu Glu Ser Ile Lys Asn Ser Thr Glu Tyr Ala Ile Glu Asn Leu
            275                 280                 285 aaa gca tct tat gct caa ata aaa gat gct aca atg aca gat gag gtt        912
Lys Ala Ser Tyr Ala Gln Ile Lys Asp Ala Thr Met Thr Asp Glu Val
        290                 295                 300 gta gca gct aca act aat agt att tta act caa tct gca atg gca atg        960
Val Ala Ala Thr Thr Asn Ser Ile Leu Thr Gln Ser Ala Met Ala Met
305                 310                 315                 320 att gca cag gct aat caa gtt cct caa tat gtt ttg tca ttg ctt aga       1008
Ile Ala Gln Ala Asn Gln Val Pro Gln Tyr Val Leu Ser Leu Leu Arg
                325                 330                 335 taa                                                                    1011
*
```

<210> SEQ ID NO 52
<211> LENGTH: 336
<212> TYPE: PRT
<213> ORGANISM: Borrelia burgdorferi

<400> SEQUENCE: 52

```
Met Ile Ile Asn His Asn Thr Ser Ala Ile Asn Ala Ser Arg Asn Asn
 1               5                  10                  15

Ala Ile Asn Ala Ala Asn Leu Ser Lys Thr Gln Glu Lys Leu Ser Ser
            20                  25                  30

Gly Tyr Arg Ile Asn Arg Ala Ser Asp Ala Ala Gly Met Gly Val
        35                  40                  45

Ser Gly Lys Ile Asn Ala Gln Ile Thr Gly Leu Ser Gln Ala Ser Arg
    50                  55                  60

Asn Thr Ser Lys Ala Ile Asn Phe Ile Gln Thr Thr Glu Gly Asn Leu
65                  70                  75                  80

Asn Glu Val Glu Lys Val Leu Val Arg Met Lys Glu Leu Ala Val Gln
                85                  90                  95

Ser Gly Asn Gly Thr Tyr Ser Asp Ala Asp Arg Gly Ser Ile Gln Ile
            100                 105                 110

Glu Ile Glu Gln Leu Thr Asp Glu Ile Asn Arg Ile Ala Asp Gln Ala
        115                 120                 125

Gln Tyr Asn Gln Met His Met Leu Ser Asn Lys Ser Ala Ser Gln Asn
    130                 135                 140

Val Lys Thr Ala Glu Glu Leu Gly Met Gln Pro Ala Lys Ile Asn Thr
145                 150                 155                 160

Pro Ala Ser Leu Ser Gly Ser Gln Ala Ser Trp Thr Leu Arg Val His
                165                 170                 175

Val Gly Ala Asn Gln Asp Glu Ala Ile Ala Val Asn Ile Tyr Ser Ala
            180                 185                 190

Asn Val Ala Asn Leu Phe Ala Gly Glu Gly Ala Gln Ala Ala Gln Ala
        195                 200                 205

Ala Pro Val Gln Glu Gly Ala Gln Glu Gly Ala Gln Gln Pro Thr
    210                 215                 220

Pro Ala Thr Ala Pro Thr Gln Gly Gly Val Asn Ser Pro Val Asn Val
225                 230                 235                 240

Thr Thr Thr Val Asp Ala Asn Thr Ser Leu Ala Lys Ile Glu Asn Ala
                245                 250                 255

Ile Arg Met Ile Ser Asp Gln Arg Ala Asn Leu Gly Ala Phe Gln Asn
            260                 265                 270

Arg Leu Glu Ser Ile Lys Asn Ser Thr Glu Tyr Ala Ile Glu Asn Leu
        275                 280                 285
```

```
Lys Ala Ser Tyr Ala Gln Ile Lys Asp Ala Thr Met Thr Asp Glu Val
        290                 295                 300

Val Ala Ala Thr Thr Asn Ser Ile Leu Thr Gln Ser Ala Met Ala Met
305                 310                 315                 320

Ile Ala Gln Ala Asn Gln Val Pro Gln Tyr Val Leu Ser Leu Leu Arg
                325                 330                 335

<210> SEQ ID NO 53
<211> LENGTH: 1008
<212> TYPE: DNA
<213> ORGANISM: Borrelia burgdorferi
<220> FEATURE:
<221> NAME/KEY: CDS
<222> LOCATION: (1)...(1008)

<400> SEQUENCE: 53 atg att atc aat cat aat aca tca gct att aat gct tca aga aat aat      48
Met Ile Ile Asn His Asn Thr Ser Ala Ile Asn Ala Ser Arg Asn Asn
 1               5                  10                  15 ggt att aat gct gct aat ctt agt aaa act caa gag aag ctt tct agt      96
Gly Ile Asn Ala Ala Asn Leu Ser Lys Thr Gln Glu Lys Leu Ser Ser
             20                  25                  30 ggt tac aga att aat aga gct tct gat gat gct gct ggt atg ggg gtt     144
Gly Tyr Arg Ile Asn Arg Ala Ser Asp Asp Ala Ala Gly Met Gly Val
         35                  40                  45 tct ggg aag att aat gct caa ata aga ggt tta tca caa gct tct aga     192
Ser Gly Lys Ile Asn Ala Gln Ile Arg Gly Leu Ser Gln Ala Ser Arg
     50                  55                  60 aac act tca aaa gct att aat ttt att cag aca aca gaa gga aat ttg     240
Asn Thr Ser Lys Ala Ile Asn Phe Ile Gln Thr Thr Glu Gly Asn Leu
 65                  70                  75                  80 aat gaa gta gaa aaa gtt tta gta aga atg aaa gaa tta gca gtt caa     288
Asn Glu Val Glu Lys Val Leu Val Arg Met Lys Glu Leu Ala Val Gln
                 85                  90                  95 tca ggt aac ggt aca tat tca gac gca gac aga ggt tct ata caa att     336
Ser Gly Asn Gly Thr Tyr Ser Asp Ala Asp Arg Gly Ser Ile Gln Ile
            100                 105                 110 gaa ata gag caa ctt aca gac gaa att aat aga att gct gat caa gct     384
Glu Ile Glu Gln Leu Thr Asp Glu Ile Asn Arg Ile Ala Asp Gln Ala
        115                 120                 125 caa tat aac caa atg cac atg ttg tca aac aaa tct gct tcc caa aat     432
Gln Tyr Asn Gln Met His Met Leu Ser Asn Lys Ser Ala Ser Gln Asn
    130                 135                 140 gta aga aca gct gaa gaa ctt gga atg caa cct gca aaa atc aac aca     480
Val Arg Thr Ala Glu Glu Leu Gly Met Gln Pro Ala Lys Ile Asn Thr
145                 150                 155                 160 cca gcg tca ctt tca gga tct caa gct tct tgg act tta aga gtt cat     528
Pro Ala Ser Leu Ser Gly Ser Gln Ala Ser Trp Thr Leu Arg Val His
                165                 170                 175 gtg gga gca aat caa gat gaa gcg att gct gta aat att tat gct gct     576
Val Gly Ala Asn Gln Asp Glu Ala Ile Ala Val Asn Ile Tyr Ala Ala
            180                 185                 190 aat gtt gca aat cta ttc tct ggt gaa gga gct cag gct gct cag act     624
Asn Val Ala Asn Leu Phe Ser Gly Glu Gly Ala Gln Ala Ala Gln Thr
        195                 200                 205 gca cct gtt caa gaa ggt gct caa caa gaa gga gct caa caa cca gca     672
Ala Pro Val Gln Glu Gly Ala Gln Gln Glu Gly Ala Gln Gln Pro Ala
    210                 215                 220 cct gct aca gcg cct tct cag ggt gga gtt aat tct cct gtt aat gtt     720
Pro Ala Thr Ala Pro Ser Gln Gly Gly Val Asn Ser Pro Val Asn Val
```

-continued

```
                225                 230                 235                 240
aca act aca gtt gac gct aat aca tct ctt gct aaa ata gaa aat gct       768
Thr Thr Thr Val Asp Ala Asn Thr Ser Leu Ala Lys Ile Glu Asn Ala
                245                 250                 255 att aga atg ata agt gat caa aga gca aat tta ggt gct ttc caa aat       816
Ile Arg Met Ile Ser Asp Gln Arg Ala Asn Leu Gly Ala Phe Gln Asn
                260                 265                 270 aga ctt gag tct ata aag gat agt act gag tat gct att gaa aac cta       864
Arg Leu Glu Ser Ile Lys Asp Ser Thr Glu Tyr Ala Ile Glu Asn Leu
            275                 280                 285 aaa gca tct tat gct caa ata aaa gat gct aca atg aca gat gag gtt       912
Lys Ala Ser Tyr Ala Gln Ile Lys Asp Ala Thr Met Thr Asp Glu Val
        290                 295                 300 gta gca gct aca act aat agt att tta aca caa tgt gca atg gca atg       960
Val Ala Ala Thr Thr Asn Ser Ile Leu Thr Gln Cys Ala Met Ala Met
305                 310                 315                 320 att gcg caa gct aat caa gtt cct caa tat gtt ttg tca ttg ctt aga      1008
Ile Ala Gln Ala Asn Gln Val Pro Gln Tyr Val Leu Ser Leu Leu Arg
                325                 330                 335

<210> SEQ ID NO 54
<211> LENGTH: 336
<212> TYPE: PRT
<213> ORGANISM: Borrelia burgdorferi

<400> SEQUENCE: 54

Met Ile Ile Asn His Asn Thr Ser Ala Ile Asn Ala Ser Arg Asn Asn
1               5                   10                  15

Gly Ile Asn Ala Ala Asn Leu Ser Lys Thr Gln Glu Lys Leu Ser Ser
            20                  25                  30

Gly Tyr Arg Ile Asn Arg Ala Ser Asp Asp Ala Ala Gly Met Gly Val
        35                  40                  45

Ser Gly Lys Ile Asn Ala Gln Ile Arg Gly Leu Ser Gln Ala Ser Arg
    50                  55                  60

Asn Thr Ser Lys Ala Ile Asn Phe Ile Gln Thr Thr Glu Gly Asn Leu
65                  70                  75                  80

Asn Glu Val Glu Lys Val Leu Val Arg Met Lys Glu Leu Ala Val Gln
                85                  90                  95

Ser Gly Asn Gly Thr Tyr Ser Asp Ala Asp Arg Gly Ser Ile Gln Ile
            100                 105                 110

Glu Ile Glu Gln Leu Thr Asp Glu Ile Asn Arg Ile Ala Asp Gln Ala
        115                 120                 125

Gln Tyr Asn Gln Met His Met Leu Ser Asn Lys Ser Ala Ser Gln Asn
    130                 135                 140

Val Arg Thr Ala Glu Glu Leu Gly Met Gln Pro Ala Lys Ile Asn Thr
145                 150                 155                 160

Pro Ala Ser Leu Ser Gly Ser Gln Ala Ser Trp Thr Leu Arg Val His
                165                 170                 175

Val Gly Ala Asn Gln Asp Glu Ala Ile Ala Val Asn Ile Tyr Ala Ala
            180                 185                 190

Asn Val Ala Asn Leu Phe Ser Gly Glu Gly Ala Gln Ala Ala Gln Thr
        195                 200                 205

Ala Pro Val Gln Glu Gly Ala Gln Gln Glu Gly Ala Gln Gln Pro Ala
    210                 215                 220

Pro Ala Thr Ala Pro Ser Gln Gly Gly Val Asn Ser Pro Val Asn Val
225                 230                 235                 240
```

```
Thr Thr Thr Val Asp Ala Asn Thr Ser Leu Ala Lys Ile Glu Asn Ala
            245                 250                 255

Ile Arg Met Ile Ser Asp Gln Arg Ala Asn Leu Gly Ala Phe Gln Asn
            260                 265                 270

Arg Leu Glu Ser Ile Lys Asp Ser Thr Glu Tyr Ala Ile Glu Asn Leu
            275                 280                 285

Lys Ala Ser Tyr Ala Gln Ile Lys Asp Ala Thr Met Thr Asp Glu Val
            290                 295                 300

Val Ala Ala Thr Thr Asn Ser Ile Leu Thr Gln Cys Ala Met Ala Met
305                 310                 315                 320

Ile Ala Gln Ala Asn Gln Val Pro Gln Tyr Val Leu Ser Leu Leu Arg
            325                 330                 335

<210> SEQ ID NO 55
<211> LENGTH: 821
<212> TYPE: DNA
<213> ORGANISM: Borrelia burgdorferi

<400> SEQUENCE: 55
atgaaaaaat atttattggg aataggtcta atattagcct taatagcatg caagcaaaat   60
    gttagcagcc ttgatgaaaa aaacagcgct tcagtagatt tgcctggtga gatgaaagtt  120
    cttgtaagta agaaaaaga caaagacggt aagtacagtc taaggcaac agtagacaag   180
    attgagctaa aggaacttc tgataaagac aatggttctg ggtgcttga aggtacaaaa   240
    gatgacaaaa gtaaagcaaa attaacaatt gctgacgatc taggtaaaac cacattcgaa  300
    cttttcaaag aagatggcaa aacattagtg tcaagaaaag taagttctaa agacaaaaca  360
    tcaacagatg aaatgttcaa tgaaaaaggt gaattgtctg caaaaaccat gacaagagaa  420
    aatggaacca aacttgaata tacagaaatg aaaagcgatg gaaccggaaa agctaaagaa  480
    gttttaaaaa actttactct tgaaggaaaa gtagctaatg ataaagtaac attggaagta  540
    aaagaaggaa ccgttacttt aagtaaggaa attgcaaaat ctggagaagt aacagttgct  600
    cttaatgaca ctaacactac tcaggctact aaaaaaactg gcgcatggga ttcaaaaact  660
    tctactttaa caattagtgt taacagcaaa aaaactacac aacttgtgtt tactaaacaa  720
    gacacaataa ctgtacaaaa atacgactcc gcaggtacca atttagaagg cacagcagtc  780
    gaaattaaaa cacttgatga acttaaaaac gctttaaaat a                      821

<210> SEQ ID NO 56
<211> LENGTH: 821
<212> TYPE: DNA
<213> ORGANISM: Borrelia burgdorferi

<400> SEQUENCE: 56
atgaaaaaat atttattggg aataggtcta atattagcct taatagcatg caagcaaaat   60
    gttagcagcc ttgatgaaaa aaacagcgct tcagtagatt tgcctggtga gattaaagtt  120
    cttgtaagta agaaaaaga caaagacggt aagtacagtc taaggcaac agtagacaag   180
    attgagctaa aggaacttc tgataaagac aatggttctg gagtgcttga aggtacaaaa  240
    gatgacaaaa gtaaagcaaa attaacaatt gctgacgatc tagtaaaac cacattcgaa  300
    cttttcaaag aagatggcaa aacattagtg tcaagaaaag taagttctaa agacaaaaca  360
    tcaacagatg aaatgttcaa tgaaaaaggt gaattgtctg caaaaaccat gacaagagaa  420
    aatggaacca aacttgaata tacagaaatg aaaagcgatg gaaccggaaa agctaaagaa  480
    gttttaaaaa actttactct tgaaggaaaa gtagctaatg ataaagtaac attggaagta  540
    aaagaaggaa ccgttacttt aagtaaggaa attgcaaaat ctggagaagt aacagttgct  600
    cttaatgaca ctaacactac tcaggctact aaaaaaactg gcgcatggga ttcaaaaact  660
    tctactttaa caattagtgt taacagtaaa aaaactacac aacttgtgtt tactaaacaa  720
    gacacaataa ctgtacaaaa atacgactcc gcaggtacca atttagaagg cacagcagtc  780
    gaaattaaaa cacttgatga acttaaaaac gctttaaaat a                      821

<210> SEQ ID NO 57
<211> LENGTH: 821
<212> TYPE: DNA
<213> ORGANISM: Borrelia burgdorferi

<400> SEQUENCE: 57
atgaaaaaat atttattggg aataggtcta atattagcct taatagcatg caagcaaaat   60
    gttagcagcc ttgatgaaaa aaacagcgct tcagtagatt tgcctggtga gatgaaagtt  120
    cttgtaagta agaaaaaga caaagacggt aagtacagtc taaggcaac agtagacaag   180
    attgagctaa aggaacttc tgataaagac aatggttctg ggtgcttga aggtacaaaa   240
    gatgacaaaa gtaaagcaaa attaacaatt gctgacgatc taggtaaaac cacattcgaa  300
    cttttcaaag aagatggcaa aacattagtg tcaagaaaag taagttctaa agacaaaaca  360
    tcaacagatg aaatgttcaa tgaaaaaggt gaattgtctg caaaaaccat gacaagagaa  420
```

```
aatggaacca aacttgaata tacagaaatg aaaagcgatg gaaccggaaa agctaaagaa    480
gttttaaaaa actttactct tgaaggaaaa gtagctaatg ataaagtaac attggaagta    540
aaagaaggaa ccgttacttt aagtaaggaa attgcaaaat ctggagaagt aacagttgct    600
cttaatgaca ctaacactac tcaggctact aaaaaaactg gcgcatggga ttcaaaaact    660
tctactttaa caattagtgt taacagcaaa aaaactacac aacttgtgtt tactaaacaa    720
gacacaataa ctgtacaaaa atacgactcc gcaggtacca atttagaagg cacagcagtc    780
gaaattaaaa cacttgatga acttaaaaac gctttaaaat a                        821
```

<210> SEQ ID NO 58
<211> LENGTH: 822
<212> TYPE: DNA
<213> ORGANISM: Borrelia burgdorferi

<400> SEQUENCE: 58

```
atgaaaaaat atttattggg aataggtcta atattagcct taatagcatg caagcaaaat     60
gttagcagcc ttgatgaaaa aaacagcgct tcagtagatt tgcctggtga gatgaaagtt    120
cttgtaagta aagaaaaaga caaagacggt aagtacagtc taaaggcaac agtagacaag    180
attgagctaa aaggaacttc tgataaagac aatggttctg gagtgcttga aggtacaaaa    240
gatgacaaaa gtaaagcaaa attaacaatt gctgacgata taagtaaaac cacattcgaa    300
cttttcaaag aagatggcaa aacattagtg tcaagaaaag taagttctaa agacaaaaca    360
tcaacagatg aaatgttcaa tgaaaaggt gaattgtctg caaaaaccat gacaagagaa    420
aatggaacca aacttgaata tacagaaatg aaaagcgatg gaaccggaaa agctaaagaa    480
gttttaaaaa actttactct tgaaggaaaa gtagctaatg ataaagtaac attggaagta    540
aaagaaggaa ccgttacttt aagtaaggaa attgcaaaat ctggagaagt aacagttgct    600
cttaatgaca ctaacactac tcaggctact aaaaaaactg gcgcatggga ttcaaaaact    660
tctactttaa caattagtgt taacagcaaa aaaactacac aacttgtgtt tactaaacaa    720
gacacaataa ctgtacaaaa atacgactcc gcaggtacca atttagaagg cacagcagtc    780
gaaattaaaa cacttgatga acttaaaaac gctttgaaat aa                       822
```

<210> SEQ ID NO 59
<211> LENGTH: 37
<212> TYPE: DNA
<213> ORGANISM: Artificial Sequence
<220> FEATURE:
<223> OTHER INFORMATION: Oligonucleotide Primer

<400> SEQUENCE: 59

```
ttggatccgg tcaccccatg gctcaatata accaatg                              37
```

<210> SEQ ID NO 60
<211> LENGTH: 37
<212> TYPE: DNA
<213> ORGANISM: Artificial Sequence
<220> FEATURE:
<223> OTHER INFORMATION: Oligonucleotide Primer

<400> SEQUENCE: 60

```
ttggatccgg tcaccccatg gcttctcaaa atgtaag                              37
```

<210> SEQ ID NO 61
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 61

```
ttggatccgg tgaccaactc cgccttgaga agg                                  33
```

<210> SEQ ID NO 62
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 62

```
ttggatccgg tgacctattt gagcataaga tgc                                  33
```

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 63
ggtgaattta gttggtaagg                                          20

<210> SEQ ID NO 64
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 64
caccagtttc tttaagctgc tcctgc                                   26

<210> SEQ ID NO 65
<211> LENGTH: 2102
<212> TYPE: DNA
<213> ORGANISM: Borrelia burgdorferi
<220> FEATURE:
<221> NAME/KEY: CDS
<222> LOCATION: (1)...(2100)

<400> SEQUENCE: 65

```
atg aaa aaa atg tta cta atc ttt agt ttt ttt ctt att ttc ttg aat      48
Met Lys Lys Met Leu Leu Ile Phe Ser Phe Phe Leu Ile Phe Leu Asn
 1               5                  10                  15 gga ttt cct gtt agt gca aga gaa gtt gat agg gaa aaa tta aag gac      96
Gly Phe Pro Val Ser Ala Arg Glu Val Asp Arg Glu Lys Leu Lys Asp
             20                  25                  30 ttt gtt aat atg gat ctt gag ttt gta aat tat aaa ggc cct tat gat     144
Phe Val Asn Met Asp Leu Glu Phe Val Asn Tyr Lys Gly Pro Tyr Asp
         35                  40                  45 tct aca aat aca tat gaa caa ata gtg ggt att ggg gag ttt tta gca     192
Ser Thr Asn Thr Tyr Glu Gln Ile Val Gly Ile Gly Glu Phe Leu Ala
     50                  55                  60 aga ccg ttg acc aat tcc aat agc aac tca agt tat tat ggt aaa tat     240
Arg Pro Leu Thr Asn Ser Asn Ser Asn Ser Ser Tyr Tyr Gly Lys Tyr
 65                  70                  75                  80 ttt att aat aga ttt att gat gat caa gat aaa aaa gca agc gtt gat     288
Phe Ile Asn Arg Phe Ile Asp Asp Gln Asp Lys Lys Ala Ser Val Asp
                 85                  90                  95 gtt ttt tct att ggt agt aag tca gag ctt gac agt ata ttg aat tta     336
Val Phe Ser Ile Gly Ser Lys Ser Glu Leu Asp Ser Ile Leu Asn Leu
            100                 105                 110 aga aga att ctt aca ggg tat tta ata aag tct ttc gat tat gac agg     384
Arg Arg Ile Leu Thr Gly Tyr Leu Ile Lys Ser Phe Asp Tyr Asp Arg
        115                 120                 125 tct agt gca gaa tta att gct aag gtt att aca ata tat aat gct gtt     432
Ser Ser Ala Glu Leu Ile Ala Lys Val Ile Thr Ile Tyr Asn Ala Val
    130                 135                 140 tat aga gga gat ttg gat tat tat aaa ggg ttt tat att gag gct gct     480
Tyr Arg Gly Asp Leu Asp Tyr Tyr Lys Gly Phe Tyr Ile Glu Ala Ala
145                 150                 155                 160 tta aag tct tta agt aaa gaa aat gca ggt ctt tct agg gtt tat agt     528
Leu Lys Ser Leu Ser Lys Glu Asn Ala Gly Leu Ser Arg Val Tyr Ser
                165                 170                 175
```

```
cag tgg gct gga aag aca caa ata ttt att cct ctt aaa aag gat att    576
Gln Trp Ala Gly Lys Thr Gln Ile Phe Ile Pro Leu Lys Lys Asp Ile
            180                 185                 190 ttg tct gga aat att gag tct gac att gat att gac agt tta gtt aca    624
Leu Ser Gly Asn Ile Glu Ser Asp Ile Asp Ile Asp Ser Leu Val Thr
        195                 200                 205 gat aag gtg gtg gca gct ctt tta agt gaa aat gaa gca ggt gtt aac    672
Asp Lys Val Val Ala Ala Leu Leu Ser Glu Asn Glu Ala Gly Val Asn
    210                 215                 220 ttt gca aga gat att aca gat att caa ggc gaa act cat aag gca gat    720
Phe Ala Arg Asp Ile Thr Asp Ile Gln Gly Glu Thr His Lys Ala Asp
225                 230                 235                 240 caa gat aaa att gat att gaa tta gac aat att cat gaa agt gat tcc    768
Gln Asp Lys Ile Asp Ile Glu Leu Asp Asn Ile His Glu Ser Asp Ser
                245                 250                 255 aat ata aca gaa act att gaa aat tta agg gat cag ctt gaa aaa gct    816
Asn Ile Thr Glu Thr Ile Glu Asn Leu Arg Asp Gln Leu Glu Lys Ala
            260                 265                 270 aca gat gaa gag cat aaa aaa gag att gaa agt cag gtt gat gct aaa    864
Thr Asp Glu Glu His Lys Lys Glu Ile Glu Ser Gln Val Asp Ala Lys
        275                 280                 285 aag aaa caa aag gaa gag cta gat aaa aag gca ata aat ctt gat aaa    912
Lys Lys Gln Lys Glu Glu Leu Asp Lys Lys Ala Ile Asn Leu Asp Lys
    290                 295                 300 gct cag caa aaa tta gat tct gct gaa gat aat tta gat gtt caa aga    960
Ala Gln Gln Lys Leu Asp Ser Ala Glu Asp Asn Leu Asp Val Gln Arg
305                 310                 315                 320 aat act gtt aga gag aaa att caa gag gat att aac gaa att aac aag   1008
Asn Thr Val Arg Glu Lys Ile Gln Glu Asp Ile Asn Glu Ile Asn Lys
                325                 330                 335 gaa aag aat tta cca aag cct ggt gat gta agt tct cct aaa gtt gat   1056
Glu Lys Asn Leu Pro Lys Pro Gly Asp Val Ser Ser Pro Lys Val Asp
            340                 345                 350 aag caa cta caa ata aaa gag agc ctg gaa gat ttg cag gag cag ctt   1104
Lys Gln Leu Gln Ile Lys Glu Ser Leu Glu Asp Leu Gln Glu Gln Leu
        355                 360                 365 aaa gaa act ggt gat gaa aat cag aaa aga gaa att gaa aag caa att   1152
Lys Glu Thr Gly Asp Glu Asn Gln Lys Arg Glu Ile Glu Lys Gln Ile
    370                 375                 380 gaa atc aaa aaa agt gat gaa aag ctt tta aaa agt aaa gat gat aaa   1200
Glu Ile Lys Lys Ser Asp Glu Lys Leu Leu Lys Ser Lys Asp Asp Lys
385                 390                 395                 400 gca agt aaa gat ggt aaa gcc ttg gat ctt gat cga gaa tta aat tct   1248
Ala Ser Lys Asp Gly Lys Ala Leu Asp Leu Asp Arg Glu Leu Asn Ser
                405                 410                 415 aaa gct tct agc aaa gaa aaa agt aaa gcc aag gaa gaa gaa ata acc   1296
Lys Ala Ser Ser Lys Glu Lys Ser Lys Ala Lys Glu Glu Glu Ile Thr
            420                 425                 430 aag ggt aag tca cag aaa agc tta ggc gat ttg aat aat gat gaa aat   1344
Lys Gly Lys Ser Gln Lys Ser Leu Gly Asp Leu Asn Asn Asp Glu Asn
        435                 440                 445 ctt atg atg cca gaa gat caa aaa tta cct gag gtt aaa aaa tta gat   1392
Leu Met Met Pro Glu Asp Gln Lys Leu Pro Glu Val Lys Lys Leu Asp
    450                 455                 460 agc aaa aaa gaa ttt aaa cct gtt tct gag gtt gag aaa tta gat aag   1440
Ser Lys Lys Glu Phe Lys Pro Val Ser Glu Val Glu Lys Leu Asp Lys
465                 470                 475                 480 att ttc aag tct aat aac aat gtt gga gaa tta tca ccg tta gat aaa   1488
Ile Phe Lys Ser Asn Asn Asn Val Gly Glu Leu Ser Pro Leu Asp Lys
                485                 490                 495
```

```
tct tct tat aaa gac att gat tca aaa gag gag aca gtt aat

-continued

```
Val Phe Ser Ile Gly Ser Lys Ser Glu Leu Asp Ser Ile Leu Asn Leu
            100                 105                 110

Arg Arg Ile Leu Thr Gly Tyr Leu Ile Lys Ser Phe Asp Tyr Asp Arg
            115                 120                 125

Ser Ser Ala Glu Leu Ile Ala Lys Val Ile Thr Ile Tyr Asn Ala Val
        130                 135                 140

Tyr Arg Gly Asp Leu Asp Tyr Tyr Lys Gly Phe Tyr Ile Glu Ala Ala
145                 150                 155                 160

Leu Lys Ser Leu Ser Lys Glu Asn Ala Gly Leu Ser Arg Val Tyr Ser
                165                 170                 175

Gln Trp Ala Gly Lys Thr Gln Ile Phe Ile Pro Leu Lys Lys Asp Ile
            180                 185                 190

Leu Ser Gly Asn Ile Glu Ser Asp Ile Asp Ile Asp Ser Leu Val Thr
            195                 200                 205

Asp Lys Val Val Ala Ala Leu Leu Ser Glu Asn Glu Ala Gly Val Asn
        210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Ile His Glu Ser Asp Ser
                245                 250                 255

Asn Ile Thr Glu Thr Ile Glu Asn Leu Arg Asp Gln Leu Glu Lys Ala
            260                 265                 270

Thr Asp Glu Glu His Lys Lys Glu Ile Glu Ser Gln Val Asp Ala Lys
            275                 280                 285

Lys Lys Gln Lys Glu Glu Leu Asp Lys Lys Ala Ile Asn Leu Asp Lys
        290                 295                 300

Ala Gln Gln Lys Leu Asp Ser Ala Glu Asp Asn Leu Asp Val Gln Arg
305                 310                 315                 320

Asn Thr Val Arg Glu Lys Ile Gln Glu Asp Ile Asn Glu Ile Asn Lys
                325                 330                 335

Glu Lys Asn Leu Pro Lys Pro Gly Asp Val Ser Ser Pro Lys Val Asp
            340                 345                 350

Lys Gln Leu Gln Ile Lys Glu Ser Leu Glu Asp Leu Gln Glu Gln Leu
            355                 360                 365

Lys Glu Thr Gly Asp Glu Asn Gln Lys Arg Glu Ile Glu Lys Gln Ile
        370                 375                 380

Glu Ile Lys Lys Ser Asp Glu Lys Leu Leu Ser Lys Asp Asp Lys
385                 390                 395                 400

Ala Ser Lys Asp Gly Lys Ala Leu Asp Leu Asp Arg Glu Leu Asn Ser
                405                 410                 415

Lys Ala Ser Ser Lys Glu Lys Ser Lys Ala Lys Glu Glu Glu Ile Thr
            420                 425                 430

Lys Gly Lys Ser Gln Lys Ser Leu Gly Asp Leu Asn Asn Asp Glu Asn
            435                 440                 445

Leu Met Met Pro Glu Asp Gln Lys Leu Pro Glu Val Lys Lys Leu Asp
        450                 455                 460

Ser Lys Lys Glu Phe Lys Pro Val Ser Glu Val Lys Leu Asp Lys
465                 470                 475                 480

Ile Phe Lys Ser Asn Asn Val Gly Glu Leu Ser Pro Leu Asp Lys
                485                 490                 495

Ser Ser Tyr Lys Asp Ile Asp Ser Lys Glu Glu Thr Val Asn Lys Asp
            500                 505                 510

Val Asn Leu Gln Lys Thr Lys Pro Gln Val Lys Asp Gln Val Thr Ser
```

-continued

```
                515                 520                 525
Leu Asn Glu Asp Leu Thr Thr Met Ser Ile Asp Ser Ser Pro Val
    530                 535                 540

Phe Leu Glu Val Ile Asp Pro Ile Thr Asn Leu Gly Thr Leu Gln Leu
545                 550                 555                 560

Ile Asp Leu Asn Thr Gly Val Arg Leu Lys Glu Ser Thr Gln Gln Gly
                565                 570                 575

Ile Gln Arg Tyr Gly Ile Tyr Glu Arg Glu Lys Asp Leu Val Val Ile
            580                 585                 590

Lys Met Asp Ser Gly Lys Ala Lys Leu Gln Ile Leu Asp Lys Leu Glu
        595                 600                 605

Asn Leu Lys Val Val Ser Glu Ser Asn Phe Glu Ile Asn Lys Asn Ser
    610                 615                 620

Ser Leu Tyr Val Asp Ser Lys Met Ile Leu Val Ala Val Arg Asp Lys
625                 630                 635                 640

Asp Ser Ser Asn Asp Trp Arg Leu Ala Lys Phe Ser Pro Lys Asn Leu
                645                 650                 655

Asp Glu Phe Ile Leu Ser Glu Asn Lys Ile Met Pro Phe Thr Ser Phe
            660                 665                 670

Ser Val Arg Lys Asn Phe Ile Tyr Leu Gln Asp Glu Phe Lys Ser Leu
        675                 680                 685

Val Ile Leu Asp Val Asn Thr Leu Lys Lys Val Lys
    690                 695                 700
```

<210> SEQ ID NO 67
<211> LENGTH: 2081
<212> TYPE: DNA
<213> ORGANISM: Borrelia burgdorferi
<220> FEATURE:
<221> NAME/KEY: CDS
<222> LOCATION: (1)...(2079)

<400> SEQUENCE: 67

```
atg aaa aaa ttg tta cta atc ttt agt ttt ttt ctt att tct ttg aat       48
Met Lys Lys Leu Leu Leu Ile Phe Ser Phe Phe Leu Ile Ser Leu Asn
  1               5                  10                  15 gga ttt cct ctt aat tca agg gaa gtt gat aag gaa aaa tta aag gat       96
Gly Phe Pro Leu Asn Ser Arg Glu Val Asp Lys Glu Lys Leu Lys Asp
             20                  25                  30 ttt gtt aat atg gat ctt gag ttt gta aac tat aaa ggt cct tat gat      144
Phe Val Asn Met Asp Leu Glu Phe Val Asn Tyr Lys Gly Pro Tyr Asp
         35                  40                  45 tct aca aat aca tat gaa caa ata gta ggt att ggt gag ttt tta gca      192
Ser Thr Asn Thr Tyr Glu Gln Ile Val Gly Ile Gly Glu Phe Leu Ala
     50                  55                  60 aga cca ttg att aat tcc aat agc aac tca att tat tat ggt aaa tat      240
Arg Pro Leu Ile Asn Ser Asn Ser Asn Ser Ile Tyr Tyr Gly Lys Tyr
 65                  70                  75                  80 ttt att aat aga ttt att gat gat caa gat aaa aaa gca agc gtt gat      288
Phe Ile Asn Arg Phe Ile Asp Asp Gln Asp Lys Lys Ala Ser Val Asp
                 85                  90                  95 gtt ttt tct att ggt agt agg tca cag ctt gac agt ata ttg aat cta      336
Val Phe Ser Ile Gly Ser Arg Ser Gln Leu Asp Ser Ile Leu Asn Leu
            100                 105                 110 aga aga att ctt aca ggg tat ttg ata aag tct ttt gat tat gaa aga      384
Arg Arg Ile Leu Thr Gly Tyr Leu Ile Lys Ser Phe Asp Tyr Glu Arg
        115                 120                 125 tct agt gct gaa tta att gct aag gtt att aca ata cat aat gct gtt      432
```

```
Ser Ser Ala Glu Leu Ile Ala Lys Val Ile Thr Ile His Asn Ala Val
    130                 135                 140 tat aga ggg gat tta aat tat tat aaa gag gtt tat att gag gct gct        480
Tyr Arg Gly Asp Leu Asn Tyr Tyr Lys Glu Val Tyr Ile Glu Ala Ala
145                 150                 155                 160 tta aag tct tta act aaa gaa aat gca ggt ctt tct aga gtg tac agt        528
Leu Lys Ser Leu Thr Lys Glu Asn Ala Gly Leu Ser Arg Val Tyr Ser
                165                 170                 175 caa tgg gct gga aag aca caa ata ttt att cct ctt aaa aag aat att        576
Gln Trp Ala Gly Lys Thr Gln Ile Phe Ile Pro Leu Lys Lys Asn Ile
            180                 185                 190 tta tct gga aaa gtt gag tct gac att gat att gac agt ttg gtt aca        624
Leu Ser Gly Lys Val Glu Ser Asp Ile Asp Ile Asp Ser Leu Val Thr
        195                 200                 205 gat aag gtt gtg gca gct ctt tta agc gag aat gaa gca ggt gtt aac        672
Asp Lys Val Val Ala Ala Leu Leu Ser Glu Asn Glu Ala Gly Val Asn
    210                 215                 220 ttt gca aga gat att aca gat att caa ggc gaa act cat aaa gca gat        720
Phe Ala Arg Asp Ile Thr Asp Ile Gln Gly Glu Thr His Lys Ala Asp
225                 230                 235                 240 caa gat aaa att gat att gaa tta gat aat gtt cat aaa agt gat tcc        768
Gln Asp Lys Ile Asp Ile Glu Leu Asp Asn Val His Lys Ser Asp Ser
                245                 250                 255 aat ata aca gag act att gag aat tta aga gat cag ctt gaa aag gct        816
Asn Ile Thr Glu Thr Ile Glu Asn Leu Arg Asp Gln Leu Glu Lys Ala
            260                 265                 270 aca gat gaa gag cat aga aaa gag att gaa agt cag gtt gat gct aaa        864
Thr Asp Glu Glu His Arg Lys Glu Ile Glu Ser Gln Val Asp Ala Lys
        275                 280                 285 aag aaa caa aaa gaa gaa cta gat aaa aag gca atc gat ctt gat aaa        912
Lys Lys Gln Lys Glu Glu Leu Asp Lys Lys Ala Ile Asp Leu Asp Lys
    290                 295                 300 gcc caa caa aaa tta gat tct tct gaa gat aat tta gat att caa agg        960
Ala Gln Gln Lys Leu Asp Ser Ser Glu Asp Asn Leu Asp Ile Gln Arg
305                 310                 315                 320 gat act gtt aga gag aag att caa gag gat att gac gag att aat aaa       1008
Asp Thr Val Arg Glu Lys Ile Gln Glu Asp Ile Asp Glu Ile Asn Lys
                325                 330                 335 gaa aag aat ttg cca aaa cct ggt gat gta agt tct cct aaa gtt gat       1056
Glu Lys Asn Leu Pro Lys Pro Gly Asp Val Ser Ser Pro Lys Val Asp
            340                 345                 350 aag cag cta caa ata aaa gag agt cta gaa gac ttg cag gaa cag ctt       1104
Lys Gln Leu Gln Ile Lys Glu Ser Leu Glu Asp Leu Gln Glu Gln Leu
        355                 360                 365 aaa gaa act agc gat gaa aat caa aaa aga gaa att gaa aag caa att       1152
Lys Glu Thr Ser Asp Glu Asn Gln Lys Arg Glu Ile Glu Lys Gln Ile
    370                 375                 380 gaa atc aaa aaa agt gat gaa gaa ctt tta aaa agt aaa gat cct aaa       1200
Glu Ile Lys Lys Ser Asp Glu Glu Leu Leu Lys Ser Lys Asp Pro Lys
385                 390                 395                 400 gca tta gat ctt aat gga gat tta aat tct aaa gtt tct agt aaa gaa       1248
Ala Leu Asp Leu Asn Gly Asp Leu Asn Ser Lys Val Ser Ser Lys Glu
                405                 410                 415 aaa att aaa ggc aaa gga gaa ata gtc aaa gag gaa tca aag gca            1296
Lys Ile Lys Gly Lys Gly Glu Ile Val Lys Glu Glu Ser Lys Ala
            420                 425                 430 agt tta gct gat ttg aat aat gac gaa aat ctt atg agg ccg gaa gat       1344
Ser Leu Ala Asp Leu Asn Asn Asp Glu Asn Leu Met Arg Pro Glu Asp
        435                 440                 445 caa aaa tta tct gag gat aaa aaa tta gat agt aaa aaa aat tta aaa       1392
Gln Lys Leu Ser Glu Asp Lys Lys Leu Asp Ser Lys Lys Asn Leu Lys
    450                 455                 460 cct gtt tct gag att gag aga gta aat gaa att tcg aag tct aac aac       1440
Pro Val Ser Glu Ile Glu Arg Val Asn Glu Ile Ser Lys Ser Asn Asn
465                 470                 475                 480 aat gag att agt gaa tca tca cca tta tat aag cct tct tat agc gat       1488
Asn Glu Ile Ser Glu Ser Ser Pro Leu Tyr Lys Pro Ser Tyr Ser Asp
```

-continued

```
                485                 490                 495
atg gat tca aaa gag ggt ata gat aat aaa gat gtt aac ttg caa gaa      1536
Met Asp Ser Lys Glu Gly Ile Asp Asn Lys Asp Val Asn Leu Gln Glu
            500                 505                 510
acc aag tct caa act aaa agt caa cct act tct tta aat caa gat ttg      1584
Thr Lys Ser Gln Thr Lys Ser Gln Pro Thr Ser Leu Asn Gln Asp Leu
        515                 520                 525
act act atg tct ata gat tct agt aat cct gta ttt tta gag gtt att      1632
Thr Thr Met Ser Ile Asp Ser Ser Asn Pro Val Phe Leu Glu Val Ile
    530                 535                 540
gat cct att aca aat tta gga acg ctt caa ctt att gat ttg aat acc      1680
Asp Pro Ile Thr Asn Leu Gly Thr Leu Gln Leu Ile Asp Leu Asn Thr
545                 550                 555                 560
ggt gtt aga ctt aaa gaa agt act cag caa ggc att cag cgg tat gga      1728
Gly Val Arg Leu Lys Glu Ser Thr Gln Gln Gly Ile Gln Arg Tyr Gly
                565                 570                 575
att tat gaa cgt gaa aaa gat tta gtt gtt att aaa atg gat tca gga      1776
Ile Tyr Glu Arg Glu Lys Asp Leu Val Val Ile Lys Met Asp Ser Gly
            580                 585                 590
aaa gcc aag ctt caa ata ctt aat aaa ctt gag aat tta aaa gtg ata      1824
Lys Ala Lys Leu Gln Ile Leu Asn Lys Leu Glu Asn Leu Lys Val Ile
        595                 600                 605
tcg gag tct aat ttt gag att aat aaa aat tca tct ctt tat gtt gac      1872
Ser Glu Ser Asn Phe Glu Ile Asn Lys Asn Ser Ser Leu Tyr Val Asp
    610                 615                 620
tct aaa atg att tta gta gtt gtg aga gat agt ggt aat gtt tgg aga      1920
Ser Lys Met Ile Leu Val Val Val Arg Asp Ser Gly Asn Val Trp Arg
625                 630                 635                 640
ttg gct aaa ttt tct cct aaa aat tta aat gag ttt att ctt tca gag      1968
Leu Ala Lys Phe Ser Pro Lys Asn Leu Asn Glu Phe Ile Leu Ser Glu
                645                 650                 655
aat aaa att ttg cct ttt act agc ttt tct gtg aga aag aat ttt att      2016
Asn Lys Ile Leu Pro Phe Thr Ser Phe Ser Val Arg Lys Asn Phe Ile
            660                 665                 670
tat ttg cag gat gag ttt aaa agt ctt att act tta gat gta aat act      2064
Tyr Leu Gln Asp Glu Phe Lys Ser Leu Ile Thr Leu Asp Val Asn Thr
        675                 680                 685
tta aaa aaa gtt aag ta                                               2081
Leu Lys Lys Val Lys
    690
```

<210> SEQ ID NO 68
<211> LENGTH: 693
<212> TYPE: PRT
<213> ORGANISM: Borrelia burgdorferi

<400> SEQUENCE: 68

```
Met Lys Lys Leu Leu Ile Phe Ser Phe Phe Leu Ile Ser Leu Asn
 1               5                  10                  15

Gly Phe Pro Leu Asn Ser Arg Glu Val Asp Lys Glu Lys Leu Lys Asp
            20                  25                  30

Phe Val Asn Met Asp Leu Glu Phe Val Asn Tyr Lys Gly Pro Tyr Asp
        35                  40                  45

Ser Thr Asn Thr Tyr Glu Gln Ile Val Gly Ile Gly Glu Phe Leu Ala
    50                  55                  60

Arg Pro Leu Ile Asn Ser Asn Ser Asn Ser Ile Tyr Gly Lys Tyr
65                  70                  75                  80

Phe Ile Asn Arg Phe Ile Asp Asp Gln Asp Lys Lys Ala Ser Val Asp
                85                  90                  95

Val Phe Ser Ile Gly Ser Arg Ser Gln Leu Asp Ser Ile Leu Asn Leu
            100                 105                 110

Arg Arg Ile Leu Thr Gly Tyr Leu Ile Lys Ser Phe Asp Tyr Glu Arg
        115                 120                 125

Ser Ser Ala Glu Leu Ile Ala Lys Val Ile Thr Ile His Asn Ala Val
    130                 135                 140

Tyr Arg Gly Asp Leu Asn Tyr Tyr Lys Glu Val Tyr Ile Glu Ala Ala
145                 150                 155                 160
```

```
Leu Lys Ser Leu Thr Lys Glu Asn Ala Gly Leu Ser Arg Val Tyr Ser
                165                 170                 175
Gln Trp Ala Gly Lys Thr Gln Ile Phe Ile Pro Leu Lys Lys Asn Ile
            180                 185                 190
Leu Ser Gly Lys Val Glu Ser Asp Ile Asp Ile Asp Ser Leu Val Thr
        195                 200                 205
Asp Lys Val Val Ala Ala Leu Leu Ser Glu Asn Glu Ala Gly Val Asn
    210                 215                 220
Phe Ala Arg Asp Ile Thr Asp Ile Gln Gly Glu Thr His Lys Ala Asp
225                 230                 235                 240
Gln Asp Lys Ile Asp Ile Glu Leu Asp Asn Val His Lys Ser Asp Ser
                245                 250                 255
Asn Ile Thr Glu Thr Ile Glu Asn Leu Arg Asp Gln Leu Glu Lys Ala
            260                 265                 270
Thr Asp Glu Glu His Arg Lys Glu Ile Glu Ser Gln Val Asp Ala Lys
        275                 280                 285
Lys Lys Gln Lys Glu Glu Leu Asp Lys Lys Ala Ile Asp Leu Asp Lys
    290                 295                 300
Ala Gln Gln Lys Leu Asp Ser Ser Glu Asp Asn Leu Asp Ile Gln Arg
305                 310                 315                 320
Asp Thr Val Arg Glu Lys Ile Gln Glu Asp Ile Asp Glu Ile Asn Lys
                325                 330                 335
Glu Lys Asn Leu Pro Lys Pro Gly Asp Val Ser Ser Pro Lys Val Asp
            340                 345                 350
Lys Gln Leu Gln Ile Lys Glu Ser Leu Glu Asp Leu Gln Glu Gln Leu
        355                 360                 365
Lys Glu Thr Ser Asp Glu Asn Gln Lys Arg Glu Ile Glu Lys Gln Ile
    370                 375                 380
Glu Ile Lys Lys Ser Asp Glu Glu Leu Leu Lys Ser Lys Asp Pro Lys
385                 390                 395                 400
Ala Leu Asp Leu Asn Gly Asp Leu Asn Ser Lys Val Ser Ser Lys Glu
                405                 410                 415
Lys Ile Lys Gly Lys Glu Gly Glu Ile Val Lys Glu Glu Ser Lys Ala
            420                 425                 430
Ser Leu Ala Asp Leu Asn Asn Asp Glu Asn Leu Met Arg Pro Glu Asp
        435                 440                 445
Gln Lys Leu Ser Glu Asp Lys Lys Leu Asp Ser Lys Lys Asn Leu Lys
    450                 455                 460
Pro Val Ser Glu Ile Glu Arg Val Asn Glu Ile Ser Lys Ser Asn Asn
465                 470                 475                 480
Asn Glu Ile Ser Glu Ser Ser Pro Leu Tyr Lys Pro Ser Tyr Ser Asp
                485                 490                 495
Met Asp Ser Lys Glu Gly Ile Asp Asn Lys Asp Val Asn Leu Gln Glu
            500                 505                 510
Thr Lys Ser Gln Thr Lys Ser Gln Pro Thr Ser Leu Asn Gln Asp Leu
        515                 520                 525
Thr Thr Met Ser Ile Asp Ser Ser Asn Pro Val Phe Leu Glu Val Ile
    530                 535                 540
Asp Pro Ile Thr Asn Leu Gly Thr Leu Gln Leu Ile Asp Leu Asn Thr
545                 550                 555                 560
Gly Val Arg Leu Lys Glu Ser Thr Gln Gln Gly Ile Gln Arg Tyr Gly
                565                 570                 575
Ile Tyr Glu Arg Glu Lys Asp Leu Val Val Ile Lys Met Asp Ser Gly
```

-continued

```
                    580                 585                 590
Lys Ala Lys Leu Gln Ile Leu Asn Lys Leu Glu Asn Leu Lys Val Ile
            595                 600                 605

Ser Glu Ser Asn Phe Glu Ile Asn Lys Asn Ser Ser Leu Tyr Val Asp
        610                 615                 620

Ser Lys Met Ile Leu Val Val Val Arg Asp Ser Gly Asn Val Trp Arg
625                 630                 635                 640

Leu Ala Lys Phe Ser Pro Lys Asn Leu Asn Glu Phe Ile Leu Ser Glu
                645                 650                 655

Asn Lys Ile Leu Pro Phe Thr Ser Phe Ser Val Arg Lys Asn Phe Ile
            660                 665                 670

Tyr Leu Gln Asp Glu Phe Lys Ser Leu Ile Thr Leu Asp Val Asn Thr
        675                 680                 685

Leu Lys Lys Val Lys
        690

<210> SEQ ID NO 69
<211> LENGTH: 1991
<212> TYPE: DNA
<213> ORGANISM: Borrelia burgdorferi
<220> FEATURE:
<221> NAME/KEY: CDS
<222> LOCATION: (1)...(1989)

<400> SEQUENCE: 69 atg aaa aaa atg tta cta atc ttt agt ttt ttt ctt gtt ttt tta aat        48
Met Lys Lys Met Leu Leu Ile Phe Ser Phe Phe Leu Val Phe Leu Asn
1               5                   10                  15 gga ttt cct ctt aat gca agg gaa gtt gat aag gaa aaa tta aag gac        96
Gly Phe Pro Leu Asn Ala Arg Glu Val Asp Lys Glu Lys Leu Lys Asp
            20                  25                  30 ttt gtt aat atg gat ctt gaa ttt gtt aat tac aag ggt cct tat gat       144
Phe Val Asn Met Asp Leu Glu Phe Val Asn Tyr Lys Gly Pro Tyr Asp
        35                  40                  45 tct aca gat aca tat gaa caa ata gta ggt att ggg gag ttt tta gca       192
Ser Thr Asp Thr Tyr Glu Gln Ile Val Gly Ile Gly Glu Phe Leu Ala
    50                  55                  60 agg ccg ttg aac aat tcc aat agt aat tca agt tat tat ggt aaa tat       240
Arg Pro Leu Asn Asn Ser Asn Ser Asn Ser Ser Tyr Tyr Gly Lys Tyr
65                  70                  75                  80 ttt gtt aat aga ttt att gac gat caa gat aaa aaa gca agt gtt gat       288
Phe Val Asn Arg Phe Ile Asp Asp Gln Asp Lys Lys Ala Ser Val Asp
                85                  90                  95 att ttt tct att ggt agt aag tca gag ctt gat agt ata tta aat cta       336
Ile Phe Ser Ile Gly Ser Lys Ser Glu Leu Asp Ser Ile Leu Asn Leu
            100                 105                 110 aga aga att ctt aca ggg tat tta atg aag tct ttt gat tat gag agg       384
Arg Arg Ile Leu Thr Gly Tyr Leu Met Lys Ser Phe Asp Tyr Glu Arg
        115                 120                 125 tct agt gcg gaa tta att gct aaa gct att aca ata tat aat gct gtt       432
Ser Ser Ala Glu Leu Ile Ala Lys Ala Ile Thr Ile Tyr Asn Ala Val
    130                 135                 140 tat aga gga gat tta gat tat tac aaa gag ttt tat att gag gct tct       480
Tyr Arg Gly Asp Leu Asp Tyr Tyr Lys Glu Phe Tyr Ile Glu Ala Ser
145                 150                 155                 160 ttg aag tct ttg act aaa gaa aat gca ggt ctt tct agg gtg tac agt       528
Leu Lys Ser Leu Thr Lys Glu Asn Ala Gly Leu Ser Arg Val Tyr Ser
                165                 170                 175 caa tgg gct ggg aag aca caa ata ttt att cct ctt aaa aag aat att       576
```

```
                                                              -continued

Gln Trp Ala Gly Lys Thr Gln Ile Phe Ile Pro Leu Lys Lys Asn Ile
            180                 185                 190 tta tct gga aat gtt gag tct gac att gat att gat agt ttg gtt aca      624
Leu Ser Gly Asn Val Glu Ser Asp Ile Asp Ile Asp Ser Leu Val Thr
        195                 200                 205 gat aag gtg gtg gca gct ctt tta agt gag aat gaa tca ggt gtt aac      672
Asp Lys Val Val Ala Ala Leu Leu Ser Glu Asn Glu Ser Gly Val Asn
    210                 215                 220 ttt gca aga gat att aca gac att caa ggc gaa act cat aaa gca gat      720
Phe Ala Arg Asp Ile Thr Asp Ile Gln Gly Glu Thr His Lys Ala Asp
225                 230                 235                 240 caa gat aaa att gat att gaa tta gat aat ttt cat gaa agt gat tcc      768
Gln Asp Lys Ile Asp Ile Glu Leu Asp Asn Phe His Glu Ser Asp Ser
                245                 250                 255 aat ata aca gaa act att gag aat tta agg gat cag ctt gaa aaa gct      816
Asn Ile Thr Glu Thr Ile Glu Asn Leu Arg Asp Gln Leu Glu Lys Ala
            260                 265                 270 aca gat gaa gag cat aaa aaa gag att gaa agt cag gtt gat gct aaa      864
Thr Asp Glu Glu His Lys Lys Glu Ile Glu Ser Gln Val Asp Ala Lys
        275                 280                 285 aag aaa caa aag gaa gaa tta gat aaa aag gca att gat ctt gat aaa      912
Lys Lys Gln Lys Glu Glu Leu Asp Lys Lys Ala Ile Asp Leu Asp Lys
    290                 295                 300 gct caa caa aaa tta gat ttt gct gaa gat aat cta gat att caa agg      960
Ala Gln Gln Lys Leu Asp Phe Ala Glu Asp Asn Leu Asp Ile Gln Arg
305                 310                 315                 320 gat act gtt aga gag aag ctt caa gaa aat att aac gag act aat aag     1008
Asp Thr Val Arg Glu Lys Leu Gln Glu Asn Ile Asn Glu Thr Asn Lys
                325                 330                 335 gaa aag aat tta cca aag cct ggt gat gta agt tct cct aag gtt gat     1056
Glu Lys Asn Leu Pro Lys Pro Gly Asp Val Ser Ser Pro Lys Val Asp
            340                 345                 350 aag cag ttg cag ata aaa gag agt cta gaa gat ttg caa gag cag ctt     1104
Lys Gln Leu Gln Ile Lys Glu Ser Leu Glu Asp Leu Gln Glu Gln Leu
        355                 360                 365 aaa gaa gct agt gat gaa aat caa aaa aga gaa ata gaa aag caa att     1152
Lys Glu Ala Ser Asp Glu Asn Gln Lys Arg Glu Ile Glu Lys Gln Ile
    370                 375                 380 gaa atc aaa aaa aat gat gaa gaa ctt ttt aaa aat aaa gat cat aaa     1200
Glu Ile Lys Lys Asn Asp Glu Glu Leu Phe Lys Asn Lys Asp His Lys
385                 390                 395                 400 gca tta gat ctt aag caa gaa tta aat tct aaa gct tct agt aaa gaa     1248
Ala Leu Asp Leu Lys Gln Glu Leu Asn Ser Lys Ala Ser Ser Lys Glu
                405                 410                 415 aaa att gaa ggc gaa gaa gag gat aaa gaa tta gat agt aaa aaa aat     1296
Lys Ile Glu Gly Glu Glu Glu Asp Lys Glu Leu Asp Ser Lys Lys Asn
            420                 425                 430 tta gag cct gtt tct gag gct gat aaa gta gat aaa att tcc aag tct     1344
Leu Glu Pro Val Ser Glu Ala Asp Lys Val Asp Lys Ile Ser Lys Ser
        435                 440                 445 aac aac aat gag gtt agt aaa tta tcc ccg tta gat gag cct tct tat     1392
Asn Asn Asn Glu Val Ser Lys Leu Ser Pro Leu Asp Glu Pro Ser Tyr
    450                 455                 460 agc gac att gat tcg aaa gag ggt gta gat aac aaa gat gtt gat ttg     1440
Ser Asp Ile Asp Ser Lys Glu Gly Val Asp Asn Lys Asp Val Asp Leu
465                 470                 475                 480 caa aaa act aaa ccc caa gtt gaa agt caa cct act tcg tta aat gaa     1488
Gln Lys Thr Lys Pro Gln Val Glu Ser Gln Pro Thr Ser Leu Asn Glu
                485                 490                 495
```

-continued

```
gat ttg att gat gtg tct ata gat tcc agt aat cct gtc ttt tta gag    1536
Asp Leu Ile Asp Val Ser Ile Asp Ser Ser Asn Pro Val Phe Leu Glu
        500                 505                 510 gtt atc gat ccg att aca aat tta gga acg ctt caa ctt att gat ttg    1584
Val Ile Asp Pro Ile Thr Asn Leu Gly Thr Leu Gln Leu Ile Asp Leu
    515                 520                 525 aat acc ggt gtt aga ctt aaa gaa agt gct caa caa ggt att cag cga    1632
Asn Thr Gly Val Arg Leu Lys Glu Ser Ala Gln Gln Gly Ile Gln Arg
530                 535                 540 tat gga att tat gaa cgt gaa aaa gat ttg gtt gtt att aaa ata gat    1680
Tyr Gly Ile Tyr Glu Arg Glu Lys Asp Leu Val Val Ile Lys Ile Asp
545                 550                 555                 560 tca gga aaa gct aag ctt cag ata ctt gat aaa ctc gag aat tta aaa    1728
Ser Gly Lys Ala Lys Leu Gln Ile Leu Asp Lys Leu Glu Asn Leu Lys
                565                 570                 575 gtg ata tca gag tct aat ttt gag att aat aaa aat tca tct ctt tat    1776
Val Ile Ser Glu Ser Asn Phe Glu Ile Asn Lys Asn Ser Ser Leu Tyr
            580                 585                 590 gtt gac tct aga atg att tta gta gtt gtt aag gac gat agt aat gct    1824
Val Asp Ser Arg Met Ile Leu Val Val Val Lys Asp Asp Ser Asn Ala
        595                 600                 605 tgg aga ttg gct aaa ttt tct cct aaa aat tta gat gaa ttt att ctg    1872
Trp Arg Leu Ala Lys Phe Ser Pro Lys Asn Leu Asp Glu Phe Ile Leu
    610                 615                 620 tca gaa aat aaa att ttg cct ttt act agc ttt gct gtg aga aag aat    1920
Ser Glu Asn Lys Ile Leu Pro Phe Thr Ser Phe Ala Val Arg Lys Asn
625                 630                 635                 640 ttt att tat ttg caa gat gaa ctt aaa agc tta gtt act tta gat gta    1968
Phe Ile Tyr Leu Gln Asp Glu Leu Lys Ser Leu Val Thr Leu Asp Val
                645                 650                 655 aat act tta aaa aaa gtt aag ta                                     1991
Asn Thr Leu Lys Lys Val Lys
                660
```

<210> SEQ ID NO 70
<211> LENGTH: 663
<212> TYPE: PRT
<213> ORGANISM: Borrelia burgdorferi

<400> SEQUENCE: 70

```
Met Lys Lys Met Leu Leu Ile Phe Ser Phe Phe Leu Val Phe Leu Asn
  1               5                  10                  15

Gly Phe Pro Leu Asn Ala Arg Glu Val Asp Lys Glu Lys Leu Lys Asp
             20                  25                  30

Phe Val Asn Met Asp Leu Glu Phe Val Asn Tyr Lys Gly Pro Tyr Asp
         35                  40                  45

Ser Thr Asp Thr Tyr Glu Gln Ile Val Gly Ile Gly Glu Phe Leu Ala
     50                  55                  60

Arg Pro Leu Asn Asn Ser Asn Ser Asn Ser Ser Tyr Tyr Gly Lys Tyr
 65                  70                  75                  80

Phe Val Asn Arg Phe Ile Asp Asp Gln Asp Lys Lys Ala Ser Val Asp
                 85                  90                  95

Ile Phe Ser Ile Gly Ser Lys Ser Glu Leu Asp Ser Ile Leu Asn Leu
            100                 105                 110

Arg Arg Ile Leu Thr Gly Tyr Leu Met Lys Ser Phe Asp Tyr Glu Arg
        115                 120                 125

Ser Ser Ala Glu Leu Ile Ala Lys Ala Ile Thr Ile Tyr Asn Ala Val
    130                 135                 140
```

-continued

```
Tyr Arg Gly Asp Leu Asp Tyr Lys Glu Phe Tyr Ile Glu Ala Ser
145                 150                 155                 160

Leu Lys Ser Leu Thr Lys Glu Asn Ala Gly Leu Ser Arg Val Tyr Ser
            165                 170                 175

Gln Trp Ala Gly Lys Thr Gln Ile Phe Ile Pro Leu Lys Lys Asn Ile
            180                 185                 190

Leu Ser Gly Asn Val Glu Ser Asp Ile Asp Ile Asp Ser Leu Val Thr
            195                 200                 205

Asp Lys Val Val Ala Ala Leu Leu Ser Glu Asn Glu Ser Gly Val Asn
210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Phe His Glu Ser Asp Ser
            245                 250                 255

Asn Ile Thr Glu Thr Ile Glu Asn Leu Arg Asp Gln Leu Glu Lys Ala
            260                 265                 270

Thr Asp Glu Glu His Lys Lys Glu Ile Glu Ser Gln Val Asp Ala Lys
        275                 280                 285

Lys Lys Gln Lys Glu Glu Leu Asp Lys Lys Ala Ile Asp Leu Asp Lys
290                 295                 300

Ala Gln Gln Lys Leu Asp Phe Ala Glu Asp Asn Leu Asp Ile Gln Arg
305                 310                 315                 320

Asp Thr Val Arg Glu Lys Leu Gln Glu Asn Ile Asn Glu Thr Asn Lys
            325                 330                 335

Glu Lys Asn Leu Pro Lys Pro Gly Asp Val Ser Pro Lys Val Asp
            340                 345                 350

Lys Gln Leu Gln Ile Lys Glu Ser Leu Glu Asp Leu Gln Glu Gln Leu
        355                 360                 365

Lys Glu Ala Ser Asp Glu Asn Gln Lys Arg Glu Ile Glu Lys Gln Ile
370                 375                 380

Glu Ile Lys Lys Asn Asp Glu Glu Leu Phe Lys Asn Lys Asp His Lys
385                 390                 395                 400

Ala Leu Asp Leu Lys Gln Glu Leu Asn Ser Lys Ala Ser Ser Lys Glu
            405                 410                 415

Lys Ile Glu Gly Glu Glu Glu Asp Lys Glu Leu Asp Ser Lys Lys Asn
            420                 425                 430

Leu Glu Pro Val Ser Glu Ala Asp Lys Val Asp Lys Ile Ser Lys Ser
        435                 440                 445

Asn Asn Asn Glu Val Ser Lys Leu Ser Pro Leu Asp Glu Pro Ser Tyr
450                 455                 460

Ser Asp Ile Asp Ser Lys Glu Gly Val Asp Asn Lys Asp Val Asp Leu
465                 470                 475                 480

Gln Lys Thr Lys Pro Gln Val Glu Ser Gln Pro Thr Ser Leu Asn Glu
            485                 490                 495

Asp Leu Ile Asp Val Ser Ile Asp Ser Ser Asn Pro Val Phe Leu Glu
            500                 505                 510

Val Ile Asp Pro Ile Thr Asn Leu Gly Thr Leu Gln Leu Ile Asp Leu
            515                 520                 525

Asn Thr Gly Val Arg Leu Lys Glu Ser Ala Gln Gln Gly Ile Gln Arg
        530                 535                 540

Tyr Gly Ile Tyr Glu Arg Glu Lys Asp Leu Val Val Ile Lys Ile Asp
545                 550                 555                 560

Ser Gly Lys Ala Lys Leu Gln Ile Leu Asp Lys Leu Glu Asn Leu Lys
```

-continued

```
                565                 570                 575
Val Ile Ser Glu Ser Asn Phe Glu Ile Asn Lys Asn Ser Ser Leu Tyr
            580                 585                 590

Val Asp Ser Arg Met Ile Leu Val Val Lys Asp Asp Ser Asn Ala
        595                 600                 605

Trp Arg Leu Ala Lys Phe Ser Pro Lys Asn Leu Asp Glu Phe Ile Leu
    610                 615                 620

Ser Glu Asn Lys Ile Leu Pro Phe Thr Ser Phe Ala Val Arg Lys Asn
625                 630                 635                 640

Phe Ile Tyr Leu Gln Asp Glu Leu Lys Ser Leu Val Thr Leu Asp Val
            645                 650                 655

Asn Thr Leu Lys Lys Val Lys
            660
```

<210> SEQ ID NO 71
<211> LENGTH: 2081
<212> TYPE: DNA
<213> ORGANISM: Borrelia burgdorferi
<220> FEATURE:
<221> NAME/KEY: CDS
<222> LOCATION: (1)...(2079)

<400> SEQUENCE: 71

```
atg aaa aaa atg tta cta atc ttt agt ttt ttt ctt att tct ttg aat    48
Met Lys Lys Met Leu Leu Ile Phe Ser Phe Phe Leu Ile Ser Leu Asn
 1               5                  10                  15 gga ttt ccc ctt aat gca agg gaa gtt gat aag gaa aaa tta aag gac    96
Gly Phe Pro Leu Asn Ala Arg Glu Val Asp Lys Glu Lys Leu Lys Asp
             20                  25                  30 ttt gtt aat atg gat ctt gag ttt gta aac tat aaa ggt cct tat gat   144
Phe Val Asn Met Asp Leu Glu Phe Val Asn Tyr Lys Gly Pro Tyr Asp
         35                  40                  45 tct aca aat aca tat gaa caa ata gta ggt att ggt gag ttt tta gca   192
Ser Thr Asn Thr Tyr Glu Gln Ile Val Gly Ile Gly Glu Phe Leu Ala
     50                  55                  60 aga cca ttg att aat ttc aat agc aac tca agt tat tat ggt aaa tat   240
Arg Pro Leu Ile Asn Phe Asn Ser Asn Ser Ser Tyr Tyr Gly Lys Tyr
 65                  70                  75                  80 ttt att aat aga ttt att gac gat caa gat aaa aaa gca agc gtt gat   288
Phe Ile Asn Arg Phe Ile Asp Asp Gln Asp Lys Lys Ala Ser Val Asp
                 85                  90                  95 gtt ttt tct att agt agt aag tca cag ctt gac agt ata ttg aat tta   336
Val Phe Ser Ile Ser Ser Lys Ser Gln Leu Asp Ser Ile Leu Asn Leu
            100                 105                 110 aga aga att ctt aca ggg tat ttg ata aag tct ttt gat tat gaa aga   384
Arg Arg Ile Leu Thr Gly Tyr Leu Ile Lys Ser Phe Asp Tyr Glu Arg
        115                 120                 125 tct agt gct gaa tta att gcc aag gtt att aca ata cat aat gct gtt   432
Ser Ser Ala Glu Leu Ile Ala Lys Val Ile Thr Ile His Asn Ala Val
    130                 135                 140 tat aga ggt gat tta aat tat tat aaa gag ttt tat att gag tct gct   480
Tyr Arg Gly Asp Leu Asn Tyr Tyr Lys Glu Phe Tyr Ile Glu Ser Ala
145                 150                 155                 160 tta aag tct tta act aaa gaa aat gca ggt ctt tct aga gtg tac agt   528
Leu Lys Ser Leu Thr Lys Glu Asn Ala Gly Leu Ser Arg Val Tyr Ser
                165                 170                 175 caa tgg gct gga aag aca caa ata ttt att cct ctt aaa aag aat att   576
Gln Trp Ala Gly Lys Thr Gln Ile Phe Ile Pro Leu Lys Lys Asn Ile
            180                 185                 190
```

-continued

```
tta tct gga aaa att gag tct gac att gat att gat agt ttg gtt aca      624
Leu Ser Gly Lys Ile Glu Ser Asp Ile Asp Ile Asp Ser Leu Val Thr
        195                 200                 205 gat aag gtt gtg gca gct ctt tta agc gaa aat gaa gca ggt gtt aac      672
Asp Lys Val Val Ala Ala Leu Leu Ser Glu Asn Glu Ala Gly Val Asn
    210                 215                 220 ttt gca agg gat att aca gat att caa gga gaa act cat aaa gca gat      720
Phe Ala Arg Asp Ile Thr Asp Ile Gln Gly Glu Thr His Lys Ala Asp
225                 230                 235                 240 caa gat aaa att gat att gaa tta gat aat gtt cat gaa agt gat tcc      768
Gln Asp Lys Ile Asp Ile Glu Leu Asp Asn Val His Glu Ser Asp Ser
                245                 250                 255 aat ata aca gaa act att gag aat tta aga gat cag ctt gaa aag gct      816
Asn Ile Thr Glu Thr Ile Glu Asn Leu Arg Asp Gln Leu Glu Lys Ala
            260                 265                 270 aca gat gaa gag cat aga aaa gag att gaa agt caa gtt gat gct aaa      864
Thr Asp Glu Glu His Arg Lys Glu Ile Glu Ser Gln Val Asp Ala Lys
        275                 280                 285 aag aaa caa aaa gaa gaa cta gat aaa aag gca atc gat ctt gat aaa      912
Lys Lys Gln Lys Glu Glu Leu Asp Lys Lys Ala Ile Asp Leu Asp Lys
    290                 295                 300 gcc caa caa aaa tta gat ttt tct gaa gat aat tta gat att caa agg      960
Ala Gln Gln Lys Leu Asp Phe Ser Glu Asp Asn Leu Asp Ile Gln Arg
305                 310                 315                 320 gat act gtt aga gag aag att caa gag gat att aac gag att aat aag     1008
Asp Thr Val Arg Glu Lys Ile Gln Glu Asp Ile Asn Glu Ile Asn Lys
                325                 330                 335 gaa aag aat tta cca aaa cct ggt gat gta agt tct cct aaa gtt gat     1056
Glu Lys Asn Leu Pro Lys Pro Gly Asp Val Ser Ser Pro Lys Val Asp
            340                 345                 350 aag cag cta caa ata aaa gag agt cta gaa gac ttg cag gag cag ctt     1104
Lys Gln Leu Gln Ile Lys Glu Ser Leu Glu Asp Leu Gln Glu Gln Leu
        355                 360                 365 aaa gaa act agc gat gaa aat caa aaa aga gaa att gaa aag caa att     1152
Lys Glu Thr Ser Asp Glu Asn Gln Lys Arg Glu Ile Glu Lys Gln Ile
    370                 375                 380 gaa atc aaa aaa agt gat gaa gaa ctt tta aaa agc aaa gat cct aaa     1200
Glu Ile Lys Lys Ser Asp Glu Glu Leu Leu Lys Ser Lys Asp Pro Lys
385                 390                 395                 400 gca tta gat ctt aat cga gat tta aat tct aaa gct tct agt aaa gaa     1248
Ala Leu Asp Leu Asn Arg Asp Leu Asn Ser Lys Ala Ser Ser Lys Glu
                405                 410                 415 aaa att aaa ggc aaa gaa aaa gaa ata gtc aaa gag aaa tca aag gta     1296
Lys Ile Lys Gly Lys Glu Lys Glu Ile Val Lys Glu Lys Ser Lys Val
            420                 425                 430 agt tta ggt gat ttg gat aat gac gaa acc ctt atg acg ccg gaa gat     1344
Ser Leu Gly Asp Leu Asp Asn Asp Glu Thr Leu Met Thr Pro Glu Asp
        435                 440                 445 caa aaa tta tct gag gat aaa aaa tta gat agt aaa aaa aat tta aaa     1392
Gln Lys Leu Ser Glu Asp Lys Lys Leu Asp Ser Lys Lys Asn Leu Lys
    450                 455                 460 cct gtt tct gag att gag aga gta aat gaa att tca aag tct aac aac     1440
Pro Val Ser Glu Ile Glu Arg Val Asn Glu Ile Ser Lys Ser Asn Asn
465                 470                 475                 480 aat gag gtt agc aaa tca tca cca tta gat aag cct tct tat agt gat     1488
Asn Glu Val Ser Lys Ser Ser Pro Leu Asp Lys Pro Ser Tyr Ser Asp
                485                 490                 495 atc gat tca aaa gag gtt gta gat aat aaa gat gtt aat ttg caa gaa     1536
Ile Asp Ser Lys Glu Val Val Asp Asn Lys Asp Val Asn Leu Gln Glu
            500                 505                 510
```

```
acc aag cct caa gct aaa agt caa tct act tct tta aat caa gat ttg    1584
Thr Lys Pro Gln Ala Lys Ser Gln Ser Thr Ser Leu Asn Gln Asp Leu
    515                 520                 525 att act atg tct ata gat tct agt aat cct gta ttt tta gag gtt att    1632
Ile Thr Met Ser Ile Asp Ser Ser Asn Pro Val Phe Leu Glu Val Ile
530                 535                 540 gat cct att aca aat tta gga atg ctt caa ctt att gat tta aat act    1680
Asp Pro Ile Thr Asn Leu Gly Met Leu Gln Leu Ile Asp Leu Asn Thr
545                 550                 555                 560 ggt gtt aga ctt aaa gaa agc act cag caa ggc att cag cgt tat gga    1728
Gly Val Arg Leu Lys Glu Ser Thr Gln Gln Gly Ile Gln Arg Tyr Gly
                565                 570                 575 att tat gaa cgt gaa aaa gat tta gtt gtt att aaa atg gat tca gga    1776
Ile Tyr Glu Arg Glu Lys Asp Leu Val Val Ile Lys Met Asp Ser Gly
            580                 585                 590 aaa gct aag ctt caa ata ctt aat aaa ctt gag aat tta aaa gtg ata    1824
Lys Ala Lys Leu Gln Ile Leu Asn Lys Leu Glu Asn Leu Lys Val Ile
        595                 600                 605 tca gag tct aat ttt gag att aat aaa aat tca tct ctt tat gtt gac    1872
Ser Glu Ser Asn Phe Glu Ile Asn Lys Asn Ser Ser Leu Tyr Val Asp
    610                 615                 620 tct aaa atg att tta gta gct gtg aaa gat agt ggt aat gtt tgg aga    1920
Ser Lys Met Ile Leu Val Ala Val Lys Asp Ser Gly Asn Val Trp Arg
625                 630                 635                 640 ttg gct aaa ttt tct cct aaa aat tta gat gag ttt att ctt tca gag    1968
Leu Ala Lys Phe Ser Pro Lys Asn Leu Asp Glu Phe Ile Leu Ser Glu
                645                 650                 655 aat aaa att ttg cct ttt act agc ttt tct gtg aga aag aat ttt att    2016
Asn Lys Ile Leu Pro Phe Thr Ser Phe Ser Val Arg Lys Asn Phe Ile
            660                 665                 670 tat ttg caa gat gag ttt aaa agt ctt att act tta gat gta aat act    2064
Tyr Leu Gln Asp Glu Phe Lys Ser Leu Ile Thr Leu Asp Val Asn Thr
        675                 680                 685 tta aaa aaa gtt aag ta                                              2081
Leu Lys Lys Val Lys
    690

<210> SEQ ID NO 72
<211> LENGTH: 693
<212> TYPE: PRT
<213> ORGANISM: Borrelia burgdorferi

<400> SEQUENCE: 72

Met Lys Lys Met Leu Leu Ile Phe Ser Phe Phe Leu Ile Ser Leu Asn
1               5                   10                  15

Gly Phe Pro Leu Asn Ala Arg Glu Val Asp Lys Glu Lys Leu Lys Asp
            20                  25                  30

Phe Val Asn Met Asp Leu Glu Phe Val Asn Tyr Lys Gly Pro Tyr Asp
        35                  40                  45

Ser Thr Asn Thr Tyr Glu Gln Ile Val Gly Ile Gly Glu Phe Leu Ala
    50                  55                  60

Arg Pro Leu Ile Asn Phe Asn Ser Asn Ser Tyr Tyr Gly Lys Tyr
65                  70                  75                  80

Phe Ile Asn Arg Phe Ile Asp Asp Gln Asp Lys Lys Ala Ser Val Asp
                85                  90                  95

Val Phe Ser Ile Ser Ser Lys Ser Gln Leu Asp Ser Ile Leu Asn Leu
            100                 105                 110

Arg Arg Ile Leu Thr Gly Tyr Leu Ile Lys Ser Phe Asp Tyr Glu Arg
```

```
                  115                 120                 125
Ser Ser Ala Glu Leu Ile Ala Lys Val Ile Thr Ile His Asn Ala Val
    130                 135                 140

Tyr Arg Gly Asp Leu Asn Tyr Tyr Lys Glu Phe Tyr Ile Glu Ser Ala
145                 150                 155                 160

Leu Lys Ser Leu Thr Lys Glu Asn Ala Gly Leu Ser Arg Val Tyr Ser
                165                 170                 175

Gln Trp Ala Gly Lys Thr Gln Ile Phe Ile Pro Leu Lys Lys Asn Ile
            180                 185                 190

Leu Ser Gly Lys Ile Glu Ser Asp Ile Asp Ile Asp Ser Leu Val Thr
        195                 200                 205

Asp Lys Val Val Ala Ala Leu Leu Ser Glu Asn Glu Ala Gly Val Asn
    210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Val His Glu Ser Asp Ser
                245                 250                 255

Asn Ile Thr Glu Thr Ile Glu Asn Leu Arg Asp Gln Leu Glu Lys Ala
            260                 265                 270

Thr Asp Glu Glu His Arg Lys Glu Ile Glu Ser Gln Val Asp Ala Lys
        275                 280                 285

Lys Lys Gln Lys Glu Glu Leu Asp Lys Lys Ala Ile Asp Leu Asp Lys
    290                 295                 300

Ala Gln Gln Lys Leu Asp Phe Ser Glu Asp Asn Leu Asp Ile Gln Arg
305                 310                 315                 320

Asp Thr Val Arg Glu Lys Ile Gln Glu Asp Ile Asn Glu Ile Asn Lys
                325                 330                 335

Glu Lys Asn Leu Pro Lys Pro Gly Asp Val Ser Ser Pro Lys Val Asp
            340                 345                 350

Lys Gln Leu Gln Ile Lys Glu Ser Leu Glu Asp Leu Gln Glu Gln Leu
        355                 360                 365

Lys Glu Thr Ser Asp Glu Asn Gln Lys Arg Glu Ile Glu Lys Gln Ile
    370                 375                 380

Glu Ile Lys Lys Ser Asp Glu Glu Leu Leu Lys Ser Lys Asp Pro Lys
385                 390                 395                 400

Ala Leu Asp Leu Asn Arg Asp Leu Asn Ser Lys Ala Ser Ser Lys Glu
                405                 410                 415

Lys Ile Lys Gly Lys Glu Lys Glu Ile Val Lys Glu Lys Ser Lys Val
            420                 425                 430

Ser Leu Gly Asp Leu Asp Asn Asp Glu Thr Leu Met Thr Pro Glu Asp
        435                 440                 445

Gln Lys Leu Ser Glu Asp Lys Lys Leu Asp Ser Lys Lys Asn Leu Lys
    450                 455                 460

Pro Val Ser Glu Ile Glu Arg Val Asn Glu Ile Ser Lys Ser Asn Asn
465                 470                 475                 480

Asn Glu Val Ser Lys Ser Ser Pro Leu Asp Lys Pro Ser Tyr Ser Asp
                485                 490                 495

Ile Asp Ser Lys Glu Val Val Asp Asn Lys Asp Val Asn Leu Gln Glu
            500                 505                 510

Thr Lys Pro Gln Ala Lys Ser Gln Ser Thr Ser Leu Asn Gln Asp Leu
        515                 520                 525

Ile Thr Met Ser Ile Asp Ser Ser Asn Pro Val Phe Leu Glu Val Ile
    530                 535                 540
```

```
Asp Pro Ile Thr Asn Leu Gly Met Leu Gln Leu Ile Asp Leu Asn Thr
545                 550                 555                 560

Gly Val Arg Leu Lys Glu Ser Thr Gln Gln Gly Ile Gln Arg Tyr Gly
                565                 570                 575

Ile Tyr Glu Arg Glu Lys Asp Leu Val Val Ile Lys Met Asp Ser Gly
            580                 585                 590

Lys Ala Lys Leu Gln Ile Leu Asn Lys Leu Glu Asn Leu Lys Val Ile
        595                 600                 605

Ser Glu Ser Asn Phe Glu Ile Asn Lys Asn Ser Ser Leu Tyr Val Asp
    610                 615                 620

Ser Lys Met Ile Leu Val Ala Val Lys Asp Ser Gly Asn Val Trp Arg
625                 630                 635                 640

Leu Ala Lys Phe Ser Pro Lys Asn Leu Asp Glu Phe Ile Leu Ser Glu
                645                 650                 655

Asn Lys Ile Leu Pro Phe Thr Ser Phe Ser Val Arg Lys Asn Phe Ile
            660                 665                 670

Tyr Leu Gln Asp Glu Phe Lys Ser Leu Ile Thr Leu Asp Val Asn Thr
        675                 680                 685

Leu Lys Lys Val Lys
    690
```

<210> SEQ ID NO 73
<211> LENGTH: 2107
<212> TYPE: DNA
<213> ORGANISM: Borrelia burgdorferi
<220> FEATURE:
<221> NAME/KEY: CDS
<222> LOCATION: (1)...(2

```
                                                         -continued

Tyr Arg Gly Asp Leu Asp Tyr Tyr Lys Glu Phe Tyr Ile Glu Ala Ser
145                 150                 155                 160 ttg aag tct ttg act aaa gaa aat gca ggt ctt tct agg gtg tac agt      528
Leu Lys Ser Leu Thr Lys Glu Asn Ala Gly Leu Ser Arg Val Tyr Ser
                    165                 170                 175 caa tgg gct ggg aag aca caa ata ttt att cct ctt aaa aag aat att      576
Gln Trp Ala Gly Lys Thr Gln Ile Phe Ile Pro Leu Lys Lys Asn Ile
                180                 185                 190 tta tct gga aat gtt gag tct gac att gat att gat agt ttg gtt aca      624
Leu Ser Gly Asn Val Glu Ser Asp Ile Asp Ile Asp Ser Leu Val Thr
            195                 200                 205 gat aag gtg gtg gca gct ctt tta agt gag aat gaa tca ggt gtt aac      672
Asp Lys Val Val Ala Ala Leu Leu Ser Glu Asn Glu Ser Gly Val Asn
        210                 215                 220 ttt gca aga gat att aca gac att caa ggc gaa act cat aaa gca gat      720
Phe Ala Arg Asp Ile Thr Asp Ile Gln Gly Glu Thr His Lys Ala Asp
225                 230                 235                 240 caa gat aaa att gat att gaa tta gat aat att cat gaa agt gat tcc      768
Gln Asp Lys Ile Asp Ile Glu Leu Asp Asn Ile His Glu Ser Asp Ser
                245                 250                 255 aat ata aca gaa act att gag aat tta agg gat cag ctt gaa aaa gct      816
Asn Ile Thr Glu Thr Ile Glu Asn Leu Arg Asp Gln Leu Glu Lys Ala
                260                 265                 270 aca gat gaa gag cat aaa aaa gag att gaa agt cag gtt gat gct aaa      864
Thr Asp Glu Glu His Lys Lys Glu Ile Glu Ser Gln Val Asp Ala Lys
            275                 280                 285 aag aaa caa aag gaa gaa tta gat aaa aag gca att gat ctt gat aaa      912
Lys Lys Gln Lys Glu Glu Leu Asp Lys Lys Ala Ile Asp Leu Asp Lys
        290                 295                 300 gct caa caa aaa tta gat ttt gct gaa gat aat cta gat att caa agg      960
Ala Gln Gln Lys Leu Asp Phe Ala Glu Asp Asn Leu Asp Ile Gln Arg
305                 310                 315                 320 gat act gtt aga gag aag ctt caa gag aat att aac gag act aat aag     1008
Asp Thr Val Arg Glu Lys Leu Gln Glu Asn Ile Asn Glu Thr Asn Lys
                325                 330                 335 gaa aag aat tta cca aag cct ggt gat gta agt tct cct aaa gtt gat     1056
Glu Lys Asn Leu Pro Lys Pro Gly Asp Val Ser Ser Pro Lys Val Asp
                340                 345                 350 aag caa cta caa ata aaa gag agc ctg gaa gat ttg cag gag cag ctt     1104
Lys Gln Leu Gln Ile Lys Glu Ser Leu Glu Asp Leu Gln Glu Gln Leu
            355                 360                 365 aaa gaa act ggt gat gaa aat cag aaa aga gaa att gaa aag caa att     1152
Lys Glu Thr Gly Asp Glu Asn Gln Lys Arg Glu Ile Glu Lys Gln Ile
        370                 375                 380 gaa atc aaa aaa agt gat gaa aag ctt tta aaa agt aaa gat gat aaa     1200
Glu Ile Lys Lys Ser Asp Glu Lys Leu Leu Lys Ser Lys Asp Asp Lys
385                 390                 395                 400 gca agt aaa gat ggt aaa gcc ttg gat ctt gat cga gaa tta aat tct     1248
Ala Ser Lys Asp Gly Lys Ala Leu Asp Leu Asp Arg Glu Leu Asn Ser
                405                 410                 415 aaa gct tct agc aaa gaa aaa agt aaa gcc aag gaa gaa gaa ata acc     1296
Lys Ala Ser Ser Lys Glu Lys Ser Lys Ala Lys Glu Glu Glu Ile Thr
                420                 425                 430 aag ggt aag tca cag aaa agc tta ggc gat ttg aat aat gat gaa aat     1344
Lys Gly Lys Ser Gln Lys Ser Leu Gly Asp Leu Asn Asn Asp Glu Asn
            435                 440                 445 ctt atg atg cca gaa gat caa aaa tta cct gag gtt aaa aaa tta gat     1392
Leu Met Met Pro Glu Asp Gln Lys Leu Pro Glu Val Lys Lys Leu Asp
        450                 455                 460
```

-continued

| | | |
|---|---|---|
| agc aaa aaa gaa ttt aaa cct gtt tct gag gtt gag aaa tta gat aag<br>Ser Lys Lys Glu Phe Lys Pro Val Ser Glu Val Glu Lys Leu Asp Lys<br>465                     470                          475                     480 | | 1440 |
| att ttc aag tct aat aac aat gtt gga gaa tta tca ccg tta gat aaa<br>Ile Phe Lys Ser Asn Asn Asn Val Gly Glu Leu Ser Pro Leu Asp Lys<br>                         485                         490                         495 | | 1488 |
| tct tct tat aaa gac att gat tca aaa gag gag aca gtt aat aaa gat<br>Ser Ser Tyr Lys Asp Ile Asp Ser Lys Glu Glu Thr Val Asn Lys Asp<br>           500                          505                         510 | | 1536 |
| gtt aat ttg caa aag act aag cct cag gtt aaa gac caa gtt act tct<br>Val Asn Leu Gln Lys Thr Lys Pro Gln Val Lys Asp Gln Val Thr Ser<br>           515                          520                         525 | | 1584 |
| ttg aat gaa gat ttg act act atg tct ata gat tcc agt agt cct gta<br>Leu Asn Glu Asp Leu Thr Thr Met Ser Ile Asp Ser Ser Ser Pro Val<br>530                     535                          540 | | 1632 |
| ttt tta gag gtt att gat cca att aca aat tta gga act ctt caa ctt<br>Phe Leu Glu Val Ile Asp Pro Ile Thr Asn Leu Gly Thr Leu Gln Leu<br>545                     550                     555                     560 | | 1680 |
| att gat tta aat act ggt gtt agg ctt aaa gaa agc act cag caa ggc<br>Ile Asp Leu Asn Thr Gly Val Arg Leu Lys Glu Ser Thr Gln Gln Gly<br>                   565                     570                     575 | | 1728 |
| att cag cgg tat gga att tat gaa cgt gaa aaa gat ttg gtt gtt att<br>Ile Gln Arg Tyr Gly Ile Tyr Glu Arg Glu Lys Asp Leu Val Val Ile<br>           580                          585                         590 | | 1776 |
| aaa atg gat tca gga aaa gct aag ctt cag ata ctt gat aaa ctt gaa<br>Lys Met Asp Ser Gly Lys Ala Lys Leu Gln Ile Leu Asp Lys Leu Glu<br>               595                     600                     605 | | 1824 |
| aat tta aaa gtg gta tca gag tct aat ttt gag att aat aaa aat tca<br>Asn Leu Lys Val Val Ser Glu Ser Asn Phe Glu Ile Asn Lys Asn Ser<br>610                     615                     620 | | 1872 |
| tct ctt tat gtt gat tct aaa atg att tta gta gct gtt agg gat aaa<br>Ser Leu Tyr Val Asp Ser Lys Met Ile Leu Val Ala Val Arg Asp Lys<br>625                     630                     635                     640 | | 1920 |
| gat agt agt aat gat tgg aga ttg gcc aaa ttt tct cct aaa aat tta<br>Asp Ser Ser Asn Asp Trp Arg Leu Ala Lys Phe Ser Pro Lys Asn Leu<br>                         645                     650                     655 | | 1968 |
| gat gag ttt att ctt tca gag aat aaa att atg cct ttt act agc ttt<br>Asp Glu Phe Ile Leu Ser Glu Asn Lys Ile Met Pro Phe Thr Ser Phe<br>           660                          665                         670 | | 2016 |
| tct gtg aga aaa aat ttt att tat ttg caa gat gag ttt aaa agt cta<br>Ser Val Arg Lys Asn Phe Ile Tyr Leu Gln Asp Glu Phe Lys Ser Leu<br>           675                          680                         685 | | 2064 |
| gtt att tta gat gta aat act tta aaa aaa gtt aag taaagcc<br>Val Ile Leu Asp Val Asn Thr Leu Lys Lys Val Lys<br>690                     695                     700 | | 2107 |

<210> SEQ ID NO 74
<211> LENGTH: 700
<212> TYPE: PRT
<213> ORGANISM: Borrelia burgdorferi

<400> SEQUENCE: 74

Met Lys Lys Met Leu Leu Ile Phe Ser Phe Phe Leu Val Phe Leu Asn
1                    5                       10                     15

Gly Phe Pro Leu Asn Ala Arg Glu Val Asp Lys Glu Lys Leu Lys Asp
                 20                       25                       30

Phe Val Asn Met Asp Leu Glu Phe Val Asn Tyr Lys Gly Pro Tyr Asp
                     35                       40                       45

Ser Thr Asn Thr Tyr Glu Gln Ile Val Gly Ile Gly Glu Phe Leu Ala
       50                       55                       60

-continued

```
Arg Pro Leu Ile Asn Ser Asn Ser Asn Ser Ser Tyr Tyr Gly Lys Tyr
 65                  70                  75                  80

Phe Val Asn Arg Phe Ile Asp Asp Gln Asp Lys Lys Ala Ser Val Asp
                 85                  90                  95

Ile Phe Ser Ile Gly Ser Lys Ser Glu Leu Asp Ser Ile Leu Asn Leu
                100                 105                 110

Arg Arg Ile Leu Thr Gly Tyr Leu Met Lys Ser Phe Asp Tyr Glu Arg
                115                 120                 125

Ser Ser Ala Glu Leu Ile Ala Lys Ala Ile Thr Ile Tyr Asn Ala Val
            130                 135                 140

Tyr Arg Gly Asp Leu Asp Tyr Tyr Lys Glu Phe Tyr Ile Glu Ala Ser
145                 150                 155                 160

Leu Lys Ser Leu Thr Lys Glu Asn Ala Gly Leu Ser Arg Val Tyr Ser
                165                 170                 175

Gln Trp Ala Gly Lys Thr Gln Ile Phe Ile Pro Leu Lys Lys Asn Ile
            180                 185                 190

Leu Ser Gly Asn Val Glu Ser Asp Ile Asp Ile Asp Ser Leu Val Thr
            195                 200                 205

Asp Lys Val Val Ala Ala Leu Leu Ser Glu Asn Glu Ser Gly Val Asn
210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Ile His Glu Ser Asp Ser
                245                 250                 255

Asn Ile Thr Glu Thr Ile Glu Asn Leu Arg Asp Gln Leu Glu Lys Ala
                260                 265                 270

Thr Asp Glu Glu His Lys Lys Glu Ile Glu Ser Gln Val Asp Ala Lys
                275                 280                 285

Lys Lys Gln Lys Glu Glu Leu Asp Lys Lys Ala Ile Asp Leu Asp Lys
            290                 295                 300

Ala Gln Gln Lys Leu Asp Phe Ala Glu Asp Asn Leu Asp Ile Gln Arg
305                 310                 315                 320

Asp Thr Val Arg Glu Lys Leu Gln Glu Asn Ile Asn Glu Thr Asn Lys
                325                 330                 335

Glu Lys Asn Leu Pro Lys Pro Gly Asp Val Ser Ser Pro Lys Val Asp
                340                 345                 350

Lys Gln Leu Gln Ile Lys Glu Ser Leu Glu Asp Leu Gln Glu Gln Leu
            355                 360                 365

Lys Glu Thr Gly Asp Glu Asn Gln Lys Arg Glu Ile Glu Lys Gln Ile
370                 375                 380

Glu Ile Lys Lys Ser Asp Glu Lys Leu Leu Lys Ser Lys Asp Asp Lys
385                 390                 395                 400

Ala Ser Lys Asp Gly Lys Ala Leu Asp Leu Asp Arg Glu Leu Asn Ser
                405                 410                 415

Lys Ala Ser Ser Lys Glu Lys Ser Lys Ala Lys Glu Glu Glu Ile Thr
                420                 425                 430

Lys Gly Lys Ser Gln Lys Ser Leu Gly Asp Leu Asn Asn Asp Glu Asn
            435                 440                 445

Leu Met Met Pro Glu Asp Gln Lys Leu Pro Glu Val Lys Lys Leu Asp
            450                 455                 460

Ser Lys Lys Glu Phe Lys Pro Val Ser Glu Val Glu Lys Leu Asp Lys
465                 470                 475                 480
```

```
Ile Phe Lys Ser Asn Asn Asn Val Gly Glu Leu Ser Pro Leu Asp Lys
                485                 490                 495

Ser Ser Tyr Lys Asp Ile Asp Ser Lys Glu Thr Val Asn Lys Asp
            500                 505                 510

Val Asn Leu Gln Lys Thr Lys Pro Gln Val Lys Asp Gln Val Thr Ser
            515                 520                 525

Leu Asn Glu Asp Leu Thr Thr Met Ser Ile Asp Ser Ser Pro Val
530                 535                 540

Phe Leu Glu Val Ile Asp Pro Ile Thr Asn Leu Gly Thr Leu Gln Leu
545                 550                 555                 560

Ile Asp Leu Asn Thr Gly Val Arg Leu Lys Glu Ser Thr Gln Gln Gly
                565                 570                 575

Ile Gln Arg Tyr Gly Ile Tyr Glu Arg Glu Lys Asp Leu Val Val Ile
            580                 585                 590

Lys Met Asp Ser Gly Lys Ala Lys Leu Gln Ile Leu Asp Lys Leu Glu
            595                 600                 605

Asn Leu Lys Val Val Ser Glu Ser Asn Phe Glu Ile Asn Lys Asn Ser
            610                 615                 620

Ser Leu Tyr Val Asp Ser Lys Met Ile Leu Val Ala Val Arg Asp Lys
625                 630                 635                 640

Asp Ser Ser Asn Asp Trp Arg Leu Ala Lys Phe Ser Pro Lys Asn Leu
                645                 650                 655

Asp Glu Phe Ile Leu Ser Glu Asn Lys Ile Met Pro Phe Thr Ser Phe
                660                 665                 670

Ser Val Arg Lys Asn Phe Ile Tyr Leu Gln Asp Glu Phe Lys Ser Leu
            675                 680                 685

Val Ile Leu Asp Val Asn Thr Leu Lys Lys Val Lys
            690                 695                 700

<210> SEQ ID NO 75
<211> LENGTH: 2126
<212> TYPE: DNA
<213> ORGANISM: Borrelia burgdorferi
<220> FEATURE:
<221> NAME/KEY: CDS
<222> LOCATION: (1)...(2124)

<400> SEQUENCE: 75 atg aaa aaa atg tta cta atc ttt agt ttt ttt ctt att ttt ttg aat      48
Met Lys Lys Met Leu Leu Ile Phe Ser Phe Phe Leu Ile Phe Leu Asn
 1               5                  10                  15 gga ttt cct ctt aat gca agg aaa gtt gat aag gaa aaa tta aag gat      96
Gly Phe Pro Leu Asn Ala Arg Lys Val Asp Lys Glu Lys Leu Lys Asp
            20                  25                  30 ttt gtt aat atg gat ctt gag ttt gta aat tat aaa ggt cct tat gat     144
Phe Val Asn Met Asp Leu Glu Phe Val Asn Tyr Lys Gly Pro Tyr Asp
        35                  40                  45 tct aca aat acg tat gaa caa ata gtg ggt att ggg gag ttt tta gca     192
Ser Thr Asn Thr Tyr Glu Gln Ile Val Gly Ile Gly Glu Phe Leu Ala
    50                  55                  60 aga ccg ctg acc aat tcc aat agc aac tca agt tat tat ggc aaa tat     240
Arg Pro Leu Thr Asn Ser Asn Ser Asn Ser Ser Tyr Tyr Gly Lys Tyr
65                  70                  75                  80 ttt att aat aga ttt att gat gat caa gat aaa aaa gca agt gtt gat     288
Phe Ile Asn Arg Phe Ile Asp Asp Gln Asp Lys Lys Ala Ser Val Asp
                85                  90                  95 gtt ttt tct ata agc agc aaa tca gag ctt gac agt ata ttg aat tta     336
Val Phe Ser Ile Ser Ser Lys Ser Glu Leu Asp Ser Ile Leu Asn Leu
```

-continued

```
                  100                 105                 110
aga aga att ctt aca ggg tat ata ata aag tct ttc gat tat gac agg       384
Arg Arg Ile Leu Thr Gly Tyr Ile Ile Lys Ser Phe Asp Tyr Asp Arg
            115                 120                 125 tct agt gca gaa tta att gct aag gtt att aca ata tat aat gct gtt       432
Ser Ser Ala Glu Leu Ile Ala Lys Val Ile Thr Ile Tyr Asn Ala Val
        130                 135                 140 tat aga gga gat ttg gat tat tat aaa ggg ttt tat att gag cct gct       480
Tyr Arg Gly Asp Leu Asp Tyr Tyr Lys Gly Phe Tyr Ile Glu Pro Ala
145                 150                 155                 160 ttg aag tct tta act aaa gaa aac gca ggt ctt tct agg gtt tac agt       528
Leu Lys Ser Leu Thr Lys Glu Asn Ala Gly Leu Ser Arg Val Tyr Ser
                165                 170                 175 cag tgg gct gga aag act caa ata ttt att cct ctt aaa aag gat att       576
Gln Trp Ala Gly Lys Thr Gln Ile Phe Ile Pro Leu Lys Lys Asp Ile
            180                 185                 190 ttg tct gga aat att gaa tct gac att gat att gac agt ttg gtt aca       624
Leu Ser Gly Asn Ile Glu Ser Asp Ile Asp Ile Asp Ser Leu Val Thr
        195                 200                 205 gat aag gtg ata gca gct ctt tta agc gaa aat gaa gca ggc gtt aac       672
Asp Lys Val Ile Ala Ala Leu Leu Ser Glu Asn Glu Ala Gly Val Asn
210                 215                 220 ttt gca aga gat att aca gat att caa ggc gaa act cat aag gca gat       720
Phe Ala Arg Asp Ile Thr Asp Ile Gln Gly Glu Thr His Lys Ala Asp
225                 230                 235                 240 caa gat aag att gat act gaa tta gac aat atc cat gaa agc gat tct       768
Gln Asp Lys Ile Asp Thr Glu Leu Asp Asn Ile His Glu Ser Asp Ser
                245                 250                 255 aat ata aca gaa act att gaa aat tta agg gat cag ctt gaa aaa gct       816
Asn Ile Thr Glu Thr Ile Glu Asn Leu Arg Asp Gln Leu Glu Lys Ala
            260                 265                 270 aca gat gaa gag cat aaa aaa gag att gaa agt cag gtt gat gct aaa       864
Thr Asp Glu Glu His Lys Lys Glu Ile Glu Ser Gln Val Asp Ala Lys
        275                 280                 285 aag aaa gaa aag gaa gag cta gat aaa aag gca atc aat ctt gat aaa       912
Lys Lys Glu Lys Glu Glu Leu Asp Lys Lys Ala Ile Asn Leu Asp Lys
290                 295                 300 gct cag caa aaa tta gac tct gct gaa gat aat tta gat gtt caa aga       960
Ala Gln Gln Lys Leu Asp Ser Ala Glu Asp Asn Leu Asp Val Gln Arg
305                 310                 315                 320 gat act gtt aga gag aaa att caa gag gat att aat gag att aat aag      1008
Asp Thr Val Arg Glu Lys Ile Gln Glu Asp Ile Asn Glu Ile Asn Lys
                325                 330                 335 gaa aag aat ttg cca aaa cct ggt gat gta agt tct cct aaa gtt gat      1056
Glu Lys Asn Leu Pro Lys Pro Gly Asp Val Ser Ser Pro Lys Val Asp
            340                 345                 350 aag caa ctg caa ata aaa gag agt cta gaa gat ttg cag gag cag ctt      1104
Lys Gln Leu Gln Ile Lys Glu Ser Leu Glu Asp Leu Gln Glu Gln Leu
        355                 360                 365 aaa gaa gct ggt gat gaa aat cag aaa aga gaa att gag aag caa att      1152
Lys Glu Ala Gly Asp Glu Asn Gln Lys Arg Glu Ile Glu Lys Gln Ile
370                 375                 380 gaa atc aaa aaa agg gac gaa gaa ctt tta aaa agt aaa gat ggc aaa      1200
Glu Ile Lys Lys Arg Asp Glu Glu Leu Leu Lys Ser Lys Asp Gly Lys
385                 390                 395                 400 gta agt aaa gat tat gaa gca tta gat ctt gat cga gaa tta tcc aaa      1248
Val Ser Lys Asp Tyr Glu Ala Leu Asp Leu Asp Arg Glu Leu Ser Lys
                405                 410                 415 gct tct agt aaa gaa aaa agt aag gtc aag gaa gaa gaa ata act aaa      1296
```

```
                Ala Ser Ser Lys Glu Lys Ser Lys Val Lys Glu Glu Ile Thr Lys
                    420                 425                 430 ggt aaa tca cgg gca agc tta ggc gat ttg aat aat gat aaa aac ctt          1344
Gly Lys Ser Arg Ala Ser Leu Gly Asp Leu Asn Asn Asp Lys Asn Leu
        435                 440                 445 atg ttg cca gaa gat caa aaa tta cct gaa gat aaa aaa ttg gat agt          1392
Met Leu Pro Glu Asp Gln Lys Leu Pro Glu Asp Lys Lys Leu Asp Ser
450                 455                 460 aaa tta gat ggt aaa aaa gaa ttt aaa cca gtt tct gag gtt gaa aaa          1440
Lys Leu Asp Gly Lys Lys Glu Phe Lys Pro Val Ser Glu Val Glu Lys
465                 470                 475                 480 tta gat aag att tcc aag tct aat aac aat gag gtt ggc aag tta tca          1488
Leu Asp Lys Ile Ser Lys Ser Asn Asn Asn Glu Val Gly Lys Leu Ser
                485                 490                 495 cca tta gat aag cct tct tat gat gat att gat tca aaa gag gag gta          1536
Pro Leu Asp Lys Pro Ser Tyr Asp Asp Ile Asp Ser Lys Glu Glu Val
            500                 505                 510 gat aat aaa gct att aat ttg caa aag atc gac cct aaa gtt aaa gac          1584
Asp Asn Lys Ala Ile Asn Leu Gln Lys Ile Asp Pro Lys Val Lys Asp
        515                 520                 525 caa act act tct ttg aat gaa gat ttg gat aaa gat ttg act act atg          1632
Gln Thr Thr Ser Leu Asn Glu Asp Leu Asp Lys Asp Leu Thr Thr Met
530                 535                 540 tct ata gat tcc agc agt cct gta ttt cta gag gtt att gat cct att          1680
Ser Ile Asp Ser Ser Ser Pro Val Phe Leu Glu Val Ile Asp Pro Ile
545                 550                 555                 560 aca aat tta gga acc ctg cag ctt att gat tta aat act ggg gtt agg          1728
Thr Asn Leu Gly Thr Leu Gln Leu Ile Asp Leu Asn Thr Gly Val Arg
                565                 570                 575 ctt aag gaa agc act cag caa ggc att cag cgg tat gga att tat gaa          1776
Leu Lys Glu Ser Thr Gln Gln Gly Ile Gln Arg Tyr Gly Ile Tyr Glu
            580                 585                 590 cgt gaa aaa gat ttg gtt gtt att aaa atg gat tca gga aag gct aag          1824
Arg Glu Lys Asp Leu Val Val Ile Lys Met Asp Ser Gly Lys Ala Lys
        595                 600                 605 ctt caa ata ctt aat aag ctt gaa aat ttg aaa gtg gta tca gag tct          1872
Leu Gln Ile Leu Asn Lys Leu Glu Asn Leu Lys Val Val Ser Glu Ser
610                 615                 620 aat ttt gag atc aat aaa aat tca tct ctt tat gtt gac tct aaa atg          1920
Asn Phe Glu Ile Asn Lys Asn Ser Ser Leu Tyr Val Asp Ser Lys Met
625                 630                 635                 640 att ttg gca gct gtt aga gat aag gat gat agc aat gct tgg aga ttg          1968
Ile Leu Ala Ala Val Arg Asp Lys Asp Asp Ser Asn Ala Trp Arg Leu
                645                 650                 655 gct aaa ttt tct cct aaa aat ttg gat gag ttt att ctt tca gag aat          2016
Ala Lys Phe Ser Pro Lys Asn Leu Asp Glu Phe Ile Leu Ser Glu Asn
            660                 665                 670 aaa att ttg cct ttt act agc ttt tct gtg aga aaa aat ttt att tat          2064
Lys Ile Leu Pro Phe Thr Ser Phe Ser Val Arg Lys Asn Phe Ile Tyr
        675                 680                 685 ttg caa gat gag ctt aaa aat cta gtt att tta gat gta aat act tta          2112
Leu Gln Asp Glu Leu Lys Asn Leu Val Ile Leu Asp Val Asn Thr Leu
    690                 695                 700 aaa aaa gtt aag ta                                                        2126
Lys Lys Val Lys
705

<210> SEQ ID NO 76
<211> LENGTH: 708
<212> TYPE: PRT
```

<213> ORGANISM: Borrelia burgdorferi

<400> SEQUENCE: 76

| | | | | | | | | | | | | | | |
|---|---|---|---|---|---|---|---|---|---|---|---|---|---|---|
| Met | Lys | Lys | Met | Leu | Leu | Ile | Phe | Ser | Phe | Leu | Ile | Phe | Leu | Asn |
| 1 | | | | 5 | | | | | 10 | | | | | 15 |
| Gly | Phe | Pro | Leu | Asn | Ala | Arg | Lys | Val | Asp | Lys | Glu | Lys | Leu | Lys | Asp |
| | | | 20 | | | | | 25 | | | | | 30 | | |
| Phe | Val | Asn | Met | Asp | Leu | Glu | Phe | Val | Asn | Tyr | Lys | Gly | Pro | Tyr | Asp |
| | | 35 | | | | | 40 | | | | | 45 | | | |
| Ser | Thr | Asn | Thr | Tyr | Glu | Gln | Ile | Val | Gly | Ile | Gly | Glu | Phe | Leu | Ala |
| 50 | | | | | 55 | | | | | 60 | | | | | |
| Arg | Pro | Leu | Thr | Asn | Ser | Asn | Ser | Asn | Ser | Ser | Tyr | Tyr | Gly | Lys | Tyr |
| 65 | | | | | 70 | | | | | 75 | | | | | 80 |
| Phe | Ile | Asn | Arg | Phe | Ile | Asp | Asp | Gln | Asp | Lys | Lys | Ala | Ser | Val | Asp |
| | | | | 85 | | | | | 90 | | | | | 95 | |
| Val | Phe | Ser | Ile | Ser | Ser | Lys | Ser | Glu | Leu | Asp | Ser | Ile | Leu | Asn | Leu |
| | | | | 100 | | | | | 105 | | | | | 110 | |
| Arg | Arg | Ile | Leu | Thr | Gly | Tyr | Ile | Ile | Lys | Ser | Phe | Asp | Tyr | Asp | Arg |
| | | | 115 | | | | | 120 | | | | | 125 | | |
| Ser | Ser | Ala | Glu | Leu | Ile | Ala | Lys | Val | Ile | Thr | Ile | Tyr | Asn | Ala | Val |
| 130 | | | | | 135 | | | | | 140 | | | | | |
| Tyr | Arg | Gly | Asp | Leu | Asp | Tyr | Tyr | Lys | Gly | Phe | Tyr | Ile | Glu | Pro | Ala |
| 145 | | | | | 150 | | | | | 155 | | | | | 160 |
| Leu | Lys | Ser | Leu | Thr | Lys | Glu | Asn | Ala | Gly | Leu | Ser | Arg | Val | Tyr | Ser |
| | | | | 165 | | | | | 170 | | | | | 175 | |
| Gln | Trp | Ala | Gly | Lys | Thr | Gln | Ile | Phe | Ile | Pro | Leu | Lys | Lys | Asp | Ile |
| | | | 180 | | | | | 185 | | | | | 190 | | |
| Leu | Ser | Gly | Asn | Ile | Glu | Ser | Asp | Ile | Asp | Ile | Asp | Ser | Leu | Val | Thr |
| | | | | 195 | | | | | 200 | | | | | 205 | |
| Asp | Lys | Val | Ile | Ala | Ala | Leu | Leu | Ser | Glu | Asn | Glu | Ala | Gly | Val | Asn |
| 210 | | | | | 215 | | | | | 220 | | | | | |
| Phe | Ala | Arg | Asp | Ile | Thr | Asp | Ile | Gln | Gly | Glu | Thr | His | Lys | Ala | Asp |
| 225 | | | | | 230 | | | | | 235 | | | | | 240 |
| Gln | Asp | Lys | Ile | Asp | Thr | Glu | Leu | Asp | Asn | Ile | His | Glu | Ser | Asp | Ser |
| | | | | 245 | | | | | 250 | | | | | 255 | |
| Asn | Ile | Thr | Glu | Thr | Ile | Glu | Asn | Leu | Arg | Asp | Gln | Leu | Glu | Lys | Ala |
| | | | 260 | | | | | 265 | | | | | 270 | | |
| Thr | Asp | Glu | Glu | His | Lys | Lys | Glu | Ile | Glu | Ser | Gln | Val | Asp | Ala | Lys |
| | | | | 275 | | | | | 280 | | | | | 285 | |
| Lys | Lys | Glu | Lys | Glu | Glu | Leu | Asp | Lys | Lys | Ala | Ile | Asn | Leu | Asp | Lys |
| | | 290 | | | | | 295 | | | | | 300 | | | |
| Ala | Gln | Gln | Lys | Leu | Asp | Ser | Ala | Glu | Asp | Asn | Leu | Asp | Val | Gln | Arg |
| 305 | | | | | 310 | | | | | 315 | | | | | 320 |
| Asp | Thr | Val | Arg | Glu | Lys | Ile | Gln | Glu | Asp | Ile | Asn | Glu | Ile | Asn | Lys |
| | | | | 325 | | | | | 330 | | | | | 335 | |
| Glu | Lys | Asn | Leu | Pro | Lys | Pro | Gly | Asp | Val | Ser | Ser | Pro | Lys | Val | Asp |
| | | | 340 | | | | | 345 | | | | | 350 | | |
| Lys | Gln | Leu | Gln | Ile | Lys | Glu | Ser | Leu | Glu | Asp | Leu | Gln | Glu | Gln | Leu |
| | | 355 | | | | | 360 | | | | | 365 | | | |
| Lys | Glu | Ala | Gly | Asp | Glu | Asn | Gln | Lys | Arg | Glu | Ile | Glu | Lys | Gln | Ile |
| | | 370 | | | | | 375 | | | | | 380 | | | |
| Glu | Ile | Lys | Lys | Arg | Asp | Glu | Glu | Leu | Leu | Lys | Ser | Lys | Asp | Gly | Lys |
| 385 | | | | | 390 | | | | | 395 | | | | | 400 |

```
Val Ser Lys Asp Tyr Glu Ala Leu Asp Leu Asp Arg Glu Leu Ser Lys
            405                 410                 415

Ala Ser Ser Lys Glu Lys Ser Lys Val Lys Glu Glu Ile Thr Lys
        420                 425                 430

Gly Lys Ser Arg Ala Ser Leu Gly Asp Leu Asn Asn Asp Lys Asn Leu
            435                 440                 445

Met Leu Pro Glu Asp Gln Lys Leu Pro Glu Asp Lys Lys Leu Asp Ser
    450                 455                 460

Lys Leu Asp Gly Lys Lys Glu Phe Lys Pro Val Ser Glu Val Glu Lys
465                 470                 475                 480

Leu Asp Lys Ile Ser Lys Ser Asn Asn Asn Glu Val Gly Lys Leu Ser
                485                 490                 495

Pro Leu Asp Lys Pro Ser Tyr Asp Asp Ile Asp Ser Lys Glu Glu Val
            500                 505                 510

Asp Asn Lys Ala Ile Asn Leu Gln Lys Ile Asp Pro Lys Val Lys Asp
            515                 520                 525

Gln Thr Thr Ser Leu Asn Glu Asp Leu Asp Lys Asp Leu Thr Thr Met
        530                 535                 540

Ser Ile Asp Ser Ser Ser Pro Val Phe Leu Glu Val Ile Asp Pro Ile
545                 550                 555                 560

Thr Asn Leu Gly Thr Leu Gln Leu Ile Asp Leu Asn Thr Gly Val Arg
            565                 570                 575

Leu Lys Glu Ser Thr Gln Gln Gly Ile Gln Arg Tyr Gly Ile Tyr Glu
            580                 585                 590

Arg Glu Lys Asp Leu Val Val Ile Lys Met Asp Ser Gly Lys Ala Lys
        595                 600                 605

Leu Gln Ile Leu Asn Lys Leu Glu Asn Leu Lys Val Val Ser Glu Ser
    610                 615                 620

Asn Phe Glu Ile Asn Lys Asn Ser Ser Leu Tyr Val Asp Ser Lys Met
625                 630                 635                 640

Ile Leu Ala Ala Val Arg Asp Lys Asp Asp Ser Asn Ala Trp Arg Leu
            645                 650                 655

Ala Lys Phe Ser Pro Lys Asn Leu Asp Glu Phe Ile Leu Ser Glu Asn
            660                 665                 670

Lys Ile Leu Pro Phe Thr Ser Phe Ser Val Arg Lys Asn Phe Ile Tyr
            675                 680                 685

Leu Gln Asp Glu Leu Lys Asn Leu Val Ile Leu Asp Val Asn Thr Leu
    690                 695                 700

Lys Lys Val Lys
705
```

<210> SEQ ID NO 77
<211> LENGTH: 1991
<212> TYPE: DNA
<213> ORGANISM: Borrelia burgdorferi
<220> FEATURE:
<221> NAME/KEY: CDS
<222> LOCATION: (1)...(1989)

<400> SEQUENCE: 77

```
atg aaa aaa atg tta cta atc

```
ttt gtt aat atg gat ctt gaa ttt gtt aat tac aag ggt cct tat gat      144
Phe Val Asn Met Asp Leu Glu Phe Val Asn Tyr Lys Gly Pro Tyr Asp
         35                  40                  45 tct aca aat aca tat gaa caa ata gta ggt att ggg gag ttt tta gca      192
Ser Thr Asn Thr Tyr Glu Gln Ile Val Gly Ile Gly Glu Phe Leu Ala
 50                  55                  60 agg ccg ttg atc aat tcc aat agt aat tca agt tat tat ggt aaa tat      240
Arg Pro Leu Ile Asn Ser Asn Ser Asn Ser Ser Tyr Tyr Gly Lys Tyr
 65                  70                  75                  80 ttt gtt aat aga ttt att gac gat caa gat aaa aaa gca agt gtt gat      288
Phe Val Asn Arg Phe Ile Asp Asp Gln Asp Lys Lys Ala Ser Val Asp
                 85                  90                  95 att ttt tct att ggt agt aag tca gag ctt gat agt ata tta aat cta      336
Ile Phe Ser Ile Gly Ser Lys Ser Glu Leu Asp Ser Ile Leu Asn Leu
            100                 105                 110 aga aga att ctt aca ggg tat tta atg aag tct ttt gat tat gag agg      384
Arg Arg Ile Leu Thr Gly Tyr Leu Met Lys Ser Phe Asp Tyr Glu Arg
        115                 120                 125 tct agt gcg gaa tta att gct aaa gct att aca ata tat aat gct gtt      432
Ser Ser Ala Glu Leu Ile Ala Lys Ala Ile Thr Ile Tyr Asn Ala Val
130                 135                 140 tat aga gga gat tta gat tat tac aaa gag ttt tat att gag gct tct      480
Tyr Arg Gly Asp Leu Asp Tyr Tyr Lys Glu Phe Tyr Ile Glu Ala Ser
145                 150                 155                 160 ttg aag tct ttg act aaa gaa aat gca ggt ctt tct agg gtg tac agt      528
Leu Lys Ser Leu Thr Lys Glu Asn Ala Gly Leu Ser Arg Val Tyr Ser
                165                 170                 175 caa tgg gct ggg aag aca caa ata ttt att cct ctt aaa aag aat att      576
Gln Trp Ala Gly Lys Thr Gln Ile Phe Ile Pro Leu Lys Lys Asn Ile
            180                 185                 190 tta tct gga aat gtt gag tct gac att gat att gat agt ttg gtt aca      624
Leu Ser Gly Asn Val Glu Ser Asp Ile Asp Ile Asp Ser Leu Val Thr
        195                 200                 205 gat aag gtg gtg gca gct ctt tta agt gag aat gaa tca ggt gtt aac      672
Asp Lys Val Val Ala Ala Leu Leu Ser Glu Asn Glu Ser Gly Val Asn
210                 215                 220 ttt gca aga gat att aca gac att caa ggc gaa act cat aaa gca gat      720
Phe Ala Arg Asp Ile Thr Asp Ile Gln Gly Glu Thr His Lys Ala Asp
225                 230                 235                 240 caa gat aaa att gat att gaa tta gat aat ttt cat gaa agt gat tcc      768
Gln Asp Lys Ile Asp Ile Glu Leu Asp Asn Phe His Glu Ser Asp Ser
                245                 250                 255 aat ata aca gaa act att gag aat tta agg gat cag ctt gaa aaa gct      816
Asn Ile Thr Glu Thr Ile Glu Asn Leu Arg Asp Gln Leu Glu Lys Ala
            260                 265                 270 aca gat gaa gag cat aaa aaa gag att gaa agt cag gtt gat gct aaa      864
Thr Asp Glu Glu His Lys Lys Glu Ile Glu Ser Gln Val Asp Ala Lys
        275                 280                 285 aag aaa caa aag gaa gaa tta gat aaa aag gca att gat ctt gat aaa      912
Lys Lys Gln Lys Glu Glu Leu Asp Lys Lys Ala Ile Asp Leu Asp Lys
290                 295                 300 gct caa caa aaa tta gat ttt gct gaa gat aat cta gat att caa agg      960
Ala Gln Gln Lys Leu Asp Phe Ala Glu Asp Asn Leu Asp Ile Gln Arg
305                 310                 315                 320 gat act gtt aga gag aag ctt caa gaa aat att aac gag act aat aag     1008
Asp Thr Val Arg Glu Lys Leu Gln Glu Asn Ile Asn Glu Thr Asn Lys
                325                 330                 335 gaa aag aat tta cca aag cct ggt gat gta agt tct cct aag gtt gat     1056
Glu Lys Asn Leu Pro Lys Pro Gly Asp Val Ser Ser Pro Lys Val Asp
            340                 345                 350
```

```
aag cag ttg cag ata aaa gag agt cta gaa gat ttg caa gag cag ctt    1104
Lys Gln Leu Gln Ile Lys Glu Ser Leu Glu Asp Leu Gln Glu Gln Leu
            355                 360                 365 aaa gaa gct agt gat gaa aat caa aaa aga gaa ata gaa aag caa att    1152
Lys Glu Ala Ser Asp Glu Asn Gln Lys Arg Glu Ile Glu Lys Gln Ile
370                 375                 380 gaa atc aaa aaa aat gat gaa gaa ctt ttt aaa aat aaa gat cat aaa    1200
Glu Ile Lys Lys Asn Asp Glu Glu Leu Phe Lys Asn Lys Asp His Lys
385                 390                 395                 400 gca tta gat ctt aag caa gaa tta aat tct aaa gct tct agt aaa gaa    1248
Ala Leu Asp Leu Lys Gln Glu Leu Asn Ser Lys Ala Ser Ser Lys Glu
            405                 410                 415 aaa att gaa ggc gaa gaa gag gat aaa gaa tta gat agt aaa aaa aat    1296
Lys Ile Glu Gly Glu Glu Glu Asp Lys Glu Leu Asp Ser Lys Lys Asn
            420                 425                 430 tta gag cct gtt tct gag gct gat aaa gta gat aaa att tcc aag tct    1344
Leu Glu Pro Val Ser Glu Ala Asp Lys Val Asp Lys Ile Ser Lys Ser
            435                 440                 445 aac aac aat gag gtt agt aaa tta tcc ccg tta gat gag cct tct tat    1392
Asn Asn Asn Glu Val Ser Lys Leu Ser Pro Leu Asp Glu Pro Ser Tyr
450                 455                 460 agc gac att gat tcg aaa gag ggt gta gat aac aaa gat gtt gat ttg    1440
Ser Asp Ile Asp Ser Lys Glu Gly Val Asp Asn Lys Asp Val Asp Leu
465                 470                 475                 480 caa aaa act aaa ccc caa gtt gaa agt caa cct act tcg tta aat gaa    1488
Gln Lys Thr Lys Pro Gln Val Glu Ser Gln Pro Thr Ser Leu Asn Glu
            485                 490                 495 gac ttg att gat gtg tct ata gat tcc agt aat cct gtc ttt tta gag    1536
Asp Leu Ile Asp Val Ser Ile Asp Ser Ser Asn Pro Val Phe Leu Glu
            500                 505                 510 gtt atc gat ccg att aca aat tta gga acg ctt caa ctt att gat ttg    1584
Val Ile Asp Pro Ile Thr Asn Leu Gly Thr Leu Gln Leu Ile Asp Leu
            515                 520                 525 aat acc ggt gtt aga ctt aaa gaa agt gct caa caa ggt att cag cga    1632
Asn Thr Gly Val Arg Leu Lys Glu Ser Ala Gln Gln Gly Ile Gln Arg
530                 535                 540 tat gga att tat gaa cgt gaa aaa gat ttg gtt gtt att aaa ata gat    1680
Tyr Gly Ile Tyr Glu Arg Glu Lys Asp Leu Val Val Ile Lys Ile Asp
545                 550                 555                 560 tca gga aaa gct aag ctt cag ata ctt gat aaa ctc gag aat tta aaa    1728
Ser Gly Lys Ala Lys Leu Gln Ile Leu Asp Lys Leu Glu Asn Leu Lys
            565                 570                 575 gtg ata tca gag tct aat ttt gag att aat aaa aat tca tct ctt tat    1776
Val Ile Ser Glu Ser Asn Phe Glu Ile Asn Lys Asn Ser Ser Leu Tyr
            580                 585                 590 gtt gac tct aga atg att tta gta gtt gtt aag gac gat agt aat gct    1824
Val Asp Ser Arg Met Ile Leu Val Val Lys Asp Asp Ser Asn Ala
            595                 600                 605 tgg aga ttg gct aaa ttt tct cct aaa aat tta gat gaa ttt att ctg    1872
Trp Arg Leu Ala Lys Phe Ser Pro Lys Asn Leu Asp Glu Phe Ile Leu
610                 615                 620 tca gaa aat aaa att ttg cct ttt act agc ttt gct gtg aga aag aat    1920
Ser Glu Asn Lys Ile Leu Pro Phe Thr Ser Phe Ala Val Arg Lys Asn
625                 630                 635                 640 ttt att tat ttg caa gat gaa ctt aaa agc tta gtt act tta gat gta    1968
Phe Ile Tyr Leu Gln Asp Glu Leu Lys Ser Leu Val Thr Leu Asp Val
            645                 650                 655 aat act tta aaa aaa gtt aag ta                                    1991
Asn Thr Leu Lys Lys Val Lys
```

-continued

```
                660

<210> SEQ ID NO 78
<211> LENGTH: 663
<212> TYPE: PRT
<213> ORGANISM: Borrelia burgdorferi

<400> SEQUENCE: 78

Met Lys Lys Met Leu Leu Ile Phe Ser Phe Phe Leu Val Phe Leu Asn
 1               5                  10                  15

Gly Phe Pro Leu Asn Ala Arg Glu Val Asp Lys Glu Lys Leu Lys Asp
            20                  25                  30

Phe Val Asn Met Asp Leu Glu Phe Val Asn Tyr Lys Gly Pro Tyr Asp
         35                  40                  45

Ser Thr Asn Thr Tyr Glu Gln Ile Val Gly Ile Gly Glu Phe Leu Ala
     50                  55                  60

Arg Pro Leu Ile Asn Ser Asn Ser Asn Ser Ser Tyr Tyr Gly Lys Tyr
 65                  70                  75                  80

Phe Val Asn Arg Phe Ile Asp Asp Gln Asp Lys Lys Ala Ser Val Asp
                85                  90                  95

Ile Phe Ser Ile Gly Ser Lys Ser Glu Leu Asp Ser Ile Leu Asn Leu
            100                 105                 110

Arg Arg Ile Leu Thr Gly Tyr Leu Met Lys Ser Phe Asp Tyr Glu Arg
        115                 120                 125

Ser Ser Ala Glu Leu Ile Ala Lys Ala Ile Thr Ile Tyr Asn Ala Val
    130                 135                 140

Tyr Arg Gly Asp Leu Asp Tyr Tyr Lys Glu Phe Tyr Ile Glu Ala Ser
145                 150                 155                 160

Leu Lys Ser Leu Thr Lys Glu Asn Ala Gly Leu Ser Arg Val Tyr Ser
                165                 170                 175

Gln Trp Ala Gly Lys Thr Gln Ile Phe Ile Pro Leu Lys Lys Asn Ile
            180                 185                 190

Leu Ser Gly Asn Val Glu Ser Asp Ile Asp Ile Asp Ser Leu Val Thr
        195                 200                 205

Asp Lys Val Ala Ala Leu Leu Ser Glu Asn Glu Ser Gly Val Asn
    210                 215                 220

Phe Ala Arg Asp Ile Thr Asp Ile Gln Gly Thr His Lys Ala Asp
225                 230                 235                 240

Gln Asp Lys Ile Asp Ile Glu Leu Asp Asn Phe His Glu Ser Asp Ser
                245                 250                 255

Asn Ile Thr Glu Thr Ile Glu Asn Leu Arg Asp Gln Leu Glu Lys Ala
            260                 265                 270

Thr Asp Glu Glu His Lys Lys Glu Ile Glu Ser Gln Val Asp Ala Lys
        275                 280                 285

Lys Lys Gln Lys Glu Glu Leu Asp Lys Lys Ala Ile Asp Leu Asp Lys
    290                 295                 300

Ala Gln Gln Lys Leu Asp Phe Ala Glu Asp Asn Leu Asp Ile Gln Arg
305                 310                 315                 320

Asp Thr Val Arg Glu Lys Leu Gln Glu Asn Ile Asn Glu Thr Asn Lys
                325                 330                 335

Glu Lys Asn Leu Pro Lys Pro Gly Asp Val Ser Ser Pro Lys Val Asp
            340                 345                 350

Lys Gln Leu Gln Ile Lys Glu Ser Leu Glu Asp Leu Gln Glu Gln Leu
        355                 360                 365
```

```
Lys Glu Ala Ser Asp Glu Asn Gln Lys Arg Glu Ile Glu Lys Gln Ile
        370                 375                 380

Glu Ile Lys Lys Asn Asp Glu Glu Leu Phe Lys Asn Lys Asp His Lys
385                 390                 395                 400

Ala Leu Asp Leu Lys Gln Glu Leu Asn Ser Lys Ala Ser Ser Lys Glu
                405                 410                 415

Lys Ile Glu Gly Glu Glu Glu Asp Lys Glu Leu Asp Ser Lys Lys Asn
                420                 425                 430

Leu Glu Pro Val Ser Glu Ala Asp Lys Val Asp Lys Ile Ser Lys Ser
            435                 440                 445

Asn Asn Asn Glu Val Ser Lys Leu Ser Pro Leu Asp Glu Pro Ser Tyr
450                 455                 460

Ser Asp Ile Asp Ser Lys Glu Gly Val Asp Asn Lys Asp Val Asp Leu
465                 470                 475                 480

Gln Lys Thr Lys Pro Gln Val Glu Ser Gln Pro Thr Ser Leu Asn Glu
                485                 490                 495

Asp Leu Ile Asp Val Ser Ile Asp Ser Ser Asn Pro Val Phe Leu Glu
                500                 505                 510

Val Ile Asp Pro Ile Thr Asn Leu Gly Thr Leu Gln Leu Ile Asp Leu
            515                 520                 525

Asn Thr Gly Val Arg Leu Lys Glu Ser Ala Gln Gln Gly Ile Gln Arg
530                 535                 540

Tyr Gly Ile Tyr Glu Arg Glu Lys Asp Leu Val Val Ile Lys Ile Asp
545                 550                 555                 560

Ser Gly Lys Ala Lys Leu Gln Ile Leu Asp Lys Leu Glu Asn Leu Lys
                565                 570                 575

Val Ile Ser Glu Ser Asn Phe Glu Ile Asn Lys Asn Ser Ser Leu Tyr
                580                 585                 590

Val Asp Ser Arg Met Ile Leu Val Val Lys Asp Asp Ser Asn Ala
            595                 600                 605

Trp Arg Leu Ala Lys Phe Ser Pro Lys Asn Leu Asp Glu Phe Ile Leu
        610                 615                 620

Ser Glu Asn Lys Ile Leu Pro Phe Thr Ser Phe Ala Val Arg Lys Asn
625                 630                 635                 640

Phe Ile Tyr Leu Gln Asp Glu Leu Lys Ser Leu Val Thr Leu Asp Val
                645                 650                 655

Asn Thr Leu Lys Lys Val Lys
            660

<210> SEQ ID NO 79
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 79
ccggtcaccc catggctgct ttaaagtctt ta                                32

<210> SEQ ID NO 80
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 80
```

```
                                           -continued ccggtcaccc catgaatctt gataaagctc ag                              32

<210> SEQ ID NO 81
<211> LENGTH: 35
<212> TYPE: DNA
<213> ORGANISM: Artificial Sequence
<220> FEATURE:
<223> OTHER INFORMATION: Oligonucleotide Primer

<400> SEQUENCE: 81
ccggtcaccc catggatgaa aagcttttaa aaagt                           35

<210> SEQ ID NO 82
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 82
ccggtcaccc ccatggttga gaaattagat aag                             33

<210> SEQ ID NO 83
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 83
ttggatccgg tgacccttaa cttttttta ag                               32

<210> SEQ ID NO 84
<211> LENGTH: 38
<212> TYPE: DNA
<213> ORGANISM: Artificial Sequence
<220> FEATURE:
<223> OTHER INFORMATION: Oligonucleotide Primer

<400> SEQUENCE: 84
aaagtagaag ttttttgaatc ccattttcca gttttttt                       38

<210> SEQ ID NO 85
<211> LENGTH: 825
<212> TYPE: DNA
<213> ORGANISM: Artificial Sequence
<220> FEATURE:
<221> NAME/KEY: CDS
<222> LOCATION: (1)...(825)
<223> OTHER INFORMATION: Chimeric nucleic acid

<400> SEQUENCE: 85 atg aaa aaa tat tta ttg gga ata ggt cta ata tta gcc tta ata gca    48
Met Lys Lys Tyr Leu Leu Gly Ile Gly Leu Ile Leu Ala Leu Ile Ala
 1               5                  10                  15 tgt aag caa aat gtt agc agc ctt gat gaa aaa aat agc gtt tca gta    96
Cys Lys Gln Asn Val Ser Ser Leu Asp Glu Lys Asn Ser Val Ser Val
             20                  25                  30 gat tta cct ggt gga atg aca gtt ctt gta agt aaa gaa aaa gac aaa   144
Asp Leu Pro Gly Gly Met Thr Val Leu Val Ser Lys Glu Lys Asp Lys
         35                  40                  45 gac ggt aaa tac agt cta gag gca aca gta gac aag ctt gag ctt aaa   192
Asp Gly Lys Tyr Ser Leu Glu Ala Thr Val Asp Lys Leu Glu Leu Lys
     50                  55                  60 gga act tct gat aaa aac aac ggt tct gga aca ctt gaa ggt gaa aaa   240
```

```
Gly Thr Ser Asp Lys Asn Asn Gly Ser Gly Thr Leu Glu Gly Glu Lys
 65                  70                  75                  80 act gac aaa agt aaa gta aaa tta aca att gct gat gac cta agt caa      288
Thr Asp Lys Ser Lys Val Lys Leu Thr Ile Ala Asp Asp Leu Ser Gln
                 85                  90                  95 act aaa ttt gaa att ttc aaa gaa gat gcc aaa aca tta gta tca aaa      336
Thr Lys Phe Glu Ile Phe Lys Glu Asp Ala Lys Thr Leu Val Ser Lys
            100                 105                 110 aaa gta acc ctt aaa gac aag tca tca aca gaa gaa aaa ttc aac gaa      384
Lys Val Thr Leu Lys Asp Lys Ser Ser Thr Glu Glu Lys Phe Asn Glu
        115                 120                 125 aag ggt gaa aca tct gaa aaa aca ata gta aga gca aat gga acc aga      432
Lys Gly Glu Thr Ser Glu Lys Thr Ile Val Arg Ala Asn Gly Thr Arg
    130                 135                 140 ctt gaa tac aca gac ata aaa agc gat gga tcc gga aaa gct aaa gaa      480
Leu Glu Tyr Thr Asp Ile Lys Ser Asp Gly Ser Gly Lys Ala Lys Glu
145                 150                 155                 160 gtt tta aaa gac ttt act ctt gaa gga act cta gct gct gac ggc aaa      528
Val Leu Lys Asp Phe Thr Leu Glu Gly Thr Leu Ala Ala Asp Gly Lys
                165                 170                 175 aca aca ttg aaa gtt aca gaa ggc act gtt gtt tta agc aag aac att      576
Thr Thr Leu Lys Val Thr Glu Gly Thr Val Val Leu Ser Lys Asn Ile
            180                 185                 190 tta aaa tcc gga gaa ata aca gtt gca ctt gat gac tct gac act act      624
Leu Lys Ser Gly Glu Ile Thr Val Ala Leu Asp Asp Ser Asp Thr Thr
        195                 200                 205 cag gct act aaa aaa act gga aaa tgg gat tca aaa act tct act tta      672
Gln Ala Thr Lys Lys Thr Gly Lys Trp Asp Ser Lys Thr Ser Thr Leu
    210                 215                 220 aca att agt gtt aac agc aaa aaa act aca caa ctt gtg ttt act aaa      720
Thr Ile Ser Val Asn Ser Lys Lys Thr Thr Gln Leu Val Phe Thr Lys
225                 230                 235                 240 caa tac aca ata act gta aaa caa tac gac tcc gca ggt acc aat tta      768
Gln Tyr Thr Ile Thr Val Lys Gln Tyr Asp Ser Ala Gly Thr Asn Leu
                245                 250                 255 gaa ggc aca gca gtc gaa att aaa aca ctt gat gaa ctt aaa aac gct      816
Glu Gly Thr Ala Val Glu Ile Lys Thr Leu Asp Glu Leu Lys Asn Ala
            260                 265                 270 tta aaa taa                                                          825
Leu Lys *

<210> SEQ ID NO 86
<211> LENGTH: 274
<212> TYPE: PRT
<213> ORGANISM: Artificial Sequence
<220> FEATURE:
<223> OTHER INFORMATION: Chimeric Protein

<400> SEQUENCE: 86

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                20                  25                  30

Asp Leu Pro Gly Gly Met Thr Val Leu Val Ser Lys Glu Lys Asp Lys
            35                  40                  45

Asp Gly Lys Tyr Ser Leu Glu Ala Thr Val Asp Lys Leu Glu Leu Lys
        50                  55                  60

Gly Thr Ser Asp Lys Asn Asn Gly Ser Gly Thr Leu Glu Gly Glu Lys
 65                  70                  75                  80
```

```
Thr Asp Lys Ser Lys Val Lys Leu Thr Ile Ala Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Lys Thr Ser Thr Leu
    210                 215                 220

Thr Ile Ser Val Asn Ser Lys Lys Thr Thr Gln Leu Val Phe Thr Lys
225                 230                 235                 240

Gln Tyr Thr Ile Thr Val Lys Gln Tyr Asp Ser Ala Gly Thr Asn Leu
                245                 250                 255

Glu Gly Thr Ala Val Glu Ile Lys Thr Leu Asp Glu Leu Lys Asn Ala
            260                 265                 270

Leu Lys
```

<210> SEQ ID NO 87
<211> LENGTH: 35
<212> TYPE: DNA
<213> ORGANISM: Artificial Sequence
<220> FEATURE:
<223> OTHER INFORMATION: Oligonucleotide Primer

<400> SEQUENCE: 87
aaagtagaag tttttgaatt ccaagctgca gtttt                           35

<210> SEQ ID NO 88
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric nucleic acid

<400> SEQUENCE: 88

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
 1               5                  10                  15 tgc aag caa aat gtt agc agc ctt gat gaa aaa aac agc gct tca gta      96
Cys Lys Gln Asn Val Ser Ser Leu Asp Glu Lys Asn Ser Ala Ser Val
            20                  25                  30 gat ttg cct ggt gag atg aaa gtt ctt gta agt aaa gaa aaa gac aaa     144
Asp Leu Pro Gly Glu Met Lys Val Leu Val Ser Lys Glu Lys Asp Lys
        35                  40                  45 gac ggt aag tac agt cta aag gca aca gta gac aag att gag cta aaa     192
Asp Gly Lys Tyr Ser Leu Lys Ala Thr Val Asp Lys Ile Glu Leu Lys
    50                  55                  60 gga act tct gat aaa gac aat ggt tct gga gtg ctt gaa ggt aca aaa     240
```

```
Gly Thr Ser Asp Lys Asp Asn Gly Ser Gly Val Leu Glu Gly Thr Lys
 65                  70                  75                  80 gat gac aaa agt aaa gca aaa tta aca att gct gac gat cta agt aaa    288
Asp Asp Lys Ser Lys Ala Lys Leu Thr Ile Ala Asp Asp Leu Ser Lys
                 85                  90                  95 acc aca ttc gaa ctt tta aaa gaa gat ggc aaa aca tta gtg tca aga    336
Thr Thr Phe Glu Leu Leu Lys Glu Asp Gly Lys Thr Leu Val Ser Arg
            100                 105                 110 aaa gta agt tct aga gac aaa aca tca aca gat gaa atg ttc aat gaa    384
Lys Val Ser Ser Arg Asp Lys Thr Ser Thr Asp Glu Met Phe Asn Glu
        115                 120                 125 aaa ggt gaa ttg tct gca aaa acc atg aca aga gaa aat gga acc aaa    432
Lys Gly Glu Leu Ser Ala Lys Thr Met Thr Arg Glu Asn Gly Thr Lys
    130                 135                 140 ctt gaa tat aca gaa atg aaa agc gat gga acc gga aaa gct aaa gaa    480
Leu Glu Tyr Thr Glu Met Lys Ser Asp Gly Thr Gly Lys Ala Lys Glu
145                 150                 155                 160 gtt tta aaa aag ttt act ctt gaa gga aaa gta gct aat gat aaa gta    528
Val Leu Lys Lys Phe Thr Leu Glu Gly Lys Val Ala Asn Asp Lys Val
                165                 170                 175 aca ttg gaa gta aaa gaa gga acc gtt act tta agt aag gaa att gca    576
Thr Leu Glu Val Lys Glu Gly Thr Val Thr Leu Ser Lys Glu Ile Ala
            180                 185                 190 aaa tct gga gaa gta aca gtt gct ctt aat gac act aac act act cag    624
Lys Ser Gly Glu Val Thr Val Ala Leu Asn Asp Thr Asn Thr Thr Gln
        195                 200                 205 gct act aaa aaa act ggc gca tgg gat tca aaa act tct act tta aca    672
Ala Thr Lys Lys Thr Gly Ala Trp Asp Ser Lys Thr Ser Thr Leu Thr
    210                 215                 220 att agt gtt aac agc aaa aaa act aca caa ctt gtg ttt act aaa caa    720
Ile Ser Val Asn Ser Lys Lys Thr Thr Gln Leu Val Phe Thr Lys Gln
225                 230                 235                 240 tac aca ata act gta aaa caa tac gac tcc gca ggt acc aat tta gaa    768
Tyr Thr Ile Thr Val Lys Gln Tyr Asp Ser Ala Gly Thr Asn Leu Glu
                245                 250                 255 ggc aca gca gtc gaa att aaa aca ctt gat gaa ctt aaa aac gct tta    816
Gly Thr Ala Val Glu Ile Lys Thr Leu Asp Glu Leu Lys Asn Ala Leu
            260                 265                 270 aaa taa                                                             822
Lys *

<210> SEQ ID NO 89
<211> LENGTH: 273
<212> TYPE: PRT
<213> ORGANISM: Artificial Sequence
<220> FEATURE:
<223> OTHER INFORMATION: Chimeric Protein

<400> SEQUENCE: 89

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
                 20                  25                  30

Asp Leu Pro Gly Glu Met Lys Val Leu Val Ser Lys Glu Lys Asp Lys
            35                  40                  45

Asp Gly Lys Tyr Ser Leu Lys Ala Thr Val Asp Lys Ile Glu Leu Lys
        50                  55                  60

Gly Thr Ser Asp Lys Asp Asn Gly Ser Gly Val Leu Glu Gly Thr Lys
 65                  70                  75                  80
```

```
Asp Asp Lys Ser Lys Ala Lys Leu Thr Ile Ala Asp Asp Leu Ser Lys
                 85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Tyr Thr Ile Thr Val Lys Gln Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys
```

<210> SEQ ID NO 90
<211> LENGTH: 38
<212> TYPE: DNA
<213> ORGANISM: Artificial Sequence
<220> FEATURE:
<223> OTHER INFORMATION: Oligonucleotide Primer

<400> SEQUENCE: 90
aaagtggaag ttttttgaatt ccaagctgca gttttttt          38

<210> SEQ ID NO 91
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric nucleic acid

<400> SEQUENCE: 91

```
atg aaa aaa tat tta ttg gga ata ggt cta ata tta gcc tta ata gca    48
Met Lys Lys Tyr Leu Leu Gly Ile Gly Leu Ile Leu Ala Leu Ile Ala
 1               5                  10                  15 tgt aag caa aat gtt agc agc ctt gac gag aaa aac agc gtt tca gta    96
Cys Lys Gln Asn Val Ser Ser Leu Asp Glu Lys Asn Ser Val Ser Val
                20                  25                  30 gat ttg cct ggt gaa atg aaa gtt ctt gta agc aaa gaa aaa aac aaa   144
Asp Leu Pro Gly Glu Met Lys Val Leu Val Ser Lys Glu Lys Asn Lys
            35                  40                  45 gac ggc aag tac gat cta att gca aca gta gac aag ctt gag ctt aaa   192
Asp Gly Lys Tyr Asp Leu Ile Ala Thr Val Asp Lys Leu Glu Leu Lys
        50                  55                  60 gga act tct gat aaa aac aat gga tct gga gta ctt gaa ggc gta aaa   240
```

```
Gly Thr Ser Asp Lys Asn Asn Gly Ser Gly Val Leu Glu Gly Val Lys
 65                  70                  75                  80 gct gac aaa agt aaa gta aaa tta aca att tct gac gat cta ggt caa    288
Ala Asp Lys Ser Lys Val Lys Leu Thr Ile Ser Asp Asp Leu Gly Gln
                 85                  90                  95 acc aca ctt gaa gtt ttc aaa gaa gat ggc aaa aca cta gta tca aaa    336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa    384
Lys Val Thr Ser Lys Asp Lys Ser Ser Thr Glu Glu Lys Phe Asn Glu
        115                 120                 125 aaa ggt gaa gta tct gaa aaa ata ata aca aga gca gac gga acc aga    432
Lys Gly Glu Val Ser Glu Lys Ile Ile Thr Arg Ala Asp Gly Thr Arg
    130                 135                 140 ctt gaa tac aca gga att aaa agc gat gga tct gga aaa gct aaa gag    480
Leu Glu Tyr Thr Gly Ile Lys Ser Asp Gly Ser Gly Lys Ala Lys Glu
145                 150                 155                 160 gtt tta aaa ggc tat gtt ctt gaa gga act cta act gct gaa aaa aca    528
Val Leu Lys Gly Tyr Val Leu Glu Gly Thr Leu Thr Ala Glu Lys Thr
                165                 170                 175 aca ttg gtg gtt aaa gaa gga act gtt act tta agc aaa aat att tca    576
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct    624
Lys Ser Gly Glu Val Ser Val Glu Leu Asn Asp Thr Asp Ser Ser Ala
        195                 200                 205 gct act aaa aaa act gca gct tgg aat tca aaa act tcc act tta aca    672
Ala Thr Lys Lys Thr Ala Ala Trp Asn Ser Lys Thr Ser Thr Leu Thr
    210                 215                 220 att agt gtg aat agc caa aaa acc aaa aac ctt gta ttc aca aaa gaa    720
Ile Ser Val Asn Ser Gln Lys Thr Lys Asn Leu Val Phe Thr Lys Glu
225                 230                 235                 240 gac aca ata aca gta caa aaa tac gac tca gca ggc acc aat cta gaa    768
Asp Thr Ile Thr Val Gln Lys Tyr Asp Ser Ala Gly Thr Asn Leu Glu
                245                 250                 255 ggc aaa gca gtc gaa att aca aca ctt aaa gaa ctt aaa aac gct tta    816
Gly Lys Ala Val Glu Ile Thr Thr Leu Lys Glu Leu Lys Asn Ala Leu
            260                 265                 270 aaa taa                                                             822
Lys *
```

<210> SEQ ID NO 92
<211> LENGTH: 273
<212> TYPE: PRT
<213> ORGANISM: Artificial Sequence
<220> FEATURE:
<223> OTHER INFORMATION: Chimeric Protein

<400> SEQUENCE: 92

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                 20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
 65                  70                  75                  80
```

-continued

```
Ala Asp Lys Ser Lys Val Lys Leu Thr Ile Ser Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
            115                 120                 125

Lys Gly Glu Val Ser Glu Lys Ile Ile Thr Arg Ala Asp Gly Thr Arg
130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
            195                 200                 205

Ala Thr Lys Lys Thr Ala Ala Trp Asn Ser Lys Thr Ser Thr Leu Thr
210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys

<210> SEQ ID NO 93
<211> LENGTH: 35
<212> TYPE: DNA
<213> ORGANISM: Artificial Sequence
<220> FEATURE:
<223> OTHER INFORMATION: Oligonucleotide Primer

<400> SEQUENCE: 93
taaagttgaa gtgcctgcat tccaagctgc agttt                               35

<210> SEQ ID NO 94
<211> LENGTH: 819
<212> TYPE: DNA
<213> ORGANISM: Artificial Sequence
<220> FEATURE:
<221> NAME/KEY: CDS
<222> LOCATION: (1)...(819)
<223> OTHER INFORMATION: Chimeric nucleic acid

<400> SEQUENCE: 94 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
                20                  25                  30 gat ttg cct ggt gaa atg aaa gtt ctt gta agc aaa gaa aaa aac aaa     144
Asp Leu Pro Gly Glu Met Lys Val Leu Val Ser Lys Glu Lys Asn Lys
            35                  40                  45 gac ggc aag tac gat cta att gca aca gta gac aag ctt gag ctt aaa     192
Asp Gly Lys Tyr Asp Leu Ile Ala Thr Val Asp Lys Leu Glu Leu Lys
        50                  55                  60 gga act tct gat aaa aac aat gga tct gga gta ctt gaa ggc gta aaa     240
```

```
Gly Thr Ser Asp Lys Asn Asn Gly Ser Gly Val Leu Glu Gly Val Lys
 65                  70                  75                  80 gct gac aaa agt aaa gta aaa tta aca att tct gac gat cta ggt caa    288
Ala Asp Lys Ser Lys Val Lys Leu Thr Ile Ser Asp Asp Leu Gly Gln
                 85                  90                  95 acc aca ctt gaa gtt ttc aaa gaa gat ggc aaa aca cta gta tca aaa    336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa    384
Lys Val Thr Ser Lys Asp Lys Ser Ser Thr Glu Glu Lys Phe Asn Glu
        115                 120                 125 aaa ggt gaa gta tct gaa aaa ata ata aca aga gca gac gga acc aga    432
Lys Gly Glu Val Ser Glu Lys Ile Ile Thr Arg Ala Asp Gly Thr Arg
    130                 135                 140 ctt gaa tac aca gga att aaa agc gat gga tct gga aaa gct aaa gag    480
Leu Glu Tyr Thr Gly Ile Lys Ser Asp Gly Ser Gly Lys Ala Lys Glu
145                 150                 155                 160 gtt tta aaa ggc tat gtt ctt gaa gga act cta act gct gaa aaa aca    528
Val Leu Lys Gly Tyr Val Leu Glu Gly Thr Leu Thr Ala Glu Lys Thr
                165                 170                 175 aca ttg gtg gtt aaa gaa gga act gtt act tta agc aaa aat att tca    576
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct    624
Lys Ser Gly Glu Val Ser Val Glu Leu Asn Asp Thr Asp Ser Ser Ala
        195                 200                 205 gct act aaa aaa act gca gct tgg aat gca ggc act tca act tta aca    672
Ala Thr Lys Lys Thr Ala Ala Trp Asn Ala Gly Thr Ser Thr Leu Thr
    210                 215                 220 att act gta aac aac aaa aaa act aaa gcc ctt gta ttt aca aaa caa    720
Ile Thr Val Asn Asn Lys Lys Thr Lys Ala Leu Val Phe Thr Lys Gln
225                 230                 235                 240 gac aca att aca tca caa aaa tac gac tca gca gga acc aac ttg gaa    768
Asp Thr Ile Thr Ser Gln Lys Tyr Asp Ser Ala Gly Thr Asn Leu Glu
                245                 250                 255 ggc aca gca gtc gaa att aaa aca ctt gat gaa ctt aaa aac gct tta    816
Gly Thr Ala Val Glu Ile Lys Thr Leu Asp Glu Leu Lys Asn Ala Leu
            260                 265                 270 aga                                                                819
Arg

<210> SEQ ID NO 95
<211> LENGTH: 273
<212> TYPE: PRT
<213> ORGANISM: Artificial Sequence
<220> FEATURE:
<223> OTHER INFORMATION: Chimeric Protein

<400> SEQUENCE: 95

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                 20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
 65                  70                  75                  80
```

```
Ala Asp Lys Ser Lys Val Lys Leu Thr Ile Ser Asp Asp Leu Gly Gln
            85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
            115                 120                 125

Lys Gly Glu Val Ser Glu Lys Ile Ile Thr Arg Ala Asp Gly Thr Arg
        130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ala Gly Thr Ser Thr Leu Thr
    210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Arg
```

<210> SEQ ID NO 96
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 96
ccccagattt tgaaatcttg cttaaaacaa c        31

<210> SEQ ID NO 97
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric nucleic acid

<400> SEQUENCE: 97

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
 1               5                  10                  15 tgt aag caa aat gtt agc agc ctt gat gaa aaa aat agc gtt tca gta      96
Cys Lys Gln Asn Val Ser Ser Leu Asp Glu Lys Asn Ser Val Ser Val
                20                  25                  30 gat tta cct ggt gga atg aca gtt ctt gta agt aaa gaa aaa gac aaa     144
Asp Leu Pro Gly Gly Met Thr Val Leu Val Ser Lys Glu Lys Asp Lys
            35                  40                  45 gac ggt aaa tac agt cta gag gca aca gta gac aag ctt gag ctt aaa     192
Asp Gly Lys Tyr Ser Leu Glu Ala Thr Val Asp Lys Leu Glu Leu Lys
        50                  55                  60 gga act tct gat aaa aac aac ggt tct gga aca ctt gaa ggt gaa aaa     240
```

```
Gly Thr Ser Asp Lys Asn Asn Gly Ser Gly Thr Leu Glu Gly Glu Lys
 65                  70                  75                  80 act gac aaa agt aaa gta aaa tta aca att gct gat gac cta agt caa     288
Thr Asp Lys Ser Lys Val Lys Leu Thr Ile Ala Asp Asp Leu Ser Gln
                 85                  90                  95 act aaa ttt gaa att ttc aaa gaa gat gcc aaa aca tta gta tca aaa     336
Thr Lys Phe Glu Ile Phe Lys Glu Asp Ala Lys Thr Leu Val Ser Lys
            100                 105                 110 aaa gta acc ctt aaa gac aag tca tca aca gaa gaa aaa ttc aac gaa     384
Lys Val Thr Leu Lys Asp Lys Ser Ser Thr Glu Glu Lys Phe Asn Glu
        115                 120                 125 aag ggt gaa aca tct gaa aaa aca ata gta aga gca aat gga acc aga     432
Lys Gly Glu Thr Ser Glu Lys Thr Ile Val Arg Ala Asn Gly Thr Arg
    130                 135                 140 ctt gaa tac aca gac ata aaa agc gat gga tcc gga aaa gct aaa gaa     480
Leu Glu Tyr Thr Asp Ile Lys Ser Asp Gly Ser Gly Lys Ala Lys Glu
145                 150                 155                 160 gtt tta aaa gac ttt act ctt gaa gga act cta gct gct gac ggc aaa     528
Val Leu Lys Asp Phe Thr Leu Glu Gly Thr Leu Ala Ala Asp Gly Lys
                165                 170                 175 aca aca ttg aaa gtt aca gaa ggc act gtt gtt tta agc aag att tca     576
Thr Thr Leu Lys Val Thr Glu Gly Thr Val Val Leu Ser Lys Ile Ser
            180                 185                 190 aaa tct ggg gaa gtt tca gtt gaa ctt aat gac act gac agt agt gct     624
Lys Ser Gly Glu Val Ser Val Glu Leu Asn Asp Thr Asp Ser Ser Ala
        195                 200                 205 gct act aaa aaa act gca gct tgg aat tca aaa act tcc act tta aca     672
Ala Thr Lys Lys Thr Ala Ala Trp Asn Ser Lys Thr Ser Thr Leu Thr
    210                 215                 220 att agt gtg aat agc caa aaa acc aaa aac ctt gta ttc aca aaa gaa     720
Ile Ser Val Asn Ser Gln Lys Thr Lys Asn Leu Val Phe Thr Lys Glu
225                 230                 235                 240 gac aca ata aca gta caa aaa tac gac tca gca ggc acc aat cta gaa     768
Asp Thr Ile Thr Val Gln Lys Tyr Asp Ser Ala Gly Thr Asn Leu Glu
                245                 250                 255 ggc aaa gca gtc gaa att aca aca ctt aaa gaa ctt aaa aac gct tta     816
Gly Lys Ala Val Glu Ile Thr Thr Leu Lys Glu Leu Lys Asn Ala Leu
            260                 265                 270 aaa taa                                                             822
Lys *

<210> SEQ ID NO 98
<211> LENGTH: 273
<212> TYPE: PRT
<213> ORGANISM: Artificial Sequence
<220> FEATURE:
<223> OTHER INFORMATION: Chimeric Protein

<400> SEQUENCE: 98

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                 20                  25                  30

Asp Leu Pro Gly Gly Met Thr Val Leu Val Ser Lys Glu Lys Asp Lys
            35                  40                  45

Asp Gly Lys Tyr Ser Leu Glu Ala Thr Val Asp Lys Leu Glu Leu Lys
        50                  55                  60

Gly Thr Ser Asp Lys Asn Asn Gly Ser Gly Thr Leu Glu Gly Glu Lys
 65                  70                  75                  80
```

-continued

```
Thr Asp Lys Ser Lys Val Lys Leu Thr Ile Ala Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys
```

<210> SEQ ID NO 99
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 99
caagtctggt tccaatttgc tcttgttatt at                32

<210> SEQ ID NO 100
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric nucleic acid

<400> SEQUENCE: 100

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15 tgt aag caa aat gtt agc agc ctt gat gaa aaa aat agc gtt tca gta       96
Cys Lys Gln Asn Val Ser Ser Leu Asp Glu Lys Asn Ser Val Ser Val
                20                  25                  30 gat tta cct ggt gga atg aca gtt ctt gta agt aaa gaa aaa gac aaa      144
Asp Leu Pro Gly Gly Met Thr Val Leu Val Ser Lys Glu Lys Asp Lys
            35                  40                  45 gac ggt aaa tac agt cta gag gca aca gta gac aag ctt gag ctt aaa      192
Asp Gly Lys Tyr Ser Leu Glu Ala Thr Val Asp Lys Leu Glu Leu Lys
        50                  55                  60 gga act tct gat aaa aac aac ggt tct gga aca ctt gaa ggt gaa aaa      240
```

```
Gly Thr Ser Asp Lys Asn Asn Gly Ser Gly Thr Leu Glu Gly Glu Lys
 65                  70                  75                  80 act gac aaa agt aaa gta aaa tta aca att gct gat gac cta agt caa      288
Thr Asp Lys Ser Lys Val Lys Leu Thr Ile Ala Asp Asp Leu Ser Gln
                 85                  90                  95 act aaa ttt gaa att ttc aaa gaa gat gcc aaa aca tta gta tca aaa      336
Thr Lys Phe Glu Ile Phe Lys Glu Asp Ala Lys Thr Leu Val Ser Lys
            100                 105                 110 aaa gta acc ctt aaa gac aag tca tca aca gaa gaa aaa ttc aac gaa      384
Lys Val Thr Leu Lys Asp Lys Ser Ser Thr Glu Glu Lys Phe Asn Glu
        115                 120                 125 aag ggt gaa aca tct gaa aaa aca ata gta aga gca aat gga acc aga      432
Lys Gly Glu Thr Ser Glu Lys Thr Ile Val Arg Ala Asn Gly Thr Arg
    130                 135                 140 ctt gaa tac aca gac ata aaa agc gat gga tcc gga aaa gct aaa gaa      480
Leu Glu Tyr Thr Asp Ile Lys Ser Asp Gly Ser Gly Lys Ala Lys Glu
145                 150                 155                 160 gtt tta aaa gac ttt act ctt gaa gga act cta gct gct gac ggc aaa      528
Val Leu Lys Asp Phe Thr Leu Glu Gly Thr Leu Ala Ala Asp Gly Lys
                165                 170                 175 aca aca ttg aaa gtt aca gaa ggc act gtt gtt tta agc aag att tca      576
Thr Thr Leu Lys Val Thr Glu Gly Thr Val Val Leu Ser Lys Ile Ser
            180                 185                 190 aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205 gct act aaa aaa act gca gct tgg aat tca aaa act tcc act tta aca      672
Ala Thr Lys Lys Thr Ala Ala Trp Asn Ser Lys Thr Ser Thr Leu Thr
    210                 215                 220 att agt gtg aat agc caa aaa acc aaa aac ctt gta ttc aca aaa gaa      720
Ile Ser Val Asn Ser Gln Lys Thr Lys Asn Leu Val Phe Thr Lys Glu
225                 230                 235                 240 gac aca ata aca gta caa aaa tac gac tca gca ggc acc aat cta gaa      768
Asp Thr Ile Thr Val Gln Lys Tyr Asp Ser Ala Gly Thr Asn Leu Glu
                245                 250                 255 ggc aaa gca gtc gaa att aca aca ctt aaa gaa ctt aaa aac gct tta      816
Gly Lys Ala Val Glu Ile Thr Thr Leu Lys Glu Leu Lys Asn Ala Leu
            260                 265                 270 aaa taa                                                              822
Lys *

<210> SEQ ID NO 101
<211> LENGTH: 273
<212> TYPE: PRT
<213> ORGANISM: Artificial Sequence
<220> FEATURE:
<223> OTHER INFORMATION: Chimeric Protein

<400> SEQUENCE: 101

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                 20                  25                  30

Asp Leu Pro Gly Gly Met Thr Val Leu Val Ser Lys Glu Lys Asp Lys
            35                  40                  45

Asp Gly Lys Tyr Ser Leu Glu Ala Thr Val Asp Lys Leu Glu Leu Lys
        50                  55                  60

Gly Thr Ser Asp Lys Asn Asn Gly Ser Gly Thr Leu Glu Gly Glu Lys
 65                  70                  75                  80
```

-continued

```
Thr Asp Lys Ser Lys Val Lys Leu Thr Ile Ala Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys

<210> SEQ ID NO 102
<211> LENGTH: 41
<212> TYPE: DNA
<213> ORGANISM: Artificial Sequence
<220> FEATURE:
<223> OTHER INFORMATION: Oligonucleotide Primer

<400> SEQUENCE: 102
gttaaagtgc tagtactgtc attccaagct gcagtttttt t            41

<210> SEQ ID NO 103
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric nucleic acid

<400> SEQUENCE: 103 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta      96
Cys Lys Gln Asn Val Ser Ser Leu Asp Glu Lys Asn Ser Val Ser Val
                20                  25                  30 gat ttg cct ggt gaa atg aaa gtt ctt gta agc aaa gaa aaa aac aaa     144
Asp Leu Pro Gly Glu Met Lys Val Leu Val Ser Lys Glu Lys Asn Lys
            35                  40                  45 gac ggc aag tac gat cta att gca aca gta gac aag ctt gag ctt aaa     192
Asp Gly Lys Tyr Asp Leu Ile Ala Thr Val Asp Lys Leu Glu Leu Lys
        50                  55                  60 gga act tct gat aaa aac aat gga tct gga gta ctt gaa ggc gta aaa     240
```

|  |  |  |  |  |  |  |  |  |  |  |  |  |  |  |  |
|---|---|---|---|---|---|---|---|---|---|---|---|---|---|---|---|
| Gly | Thr | Ser | Asp | Lys | Asn | Asn | Gly | Ser | Gly | Val | Leu | Glu | Gly | Val | Lys |
| 65 |  |  |  |  | 70 |  |  |  |  | 75 |  |  |  |  | 80 |

| gct | gac | aaa | agt | aaa | gta | aaa | tta | aca | att | tct | gac | gat | cta | ggt | caa | 288 |
|---|---|---|---|---|---|---|---|---|---|---|---|---|---|---|---|---|
| Ala | Asp | Lys | Ser | Lys | Val | Lys | Leu | Thr | Ile | Ser | Asp | Asp | Leu | Gly | Gln |  |
|  |  |  | 85 |  |  |  |  | 90 |  |  |  |  | 95 |  |  |  |

| acc | aca | ctt | gaa | gtt | ttc | aaa | gaa | gat | ggc | aaa | aca | cta | gta | tca | aaa | 336 |
|---|---|---|---|---|---|---|---|---|---|---|---|---|---|---|---|---|
| Thr | Thr | Leu | Glu | Val | Phe | Lys | Glu | Asp | Gly | Lys | Thr | Leu | Val | Ser | Lys |  |
|  |  |  | 100 |  |  |  |  | 105 |  |  |  |  | 110 |  |  |  |

| aaa | gta | act | tcc | aaa | gac | aag | tca | tca | aca | gaa | gaa | aaa | ttc | aat | gaa | 384 |
|---|---|---|---|---|---|---|---|---|---|---|---|---|---|---|---|---|
| Lys | Val | Thr | Ser | Lys | Asp | Lys | Ser | Ser | Thr | Glu | Glu | Lys | Phe | Asn | Glu |  |
|  |  |  | 115 |  |  |  |  | 120 |  |  |  |  | 125 |  |  |  |

| aaa | ggt | gaa | gta | tct | gaa | aaa | ata | ata | aca | aga | gca | gac | gga | acc | aga | 432 |
|---|---|---|---|---|---|---|---|---|---|---|---|---|---|---|---|---|
| Lys | Gly | Glu | Val | Ser | Glu | Lys | Ile | Ile | Thr | Arg | Ala | Asp | Gly | Thr | Arg |  |
|  | 130 |  |  |  |  | 135 |  |  |  |  | 140 |  |  |  |  |  |

| ctt | gaa | tac | aca | gga | att | aaa | agc | gat | gga | tct | gga | aaa | gct | aaa | gag | 480 |
|---|---|---|---|---|---|---|---|---|---|---|---|---|---|---|---|---|
| Leu | Glu | Tyr | Thr | Gly | Ile | Lys | Ser | Asp | Gly | Ser | Gly | Lys | Ala | Lys | Glu |  |
| 145 |  |  |  |  | 150 |  |  |  |  | 155 |  |  |  |  | 160 |  |

| gtt | tta | aaa | ggc | tat | gtt | ctt | gaa | gga | act | cta | act | gct | gaa | aaa | aca | 528 |
|---|---|---|---|---|---|---|---|---|---|---|---|---|---|---|---|---|
| Val | Leu | Lys | Gly | Tyr | Val | Leu | Glu | Gly | Thr | Leu | Thr | Ala | Glu | Lys | Thr |  |
|  |  |  | 165 |  |  |  |  | 170 |  |  |  |  | 175 |  |  |  |

| aca | ttg | gtg | gtt | aaa | gaa | gga | act | gtt | act | tta | agc | aaa | aat | att | tca | 576 |
|---|---|---|---|---|---|---|---|---|---|---|---|---|---|---|---|---|
| Thr | Leu | Val | Val | Lys | Glu | Gly | Thr | Val | Thr | Leu | Ser | Lys | Asn | Ile | Ser |  |
|  |  |  | 180 |  |  |  |  | 185 |  |  |  |  | 190 |  |  |  |

| aaa | tct | ggg | gaa | gtt | tca | gtt | gaa | ctt | aat | gac | act | gac | agt | agt | gct | 624 |
|---|---|---|---|---|---|---|---|---|---|---|---|---|---|---|---|---|
| Lys | Ser | Gly | Glu | Val | Ser | Val | Glu | Leu | Asn | Asp | Thr | Asp | Ser | Ser | Ala |  |
|  |  | 195 |  |  |  |  | 200 |  |  |  |  | 205 |  |  |  |  |

| gct | act | aaa | aaa | act | gca | gct | tgg | aat | gac | agt | act | agc | act | tta | aca | 672 |
|---|---|---|---|---|---|---|---|---|---|---|---|---|---|---|---|---|
| Ala | Thr | Lys | Lys | Thr | Ala | Ala | Trp | Asn | Asp | Ser | Thr | Ser | Thr | Leu | Thr |  |
|  | 210 |  |  |  |  | 215 |  |  |  |  | 220 |  |  |  |  |  |

| att | agt | gct | gac | agc | aaa | aaa | act | aaa | gat | ttg | gtg | ttc | tta | aca | gat | 720 |
|---|---|---|---|---|---|---|---|---|---|---|---|---|---|---|---|---|
| Ile | Ser | Ala | Asp | Ser | Lys | Lys | Thr | Lys | Asp | Leu | Val | Phe | Leu | Thr | Asp |  |
| 225 |  |  |  |  | 230 |  |  |  |  | 235 |  |  |  |  | 240 |  |

| ggt | aca | att | aca | gta | caa | caa | tac | aac | aca | gct | gga | acc | agc | cta | gaa | 768 |
|---|---|---|---|---|---|---|---|---|---|---|---|---|---|---|---|---|
| Gly | Thr | Ile | Thr | Val | Gln | Gln | Tyr | Asn | Thr | Ala | Gly | Thr | Ser | Leu | Glu |  |
|  |  |  | 245 |  |  |  |  | 250 |  |  |  |  | 255 |  |  |  |

| gga | tca | gca | agt | gaa | att | aaa | aat | ctt | tca | gag | ctt | aaa | aac | gct | tta | 816 |
|---|---|---|---|---|---|---|---|---|---|---|---|---|---|---|---|---|
| Gly | Ser | Ala | Ser | Glu | Ile | Lys | Asn | Leu | Ser | Glu | Leu | Lys | Asn | Ala | Leu |  |
|  |  | 260 |  |  |  |  | 265 |  |  |  |  | 270 |  |  |  |  |

| aaa | taa |  | 822 |
|---|---|---|---|
| Lys | * |  |  |

<210> SEQ ID NO 104
<211> LENGTH: 273
<212> TYPE: PRT
<213> ORGANISM: Artificial Sequence
<220> FEATURE:
<223> OTHER INFORMATION: Chimeric Protein

<400> SEQUENCE: 104

|  |  |  |  |  |  |  |  |  |  |  |  |  |  |  |  |
|---|---|---|---|---|---|---|---|---|---|---|---|---|---|---|---|
| Met | Lys | Lys | Tyr | Leu | Leu | Gly | Ile | Gly | Leu | Ile | Leu | Ala | Leu | Ile | Ala |
| 1 |  |  |  | 5 |  |  |  |  | 10 |  |  |  |  | 15 |  |

|  |  |  |  |  |  |  |  |  |  |  |  |  |  |  |  |
|---|---|---|---|---|---|---|---|---|---|---|---|---|---|---|---|
| Cys | Lys | Gln | Asn | Val | Ser | Ser | Leu | Asp | Glu | Lys | Asn | Ser | Val | Ser | Val |
|  |  |  | 20 |  |  |  |  | 25 |  |  |  |  | 30 |  |  |

|  |  |  |  |  |  |  |  |  |  |  |  |  |  |  |  |
|---|---|---|---|---|---|---|---|---|---|---|---|---|---|---|---|
| Asp | Leu | Pro | Gly | Glu | Met | Lys | Val | Leu | Val | Ser | Lys | Glu | Lys | Asn | Lys |
|  |  | 35 |  |  |  |  | 40 |  |  |  |  | 45 |  |  |  |

|  |  |  |  |  |  |  |  |  |  |  |  |  |  |  |  |
|---|---|---|---|---|---|---|---|---|---|---|---|---|---|---|---|
| Asp | Gly | Lys | Tyr | Asp | Leu | Ile | Ala | Thr | Val | Asp | Lys | Leu | Glu | Leu | Lys |
|  | 50 |  |  |  |  | 55 |  |  |  |  | 60 |  |  |  |  |

|  |  |  |  |  |  |  |  |  |  |  |  |  |  |  |  |
|---|---|---|---|---|---|---|---|---|---|---|---|---|---|---|---|
| Gly | Thr | Ser | Asp | Lys | Asn | Asn | Gly | Ser | Gly | Val | Leu | Glu | Gly | Val | Lys |
| 65 |  |  |  |  | 70 |  |  |  |  | 75 |  |  |  |  | 80 |

-continued

```
Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Asp Ser Thr Ser Thr Leu Thr
    210                 215                 220

Ile Ser Ala Asp Ser Lys Lys Thr Lys Asp Leu Val Phe Leu Thr Asp
225                 230                 235                 240

Gly Thr Ile Thr Val Gln Gln Tyr Asn Thr Ala Gly Thr Ser Leu Glu
                245                 250                 255

Gly Ser Ala Ser Glu Ile Lys Asn Leu Ser Glu Leu Lys Asn Ala Leu
            260                 265                 270

Lys

<210> SEQ ID NO 105
<211> LENGTH: 39
<212> TYPE: DNA
<213> ORGANISM: Artificial Sequence
<220> FEATURE:
<223> OTHER INFORMATION: Oligonucleotide Primer

<400> SEQUENCE: 105
tgcagatgta atcccatccg ccatttttaa agcgttttt                              39

<210> SEQ ID NO 106
<211> LENGTH: 1401
<212> TYPE: DNA
<213> ORGANISM: Artificial Sequence
<220> FEATURE:
<221> NAME/KEY: CDS
<222> LOCATION: (1)...(1401)
<223> OTHER INFORMATION: Chimeric nucleic acid

<400> SEQUENCE: 106 atg aaa aaa tat tta ttg gga ata ggt cta ata tta gcc tta ata gca     48
Met Lys Lys Tyr Leu Leu Gly Ile Gly Leu Ile Leu Ala Leu Ile Ala
 1               5                  10                  15 tgt aag caa aat gtt agc agc ctt gac gag aaa aac agc gtt tca gta     96
Cys Lys Gln Asn Val Ser Ser Leu Asp Glu Lys Asn Ser Val Ser Val
                20                  25                  30 gat ttg cct ggt gaa atg aaa gtt ctt gta agc aaa gaa aaa aac aaa    144
Asp Leu Pro Gly Glu Met Lys Val Leu Val Ser Lys Glu Lys Asn Lys
            35                  40                  45 gac ggc aag tac gat cta att gca aca gta gac aag ctt gag ctt aaa    192
Asp Gly Lys Tyr Asp Leu Ile Ala Thr Val Asp Lys Leu Glu Leu Lys
        50                  55                  60 gga act tct gat aaa aac aat gga tct gga gta ctt gaa ggc gta aaa    240
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Gly | Thr | Ser | Asp | Lys | Asn | Asn | Gly | Ser | Gly | Val | Leu | Glu | Gly | Val | Lys |      |
| 65  |     |     |     |     | 70  |     |     |     |     | 75  |     |     |     |     | 80  |      |

```
gct gac aaa agt aaa gta aaa tta aca att tct gac gat cta ggt caa      288
Ala Asp Lys Ser Lys Val Lys Leu Thr Ile Ser Asp Asp Leu Gly Gln
            85                  90                  95 acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
            115                 120                 125 aaa ggt gaa gta tct gaa aaa ata ata aca aga gca gac gga acc aga      432
Lys Gly Glu Val Ser Glu Lys Ile Ile Thr Arg Ala Asp Gly Thr Arg
        130                 135                 140 ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145             150                 155                 160 gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175 aca ttg gtg gtt aaa gaa gga act gtt act tta agc aaa aat att tca      576
Thr Leu Val Val Lys Glu Gly Thr Val Thr Leu Ser Lys Asn Ile Ser
                180                 185                 190 aaa tct ggg gaa gtt tca gtt gaa ctt aat gac act gac agt agt gct      624
Lys Ser Gly Glu Val Ser Val Glu Leu Asn Asp Thr Asp Ser Ser Ala
            195                 200                 205 gct act aaa aaa act gca gct tgg aat gac agt act agc act tta aca      672
Ala Thr Lys Lys Thr Ala Ala Trp Asn Asp Ser Thr Ser Thr Leu Thr
            210                 215                 220 att agt gct gac agc aaa aaa act aaa gat ttg gtg ttc tta aca gat      720
Ile Ser Ala Asp Ser Lys Lys Thr Lys Asp Leu Val Phe Leu Thr Asp
225             230                 235                 240 ggt aca att aca gta caa caa tac aac aca gct gga acc agc cta gaa      768
Gly Thr Ile Thr Val Gln Gln Tyr Asn Thr Ala Gly Thr Ser Leu Glu
                245                 250                 255 gga tca gca agt gaa att aaa aat ctt tca gag ctt aaa aac gct tta      816
Gly Ser Ala Ser Glu Ile Lys Asn Leu Ser Glu Leu Lys Asn Ala Leu
            260                 265                 270 aaa atg gct aat aat tca ggg aaa gat ggg aat aca tct gca aat tct      864
Lys Met Ala Asn Asn Ser Gly Lys Asp Gly Asn Thr Ser Ala Asn Ser
            275                 280                 285 gct gat gag tct gtt aaa ggg cct aat ctt aca gaa ata agt aaa aaa      912
Ala Asp Glu Ser Val Lys Gly Pro Asn Leu Thr Glu Ile Ser Lys Lys
            290                 295                 300 att acg gat tct aat gcg gtt tta ctt gct gtg aaa gag gtt gaa gcg      960
Ile Thr Asp Ser Asn Ala Val Leu Leu Ala Val Lys Glu Val Glu Ala
305             310                 315                 320 ttg ctg tca tct ata gat gaa att gct gct aaa gct att ggt aaa aaa     1008
Leu Leu Ser Ser Ile Asp Glu Ile Ala Ala Lys Ala Ile Gly Lys Lys
                325                 330                 335 ata cac caa aat aat ggt ttg gat acc gaa tat aat cac aat gga tca     1056
Ile His Gln Asn Asn Gly Leu Asp Thr Glu Tyr Asn His Asn Gly Ser
            340                 345                 350 ttg tta gcg gga cgt tat gca ata tca acc cta ata aaa caa aaa tta     1104
Leu Leu Ala Gly Arg Tyr Ala Ile Ser Thr Leu Ile Lys Gln Lys Leu
            355                 360                 365 gat gga ttg aaa aat gaa gga tta aag gaa aaa att gat gcg gct aag     1152
Asp Gly Leu Lys Asn Glu Gly Leu Lys Glu Lys Ile Asp Ala Ala Lys
370             375                 380
```

```
aaa tgt tct gaa aca ttt act aat aaa tta aaa gca aaa cac aca gat    1200
Lys Cys Ser Glu Thr Phe Thr Asn Lys Leu Lys Ala Lys His Thr Asp
385                 390                 395                 400 ctt ggt aaa gaa ggt gtt act gat gct gat gca aaa gaa gcc att tta    1248
Leu Gly Lys Glu Gly Val Thr Asp Ala Asp Ala Lys Glu Ala Ile Leu
                405                 410                 415 aaa aca aat ggt act aaa act aaa ggt gct gaa gaa ctt gga aaa tta    1296
Lys Thr Asn Gly Thr Lys Thr Lys Gly Ala Glu Glu Leu Gly Lys Leu
            420                 425                 430 ttt gaa tca gta gag gtc ttg tca aaa gca gct aaa gag atg ctt gct    1344
Phe Glu Ser Val Glu Val Leu Ser Lys Ala Ala Lys Glu Met Leu Ala
                435                 440                 445 aat tca gtt aaa gag ctt aca agc cct gtt gtg gca gaa agt cca aaa    1392
Asn Ser Val Lys Glu Leu Thr Ser Pro Val Val Ala Glu Ser Pro Lys
        450                 455                 460 aaa cct taa                                                         1401
Lys Pro *
465

<210> SEQ ID NO 107
<211> LENGTH: 466
<212> TYPE: PRT
<213> ORGANISM: Artificial Sequence
<220> FEATURE:
<223> OTHER INFORMATION: Chimeric Protien

<400> SEQUENCE: 107

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Asp Ser Thr Ser Thr Leu Thr
    210                 215                 220

Ile Ser Ala Asp Ser Lys Lys Thr Lys Asp Leu Val Phe Leu Thr Asp
225                 230                 235                 240
```

```
                         -continued

Gly Thr Ile Thr Val Gln Gln Tyr Asn Thr Ala Gly Thr Ser Leu Glu
                245                 250                 255

Gly Ser Ala Ser Glu Ile Lys Asn Leu Ser Glu Leu Lys Asn Ala Leu
            260                 265                 270

Lys Met Ala Asn Asn Ser Gly Lys Asp Gly Asn Thr Ser Ala Asn Ser
        275                 280                 285

Ala Asp Glu Ser Val Lys Gly Pro Asn Leu Thr Glu Ile Ser Lys Lys
    290                 295                 300

Ile Thr Asp Ser Asn Ala Val Leu Leu Ala Val Lys Glu Val Glu Ala
305                 310                 315                 320

Leu Leu Ser Ser Ile Asp Glu Ile Ala Ala Lys Ala Ile Gly Lys Lys
                325                 330                 335

Ile His Gln Asn Asn Gly Leu Asp Thr Glu Tyr Asn His Asn Gly Ser
            340                 345                 350

Leu Leu Ala Gly Arg Tyr Ala Ile Ser Thr Leu Ile Lys Gln Lys Leu
        355                 360                 365

Asp Gly Leu Lys Asn Glu Gly Leu Lys Glu Lys Ile Asp Ala Ala Lys
    370                 375                 380

Lys Cys Ser Glu Thr Phe Thr Asn Lys Leu Lys Ala Lys His Thr Asp
385                 390                 395                 400

Leu Gly Lys Glu Gly Val Thr Asp Ala Asp Ala Lys Glu Ala Ile Leu
                405                 410                 415

Lys Thr Asn Gly Thr Lys Thr Lys Gly Ala Glu Glu Leu Gly Lys Leu
            420                 425                 430

Phe Glu Ser Val Glu Val Leu Ser Lys Ala Ala Lys Glu Met Leu Ala
        435                 440                 445

Asn Ser Val Lys Glu Leu Thr Ser Pro Val Val Ala Glu Ser Pro Lys
    450                 455                 460

Lys Pro
465

<210> SEQ ID NO 108
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 108
gctgctaaca ttttgcttag gttttttttgg actttc                    36

<210> SEQ ID NO 109
<211> LENGTH: 1401
<212> TYPE: DNA
<213> ORGANISM: Artificial Sequence
<220> FEATURE:
<221> NAME/KEY: CDS
<222> LOCATION: (1)...(1401)
<223> OTHER INFORMATION: Chimeric Nucleic Acid

<400> SEQUENCE: 109 atg aaa aag aat aca tta agt gcg ata tta atg act tta ttt tta ttt      48
Met Lys Lys Asn Thr Leu Ser Ala Ile Leu Met Thr Leu Phe Leu Phe
 1               5                  10                  15 ata tct tgt aat aat tca ggg aaa gat ggg aat aca tct gca aat tct      96
Ile Ser Cys Asn Asn Ser Gly Lys Asp Gly Asn Thr Ser Ala Asn Ser
                20                  25                  30 gct gat gag tct gtt aaa ggg cct aat ctt aca gaa ata agt aaa aaa     144
Ala Asp Glu Ser Val Lys Gly Pro Asn Leu Thr Glu Ile Ser Lys Lys
```

```
             35                  40                  45
att acg gat tct aat gcg gtt tta ctt gct gtg aaa gag gtt gaa gcg     192
Ile Thr Asp Ser Asn Ala Val Leu Leu Ala Val Lys Glu Val Glu Ala
         50                  55                  60 ttg ctg tca tct ata gat gaa att gct gct aaa gct att ggt aaa aaa     240
Leu Leu Ser Ser Ile Asp Glu Ile Ala Ala Lys Ala Ile Gly Lys Lys
 65                  70                  75                  80 ata cac caa aat aat ggt ttg gat acc gaa tat aat cac aat gga tca     288
Ile His Gln Asn Asn Gly Leu Asp Thr Glu Tyr Asn His Asn Gly Ser
                 85                  90                  95 ttg tta gcg gga cgt tat gca ata tca acc cta ata aaa caa aaa tta     336
Leu Leu Ala Gly Arg Tyr Ala Ile Ser Thr Leu Ile Lys Gln Lys Leu
            100                 105                 110 gat gga ttg aaa aat gaa gga tta aag gaa aaa att gat gcg gct aag     384
Asp Gly Leu Lys Asn Glu Gly Leu Lys Glu Lys Ile Asp Ala Ala Lys
        115                 120                 125 aaa tgt tct gaa aca ttt act aat aaa tta aaa gca aaa cac aca gat     432
Lys Cys Ser Glu Thr Phe Thr Asn Lys Leu Lys Ala Lys His Thr Asp
130                 135                 140 ctt ggt aaa gaa ggt gtt act gat gct gat gca aaa gaa gcc att tta     480
Leu Gly Lys Glu Gly Val Thr Asp Ala Asp Ala Lys Glu Ala Ile Leu
145                 150                 155                 160 aaa aca aat ggt act aaa act aaa ggt gct gaa gaa ctt gga aaa tta     528
Lys Thr Asn Gly Thr Lys Thr Lys Gly Ala Glu Glu Leu Gly Lys Leu
                165                 170                 175 ttt gaa tca gta gag gtc ttg tca aaa gca gct aaa gag atg ctt gct     576
Phe Glu Ser Val Glu Val Leu Ser Lys Ala Ala Lys Glu Met Leu Ala
            180                 185                 190 aat tca gtt aaa gag ctt aca agc cct gtt gtg gca gaa agt cca aaa     624
Asn Ser Val Lys Glu Leu Thr Ser Pro Val Val Ala Glu Ser Pro Lys
        195                 200                 205 aaa cct aag caa aat gtt agc agc ctt gac gag aaa aac agc gtt tca     672
Lys Pro Lys Gln Asn Val Ser Ser Leu Asp Glu Lys Asn Ser Val Ser
    210                 215                 220 gta gat ttg cct ggt gaa atg aaa gtt ctt gta agc aaa gaa aaa aac     720
Val Asp Leu Pro Gly Glu Met Lys Val Leu Val Ser Lys Glu Lys Asn
225                 230                 235                 240 aaa gac ggc aag tac gat cta att gca aca gta gac aag ctt gag ctt     768
Lys Asp Gly Lys Tyr Asp Leu Ile Ala Thr Val Asp Lys Leu Glu Leu
                245                 250                 255 aaa gga act tct gat aaa aac aat gga tct gga gta ctt gaa ggc gta     816
Lys Gly Thr Ser Asp Lys Asn Asn Gly Ser Gly Val Leu Glu Gly Val
            260                 265                 270 aaa gct gac aaa agt aaa gta aaa tta aca att tct gac gat cta ggt     864
Lys Ala Asp Lys Ser Lys Val Lys Leu Thr Ile Ser Asp Asp Leu Gly
        275                 280                 285 caa acc aca ctt gaa gtt ttc aaa gaa gat ggc aaa aca cta gta tca     912
Gln Thr Thr Leu Glu Val Phe Lys Glu Asp Gly Lys Thr Leu Val Ser
    290                 295                 300 aaa aaa gta act tcc aaa gac aag tca tca aca gaa gaa aaa ttc aat     960
Lys Lys Val Thr Ser Lys Asp Lys Ser Ser Thr Glu Glu Lys Phe Asn
305                 310                 315                 320 gaa aaa ggt gaa gta tct gaa aaa ata ata aca aga gca gac gga acc     1008
Glu Lys Gly Glu Val Ser Glu Lys Ile Ile Thr Arg Ala Asp Gly Thr
                325                 330                 335 aga ctt gaa tac aca gga att aaa agc gat gga tct gga aaa gct aaa     1056
Arg Leu Glu Tyr Thr Gly Ile Lys Ser Asp Gly Ser Gly Lys Ala Lys
            340                 345                 350 gag gtt tta aaa ggc tat gtt ctt gaa gga act cta act gct gaa aaa     1104
```

```
                Glu Val Leu Lys Gly Tyr Val Leu Glu Gly Thr Leu Thr Ala Glu Lys
                                355                 360                 365 aca aca ttg gtg gtt aaa gaa gga act gtt act tta agc aaa aat att              1152
Thr Thr Leu Val Val Lys Glu Gly Thr Val Thr Leu Ser Lys Asn Ile
        370                 375                 380 tca aaa tct ggg gaa gtt tca gtt gaa ctt aat gac act gac agt agt              1200
Ser Lys Ser Gly Glu Val Ser Val Glu Leu Asn Asp Thr Asp Ser Ser
385                 390                 395                 400 gct gct act aaa aaa act gca gct tgg aat gac agt act agc act tta              1248
Ala Ala Thr Lys Lys Thr Ala Ala Trp Asn Asp Ser Thr Ser Thr Leu
                405                 410                 415 aca att agt gct gac agc aaa aaa act aaa gat ttg gtg ttc tta aca              1296
Thr Ile Ser Ala Asp Ser Lys Lys Thr Lys Asp Leu Val Phe Leu Thr
            420                 425                 430 gat ggt aca att aca gta caa caa tac aac aca gct gga acc agc cta              1344
Asp Gly Thr Ile Thr Val Gln Gln Tyr Asn Thr Ala Gly Thr Ser Leu
        435                 440                 445 gaa gga tca gca agt gaa att aaa aat ctt tca gag ctt aaa aac gct              1392
Glu Gly Ser Ala Ser Glu Ile Lys Asn Leu Ser Glu Leu Lys Asn Ala
    450                 455                 460 tta aaa taa                                                                  1401
Leu Lys  *
465

<210> SEQ ID NO 110
<211> LENGTH: 466
<212> TYPE: PRT
<213> ORGANISM: Artificial Sequence
<220> FEATURE:
<223> OTHER INFORMATION: Chimeric Protein

<400> SEQUENCE: 110

Met Lys Lys Asn Thr Leu Ser Ala Ile Leu Met Thr Leu Phe Leu Phe
  1               5                  10                  15

Ile Ser Cys Asn Asn Ser Gly Lys Asp Gly Asn Thr Ser Ala Asn Ser
                 20                  25                  30

Ala Asp Glu Ser Val Lys Gly Pro Asn Leu Thr Glu Ile Ser Lys Lys
             35                  40                  45

Ile Thr Asp Ser Asn Ala Val Leu Leu Ala Val Lys Glu Val Glu Ala
         50                  55                  60

Leu Leu Ser Ser Ile Asp Glu Ile Ala Ala Lys Ala Ile Gly Lys Lys
 65                  70                  75                  80

Ile His Gln Asn Asn Gly Leu Asp Thr Glu Tyr Asn His Asn Gly Ser
                 85                  90                  95

Leu Leu Ala Gly Arg Tyr Ala Ile Ser Thr Leu Ile Lys Gln Lys Leu
                100                 105                 110

Asp Gly Leu Lys Asn Glu Gly Leu Lys Glu Lys Ile Asp Ala Ala Lys
            115                 120                 125

Lys Cys Ser Glu Thr Phe Thr Asn Lys Leu Lys Ala Lys His Thr Asp
        130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205
```

-continued

```
Lys Pro Lys Gln Asn Val Ser Ser Leu Asp Glu Lys Asn Ser Val Ser
        210                 215                 220
Val Asp Leu Pro Gly Glu Met Lys Val Leu Val Ser Lys Glu Lys Asn
225                 230                 235                 240
Lys Asp Gly Lys Tyr Asp Leu Ile Ala Thr Val Asp Lys Leu Glu Leu
                245                 250                 255
Lys Gly Thr Ser Asp Lys Asn Asn Gly Ser Gly Val Leu Glu Gly Val
            260                 265                 270
Lys Ala Asp Lys Ser Lys Val Lys Leu Thr Ile Ser Asp Asp Leu Gly
        275                 280                 285
Gln Thr Thr Leu Glu Val Phe Lys Glu Asp Gly Lys Thr Leu Val Ser
    290                 295                 300
Lys Lys Val Thr Ser Lys Asp Lys Ser Ser Thr Glu Glu Lys Phe Asn
305                 310                 315                 320
Glu Lys Gly Glu Val Ser Glu Lys Ile Ile Thr Arg Ala Asp Gly Thr
                325                 330                 335
Arg Leu Glu Tyr Thr Gly Ile Lys Ser Asp Gly Ser Gly Lys Ala Lys
            340                 345                 350
Glu Val Leu Lys Gly Tyr Val Leu Glu Gly Thr Leu Thr Ala Glu Lys
        355                 360                 365
Thr Thr Leu Val Val Lys Glu Gly Thr Val Thr Leu Ser Lys Asn Ile
    370                 375                 380
Ser Lys Ser Gly Glu Val Ser Val Glu Leu Asn Asp Thr Asp Ser Ser
385                 390                 395                 400
Ala Ala Thr Lys Lys Thr Ala Ala Trp Asn Asp Ser Thr Ser Thr Leu
                405                 410                 415
Thr Ile Ser Ala Asp Ser Lys Lys Thr Lys Asp Leu Val Phe Leu Thr
            420                 425                 430
Asp Gly Thr Ile Thr Val Gln Gln Tyr Asn Thr Ala Gly Thr Ser Leu
        435                 440                 445
Glu Gly Ser Ala Ser Glu Ile Lys Asn Leu Ser Glu Leu Lys Asn Ala
    450                 455                 460
Leu Lys
465
```

<210> SEQ ID NO 111
<211> LENGTH: 1720
<212> TYPE: DNA
<213> ORGANISM: Artificial Sequence
<220> FEATURE:
<221> NAME/KEY: CDS
<222> LOCATION: (1)...(1719)
<223> OTHER INFORMATION: Chimeric Nucleic Acid

<400> SEQUENCE: 111

```
aag caa aat gtt agc agc ctt gac gag aaa aac agc gtt tca gta gat      48
Lys Gln Asn Val Ser Ser Leu Asp Glu Lys Asn Ser Val Ser Val Asp
  1               5                  10                  15 ttg cct ggt gaa atg aaa gtt ctt gta agc aaa gaa aaa aac aaa gac      96
Leu Pro Gly Glu Met Lys Val Leu Val Ser Lys Glu Lys Asn Lys Asp
             20                  25                  30 ggc aag tac gat cta att gca aca gta gac aag ctt gag ctt aaa gga     144
Gly Lys Tyr Asp Leu Ile Ala Thr Val Asp Lys Leu Glu Leu Lys Gly
         35                  40                  45 act tct gat aaa aac aat gga tct gga gta ctt gaa ggc gta aaa gct     192
Thr Ser Asp Lys Asn Asn Gly Ser Gly Val Leu Glu Gly Val Lys Ala
     50                  55                  60
```

```
gac aaa agt aaa gta aaa tta aca att tct gac gat cta ggt caa acc     240
Asp Lys Ser Lys Val Lys Leu Thr Ile Ser Asp Asp Leu Gly Gln Thr
 65                  70                  75                  80 aca ctt gaa gtt ttc aaa gaa gat ggc aaa aca cta gta tca aaa aaa     288
Thr Leu Glu Val Phe Lys Glu Asp Gly Lys Thr Leu Val Ser Lys Lys
                 85                  90                  95 gta act tcc aaa gac aag tca tca aca gaa gaa aaa ttc aat gaa aaa     336
Val Thr Ser Lys Asp Lys Ser Ser Thr Glu Glu Lys Phe Asn Glu Lys
            100                 105                 110 ggt gaa gta tct gaa aaa ata ata aca aga gca gac gga acc aga ctt     384
Gly Glu Val Ser Glu Lys Ile Ile Thr Arg Ala Asp Gly Thr Arg Leu
        115                 120                 125 gaa tac aca gga att aaa agc gat gga tct gga aaa gct aaa gag gtt     432
Glu Tyr Thr Gly Ile Lys Ser Asp Gly Ser Gly Lys Ala Lys Glu Val
    130                 135                 140 tta aaa ggc tat gtt ctt gaa gga act cta act gct gaa aaa aca aca     480
Leu Lys Gly Tyr Val Leu Glu Gly Thr Leu Thr Ala Glu Lys Thr Thr
145                 150                 155                 160 ttg gtg gtt aaa gaa gga act gtt act tta agc aaa aat att tca aaa     528
Leu Val Val Lys Glu Gly Thr Val Thr Leu Ser Lys Asn Ile Ser Lys
                165                 170                 175 tct ggg gaa gtt tca gtt gaa ctt aat gac act gac agt agt gct gct     576
Ser Gly Glu Val Ser Val Glu Leu Asn Asp Thr Asp Ser Ser Ala Ala
            180                 185                 190 act aaa aaa act gca gct tgg aat tca ggc act tca act tta aca att     624
Thr Lys Lys Thr Ala Ala Trp Asn Ser Gly Thr Ser Thr Leu Thr Ile
        195                 200                 205 act gta aac agt aaa aaa act aaa gac ctt gtg ttt aca aaa gaa aac     672
Thr Val Asn Ser Lys Lys Thr Lys Asp Leu Val Phe Thr Lys Glu Asn
    210                 215                 220 aca att aca gta caa caa tac gac tca aat ggc acc aaa tta gag ggg     720
Thr Ile Thr Val Gln Gln Tyr Asp Ser Asn Gly Thr Lys Leu Glu Gly
225                 230                 235                 240 tca gca gtt gaa att aca aaa ctt gat gaa att aaa aac gct tta aaa     768
Ser Ala Val Glu Ile Thr Lys Leu Asp Glu Ile Lys Asn Ala Leu Lys
                245                 250                 255 ggt cac ccc atg gat gaa aag ctt tta aaa agt aaa gat gat aaa gca     816
Gly His Pro Met Asp Glu Lys Leu Leu Lys Ser Lys Asp Asp Lys Ala
            260                 265                 270 agt aaa gat ggt aaa gcc ttg gat ctt gat cga gaa tta aat tct aaa     864
Ser Lys Asp Gly Lys Ala Leu Asp Leu Asp Arg Glu Leu Asn Ser Lys
        275                 280                 285 gct tct agc aaa gaa aaa agt aaa gcc aag gaa gaa gaa ata acc aag     912
Ala Ser Ser Lys Glu Lys Ser Lys Ala Lys Glu Glu Glu Ile Thr Lys
    290                 295                 300 ggt aag tca cag aaa agc tta ggc gat ttg aat aat gat gaa aat ctt     960
Gly Lys Ser Gln Lys Ser Leu Gly Asp Leu Asn Asn Asp Glu Asn Leu
305                 310                 315                 320 atg atg cca gaa gat caa aaa tta cct gag gtt aaa aaa tta gat agc    1008
Met Met Pro Glu Asp Gln Lys Leu Pro Glu Val Lys Lys Leu Asp Ser
                325                 330                 335 aaa aaa gaa ttt aaa cct gtt tct gag gtt gag aaa tta gat aag att    1056
Lys Lys Glu Phe Lys Pro Val Ser Glu Val Glu Lys Leu Asp Lys Ile
            340                 345                 350 ttc aag tct aat aac aat gtt gga gaa tta tca ccg tta gat aaa tct    1104
Phe Lys Ser Asn Asn Asn Val Gly Glu Leu Ser Pro Leu Asp Lys Ser
        355                 360                 365 tct tat aaa gac att gat tca aaa gag gag aca gtt aat aaa gat gtt    1152
Ser Tyr Lys Asp Ile Asp Ser Lys Glu Glu Thr Val Asn Lys Asp Val
```

-continued

```
      370                 375                 380
aat ttg caa aag act aag cct cag gtt aaa gac caa gtt act tct ttg    1200
Asn Leu Gln Lys Thr Lys Pro Gln Val Lys Asp Gln Val Thr Ser Leu
385                 390                 395                 400 aat gaa gat ttg act act atg tct ata gat tcc agt agt cct gta ttt    1248
Asn Glu Asp Leu Thr Thr Met Ser Ile Asp Ser Ser Pro Val Phe
        405                 410                 415 tta gag gtt att gat cca att aca aat tta gga act ctt caa ctt att    1296
Leu Glu Val Ile Asp Pro Ile Thr Asn Leu Gly Thr Leu Gln Leu Ile
            420                 425                 430 gat tta aat act ggt gtt agg ctt aaa gaa agc act cag caa ggc att    1344
Asp Leu Asn Thr Gly Val Arg Leu Lys Glu Ser Thr Gln Gln Gly Ile
                435                 440                 445 cag cgg tat gga att tat gaa cgt gaa aaa gat ttg gtt gtt att aaa    1392
Gln Arg Tyr Gly Ile Tyr Glu Arg Glu Lys Asp Leu Val Val Ile Lys
            450                 455                 460 atg gat tca gga aaa gct aag ctt cag ata ctt gat aaa ctt gaa aat    1440
Met Asp Ser Gly Lys Ala Lys Leu Gln Ile Leu Asp Lys Leu Glu Asn
465                 470                 475                 480 tta aaa gtg gta tca gag tct aat ttt gag att aat aaa aat tca tct    1488
Leu Lys Val Val Ser Glu Ser Asn Phe Glu Ile Asn Lys Asn Ser Ser
                485                 490                 495 ctt tat gtt gat tct aaa atg att tta gta gct gtt agg gat aaa gat    1536
Leu Tyr Val Asp Ser Lys Met Ile Leu Val Ala Val Arg Asp Lys Asp
            500                 505                 510 agt agt aat gat tgg aga ttg gcc aaa ttt tct cct aaa aat tta gat    1584
Ser Ser Asn Asp Trp Arg Leu Ala Lys Phe Ser Pro Lys Asn Leu Asp
            515                 520                 525 gag ttt att ctt tca gag aat aaa att atg cct ttt act agc ttt tct    1632
Glu Phe Ile Leu Ser Glu Asn Lys Ile Met Pro Phe Thr Ser Phe Ser
530                 535                 540 gtg aga aaa aat ttt att tat ttg caa gat gag ttt aaa agt cta gtt    1680
Val Arg Lys Asn Phe Ile Tyr Leu Gln Asp Glu Phe Lys Ser Leu Val
545                 550                 555                 560 att tta gat gta aat act tta aaa aaa gtt aag ggt cac c              1720
Ile Leu Asp Val Asn Thr Leu Lys Lys Val Lys Gly His
                565                 570
```

<210> SEQ ID NO 112
<211> LENGTH: 573
<212> TYPE: PRT
<213> ORGANISM: Artificial Sequence
<220> FEATURE:
<223> OTHER INFORMATION: Chimeric Protein

<400> SEQUENCE: 112

```
Lys Gln Asn Val Ser Ser Leu Asp Glu Lys Asn Ser Val Ser Val Asp
1               5                   10                  15

Leu Pro Gly Glu Met Lys Val Leu Val Ser Lys Glu Lys Asn Lys Asp
            20                  25                  30

Gly Lys Tyr Asp Leu Ile Ala Thr Val Asp Lys Leu Glu Leu Lys Gly
        35                  40                  45

Thr Ser Asp Lys Asn Asn Gly Ser Gly Val Leu Glu Gly Val Lys Ala
    50                  55                  60

Asp Lys Ser Lys Val Lys Leu Thr Ile Ser Asp Asp Leu Gly Gln Thr
65                  70                  75                  80

Thr Leu Glu Val Phe Lys Glu Asp Gly Lys Thr Leu Val Ser Lys Lys
                85                  90                  95

Val Thr Ser Lys Asp Lys Ser Ser Thr Glu Glu Lys Phe Asn Glu Lys
```

-continued

```
                    100                 105                 110
Gly Glu Val Ser Glu Lys Ile Ile Thr Arg Ala Asp Gly Thr Arg Leu
            115                 120                 125
Glu Tyr Thr Gly Ile Lys Ser Asp Gly Ser Gly Lys Ala Lys Glu Val
130                 135                 140
Leu Lys Gly Tyr Val Leu Glu Gly Thr Leu Thr Ala Glu Lys Thr Thr
145                 150                 155                 160
Leu Val Val Lys Glu Gly Thr Val Thr Leu Ser Lys Asn Ile Ser Lys
                    165                 170                 175
Ser Gly Glu Val Ser Val Glu Leu Asn Asp Thr Asp Ser Ser Ala Ala
            180                 185                 190
Thr Lys Lys Thr Ala Ala Trp Asn Ser Gly Thr Ser Thr Leu Thr Ile
        195                 200                 205
Thr Val Asn Ser Lys Lys Thr Lys Asp Leu Val Phe Thr Lys Glu Asn
    210                 215                 220
Thr Ile Thr Val Gln Gln Tyr Asp Ser Asn Gly Thr Lys Leu Glu Gly
225                 230                 235                 240
Ser Ala Val Glu Ile Thr Lys Leu Asp Glu Ile Lys Asn Ala Leu Lys
                    245                 250                 255
Gly His Pro Met Asp Glu Lys Leu Leu Lys Ser Lys Asp Asp Lys Ala
            260                 265                 270
Ser Lys Asp Gly Lys Ala Leu Asp Leu Asp Arg Glu Leu Asn Ser Lys
        275                 280                 285
Ala Ser Ser Lys Glu Lys Ser Lys Ala Lys Glu Glu Ile Thr Lys
    290                 295                 300
Gly Lys Ser Gln Lys Ser Leu Gly Asp Leu Asn Asn Asp Glu Asn Leu
305                 310                 315                 320
Met Met Pro Glu Asp Gln Lys Leu Pro Glu Val Lys Lys Leu Asp Ser
                    325                 330                 335
Lys Lys Glu Phe Lys Pro Val Ser Glu Val Glu Lys Leu Asp Lys Ile
            340                 345                 350
Phe Lys Ser Asn Asn Asn Val Gly Glu Leu Ser Pro Leu Asp Lys Ser
        355                 360                 365
Ser Tyr Lys Asp Ile Asp Ser Lys Glu Glu Thr Val Asn Lys Asp Val
    370                 375                 380
Asn Leu Gln Lys Thr Lys Pro Gln Val Lys Asp Gln Val Thr Ser Leu
385                 390                 395                 400
Asn Glu Asp Leu Thr Thr Met Ser Ile Asp Ser Ser Pro Val Phe
                    405                 410                 415
Leu Glu Val Ile Asp Pro Ile Thr Asn Leu Gly Thr Leu Gln Leu Ile
            420                 425                 430
Asp Leu Asn Thr Gly Val Arg Leu Lys Glu Ser Thr Gln Gln Gly Ile
        435                 440                 445
Gln Arg Tyr Gly Ile Tyr Glu Arg Lys Asp Leu Val Val Ile Lys
    450                 455                 460
Met Asp Ser Gly Lys Ala Lys Leu Gln Ile Leu Asp Lys Leu Glu Asn
465                 470                 475                 480
Leu Lys Val Val Ser Glu Ser Asn Phe Glu Ile Asn Lys Asn Ser Ser
                    485                 490                 495
Leu Tyr Val Asp Ser Lys Met Ile Leu Val Ala Val Arg Asp Lys Asp
            500                 505                 510
Ser Ser Asn Asp Trp Arg Leu Ala Lys Phe Ser Pro Lys Asn Leu Asp
        515                 520                 525
```

```
Glu Phe Ile Leu Ser Glu Asn Lys Ile Met Pro Phe Thr Ser Phe Ser
    530                 535                 540

Val Arg Lys Asn Phe Ile Tyr Leu Gln Asp Glu Phe Lys Ser Leu Val
545                 550                 555                 560

Ile Leu Asp Val Asn Thr Leu Lys Lys Val Lys Gly His
                565                 570

<210> SEQ ID NO 113
<211> LENGTH: 1180
<212> TYPE: DNA
<213> ORGANISM: Artificial Sequence
<220> FEATURE:
<221> NAME/KEY: CDS
<222> LOCATION: (1)...(1179)
<223> OTHER INFORMATION: Chimeric Nucleic Acid

<400> SEQUENCE: 113 gca caa aaa ggt gct gag tca att ggt tct caa aaa gaa aat gat cta      48
Ala Gln Lys Gly Ala Glu Ser Ile Gly Ser Gln Lys Glu Asn Asp Leu
 1               5                  10                  15 aac ctt gaa gac tct agt aaa aaa tca cat caa aac gct aaa caa gac      96
Asn Leu Glu Asp Ser Ser Lys Lys Ser His Gln Asn Ala Lys Gln Asp
                20                  25                  30 ctt cct gcg gtg aca gaa gac tca gtg tct ttg ttt aat ggt aat aaa     144
Leu Pro Ala Val Thr Glu Asp Ser Val Ser Leu Phe Asn Gly Asn Lys
            35                  40                  45 att ttt gta agc aaa gaa aaa aat agc tcc ggc aaa tat gat tta aga     192
Ile Phe Val Ser Lys Glu Lys Asn Ser Ser Gly Lys Tyr Asp Leu Arg
 50                  55                  60 gca aca att gat cag gtt gaa ctt aaa gga act tcc gat aaa aac aat     240
Ala Thr Ile Asp Gln Val Glu Leu Lys Gly Thr Ser Asp Lys Asn Asn
 65                  70                  75                  80 ggt tct gga acc ctt gaa ggt tca aag cct gac aag agt aaa gta aaa     288
Gly Ser Gly Thr Leu Glu Gly Ser Lys Pro Asp Lys Ser Lys Val Lys
                85                  90                  95 tta aca gtt tct gct gat tta aac aca gta acc tta gaa gca ttt gat     336
Leu Thr Val Ser Ala Asp Leu Asn Thr Val Thr Leu Glu Ala Phe Asp
            100                 105                 110 gcc agc aac caa aaa att tca agt aaa gtt act aaa aaa cag ggg tca     384
Ala Ser Asn Gln Lys Ile Ser Ser Lys Val Thr Lys Lys Gln Gly Ser
        115                 120                 125 ata aca gag gaa act ctc aaa gct aat aaa tta gac tca aag aaa tta     432
Ile Thr Glu Glu Thr Leu Lys Ala Asn Lys Leu Asp Ser Lys Lys Leu
    130                 135                 140 aca aga tca aac gga act aca ctt gaa tac tca caa ata aca gat gct     480
Thr Arg Ser Asn Gly Thr Thr Leu Glu Tyr Ser Gln Ile Thr Asp Ala
145                 150                 155                 160 gac aat gct aca aaa gca gta gaa act cta aaa aat agc att aag ctt     528
Asp Asn Ala Thr Lys Ala Val Glu Thr Leu Lys Asn Ser Ile Lys Leu
                165                 170                 175 gaa gga agt ctt gta gtc gga aaa aca aca gtg gaa att aaa gaa ggt     576
Glu Gly Ser Leu Val Val Gly Lys Thr Thr Val Glu Ile Lys Glu Gly
            180                 185                 190 act gtt act cta aaa aga gaa att gaa aaa gat gga aaa gta aaa gtc     624
Thr Val Thr Leu Lys Arg Glu Ile Glu Lys Asp Gly Lys Val Lys Val
        195                 200                 205 ttt ttg aat gac act gca ggt tct aac aaa aaa aca ggt aaa tgg gaa     672
Phe Leu Asn Asp Thr Ala Gly Ser Asn Lys Lys Thr Gly Lys Trp Glu
    210                 215                 220 gac agt act agc act tta aca att agt gct gac agc aaa aaa act aaa     720
```

-continued

| | | | | | | | | | | | | |
|---|---|---|---|---|---|---|---|---|---|---|---|---|
| Asp | Ser | Thr | Ser | Thr | Leu | Thr | Ile | Ser | Ala | Asp | Ser | Lys | Lys | Thr | Lys |
| 225 | | | | 230 | | | | | 235 | | | | | 240 | |

| gat | ttg | gtg | ttc | tta | aca | gat | ggt | aca | att | aca | gta | caa | caa | tac | aac | 768 |
|---|---|---|---|---|---|---|---|---|---|---|---|---|---|---|---|---|
| Asp | Leu | Val | Phe | Leu | Thr | Asp | Gly | Thr | Ile | Thr | Val | Gln | Gln | Tyr | Asn | |
| | | | | 245 | | | | | 250 | | | | | 255 | | |

| aca | gct | gga | acc | agc | cta | gaa | gga | tca | gca | agt | gaa | att | aaa | aat | ctt | 816 |
|---|---|---|---|---|---|---|---|---|---|---|---|---|---|---|---|---|
| Thr | Ala | Gly | Thr | Ser | Leu | Glu | Gly | Ser | Ala | Ser | Glu | Ile | Lys | Asn | Leu | |
| | | 260 | | | | | 265 | | | | | 270 | | | | |

| tca | gag | ctt | aaa | aac | gct | tta | aaa | ggt | cac | ccc | atg | gct | caa | tat | aac | 864 |
|---|---|---|---|---|---|---|---|---|---|---|---|---|---|---|---|---|
| Ser | Glu | Leu | Lys | Asn | Ala | Leu | Lys | Gly | His | Pro | Met | Ala | Gln | Tyr | Asn | |
| | | 275 | | | | | 280 | | | | | 285 | | | | |

| caa | atg | cac | atg | tta | tca | aac | aaa | tct | gct | tct | caa | aat | gta | aga | aca | 912 |
|---|---|---|---|---|---|---|---|---|---|---|---|---|---|---|---|---|
| Gln | Met | His | Met | Leu | Ser | Asn | Lys | Ser | Ala | Ser | Gln | Asn | Val | Arg | Thr | |
| 290 | | | | | 295 | | | | | 300 | | | | | | |

| gct | gaa | gag | ctt | gga | atg | cag | cct | gca | aaa | att | aac | aca | cca | gca | tca | 960 |
|---|---|---|---|---|---|---|---|---|---|---|---|---|---|---|---|---|
| Ala | Glu | Glu | Leu | Gly | Met | Gln | Pro | Ala | Lys | Ile | Asn | Thr | Pro | Ala | Ser | |
| 305 | | | | 310 | | | | | 315 | | | | | 320 | | |

| ctt | tca | ggg | ctt | caa | gcg | tct | tgg | act | tta | aga | gtt | cat | gtt | gga | gca | 1008 |
|---|---|---|---|---|---|---|---|---|---|---|---|---|---|---|---|---|
| Leu | Ser | Gly | Leu | Gln | Ala | Ser | Trp | Thr | Leu | Arg | Val | His | Val | Gly | Ala | |
| | | | | 325 | | | | | 330 | | | | | 335 | | |

| acc | caa | gat | gaa | gct | att | gct | gta | aat | att | tat | gca | gct | aat | gtt | gca | 1056 |
|---|---|---|---|---|---|---|---|---|---|---|---|---|---|---|---|---|
| Thr | Gln | Asp | Glu | Ala | Ile | Ala | Val | Asn | Ile | Tyr | Ala | Ala | Asn | Val | Ala | |
| | | 340 | | | | | 345 | | | | | 350 | | | | |

| aat | ctt | ttc | tct | ggt | gag | gga | gct | caa | act | gct | cag | gct | gca | ccg | gtt | 1104 |
|---|---|---|---|---|---|---|---|---|---|---|---|---|---|---|---|---|
| Asn | Leu | Phe | Ser | Gly | Glu | Gly | Ala | Gln | Thr | Ala | Gln | Ala | Ala | Pro | Val | |
| | | 355 | | | | | 360 | | | | | 365 | | | | |

| caa | gag | ggt | gtt | caa | cag | gaa | gga | gct | caa | cag | cca | gca | cct | gct | aca | 1152 |
|---|---|---|---|---|---|---|---|---|---|---|---|---|---|---|---|---|
| Gln | Glu | Gly | Val | Gln | Gln | Glu | Gly | Ala | Gln | Gln | Pro | Ala | Pro | Ala | Thr | |
| 370 | | | | | 375 | | | | | 380 | | | | | | |

| gca | cct | tct | caa | ggc | gga | gtt | ggt | cac | c | | | | | | | 1180 |
|---|---|---|---|---|---|---|---|---|---|---|---|---|---|---|---|---|
| Ala | Pro | Ser | Gln | Gly | Gly | Val | Gly | His | | | | | | | | |
| 385 | | | | | 390 | | | | | | | | | | | |

<210> SEQ ID NO 114
<211> LENGTH: 393
<212> TYPE: PRT
<213> ORGANISM: Artificial Sequence
<220> FEATURE:
<223> OTHER INFORMATION: Chimeric Protein

<400> SEQUENCE: 114

| | | | | | | | | | | | | |
|---|---|---|---|---|---|---|---|---|---|---|---|---|
| Ala | Gln | Lys | Gly | Ala | Glu | Ser | Ile | Gly | Ser | Gln | Lys | Glu | Asn | Asp | Leu |
| 1 | | | | 5 | | | | | 10 | | | | | 15 | |

| | | | | | | | | | | | | |
|---|---|---|---|---|---|---|---|---|---|---|---|---|
| Asn | Leu | Glu | Asp | Ser | Ser | Lys | Lys | Ser | His | Gln | Asn | Ala | Lys | Gln | Asp |
| | | | 20 | | | | | 25 | | | | | 30 | | |

| | | | | | | | | | | | | |
|---|---|---|---|---|---|---|---|---|---|---|---|---|
| Leu | Pro | Ala | Val | Thr | Glu | Asp | Ser | Val | Ser | Leu | Phe | Asn | Gly | Asn | Lys |
| | | 35 | | | | | 40 | | | | | 45 | | | |

| | | | | | | | | | | | | |
|---|---|---|---|---|---|---|---|---|---|---|---|---|
| Ile | Phe | Val | Ser | Lys | Glu | Lys | Asn | Ser | Ser | Gly | Lys | Tyr | Asp | Leu | Arg |
| 50 | | | | | 55 | | | | | 60 | | | | | |

| | | | | | | | | | | | | |
|---|---|---|---|---|---|---|---|---|---|---|---|---|
| Ala | Thr | Ile | Asp | Gln | Val | Glu | Leu | Lys | Gly | Thr | Ser | Asp | Lys | Asn | Asn |
| 65 | | | | 70 | | | | | 75 | | | | | 80 | |

| | | | | | | | | | | | | |
|---|---|---|---|---|---|---|---|---|---|---|---|---|
| Gly | Ser | Gly | Thr | Leu | Glu | Gly | Ser | Lys | Pro | Asp | Lys | Ser | Lys | Val | Lys |
| | | | | 85 | | | | | 90 | | | | | 95 | |

| | | | | | | | | | | | | |
|---|---|---|---|---|---|---|---|---|---|---|---|---|
| Leu | Thr | Val | Ser | Ala | Asp | Leu | Asn | Thr | Val | Thr | Leu | Glu | Ala | Phe | Asp |
| | | | 100 | | | | | 105 | | | | | 110 | | |

| | | | | | | | | | | | | |
|---|---|---|---|---|---|---|---|---|---|---|---|---|
| Ala | Ser | Asn | Gln | Lys | Ile | Ser | Ser | Lys | Val | Thr | Lys | Lys | Gln | Gly | Ser |
| | | 115 | | | | | 120 | | | | | 125 | | | |

| | | | | | | | | | | | | |
|---|---|---|---|---|---|---|---|---|---|---|---|---|
| Ile | Thr | Glu | Glu | Thr | Leu | Lys | Ala | Asn | Lys | Leu | Asp | Ser | Lys | Lys | Leu |
| 130 | | | | | 135 | | | | | 140 | | | | | |

```
Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
            165                 170                 175

Glu Gly Ser Leu Val Val Gly Lys Thr Thr Val Glu Ile Lys Glu Gly
            180                 185                 190

Thr Val Thr Leu Lys Arg Glu Ile Glu Lys Asp Gly Lys Val Lys Val
        195                 200                 205

Phe Leu Asn Asp Thr Ala Gly Ser Asn Lys Lys Thr Gly Lys Trp Glu
    210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
            260                 265                 270

Ser Glu Leu Lys Asn Ala Leu Lys Gly His Pro Met Ala Gln Tyr Asn
        275                 280                 285

Gln Met His Met Leu Ser Asn Lys Ser Ala Ser Gln Asn Val Arg Thr
    290                 295                 300

Ala Glu Glu Leu Gly Met Gln Pro Ala Lys Ile Asn Thr Pro Ala Ser
305                 310                 315                 320

Leu Ser Gly Leu Gln Ala Ser Trp Thr Leu Arg Val His Val Gly Ala
                325                 330                 335

Thr Gln Asp Glu Ala Ile Ala Val Asn Ile Tyr Ala Ala Asn Val Ala
            340                 345                 350

Asn Leu Phe Ser Gly Glu Gly Ala Gln Thr Ala Gln Ala Ala Pro Val
        355                 360                 365

Gln Glu Gly Val Gln Gln Glu Gly Ala Gln Gln Pro Ala Pro Ala Thr
    370                 375                 380

Ala Pro Ser Gln Gly Gly Val Gly His
385                 390

<210> SEQ ID NO 115
<211> LENGTH: 1363
<212> TYPE: DNA
<213> ORGANISM: Artificial Sequence
<220> FEATURE:
<221> NAME/KEY: CDS
<222> LOCATION: (1)...(1362)
<223> OTHER INFORMATION: Chimeric nucleic acid

<400> SEQUENCE: 115 gca caa aaa ggt gct gag tca att ggt tct caa aaa gaa aat gat cta      48
Ala Gln Lys Gly Ala Glu Ser Ile Gly Ser Gln Lys Glu Asn Asp Leu
1               5                   10                  15 aac ctt gaa gac tct agt aaa aaa tca cat caa aac gct aaa caa gac      96
Asn Leu Glu Asp Ser Ser Lys Lys Ser His Gln Asn Ala Lys Gln Asp
            20                  25                  30 ctt cct gcg gtg aca gaa gac tca gtg tct ttg ttt aat ggt aat aaa     144
Leu Pro Ala Val Thr Glu Asp Ser Val Ser Leu Phe Asn Gly Asn Lys
        35                  40                  45 att ttt gta agc aaa gaa aaa aat agc tcc ggc aaa tat gat tta aga     192
Ile Phe Val Ser Lys Glu Lys Asn Ser Ser Gly Lys Tyr Asp Leu Arg
    50                  55                  60 gca aca att gat cag gtt gaa ctt aaa gga act tcc gat aaa aac aat     240
Ala Thr Ile Asp Gln Val Glu Leu Lys Gly Thr Ser Asp Lys Asn Asn
```

-continued

```
                65                  70                  75                  80 ggt tct gga acc ctt gaa ggt tca aag cct gac aag agt aaa gta aaa        288
Gly Ser Gly Thr Leu Glu Gly Ser Lys Pro Asp Lys Ser Lys Val Lys
                    85                  90                  95 tta aca gtt tct gct gat tta aac aca gta acc tta gaa gca ttt gat        336
Leu Thr Val Ser Ala Asp Leu Asn Thr Val Thr Leu Glu Ala Phe Asp
                    100                 105                 110 gcc agc aac caa aaa att tca agt aaa gtt act aaa aaa cag ggg tca        384
Ala Ser Asn Gln Lys Ile Ser Ser Lys Val Thr Lys Lys Gln Gly Ser
                    115                 120                 125 ata aca gag gaa act ctc aaa gct aat aaa tta gac tca aag aaa tta        432
Ile Thr Glu Glu Thr Leu Lys Ala Asn Lys Leu Asp Ser Lys Lys Leu
    130                 135                 140 aca aga tca aac gga act aca ctt gaa tac tca caa ata aca gat gct        480
Thr Arg Ser Asn Gly Thr Thr Leu Glu Tyr Ser Gln Ile Thr Asp Ala
145                 150                 155                 160 gac aat gct aca aaa gca gta gaa act cta aaa aat agc att aag ctt        528
Asp Asn Ala Thr Lys Ala Val Glu Thr Leu Lys Asn Ser Ile Lys Leu
                    165                 170                 175 gaa gga agt ctt gta gtc gga aaa aca aca gtg gaa att aaa gaa ggt        576
Glu Gly Ser Leu Val Val Gly Lys Thr Thr Val Glu Ile Lys Glu Gly
                    180                 185                 190 act gtt act cta aaa aga gaa att gaa aaa gat gga aaa gta aaa gtc        624
Thr Val Thr Leu Lys Arg Glu Ile Glu Lys Asp Gly Lys Val Lys Val
                    195                 200                 205 ttt ttg aat gac act gca ggt tct aac aaa aaa aca ggt aaa tgg gaa        672
Phe Leu Asn Asp Thr Ala Gly Ser Asn Lys Lys Thr Gly Lys Trp Glu
    210                 215                 220 gac agt act agc act tta aca att agt gct gac agc aaa aaa act aaa        720
Asp Ser Thr Ser Thr Leu Thr Ile Ser Ala Asp Ser Lys Lys Thr Lys
225                 230                 235                 240 gat ttg gtg ttc tta aca gat ggt aca att aca gta caa caa tac aac        768
Asp Leu Val Phe Leu Thr Asp Gly Thr Ile Thr Val Gln Gln Tyr Asn
                    245                 250                 255 aca gct gga acc agc cta gaa gga tca gca agt gaa att aaa aat ctt        816
Thr Ala Gly Thr Ser Leu Glu Gly Ser Ala Ser Glu Ile Lys Asn Leu
                    260                 265                 270 tca gag ctt aaa aac gct tta aaa ggt cac ccc atg gct caa tat aac        864
Ser Glu Leu Lys Asn Ala Leu Lys Gly His Pro Met Ala Gln Tyr Asn
                    275                 280                 285 caa atg cac atg tta tca aac aaa tct gct tct caa aat gta aga aca        912
Gln Met His Met Leu Ser Asn Lys Ser Ala Ser Gln Asn Val Arg Thr
                    290                 295                 300 gct gaa gag ctt gga atg cag cct gca aaa att aac aca cca gca tca        960
Ala Glu Glu Leu Gly Met Gln Pro Ala Lys Ile Asn Thr Pro Ala Ser
305                 310                 315                 320 ctt tca ggg ctt caa gcg tct tgg act tta aga gtt cat gtt gga gca       1008
Leu Ser Gly Leu Gln Ala Ser Trp Thr Leu Arg Val His Val Gly Ala
                    325                 330                 335 acc caa gat gaa gct att gct gta aat att tat gca gct aat gtt gca       1056
Thr Gln Asp Glu Ala Ile Ala Val Asn Ile Tyr Ala Ala Asn Val Ala
                    340                 345                 350 aat ctt ttc tct ggt gag gga gct caa act gct cag gct gca ccg gtt       1104
Asn Leu Phe Ser Gly Glu Gly Ala Gln Thr Ala Gln Ala Ala Pro Val
                    355                 360                 365 caa gag ggt gtt caa cag gaa gga gct caa cag cca gca cct gct aca       1152
Gln Glu Gly Val Gln Gln Glu Gly Ala Gln Gln Pro Ala Pro Ala Thr
                    370                 375                 380 gca cct tct caa ggc gga gtt aat tct cct gtt aat gtt aca act aca       1200
```

```
Ala Pro Ser Gln Gly Gly Val Asn Ser Pro Val Asn Val Thr Thr Thr
385                 390                 395                 400 gtt gat gct aat aca tca ctt gct aaa att gaa aat gct att aga atg    1248
Val Asp Ala Asn Thr Ser Leu Ala Lys Ile Glu Asn Ala Ile Arg Met
                405                 410                 415 ata agt gat caa agg gca aat tta ggt gct ttc caa aat aga ctt gaa    1296
Ile Ser Asp Gln Arg Ala Asn Leu Gly Ala Phe Gln Asn Arg Leu Glu
            420                 425                 430 tct ata aag aat agt act gag tat gca att gaa aat cta aaa gca tct    1344
Ser Ile Lys Asn Ser Thr Glu Tyr Ala Ile Glu Asn Leu Lys Ala Ser
        435                 440                 445 tat gct caa ata ggt cac c                                          1363
Tyr Ala Gln Ile Gly His
    450

<210> SEQ ID NO 116
<211> LENGTH: 454
<212> TYPE: PRT
<213> ORGANISM: Artificial Sequence
<220> FEATURE:
<223> OTHER INFORMATION: Chimeric Protein

<400> SEQUENCE: 116

Ala Gln Lys Gly Ala Glu Ser Ile Gly Ser Gln Lys Glu Asn Asp Leu
1               5                   10                  15

Asn Leu Glu Asp Ser Ser Lys Lys Ser His Gln Asn Ala Lys Gln Asp
            20                  25                  30

Leu Pro Ala Val Thr Glu Asp Ser Val Ser Leu Phe Asn Gly Asn Lys
        35                  40                  45

Ile Phe Val Ser Lys Glu Lys Asn Ser Ser Gly Lys Tyr Asp Leu Arg
    50                  55                  60

Ala Thr Ile Asp Gln Val Glu Leu Lys Gly Thr Ser Asp Lys Asn Asn
65                  70                  75                  80

Gly Ser Gly Thr Leu Glu Gly Ser Lys Pro Asp Lys Ser Lys Val Lys
                85                  90                  95

Leu Thr Val Ser Ala Asp Leu Asn Thr Val Thr Leu Glu Ala Phe Asp
            100                 105                 110

Ala Ser Asn Gln Lys Ile Ser Ser Lys Val Thr Lys Lys Gln Gly Ser
        115                 120                 125

Ile Thr Glu Glu Thr Leu Lys Ala Asn Lys Leu Asp Ser Lys Lys Leu
    130                 135                 140

Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
                165                 170                 175

Glu Gly Ser Leu Val Val Gly Lys Thr Thr Val Glu Ile Lys Glu Gly
            180                 185                 190

Thr Val Thr Leu Lys Arg Glu Ile Glu Lys Asp Gly Lys Val Lys Val
        195                 200                 205

Phe Leu Asn Asp Thr Ala Gly Ser Asn Lys Lys Thr Gly Lys Trp Glu
    210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
            260                 265                 270
```

-continued

```
Ser Glu Leu Lys Asn Ala Leu Lys Gly His Pro Met Ala Gln Tyr Asn
        275                 280                 285

Gln Met His Met Leu Ser Asn Lys Ser Ala Ser Gln Asn Val Arg Thr
    290                 295                 300

Ala Glu Glu Leu Gly Met Gln Pro Ala Lys Ile Asn Thr Pro Ala Ser
305                 310                 315                 320

Leu Ser Gly Leu Gln Ala Ser Trp Thr Leu Arg Val His Val Gly Ala
                325                 330                 335

Thr Gln Asp Glu Ala Ile Ala Val Asn Ile Tyr Ala Ala Asn Val Ala
            340                 345                 350

Asn Leu Phe Ser Gly Glu Gly Ala Gln Thr Ala Gln Ala Ala Pro Val
        355                 360                 365

Gln Glu Gly Val Gln Gln Gly Ala Gln Gln Pro Ala Pro Ala Thr
    370                 375                 380

Ala Pro Ser Gln Gly Gly Val Asn Ser Pro Val Asn Val Thr Thr Thr
385                 390                 395                 400

Val Asp Ala Asn Thr Ser Leu Ala Lys Ile Glu Asn Ala Ile Arg Met
                405                 410                 415

Ile Ser Asp Gln Arg Ala Asn Leu Gly Ala Phe Gln Asn Arg Leu Glu
            420                 425                 430

Ser Ile Lys Asn Ser Thr Glu Tyr Ala Ile Glu Asn Leu Lys Ala Ser
        435                 440                 445

Tyr Ala Gln Ile Gly His
    450
```

<210> SEQ ID NO 117
<211> LENGTH: 1141
<212> TYPE: DNA
<213> ORGANISM: Artificial Sequence
<220> FEATURE:
<221> NAME/KEY: CDS
<222> LOCATION: (1)...(1140)
<223> OTHER INFORMATION: Chimeric nucleic acid

<400> SEQUENCE: 117

```
gca caa aaa ggt gct gag tca att ggt tct caa aaa gaa aat gat cta      48
Ala Gln Lys Gly Ala Glu Ser Ile Gly Ser Gln Lys Glu Asn Asp Leu
1               5                   10                  15 aac ctt gaa gac tct agt aaa aaa tca cat caa aac gct aaa caa gac      96
Asn Leu Glu Asp Ser Ser Lys Lys Ser His Gln Asn Ala Lys Gln Asp
                20                  25                  30 ctt cct gcg gtg aca gaa gac tca gtg tct ttg ttt aat ggt aat aaa     144
Leu Pro Ala Val Thr Glu Asp Ser Val Ser Leu Phe Asn Gly Asn Lys
            35                  40                  45 att ttt gta agc aaa gaa aaa aat agc tcc ggc aaa tat gat tta aga     192
Ile Phe Val Ser Lys Glu Lys Asn Ser Ser Gly Lys Tyr Asp Leu Arg
        50                  55                  60 gca aca att gat cag gtt gaa ctt aaa gga act tcc gat aaa aac aat     240
Ala Thr Ile Asp Gln Val Glu Leu Lys Gly Thr Ser Asp Lys Asn Asn
65                  70                  75                  80 ggt tct gga acc ctt gaa ggt tca aag cct gac aag agt aaa gta aaa     288
Gly Ser Gly Thr Leu Glu Gly Ser Lys Pro Asp Lys Ser Lys Val Lys
                85                  90                  95 tta aca gtt tct gct gat tta aac aca gta acc tta gaa gca ttt gat     336
Leu Thr Val Ser Ala Asp Leu Asn Thr Val Thr Leu Glu Ala Phe Asp
            100                 105                 110 gcc agc aac caa aaa att tca agt aaa gtt act aaa aaa cag ggg tca     384
Ala Ser Asn Gln Lys Ile Ser Ser Lys Val Thr Lys Lys Gln Gly Ser
```

```
                    115                 120                 125
ata aca gag gaa act ctc aaa gct aat aaa tta gac tca aag aaa tta     432
Ile Thr Glu Glu Thr Leu Lys Ala Asn Lys Leu Asp Ser Lys Lys Leu
    130                 135                 140 aca aga tca aac gga act aca ctt gaa tac tca caa ata aca gat gct     480
Thr Arg Ser Asn Gly Thr Thr Leu Glu Tyr Ser Gln Ile Thr Asp Ala
145                 150                 155                 160 gac aat gct aca aaa gca gta gaa act cta aaa aat agc att aag ctt     528
Asp Asn Ala Thr Lys Ala Val Glu Thr Leu Lys Asn Ser Ile Lys Leu
                165                 170                 175 gaa gga agt ctt gta gtc gga aaa aca aca gtg gaa att aaa gaa ggt     576
Glu Gly Ser Leu Val Val Gly Lys Thr Thr Val Glu Ile Lys Glu Gly
            180                 185                 190 act gtt act cta aaa aga gaa att gaa aaa gat gga aaa gta aaa gtc     624
Thr Val Thr Leu Lys Arg Glu Ile Glu Lys Asp Gly Lys Val Lys Val
        195                 200                 205 ttt ttg aat gac act gca ggt tct aac aaa aaa aca ggt aaa tgg gaa     672
Phe Leu Asn Asp Thr Ala Gly Ser Asn Lys Lys Thr Gly Lys Trp Glu
    210                 215                 220 gac agt act agc act tta aca att agt gct gac agc aaa aaa act aaa     720
Asp Ser Thr Ser Thr Leu Thr Ile Ser Ala Asp Ser Lys Lys Thr Lys
225                 230                 235                 240 gat ttg gtg ttc tta aca gat ggt aca att aca gta caa caa tac aac     768
Asp Leu Val Phe Leu Thr Asp Gly Thr Ile Thr Val Gln Gln Tyr Asn
                245                 250                 255 aca gct gga acc agc cta gaa gga tca gca agt gaa att aaa aat ctt     816
Thr Ala Gly Thr Ser Leu Glu Gly Ser Ala Ser Glu Ile Lys Asn Leu
            260                 265                 270 tca gag ctt aaa aac gct tta aaa ggt cac ccc atg gct tct caa aat     864
Ser Glu Leu Lys Asn Ala Leu Lys Gly His Pro Met Ala Ser Gln Asn
        275                 280                 285 gta aga aca gct gaa gag ctt gga atg cag cct gca aaa att aac aca     912
Val Arg Thr Ala Glu Glu Leu Gly Met Gln Pro Ala Lys Ile Asn Thr
    290                 295                 300 cca gca tca ctt tca ggg ctt caa gcg tct tgg act tta aga gtt cat     960
Pro Ala Ser Leu Ser Gly Leu Gln Ala Ser Trp Thr Leu Arg Val His
305                 310                 315                 320 gtt gga gca acc caa gat gaa gct att gct gta aat att tat gca gct    1008
Val Gly Ala Thr Gln Asp Glu Ala Ile Ala Val Asn Ile Tyr Ala Ala
                325                 330                 335 aat gtt gca aat ctt ttc tct ggt gag gga gct caa act gct cag gct    1056
Asn Val Ala Asn Leu Phe Ser Gly Glu Gly Ala Gln Thr Ala Gln Ala
            340                 345                 350 gca ccg gtt caa gag ggt gtt caa cag gaa gga gct caa cag cca gca    1104
Ala Pro Val Gln Glu Gly Val Gln Gln Glu Gly Ala Gln Gln Pro Ala
        355                 360                 365 cct gct aca gca cct tct caa ggc gga gtt ggt cac c                  1141
Pro Ala Thr Ala Pro Ser Gln Gly Gly Val Gly His
    370                 375                 380

<210> SEQ ID NO 118
<211> LENGTH: 380
<212> TYPE: PRT
<213> ORGANISM: Artificial Sequence
<220> FEATURE:
<223> OTHER INFORMATION: Chimeric Protein

<400> SEQUENCE: 118

Ala Gln Lys Gly Ala Glu Ser Ile Gly Ser Gln Lys Glu Asn Asp Leu
1               5                   10                  15
```

```
Asn Leu Glu Asp Ser Ser Lys Lys Ser His Gln Asn Ala Lys Gln Asp
            20                  25                  30

Leu Pro Ala Val Thr Glu Asp Ser Val Ser Leu Phe Asn Gly Asn Lys
        35                  40                  45

Ile Phe Val Ser Lys Glu Lys Asn Ser Ser Gly Lys Tyr Asp Leu Arg
 50                  55                  60

Ala Thr Ile Asp Gln Val Glu Leu Lys Gly Thr Ser Asp Lys Asn Asn
 65                  70                  75                  80

Gly Ser Gly Thr Leu Glu Gly Ser Lys Pro Asp Lys Ser Lys Val Lys
                85                  90                  95

Leu Thr Val Ser Ala Asp Leu Asn Thr Val Thr Leu Glu Ala Phe Asp
            100                 105                 110

Ala Ser Asn Gln Lys Ile Ser Ser Lys Val Thr Lys Gln Gly Ser
        115                 120                 125

Ile Thr Glu Glu Thr Leu Lys Ala Asn Lys Leu Asp Ser Lys Lys Leu
130                 135                 140

Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
                165                 170                 175

Glu Gly Ser Leu Val Val Gly Lys Thr Thr Val Glu Ile Lys Glu Gly
            180                 185                 190

Thr Val Thr Leu Lys Arg Glu Ile Glu Lys Asp Gly Lys Val Lys Val
        195                 200                 205

Phe Leu Asn Asp Thr Ala Gly Ser Asn Lys Lys Thr Gly Lys Trp Glu
210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
            260                 265                 270

Ser Glu Leu Lys Asn Ala Leu Lys Gly His Pro Met Ala Ser Gln Asn
        275                 280                 285

Val Arg Thr Ala Glu Glu Leu Gly Met Gln Pro Ala Lys Ile Asn Thr
290                 295                 300

Pro Ala Ser Leu Ser Gly Leu Gln Ala Ser Trp Thr Leu Arg Val His
305                 310                 315                 320

Val Gly Ala Thr Gln Asp Glu Ala Ile Ala Val Asn Ile Tyr Ala Ala
                325                 330                 335

Asn Val Ala Asn Leu Phe Ser Gly Glu Gly Ala Gln Thr Ala Gln Ala
            340                 345                 350

Ala Pro Val Gln Glu Gly Val Gln Gln Glu Gly Ala Gln Gln Pro Ala
        355                 360                 365

Pro Ala Thr Ala Pro Ser Gln Gly Gly Val Gly His
370                 375                 380

<210> SEQ ID NO 119
<211> LENGTH: 1324
<212> TYPE: DNA
<213> ORGANISM: Artificial Sequence
<220> FEATURE:
<221> NAME/KEY: CDS
<222> LOCATION: (1)...(1323)
<223> OTHER INFORMATION: Chimeric nucleic acid
```

```
<400> SEQUENCE: 119 gca caa aaa ggt gct gag tca att ggt tct caa aaa gaa aat gat cta      48
Ala Gln Lys Gly Ala Glu Ser Ile Gly Ser Gln Lys Glu Asn Asp Leu
 1               5                  10                  15 aac ctt gaa gac tct agt aaa aaa tca cat caa aac gct aaa caa gac      96
Asn Leu Glu Asp Ser Ser Lys Lys Ser His Gln Asn Ala Lys Gln Asp
             20                  25                  30 ctt cct gcg gtg aca gaa gac tca gtg tct ttg ttt aat ggt aat aaa     144
Leu Pro Ala Val Thr Glu Asp Ser Val Ser Leu Phe Asn Gly Asn Lys
         35                  40                  45 att ttt gta agc aaa gaa aaa aat agc tcc ggc aaa tat gat tta aga     192
Ile Phe Val Ser Lys Glu Lys Asn Ser Ser Gly Lys Tyr Asp Leu Arg
     50                  55                  60 gca aca att gat cag gtt gaa ctt aaa gga act tcc gat aaa aac aat     240
Ala Thr Ile Asp Gln Val Glu Leu Lys Gly Thr Ser Asp Lys Asn Asn
 65                  70                  75                  80 ggt tct gga acc ctt gaa ggt tca aag cct gac aag agt aaa gta aaa     288
Gly Ser Gly Thr Leu Glu Gly Ser Lys Pro Asp Lys Ser Lys Val Lys
                 85                  90                  95 tta aca gtt tct gct gat tta aac aca gta acc tta gaa gca ttt gat     336
Leu Thr Val Ser Ala Asp Leu Asn Thr Val Thr Leu Glu Ala Phe Asp
            100                 105                 110 gcc agc aac caa aaa att tca agt aaa gtt act aaa aaa cag ggg tca     384
Ala Ser Asn Gln Lys Ile Ser Ser Lys Val Thr Lys Lys Gln Gly Ser
        115                 120                 125 ata aca gag gaa act ctc aaa gct aat aaa tta gac tca aag aaa tta     432
Ile Thr Glu Glu Thr Leu Lys Ala Asn Lys Leu Asp Ser Lys Lys Leu
    130                 135                 140 aca aga tca aac gga act aca ctt gaa tac tca caa ata aca gat gct     480
Thr Arg Ser Asn Gly Thr Thr Leu Glu Tyr Ser Gln Ile Thr Asp Ala
145                 150                 155                 160 gac aat gct aca aaa gca gta gaa act cta aaa aat agc att aag ctt     528
Asp Asn Ala Thr Lys Ala Val Glu Thr Leu Lys Asn Ser Ile Lys Leu
                165                 170                 175 gaa gga agt ctt gta gtc gga aaa aca aca gtg gaa att aaa gaa ggt     576
Glu Gly Ser Leu Val Val Gly Lys Thr Thr Val Glu Ile Lys Glu Gly
            180                 185                 190 act gtt act cta aaa aga gaa att gaa aaa gat gga aaa gta aaa gtc     624
Thr Val Thr Leu Lys Arg Glu Ile Glu Lys Asp Gly Lys Val Lys Val
        195                 200                 205 ttt ttg aat gac act gca ggt tct aac aaa aaa aca ggt aaa tgg gaa     672
Phe Leu Asn Asp Thr Ala Gly Ser Asn Lys Lys Thr Gly Lys Trp Glu
    210                 215                 220 gac agt act agc act tta aca att agt gct gac agc aaa aaa act aaa     720
Asp Ser Thr Ser Thr Leu Thr Ile Ser Ala Asp Ser Lys Lys Thr Lys
225                 230                 235                 240 gat ttg gtg ttc tta aca gat ggt aca att aca gta caa caa tac aac     768
Asp Leu Val Phe Leu Thr Asp Gly Thr Ile Thr Val Gln Gln Tyr Asn
                245                 250                 255 aca gct gga acc agc cta gaa gga tca gca agt gaa att aaa aat ctt     816
Thr Ala Gly Thr Ser Leu Glu Gly Ser Ala Ser Glu Ile Lys Asn Leu
            260                 265                 270 tca gag ctt aaa aac gct tta aaa ggt cac ccc atg gct tct caa aat     864
Ser Glu Leu Lys Asn Ala Leu Lys Gly His Pro Met Ala Ser Gln Asn
        275                 280                 285 gta aga aca gct gaa gag ctt gga atg cag cct gca aaa att aac aca     912
Val Arg Thr Ala Glu Glu Leu Gly Met Gln Pro Ala Lys Ile Asn Thr
    290                 295                 300 cca gca tca ctt tca ggg ctt caa gcg tct tgg act tta aga gtt cat     960
```

-continued

```
Pro Ala Ser Leu Ser Gly Leu Gln Ala Ser Trp Thr Leu Arg Val His
305                 310                 315                 320 gtt gga gca acc caa gat gaa gct att gct gta aat att tat gca gct      1008
Val Gly Ala Thr Gln Asp Glu Ala Ile Ala Val Asn Ile Tyr Ala Ala
                325                 330                 335 aat gtt gca aat ctt ttc tct ggt gag gga gct caa act gct cag gct      1056
Asn Val Ala Asn Leu Phe Ser Gly Glu Gly Ala Gln Thr Ala Gln Ala
            340                 345                 350 gca ccg gtt caa gag ggt gtt caa cag gaa gga gct caa cag cca gca      1104
Ala Pro Val Gln Glu Gly Val Gln Gln Glu Gly Ala Gln Gln Pro Ala
        355                 360                 365 cct gct aca gca cct tct caa ggc gga gtt aat tct cct gtt aat gtt      1152
Pro Ala Thr Ala Pro Ser Gln Gly Gly Val Asn Ser Pro Val Asn Val
    370                 375                 380 aca act aca gtt gat gct aat aca tca ctt gct aaa att gaa aat gct      1200
Thr Thr Thr Val Asp Ala Asn Thr Ser Leu Ala Lys Ile Glu Asn Ala
385                 390                 395                 400 att aga atg ata agt gat caa agg gca aat tta ggt gct ttc caa aat      1248
Ile Arg Met Ile Ser Asp Gln Arg Ala Asn Leu Gly Ala Phe Gln Asn
                405                 410                 415 aga ctt gaa tct ata aag aat agt act gag tat gca att gaa aat cta      1296
Arg Leu Glu Ser Ile Lys Asn Ser Thr Glu Tyr Ala Ile Glu Asn Leu
            420                 425                 430 aaa gca tct tat gct caa ata ggt cac c                                1324
Lys Ala Ser Tyr Ala Gln Ile Gly His
        435                 440
```

<210> SEQ ID NO 120
<211> LENGTH: 441
<212> TYPE: PRT
<213> ORGANISM: Artificial Sequence
<220> FEATURE:
<223> OTHER INFORMATION: Chimeric Protein

<400> SEQUENCE: 120

```
Ala Gln Lys Gly Ala Glu Ser Ile Gly Ser Gln Lys Glu Asn Asp Leu
1               5                   10                  15

Asn Leu Glu Asp Ser Ser Lys Lys Ser His Gln Asn Ala Lys Gln Asp
            20                  25                  30

Leu Pro Ala Val Thr Glu Asp Ser Val Ser Leu Phe Asn Gly Asn Lys
        35                  40                  45

Ile Phe Val Ser Lys Glu Lys Asn Ser Ser Gly Lys Tyr Asp Leu Arg
    50                  55                  60

Ala Thr Ile Asp Gln Val Glu Leu Lys Gly Thr Ser Asp Lys Asn Asn
65                  70                  75                  80

Gly Ser Gly Thr Leu Glu Gly Ser Lys Pro Asp Lys Ser Lys Val Lys
                85                  90                  95

Leu Thr Val Ser Ala Asp Leu Asn Thr Val Thr Leu Glu Ala Phe Asp
            100                 105                 110

Ala Ser Asn Gln Lys Ile Ser Ser Lys Val Thr Lys Gln Gly Ser
        115                 120                 125

Ile Thr Glu Glu Thr Leu Lys Ala Asn Lys Leu Asp Ser Lys Lys Leu
    130                 135                 140

Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
                165                 170                 175

Glu Gly Ser Leu Val Val Gly Lys Thr Thr Val Glu Ile Lys Glu Gly
```

```
                        180                 185                 190
Thr Val Thr Leu Lys Arg Glu Ile Glu Lys Asp Gly Lys Val Lys Val
            195                 200                 205

Phe Leu Asn Asp Thr Ala Gly Ser Asn Lys Lys Thr Gly Lys Trp Glu
210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
            260                 265                 270

Ser Glu Leu Lys Asn Ala Leu Lys Gly His Pro Met Ala Ser Gln Asn
        275                 280                 285

Val Arg Thr Ala Glu Glu Leu Gly Met Gln Pro Ala Lys Ile Asn Thr
    290                 295                 300

Pro Ala Ser Leu Ser Gly Leu Gln Ala Ser Trp Thr Leu Arg Val His
305                 310                 315                 320

Val Gly Ala Thr Gln Asp Glu Ala Ile Ala Val Asn Ile Tyr Ala Ala
                325                 330                 335

Asn Val Ala Asn Leu Phe Ser Gly Glu Gly Ala Gln Thr Ala Gln Ala
            340                 345                 350

Ala Pro Val Gln Glu Gly Val Gln Gln Gly Ala Gln Gln Pro Ala
        355                 360                 365

Pro Ala Thr Ala Pro Ser Gln Gly Gly Val Asn Ser Pro Val Asn Val
    370                 375                 380

Thr Thr Thr Val Asp Ala Asn Thr Ser Leu Ala Lys Ile Glu Asn Ala
385                 390                 395                 400

Ile Arg Met Ile Ser Asp Gln Arg Ala Asn Leu Gly Ala Phe Gln Asn
                405                 410                 415

Arg Leu Glu Ser Ile Lys Asn Ser Thr Glu Tyr Ala Ile Glu Asn Leu
            420                 425                 430

Lys Ala Ser Tyr Ala Gln Ile Gly His
        435                 440

<210> SEQ ID NO 121
<211> LENGTH: 1765
<212> TYPE: DNA
<213> ORGANISM: Artificial Sequence
<220> FEATURE:
<221> NAME/KEY: CDS
<222> LOCATION: (1)...(1764)
<223> OTHER INFORMATION: Chimeric nucleic acid

<400> SEQUENCE: 121 gca caa aaa ggt gct gag tca att ggt tct caa aaa gaa aat gat cta     48
Ala Gln Lys Gly Ala Glu Ser Ile Gly Ser Gln Lys Glu Asn Asp Leu
1               5                   10                  15 aac ctt gaa gac tct agt aaa aaa tca cat caa aac gct aaa caa gac    96
Asn Leu Glu Asp Ser Ser Lys Lys Ser His Gln Asn Ala Lys Gln Asp
            20                  25                  30 ctt cct gcg gtg aca gaa gac tca gtg tct ttg ttt aat ggt aat aaa   144
Leu Pro Ala Val Thr Glu Asp Ser Val Ser Leu Phe Asn Gly Asn Lys
        35                  40                  45 att ttt gta agc aaa gaa aaa aat agc tcc ggc aaa tat gat tta aga   192
Ile Phe Val Ser Lys Glu Lys Asn Ser Ser Gly Lys Tyr Asp Leu Arg
    50                  55                  60 gca aca att gat cag gtt gaa ctt aaa gga act tcc gat aaa aac aat   240
```

```
                                                                                    -continued Ala Thr Ile Asp Gln Val Glu Leu Lys Gly Thr Ser Asp Lys Asn Asn
 65                  70                  75                  80 ggt tct gga acc ctt gaa ggt tca aag cct gac aag agt aaa gta aaa        288
Gly Ser Gly Thr Leu Glu Gly Ser Lys Pro Asp Lys Ser Lys Val Lys
                 85                  90                  95 tta aca gtt tct gct gat tta aac aca gta acc tta gaa gca ttt gat        336
Leu Thr Val Ser Ala Asp Leu Asn Thr Val Thr Leu Glu Ala Phe Asp
             100                 105                 110 gcc agc aac caa aaa att tca agt aaa gtt act aaa aaa cag ggg tca        384
Ala Ser Asn Gln Lys Ile Ser Ser Lys Val Thr Lys Lys Gln Gly Ser
         115                 120                 125 ata aca gag gaa act ctc aaa gct aat aaa tta gac tca aag aaa tta        432
Ile Thr Glu Glu Thr Leu Lys Ala Asn Lys Leu Asp Ser Lys Lys Leu
    130                 135                 140 aca aga tca aac gga act aca ctt gaa tac tca caa ata aca gat gct        480
Thr Arg Ser Asn Gly Thr Thr Leu Glu Tyr Ser Gln Ile Thr Asp Ala
145                 150                 155                 160 gac aat gct aca aaa gca gta gaa act cta aaa aat agc att aag ctt        528
Asp Asn Ala Thr Lys Ala Val Glu Thr Leu Lys Asn Ser Ile Lys Leu
                165                 170                 175 gaa gga agt ctt gta gtc gga aaa aca aca gtg gaa att aaa gaa ggt        576
Glu Gly Ser Leu Val Val Gly Lys Thr Thr Val Glu Ile Lys Glu Gly
            180                 185                 190 act gtt act cta aaa aga gaa att gaa aaa gat gga aaa gta aaa gtc        624
Thr Val Thr Leu Lys Arg Glu Ile Glu Lys Asp Gly Lys Val Lys Val
        195                 200                 205 ttt ttg aat gac act gca ggt tct aac aaa aaa aca ggt aaa tgg gaa        672
Phe Leu Asn Asp Thr Ala Gly Ser Asn Lys Lys Thr Gly Lys Trp Glu
210                 215                 220 gac agt act agc act tta aca att agt gct gac agc aaa aaa act aaa        720
Asp Ser Thr Ser Thr Leu Thr Ile Ser Ala Asp Ser Lys Lys Thr Lys
225                 230                 235                 240 gat ttg gtg ttc tta aca gat ggt aca att aca gta caa caa tac aac        768
Asp Leu Val Phe Leu Thr Asp Gly Thr Ile Thr Val Gln Gln Tyr Asn
                245                 250                 255 aca gct gga acc agc cta gaa gga tca gca agt gaa att aaa aat ctt        816
Thr Ala Gly Thr Ser Leu Glu Gly Ser Ala Ser Glu Ile Lys Asn Leu
            260                 265                 270 tca gag ctt aaa aac gct tta aaa ggt cac ccc atg gga aat aat tca        864
Ser Glu Leu Lys Asn Ala Leu Lys Gly His Pro Met Gly Asn Asn Ser
        275                 280                 285 ggg aaa gat ggg aat aca tct gca aat tct gct gat gag tct gtt aaa        912
Gly Lys Asp Gly Asn Thr Ser Ala Asn Ser Ala Asp Glu Ser Val Lys
290                 295                 300 ggg cct aat ctt aca gaa ata agt aaa aaa att acg gat tct aat gcg        960
Gly Pro Asn Leu Thr Glu Ile Ser Lys Lys Ile Thr Asp Ser Asn Ala
305                 310                 315                 320 gtt tta ctt gct gtg aaa gag gtt gaa gcg ttg ctg tca tct ata gat       1008
Val Leu Leu Ala Val Lys Glu Val Glu Ala Leu Leu Ser Ser Ile Asp
                325                 330                 335 gaa att gct gct aaa gct att ggt aaa aaa ata cac caa aat aat ggt       1056
Glu Ile Ala Ala Lys Ala Ile Gly Lys Lys Ile His Gln Asn Asn Gly
            340                 345                 350 ttg gat acc gaa tat aat cac aat gga tca ttg tta gcg gga cgt tat       1104
Leu Asp Thr Glu Tyr Asn His Asn Gly Ser Leu Leu Ala Gly Arg Tyr
        355                 360                 365 gca ata tca acc cta ata aaa caa aaa tta gat gga ttg aaa aat gaa       1152
Ala Ile Ser Thr Leu Ile Lys Gln Lys Leu Asp Gly Leu Lys Asn Glu
370                 375                 380
```

-continued

| | | |
|---|---|---|
| gga tta aag gaa aaa att gat gcg gct aag aaa tgt tct gaa aca ttt<br>Gly Leu Lys Glu Lys Ile Asp Ala Ala Lys Lys Cys Ser Glu Thr Phe<br>385                           390                     395                      400 | | 1200 |
| act aat aaa tta aaa gaa aaa cac aca gat ctt ggt aaa gaa ggt gtt<br>Thr Asn Lys Leu Lys Glu Lys His Thr Asp Leu Gly Lys Glu Gly Val<br>                       405                      410                     415 | | 1248 |
| act gat gct gat gca aaa gaa gcc att tta aaa aca aat ggt act aaa<br>Thr Asp Ala Asp Ala Lys Glu Ala Ile Leu Lys Thr Asn Gly Thr Lys<br>             420                     425                     430 | | 1296 |
| act aaa ggt gct gaa gaa ctt gga aaa tta ttt gaa tca gta gag gtc<br>Thr Lys Gly Ala Glu Glu Leu Gly Lys Leu Phe Glu Ser Val Glu Val<br>                 435                   440                     445 | | 1344 |
| ttg tca aaa gca gct aaa gag atg ctt gct aat tca gtt aaa gag ctt<br>Leu Ser Lys Ala Ala Lys Glu Met Leu Ala Asn Ser Val Lys Glu Leu<br>450                           455                     460 | | 1392 |
| aca agc cct gtt gtg gca gaa agt cca aaa aaa cct ggt acc atg gct<br>Thr Ser Pro Val Val Ala Glu Ser Pro Lys Lys Pro Gly Thr Met Ala<br>465                           470                     475                     480 | | 1440 |
| caa tat aac caa atg cac atg tta tca aac aaa tct gct tct caa aat<br>Gln Tyr Asn Gln Met His Met Leu Ser Asn Lys Ser Ala Ser Gln Asn<br>                       485                      490                     495 | | 1488 |
| gta aga aca gct gaa gag ctt gga atg cag cct gca aaa att aac aca<br>Val Arg Thr Ala Glu Glu Leu Gly Met Gln Pro Ala Lys Ile Asn Thr<br>             500                     505                     510 | | 1536 |
| cca gca tca ctt tca ggg ctt caa gcg tct tgg act tta aga gtt cat<br>Pro Ala Ser Leu Ser Gly Leu Gln Ala Ser Trp Thr Leu Arg Val His<br>                 515                     520                     525 | | 1584 |
| gtt gga gca acc caa gat gaa gct att gct gta aat att tat gca gct<br>Val Gly Ala Thr Gln Asp Glu Ala Ile Ala Val Asn Ile Tyr Ala Ala<br>530                           535                     540 | | 1632 |
| aat gtt gca aat ctt ttc tct ggt gag gga gct caa act gct cag gct<br>Asn Val Ala Asn Leu Phe Ser Gly Glu Gly Ala Gln Thr Ala Gln Ala<br>545                           550                     555                     560 | | 1680 |
| gca ccg gtt caa gag ggt gtt caa cag gaa gga gct caa cag cca gca<br>Ala Pro Val Gln Glu Gly Val Gln Gln Glu Gly Ala Gln Gln Pro Ala<br>                       565                      570                     575 | | 1728 |
| cct gct aca gca cct tct caa ggc gga gtt ggt cac c<br>Pro Ala Thr Ala Pro Ser Gln Gly Gly Val Gly His<br>             580                     585 | | 1765 |

<210> SEQ ID NO 122
<211> LENGTH: 588
<212> TYPE: PRT
<213> ORGANISM: Artificial Sequence
<220> FEATURE:
<223> OTHER INFORMATION: Chimeric Protein

<400> SEQUENCE: 122

Ala Gln Lys Gly Ala Glu Ser Ile Gly Ser Gln Lys Glu Asn Asp Leu
1               5                   10                  15

Asn Leu Glu Asp Ser Ser Lys Lys Ser His Gln Asn Ala Lys Gln Asp
                20                  25                  30

Leu Pro Ala Val Thr Glu Asp Ser Val Ser Leu Phe Asn Gly Asn Lys
            35                  40                  45

Ile Phe Val Ser Lys Glu Lys Asn Ser Ser Gly Lys Tyr Asp Leu Arg
        50                  55                  60

Ala Thr Ile Asp Gln Val Glu Leu Lys Gly Thr Ser Asp Lys Asn Asn
65                  70                  75                  80

Gly Ser Gly Thr Leu Glu Gly Ser Lys Pro Asp Lys Ser Lys Val Lys
                85                  90                  95

```
Leu Thr Val Ser Ala Asp Leu Asn Thr Val Thr Leu Glu Ala Phe Asp
            100                 105                 110

Ala Ser Asn Gln Lys Ile Ser Ser Lys Val Thr Lys Gln Gly Ser
        115                 120                 125

Ile Thr Glu Thr Leu Lys Ala Asn Lys Leu Asp Ser Lys Lys Leu
        130                 135                 140

Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
                165                 170                 175

Glu Gly Ser Leu Val Val Gly Lys Thr Thr Val Glu Ile Lys Glu Gly
                180                 185                 190

Thr Val Thr Leu Lys Arg Glu Ile Glu Lys Asp Gly Lys Val Lys Val
                195                 200                 205

Phe Leu Asn Asp Thr Ala Gly Ser Asn Lys Lys Thr Gly Lys Trp Glu
        210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
                260                 265                 270

Ser Glu Leu Lys Asn Ala Leu Lys Gly His Pro Met Gly Asn Asn Ser
                275                 280                 285

Gly Lys Asp Gly Asn Thr Ser Ala Asn Ser Ala Asp Glu Ser Val Lys
        290                 295                 300

Gly Pro Asn Leu Thr Glu Ile Ser Lys Lys Ile Thr Asp Ser Asn Ala
305                 310                 315                 320

Val Leu Leu Ala Val Lys Glu Val Glu Ala Leu Leu Ser Ser Ile Asp
                325                 330                 335

Glu Ile Ala Ala Lys Ala Ile Gly Lys Lys Ile His Gln Asn Asn Gly
                340                 345                 350

Leu Asp Thr Glu Tyr Asn His Asn Gly Ser Leu Leu Ala Gly Arg Tyr
        355                 360                 365

Ala Ile Ser Thr Leu Ile Lys Gln Lys Leu Asp Gly Leu Lys Asn Glu
        370                 375                 380

Gly Leu Lys Glu Lys Ile Asp Ala Ala Lys Lys Cys Ser Glu Thr Phe
385                 390                 395                 400

Thr Asn Lys Leu Lys Glu Lys His Thr Asp Leu Gly Lys Glu Gly Val
                405                 410                 415

Thr Asp Ala Asp Ala Lys Glu Ala Ile Leu Lys Thr Asn Gly Thr Lys
                420                 425                 430

Thr Lys Gly Ala Glu Glu Leu Gly Lys Leu Phe Glu Ser Val Glu Val
        435                 440                 445

Leu Ser Lys Ala Ala Lys Glu Met Leu Ala Asn Ser Val Lys Glu Leu
        450                 455                 460

Thr Ser Pro Val Val Ala Glu Ser Pro Lys Lys Pro Gly Thr Met Ala
465                 470                 475                 480

Gln Tyr Asn Gln Met His Met Leu Ser Asn Lys Ser Ala Ser Gln Asn
                485                 490                 495

Val Arg Thr Ala Glu Glu Leu Gly Met Gln Pro Ala Lys Ile Asn Thr
                500                 505                 510
```

```
Pro Ala Ser Leu Ser Gly Leu Gln Ala Ser Trp Thr Leu Arg Val His
        515                 520                 525

Val Gly Ala Thr Gln Asp Glu Ala Ile Ala Val Asn Ile Tyr Ala Ala
            530                 535                 540

Asn Val Ala Asn Leu Phe Ser Gly Glu Gly Ala Gln Thr Ala Gln Ala
545                 550                 555                 560

Ala Pro Val Gln Glu Gly Val Gln Gln Glu Gly Ala Gln Gln Pro Ala
                565                 570                 575

Pro Ala Thr Ala Pro Ser Gln Gly Gly Val Gly His
            580                 585
```

<210> SEQ ID NO 123
<211> LENGTH: 704
<212> TYPE: DNA
<213> ORGANISM: Borrelia burgdorferi

<400> SEQUENCE: 123

```
ctactgttaa gtttattttt attgctctca atatcttgtt ctttagataa tgaaggtgta    60
aactcaaaag attacgagtc aaaaaaacag agtatactag gtgaattaaa tcagctattg   120
gggcaaacta caaattcact aaaagaagca aaaaatacaa cagataattt aaatgcatca   180
aatgaggcaa ataagttgt agaagcagtt ataagtgtgg ttaatttaat ttcatctgct    240
gcagatcagg taaaggtca acaacaaata tgcacgattt agctcaaatg cagaaatag    300
atttagaaaa aataaggaa tctagtgata agtaatagt tgcggctaat gttgcgaaag    360
aagcatataa ccttactaaa gcagtagaac aaaatatgca aaaactgtac aaagagcaag   420
aagagcaact aaaacactat ctgattctga tgaaacagaa cgagtttctg atgaaataaa   480
acaagctaaa gaggctgtag aaatagcttg gaaagccaca gtaaaagtaa aagatgagtt   540
aattgatgta gaaatgcag tcaaagaggc attggataaa ataaagacag aaaccgcgaa    600
caatacaaaa cttacagata tagaagaagt agcagagtta gtattacaga tagccaaaaa   660
tgtagcggaa atagcgcaag aagttgtggc cttgttaaat actt               704
```

<210> SEQ ID NO 124
<211> LENGTH: 704
<212> TYPE: DNA
<213> ORGANISM: Borrelia burgdorferi

<400> SEQUENCE: 124

```
      ctactgttaa gtttattttt attgctctca atatcttgtt atttagataa tgaaggtgta 60
      aactcaaaag attacgagtc aaaaaaacag agtatactag gtgaattaaa tcagctattg 120
      gggcaaacta caaattcact aaaagaagca aaaaatacaa cagataattt aaatgcatca 180
      aatgaggcaa ataagttgt agaagcagtt ataagtgtgg ttaatttaat ttcatctgct  240
      gcagatcagg taaaggtca acaacaaata tgcacgattt agctcaaatg cagaaatag   300
      atttagaaaa aataaggaa tctagtgata agtaatagt tgcggctaat gttgcgaaag   360
      aagcatataa ccttactaaa gcagtagaac aaaatatgca aaaactgtac aaagagcaag 420
      aagagcaact aaaacactat ctgattctga tgaaacagaa cgagtttctg atgaaataaa 480
      acaagctaaa gaggctgtag aaatagcttg gaaagccaca gtaaaagtaa aagatgagtt 540
      aattgatgta gaaatgcag tcaaagaggc attggataaa ataaagacag aaaccgcgaa  600
      caatacaaaa cttacagata tagaagaagt agcagagtta gtattacaaa tagccaaaaa 660
      tgtagcggaa atagcgcaag aagttgtggc cttgttaaat actt               704
```

<210> SEQ ID NO 125
<211> LENGTH: 704
<212> TYPE: DNA
<213> ORGANISM: Borrelia burgdorferi

<400> SEQUENCE: 125

```
ctactgctaa gtttattttt attgctctca atatctggtt ctttagataa tgaaggtgta    60
aactcaaaag attacgagtc aaaaaaacag agtatactag gtgaattaaa tcagctattg   120
```

-continued

```
gggcaaacta caaattcact aaaagaagca aaaaatacaa cagataattt aaatgcatca      180
aatgaggcaa ataaagttgt agaagcagtt ataagtgtgg ttaatttaat ttcatctgct      240
gcagatcagg tgaaaggtca acaacaaata tgcacgattt agctcaaatg cagaaaatag      300
atttagaaaa aataaaggaa tctagtgata agtaatagt tgcggctaat gttgcgaaag       360
aagcatataa ccttactaaa gcagtagaac aaaatatgca aaaactgtac aaagagcaag      420
aagagcaact aaaacactat ctgattctga tgaagcagaa cgagtttctg atgaaataaa      480
acaagctaaa gaggctgtag aaatagcttg gaaagccaca gtaaaagtaa agatgagtt      540 aattgatgta gaaaatgcag tcaaagaggc attggataaa ataaagacag aaccgcgaa       600 caatacaaaa cttacagata tagaagaagt agcagagtta gtattacaaa tagccaaaaa      660
tgtagcggaa atagcgcaag aagttgtggc cttgttaaat actt                       704
```

<210> SEQ ID NO 126
<211> LENGTH: 704
<212> TYPE: DNA
<213> ORGANISM: Borrelia burgdorferi

<400> SEQUENCE: 126

```
ctactgttaa gtttattttt attgctctca atatcttgtt ctttagataa tgaaggtgta       60
agctcaaaag attacgagtc aaaaaaacag agtatactag gtgaattaaa tcagctattg      120
gggcaaacta caaattcact aaaagaagca aaaaatacaa cagataattt aaatgcatca      180
aatgaggcaa ataaagttgt agaagcagtt ataagtgtgg ttaatttaat ttcatctgct      240
gcagatcagg tgaaaggtca acaacaaata tgcacgattt agctcaaatg cagaaaatag      300
atttagaaaa aataaaggaa tctagtgata agtaatagt tgcggctaat gttgcgaaag       360
aagcatataa ccttactaaa gcagtagaac aaaatatgca aaaactgtac aaagagcaag      420
aagagcaact aaaacactat ctgattctga tgaagcagaa cgagtttctg atgaaataaa      480
acaagctaaa gaggctgtag aaatagcttg gaaagccaca gtaaaagtaa agatgagtt      540 aattgatgta gaaaatgcag tcaaagaggc attggataaa ataaagacag gaaccgcgaa      600
caatacaaaa cttacagata tagaagaagt agcagagtta gtattacaaa tagccaaaaa      660
tgtagcggaa atagcgcaag aagttgtggc cttgttaaat actt                       704
```

<210> SEQ ID NO 127
<211> LENGTH: 1011
<212> TYPE: DNA
<213> ORGANISM: Borrelia burgdorferi
<220> FEATURE:
<221> NAME/KEY: CDS
<222> LOCATION: (1)...(1011)

<400> SEQUENCE: 127

```
atg att atc aat cat aat aca tca gct att aat gct tca aga aat aat       48
Met Ile Ile Asn His Asn Thr Ser Ala Ile Asn Ala Ser Arg Asn Asn
 1               5                  10                  15 ggc att aac gct gct aat ctt agt aaa act caa gaa aag ctt tct agt       96
Gly Ile Asn Ala Ala Asn Leu Ser Lys Thr Gln Glu Lys Leu Ser Ser
            20                  25                  30 ggc tac aga att aat cga gct tct gat gat gct gct ggc atg gga gtt      144
Gly Tyr Arg Ile Asn Arg Ala Ser Asp Asp Ala Ala Gly Met Gly Val
        35                  40                  45 tct ggt aag att aat gct caa ata aga ggt ttg tca caa gct tct aga      192
Ser Gly Lys Ile Asn Ala Gln Ile Arg Gly Leu Ser Gln Ala Ser Arg
    50                  55                  60
```

```
aat act tca aag gct att aat ttt att cag aca aca gaa ggg aat tta        240
Asn Thr Ser Lys Ala Ile Asn Phe Ile Gln Thr Thr Glu Gly Asn Leu
 65                  70                  75                  80 aat gaa gta gaa aaa gtc tta gta aga atg aag gaa ttg gca gtt caa        288
Asn Glu Val Glu Lys Val Leu Val Arg Met Lys Glu Leu Ala Val Gln
                 85                  90                  95 tca ggt aac ggc aca tat tca gat gca gac aga ggt tct ata caa att        336
Ser Gly Asn Gly Thr Tyr Ser Asp Ala Asp Arg Gly Ser Ile Gln Ile
            100                 105                 110 gaa ata gag caa ctt aca gac gaa att aat aga att gct gat caa gct        384
Glu Ile Glu Gln Leu Thr Asp Glu Ile Asn Arg Ile Ala Asp Gln Ala
        115                 120                 125 caa tat aac caa atg cac atg tta tca aac aaa tct gct tct caa aat        432
Gln Tyr Asn Gln Met His Met Leu Ser Asn Lys Ser Ala Ser Gln Asn
130                 135                 140 gta aga aca gct gaa gag ctt gga atg cag cct gca aaa att aac aca        480
Val Arg Thr Ala Glu Glu Leu Gly Met Gln Pro Ala Lys Ile Asn Thr
145                 150                 155                 160 cca gca tca ctt tca ggg ctt caa gcg tct tgg act tta aga gtt cat        528
Pro Ala Ser Leu Ser Gly Leu Gln Ala Ser Trp Thr Leu Arg Val His
                165                 170                 175 gtt gga gca acc caa gat gaa gct att gct gta aat att tat gca gct        576
Val Gly Ala Thr Gln Asp Glu Ala Ile Ala Val Asn Ile Tyr Ala Ala
            180                 185                 190 aat gtt gca aat ctt ttc tct ggt gag gga gct caa act gct cag gct        624
Asn Val Ala Asn Leu Phe Ser Gly Glu Gly Ala Gln Thr Ala Gln Ala
        195                 200                 205 gca ccg gtt caa gag ggt gtt caa cag gaa gga gct caa cag cca gca        672
Ala Pro Val Gln Glu Gly Val Gln Gln Glu Gly Ala Gln Gln Pro Ala
210                 215                 220 cct gct aca gca cct tct caa ggc gga gtt aat tct cct gtt aat gtt        720
Pro Ala Thr Ala Pro Ser Gln Gly Gly Val Asn Ser Pro Val Asn Val
225                 230                 235                 240 aca act aca gtt gat gct aat aca tca ctt gct aaa att gaa aat gct        768
Thr Thr Thr Val Asp Ala Asn Thr Ser Leu Ala Lys Ile Glu Asn Ala
                245                 250                 255 att aga atg ata agt gat caa agg gca aat tta ggt gct ttc caa aat        816
Ile Arg Met Ile Ser Asp Gln Arg Ala Asn Leu Gly Ala Phe Gln Asn
            260                 265                 270 aga ctt gaa tct ata aag aat agt act gag tat gca att gaa aat cta        864
Arg Leu Glu Ser Ile Lys Asn Ser Thr Glu Tyr Ala Ile Glu Asn Leu
        275                 280                 285 aaa gca tct tat gct caa ata aaa gat gct aca atg aca gat gag gtt        912
Lys Ala Ser Tyr Ala Gln Ile Lys Asp Ala Thr Met Thr Asp Glu Val
290                 295                 300 gta gca gca aca act aat atg att tta aca caa tct gca atg gca atg        960
Val Ala Ala Thr Thr Asn Met Ile Leu Thr Gln Ser Ala Met Ala Met
305                 310                 315                 320 att gcg cag gct aat caa gtt ccc caa tat gtt ttg tca ttg ctt aga       1008
Ile Ala Gln Ala Asn Gln Val Pro Gln Tyr Val Leu Ser Leu Leu Arg
                325                 330                 335 taa                                                                   1011
 *

<210> SEQ ID NO 128
<211> LENGTH: 336
<212> TYPE: PRT
<213> ORGANISM: Borrelia burgdorferi

<400> SEQUENCE: 128
```

```
Met Ile Ile Asn His Asn Thr Ser Ala Ile Asn Ala Ser Arg Asn Asn
  1               5                  10                  15

Gly Ile Asn Ala Ala Asn Leu Ser Lys Thr Gln Glu Lys Leu Ser Ser
                 20                  25                  30

Gly Tyr Arg Ile Asn Arg Ala Ser Asp Asp Ala Ala Gly Met Gly Val
             35                  40                  45

Ser Gly Lys Ile Asn Ala Gln Ile Arg Gly Leu Ser Gln Ala Ser Arg
 50                  55                  60

Asn Thr Ser Lys Ala Ile Asn Phe Ile Gln Thr Thr Glu Gly Asn Leu
 65                  70                  75                  80

Asn Glu Val Glu Lys Val Leu Val Arg Met Lys Glu Leu Ala Val Gln
                 85                  90                  95

Ser Gly Asn Gly Thr Tyr Ser Asp Ala Asp Arg Gly Ser Ile Gln Ile
                100                 105                 110

Glu Ile Glu Gln Leu Thr Asp Glu Ile Asn Arg Ile Ala Asp Gln Ala
             115                 120                 125

Gln Tyr Asn Gln Met His Met Leu Ser Asn Lys Ser Ala Ser Gln Asn
130                 135                 140

Val Arg Thr Ala Glu Glu Leu Gly Met Gln Pro Ala Lys Ile Asn Thr
145                 150                 155                 160

Pro Ala Ser Leu Ser Gly Leu Gln Ala Ser Trp Thr Leu Arg Val His
                165                 170                 175

Val Gly Ala Thr Gln Asp Glu Ala Ile Ala Val Asn Ile Tyr Ala Ala
            180                 185                 190

Asn Val Ala Asn Leu Phe Ser Gly Glu Gly Ala Gln Thr Ala Gln Ala
            195                 200                 205

Ala Pro Val Gln Glu Gly Val Gln Gln Glu Gly Ala Gln Gln Pro Ala
210                 215                 220

Pro Ala Thr Ala Pro Ser Gln Gly Gly Val Asn Ser Pro Val Asn Val
225                 230                 235                 240

Thr Thr Thr Val Asp Ala Asn Thr Ser Leu Ala Lys Ile Glu Asn Ala
            245                 250                 255

Ile Arg Met Ile Ser Asp Gln Arg Ala Asn Leu Gly Ala Phe Gln Asn
            260                 265                 270

Arg Leu Glu Ser Ile Lys Asn Ser Thr Glu Tyr Ala Ile Glu Asn Leu
            275                 280                 285

Lys Ala Ser Tyr Ala Gln Ile Lys Asp Ala Thr Met Thr Asp Glu Val
290                 295                 300

Val Ala Ala Thr Thr Asn Met Ile Leu Thr Gln Ser Ala Met Ala Met
305                 310                 315                 320

Ile Ala Gln Ala Asn Gln Val Pro Gln Tyr Val Leu Ser Leu Leu Arg
                325                 330                 335
```

<210> SEQ ID NO 129
<211> LENGTH: 1008
<212> TYPE: DNA
<213> ORGANISM: Borrelia burgdorferi

<400> SEQUENCE: 129

| | | | | |
|---|---|---|---|---|
| atgattatca atcataatac atcagctatt aatgcttcaa gaaataatgg cattaacgct | 60 |
| gctaatctta gtaaaactca agaaaagctt tctagtgggt acagaattaa tcgagcttct | 120 |
| gatgatgctg ctggcatggg agtttctggt aagattaatg ctcaaataag gggtttgtca | 180 |
| caagcttcta gaaatacttc aaaggctatt aattttattc agacaacaga agggaattta | 240 |

| | |
|---|---|
| aatgaagtag aaaaagtctt agtaagaatg aaggaattgg c

```
gctaatctta gtaaaaccca agagaagcct tctagtggtt acagaattaa tcgagcttct    120
gatgatgctg ctggtatggg ggtttctggc aagattaatg ctcaaataag aggcttatca    180
caagcttcta gaaacacttc aaaagctatc aattttattc agacaacaga aggaaattta    240
aatgaagtag aaaaagtttt agtaagaatg aaagaattag cagttcaatc aggtaacgga    300
acgtattcag actcagacag aggttctata cagattgaaa tagagcaact tacagacgaa    360
attaatagaa ttgctgatca ggctcaatat aaccaaatgc acatgttgtc aaacaaatct    420
gcttcccaaa atgtaaaaac agctgaagag cttggaatgc agcctgcaaa aattaacaca    480
ccagcatcac tttcaggatc tcaagcttct tggactttaa gagttcatgt gggagcaaat    540
caagatgaag caattgctgt aaatatttat tcagctaatg ttgcaaatct ttttgctggt    600
gagggagctc aagctgctca ggctgcacct gttcaagagg gtgctcaaga agaaggagct    660
cagcaaccaa cacctgctac agcacctact caaggtggag ttaattctcc tgttaatgtt    720
acaaccacag ttgatgctaa tacatcactt gctaaaatga aaatgctat tagaatgata    780 agtgatcaaa gagcaaattt aggtgctttc aaaatagac ttgaatctat aaagaatagc    840
actgagtatg ctattgaaaa tctaaaagca tcttatgctc aaataaaaga tgctacaatg    900
acagatgagg ttgtagcagc tacaactaaa agtattttaa ctcaatctgc aatggcaatg    960
attgcacagg ctaatcaagt tcctcaatat gttttgtcat tgcttaga             1008

<210> SEQ ID NO 132
<211> LENGTH: 822
<212> TYPE: DNA
<213> ORGANISM: Borrelia burgdorferi

<400> SEQUENCE: 132
atgaaaaaat atttattggg aataggtcta atattagcct aatagcatg taagcaaaat     60 gttagcagcc ttgacgagaa aaacagcgtt tcagtagatt tgcctggtga atgaaagtt    120 cttgtaagca agaaaaaaa caaagacggc aagtacgatc taattgcaac agtagacaag    180
cttgagctta aggaacttc tgataaaaac aatggatctg gagtacttga aggcgtaaaa    240
gctgacaaaa gtaaagtaaa attaacaatt tctgacgatc taggtcaaac cacacttgaa    300
gttttcaaag aagatggcaa aacactagta tcaaaaaaag taacttccaa agacaagtca    360
tcaacagaag aaaaattcaa tgaaaaaggt gaagtatctg aaaaaataat aacaagagca    420
gacggaacca gacttgaata cacaggaatt aaaagcgatg gatctggaaa agctaaagag    480
gttttaaaag gctatgttct tgaaggaact ctaactgctg aaaaaacaac attggtggtt    540
aaagaaggaa ctgttacttt aagcaaaaat atttcaaaat ctggggaagt ttcagttgaa    600
cttaatgaca ctgacagtag tgctgctact aaaaaaactg cagcttggaa ttcaggcact    660
tcaactttaa caattactgt aaacagtaaa aaaactaaag accttgtgtt tacaaaagaa    720
aacacaatta cagtacaaca atacgactca atggcacca attagagggg gtcagcagtt    780
gaaattacaa aacttgatga aattaaaaac gctttaaaat aa                       822

<210> SEQ ID NO 133
<211> LENGTH: 822
<212> TYPE: DNA
<213> ORGANISM: Borrelia burgdorferi

<400> SEQUENCE: 133
atgaaaaaat atttattggg aataggtcta atattagcct aatagcatg taagcaaaat     60 gttagcagcc ttgacgagaa aaacagcgtt tcagtagatt tgcctggtga atgaacgtt    120
```

```
cttgtaagca aagaaaaaaa caaagacggc aagtacgatc taattgcaac agtagacaag    180
cttgagctta aaggaacttc tgataaaaac aatggatctg gagtacttga aggcgtaaaa    240
gctgacaaaa gtaaagtaaa attaacaatt tctgacgatc taggtcaaac cacacttgaa    300
gttttcaaag aagatggcaa acactagta tcaaaaaaag taacttccaa agacaagtca     360
tcaacagaag aaaaattcaa tgaaaaaggt gaagtatctg aaaaaataat aacaagagca    420
gacggaacca gacttgaata cacagaaatt aaaagcgatg gatctggaaa agctaaagag    480
gttttaaaag gctatgttct tgaaggaact ctaactgctg aaaaaacaac attggtggtt    540
aaagaaggaa ctgttacttt aagcaaaaat atttcaaaat ctggggaagt ttcagttgaa    600
cttaatgaca ctgacagtag tgctgctact aaaaaaactg cagcttggaa ttcaggcact    660
tcaactttaa caattactgt aaacagtaaa aaaactaaag accttgtgtt tacaaaagaa    720
aacacaatta cagtacaaca atacgactca aatggcacca aattagaggg gtcagcagtt    780
gaaattacaa aacttgatga aattaaaaac gctttaaaat aa                       822

<210> SEQ ID NO 134
<211> LENGTH: 822
<212> TYPE: DNA
<213> ORGANISM: Borrelia burgdorferi

<400> SEQUENCE: 134
atgaaaaaat atttattggg aataggtcta atattagcct taatagcatg taagcaaaat     60
gttagcagcc ttgacgagaa aaacagcgtt tcagtagatt tgcctggtga atgaacgtt    120 cttgtaagca aagaaaaaaa caaagacggc aagtacgatc taattgcaac agtagacaag    180
cttgagctta aaggaacttc tgataaaaac aatggatctg gagtacttga aggcgtaaaa    240
gctgacaaaa gtaaagtaaa attaacaatt tctgacgatc taggtcaaac cacacttgaa    300
gttttcaaag aagatggcaa acactagta tcaaaaaaag taacttccaa agacaagtca     360
tcaacagaag aaaaattcaa tgaaaaaggt gaagtatctg aaaaaataat aacaagagca    420
gacggaacca gacttgaata cacagaaatt aaaagcgatg gatctggaaa agctaaagag    480
gttttaaaaa gctatgttct tgaaggaact ttaactgctg aaaaaacaac attggtggtt    540
aaagaaggaa ctgttacttt aagcaaaaat atttcaaaat ctggggaagt ttcagttgaa    600
cttaatgaca ctgacagtag tgctgctact aaaaaaactg cagcttggaa ttcaggcact    660
tcaactttaa caattactgt aaacagtaaa aaaactaaag accttgtgtt tacaaaagaa    720
aacacaatta cagtacaaca atacgactca aatggcacca aattagaggg gtcagcagtt    780
gaaattacaa aacttgatga aattaaaaac gctttaaaat aa                       822

<210> SEQ ID NO 135
<211> LENGTH: 821
<212> TYPE: DNA
<213> ORGANISM: Borrelia burgdorferi

<400> SEQUENCE: 135
atgaaaaaat atttattggg aataggtcta atattagcct taatagcatg taagcaaaat     60
gttagcagcc ttgatgagaa aaacagcgtt tcagtagatt tacctggtga atgaaagtt    120 cttgtaagca aagaaaaaga caaagatggt aaatacagtc taatggcaac agtagacaag    180
ctagagctta aggaacttc tgataaaagc aacggttctg gaacacttga aggtgaaaaa    240
tctgacaaaa gtaaagcaaa attaacaatt tctgaagatc taagtaaaac cacatttgaa    300
```

```
attttcaaag aagatggcaa aacattagta tcaaaaaaag taaattctaa agataagtca      360
tcaatagaag aaaaattcaa cgcaaaaggt gaattatctg aaaaaacaat actaagagca      420
aacggaacca ggcttgaata cacagaaata aaaagcgatg gaaccggaaa agctaaagaa      480
gctttaaaag actttgctct tgaaggaact ctagctgccg acaaaacaac attgaaagtt      540
acagaaggca ctgttgtttt aagcaaacac attccaaact ctggagaaat aacagttgag      600
cttaatgact ctaactctac tcaggctact aaaaaaactg gaaaatggga ttcaaatact      660
tccactttaa caattagtgt gaatagcaaa aaaactaaaa acattgtatt tacaaaagaa      720
gacacaataa cagtacaaaa atacgactca gcaggcacca atctagaagg caacgcagtc      780
gaaattaaaa cacttgatga acttaaaaac gctttaaaat a                         821

<210> SEQ ID NO 136
<211> LENGTH: 821
<212> TYPE: DNA
<213> ORGANISM: Borrelia burgdorferi

<400> SEQUENCE: 136
atgaaaaaat atttattggg aataggtc

```
                    Asp Gly Lys Tyr Ser Leu Glu Ala Thr Val Asp Lys Leu Glu Leu Lys
                         50                  55                  60 gga act tct gat aaa aac aac ggt tct gga aca ctt gaa ggt gaa aaa                240
Gly Thr Ser Asp Lys Asn Asn Gly Ser Gly Thr Leu Glu Gly Glu Lys
 65                  70                  75                  80 act gac aaa agt aaa gta aaa tta aca att gct gat gac cta agt caa                288
Thr Asp Lys Ser Lys Val Lys Leu Thr Ile Ala Asp Asp Leu Ser Gln
                 85                  90                  95 act aaa ttt gaa att ttc aaa gaa gat gcc aaa aca tta gta tca aaa                336
Thr Lys Phe Glu Ile Phe Lys Glu Asp Ala Lys Thr Leu Val Ser Lys
            100                 105                 110 aaa gta acc ctt aaa gac aag tca tca aca gaa gaa aaa ttc aac gaa                384
Lys Val Thr Leu Lys Asp Lys Ser Ser Thr Glu Glu Lys Phe Asn Glu
        115                 120                 125 aag ggt gaa aca tct gaa aaa aca ata gta aga gca aat gga acc aga                432
Lys Gly Glu Thr Ser Glu Lys Thr Ile Val Arg Ala Asn Gly Thr Arg
    130                 135                 140 ctt gaa tac aca gac ata aaa agc gat gga tcc gga aaa gct aaa gaa                480
Leu Glu Tyr Thr Asp Ile Lys Ser Asp Gly Ser Gly Lys Ala Lys Glu
145                 150                 155                 160 gtt tta aaa gac ttt act ctt gaa gga act cta gct gct gac ggc aaa                528
Val Leu Lys Asp Phe Thr Leu Glu Gly Thr Leu Ala Ala Asp Gly Lys
                165                 170                 175 aca aca ttg aaa gtt aca gaa ggc act gtt gtt tta agc aag aac att                576
Thr Thr Leu Lys Val Thr Glu Gly Thr Val Val Leu Ser Lys Asn Ile
            180                 185                 190 tta aaa tcc gga gaa ata aca gtt gca ctt gat gac tct gac act act                624
Leu Lys Ser Gly Glu Ile Thr Val Ala Leu Asp Asp Ser Asp Thr Thr
        195                 200                 205 cag gct act aaa aaa act gga aaa tgg gat tca aat act tcc act tta                672
Gln Ala Thr Lys Lys Thr Gly Lys Trp Asp Ser Asn Thr Ser Thr Leu
    210                 215                 220 aca att agt gtg aat agc aaa aaa act aaa aac att gta ttt aca aaa                720
Thr Ile Ser Val Asn Ser Lys Lys Thr Lys Asn Ile Val Phe Thr Lys
225                 230                 235                 240 gaa gac aca ata aca gta caa aaa tac gac tca gca ggc acc aat cta                768
Glu Asp Thr Ile Thr Val Gln Lys Tyr Asp Ser Ala Gly Thr Asn Leu
                245                 250                 255 gaa ggc aac gca gtc gaa att aaa act ctt gat gaa ctt aaa aac gct                816
Glu Gly Asn Ala Val Glu Ile Lys Thr Leu Asp Glu Leu Lys Asn Ala
            260                 265                 270 tta aaa taa                                                                    825
Leu Lys  *

<210> SEQ ID NO 138
<211> LENGTH: 274
<212> TYPE: PRT
<213> ORGANISM: Artificial Sequence
<220> FEATURE:
<223> OTHER INFORMATION: Chimeric Protein

<400> SEQUENCE: 138

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                20                  25                  30

Asp Leu Pro Gly Gly Met Thr Val Leu Val Ser Lys Glu Lys Asp Lys
            35                  40                  45

Asp Gly Lys Tyr Ser Leu Glu Ala Thr Val Asp Lys Leu Glu Leu Lys
        50                  55                  60
```

-continued

```
Gly Thr Ser Asp Lys Asn Asn Gly Ser Gly Thr Leu Glu Gly Glu Lys
 65                  70                  75                  80

Thr Asp Lys Ser Lys Val Lys Leu Thr Ile Ala Asp Asp Leu Ser Gln
                 85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Asn Thr Ser Thr Leu
    210                 215                 220

Thr Ile Ser Val Asn Ser Lys Lys Thr Lys Asn Ile Val Phe Thr Lys
225                 230                 235                 240

Glu Asp Thr Ile Thr Val Gln Lys Tyr Asp Ser Ala Gly Thr Asn Leu
                245                 250                 255

Glu Gly Asn Ala Val Glu Ile Lys Thr Leu Asp Glu Leu Lys Asn Ala
            260                 265                 270

Leu Lys
```

<210> SEQ ID NO 139
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric Nucleic Acid

<400> SEQUENCE: 139

```
atg aaa aaa tat tta ttg gga ata ggt cta ata tta gcc tta ata gca      48
Met Lys Lys Tyr Leu Leu Gly Ile Gly Leu Ile Leu Ala Leu Ile Ala
  1               5                  10                  15 tgc aag caa aat gtt agc agc ctt gat gaa aaa aac agc gct tca gta      96
Cys Lys Gln Asn Val Ser Ser Leu Asp Glu Lys Asn Ser Ala Ser Val
             20                  25                  30 gat ttg cct ggt gag atg aaa gtt ctt gta agt aaa gaa aaa gac aaa     144
Asp Leu Pro Gly Glu Met Lys Val Leu Val Ser Lys Glu Lys Asp Lys
         35                  40                  45 gac ggt aag tac agt cta aag gca aca gta gac aag att gag cta aaa     192
Asp Gly Lys Tyr Ser Leu Lys Ala Thr Val Asp Lys Ile Glu Leu Lys
     50                  55                  60 gga act tct gat aaa gac aat ggt tct gga gtg ctt gaa ggt aca aaa     240
Gly Thr Ser Asp Lys Asp Asn Gly Ser Gly Val Leu Glu Gly Thr Lys
 65                  70                  75                  80 gat gac aaa agt aaa gca aaa tta aca att gct gac gat cta agt aaa     288
Asp Asp Lys Ser Lys Ala Lys Leu Thr Ile Ala Asp Asp Leu Ser Lys
                 85                  90                  95 acc aca ttc gaa ctt tta aaa gaa gat ggc aaa aca tta gtg tca aga     336
Thr Thr Phe Glu Leu Leu Lys Glu Asp Gly Lys Thr Leu Val Ser Arg
```

| | | |
|---|---|---|
| Thr Thr Phe Glu Leu Leu Lys Glu Asp Gly Lys Thr Leu Val Ser Arg<br>               100                 105              110 | |
| aaa gta agt tct aga gac aaa aca tca aca gat gaa atg ttc aat gaa<br>Lys Val Ser Ser Arg Asp Lys Thr Ser Thr Asp Glu Met Phe Asn Glu<br>           115               120              125 | 384 |
| aaa ggt gaa ttg tct gca aaa acc atg aca aga gaa aat gga acc aaa<br>Lys Gly Glu Leu Ser Ala Lys Thr Met Thr Arg Glu Asn Gly Thr Lys<br>130                 135               140 | 432 |
| ctt gaa tat aca gaa atg aaa agc gat gga acc gga aaa gct aaa gaa<br>Leu Glu Tyr Thr Glu Met Lys Ser Asp Gly Thr Gly Lys Ala Lys Glu<br>145                 150               155              160 | 480 |
| gtt tta aaa aag ttt act ctt gaa gga aaa gta gct aat gat aaa gta<br>Val Leu Lys Lys Phe Thr Leu Glu Gly Lys Val Ala Asn Asp Lys Val<br>                165               170              175 | 528 |
| aca ttg gaa gta aaa gaa gga acc gtt act tta agt aag gaa att gca<br>Thr Leu Glu Val Lys Glu Gly Thr Val Thr Leu Ser Lys Glu Ile Ala<br>           180               185              190 | 576 |
| aaa tct gga gaa gta aca gtt gct ctt aat gac act aac act act cag<br>Lys Ser Gly Glu Val Thr Val Ala Leu Asn Asp Thr Asn Thr Thr Gln<br>              195               200              205 | 624 |
| gct act aaa aaa act ggc gca tgg gat tca aaa act tct act tta aca<br>Ala Thr Lys Lys Thr Gly Ala Trp Asp Ser Lys Thr Ser Thr Leu Thr<br>210                 215               220 | 672 |
| att agt gtt aac agc aaa aaa act aca caa ctt gtg ttt act aaa caa<br>Ile Ser Val Asn Ser Lys Lys Thr Thr Gln Leu Val Phe Thr Lys Gln<br>225                 230               235              240 | 720 |
| gac aca ata act gta caa aaa tac gac tcc gca ggt acc aat tta gaa<br>Asp Thr Ile Thr Val Gln Lys Tyr Asp Ser Ala Gly Thr Asn Leu Glu<br>              245               250              255 | 768 |
| ggc aca gca gtc gaa att aaa aca ctt gat gaa ctt aaa aac gct tta<br>Gly Thr Ala Val Glu Ile Lys Thr Leu Asp Glu Leu Lys Asn Ala Leu<br>           260               265              270 | 816 |
| aaa taa<br>Lys * | 822 |

<210> SEQ ID NO 140
<211> LENGTH: 273
<212> TYPE: PRT
<213> ORGANISM: Artificial Sequence
<220> FEATURE:
<223> OTHER INFORMATION: Chimeric Protein

<400> SEQUENCE: 140

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

```
Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys

<210> SEQ ID NO 141
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric Nucleic Acid

<400> SEQUENCE: 141 atg aaa aaa tat tta ttg gga ata ggt cta ata tta gcc tta ata gca      48
Met Lys Lys Tyr Leu Leu Gly Ile Gly Leu Ile Leu Ala Leu Ile Ala
  1               5                  10                  15 tgc aag caa aat gtt agc agc ctt gat gaa aaa aac agc gct tca gta      96
Cys Lys Gln Asn Val Ser Ser Leu Asp Glu Lys Asn Ser Ala Ser Val
             20                  25                  30 gat ttg cct ggt gag atg aaa gtt ctt gta agt aaa gaa aaa gac aaa     144
Asp Leu Pro Gly Glu Met Lys Val Leu Val Ser Lys Glu Lys Asp Lys
         35                  40                  45 gac ggt aag tac agt cta aag gca aca gta gac aag att gag cta aaa     192
Asp Gly Lys Tyr Ser Leu Lys Ala Thr Val Asp Lys Ile Glu Leu Lys
     50                  55                  60 gga act tct gat aaa gac aat ggt tct gga gtg ctt gaa ggt aca aaa     240
Gly Thr Ser Asp Lys Asp Asn Gly Ser Gly Val Leu Glu Gly Thr Lys
 65                  70                  75                  80 gat gac aaa agt aaa gca aaa tta aca att gct gac gat cta agt aaa     288
Asp Asp Lys Ser Lys Ala Lys Leu Thr Ile Ala Asp Asp Leu Ser Lys
                 85                  90                  95 acc aca ttc gaa ctt tta aaa gaa gat ggc aaa aca tta gtg tca aga     336
Thr Thr Phe Glu Leu Leu Lys Glu Asp Gly Lys Thr Leu Val Ser Arg
            100                 105                 110 aaa gta agt tct aga gac aaa aca tca aca gat gaa atg ttc aat gaa     384
Lys Val Ser Ser Arg Asp Lys Thr Ser Thr Asp Glu Met Phe Asn Glu
        115                 120                 125 aaa ggt gaa ttg tct gca aaa acc atg aca aga gaa aat gga acc aaa     432
Lys Gly Glu Leu Ser Ala Lys Thr Met Thr Arg Glu Asn Gly Thr Lys
    130                 135                 140 ctt gaa tat aca gaa atg aaa agc gat gga acc gga aaa gct aaa gaa     480
```

-continued

```
Leu Glu Tyr Thr Glu Met Lys Ser Asp Gly Thr Gly Lys Ala Lys Glu
145                 150                 155                 160 gtt tta aaa aag ttt act ctt gaa gga aaa gta gct aat gat aaa gta      528
Val Leu Lys Lys Phe Thr Leu Glu Gly Lys Val Ala Asn Asp Lys Val
                165                 170                 175 aca ttg gaa gta aaa gaa gga acc gtt act tta agt aag gaa att tca      576
Thr Leu Glu Val Lys Glu Gly Thr Val Thr Leu Ser Lys Glu Ile Ser
            180                 185                 190 aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205 gct act aaa aaa act gca gct tgg aat tca aaa act tcc act tta aca      672
Ala Thr Lys Lys Thr Ala Ala Trp Asn Ser Lys Thr Ser Thr Leu Thr
    210                 215                 220 att agt gtg aat agc caa aaa acc aaa aac ctt gta ttc aca aaa gaa      720
Ile Ser Val Asn Ser Gln Lys Thr Lys Asn Leu Val Phe Thr Lys Glu
225                 230                 235                 240 gac aca ata aca gta caa aaa tac gac tca gca ggc acc aat cta gaa      768
Asp Thr Ile Thr Val Gln Lys Tyr Asp Ser Ala Gly Thr Asn Leu Glu
                245                 250                 255 ggc aaa gca gtc gaa att aca aca ctt aaa gaa ctt aaa aac gct tta      816
Gly Lys Ala Val Glu Ile Thr Thr Leu Lys Glu Leu Lys Asn Ala Leu
            260                 265                 270 aaa taa                                                              822
Lys *

<210> SEQ ID NO 142
<211> LENGTH: 273
<212> TYPE: PRT
<213> ORGANISM: Artificial Sequence
<220> FEATURE:
<223> OTHER INFORMATION: Chimeric Protein

<400> SEQUENCE: 142

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ser
            180                 185                 190
```

```
Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys

<210> SEQ ID NO 143
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric Nucleic Acid

<400> SEQUENCE: 143 atg aaa aaa tat tta ttg gga ata ggt cta ata tta gcc tta ata gca        48
Met Lys Lys Tyr Leu Leu Gly Ile Gly Leu Ile Leu Ala Leu Ile Ala
1               5                   10                  15 tgt aag caa aat gtt agc agc ctt gac gag aaa aac agc gtt tca gta        96
Cys Lys Gln Asn Val Ser Ser Leu Asp Glu Lys Asn Ser Val Ser Val
            20                  25                  30 gat ttg cct ggt gaa atg aaa gtt ctt gta agc aaa gaa aaa aac aaa       144
Asp Leu Pro Gly Glu Met Lys Val Leu Val Ser Lys Glu Lys Asn Lys
        35                  40                  45 gac ggc aag tac gat cta att gca aca gta gac aag ctt gag ctt aaa       192
Asp Gly Lys Tyr Asp Leu Ile Ala Thr Val Asp Lys Leu Glu Leu Lys
    50                  55                  60 gga act tct gat aaa aac aat gga tct gga gta ctt gaa ggc gta aaa       240
Gly Thr Ser Asp Lys Asn Asn Gly Ser Gly Val Leu Glu Gly Val Lys
65                  70                  75                  80 gct gac aaa agt aaa gta aaa tta aca att tct gac gat cta ggt caa       288
Ala Asp Lys Ser Lys Val Lys Leu Thr Ile Ser Asp Asp Leu Gly Gln
                85                  90                  95 acc aca ctt gaa gtt ttc aaa gaa gat ggc aaa aca cta gta tca aaa       336
Thr Thr Leu Glu Val Phe Lys Glu Asp Gly Lys Thr Leu Val Ser Lys
            100                 105                 110 aaa gta act tcc aaa gac aag tca tca aca gaa gaa aaa ttc aat gaa       384
Lys Val Thr Ser Lys Asp Lys Ser Ser Thr Glu Glu Lys Phe Asn Glu
        115                 120                 125 aaa ggt gaa gta tct gaa aaa ata ata aca aga gca aat gga acc aaa       432
Lys Gly Glu Val Ser Glu Lys Ile Ile Thr Arg Ala Asn Gly Thr Lys
    130                 135                 140 ctt gaa tat aca gaa atg aaa agc gat gga acc gga aaa gct aaa gaa       480
Leu Glu Tyr Thr Glu Met Lys Ser Asp Gly Thr Gly Lys Ala Lys Glu
145                 150                 155                 160 gtt tta aaa aag ttt act ctt gaa gga aaa gta gct aat gat aaa gta       528
Val Leu Lys Lys Phe Thr Leu Glu Gly Lys Val Ala Asn Asp Lys Val
                165                 170                 175 aca ttg gaa gta aaa gaa gga acc gtt act tta agt aag gaa att tca       576
Thr Leu Glu Val Lys Glu Gly Thr Val Thr Leu Ser Lys Glu Ile Ser
            180                 185                 190 aaa tct ggg gaa gtt tca gtt gaa ctt aat gac act gac agt agt gct       624
Lys Ser Gly Glu Val Ser Val Glu Leu Asn Asp Thr Asp Ser Ser Ala
```

```
Lys Ser Gly Glu Val Ser Val Glu Leu Asn Asp Thr Asp Ser Ser Ala
            195                 200                 205 gct act aaa aaa act gca gct tgg aat tca aaa act tcc act tta aca      672
Ala Thr Lys Lys Thr Ala Ala Trp Asn Ser Lys Thr Ser Thr Leu Thr
    210                 215                 220 att agt gtg aat agc caa aaa acc aaa aac ctt gta ttc aca aaa gaa      720
Ile Ser Val Asn Ser Gln Lys Thr Lys Asn Leu Val Phe Thr Lys Glu
225                 230                 235                 240 gac aca ata aca gta caa aaa tac gac tca gca ggc acc aat cta gaa      768
Asp Thr Ile Thr Val Gln Lys Tyr Asp Ser Ala Gly Thr Asn Leu Glu
                245                 250                 255 ggc aaa gca gtc gaa att aca aca ctt aaa gaa ctt aaa aac gct tta      816
Gly Lys Ala Val Glu Ile Thr Thr Leu Lys Glu Leu Lys Asn Ala Leu
            260                 265                 270 aaa taa                                                              822
Lys *

<210> SEQ ID NO 144
<211> LENGTH: 273
<212> TYPE: PRT
<213> ORGANISM: Artificial Sequence
<220> FEATURE:
<223> OTHER INFORMATION: Chimeric Protein

<400> SEQUENCE: 144

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255
```

```
Gly Lys Ala Val Glu Ile Thr Thr Leu Lys Glu Leu Lys Asn Ala Leu
            260                 265                 270

Lys

<210> SEQ ID NO 145
<211> LENGTH: 1362
<212> TYPE: DNA
<213> ORGANISM: Artificial Sequence
<220> FEATURE:
<221> NAME/KEY: CDS
<222> LOCATION: (1)...(1362)
<223> OTHER INFORMATION: Chimeric nucleic acid

<400> SEQUENCE: 145 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
                20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
            35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
        50                  55                  60 ata cac caa aat aat ggt ttg gat acc gaa aat aat cac aat gga tca     240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
               100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
            115                 120                 125 ctt ggt aaa gaa ggt gtt act gat gct gat gca aaa gaa gcc att tta     432
Leu Gly Lys Glu Gly Val Thr Asp Ala Asp Ala Lys Glu Ala Ile Leu
        130                 135                 140 aaa gca aat ggt act aaa act aaa ggt gct gaa gaa ctt gga aaa tta     480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct     528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa     576
Asn Ser Val Lys Glu Leu Thr Ser Pro Val Val Ala Glu Ser Pro Lys
            180                 185                 190 aaa cct tcc atg gcc aag caa aat gtt agc agc ctt gac gag aaa aac     624
Lys Pro Ser Met Ala Lys Gln Asn Val Ser Ser Leu Asp Glu Lys Asn
        195                 200                 205 agc gtt tca gta gat ttg cct ggt gaa atg aaa gtt ctt gta agc aaa     672
Ser Val Ser Val Asp Leu Pro Gly Glu Met Lys Val Leu Val Ser Lys
    210                 215                 220 gaa aaa aac aaa gac ggc aag tac gat cta att gca aca gta gac aag     720
Glu Lys Asn Lys Asp Gly Lys Tyr Asp Leu Ile Ala Thr Val Asp Lys
225                 230                 235                 240 ctt gag ctt aaa gga act tct gat aaa aac aat gga tct gga gta ctt     768
```

| | | | | | | | | | | | | |
|---|---|---|---|---|---|---|---|---|---|---|---|---|
| Leu | Glu | Leu | Lys | Gly<br>245 | Thr | Ser | Asp | Lys | Asn<br>250 | Asn | Gly | Ser | Gly | Val<br>255 | Leu |

```
gaa ggc gta aaa gct gac aaa agt aaa gta aaa tta aca att tct gac    816
Glu Gly Val Lys Ala Asp Lys Ser Lys Val Lys Leu Thr Ile Ser Asp
            260             265             270 gat cta ggt caa acc aca ctt gaa gtt ttc aaa gaa gat ggc aaa aca    864
Asp Leu Gly Gln Thr Thr Leu Glu Val Phe Lys Glu Asp Gly Lys Thr
        275             280             285 cta gta tca aaa aaa gta act tcc aaa gac aag tca tca aca gaa gaa    912
Leu Val Ser Lys Lys Val Thr Ser Lys Asp Lys Ser Ser Thr Glu Glu
    290             295             300 aaa ttc aat gaa aaa ggt gaa gta tct gaa aaa ata ata aca aga gca    960
Lys Phe Asn Glu Lys Gly Glu Val Ser Glu Lys Ile Ile Thr Arg Ala
305             310             315             320 gac gga acc aga ctt gaa tac aca gga att aaa agc gat gga tct gga   1008
Asp Gly Thr Arg Leu Glu Tyr Thr Gly Ile Lys Ser Asp Gly Ser Gly
            325             330             335 aaa gct aaa gag gtt tta aaa ggc tat gtt ctt gaa gga act cta act   1056
Lys Ala Lys Glu Val Leu Lys Gly Tyr Val Leu Glu Gly Thr Leu Thr
        340             345             350 gct gaa aaa aca aca ttg gtg gtt aaa gaa gga act gtt act tta agc   1104
Ala Glu Lys Thr Thr Leu Val Val Lys Glu Gly Thr Val Thr Leu Ser
    355             360             365 aaa aat att tca aaa tct ggg gaa gtt tca gtt gaa ctt aat gac act   1152
Lys Asn Ile Ser Lys Ser Gly Glu Val Ser Val Glu Leu Asn Asp Thr
370             375             380 gac agt agt gct gct act aaa aaa act gca gct tgg aat tca ggc act   1200
Asp Ser Ser Ala Ala Thr Lys Lys Thr Ala Ala Trp Asn Ser Gly Thr
385             390             395             400 tca act tta aca att act gta aac agt aaa aaa act aaa gac ctt gtg   1248
Ser Thr Leu Thr Ile Thr Val Asn Ser Lys Lys Thr Lys Asp Leu Val
            405             410             415 ttt aca aaa gaa aac aca att aca gta caa caa tac gac tca aat ggc   1296
Phe Thr Lys Glu Asn Thr Ile Thr Val Gln Gln Tyr Asp Ser Asn Gly
        420             425             430 acc aaa tta gag ggg tca gca gtt gaa att aca aaa ctt gat gaa att   1344
Thr Lys Leu Glu Gly Ser Ala Val Glu Ile Thr Lys Leu Asp Glu Ile
    435             440             445 aaa aac gct tta aaa taa                                           1362
Lys Asn Ala Leu Lys *
450

<210> SEQ ID NO 146
<211> LENGTH: 453
<212> TYPE: PRT
<213> ORGANISM: Artificial Sequence
<220> FEATURE:
<223> OTHER INFORMATION: Chimeric Protein

<400> SEQUENCE: 146

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80
```

```
Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Glu Met Lys Val Leu Val Ser Lys
    210                 215                 220

Glu Lys Asn Lys Asp Gly Lys Tyr Asp Leu Ile Ala Thr Val Asp Lys
225                 230                 235                 240

Leu Glu Leu Lys Gly Thr Ser Asp Lys Asn Asn Gly Ser Gly Val Leu
                245                 250                 255

Glu Gly Val Lys Ala Asp Lys Ser Lys Val Lys Leu Thr Ile Ser Asp
            260                 265                 270

Asp Leu Gly Gln Thr Thr Leu Glu Val Phe Lys Glu Asp Gly Lys Thr
        275                 280                 285

Leu Val Ser Lys Lys Val Thr Ser Lys Asp Lys Ser Ser Thr Glu Glu
    290                 295                 300

Lys Phe Asn Glu Lys Gly Glu Val Ser Glu Lys Ile Ile Thr Arg Ala
305                 310                 315                 320

Asp Gly Thr Arg Leu Glu Tyr Thr Gly Ile Lys Ser Asp Gly Ser Gly
                325                 330                 335

Lys Ala Lys Glu Val Leu Lys Gly Tyr Val Leu Glu Gly Thr Leu Thr
            340                 345                 350

Ala Glu Lys Thr Thr Leu Val Val Lys Glu Gly Thr Val Thr Leu Ser
        355                 360                 365

Lys Asn Ile Ser Lys Ser Gly Glu Val Ser Val Glu Leu Asn Asp Thr
    370                 375                 380

Asp Ser Ser Ala Ala Thr Lys Lys Thr Ala Ala Trp Asn Ser Gly Thr
385                 390                 395                 400

Ser Thr Leu Thr Ile Thr Val Asn Ser Lys Lys Thr Lys Asp Leu Val
                405                 410                 415

Phe Thr Lys Glu Asn Thr Ile Thr Val Gln Gln Tyr Asp Ser Asn Gly
            420                 425                 430

Thr Lys Leu Glu Gly Ser Ala Val Glu Ile Thr Lys Leu Asp Glu Ile
        435                 440                 445

Lys Asn Ala Leu Lys
    450

<210> SEQ ID NO 147
<211> LENGTH: 1353
<212> TYPE: DNA
<213> ORGANISM: Artificial Sequence
<220> FEATURE:
```

```
<221> NAME/KEY: CDS
<222> LOCATION: (1)...(1353)
<223> OTHER INFORMATION: Chimeric nucleic acid

<400> SEQUENCE: 147 atg gct tgt aat aat tca ggg aaa gat ggg aat aca tct gca aat tct        48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata aat aaa aaa        96
Ala Asp Glu Ser Val Lys Gly Pro Asn Leu Thr Glu Ile Asn Lys Lys
            20                  25                  30 att acg gat tct aat gcg gtt tta ctt gct gtg aaa gag gtt gaa gcg       144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa       192
Leu Leu Ser Ser Ile Asp Glu Ile Ala Ala Lys Ala Ile Gly Lys Lys
    50                  55                  60 ata cac caa aat aat ggt ttg gat acc gaa aat aat cac aat gga tca       240
Ile His Gln Asn Asn Gly Leu Asp Thr Glu Asn Asn His Asn Gly Ser
65                  70                  75                  80 ttg tta gcg gga gct tat gca ata tca acc cta ata aaa caa aaa tta       288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag       336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat       384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta       432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta       480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct       528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca gcc       576
Asn Ser Val Lys Glu Leu Thr Ser Pro Val Val Ala Glu Ser Pro Ala
            180                 185                 190 atg gcc aag caa aat gtt agc agc ctt gac gag aaa aac agc gtt tca       624
Met Ala Lys Gln Asn Val Ser Ser Leu Asp Glu Lys Asn Ser Val Ser
        195                 200                 205 gta gat ttg cct ggt gaa atg aaa gtt ctt gta agc aaa gaa aaa aac       672
Val Asp Leu Pro Gly Glu Met Lys Val Leu Val Ser Lys Glu Lys Asn
    210                 215                 220 aaa gac ggc aag tac gat cta att gca aca gta gac aag ctt gag ctt       720
Lys Asp Gly Lys Tyr Asp Leu Ile Ala Thr Val Asp Lys Leu Glu Leu
225                 230                 235                 240 aaa gga act tct gat aaa aac aat gga tct gga gta ctt gaa ggc gta       768
Lys Gly Thr Ser Asp Lys Asn Asn Gly Ser Gly Val Leu Glu Gly Val
                245                 250                 255 aaa gct gac aaa agt aaa gta aaa tta aca att tct gac gat cta ggt       816
Lys Ala Asp Lys Ser Lys Val Lys Leu Thr Ile Ser Asp Asp Leu Gly
            260                 265                 270 caa acc aca ctt gaa gtt ttc aaa gaa gat ggc aaa aca cta gta tca       864
Gln Thr Thr Leu Glu Val Phe Lys Glu Asp Gly Lys Thr Leu Val Ser
        275                 280                 285 aaa aaa gta act tcc aaa gac aag tca tca aca gaa gaa aaa ttc aat       912
```

```
                                                                          -continued Lys Lys Val Thr Ser Lys Asp Lys Ser Ser Thr Glu Glu Lys Phe Asn
        290                 295                 300 gaa aaa ggt gaa gta tct gaa aaa ata ata aca aga gca gac gga acc        960
Glu Lys Gly Glu Val Ser Glu Lys Ile Ile Thr Arg Ala Asp Gly Thr
305                 310                 315                 320 aga ctt gaa tac aca gga att aaa agc gat gga tct gga aaa gct aaa       1008
Arg Leu Glu Tyr Thr Gly Ile Lys Ser Asp Gly Ser Gly Lys Ala Lys
                325                 330                 335 gag gtt tta aaa ggc tat gtt ctt gaa gga act cta act gct gaa aaa       1056
Glu Val Leu Lys Gly Tyr Val Leu Glu Gly Thr Leu Thr Ala Glu Lys
            340                 345                 350 aca aca ttg gtg gtt aaa gaa gga act gtt act tta agc aaa aat att       1104
Thr Thr Leu Val Val Lys Glu Gly Thr Val Thr Leu Ser Lys Asn Ile
        355                 360                 365 tca aaa tct ggg gaa gtt tca gtt gaa ctt aat gac act gac agt agt       1152
Ser Lys Ser Gly Glu Val Ser Val Glu Leu Asn Asp Thr Asp Ser Ser
370                 375                 380 gct gct act aaa aaa act gca gct tgg aat tca ggc act tca act tta       1200
Ala Ala Thr Lys Lys Thr Ala Ala Trp Asn Ser Gly Thr Ser Thr Leu
385                 390                 395                 400 aca att act gta aac agt aaa aaa act aaa gac ctt gtg ttt aca aaa       1248
Thr Ile Thr Val Asn Ser Lys Lys Thr Lys Asp Leu Val Phe Thr Lys
                405                 410                 415 gaa aac aca att aca gta caa caa tac gac tca aat ggc acc aaa tta       1296
Glu Asn Thr Ile Thr Val Gln Gln Tyr Asp Ser Asn Gly Thr Lys Leu
            420                 425                 430 gag ggg tca gca gtt gaa att aca aaa ctt gat gaa att aaa aac gct       1344
Glu Gly Ser Ala Val Glu Ile Thr Lys Leu Asp Glu Ile Lys Asn Ala
        435                 440                 445 tta aaa taa                                                           1353
Leu Lys  *
    450

<210> SEQ ID NO 148
<211> LENGTH: 450
<212> TYPE: PRT
<213> ORGANISM: Artificial Sequence
<220> FEATURE:
<223> OTHER INFORMATION: Chimeric Protein

<400> SEQUENCE: 148

Met Ala Cys Asn Asn Ser Gly Lys Asp Gly Asn Thr Ser Ala Asn Ser
1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140
```

```
Lys Ala Asn Gly Thr Lys Thr Lys Gly Ala Glu Glu Leu Gly Lys Leu
145                 150                 155                 160

Phe Glu Ser Val Glu Val Leu Ser Lys Ala Lys Glu Met Leu Ala
            165                 170                 175

Asn Ser Val Lys Glu Leu Thr Ser Pro Val Val Ala Glu Ser Pro Ala
            180                 185                 190

Met Ala Lys Gln Asn Val Ser Ser Leu Asp Lys Asn Ser Val Ser
    195                 200                 205

Val Asp Leu Pro Gly Glu Met Lys Val Leu Val Ser Lys Glu Lys Asn
210                 215                 220

Lys Asp Gly Lys Tyr Asp Leu Ile Ala Thr Val Asp Lys Leu Glu Leu
225                 230                 235                 240

Lys Gly Thr Ser Asp Lys Asn Asn Gly Ser Gly Val Leu Glu Gly Val
            245                 250                 255

Lys Ala Asp Lys Ser Lys Val Lys Leu Thr Ile Ser Asp Asp Leu Gly
            260                 265                 270

Gln Thr Thr Leu Glu Val Phe Lys Glu Asp Gly Lys Thr Leu Val Ser
    275                 280                 285

Lys Lys Val Thr Ser Lys Asp Lys Ser Ser Thr Glu Glu Lys Phe Asn
290                 295                 300

Glu Lys Gly Glu Val Ser Glu Lys Ile Ile Thr Arg Ala Asp Gly Thr
305                 310                 315                 320

Arg Leu Glu Tyr Thr Gly Ile Lys Ser Asp Gly Ser Gly Lys Ala Lys
            325                 330                 335

Glu Val Leu Lys Gly Tyr Val Leu Glu Gly Thr Leu Thr Ala Glu Lys
            340                 345                 350

Thr Thr Leu Val Val Lys Glu Gly Thr Val Thr Leu Ser Lys Asn Ile
    355                 360                 365

Ser Lys Ser Gly Glu Val Ser Val Glu Leu Asn Asp Thr Asp Ser Ser
370                 375                 380

Ala Ala Thr Lys Lys Thr Ala Ala Trp Asn Ser Gly Thr Ser Thr Leu
385                 390                 395                 400

Thr Ile Thr Val Asn Ser Lys Lys Thr Lys Asp Leu Val Phe Thr Lys
            405                 410                 415

Glu Asn Thr Ile Thr Val Gln Gln Tyr Asp Ser Asn Gly Thr Lys Leu
            420                 425                 430

Glu Gly Ser Ala Val Glu Ile Thr Lys Leu Asp Glu Ile Lys Asn Ala
    435                 440                 445

Leu Lys
    450

<210> SEQ ID NO 149
<211> LENGTH: 1341
<212> TYPE: DNA
<213> ORGANISM: Artificial Sequence
<220> FEATURE:
<221> NAME/KEY: CDS
<222> LOCATION: (1)...(1341)
<223> OTHER INFORMATION: Chimeric nucleic acid

<400> SEQUENCE: 149 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
```

```
                    20                  25                  30
att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45 ttg ctg tca tct ata gat gag ctt gct aaa gct att ggt aaa aaa ata      192
Leu Leu Ser Ser Ile Asp Glu Leu Ala Lys Ala Ile Gly Lys Lys Ile
 50                  55                  60 aaa aac gat ggt agt tta gat aat gaa gca aat cgc aac gag tca ttg      240
Lys Asn Asp Gly Ser Leu Asp Asn Glu Ala Asn Arg Asn Glu Ser Leu
 65                  70                  75                  80 tta gca gga gct tat aca ata tca acc tta ata aca caa aaa tta agt      288
Leu Ala Gly Ala Tyr Thr Ile Ser Thr Leu Ile Thr Gln Lys Leu Ser
                 85                  90                  95 aaa tta aac gga tca gaa ggt tta aag gaa aag att gcc gca gct aag      336
Lys Leu Asn Gly Ser Glu Gly Leu Lys Glu Lys Ile Ala Ala Ala Lys
                100                 105                 110 aaa tgc tct gaa gag ttt agt act aaa cta aaa gat aat cat gca cag      384
Lys Cys Ser Glu Glu Phe Ser Thr Lys Leu Lys Asp Asn His Ala Gln
            115                 120                 125 ctt ggt ata cag ggc gtt act gat gaa aat gca aaa aaa gct att tta      432
Leu Gly Ile Gln Gly Val Thr Asp Glu Asn Ala Lys Lys Ala Ile Leu
        130                 135                 140 aaa gca aat gca gcg ggt aaa gat aag ggc gtt gaa gaa ctt gaa aag      480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt      528
Leu Ser Gly Ser Leu Glu Ser Leu Ser Lys Ala Ala Lys Glu Met Leu
                165                 170                 175 gct aat tca gtt aaa gag ctt aca agc cct gtt gtc cat ggc aag caa      576
Ala Asn Ser Val Lys Glu Leu Thr Ser Pro Val Val His Gly Lys Gln
                180                 185                 190 aat gtt agc agc ctt gac gag aaa aac agc gtt tca gta gat ttg cct      624
Asn Val Ser Ser Leu Asp Glu Lys Asn Ser Val Ser Val Asp Leu Pro
            195                 200                 205 ggt gaa atg aaa gtt ctt gta agc aaa gaa aaa aac aaa gac ggc aag      672
Gly Glu Met Lys Val Leu Val Ser Lys Glu Lys Asn Lys Asp Gly Lys
        210                 215                 220 tac gat cta att gca aca gta gac aag ctt gag ctt aaa gga act tct      720
Tyr Asp Leu Ile Ala Thr Val Asp Lys Leu Glu Leu Lys Gly Thr Ser
225                 230                 235                 240 gat aaa aac aat gga tct gga gta ctt gaa ggc gta aaa gct gac aaa      768
Asp Lys Asn Asn Gly Ser Gly Val Leu Glu Gly Val Lys Ala Asp Lys
                245                 250                 255 agt aaa gta aaa tta aca att tct gac gat cta ggt caa acc aca ctt      816
Ser Lys Val Lys Leu Thr Ile Ser Asp Asp Leu Gly Gln Thr Thr Leu
                260                 265                 270 gaa gtt ttc aaa gaa gat ggc aaa aca cta gta tca aaa aaa gta act      864
Glu Val Phe Lys Glu Asp Gly Lys Thr Leu Val Ser Lys Lys Val Thr
            275                 280                 285 tcc aaa gac aag tca tca aca gaa gaa aaa ttc aat gaa aaa ggt gaa      912
Ser Lys Asp Lys Ser Ser Thr Glu Glu Lys Phe Asn Glu Lys Gly Glu
        290                 295                 300 gta tct gaa aaa ata ata aca aga gca gac gga acc aga ctt gaa tac      960
Val Ser Glu Lys Ile Ile Thr Arg Ala Asp Gly Thr Arg Leu Glu Tyr
305                 310                 315                 320 aca gga att aaa agc gat gga tct gga aaa gct aaa gag gtt tta aaa     1008
Thr Gly Ile Lys Ser Asp Gly Ser Gly Lys Ala Lys Glu Val Leu Lys
                325                 330                 335 ggc tat gtt ctt gaa gga act cta act gct gaa aaa aca aca ttg gtg     1056
Gly Tyr Val Leu Glu Gly Thr Leu Thr Ala Glu Lys Thr Thr Leu Val
```

```
Gly Tyr Val Leu Glu Gly Thr Leu Thr Ala Glu Lys Thr Thr Leu Val
                340                 345                 350 gtt aaa gaa gga act gtt act tta agc aaa aat att tca aaa tct ggg    1104
Val Lys Glu Gly Thr Val Thr Leu Ser Lys Asn Ile Ser Lys Ser Gly
            355                 360                 365 gaa gtt tca gtt gaa ctt aat gac act gac agt agt gct gct act aaa    1152
Glu Val Ser Val Glu Leu Asn Asp Thr Asp Ser Ser Ala Ala Thr Lys
    370                 375                 380 aaa act gca gct tgg aat tca ggc act tca act tta aca att act gta    1200
Lys Thr Ala Ala Trp Asn Ser Gly Thr Ser Thr Leu Thr Ile Thr Val
385                 390                 395                 400 aac agt aaa aaa act aaa gac ctt gtg ttt aca aaa gaa aac aca att    1248
Asn Ser Lys Lys Thr Lys Asp Leu Val Phe Thr Lys Glu Asn Thr Ile
                405                 410                 415 aca gta caa caa tac gac tca aat ggc acc aaa tta gag ggg tca gca    1296
Thr Val Gln Gln Tyr Asp Ser Asn Gly Thr Lys Leu Glu Gly Ser Ala
            420                 425                 430 gtt gaa att aca aaa ctt gat gaa att aaa aac gct tta aaa taa        1341
Val Glu Ile Thr Lys Leu Asp Glu Ile Lys Asn Ala Leu Lys *
    435                 440                 445

<210> SEQ ID NO 150
<211> LENGTH: 446
<212> TYPE: PRT
<213> ORGANISM: Artificial Sequence
<220> FEATURE:
<223> OTHER INFORMATION: Chimeric Protein

<400> SEQUENCE: 150

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
                20                  25                  30

Ile Thr Asp Ser Asn Ala Val Leu Leu Ala Val Lys Glu Val Glu Ala
            35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
                100                 105                 110

Lys Cys Ser Glu Glu Phe Ser Thr Lys Leu Lys Asp Asn His Ala Gln
            115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
    195                 200                 205

Gly Glu Met Lys Val Leu Val Ser Lys Glu Lys Asn Lys Asp Gly Lys
    210                 215                 220
```

```
Tyr Asp Leu Ile Ala Thr Val Asp Lys Leu Glu Leu Lys Gly Thr Ser
225                 230                 235                 240

Asp Lys Asn Asn Gly Ser Gly Val Leu Glu Gly Val Lys Ala Asp Lys
            245                 250                 255

Ser Lys Val Lys Leu Thr Ile Ser Asp Asp Leu Gly Gln Thr Thr Leu
        260                 265                 270

Glu Val Phe Lys Glu Asp Gly Lys Thr Leu Val Ser Lys Val Thr
    275                 280                 285

Ser Lys Asp Lys Ser Ser Thr Glu Glu Lys Phe Asn Glu Lys Gly Glu
    290                 295                 300

Val Ser Glu Lys Ile Ile Thr Arg Ala Asp Gly Thr Arg Leu Glu Tyr
305                 310                 315                 320

Thr Gly Ile Lys Ser Asp Gly Ser Gly Lys Ala Lys Glu Val Leu Lys
                325                 330                 335

Gly Tyr Val Leu Glu Gly Thr Leu Thr Ala Glu Lys Thr Thr Leu Val
            340                 345                 350

Val Lys Glu Gly Thr Val Thr Leu Ser Lys Asn Ile Ser Lys Ser Gly
        355                 360                 365

Glu Val Ser Val Glu Leu Asn Asp Thr Asp Ser Ser Ala Ala Thr Lys
    370                 375                 380

Lys Thr Ala Ala Trp Asn Ser Gly Thr Ser Thr Leu Thr Ile Thr Val
385                 390                 395                 400

Asn Ser Lys Lys Thr Lys Asp Leu Val Phe Thr Lys Glu Asn Thr Ile
                405                 410                 415

Thr Val Gln Gln Tyr Asp Ser Asn Gly Thr Lys Leu Glu Gly Ser Ala
            420                 425                 430

Val Glu Ile Thr Lys Leu Asp Glu Ile Lys Asn Ala Leu Lys
            435                 440                 445

<210> SEQ ID NO 151
<211> LENGTH: 1362
<212> TYPE: DNA
<213> ORGANISM: Artificial Sequence
<220> FEATURE:
<221> NAME/KEY: CDS
<222> LOCATION: (1)...(1362)
<223> OTHER INFORMATION: Chimeric nucleic acid

<400> SEQUENCE: 151 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
             20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
         35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
     50                  55                  60 ata cac caa aat aat ggt ttg gat acc gaa aat aat cac aat gga tca     240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag     336
```

```
                    -continued

Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190 aaa cct tcc atg gcc aag caa aat gtt agc agc ctt gac gag aaa aac      624
Lys Pro Ser Met Ala Lys Gln Asn Val Ser Ser Leu Asp Glu Lys Asn
        195                 200                 205 agc gtt tca gta gat ttg cct ggt gaa atg aaa gtt ctt gta agc aaa      672
Ser Val Ser Val Asp Leu Pro Gly Glu Met Lys Val Leu Val Ser Lys
    210                 215                 220 gaa aaa aac aaa gac ggc aag tac gat cta att gca aca gta gac aag      720
Glu Lys Asn Lys Asp Gly Lys Tyr Asp Leu Ile Ala Thr Val Asp Lys
225                 230                 235                 240 ctt gag ctt aaa gga act tct gat aaa aac aat gga tct gga gta ctt      768
Leu Glu Leu Lys Gly Thr Ser Asp Lys Asn Asn Gly Ser Gly Val Leu
                245                 250                 255 gaa ggc gta aaa gct gac aaa agt aaa gta aaa tta aca att tct gac      816
Glu Gly Val Lys Ala Asp Lys Ser Lys Val Lys Leu Thr Ile Ser Asp
            260                 265                 270 gat cta ggt caa acc aca ctt gaa gtt ttc aaa gaa gat ggc aaa aca      864
Asp Leu Gly Gln Thr Thr Leu Glu Val Phe Lys Glu Asp Gly Lys Thr
        275                 280                 285 cta gta tca aaa aaa gta act tcc aaa gac aag tca tca aca gaa gaa      912
Leu Val Ser Lys Lys Val Thr Ser Lys Asp Lys Ser Ser Thr Glu Glu
    290                 295                 300 aaa ttc aat gaa aaa ggt gaa gta tct gaa aaa ata ata aca aga gca      960
Lys Phe Asn Glu Lys Gly Glu Val Ser Glu Lys Ile Ile Thr Arg Ala
305                 310                 315                 320 gac gga acc aga ctt gaa tac aca gga att aaa agc gat gga tct gga     1008
Asp Gly Thr Arg Leu Glu Tyr Thr Gly Ile Lys Ser Asp Gly Ser Gly
                325                 330                 335 aaa gct aaa gag gtt tta aaa ggc tat gtt ctt gaa gga act cta act     1056
Lys Ala Lys Glu Val Leu Lys Gly Tyr Val Leu Glu Gly Thr Leu Thr
            340                 345                 350 gct gaa aaa aca aca ttg gtg gtt aaa gaa gga act gtt act tta agc     1104
Ala Glu Lys Thr Thr Leu Val Val Lys Glu Gly Thr Val Thr Leu Ser
        355                 360                 365 aaa aat att tca aaa tct ggg gaa gtt tca gtt gaa ctt aat gac act     1152
Lys Asn Ile Ser Lys Ser Gly Glu Val Ser Val Glu Leu Asn Asp Thr
    370                 375                 380 gac agt agt gct gct act aaa aaa act gca gct tgg aat tca aaa act     1200
Asp Ser Ser Ala Ala Thr Lys Lys Thr Ala Ala Trp Asn Ser Lys Thr
385                 390                 395                 400 tcc act tta aca att agt gtg aat agc caa aaa acc aaa aac ctt gta     1248
Ser Thr Leu Thr Ile Ser Val Asn Ser Gln Lys Thr Lys Asn Leu Val
                405                 410                 415
```

```
ttc aca aaa gaa gac aca ata aca gta caa aaa tac gac tca gca ggc    1296
Phe Thr Lys Glu Asp Thr Ile Thr Val Gln Lys Tyr Asp Ser Ala Gly
            420                 425                 430 acc aat cta gaa ggc aaa gca gtc gaa att aca aca ctt aaa gaa ctt    1344
Thr Asn Leu Glu Gly Lys Ala Val Glu Ile Thr Thr Leu Lys Glu Leu
            435                 440                 445 aaa aac gct tta aaa taa                                            1362
Lys Asn Ala Leu Lys *
    450
```

```
<210> SEQ ID NO 152
<211> LENGTH: 453
<212> TYPE: PRT
<213> ORGANISM: Artificial Sequence
<220> FEATURE:
<223> OTHER INFORMATION: Chimeric Protein

<400> SEQUENCE: 152
```

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Glu Met Lys Val Leu Val Ser Lys
    210                 215                 220

Glu Lys Asn Lys Asp Gly Lys Tyr Asp Leu Ile Ala Thr Val Asp Lys
225                 230                 235                 240

Leu Glu Leu Lys Gly Thr Ser Asp Lys Asn Asn Gly Ser Gly Val Leu
                245                 250                 255

Glu Gly Val Lys Ala Asp Lys Ser Lys Val Lys Leu Thr Ile Ser Asp
            260                 265                 270

Asp Leu Gly Gln Thr Thr Leu Glu Val Phe Lys Glu Asp Gly Lys Thr
        275                 280                 285

Leu Val Ser Lys Lys Val Thr Ser Lys Asp Lys Ser Ser Thr Glu Glu
    290                 295                 300
```

```
                            -continued

Lys Phe Asn Glu Lys Gly Glu Val Ser Glu Lys Ile Thr Arg Ala
305                 310                 315                 320

Asp Gly Thr Arg Leu Glu Tyr Thr Gly Ile Lys Ser Asp Gly Ser Gly
                325                 330                 335

Lys Ala Lys Glu Val Leu Lys Gly Tyr Val Leu Glu Gly Thr Leu Thr
                340                 345                 350

Ala Glu Lys Thr Thr Leu Val Val Lys Glu Gly Thr Val Thr Leu Ser
                355                 360                 365

Lys Asn Ile Ser Lys Ser Gly Glu Val Ser Val Glu Leu Asn Asp Thr
            370                 375                 380

Asp Ser Ser Ala Ala Thr Lys Lys Thr Ala Ala Trp Asn Ser Lys Thr
385                 390                 395                 400

Ser Thr Leu Thr Ile Ser Val Asn Ser Gln Lys Thr Lys Asn Leu Val
                405                 410                 415

Phe Thr Lys Glu Asp Thr Ile Thr Val Gln Lys Tyr Asp Ser Ala Gly
                420                 425                 430

Thr Asn Leu Glu Gly Lys Ala Val Glu Ile Thr Thr Leu Lys Glu Leu
            435                 440                 445

Lys Asn Ala Leu Lys
        450

<210> SEQ ID NO 153
<211> LENGTH: 1341
<212> TYPE: DNA
<213> ORGANISM: Artificial Sequence
<220> FEATURE:
<221> NAME/KEY: CDS
<222> LOCATION: (1)...(1341)
<223> OTHER INFORMATION: Chimeric nucleic acid

<400> SEQUENCE: 153 atg gct tgt aat aat tca ggg aaa gat ggg aat aca tct gca aat tct      48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
                20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
            35                  40                  45 ttg ctg tca tct ata gat gag ctt gct aaa gct att ggt aaa aaa ata     192
Leu Leu Ser Ser Ile Asp Glu Leu Ala Lys Ala Ile Gly Lys Lys Ile
        50                  55                  60 aaa aac gat ggt agt tta gat aat gaa gca aat cgc aac gag tca ttg     240
Lys Asn Asp Gly Ser Leu Asp Asn Glu Ala Asn Arg Asn Glu Ser Leu
65                  70                  75                  80 tta gca gga gct tat aca ata tca acc tta ata aca caa aaa tta agt     288
Leu Ala Gly Ala Tyr Thr Ile Ser Thr Leu Ile Thr Gln Lys Leu Ser
                85                  90                  95 aaa tta aac gga tca gaa ggt tta aag gaa aag att gcc gca gct aag     336
Lys Leu Asn Gly Ser Glu Gly Leu Lys Glu Lys Ile Ala Ala Ala Lys
                100                 105                 110 aaa tgc tct gaa gag ttt agt act aaa cta aaa gat aat cat gca cag     384
Lys Cys Ser Glu Glu Phe Ser Thr Lys Leu Lys Asp Asn His Ala Gln
                115                 120                 125 ctt ggt ata cag ggc gtt act gat gaa aat gca aaa aaa gct att tta     432
Leu Gly Ile Gln Gly Val Thr Asp Glu Asn Ala Lys Lys Ala Ile Leu
        130                 135                 140 aaa gca aat gca gcg ggt aaa gat aag ggc gtt gaa gaa ctt gaa aag     480
```

```
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt      528
Leu Ser Gly Ser Leu Glu Ser Leu Ser Lys Ala Ala Lys Glu Met Leu
                165                 170                 175 gct aat tca gtt aaa gag ctt aca agc cct gtt gtc cat ggc aag caa      576
Ala Asn Ser Val Lys Glu Leu Thr Ser Pro Val Val His Gly Lys Gln
            180                 185                 190 aat gtt agc agc ctt gac gag aaa aac agc gtt tca gta gat ttg cct      624
Asn Val Ser Ser Leu Asp Glu Lys Asn Ser Val Ser Val Asp Leu Pro
        195                 200                 205 ggt gaa atg aaa gtt ctt gta agc aaa gaa aaa aac aaa gac ggc aag      672
Gly Glu Met Lys Val Leu Val Ser Lys Glu Lys Asn Lys Asp Gly Lys
    210                 215                 220 tac gat cta att gca aca gta gac aag ctt gag ctt aaa gga act tct      720
Tyr Asp Leu Ile Ala Thr Val Asp Lys Leu Glu Leu Lys Gly Thr Ser
225                 230                 235                 240 gat aaa aac aat gga tct gga gta ctt gaa ggc gta aaa gct gac aaa      768
Asp Lys Asn Asn Gly Ser Gly Val Leu Glu Gly Val Lys Ala Asp Lys
                245                 250                 255 agt aaa gta aaa tta aca att tct gac gat cta ggt caa acc aca ctt      816
Ser Lys Val Lys Leu Thr Ile Ser Asp Asp Leu Gly Gln Thr Thr Leu
            260                 265                 270 gaa gtt ttc aaa gaa gat ggc aaa aca cta gta tca aaa aaa gta act      864
Glu Val Phe Lys Glu Asp Gly Lys Thr Leu Val Ser Lys Lys Val Thr
        275                 280                 285 tcc aaa gac aag tca tca aca gaa gaa aaa ttc aat gaa aaa ggt gaa      912
Ser Lys Asp Lys Ser Ser Thr Glu Glu Lys Phe Asn Glu Lys Gly Glu
    290                 295                 300 gta tct gaa aaa ata ata aca aga gca gac gga acc aga ctt gaa tac      960
Val Ser Glu Lys Ile Ile Thr Arg Ala Asp Gly Thr Arg Leu Glu Tyr
305                 310                 315                 320 aca gga att aaa agc gat gga tct gga aaa gct aaa gag gtt tta aaa     1008
Thr Gly Ile Lys Ser Asp Gly Ser Gly Lys Ala Lys Glu Val Leu Lys
                325                 330                 335 ggc tat gtt ctt gaa gga act cta act gct gaa aaa aca aca ttg gtg     1056
Gly Tyr Val Leu Glu Gly Thr Leu Thr Ala Glu Lys Thr Thr Leu Val
            340                 345                 350 gtt aaa gaa gga act gtt act tta agc aaa aat att tca aaa tct ggg     1104
Val Lys Glu Gly Thr Val Thr Leu Ser Lys Asn Ile Ser Lys Ser Gly
        355                 360                 365 gaa gtt tca gtt gaa ctt aat gac act gac agt agt gct gct act aaa     1152
Glu Val Ser Val Glu Leu Asn Asp Thr Asp Ser Ser Ala Ala Thr Lys
    370                 375                 380 aaa act gca gct tgg aat tca aaa act tcc act tta aca att agt gtg     1200
Lys Thr Ala Ala Trp Asn Ser Lys Thr Ser Thr Leu Thr Ile Ser Val
385                 390                 395                 400 aat agc caa aaa acc aaa aac ctt gta ttc aca aaa gaa gac aca ata     1248
Asn Ser Gln Lys Thr Lys Asn Leu Val Phe Thr Lys Glu Asp Thr Ile
                405                 410                 415 aca gta caa aaa tac gac tca gca ggc acc aat cta gaa ggc aaa gca     1296
Thr Val Gln Lys Tyr Asp Ser Ala Gly Thr Asn Leu Glu Gly Lys Ala
            420                 425                 430 gtc gaa att aca aca ctt aaa gaa ctt aaa aac gct tta aaa taa         1341
Val Glu Ile Thr Thr Leu Lys Glu Leu Lys Asn Ala Leu Lys *
        435                 440                 445

<210> SEQ ID NO 154
<211> LENGTH: 446
<212> TYPE: PRT
```

<213> ORGANISM: Artificial Sequence
<220> FEATURE:
<223> OTHER INFORMATION: Chimeric protein

<400> SEQUENCE: 154

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
        195                 200                 205

Gly Glu Met Lys Val Leu Val Ser Lys Glu Lys Asn Lys Asp Gly Lys
    210                 215                 220

Tyr Asp Leu Ile Ala Thr Val Asp Lys Leu Glu Leu Lys Gly Thr Ser
225                 230                 235                 240

Asp Lys Asn Asn Gly Ser Gly Val Leu Glu Gly Val Lys Ala Asp Lys
                245                 250                 255

Ser Lys Val Lys Leu Thr Ile Ser Asp Asp Leu Gly Gln Thr Thr Leu
            260                 265                 270

Glu Val Phe Lys Glu Asp Gly Lys Thr Leu Val Ser Lys Lys Val Thr
        275                 280                 285

Ser Lys Asp Lys Ser Ser Thr Glu Glu Lys Phe Asn Glu Lys Gly Glu
    290                 295                 300

Val Ser Glu Lys Ile Ile Thr Arg Ala Asp Gly Thr Arg Leu Glu Tyr
305                 310                 315                 320

Thr Gly Ile Lys Ser Asp Gly Ser Gly Lys Ala Lys Glu Val Leu Lys
                325                 330                 335

Gly Tyr Val Leu Glu Gly Thr Leu Thr Ala Glu Lys Thr Thr Leu Val
            340                 345                 350

Val Lys Glu Gly Thr Val Thr Leu Ser Lys Asn Ile Ser Lys Ser Gly
        355                 360                 365

Glu Val Ser Val Glu Leu Asn Asp Thr Asp Ser Ser Ala Ala Thr Lys
    370                 375                 380

Lys Thr Ala Ala Trp Asn Ser Lys Thr Ser Thr Leu Thr Ile Ser Val
```

```
                385                 390                 395                 400
Asn Ser Gln Lys Thr Lys Asn Leu Val Phe Thr Lys Glu Asp Thr Ile
                405                 410                 415

Thr Val Gln Lys Tyr Asp Ser Ala Gly Thr Asn Leu Glu Gly Lys Ala
                420                 425                 430

Val Glu Ile Thr Thr Leu Lys Glu Leu Lys Asn Ala Leu Lys
                435                 440                 445

<210> SEQ ID NO 155
<211> LENGTH: 1362
<212> TYPE: DNA
<213> ORGANISM: Artificial Sequence
<220> FEATURE:
<221> NAME/KEY: CDS
<222> LOCATION: (1)...(1362)
<223> OTHER INFORMATION: Chimeric nucleic acid

<400> SEQUENCE: 155 atg gct tgt aat aat tca ggg aaa gat ggg aat aca tct gca aat tct       48
Met Ala Cys Asn Asn Ser Gly Lys Asp Gly Asn Thr Ser Ala Asn Ser
  1               5                  10                  15 gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
             20                  25                  30 att acg gat tct aat gcg gtt tta ctt gct gtg aaa gag gtt gaa gcg      144
Ile Thr Asp Ser Asn Ala Val Leu Leu Ala Val Lys Glu Val Glu Ala
         35                  40                  45 ttg ctg tca tct ata gat gaa att gct gct aaa gct att ggt aaa aaa      192
Leu Leu Ser Ser Ile Asp Glu Ile Ala Ala Lys Ala Ile Gly Lys Lys
     50                  55                  60 ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80 tta tta gcg gga gct tat gca ata tca acc cta ata aaa caa aaa tta      288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190 aaa cct tcc atg gcc aag caa aat gtt agc agc ctt gac gag aaa aac      624
Lys Pro Ser Met Ala Lys Gln Asn Val Ser Ser Leu Asp Glu Lys Asn
        195                 200                 205 agc gtt tca gta gat ttg cct ggt gaa atg aaa gtt ctt gta agc aaa      672
Ser Val Ser Val Asp Leu Pro Gly Glu Met Lys Val Leu Val Ser Lys
    210                 215                 220
```

```
gaa aaa aac aaa gac ggc aag tac gat cta att gca aca gta gac aag    720
Glu Lys Asn Lys Asp Gly Lys Tyr Asp Leu Ile Ala Thr Val Asp Lys
225                 230                 235                 240 ctt gag ctt aaa gga act tct gat aaa aac aat gga tct gga gta ctt    768
Leu Glu Leu Lys Gly Thr Ser Asp Lys Asn Asn Gly Ser Gly Val Leu
                245                 250                 255 gaa ggc gta aaa gct gac aaa agt aaa gta aaa tta aca att tct gac    816
Glu Gly Val Lys Ala Asp Lys Ser Lys Val Lys Leu Thr Ile Ser Asp
            260                 265                 270 gat cta ggt caa acc aca ctt gaa gtt ttc aaa gaa gat ggc aaa aca    864
Asp Leu Gly Gln Thr Thr Leu Glu Val Phe Lys Glu Asp Gly Lys Thr
        275                 280                 285 cta gta tca aaa aaa gta act tcc aaa gac aag tca tca aca gaa gaa    912
Leu Val Ser Lys Lys Val Thr Ser Lys Asp Lys Ser Ser Thr Glu Glu
    290                 295                 300 aaa ttc aat gaa aaa ggt gaa gta tct gaa aaa ata ata aca aga gca    960
Lys Phe Asn Glu Lys Gly Glu Val Ser Glu Lys Ile Ile Thr Arg Ala
305                 310                 315                 320 gac gga acc aga ctt gaa tac aca gga att aaa agc gat gga tct gga   1008
Asp Gly Thr Arg Leu Glu Tyr Thr Gly Ile Lys Ser Asp Gly Ser Gly
                325                 330                 335 aaa gct aaa gag gtt tta aaa ggc tat gtt ctt gaa gga act cta act   1056
Lys Ala Lys Glu Val Leu Lys Gly Tyr Val Leu Glu Gly Thr Leu Thr
            340                 345                 350 gct gaa aaa aca aca ttg gtg gtt aaa gaa gga act gtt act tta agc   1104
Ala Glu Lys Thr Thr Leu Val Val Lys Glu Gly Thr Val Thr Leu Ser
        355                 360                 365 aaa aat att tca aaa tct ggg gaa gtt tca gtt gaa ctt aat gac act   1152
Lys Asn Ile Ser Lys Ser Gly Glu Val Ser Val Glu Leu Asn Asp Thr
    370                 375                 380 gac agt agt gct gct act aaa aaa act gca gct tgg aat tca aaa act   1200
Asp Ser Ser Ala Ala Thr Lys Lys Thr Ala Ala Trp Asn Ser Lys Thr
385                 390                 395                 400 tct act tta aca att agt gtt aac agc aaa aaa act aca caa ctt gtg   1248
Ser Thr Leu Thr Ile Ser Val Asn Ser Lys Lys Thr Thr Gln Leu Val
                405                 410                 415 ttt act aaa caa gac aca ata act gta caa aaa tac gac tcc gca ggt   1296
Phe Thr Lys Gln Asp Thr Ile Thr Val Gln Lys Tyr Asp Ser Ala Gly
            420                 425                 430 acc aat tta gaa ggc aca gca gtc gaa att aaa aca ctt gat gaa ctt   1344
Thr Asn Leu Glu Gly Thr Ala Val Glu Ile Lys Thr Leu Asp Glu Leu
        435                 440                 445 aaa aac gct tta aaa taa                                            1362
Lys Asn Ala Leu Lys *
    450

<210> SEQ ID NO 156
<211> LENGTH: 453
<212> TYPE: PRT
<213> ORGANISM: Artificial Sequence
<220> FEATURE:
<223> OTHER INFORMATION: Chimeric Protein

<400> SEQUENCE: 156

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45
```

```
Leu Leu Ser Ser Ile Asp Glu Ile Ala Ala Lys Ala Ile Gly Lys Lys
    50              55              60

Ile His Gln Asn Asn Gly Leu Asp Thr Glu Asn Asn His Asn Gly Ser
65              70              75              80

Leu Leu Ala Gly Ala Tyr Ala Ile Ser Thr Leu Ile Lys Gln Lys Leu
            85              90              95

Asp Gly Leu Lys Asn Glu Gly Leu Lys Glu Lys Ile Asp Ala Ala Lys
            100             105             110

Lys Cys Ser Glu Thr Phe Thr Asn Lys Leu Lys Glu Lys His Thr Asp
            115             120             125

Leu Gly Lys Glu Gly Val Thr Asp Ala Asp Ala Lys Glu Ala Ile Leu
            130             135             140

Lys Ala Asn Gly Thr Lys Thr Lys Gly Ala Glu Glu Leu Gly Lys Leu
145             150             155             160

Phe Glu Ser Val Glu Val Leu Ser Lys Ala Ala Lys Glu Met Leu Ala
            165             170             175

Asn Ser Val Lys Glu Leu Thr Ser Pro Val Ala Glu Ser Pro Lys
            180             185             190

Lys Pro Ser Met Ala Lys Gln Asn Val Ser Ser Leu Asp Glu Lys Asn
            195             200             205

Ser Val Ser Val Asp Leu Pro Gly Glu Met Lys Val Leu Val Ser Lys
    210             215             220

Glu Lys Asn Lys Asp Gly Lys Tyr Asp Leu Ile Ala Thr Val Asp Lys
225             230             235             240

Leu Glu Leu Lys Gly Thr Ser Asp Lys Asn Asn Gly Ser Gly Val Leu
            245             250             255

Glu Gly Val Lys Ala Asp Lys Ser Lys Val Lys Leu Thr Ile Ser Asp
            260             265             270

Asp Leu Gly Gln Thr Thr Leu Glu Val Phe Lys Glu Asp Gly Lys Thr
            275             280             285

Leu Val Ser Lys Lys Val Thr Ser Lys Asp Lys Ser Ser Thr Glu Glu
            290             295             300

Lys Phe Asn Glu Lys Gly Glu Val Ser Glu Lys Ile Ile Thr Arg Ala
305             310             315             320

Asp Gly Thr Arg Leu Glu Tyr Thr Gly Ile Lys Ser Asp Gly Ser Gly
            325             330             335

Lys Ala Lys Glu Val Leu Lys Gly Tyr Val Leu Glu Gly Thr Leu Thr
            340             345             350

Ala Glu Lys Thr Thr Leu Val Val Lys Glu Gly Thr Val Thr Leu Ser
            355             360             365

Lys Asn Ile Ser Lys Ser Gly Glu Val Ser Val Glu Leu Asn Asp Thr
            370             375             380

Asp Ser Ser Ala Ala Thr Lys Lys Thr Ala Ala Trp Asn Ser Lys Thr
385             390             395             400

Ser Thr Leu Thr Ile Ser Val Asn Ser Lys Lys Thr Thr Gln Leu Val
            405             410             415

Phe Thr Lys Gln Asp Thr Ile Thr Val Gln Lys Tyr Asp Ser Ala Gly
            420             425             430

Thr Asn Leu Glu Gly Thr Ala Val Glu Ile Lys Thr Leu Asp Glu Leu
            435             440             445

Lys Asn Ala Leu Lys
    450
```

```
<210> SEQ ID NO 157
<211> LENGTH: 1341
<212> TYPE: DNA
<213> ORGANISM: Artificial Sequence
<220> FEATURE:
<221> NAME/KEY: CDS
<222> LOCATION: (1)...(1341)
<223> OTHER INFORMATION: Chimeric nucleic acid

<400> SEQUENCE: 157 atg gct tgt aat aat tca ggg aaa gat ggg aat aca tct gca aat tct        48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa        96
Ala Asp Glu Ser Val Lys Gly Pro Asn Leu Thr Glu Ile Ser Lys Lys
             20                  25                  30 att acg gat tct aat gcg gtt tta ctt gct gtg aaa gag gtt gaa gcg       144
Ile Thr Asp Ser Asn Ala Val Leu Leu Ala Val Lys Glu Val Glu Ala
         35                  40                  45 ttg ctg tca tct ata gat gag ctt gct aaa gct att ggt aaa aaa ata       192
Leu Leu Ser Ser Ile Asp Glu Leu Ala Lys Ala Ile Gly Lys Lys Ile
     50                  55                  60 aaa aac gat ggt agt tta gat aat gaa gca aat cgc aac gag tca ttg       240
Lys Asn Asp Gly Ser Leu Asp Asn Glu Ala Asn Arg Asn Glu Ser Leu
 65                  70                  75                  80 tta gca gga gct tat aca ata tca acc tta ata aca caa aaa tta agt       288
Leu Ala Gly Ala Tyr Thr Ile Ser Thr Leu Ile Thr Gln Lys Leu Ser
                 85                  90                  95 aaa tta aac gga tca gaa ggt tta aag gaa aag att gcc gca gct aag       336
Lys Leu Asn Gly Ser Glu Gly Leu Lys Glu Lys Ile Ala Ala Ala Lys
            100                 105                 110 aaa tgc tct gaa gag ttt agt act aaa cta aaa gat aat cat gca cag       384
Lys Cys Ser Glu Glu Phe Ser Thr Lys Leu Lys Asp Asn His Ala Gln
        115                 120                 125 ctt ggt ata cag ggc gtt act gat gaa aat gca aaa aaa gct att tta       432
Leu Gly Ile Gln Gly Val Thr Asp Glu Asn Ala Lys Lys Ala Ile Leu
    130                 135                 140 aaa gca aat gca gcg ggt aaa gat aag ggc gtt gaa gaa ctt gaa aag       480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt       528
Leu Ser Gly Ser Leu Glu Ser Leu Ser Lys Ala Ala Lys Glu Met Leu
                165                 170                 175 gct aat tca gtt aaa gag ctt aca agc cct gtt gtc cat ggc aag caa       576
Ala Asn Ser Val Lys Glu Leu Thr Ser Pro Val Val His Gly Lys Gln
            180                 185                 190 aat gtt agc agc ctt gac gag aaa aac agc gtt tca gta gat ttg cct       624
Asn Val Ser Ser Leu Asp Glu Lys Asn Ser Val Ser Val Asp Leu Pro
        195                 200                 205 ggt gaa atg aaa gtt ctt gta agc aaa gaa aaa aac aaa gac ggc aag       672
Gly Glu Met Lys Val Leu Val Ser Lys Glu Lys Asn Lys Asp Gly Lys
    210                 215                 220 tac gat cta att gca aca gta gac aag ctt gag ctt aaa gga act tct       720
Tyr Asp Leu Ile Ala Thr Val Asp Lys Leu Glu Leu Lys Gly Thr Ser
225                 230                 235                 240 gat aaa aac aat gga tct gga gta ctt gaa ggc gta aaa gct gac aaa       768
Asp Lys Asn Asn Gly Ser Gly Val Leu Glu Gly Val Lys Ala Asp Lys
                245                 250                 255 agt aaa gta aaa tta aca att tct gac gat cta ggt caa acc aca ctt       816
Ser Lys Val Lys Leu Thr Ile Ser Asp Asp Leu Gly Gln Thr Thr Leu
            260                 265                 270
```

```
gaa gtt ttc aaa gaa gat ggc aaa aca cta gta tca aaa aaa gta act      864
Glu Val Phe Lys Glu Asp Gly Lys Thr Leu Val Ser Lys Lys Val Thr
        275                 280                 285 tcc aaa gac aag tca tca aca gaa gaa aaa ttc aat gaa aaa ggt gaa      912
Ser Lys Asp Lys Ser Ser Thr Glu Glu Lys Phe Asn Glu Lys Gly Glu
290                 295                 300 gta tct gaa aaa ata ata aca aga gca gac gga acc aga ctt gaa tac      960
Val Ser Glu Lys Ile Ile Thr Arg Ala Asp Gly Thr Arg Leu Glu Tyr
305                 310                 315                 320 aca gga att aaa agc gat gga tct gga aaa gct aaa gag gtt tta aaa     1008
Thr Gly Ile Lys Ser Asp Gly Ser Gly Lys Ala Lys Glu Val Leu Lys
                325                 330                 335 ggc tat gtt ctt gaa gga act cta act gct gaa aaa aca aca ttg gtg     1056
Gly Tyr Val Leu Glu Gly Thr Leu Thr Ala Glu Lys Thr Thr Leu Val
            340                 345                 350 gtt aaa gaa gga act gtt act tta agc aaa aat att tca aaa tct ggg     1104
Val Lys Glu Gly Thr Val Thr Leu Ser Lys Asn Ile Ser Lys Ser Gly
        355                 360                 365 gaa gtt tca gtt gaa ctt aat gac act gac agt agt gct gct act aaa     1152
Glu Val Ser Val Glu Leu Asn Asp Thr Asp Ser Ser Ala Ala Thr Lys
370                 375                 380 aaa act gca gct tgg aat tca aaa act tct act tta aca att agt gtt     1200
Lys Thr Ala Ala Trp Asn Ser Lys Thr Ser Thr Leu Thr Ile Ser Val
385                 390                 395                 400 aac agc aaa aaa act aca caa ctt gtg ttt act aaa caa tac aca ata     1248
Asn Ser Lys Lys Thr Thr Gln Leu Val Phe Thr Lys Gln Tyr Thr Ile
                405                 410                 415 act gta aaa caa tac gac tcc gca ggt acc aat tta gaa ggc aca gca     1296
Thr Val Lys Gln Tyr Asp Ser Ala Gly Thr Asn Leu Glu Gly Thr Ala
            420                 425                 430 gtc gaa att aaa aca ctt gat gaa ctt aaa aac gct tta aaa taa         1341
Val Glu Ile Lys Thr Leu Asp Glu Leu Lys Asn Ala Leu Lys *
        435                 440                 445
```

<210> SEQ ID NO 158
<211> LENGTH: 446
<212> TYPE: PRT
<213> ORGANISM: Artificial Sequence
<220> FEATURE:
<223> OTHER INFORMATION: Chimeric protein

<400> SEQUENCE: 158

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
```

```
            130                 135                 140
Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
        195                 200                 205

Gly Glu Met Lys Val Leu Val Ser Lys Glu Lys Asn Lys Asp Gly Lys
    210                 215                 220

Tyr Asp Leu Ile Ala Thr Val Asp Lys Leu Glu Leu Lys Gly Thr Ser
225                 230                 235                 240

Asp Lys Asn Asn Gly Ser Gly Val Leu Glu Gly Val Lys Ala Asp Lys
                245                 250                 255

Ser Lys Val Lys Leu Thr Ile Ser Asp Asp Leu Gly Gln Thr Thr Leu
            260                 265                 270

Glu Val Phe Lys Glu Asp Gly Lys Thr Leu Val Ser Lys Lys Val Thr
        275                 280                 285

Ser Lys Asp Lys Ser Ser Thr Glu Glu Lys Phe Asn Glu Lys Gly Glu
    290                 295                 300

Val Ser Glu Lys Ile Ile Thr Arg Ala Asp Gly Thr Arg Leu Glu Tyr
305                 310                 315                 320

Thr Gly Ile Lys Ser Asp Gly Ser Gly Lys Ala Lys Glu Val Leu Lys
                325                 330                 335

Gly Tyr Val Leu Glu Gly Thr Leu Thr Ala Glu Lys Thr Thr Leu Val
            340                 345                 350

Val Lys Glu Gly Thr Val Thr Leu Ser Lys Asn Ile Ser Lys Ser Gly
        355                 360                 365

Glu Val Ser Val Glu Leu Asn Asp Thr Asp Ser Ser Ala Ala Thr Lys
    370                 375                 380

Lys Thr Ala Ala Trp Asn Ser Lys Thr Ser Thr Leu Thr Ile Ser Val
385                 390                 395                 400

Asn Ser Lys Lys Thr Thr Gln Leu Val Phe Thr Lys Gln Tyr Thr Ile
                405                 410                 415

Thr Val Lys Gln Tyr Asp Ser Ala Gly Thr Asn Leu Glu Gly Thr Ala
            420                 425                 430

Val Glu Ile Lys Thr Leu Asp Glu Leu Lys Asn Ala Leu Lys
        435                 440                 445

<210> SEQ ID NO 159
<211> LENGTH: 1365
<212> TYPE: DNA
<213> ORGANISM: Artificial Sequence
<220> FEATURE:
<221> NAME/KEY: CDS
<222> LOCATION: (1)...(1365)
<223> OTHER INFORMATION: Chimeric nucleic acid

<400> SEQUENCE: 159 atg gct tgt aat aat tca ggg aaa gat ggg aat aca tct gca aat tct      48
Met Ala Cys Asn Asn Ser Gly Lys Asp Gly Asn Thr Ser Ala Asn Ser
  1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
             20                  25                  30
```

-continued

| | | |
|---|---|---|
| att acg gat tct aat gcg gtt tta ctt gct gtg aaa gag gtt gaa gcg<br>Ile Thr Asp Ser Asn Ala Val Leu Leu Ala Val Lys Glu Val Glu Ala<br>          35                    40                    45 | | 144 |
| ttg ctg tca tct ata gat gaa att gct gct aaa gct att ggt aaa aaa<br>Leu Leu Ser Ser Ile Asp Glu Ile Ala Ala Lys Ala Ile Gly Lys Lys<br>50                   55                    60 | | 192 |
| ata cac caa aat aat ggt ttg gat acc gaa tat aat cac aat gga tca<br>Ile His Gln Asn Asn Gly Leu Asp Thr Glu Tyr Asn His Asn Gly Ser<br>65                   70                   75                  80 | | 240 |
| ttg tta gcg gga gct tat gca ata tca acc cta ata aaa caa aaa tta<br>Leu Leu Ala Gly Ala Tyr Ala Ile Ser Thr Leu Ile Lys Gln Lys Leu<br>                   85                    90                   95 | | 288 |
| gat gga ttg aaa aat gaa gga tta aag gaa aaa att gat gcg gct aag<br>Asp Gly Leu Lys Asn Glu Gly Leu Lys Glu Lys Ile Asp Ala Ala Lys<br>                 100                 105                110 | | 336 |
| aaa tgt tct gaa aca ttt act aat aaa tta aaa gaa aaa cac aca gat<br>Lys Cys Ser Glu Thr Phe Thr Asn Lys Leu Lys Glu Lys His Thr Asp<br>                 115                 120                125 | | 384 |
| ctt ggt aaa gaa ggt gtt act gat gct gat gca aaa gaa gcc att tta<br>Leu Gly Lys Glu Gly Val Thr Asp Ala Asp Ala Lys Glu Ala Ile Leu<br>130                    135                140 | | 432 |
| aaa aca aat ggt act aaa act aaa ggt gct gaa gaa ctt gga aaa tta<br>Lys Thr Asn Gly Thr Lys Thr Lys Gly Ala Glu Glu Leu Gly Lys Leu<br>145                    150                 155                160 | | 480 |
| ttt gaa tca gta gag gtc ttg tca aaa gca gct aaa gag atg ctt gct<br>Phe Glu Ser Val Glu Val Leu Ser Lys Ala Ala Lys Glu Met Leu Ala<br>                 165                 170                175 | | 528 |
| aat tca gtt aaa gag ctt aca agc cct gtt gtg gca gaa agt cca aaa<br>Asn Ser Val Lys Glu Leu Thr Ser Pro Val Val Ala Glu Ser Pro Lys<br>                 180                 185                190 | | 576 |
| aaa cct tcc atg gcc aag caa aat gtt agc agc ctt gat gaa aaa aat<br>Lys Pro Ser Met Ala Lys Gln Asn Val Ser Ser Leu Asp Glu Lys Asn<br>                 195                 200                205 | | 624 |
| agc gtt tca gta gat tta cct ggt gga atg aca gtt ctt gta agt aaa<br>Ser Val Ser Val Asp Leu Pro Gly Gly Met Thr Val Leu Val Ser Lys<br>                 210                 215                220 | | 672 |
| gaa aaa gac aaa gac ggt aaa tac agt cta gag gca aca gta gac aag<br>Glu Lys Asp Lys Asp Gly Lys Tyr Ser Leu Glu Ala Thr Val Asp Lys<br>225                    230                 235                240 | | 720 |
| ctt gag ctt aaa gga act tct gat aaa aac aac ggt tct gga aca ctt<br>Leu Glu Leu Lys Gly Thr Ser Asp Lys Asn Asn Gly Ser Gly Thr Leu<br>                 245                 250                255 | | 768 |
| gaa ggt gaa aaa act gac aaa agt aaa gta aaa tta aca att gct gat<br>Glu Gly Glu Lys Thr Asp Lys Ser Lys Val Lys Leu Thr Ile Ala Asp<br>                 260                 265                270 | | 816 |
| gac cta agt caa act aaa ttt gaa att ttc aaa gaa gat gcc aaa aca<br>Asp Leu Ser Gln Thr Lys Phe Glu Ile Phe Lys Glu Asp Ala Lys Thr<br>                 275                 280                285 | | 864 |
| tta gta tca aaa aaa gta acc ctt aaa gac aag tca tca aca gaa gaa<br>Leu Val Ser Lys Lys Val Thr Leu Lys Asp Lys Ser Ser Thr Glu Glu<br>290                    295                300 | | 912 |
| aaa ttc aac gaa aag ggt gaa aca tct gaa aaa aca ata gta aga gca<br>Lys Phe Asn Glu Lys Gly Glu Thr Ser Glu Lys Thr Ile Val Arg Ala<br>305                    310                 315                320 | | 960 |
| aat gga acc aga ctt gaa tac aca gac ata aaa agc gat gga tcc gga<br>Asn Gly Thr Arg Leu Glu Tyr Thr Asp Ile Lys Ser Asp Gly Ser Gly<br>                 325                 330                335 | | 1008 |
| aaa gct aaa gaa gtt tta aaa gac ttt act ctt gaa gga act cta gct<br>Lys Ala Lys Glu Val Leu Lys Asp Phe Thr Leu Glu Gly Thr Leu Ala<br>                 340                 345                350 | | 1056 |

```
gct gac ggc aaa aca aca ttg aaa gtt aca gaa ggc act gtt gtt tta    1104
Ala Asp Gly Lys Thr Thr Leu Lys Val Thr Glu Gly Thr Val Val Leu
        355                 360                 365 agc aag aac att tta aaa tcc gga gaa ata aca gtt gca ctt gat gac    1152
Ser Lys Asn Ile Leu Lys Ser Gly Glu Ile Thr Val Ala Leu Asp Asp
    370                 375                 380 tct gac act act cag gct act aaa aaa act gga aaa tgg gat tca aat    1200
Ser Asp Thr Thr Gln Ala Thr Lys Lys Thr Gly Lys Trp Asp Ser Asn
385                 390                 395                 400 act tcc act tta aca att agt gtg aat agc aaa aaa act aaa aac att    1248
Thr Ser Thr Leu Thr Ile Ser Val Asn Ser Lys Lys Thr Lys Asn Ile
                405                 410                 415 gta ttt aca aaa gaa gac aca ata aca gta caa aaa tac gac tca gca    1296
Val Phe Thr Lys Glu Asp Thr Ile Thr Val Gln Lys Tyr Asp Ser Ala
            420                 425                 430 ggc acc aat cta gaa ggc aac gca gtc gaa att aaa aca ctt gat gaa    1344
Gly Thr Asn Leu Glu Gly Asn Ala Val Glu Ile Lys Thr Leu Asp Glu
        435                 440                 445 ctt aaa aac gct tta aaa tag                                        1365
Leu Lys Asn Ala Leu Lys  *
    450

<210> SEQ ID NO 160
<211> LENGTH: 454
<212> TYPE: PRT
<213> ORGANISM: Artificial Sequence
<220> FEATURE:
<223> OTHER INFORMATION: Chimeric protein

<400> SEQUENCE: 160

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Tyr Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Thr Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Gly Met Thr Val Leu Val Ser Lys
```

```
                   210                 215                 220
Glu Lys Asp Lys Asp Gly Lys Tyr Ser Leu Glu Ala Thr Val Asp Lys
225                 230                 235                 240

Leu Glu Leu Lys Gly Thr Ser Asp Lys Asn Asn Gly Ser Gly Thr Leu
                245                 250                 255

Glu Gly Glu Lys Thr Asp Lys Ser Lys Val Lys Leu Thr Ile Ala Asp
            260                 265                 270

Asp Leu Ser Gln Thr Lys Phe Glu Ile Phe Lys Glu Asp Ala Lys Thr
        275                 280                 285

Leu Val Ser Lys Val Thr Leu Lys Asp Lys Ser Ser Thr Glu Glu
    290                 295                 300

Lys Phe Asn Glu Lys Gly Glu Thr Ser Glu Lys Thr Ile Val Arg Ala
305                 310                 315                 320

Asn Gly Thr Arg Leu Glu Tyr Thr Asp Ile Lys Ser Asp Gly Ser Gly
                325                 330                 335

Lys Ala Lys Glu Val Leu Lys Asp Phe Thr Leu Glu Gly Thr Leu Ala
            340                 345                 350

Ala Asp Gly Lys Thr Thr Leu Lys Val Thr Glu Gly Thr Val Val Leu
        355                 360                 365

Ser Lys Asn Ile Leu Lys Ser Gly Glu Ile Thr Val Ala Leu Asp Asp
    370                 375                 380

Ser Asp Thr Thr Gln Ala Thr Lys Lys Thr Gly Lys Trp Asp Ser Asn
385                 390                 395                 400

Thr Ser Thr Leu Thr Ile Ser Val Asn Ser Lys Lys Thr Lys Asn Ile
                405                 410                 415

Val Phe Thr Lys Glu Asp Thr Ile Thr Val Gln Lys Tyr Asp Ser Ala
            420                 425                 430

Gly Thr Asn Leu Glu Gly Asn Ala Val Glu Ile Lys Thr Leu Asp Glu
        435                 440                 445

Leu Lys Asn Ala Leu Lys
    450

<210> SEQ ID NO 161
<211> LENGTH: 1344
<212> TYPE: DNA
<213> ORGANISM: Artificial Sequence
<220> FEATURE:
<221> NAME/KEY: CDS
<222> LOCATION: (1)...(1344)
<223> OTHER INFORMATION: Chimeric nucleic acid

<400> SEQUENCE: 161 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
                20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
            35                  40                  45 ttg ctg tca tct ata gat gag ctt gct aaa gct att ggt aaa aaa ata     192
Leu Leu Ser Ser Ile Asp Glu Leu Ala Lys Ala Ile Gly Lys Lys Ile
        50                  55                  60 aaa aac gat ggt agt tta gat aat gaa gca aat cgc aac gag tca ttg     240
Lys Asn Asp Gly Ser Leu Asp Asn Glu Ala Asn Arg Asn Glu Ser Leu
65                  70                  75                  80
```

-continued

| | | |
|---|---|---|
| tta gca gga gct tat aca ata tca acc tta ata aca caa aaa tta agt<br>Leu Ala Gly Ala Tyr Thr Ile Ser Thr Leu Ile Thr Gln Lys Leu Ser<br>                  85                          90                      95 | 288 |
| aaa tta aac gga tca gaa ggt tta aag gaa aag att gcc gca gct aag<br>Lys Leu Asn Gly Ser Glu Gly Leu Lys Glu Lys Ile Ala Ala Ala Lys<br>                100                      105                      110 | 336 |
| aaa tgc tct gaa gag ttt agt act aaa cta aaa gat aat cat gca cag<br>Lys Cys Ser Glu Glu Phe Ser Thr Lys Leu Lys Asp Asn His Ala Gln<br>              115                      120                      125 | 384 |
| ctt ggt ata cag ggc gtt act gat gaa aat gca aaa aaa gct att tta<br>Leu Gly Ile Gln Gly Val Thr Asp Glu Asn Ala Lys Lys Ala Ile Leu<br>130                      135                      140 | 432 |
| aaa gca aat gca gcg ggt aaa gat aag ggc gtt gaa gaa ctt gaa aag<br>Lys Ala Asn Ala Ala Gly Lys Asp Lys Gly Val Glu Glu Leu Glu Lys<br>145                      150                      155                      160 | 480 |
| ttg tcc gga tca tta gaa agc tta tca aaa gca gct aaa gag atg ctt<br>Leu Ser Gly Ser Leu Glu Ser Leu Ser Lys Ala Ala Lys Glu Met Leu<br>                165                      170                      175 | 528 |
| gct aat tca gtt aaa gag ctt aca agc cct gtt gtc cat ggc aag caa<br>Ala Asn Ser Val Lys Glu Leu Thr Ser Pro Val Val His Gly Lys Gln<br>                  180                      185                      190 | 576 |
| aat gtt agc agc ctt gat gaa aaa aat agc gtt tca gta gat tta cct<br>Asn Val Ser Ser Leu Asp Glu Lys Asn Ser Val Ser Val Asp Leu Pro<br>                195                      200                      205 | 624 |
| ggt gga atg aca gtt ctt gta agt aaa gaa aaa gac aaa gac ggt aaa<br>Gly Gly Met Thr Val Leu Val Ser Lys Glu Lys Asp Lys Asp Gly Lys<br>210                      215                      220 | 672 |
| tac agt cta gag gca aca gta gac aag ctt gag ctt aaa gga act tct<br>Tyr Ser Leu Glu Ala Thr Val Asp Lys Leu Glu Leu Lys Gly Thr Ser<br>225                      230                      235                      240 | 720 |
| gat aaa aac aac ggt tct gga aca ctt gaa ggt gaa aaa act gac aaa<br>Asp Lys Asn Asn Gly Ser Gly Thr Leu Glu Gly Glu Lys Thr Asp Lys<br>                245                      250                      255 | 768 |
| agt aaa gta aaa tta aca att gct gat gac cta agt caa act aaa ttt<br>Ser Lys Val Lys Leu Thr Ile Ala Asp Asp Leu Ser Gln Thr Lys Phe<br>                260                      265                      270 | 816 |
| gaa att ttc aaa gaa gat gcc aaa aca tta gta tca aaa aaa gta acc<br>Glu Ile Phe Lys Glu Asp Ala Lys Thr Leu Val Ser Lys Lys Val Thr<br>                275                      280                      285 | 864 |
| ctt aaa gac aag tca tca aca gaa gaa aaa ttc aac gaa aag ggt gaa<br>Leu Lys Asp Lys Ser Ser Thr Glu Glu Lys Phe Asn Glu Lys Gly Glu<br>290                      295                      300 | 912 |
| aca tct gaa aaa aca ata gta aga gca aat gga acc aga ctt gaa tac<br>Thr Ser Glu Lys Thr Ile Val Arg Ala Asn Gly Thr Arg Leu Glu Tyr<br>305                      310                      315                      320 | 960 |
| aca gac ata aaa agc gat gga tcc gga aaa gct aaa gaa gtt tta aaa<br>Thr Asp Ile Lys Ser Asp Gly Ser Gly Lys Ala Lys Glu Val Leu Lys<br>                325                      330                      335 | 1008 |
| gac ttt act ctt gaa gga act cta gct gct gac ggc aaa aca aca ttg<br>Asp Phe Thr Leu Glu Gly Thr Leu Ala Ala Asp Gly Lys Thr Thr Leu<br>                340                      345                      350 | 1056 |
| aaa gtt aca gaa ggc act gtt gtt tta agc aag aac att tta aaa tcc<br>Lys Val Thr Glu Gly Thr Val Val Leu Ser Lys Asn Ile Leu Lys Ser<br>                355                      360                      365 | 1104 |
| gga gaa ata aca gtt gca ctt gat gac tct gac act act cag gct act<br>Gly Glu Ile Thr Val Ala Leu Asp Asp Ser Asp Thr Thr Gln Ala Thr<br>370                      375                      380 | 1152 |
| aaa aaa act gga aaa tgg gat tca aat act tcc act tta aca att agt<br>Lys Lys Thr Gly Lys Trp Asp Ser Asn Thr Ser Thr Leu Thr Ile Ser<br>385                      390                      395                      400 | 1200 |

```
gtg aat agc aaa aaa act aaa aac att gta ttt aca aaa gaa gac aca     1248
Val Asn Ser Lys Lys Thr Lys Asn Ile Val Phe Thr Lys Glu Asp Thr
            405                 410                 415 ata aca gta caa aaa tac gac tca gca ggc acc aat cta gaa ggc aac     1296
Ile Thr Val Gln Lys Tyr Asp Ser Ala Gly Thr Asn Leu Glu Gly Asn
        420                 425                 430 gca gtc gaa att aaa aca ctt gat gaa ctt aaa aac gct tta aaa tag     1344
Ala Val Glu Ile Lys Thr Leu Asp Glu Leu Lys Asn Ala Leu Lys *
    435                 440                 445
```

<210> SEQ ID NO 162
<211> LENGTH: 447
<212> TYPE: PRT
<213> ORGANISM: Artificial Sequence
<220> FEATURE:
<223> OTHER INFORMATION: Chimeric protein

<400> SEQUENCE: 162

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Ile Ala Ala Lys
            100                 105                 110

Lys Cys Ser Glu Glu Phe Ser Thr Lys Leu Lys Asp Asn His Ala Gln
    115                 120                 125

Leu Gly Ile Gln Gly Val Thr Asp Glu Asn Ala Lys Lys Ala Ile Leu
130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
        195                 200                 205

Gly Gly Met Thr Val Leu Val Ser Lys Glu Lys Asp Lys Asp Gly Lys
    210                 215                 220

Tyr Ser Leu Glu Ala Thr Val Asp Lys Leu Glu Leu Lys Gly Thr Ser
225                 230                 235                 240

Asp Lys Asn Asn Gly Ser Gly Thr Leu Glu Gly Glu Lys Thr Asp Lys
                245                 250                 255

Ser Lys Val Lys Leu Thr Ile Ala Asp Asp Leu Ser Gln Thr Lys Phe
            260                 265                 270

Glu Ile Phe Lys Glu Asp Ala Lys Thr Leu Val Ser Lys Lys Val Thr
        275                 280                 285

Leu Lys Asp Lys Ser Ser Thr Glu Glu Lys Phe Asn Glu Lys Gly Glu
    290                 295                 300
```

```
Thr Ser Glu Lys Thr Ile Val Arg Ala Asn Gly Thr Arg Leu Glu Tyr
305                 310                 315                 320

Thr Asp Ile Lys Ser Asp Gly Ser Gly Lys Ala Lys Glu Val Leu Lys
            325                 330                 335

Asp Phe Thr Leu Glu Gly Thr Leu Ala Ala Asp Gly Lys Thr Thr Leu
            340                 345                 350

Lys Val Thr Glu Gly Thr Val Val Leu Ser Lys Asn Ile Leu Lys Ser
            355                 360                 365

Gly Glu Ile Thr Val Ala Leu Asp Asp Ser Asp Thr Thr Gln Ala Thr
            370                 375                 380

Lys Lys Thr Gly Lys Trp Asp Ser Asn Thr Ser Thr Leu Thr Ile Ser
385                 390                 395                 400

Val Asn Ser Lys Lys Thr Lys Asn Ile Val Phe Thr Lys Glu Asp Thr
                405                 410                 415

Ile Thr Val Gln Lys Tyr Asp Ser Ala Gly Thr Asn Leu Glu Gly Asn
            420                 425                 430

Ala Val Glu Ile Lys Thr Leu Asp Glu Leu Lys Asn Ala Leu Lys
            435                 440                 445

<210> SEQ ID NO 163
<211> LENGTH: 1305
<212> TYPE: DNA
<213> ORGANISM: Artificial Sequence
<220> FEATURE:
<221> NAME/KEY: CDS
<222> LOCATION: (1)...(1305)
<223> OTHER INFORMATION: Chimeric nucleic acid

<400> SEQUENCE: 163 atg gct tgt aat aat tca gga aaa gat ggg aat aca tct gca aat tct        48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa        96
Ala Asp Glu Ser Val Lys Gly Pro Asn Leu Thr Glu Ile Ser Lys Lys
                20                  25                  30 att aca gaa tct aac gca gtt gtt ctg gct gtg aaa gaa att gaa act       144
Ile Thr Glu Ser Asn Ala Val Val Leu Ala Val Lys Glu Ile Glu Thr
            35                  40                  45 ttg ctt gca tct ata gat gaa ctt gct act aaa gct att ggt aaa aaa       192
Leu Leu Ala Ser Ile Asp Glu Leu Ala Thr Lys Ala Ile Gly Lys Lys
        50                  55                  60 ata caa caa aat ggt ggt tta gct gtc gaa gcg ggg cat aat gga aca       240
Ile Gln Gln Asn Gly Gly Leu Ala Val Glu Ala Gly His Asn Gly Thr
65                  70                  75                  80 ttg tta gca ggt gct tat aca ata tca aaa cta ata aca caa aaa tta       288
Leu Leu Ala Gly Ala Tyr Thr Ile Ser Lys Leu Ile Thr Gln Lys Leu
                85                  90                  95 gat gga ttg aaa aat tca gaa aaa tta aag gaa aaa att gaa aat gct       336
Asp Gly Leu Lys Asn Ser Glu Lys Leu Lys Glu Lys Ile Glu Asn Ala
            100                 105                 110 aag aaa tgt tct gaa gat ttt act aaa aaa cta gaa gga gaa cat gcg       384
Lys Lys Cys Ser Glu Asp Phe Thr Lys Lys Leu Glu Gly Glu His Ala
        115                 120                 125 caa ctt gga att gaa aat gtt act gat gag aat gca aaa aaa gct att       432
Gln Leu Gly Ile Glu Asn Val Thr Asp Glu Asn Ala Lys Lys Ala Ile
    130                 135                 140 tta ata aca gat gca gct aaa gat aag ggc gct gca gag ctt gaa aag       480
Leu Ile Thr Asp Ala Ala Lys Asp Lys Gly Ala Ala Glu Leu Glu Lys
145                 150                 155                 160
```

| | | |
|---|---|---|
| cta ttt aaa gca gta gaa aac ttg gca aaa gca gct aaa gag atg ctt<br>Leu Phe Lys Ala Val Glu Asn Leu Ala Lys Ala Ala Lys Glu Met Leu<br>165 170 175 | | 528 |
| gct aat tca gtt aaa gag ctt aca agt cct att gtg cat ggc gtt tca<br>Ala Asn Ser Val Lys Glu Leu Thr Ser Pro Ile Val His Gly Val Ser<br>180 185 190 | | 576 |
| gta gat ttg cct ggt gaa atg aaa gtt ctt gta agc aaa gaa aaa aac<br>Val Asp Leu Pro Gly Glu Met Lys Val Leu Val Ser Lys Glu Lys Asn<br>195 200 205 | | 624 |
| aaa gac ggc aag tac gat cta att gca aca gta gac aag ctt gag ctt<br>Lys Asp Gly Lys Tyr Asp Leu Ile Ala Thr Val Asp Lys Leu Glu Leu<br>210 215 220 | | 672 |
| aaa gga act tct gat aaa aac aat gga tct gga gta ctt gaa ggc gta<br>Lys Gly Thr Ser Asp Lys Asn Asn Gly Ser Gly Val Leu Glu Gly Val<br>225 230 235 240 | | 720 |
| aaa gct gac aaa agt aaa gta aaa tta aca att tct gac gat cta ggt<br>Lys Ala Asp Lys Ser Lys Val Lys Leu Thr Ile Ser Asp Asp Leu Gly<br>245 250 255 | | 768 |
| caa acc aca ctt gaa gtt ttc aaa gaa gat ggc aaa aca cta gta tca<br>Gln Thr Thr Leu Glu Val Phe Lys Glu Asp Gly Lys Thr Leu Val Ser<br>260 265 270 | | 816 |
| aaa aaa gta act tcc aaa gac aag tca tca aca gaa gaa aaa ttc aat<br>Lys Lys Val Thr Ser Lys Asp Lys Ser Ser Thr Glu Glu Lys Phe Asn<br>275 280 285 | | 864 |
| gaa aaa ggt gaa gta tct gaa aaa ata ata aca aga gca gac gga acc<br>Glu Lys Gly Glu Val Ser Glu Lys Ile Ile Thr Arg Ala Asp Gly Thr<br>290 295 300 | | 912 |
| aga ctt gaa tac aca gga att aaa agc gat gga tct gga aaa gct aaa<br>Arg Leu Glu Tyr Thr Gly Ile Lys Ser Asp Gly Ser Gly Lys Ala Lys<br>305 310 315 320 | | 960 |
| gag gtt tta aaa aaa ttt act ctt gaa gga aaa gta gct aat gat aaa<br>Glu Val Leu Lys Lys Phe Thr Leu Glu Gly Lys Val Ala Asn Asp Lys<br>325 330 335 | | 1008 |
| gta aca ttg gaa gta aaa gaa gga acc gtt act tta agt aag aac att<br>Val Thr Leu Glu Val Lys Glu Gly Thr Val Thr Leu Ser Lys Asn Ile<br>340 345 350 | | 1056 |
| tca aaa tct ggg gaa gtt tca gtt gaa ctt aat gac act gac agt agt<br>Ser Lys Ser Gly Glu Val Ser Val Glu Leu Asn Asp Thr Asp Ser Ser<br>355 360 365 | | 1104 |
| gct gct act aaa aaa act gca gct tgg aat tca ggc act tca act tta<br>Ala Ala Thr Lys Lys Thr Ala Ala Trp Asn Ser Gly Thr Ser Thr Leu<br>370 375 380 | | 1152 |
| aca att act gta aac agt aaa aaa act aaa gac ctt gtg ttt aca aaa<br>Thr Ile Thr Val Asn Ser Lys Lys Thr Lys Asp Leu Val Phe Thr Lys<br>385 390 395 400 | | 1200 |
| gaa aac aca att aca gta caa caa tac gac tca aat ggc acc aaa tta<br>Glu Asn Thr Ile Thr Val Gln Gln Tyr Asp Ser Asn Gly Thr Lys Leu<br>405 410 415 | | 1248 |
| gag ggg tca gca gtt gaa att aca aaa ctt gat gaa att aaa aac gct<br>Glu Gly Ser Ala Val Glu Ile Thr Lys Leu Asp Glu Ile Lys Asn Ala<br>420 425 430 | | 1296 |
| tta aaa taa<br>Leu Lys * | | 1305 |

<210> SEQ ID NO 164
<211> LENGTH: 434
<212> TYPE: PRT
<213> ORGANISM: Artificial Sequence
<220> FEATURE:
<223> OTHER INFORMATION: Chimeric protein -continued

<400> SEQUENCE: 164

```
Met Ala Cys Asn Asn Ser Gly Lys Asp Gly Asn Thr Ser Ala Asn Ser
 1               5                  10                  15
Ala Asp Glu Ser Val Lys Gly Pro Asn Leu Thr Glu Ile Ser Lys Lys
             20                  25                  30
Ile Thr Glu Ser Asn Ala Val Val Leu Ala Val Lys Glu Ile Glu Thr
         35                  40                  45
Leu Leu Ala Ser Ile Asp Glu Leu Ala Thr Lys Ala Ile Gly Lys Lys
     50                  55                  60
Ile Gln Gln Asn Gly Gly Leu Ala Val Glu Ala Gly His Asn Gly Thr
 65                  70                  75                  80
Leu Leu Ala Gly Ala Tyr Thr Ile Ser Lys Leu Ile Thr Gln Lys Leu
                 85                  90                  95
Asp Gly Leu Lys Asn Ser Glu Lys Leu Lys Glu Lys Ile Glu Asn Ala
            100                 105                 110
Lys Lys Cys Ser Glu Asp Phe Thr Lys Lys Leu Glu Gly Glu His Ala
        115                 120                 125
Gln Leu Gly Ile Glu Asn Val Thr Asp Glu Asn Ala Lys Lys Ala Ile
    130                 135                 140
Leu Ile Thr Asp Ala Ala Lys Asp Lys Gly Ala Ala Glu Leu Glu Lys
145                 150                 155                 160
Leu Phe Lys Ala Val Glu Asn Leu Ala Lys Ala Ala Lys Glu Met Leu
                165                 170                 175
Ala Asn Ser Val Lys Glu Leu Thr Ser Pro Ile Val His Gly Val Ser
            180                 185                 190
Val Asp Leu Pro Gly Glu Met Lys Val Leu Val Ser Lys Glu Lys Asn
        195                 200                 205
Lys Asp Gly Lys Tyr Asp Leu Ile Ala Thr Val Asp Lys Leu Glu Leu
    210                 215                 220
Lys Gly Thr Ser Asp Lys Asn Asn Gly Ser Gly Val Leu Glu Gly Val
225                 230                 235                 240
Lys Ala Asp Lys Ser Lys Val Lys Leu Thr Ile Ser Asp Asp Leu Gly
                245                 250                 255
Gln Thr Thr Leu Glu Val Phe Lys Glu Asp Gly Lys Thr Leu Val Ser
            260                 265                 270
Lys Lys Val Thr Ser Lys Asp Lys Ser Ser Thr Glu Glu Lys Phe Asn
        275                 280                 285
Glu Lys Gly Glu Val Ser Glu Lys Ile Ile Thr Arg Ala Asp Gly Thr
    290                 295                 300
Arg Leu Glu Tyr Thr Gly Ile Lys Ser Asp Gly Ser Gly Lys Ala Lys
305                 310                 315                 320
Glu Val Leu Lys Lys Phe Thr Leu Glu Gly Lys Val Ala Asn Asp Lys
                325                 330                 335
Val Thr Leu Glu Val Lys Glu Gly Thr Val Thr Leu Ser Lys Asn Ile
            340                 345                 350
Ser Lys Ser Gly Glu Val Ser Val Glu Leu Asn Asp Thr Asp Ser Ser
        355                 360                 365
Ala Ala Thr Lys Lys Thr Ala Ala Trp Asn Ser Gly Thr Ser Thr Leu
    370                 375                 380
Thr Ile Thr Val Asn Ser Lys Lys Thr Lys Asp Leu Val Phe Thr Lys
385                 390                 395                 400
Glu Asn Thr Ile Thr Val Gln Gln Tyr Asp Ser Asn Gly Thr Lys Leu
```

-continued

```
                   405                 410                 415
Glu Gly Ser Ala Val Glu Ile Thr Lys Leu Asp Glu Ile Lys Asn Ala
            420                 425                 430

Leu Lys

<210> SEQ ID NO 165
<211> LENGTH: 1332
<212> TYPE: DNA
<213> ORGANISM: Artificial Sequence
<220> FEATURE:
<221> NAME/KEY: CDS
<222> LOCATION: (1)...(1332)
<223> OTHER INFORMATION: Chimeric nucleic acid

<400> SEQUENCE: 165 atg gct tgt agt aat tca ggg aaa ggt ggg gat tct gca tct act aat         48
Met Ala Cys Ser Asn Ser Gly Lys Gly Gly Asp Ser Ala Ser Thr Asn
1               5                   10                  15 cct gct gac gag tct gcg aaa ggg cct aat ctt aca gaa ata agc aaa         96
Pro Ala Asp Glu Ser Ala Lys Gly Pro Asn Leu Thr Glu Ile Ser Lys
            20                  25                  30 aaa att aca gat tct aat gca ttt gta ctt gct gtt aaa gaa gtt gag        144
Lys Ile Thr Asp Ser Asn Ala Phe Val Leu Ala Val Lys Glu Val Glu
        35                  40                  45 act ttg gtt tta tct ata gat gaa ctt gct aag aaa gct att ggt caa        192
Thr Leu Val Leu Ser Ile Asp Glu Leu Ala Lys Lys Ala Ile Gly Gln
    50                  55                  60 aaa ata gac aat aat aat ggt tta gct gct tta aat aat cag aat gga        240
Lys Ile Asp Asn Asn Asn Gly Leu Ala Ala Leu Asn Asn Gln Asn Gly
65                  70                  75                  80 tcg ttg tta gca gga gcc tat gca ata tca acc tta ata aca gaa aaa        288
Ser Leu Leu Ala Gly Ala Tyr Ala Ile Ser Thr Leu Ile Thr Glu Lys
                85                  90                  95 ttg agt aaa ttg aaa aat tta gaa gaa tta aag aca gaa att gca aag        336
Leu Ser Lys Leu Lys Asn Leu Glu Glu Leu Lys Thr Glu Ile Ala Lys
            100                 105                 110 gct aag aaa tgt tcc gaa gaa ttt act aat aaa cta aaa agt ggt cat        384
Ala Lys Lys Cys Ser Glu Glu Phe Thr Asn Lys Leu Lys Ser Gly His
        115                 120                 125 gca gat ctt ggc aaa cag gat gct acc gat gat cat gca aaa gca gct        432
Ala Asp Leu Gly Lys Gln Asp Ala Thr Asp Asp His Ala Lys Ala Ala
    130                 135                 140 att tta aaa aca cat gca act acc gat aaa ggt gct aaa gaa ttt aaa        480
Ile Leu Lys Thr His Ala Thr Thr Asp Lys Gly Ala Lys Glu Phe Lys
145                 150                 155                 160 gat tta ttt gaa tca gta gaa ggt ttg tta aaa gca gct caa gta gca        528
Asp Leu Phe Glu Ser Val Glu Gly Leu Leu Lys Ala Ala Gln Val Ala
                165                 170                 175 cta act aat tca gtt aaa gaa ctt aca agt cct gtt gta gca gaa agt        576
Leu Thr Asn Ser Val Lys Glu Leu Thr Ser Pro Val Val Ala Glu Ser
            180                 185                 190 cca aaa aaa cct tcc atg gcc gtt tca gta gat ttg cct ggt gaa atg        624
Pro Lys Lys Pro Ser Met Ala Val Ser Val Asp Leu Pro Gly Glu Met
        195                 200                 205 aaa gtt ctt gta agc aaa gaa aaa aac aaa gac ggc aag tac gat cta        672
Lys Val Leu Val Ser Lys Glu Lys Asn Lys Asp Gly Lys Tyr Asp Leu
    210                 215                 220 att gca aca gta gac aag ctt gag ctt aaa gga act tct gat aaa aac        720
Ile Ala Thr Val Asp Lys Leu Glu Leu Lys Gly Thr Ser Asp Lys Asn
225                 230                 235                 240
```

-continued

| | | | | | | | | | | | | | | | |
|---|---|---|---|---|---|---|---|---|---|---|---|---|---|---|---|
| aat | gga | tct | gga | gta | ctt | gaa | ggc | gta | aaa | gct | gac | aaa | agt | aaa | gta | 768 |
| Asn | Gly | Ser | Gly | Val | Leu | Glu | Gly | Val | Lys | Ala | Asp | Lys | Ser | Lys | Val | |
| | | | 245 | | | | | 250 | | | | | 255 | | | |
| aaa | tta | aca | att | tct | gac | gat | cta | ggt | caa | acc | aca | ctt | gaa | gtt | ttc | 816 |
| Lys | Leu | Thr | Ile | Ser | Asp | Asp | Leu | Gly | Gln | Thr | Thr | Leu | Glu | Val | Phe | |
| | | | 260 | | | | | 265 | | | | | 270 | | | |
| aaa | gaa | gat | ggc | aaa | aca | cta | gta | tca | aaa | aaa | gta | act | tcc | aaa | gac | 864 |
| Lys | Glu | Asp | Gly | Lys | Thr | Leu | Val | Ser | Lys | Lys | Val | Thr | Ser | Lys | Asp | |
| | | | 275 | | | | | 280 | | | | | 285 | | | |
| aag | tca | tca | aca | gaa | gaa | aaa | ttc | aat | gaa | aaa | ggt | gaa | gta | tct | gaa | 912 |
| Lys | Ser | Ser | Thr | Glu | Glu | Lys | Phe | Asn | Glu | Lys | Gly | Glu | Val | Ser | Glu | |
| | | 290 | | | | | 295 | | | | | 300 | | | | |
| aaa | ata | ata | aca | aga | gca | gac | gga | acc | aga | ctt | gaa | tac | aca | gga | att | 960 |
| Lys | Ile | Ile | Thr | Arg | Ala | Asp | Gly | Thr | Arg | Leu | Glu | Tyr | Thr | Gly | Ile | |
| 305 | | | | 310 | | | | | 315 | | | | | 320 | | |
| aaa | agc | gat | gga | tct | gga | aaa | gct | aaa | gag | gtt | tta | aaa | aaa | ttt | act | 1008 |
| Lys | Ser | Asp | Gly | Ser | Gly | Lys | Ala | Lys | Glu | Val | Leu | Lys | Lys | Phe | Thr | |
| | | | 325 | | | | | 330 | | | | | 335 | | | |
| ctt | gaa | gga | aaa | gta | gct | aat | gat | aaa | gta | aca | ttg | gaa | gta | aaa | gaa | 1056 |
| Leu | Glu | Gly | Lys | Val | Ala | Asn | Asp | Lys | Val | Thr | Leu | Glu | Val | Lys | Glu | |
| | | | 340 | | | | | 345 | | | | | 350 | | | |
| gga | acc | gtt | act | tta | agt | aag | aat | att | tca | aaa | tct | ggg | gaa | gtt | tca | 1104 |
| Gly | Thr | Val | Thr | Leu | Ser | Lys | Asn | Ile | Ser | Lys | Ser | Gly | Glu | Val | Ser | |
| | | | 355 | | | | | 360 | | | | | 365 | | | |
| gtt | gaa | ctt | aat | gac | act | gac | agt | agt | gct | gct | act | aaa | aaa | act | gca | 1152 |
| Val | Glu | Leu | Asn | Asp | Thr | Asp | Ser | Ser | Ala | Ala | Thr | Lys | Lys | Thr | Ala | |
| | | 370 | | | | | 375 | | | | | 380 | | | | |
| gct | tgg | aat | tca | aaa | act | tcc | act | tta | aca | att | agt | gtg | aat | agc | caa | 1200 |
| Ala | Trp | Asn | Ser | Lys | Thr | Ser | Thr | Leu | Thr | Ile | Ser | Val | Asn | Ser | Gln | |
| 385 | | | | 390 | | | | | 395 | | | | | 400 | | |
| aaa | acc | aaa | aac | ctt | gta | ttc | aca | aaa | gaa | gac | aca | ata | aca | gta | caa | 1248 |
| Lys | Thr | Lys | Asn | Leu | Val | Phe | Thr | Lys | Glu | Asp | Thr | Ile | Thr | Val | Gln | |
| | | | 405 | | | | | 410 | | | | | 415 | | | |
| aaa | tac | gac | tca | gca | ggc | acc | aat | cta | gaa | ggc | aaa | gca | gtc | gaa | att | 1296 |
| Lys | Tyr | Asp | Ser | Ala | Gly | Thr | Asn | Leu | Glu | Gly | Lys | Ala | Val | Glu | Ile | |
| | | | 420 | | | | | 425 | | | | | 430 | | | |
| aca | aca | ctt | aaa | gaa | ctt | aaa | aac | gct | tta | aaa | taa | | | | | 1332 |
| Thr | Thr | Leu | Lys | Glu | Leu | Lys | Asn | Ala | Leu | Lys | * | | | | | |
| | | | 435 | | | | | 440 | | | | | | | | |

<210> SEQ ID NO 166
<211> LENGTH: 443
<212> TYPE: PRT
<213> ORGANISM: Artificial Sequence
<220> FEATURE:
<223> OTHER INFORMATION: Chimeric protein

<400> SEQUENCE: 166

Met Ala Cys Ser Asn Ser Gly Lys Gly Gly Asp Ser Ala Ser Thr Asn
 1               5                  10                  15

Pro Ala Asp Glu Ser Ala Lys Gly Pro Asn Leu Thr Glu Ile Ser Lys
                20                  25                  30

Lys Ile Thr Asp Ser Asn Ala Phe Val Leu Ala Val Lys Glu Val Glu
            35                  40                  45

Thr Leu Val Leu Ser Ile Asp Glu Leu Ala Lys Lys Ala Ile Gly Gln
        50                  55                  60

Lys Ile Asp Asn Asn Asn Gly Leu Ala Ala Leu Asn Gln Asn Gly
 65                  70                  75                  80

Ser Leu Leu Ala Gly Ala Tyr Ala Ile Ser Thr Leu Ile Thr Glu Lys
                85                  90                  95

```
Leu Ser Lys Leu Lys Asn Leu Glu Glu Leu Lys Thr Glu Ile Ala Lys
            100                 105                 110
Ala Lys Lys Cys Ser Glu Glu Phe Thr Asn Lys Leu Lys Ser Gly His
        115                 120                 125
Ala Asp Leu Gly Lys Gln Asp Ala Thr Asp His Ala Lys Ala Ala
    130                 135                 140
Ile Leu Lys Thr His Ala Thr Thr Asp Lys Gly Ala Lys Glu Phe Lys
145                 150                 155                 160
Asp Leu Phe Glu Ser Val Glu Gly Leu Leu Lys Ala Ala Gln Val Ala
                165                 170                 175
Leu Thr Asn Ser Val Lys Glu Leu Thr Ser Pro Val Val Ala Glu Ser
            180                 185                 190
Pro Lys Lys Pro Ser Met Ala Val Ser Val Asp Leu Pro Gly Glu Met
        195                 200                 205
Lys Val Leu Val Ser Lys Glu Lys Asn Lys Asp Gly Lys Tyr Asp Leu
    210                 215                 220
Ile Ala Thr Val Asp Lys Leu Glu Leu Lys Gly Thr Ser Asp Lys Asn
225                 230                 235                 240
Asn Gly Ser Gly Val Leu Glu Gly Val Lys Ala Asp Lys Ser Lys Val
                245                 250                 255
Lys Leu Thr Ile Ser Asp Asp Leu Gly Gln Thr Thr Leu Glu Val Phe
            260                 265                 270
Lys Glu Asp Gly Lys Thr Leu Val Ser Lys Lys Val Thr Ser Lys Asp
        275                 280                 285
Lys Ser Ser Thr Glu Glu Lys Phe Asn Glu Lys Gly Glu Val Ser Glu
    290                 295                 300
Lys Ile Ile Thr Arg Ala Asp Gly Thr Arg Leu Glu Tyr Thr Gly Ile
305                 310                 315                 320
Lys Ser Asp Gly Ser Gly Lys Ala Lys Glu Val Leu Lys Lys Phe Thr
                325                 330                 335
Leu Glu Gly Lys Val Ala Asn Asp Lys Val Thr Leu Glu Val Lys Glu
            340                 345                 350
Gly Thr Val Thr Leu Ser Lys Asn Ile Ser Lys Ser Gly Glu Val Ser
        355                 360                 365
Val Glu Leu Asn Asp Thr Asp Ser Ser Ala Ala Thr Lys Lys Thr Ala
    370                 375                 380
Ala Trp Asn Ser Lys Thr Ser Thr Leu Thr Ile Ser Val Asn Ser Gln
385                 390                 395                 400
Lys Thr Lys Asn Leu Val Phe Thr Lys Glu Asp Thr Ile Thr Val Gln
                405                 410                 415
Lys Tyr Asp Ser Ala Gly Thr Asn Leu Glu Gly Lys Ala Val Glu Ile
            420                 425                 430
Thr Thr Leu Lys Glu Leu Lys Asn Ala Leu Lys
        435                 440

<210> SEQ ID NO 167
<211> LENGTH: 1317
<212> TYPE: DNA
<213> ORGANISM: Artificial Sequence
<220> FEATURE:
<221> NAME/KEY: CDS
<222> LOCATION: (1)...(1317)
<223> OTHER INFORMATION: Chimeric nucleic acid

<400> SEQUENCE: 167
```

```
-continued atg gct tgt aat aat tca ggt ggg gat tct gca tct act aat cct gat      48
Met Ala Cys Asn Asn Ser Gly Gly Asp Ser Ala Ser Thr Asn Pro Asp
  1               5                  10                  15 gag tct gca aaa gga cct aat ctt acc gta ata agc aaa aaa att aca      96
Glu Ser Ala Lys Gly Pro Asn Leu Thr Val Ile Ser Lys Lys Ile Thr
             20                  25                  30 gat tct aat gca ttt tta ctg gct gtg aaa gaa gtt gag gct ttg ctt     144
Asp Ser Asn Ala Phe Leu Leu Ala Val Lys Glu Val Glu Ala Leu Leu
         35                  40                  45 tca tct ata gat gaa ctt tct aaa gct att ggt aaa aaa ata aaa aat     192
Ser Ser Ile Asp Glu Leu Ser Lys Ala Ile Gly Lys Lys Ile Lys Asn
     50                  55                  60 gat ggt act tta gat aac gaa gca aat cga aac gaa tca ttg ata gca     240
Asp Gly Thr Leu Asp Asn Glu Ala Asn Arg Asn Glu Ser Leu Ile Ala
 65                  70                  75                  80 gga gct tat gaa ata tca aaa cta ata aca caa aaa tta agt gta ttg     288
Gly Ala Tyr Glu Ile Ser Lys Leu Ile Thr Gln Lys Leu Ser Val Leu
                 85                  90                  95 aat tca gaa gaa tta aag gaa aaa att aaa gag gct aag gat tgt tcc     336
Asn Ser Glu Glu Leu Lys Glu Lys Ile Lys Glu Ala Lys Asp Cys Ser
            100                 105                 110 gaa aaa ttt act act aag cta aaa gat agt cat gca gag ctt ggt ata     384
Glu Lys Phe Thr Thr Lys Leu Lys Asp Ser His Ala Glu Leu Gly Ile
        115                 120                 125 caa agc gtt cag gat gat aat gca aaa aaa gct att tta aaa aca cat     432
Gln Ser Val Gln Asp Asp Asn Ala Lys Lys Ala Ile Leu Lys Thr His
    130                 135                 140 gga act aaa gac aag ggt gct aaa gaa ctt gaa gag tta ttt aaa tca     480
Gly Thr Lys Asp Lys Gly Ala Lys Glu Leu Glu Glu Leu Phe Lys Ser
145                 150                 155                 160 cta gaa agc ttg tca aaa gca gcg caa gca gca tta act aat tca gtt     528
Leu Glu Ser Leu Ser Lys Ala Ala Gln Ala Ala Leu Thr Asn Ser Val
                165                 170                 175 aaa gag ctt aca aat cct gtt gtg gca gaa agt cca aaa aaa cct tcc     576
Lys Glu Leu Thr Asn Pro Val Val Ala Glu Ser Pro Lys Lys Pro Ser
            180                 185                 190 atg gcc gtt tca gta gat ttg cct ggt gaa atg aaa gtt ctt gta agc     624
Met Ala Val Ser Val Asp Leu Pro Gly Glu Met Lys Val Leu Val Ser
        195                 200                 205 aaa gaa aaa aac aaa gac ggc aag tac gat cta att gca aca gta gac     672
Lys Glu Lys Asn Lys Asp Gly Lys Tyr Asp Leu Ile Ala Thr Val Asp
    210                 215                 220 aag ctt gag ctt aaa gga act tct gat aaa aac aat gga tct gga gta     720
Lys Leu Glu Leu Lys Gly Thr Ser Asp Lys Asn Asn Gly Ser Gly Val
225                 230                 235                 240 ctt gaa ggc gta aaa gct gac aaa agt aaa gta aaa tta aca att tct     768
Leu Glu Gly Val Lys Ala Asp Lys Ser Lys Val Lys Leu Thr Ile Ser
                245                 250                 255 gac gat cta ggt caa acc aca ctt gaa gtt ttc aaa gaa gat ggc aaa     816
Asp Asp Leu Gly Gln Thr Thr Leu Glu Val Phe Lys Glu Asp Gly Lys
            260                 265                 270 aca cta gta tca aaa aaa gta act tcc aaa gac aag tca tca aca gaa     864
Thr Leu Val Ser Lys Lys Val Thr Ser Lys Asp Lys Ser Ser Thr Glu
        275                 280                 285 gaa aaa ttc aat gaa aaa ggt gaa gta tct gaa aaa ata ata aca aga     912
Glu Lys Phe Asn Glu Lys Gly Glu Val Ser Glu Lys Ile Ile Thr Arg
    290                 295                 300 gca gac gga acc aga ctt gaa tac aca gga att aaa agc gat gga tct     960
Ala Asp Gly Thr Arg Leu Glu Tyr Thr Gly Ile Lys Ser Asp Gly Ser
305                 310                 315                 320
```

```
gga aaa gct aaa gag gtt tta aaa aaa ttt act ctt gaa gga aaa gta      1008
Gly Lys Ala Lys Glu Val Leu Lys Lys Phe Thr Leu Glu Gly Lys Val
                325                 330                 335 gct aat gat aaa gta aca ttg gaa gta aaa gaa gga acc gtt act tta      1056
Ala Asn Asp Lys Val Thr Leu Glu Val Lys Glu Gly Thr Val Thr Leu
            340                 345                 350 agt aag aac att tca aaa tct ggg gaa gtt tca gtt gaa ctt aat gac      1104
Ser Lys Asn Ile Ser Lys Ser Gly Glu Val Ser Val Glu Leu Asn Asp
        355                 360                 365 act gac agt agt gct gct act aaa aaa act gca gct tgg aat tca aaa      1152
Thr Asp Ser Ser Ala Ala Thr Lys Lys Thr Ala Ala Trp Asn Ser Lys
    370                 375                 380 act tct act tta aca att agt gtt aac agc aaa aaa act aca caa ctt      1200
Thr Ser Thr Leu Thr Ile Ser Val Asn Ser Lys Lys Thr Thr Gln Leu
385                 390                 395                 400 gtg ttt act aaa caa gac aca ata act gta caa aaa tac gac tcc gca      1248
Val Phe Thr Lys Gln Asp Thr Ile Thr Val Gln Lys Tyr Asp Ser Ala
                405                 410                 415 ggt acc aat tta gaa ggc aca gca gtc gaa att aaa aca ctt gat gaa      1296
Gly Thr Asn Leu Glu Gly Thr Ala Val Glu Ile Lys Thr Leu Asp Glu
            420                 425                 430 ctt aaa aac gct tta aaa taa                                          1317
Leu Lys Asn Ala Leu Lys *
        435

<210> SEQ ID NO 168
<211> LENGTH: 438
<212> TYPE: PRT
<213> ORGANISM: Artificial Sequence
<220> FEATURE:
<223> OTHER INFORMATION: Chimeric protein

<400> SEQUENCE: 168

Met Ala Cys Asn Asn Ser Gly Gly Asp Ser Ala Ser Thr Asn Pro Asp
  1               5                  10                  15

Glu Ser Ala Lys Gly Pro Asn Leu Thr Val Ile Ser Lys Lys Ile Thr
             20                  25                  30

Asp Ser Asn Ala Phe Leu Leu Ala Val Lys Glu Val Glu Ala Leu Leu
         35                  40                  45

Ser Ser Ile Asp Glu Leu Ser Lys Ala Ile Gly Lys Lys Ile Lys Asn
     50                  55                  60

Asp Gly Thr Leu Asp Asn Glu Ala Asn Arg Asn Glu Ser Leu Ile Ala
 65                  70                  75                  80

Gly Ala Tyr Glu Ile Ser Lys Leu Ile Thr Gln Lys Leu Ser Val Leu
                 85                  90                  95

Asn Ser Glu Glu Leu Lys Glu Lys Ile Lys Glu Ala Lys Asp Cys Ser
            100                 105                 110

Glu Lys Phe Thr Thr Lys Leu Lys Asp Ser His Ala Glu Leu Gly Ile
        115                 120                 125

Gln Ser Val Gln Asp Asp Asn Ala Lys Lys Ala Ile Leu Lys Thr His
    130                 135                 140

Gly Thr Lys Asp Lys Gly Ala Lys Glu Leu Glu Leu Phe Lys Ser
145                 150                 155                 160

Leu Glu Ser Leu Ser Lys Ala Ala Gln Ala Ala Leu Thr Asn Ser Val
                165                 170                 175

Lys Glu Leu Thr Asn Pro Val Val Ala Glu Ser Pro Lys Lys Pro Ser
            180                 185                 190
```

-continued

```
Met Ala Val Ser Val Asp Leu Pro Gly Glu Met Lys Val Leu Val Ser
            195                 200                 205
Lys Glu Lys Asn Lys Asp Gly Lys Tyr Asp Leu Ile Ala Thr Val Asp
        210                 215                 220
Lys Leu Glu Leu Lys Gly Thr Ser Asp Lys Asn Asn Gly Ser Gly Val
225                 230                 235                 240
Leu Glu Gly Val Lys Ala Asp Lys Ser Lys Val Lys Leu Thr Ile Ser
                245                 250                 255
Asp Asp Leu Gly Gln Thr Thr Leu Glu Val Phe Lys Glu Asp Gly Lys
            260                 265                 270
Thr Leu Val Ser Lys Lys Val Thr Ser Lys Asp Lys Ser Ser Thr Glu
        275                 280                 285
Glu Lys Phe Asn Glu Lys Gly Glu Val Ser Glu Lys Ile Ile Thr Arg
    290                 295                 300
Ala Asp Gly Thr Arg Leu Glu Tyr Thr Gly Ile Lys Ser Asp Gly Ser
305                 310                 315                 320
Gly Lys Ala Lys Glu Val Leu Lys Lys Phe Thr Leu Glu Gly Lys Val
                325                 330                 335
Ala Asn Asp Lys Val Thr Leu Glu Val Lys Glu Gly Thr Val Thr Leu
            340                 345                 350
Ser Lys Asn Ile Ser Lys Ser Gly Glu Val Ser Val Glu Leu Asn Asp
        355                 360                 365
Thr Asp Ser Ser Ala Ala Thr Lys Lys Thr Ala Ala Trp Asn Ser Lys
    370                 375                 380
Thr Ser Thr Leu Thr Ile Ser Val Asn Ser Lys Lys Thr Thr Gln Leu
385                 390                 395                 400
Val Phe Thr Lys Gln Asp Thr Ile Thr Val Gln Lys Tyr Asp Ser Ala
                405                 410                 415
Gly Thr Asn Leu Glu Gly Thr Ala Val Glu Ile Lys Thr Leu Asp Glu
            420                 425                 430
Leu Lys Asn Ala Leu Lys
        435
```

<210> SEQ ID NO 169
<211> LENGTH: 1029
<212> TYPE: DNA
<213> ORGANISM: Artificial Sequence
<220> FEATURE:
<221> NAME/KEY: CDS
<222> LOCATION: (1)...(1029)
<223> OTHER INFORMATION: Chimeric nucleic acid

<400> SEQUENCE: 169

```
atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
                20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
            35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
        50                  55                  60 ata cac caa aat aat ggt ttg gat acc gaa aat aat cac aat gga tca     240
Ile His Gln Asn Asn Gly Leu Asp Thr Glu Asn Asn His Asn Gly Ser
65                  70                  75                  80
```

| | | |
|---|---|---|
| ttg tta gcg gga gct tat gca ata tca acc cta ata aaa caa aaa tta<br>Leu Leu Ala Gly Ala Tyr Ala Ile Ser Thr Leu Ile Lys Gln Lys Leu<br>                        85                    90                    95 | 288 |
| gat gga ttg aaa aat gaa gga tta aag gaa aaa att gat gcg gct aag<br>Asp Gly Leu Lys Asn Glu Gly Leu Lys Glu Lys Ile Asp Ala Ala Lys<br>         100                    105                   110 | 336 |
| aaa tgt tct gaa aca ttt act aat aaa tta aaa gaa aaa cac aca gat<br>Lys Cys Ser Glu Thr Phe Thr Asn Lys Leu Lys Glu Lys His Thr Asp<br>             115                    120                 125 | 384 |
| ctt ggt aaa gaa ggt gtt act gat gct gat gca aaa gaa gcc att tta<br>Leu Gly Lys Glu Gly Val Thr Asp Ala Asp Ala Lys Glu Ala Ile Leu<br>130                     135                   140 | 432 |
| aaa gca aat ggt act aaa act aaa ggt gct gaa gaa ctt gga aaa tta<br>Lys Ala Asn Gly Thr Lys Thr Lys Gly Ala Glu Glu Leu Gly Lys Leu<br>145                   150                   155                 160 | 480 |
| ttt gaa tca gta gag gtc ttg tca aaa gca gct aaa gag atg ctt gct<br>Phe Glu Ser Val Glu Val Leu Ser Lys Ala Ala Lys Glu Met Leu Ala<br>                     165                    170                 175 | 528 |
| aat tca gtt aaa gag ctt aca agc cct gtt gtg gca gaa agt cca aaa<br>Asn Ser Val Lys Glu Leu Thr Ser Pro Val Val Ala Glu Ser Pro Lys<br>         180                    185                   190 | 576 |
| aaa cct tcc atg gcc aag caa aat gtt tct gaa aaa ata ata aca aga<br>Lys Pro Ser Met Ala Lys Gln Asn Val Ser Glu Lys Ile Ile Thr Arg<br>             195                    200                 205 | 624 |
| gca gac gga acc aga ctt gaa tac aca gga att aaa agc gat gga tct<br>Ala Asp Gly Thr Arg Leu Glu Tyr Thr Gly Ile Lys Ser Asp Gly Ser<br>210                     215                   220 | 672 |
| gga aaa gct aaa gag gtt tta aaa ggc tat gtt ctt gaa gga act cta<br>Gly Lys Ala Lys Glu Val Leu Lys Gly Tyr Val Leu Glu Gly Thr Leu<br>225                   230                   235                 240 | 720 |
| act gct gaa aaa aca aca ttg gtg gtt aaa gaa gga act gtt act tta<br>Thr Ala Glu Lys Thr Thr Leu Val Val Lys Glu Gly Thr Val Thr Leu<br>                     245                    250                 255 | 768 |
| agc aaa aat att tca aaa tct ggg gaa gtt tca gtt gaa ctt aat gac<br>Ser Lys Asn Ile Ser Lys Ser Gly Glu Val Ser Val Glu Leu Asn Asp<br>         260                    265                   270 | 816 |
| act gac agt agt gct gct act aaa aaa act gca gct tgg aat tca ggc<br>Thr Asp Ser Ser Ala Ala Thr Lys Lys Thr Ala Ala Trp Asn Ser Gly<br>             275                    280                 285 | 864 |
| act tca act tta aca att act gta aac agt aaa aaa act aaa gac ctt<br>Thr Ser Thr Leu Thr Ile Thr Val Asn Ser Lys Lys Thr Lys Asp Leu<br>290                     295                   300 | 912 |
| gtg ttt aca aaa gaa aac aca att aca gta caa caa tac gac tca aat<br>Val Phe Thr Lys Glu Asn Thr Ile Thr Val Gln Gln Tyr Asp Ser Asn<br>305                   310                   315                 320 | 960 |
| ggc acc aaa tta gag ggg tca gca gtt gaa att aca aaa ctt gat gaa<br>Gly Thr Lys Leu Glu Gly Ser Ala Val Glu Ile Thr Lys Leu Asp Glu<br>             325                    330                 335 | 1008 |
| att aaa aac gct tta aaa taa<br>Ile Lys Asn Ala Leu Lys *<br>         340 | 1029 |

<210> SEQ ID NO 170
<211> LENGTH: 342
<212> TYPE: PRT
<213> ORGANISM: Artificial Sequence
<220> FEATURE:
<223> OTHER INFORMATION: Chimeric protein

<400> SEQUENCE: 170

| | | | | | | | | | | | | | | |
|---|---|---|---|---|---|---|---|---|---|---|---|---|---|---|
| Met | Ala | Cys | Asn | Asn | Ser | Gly | Lys | Asp | Gly | Asn | Thr | Ser | Ala | Asn | Ser |
| 1 | | | | 5 | | | | | 10 | | | | | 15 | |
| Ala | Asp | Glu | Ser | Val | Lys | Gly | Pro | Asn | Leu | Thr | Glu | Ile | Asn | Lys | Lys |
| | | | 20 | | | | | 25 | | | | | 30 | | |
| Ile | Thr | Asp | Ser | Asn | Ala | Val | Leu | Leu | Ala | Val | Lys | Glu | Val | Glu | Ala |
| | | 35 | | | | | 40 | | | | | 45 | | | |
| Leu | Leu | Ser | Ser | Ile | Asp | Glu | Ile | Ala | Ala | Lys | Ala | Ile | Gly | Lys | Lys |
| 50 | | | | | 55 | | | | | 60 | | | | | |
| Ile | His | Gln | Asn | Asn | Gly | Leu | Asp | Thr | Glu | Asn | Asn | His | Asn | Gly | Ser |
| 65 | | | | | 70 | | | | | 75 | | | | | 80 |
| Leu | Leu | Ala | Gly | Ala | Tyr | Ala | Ile | Ser | Thr | Leu | Ile | Lys | Gln | Lys | Leu |
| | | | | 85 | | | | | 90 | | | | | 95 | |
| Asp | Gly | Leu | Lys | Asn | Glu | Gly | Leu | Lys | Glu | Lys | Ile | Asp | Ala | Ala | Lys |
| | | | 100 | | | | | 105 | | | | | 110 | | |
| Lys | Cys | Ser | Glu | Thr | Phe | Thr | Asn | Lys | Leu | Lys | Glu | Lys | His | Thr | Asp |
| | | 115 | | | | | 120 | | | | | 125 | | | |
| Leu | Gly | Lys | Glu | Gly | Val | Thr | Asp | Ala | Asp | Ala | Lys | Glu | Ala | Ile | Leu |
| | 130 | | | | | 135 | | | | | 140 | | | | |
| Lys | Ala | Asn | Gly | Thr | Lys | Thr | Lys | Gly | Ala | Glu | Glu | Leu | Gly | Lys | Leu |
| 145 | | | | | 150 | | | | | 155 | | | | | 160 |
| Phe | Glu | Ser | Val | Glu | Val | Leu | Ser | Lys | Ala | Ala | Lys | Glu | Met | Leu | Ala |
| | | | | 165 | | | | | 170 | | | | | 175 | |
| Asn | Ser | Val | Lys | Glu | Leu | Thr | Ser | Pro | Val | Val | Ala | Glu | Ser | Pro | Lys |
| | | | 180 | | | | | 185 | | | | | 190 | | |
| Lys | Pro | Ser | Met | Ala | Lys | Gln | Asn | Val | Ser | Glu | Lys | Ile | Ile | Thr | Arg |
| | | 195 | | | | | 200 | | | | | 205 | | | |
| Ala | Asp | Gly | Thr | Arg | Leu | Glu | Tyr | Thr | Gly | Ile | Lys | Ser | Asp | Gly | Ser |
| | 210 | | | | | 215 | | | | | 220 | | | | |
| Gly | Lys | Ala | Lys | Glu | Val | Leu | Lys | Gly | Tyr | Val | Leu | Glu | Gly | Thr | Leu |
| 225 | | | | | 230 | | | | | 235 | | | | | 240 |
| Thr | Ala | Glu | Lys | Thr | Thr | Leu | Val | Val | Lys | Glu | Gly | Thr | Val | Thr | Leu |
| | | | | 245 | | | | | 250 | | | | | 255 | |
| Ser | Lys | Asn | Ile | Ser | Lys | Ser | Gly | Glu | Val | Ser | Val | Glu | Leu | Asn | Asp |
| | | | 260 | | | | | 265 | | | | | 270 | | |
| Thr | Asp | Ser | Ser | Ala | Ala | Thr | Lys | Lys | Thr | Ala | Ala | Trp | Asn | Ser | Gly |
| | | 275 | | | | | 280 | | | | | 285 | | | |
| Thr | Ser | Thr | Leu | Thr | Ile | Thr | Val | Asn | Ser | Lys | Lys | Thr | Lys | Asp | Leu |
| | 290 | | | | | 295 | | | | | 300 | | | | |
| Val | Phe | Thr | Lys | Glu | Asn | Thr | Ile | Thr | Val | Gln | Gln | Tyr | Asp | Ser | Asn |
| 305 | | | | | 310 | | | | | 315 | | | | | 320 |
| Gly | Thr | Lys | Leu | Glu | Gly | Ser | Ala | Val | Glu | Ile | Thr | Lys | Leu | Asp | Glu |
| | | | | 325 | | | | | 330 | | | | | 335 | |
| Ile | Lys | Asn | Ala | Leu | Lys | | | | | | | | | | |
| | | | 340 | | | | | | | | | | | | |

<210> SEQ ID NO 171
<211> LENGTH: 1029
<212> TYPE: DNA
<213> ORGANISM: Artificial Sequence
<220> FEATURE:
<221> NAME/KEY: CDS
<222> LOCATION: (1)...(1029)
<223> OTHER INFORMATION: Chimeric nucleic acid

<400> SEQUENCE: 171

| | | | | | | | | | | | | | | | | |
|---|---|---|---|---|---|---|---|---|---|---|---|---|---|---|---|---|
| atg | gct | tgt | aat | aat | tca | ggg | aaa | gat | ggg | aat | aca | tct | gca | aat | tct | 48 |

```
                                                                -continued

Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata aat aaa aaa    96
Ala Asp Glu Ser Val Lys Gly Pro Asn Leu Thr Glu Ile Asn Lys Lys
             20                  25                  30 att acg gat tct aat gcg gtt tta ctt gct gtg aaa gag gtt gaa gcg   144
Ile Thr Asp Ser Asn Ala Val Leu Leu Ala Val Lys Glu Val Glu Ala
         35                  40                  45 ttg ctg tca tct ata gat gaa att gct gct aaa gct att ggt aaa aaa   192
Leu Leu Ser Ser Ile Asp Glu Ile Ala Ala Lys Ala Ile Gly Lys Lys
     50                  55                  60 ata cac caa aat aat ggt ttg gat acc gaa aat aat cac aat gga tca   240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta   288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag   336
Asp Gly Leu Lys Asn Glu Gly Leu Lys Glu Lys Ile Asp Ala Ala Lys
             100                 105                 110 aaa tgt tct gaa aca ttt act aat aaa tta aaa gaa aaa cac aca gat   384
Lys Cys Ser Glu Thr Phe Thr Asn Lys Leu Lys Glu Lys His Thr Asp
         115                 120                 125 ctt ggt aaa gaa ggt gtt act gat gct gat gca aaa gaa gcc att tta   432
Leu Gly Lys Glu Gly Val Thr Asp Ala Asp Ala Lys Glu Ala Ile Leu
     130                 135                 140 aaa gca aat ggt act aaa act aaa ggt gct gaa gaa ctt gga aaa tta   480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct   528
Phe Glu Ser Val Glu Val Leu Ser Lys Ala Ala Lys Glu Met Leu Ala
                 165                 170                 175 aat tca gtt aaa gag ctt aca agc cct gtt gtg gca gaa agt cca aaa   576
Asn Ser Val Lys Glu Leu Thr Ser Pro Val Val Ala Glu Ser Pro Lys
             180                 185                 190 aaa cct tcc atg gcc aag caa aat gtt tct gaa aaa ata ata aca aga   624
Lys Pro Ser Met Ala Lys Gln Asn Val Ser Glu Lys Ile Ile Thr Arg
         195                 200                 205 gca gac gga acc aga ctt gaa tac aca gga att aaa agc gat gga tct   672
Ala Asp Gly Thr Arg Leu Glu Tyr Thr Gly Ile Lys Ser Asp Gly Ser
     210                 215                 220 gga aaa gct aaa gag gtt tta aaa ggc tat gtt ctt gaa gga act cta   720
Gly Lys Ala Lys Glu Val Leu Lys Gly Tyr Val Leu Glu Gly Thr Leu
225                 230                 235                 240 act gct gaa aaa aca aca ttg gtg gtt aaa gaa gga act gtt act tta   768
Thr Ala Glu Lys Thr Thr Leu Val Val Lys Glu Gly Thr Val Thr Leu
                 245                 250                 255 agc aaa aat att tca aaa tct ggg gaa gtt tca gtt gaa ctt aat gac   816
Ser Lys Asn Ile Ser Lys Ser Gly Glu Val Ser Val Glu Leu Asn Asp
             260                 265                 270 act gac agt agt gct gct act aaa aaa act gca gct tgg aat tca aaa   864
Thr Asp Ser Ser Ala Ala Thr Lys Lys Thr Ala Ala Trp Asn Ser Lys
         275                 280                 285 act tcc act tta aca att agt gtg aat agc caa aaa acc aaa aac ctt   912
Thr Ser Thr Leu Thr Ile Ser Val Asn Ser Gln Lys Thr Lys Asn Leu
     290                 295                 300 gta ttc aca aaa gaa gac aca ata aca gta caa aaa tac gac tca gca   960
Val Phe Thr Lys Glu Asp Thr Ile Thr Val Gln Lys Tyr Asp Ser Ala
305                 310                 315                 320
```

```
ggc acc aat cta gaa ggc aaa gca gtc gaa att aca aca ctt aaa gaa     1008
Gly Thr Asn Leu Glu Gly Lys Ala Val Glu Ile Thr Thr Leu Lys Glu
            325                 330                 335 ctt aaa aac gct tta aaa taa                                         1029
Leu Lys Asn Ala Leu Lys *
340
```

<210> SEQ ID NO 172
<211> LENGTH: 342
<212> TYPE: PRT
<213> ORGANISM: Artificial Sequence
<220> FEATURE:
<223> OTHER INFORMATION: Chimeric protein

<400> SEQUENCE: 172

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Glu Lys Ile Ile Thr Arg
        195                 200                 205

Ala Asp Gly Thr Arg Leu Glu Tyr Thr Gly Ile Lys Ser Asp Gly Ser
    210                 215                 220

Gly Lys Ala Lys Glu Val Leu Lys Gly Tyr Val Leu Glu Gly Thr Leu
225                 230                 235                 240

Thr Ala Glu Lys Thr Thr Leu Val Val Lys Glu Gly Thr Val Thr Leu
                245                 250                 255

Ser Lys Asn Ile Ser Lys Ser Gly Glu Val Ser Val Glu Leu Asn Asp
            260                 265                 270

Thr Asp Ser Ser Ala Ala Thr Lys Thr Ala Ala Trp Asn Ser Lys
        275                 280                 285

Thr Ser Thr Leu Thr Ile Ser Val Asn Ser Gln Lys Thr Lys Asn Leu
    290                 295                 300

Val Phe Thr Lys Glu Asp Thr Ile Thr Val Gln Lys Tyr Asp Ser Ala
305                 310                 315                 320

Gly Thr Asn Leu Glu Gly Lys Ala Val Glu Ile Thr Thr Leu Lys Glu
```

```
                        325                 330                 335
Leu Lys Asn Ala Leu Lys
            340

<210> SEQ ID NO 173
<211> LENGTH: 1029
<212> TYPE: DNA
<213> ORGANISM: Artificial Sequence
<220> FEATURE:
<221> NAME/KEY: CDS
<222> LOCATION: (1)...(1029)
<223> OTHER INFORMATION: Chimeric nucleic acid

<400> SEQUENCE: 173 atg gct tgt aat aat tca ggg aaa gat ggg aat aca tct gca aat tct       48
Met Ala Cys Asn Asn Ser Gly Lys Asp Gly Asn Thr Ser Ala Asn Ser
  1               5                  10                  15 gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
             20                  25                  30 att acg gat tct aat gcg gtt tta ctt gct gtg aaa gag gtt gaa gcg      144
Ile Thr Asp Ser Asn Ala Val Leu Leu Ala Val Lys Glu Val Glu Ala
         35                  40                  45 ttg ctg tca tct ata gat gaa att gct gct aaa gct att ggt aaa aaa      192
Leu Leu Ser Ser Ile Asp Glu Ile Ala Ala Lys Ala Ile Gly Lys Lys
     50                  55                  60 ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190 aaa cct tcc atg gcc aag caa aat gtt tct gaa aaa ata ata aca aga      624
Lys Pro Ser Met Ala Lys Gln Asn Val Ser Glu Lys Ile Ile Thr Arg
        195                 200                 205 gca gac gga acc aga ctt gaa tac aca gga att aaa agc gat gga tct      672
Ala Asp Gly Thr Arg Leu Glu Tyr Thr Gly Ile Lys Ser Asp Gly Ser
    210                 215                 220 gga aaa gct aaa gag gtt tta aaa ggc tat gtt ctt gaa gga act cta      720
Gly Lys Ala Lys Glu Val Leu Lys Gly Tyr Val Leu Glu Gly Thr Leu
225                 230                 235                 240 act gct gaa aaa aca aca ttg gtg gtt aaa gaa gga act gtt act tta      768
Thr Ala Glu Lys Thr Thr Leu Val Val Lys Glu Gly Thr Val Thr Leu
```

-continued

```
                245                 250                 255
agc aaa aat att tca aaa tct ggg gaa gtt tca gtt gaa ctt aat gac     816
Ser Lys Asn Ile Ser Lys Ser Gly Glu Val Ser Val Glu Leu Asn Asp
            260                 265                 270 act gac agt agt gct gct act aaa aaa act gca gct tgg aat tca aaa     864
Thr Asp Ser Ser Ala Ala Thr Lys Lys Thr Ala Ala Trp Asn Ser Lys
        275                 280                 285 act tct act tta aca att agt gtt aac agc aaa aaa act aca caa ctt     912
Thr Ser Thr Leu Thr Ile Ser Val Asn Ser Lys Lys Thr Thr Gln Leu
    290                 295                 300 gtg ttt act aaa caa gac aca ata act gta caa aaa tac gac tcc gca     960
Val Phe Thr Lys Gln Asp Thr Ile Thr Val Gln Lys Tyr Asp Ser Ala
305                 310                 315                 320 ggt acc aat tta gaa ggc aca gca gtc gaa att aaa aca ctt gat gaa    1008
Gly Thr Asn Leu Glu Gly Thr Ala Val Glu Ile Lys Thr Leu Asp Glu
                325                 330                 335 ctt aaa aac gct tta aaa taa                                        1029
Leu Lys Asn Ala Leu Lys  *
            340
```

<210> SEQ ID NO 174
<211> LENGTH: 342
<212> TYPE: PRT
<213> ORGANISM: Artificial Sequence
<220> FEATURE:
<223> OTHER INFORMATION: Chimeric protein

<400> SEQUENCE: 174

```
Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn His Asn Gly Ser
65              70                  75                  80

Leu Leu Ala Gly Ala Tyr Ala Ile Ser Thr Leu Ile Lys Gln Lys Leu
            85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Glu Lys Ile Ile Thr Arg
        195                 200                 205

Ala Asp Gly Thr Arg Leu Glu Tyr Thr Gly Ile Lys Ser Asp Gly Ser
    210                 215                 220

Gly Lys Ala Lys Glu Val Leu Lys Gly Tyr Val Leu Glu Gly Thr Leu
```

-continued

```
                225                 230                 235                 240
            Thr Ala Glu Lys Thr Thr Leu Val Val Lys Glu Gly Thr Val Thr Leu
                            245                 250                 255
            Ser Lys Asn Ile Ser Lys Ser Gly Glu Val Ser Val Glu Leu Asn Asp
                        260                 265                 270
            Thr Asp Ser Ser Ala Ala Thr Lys Lys Thr Ala Ala Trp Asn Ser Lys
                    275                 280                 285
            Thr Ser Thr Leu Thr Ile Ser Val Asn Ser Lys Lys Thr Thr Gln Leu
                290                 295                 300
            Val Phe Thr Lys Gln Asp Thr Ile Thr Val Gln Lys Tyr Asp Ser Ala
            305                 310                 315                 320
            Gly Thr Asn Leu Glu Gly Thr Ala Val Glu Ile Lys Thr Leu Asp Glu
                            325                 330                 335
            Leu Lys Asn Ala Leu Lys
                        340

<210> SEQ ID NO 175
<211> LENGTH: 1035
<212> TYPE: DNA
<213> ORGANISM: Artificial Sequence
<220> FEATURE:
<221> NAME/KEY: CDS
<222> LOCATION: (1)...(1035)
<223> OTHER INFORMATION: Chimeric nucleic acid

<400> SEQUENCE: 175 atg gct tgt aat aat tca ggg aaa gat ggg aat aca tct gca aat tct          48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa          96
Ala Asp Glu Ser Val Lys Gly Pro Asn Leu Thr Glu Ile Ser Lys Lys
             20                  25                  30 att acg gat tct aat gcg gtt tta ctt gct gtg aaa gag gtt gaa gcg         144
Ile Thr Asp Ser Asn Ala Val Leu Leu Ala Val Lys Glu Val Glu Ala
         35                  40                  45 ttg ctg tca tct ata gat gaa att gct gct aaa gct att ggt aaa aaa         192
Leu Leu Ser Ser Ile Asp Glu Ile Ala Ala Lys Ala Ile Gly Lys Lys
     50                  55                  60 ata cac caa aat aat ggt ttg gat acc gaa tat aat cac aat gga tca         240
Ile His Gln Asn Asn Gly Leu Asp Thr Glu Tyr Asn His Asn Gly Ser
 65                  70                  75                  80 ttg tta gcg gga gct tat gca ata tca acc cta ata aaa caa aaa tta         288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag         336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat         384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta         432
Leu Gly Lys Glu Gly Val Thr Asp Ala Asp Ala Lys Glu Ala Ile Leu
    130                 135                 140 aaa aca aat ggt act aaa act aaa ggt gct gaa gaa ctt gga aaa tta         480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct         528
Phe Glu Ser Val Glu Val Leu Ser Lys Ala Ala Lys Glu Met Leu Ala
                165                 170                 175
```

| | | | | | | | | | | | | | | | | |
|---|---|---|---|---|---|---|---|---|---|---|---|---|---|---|---|---|
| aat | tca | gtt | aaa | gag | ctt | aca | agc | cct | gtt | gtg | gca | gaa | agt | cca | aaa | 576 |
| Asn | Ser | Val | Lys | Glu | Leu | Thr | Ser | Pro | Val | Val | Ala | Glu | Ser | Pro | Lys | |
| | | | 180 | | | | | 185 | | | | | 190 | | | |
| aaa | cct | tcc | atg | gcc | aag | caa | aat | gtt | aca | tct | gaa | aaa | aca | ata | gta | 624 |
| Lys | Pro | Ser | Met | Ala | Lys | Gln | Asn | Val | Thr | Ser | Glu | Lys | Thr | Ile | Val | |
| | | 195 | | | | | 200 | | | | | 205 | | | | |
| aga | gca | aat | gga | acc | aga | ctt | gaa | tac | aca | gac | ata | aaa | agc | gat | gga | 672 |
| Arg | Ala | Asn | Gly | Thr | Arg | Leu | Glu | Tyr | Thr | Asp | Ile | Lys | Ser | Asp | Gly | |
| | 210 | | | | | 215 | | | | | 220 | | | | | |
| tcc | gga | aaa | gct | aaa | gaa | gtt | tta | aaa | gac | ttt | act | ctt | gaa | gga | act | 720 |
| Ser | Gly | Lys | Ala | Lys | Glu | Val | Leu | Lys | Asp | Phe | Thr | Leu | Glu | Gly | Thr | |
| 225 | | | | | 230 | | | | | 235 | | | | | 240 | |
| cta | gct | gct | gac | ggc | aaa | aca | aca | ttg | aaa | gtt | aca | gaa | ggc | act | gtt | 768 |
| Leu | Ala | Ala | Asp | Gly | Lys | Thr | Thr | Leu | Lys | Val | Thr | Glu | Gly | Thr | Val | |
| | | | 245 | | | | | 250 | | | | | 255 | | | |
| gtt | tta | agc | aag | aac | att | tta | aaa | tcc | gga | gaa | ata | aca | gtt | gca | ctt | 816 |
| Val | Leu | Ser | Lys | Asn | Ile | Leu | Lys | Ser | Gly | Glu | Ile | Thr | Val | Ala | Leu | |
| | | | 260 | | | | | 265 | | | | | 270 | | | |
| gat | gac | tct | gac | act | act | cag | gct | act | aaa | aaa | act | gga | aaa | tgg | gat | 864 |
| Asp | Asp | Ser | Asp | Thr | Thr | Gln | Ala | Thr | Lys | Lys | Thr | Gly | Lys | Trp | Asp | |
| | | 275 | | | | | 280 | | | | | 285 | | | | |
| tca | aat | act | tcc | act | tta | aca | att | agt | gtg | aat | agc | aaa | aaa | act | aaa | 912 |
| Ser | Asn | Thr | Ser | Thr | Leu | Thr | Ile | Ser | Val | Asn | Ser | Lys | Lys | Thr | Lys | |
| | 290 | | | | | 295 | | | | | 300 | | | | | |
| aac | att | gta | ttt | aca | aaa | gaa | gac | aca | ata | aca | gta | caa | aaa | tac | gac | 960 |
| Asn | Ile | Val | Phe | Thr | Lys | Glu | Asp | Thr | Ile | Thr | Val | Gln | Lys | Tyr | Asp | |
| 305 | | | | | 310 | | | | | 315 | | | | | 320 | |
| tca | gca | ggc | acc | aat | cta | gaa | ggc | aac | gca | gtc | gaa | att | aaa | aca | ctt | 1008 |
| Ser | Ala | Gly | Thr | Asn | Leu | Glu | Gly | Asn | Ala | Val | Glu | Ile | Lys | Thr | Leu | |
| | | | 325 | | | | | 330 | | | | | 335 | | | |
| gat | gaa | ctt | aaa | aac | gct | tta | aaa | tag | | | | | | | | 1035 |
| Asp | Glu | Leu | Lys | Asn | Ala | Leu | Lys | * | | | | | | | | |
| | | | 340 | | | | | | | | | | | | | |

<210> SEQ ID NO 176
<211> LENGTH: 344
<212> TYPE: PRT
<213> ORGANISM: Artificial Sequence
<220> FEATURE:
<223> OTHER INFORMATION: Chimeric protein

<400> SEQUENCE: 176

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
                20                  25                  30

Ile Thr Asp Ser Asn Ala Val Leu Leu Ala Val Lys Glu Val Glu Ala
            35                  40                  45

Leu Leu Ser Ser Ile Asp Glu Ile Ala Ala Lys Ala Ile Gly Lys Lys
        50                  55                  60

Ile His Gln Asn Asn Gly Leu Asp Thr Glu Tyr Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu

```
            130                 135                 140
Lys Thr Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Ala Glu Ser Pro Lys
            180                 185                 190

Lys Pro Ser Met Ala Lys Gln Asn Val Thr Ser Glu Lys Thr Ile Val
            195                 200                 205

Arg Ala Asn Gly Thr Arg Leu Glu Tyr Thr Asp Ile Lys Ser Asp Gly
210                 215                 220

Ser Gly Lys Ala Lys Glu Val Leu Lys Asp Phe Thr Leu Glu Gly Thr
225                 230                 235                 240

Leu Ala Ala Asp Gly Lys Thr Thr Leu Lys Val Thr Glu Gly Thr Val
                245                 250                 255

Val Leu Ser Lys Asn Ile Leu Lys Ser Gly Glu Ile Thr Val Ala Leu
            260                 265                 270

Asp Asp Ser Asp Thr Thr Gln Ala Thr Lys Lys Thr Gly Lys Trp Asp
            275                 280                 285

Ser Asn Thr Ser Thr Leu Thr Ile Ser Val Asn Ser Lys Lys Thr Lys
            290                 295                 300

Asn Ile Val Phe Thr Lys Glu Asp Thr Ile Thr Val Gln Lys Tyr Asp
305                 310                 315                 320

Ser Ala Gly Thr Asn Leu Glu Gly Asn Ala Val Glu Ile Lys Thr Leu
                325                 330                 335

Asp Glu Leu Lys Asn Ala Leu Lys
            340

<210> SEQ ID NO 177
<211> LENGTH: 1323
<212> TYPE: DNA
<213> ORGANISM: Artificial Sequence
<220> FEATURE:
<221> NAME/KEY: CDS
<222> LOCATION: (1)...(1323)
<223> OTHER INFORMATION: Chimeric nucleic acid

<400> SEQUENCE: 177 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata aat aaa aaa      96
Ala Asp Glu Ser Val Lys Gly Pro Asn Leu Thr Glu Ile Asn Lys Lys
                20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
            35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
        50                  55                  60 ata cac caa aat aat ggt ttg gat acc gaa aat aat cac aat gga tca     240
Ile His Gln Asn Asn Gly Leu Asp Thr Glu Asn Asn His Asn Gly Ser
 65                 70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
```

-continued

```
              100                 105                 110
aaa tgt tct gaa aca ttt act aat aaa tta aaa gaa aaa cac aca gat        384
Lys Cys Ser Glu Thr Phe Thr Asn Lys Leu Lys Glu Lys His Thr Asp
            115                 120                 125 ctt ggt aaa gaa ggt gtt act gat gct gat gca aaa gaa gcc att tta        432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta        480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct        528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa        576
Asn Ser Val Lys Glu Leu Thr Ser Pro Val Val Ala Glu Ser Pro Lys
            180                 185                 190 aaa cct tcc atg gcc gtt tca gta gat ttg cct ggt gaa atg aaa gtt        624
Lys Pro Ser Met Ala Val Ser Val Asp Leu Pro Gly Glu Met Lys Val
        195                 200                 205 ctt gta agc aaa gaa aaa aac aaa gac ggc aag tac gat cta att gca        672
Leu Val Ser Lys Glu Lys Asn Lys Asp Gly Lys Tyr Asp Leu Ile Ala
    210                 215                 220 aca gta gac aag ctt gag ctt aaa gga act tct gat aaa aac aat gga        720
Thr Val Asp Lys Leu Glu Leu Lys Gly Thr Ser Asp Lys Asn Asn Gly
225                 230                 235                 240 tct gga gta ctt gaa ggc gta aaa gct gac aaa agt aaa gta aaa tta        768
Ser Gly Val Leu Glu Gly Val Lys Ala Asp Lys Ser Lys Val Lys Leu
                245                 250                 255 aca att tct gac gat cta ggt caa acc aca ctt gaa gtt ttc aaa gaa        816
Thr Ile Ser Asp Asp Leu Gly Gln Thr Thr Leu Glu Val Phe Lys Glu
            260                 265                 270 gat ggc aaa aca cta gta tca aaa aaa gta act tcc aaa gac aag tca        864
Asp Gly Lys Thr Leu Val Ser Lys Lys Val Thr Ser Lys Asp Lys Ser
        275                 280                 285 tca aca gaa gaa aaa ttc aat gaa aaa ggt gaa gta tct gaa aaa ata        912
Ser Thr Glu Glu Lys Phe Asn Glu Lys Gly Glu Val Ser Glu Lys Ile
    290                 295                 300 ata aca aga gca gac gga acc aga ctt gaa tac aca gga att aaa agc        960
Ile Thr Arg Ala Asp Gly Thr Arg Leu Glu Tyr Thr Gly Ile Lys Ser
305                 310                 315                 320 gat gga tct gga aaa gct aaa gag gtt tta aaa ggc ttt act ctt gaa       1008
Asp Gly Ser Gly Lys Ala Lys Glu Val Leu Lys Gly Phe Thr Leu Glu
                325                 330                 335 gga aaa gta gct aat gat aaa gta aca ttg gaa gta aaa gaa gga acc       1056
Gly Lys Val Ala Asn Asp Lys Val Thr Leu Glu Val Lys Glu Gly Thr
            340                 345                 350 gtt act tta agt aag att tca aaa tct ggg gaa gtt tca gtt gaa ctt       1104
Val Thr Leu Ser Lys Ile Ser Lys Ser Gly Glu Val Ser Val Glu Leu
        355                 360                 365 aat gac act gac agt agt gct gct act aaa aaa act gca gct tgg aat       1152
Asn Asp Thr Asp Ser Ser Ala Ala Thr Lys Lys Thr Ala Ala Trp Asn
    370                 375                 380 tca aaa act tct act tta aca att agt gtt aac agc aaa aaa act aca       1200
Ser Lys Thr Ser Thr Leu Thr Ile Ser Val Asn Ser Lys Lys Thr Thr
385                 390                 395                 400 caa ctt gtg ttt act aaa caa gac aca ata act gta caa aaa tac gac       1248
Gln Leu Val Phe Thr Lys Gln Asp Thr Ile Thr Val Gln Lys Tyr Asp
                405                 410                 415 tcc gca ggt acc aat tta gaa ggc aca gca gtc gaa att aaa aca ctt       1296
```

```
Ser Ala Gly Thr Asn Leu Glu Gly Thr Ala Val Glu Ile Lys Thr Leu
            420                 425                 430 gat gaa ctt aaa aac gct tta aaa taa                                      1323
Asp Glu Leu Lys Asn Ala Leu Lys  *
            435                 440

<210> SEQ ID NO 178
<211> LENGTH: 440
<212> TYPE: PRT
<213> ORGANISM: Artificial Sequence
<220> FEATURE:
<223> OTHER INFORMATION: Chimeric protein

<400> SEQUENCE: 178

Met Ala Cys Asn Asn Ser Gly Lys Asp Gly Asn Thr Ser Ala Asn Ser
  1               5                  10                  15

Ala Asp Glu Ser Val Lys Gly Pro Asn Leu Thr Glu Ile Asn Lys Lys
             20                  25                  30

Ile Thr Asp Ser Asn Ala Val Leu Ala Val Lys Val Glu Ala
             35                  40                  45

Leu Leu Ser Ser Ile Asp Glu Ile Ala Ala Lys Ala Ile Gly Lys Lys
 50                  55                  60

Ile His Gln Asn Asn Gly Leu Asp Thr Glu Asn Asn His Asn Gly Ser
 65                  70                  75                  80

Leu Leu Ala Gly Ala Tyr Ala Ile Ser Thr Leu Ile Lys Gln Lys Leu
                 85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Val Ser Val Asp Leu Pro Gly Glu Met Lys Val
        195                 200                 205

Leu Val Ser Lys Glu Lys Asn Lys Asp Gly Lys Tyr Asp Leu Ile Ala
210                 215                 220

Thr Val Asp Lys Leu Glu Leu Lys Gly Thr Ser Asp Lys Asn Asn Gly
225                 230                 235                 240

Ser Gly Val Leu Glu Gly Val Lys Ala Asp Lys Ser Lys Val Lys Leu
                245                 250                 255

Thr Ile Ser Asp Asp Leu Gly Gln Thr Thr Leu Glu Val Phe Lys Glu
            260                 265                 270

Asp Gly Lys Thr Leu Val Ser Lys Val Thr Ser Lys Asp Lys Ser
        275                 280                 285

Ser Thr Glu Glu Lys Phe Asn Glu Lys Gly Glu Val Ser Glu Lys Ile
    290                 295                 300

Ile Thr Arg Ala Asp Gly Thr Arg Leu Glu Tyr Thr Gly Ile Lys Ser
305                 310                 315                 320

Asp Gly Ser Gly Lys Ala Lys Glu Val Leu Lys Gly Phe Thr Leu Glu
                325                 330                 335
```

```
                Gly Lys Val Ala Asn Asp Lys Val Thr Leu Glu Val Lys Glu Gly Thr
                                340                 345                 350

Val Thr Leu Ser Lys Ile Ser Lys Ser Gly Glu Val Ser Val Glu Leu
                            355                 360                 365

Asn Asp Thr Asp Ser Ser Ala Ala Thr Lys Lys Thr Ala Ala Trp Asn
                        370                 375                 380

Ser Lys Thr Ser Thr Leu Thr Ile Ser Val Asn Ser Lys Lys Thr Thr
                385                 390                 395                 400

Gln Leu Val Phe Thr Lys Gln Asp Thr Ile Thr Val Gln Lys Tyr Asp
                                405                 410                 415

Ser Ala Gly Thr Asn Leu Glu Gly Thr Ala Val Glu Ile Lys Thr Leu
                            420                 425                 430

Asp Glu Leu Lys Asn Ala Leu Lys
                        435                 440

<210> SEQ ID NO 179
<211> LENGTH: 1302
<212> TYPE: DNA
<213> ORGANISM: Artificial Sequence
<220> FEATURE:
<221> NAME/KEY: CDS
<222> LOCATION: (1)...(1302)
<223> OTHER INFORMATION: Chimeric nucleic acid

<400> SEQUENCE: 179 atg gct tgt aat aat tca ggg aaa gat ggg aat aca tct gca aat tct         48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa         96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg        144
Ile Thr Asp Ser Asn Ala Val Leu Leu Ala Val Lys Glu Val Glu Ala
        35                  40                  45 ttg ctg tca tct ata gat gag ctt gct aaa gct att ggt aaa aaa ata        192
Leu Leu Ser Ser Ile Asp Glu Leu Ala Lys Ala Ile Gly Lys Lys Ile
    50                  55                  60 aaa aac gat ggt agt tta gat aat gaa gca aat cgc aac gag tca ttg        240
Lys Asn Asp Gly Ser Leu Asp Asn Glu Ala Asn Arg Asn Glu Ser Leu
65                  70                  75                  80 tta gca gga gct tat aca ata tca acc tta ata aca caa aaa tta agt        288
Leu Ala Gly Ala Tyr Thr Ile Ser Thr Leu Ile Thr Gln Lys Leu Ser
                85                  90                  95 aaa tta aac gga tca gaa ggt tta aag gaa aag att gcc gca gct aag        336
Lys Leu Asn Gly Ser Glu Gly Leu Lys Glu Lys Ile Ala Ala Ala Lys
            100                 105                 110 aaa tgc tct gaa gag ttt agt act aaa cta aaa gat aat cat gca cag        384
Lys Cys Ser Glu Glu Phe Ser Thr Lys Leu Lys Asp Asn His Ala Gln
        115                 120                 125 ctt ggt ata cag ggc gtt act gat gaa aat gca aaa aaa gct att tta        432
Leu Gly Ile Gln Gly Val Thr Asp Glu Asn Ala Lys Lys Ala Ile Leu
    130                 135                 140 aaa gca aat gca gcg ggt aaa gat aag ggc gtt gaa gaa ctt gaa aag        480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt        528
Leu Ser Gly Ser Leu Glu Ser Leu Ser Lys Ala Ala Lys Glu Met Leu
                165                 170                 175 gct aat tca gtt aaa gag ctt aca agc cct gtt gtc cat ggc gtt tca        576
```

-continued

| | | |
|---|---|---|
| Ala Asn Ser Val Lys Glu Leu Thr Ser Pro Val Val His Gly Val Ser<br>                 180                     185                190 | | |
| gta gat ttg cct ggt gaa atg aaa gtt ctt gta agc aaa gaa aaa aac<br>Val Asp Leu Pro Gly Glu Met Lys Val Leu Val Ser Lys Glu Lys Asn<br>           195                    200                   205 | 624 | |
| aaa gac ggc aag tac gat cta att gca aca gta gac aag ctt gag ctt<br>Lys Asp Gly Lys Tyr Asp Leu Ile Ala Thr Val Asp Lys Leu Glu Leu<br>210                   215                   220 | 672 | |
| aaa gga act tct gat aaa aac aat gga tct gga gta ctt gaa ggc gta<br>Lys Gly Thr Ser Asp Lys Asn Asn Gly Ser Gly Val Leu Glu Gly Val<br>225                   230                   235                   240 | 720 | |
| aaa gct gac aaa agt aaa gta aaa tta aca att tct gac gat cta ggt<br>Lys Ala Asp Lys Ser Lys Val Lys Leu Thr Ile Ser Asp Asp Leu Gly<br>           245                    250                   255 | 768 | |
| caa acc aca ctt gaa gtt ttc aaa gaa gat ggc aaa aca cta gta tca<br>Gln Thr Thr Leu Glu Val Phe Lys Glu Asp Gly Lys Thr Leu Val Ser<br>                 260                    265               270 | 816 | |
| aaa aaa gta act tcc aaa gac aag tca tca aca gaa gaa aaa ttc aat<br>Lys Lys Val Thr Ser Lys Asp Lys Ser Ser Thr Glu Glu Lys Phe Asn<br>275                   280                   285 | 864 | |
| gaa aaa ggt gaa gta tct gaa aaa ata ata aca aga gca gac gga acc<br>Glu Lys Gly Glu Val Ser Glu Lys Ile Ile Thr Arg Ala Asp Gly Thr<br>     290                   295                   300 | 912 | |
| aga ctt gaa tac aca gga att aaa agc gat gga tct gga aaa gct aaa<br>Arg Leu Glu Tyr Thr Gly Ile Lys Ser Asp Gly Ser Gly Lys Ala Lys<br>305                   310                   315                   320 | 960 | |
| gag gtt tta aaa ggc ttt act ctt gaa gga aaa gta gct aat gat aaa<br>Glu Val Leu Lys Gly Phe Thr Leu Glu Gly Lys Val Ala Asn Asp Lys<br>                 325                    330               335 | 1008 | |
| gta aca ttg gaa gta aaa gaa gga acc gtt act tta agt aag att tca<br>Val Thr Leu Glu Val Lys Glu Gly Thr Val Thr Leu Ser Lys Ile Ser<br>           340                    345                   350 | 1056 | |
| aaa tct ggg gaa gtt tca gtt gaa ctt aat gac act gac agt agt gct<br>Lys Ser Gly Glu Val Ser Val Glu Leu Asn Asp Thr Asp Ser Ser Ala<br>355                   360                   365 | 1104 | |
| gct act aaa aaa act gca gct tgg aat tca aaa act tct act tta aca<br>Ala Thr Lys Lys Thr Ala Ala Trp Asn Ser Lys Thr Ser Thr Leu Thr<br>     370                   375                   380 | 1152 | |
| att agt gtt aac agc aaa aaa act aca caa ctt gtg ttt act aaa caa<br>Ile Ser Val Asn Ser Lys Lys Thr Thr Gln Leu Val Phe Thr Lys Gln<br>385                   390                   395                   400 | 1200 | |
| gac aca ata act gta caa aaa tac gac tcc gca ggt acc aat tta gaa<br>Asp Thr Ile Thr Val Gln Lys Tyr Asp Ser Ala Gly Thr Asn Leu Glu<br>                 405                    410               415 | 1248 | |
| ggc aca gca gtc gaa att aaa aca ctt gat gaa ctt aaa aac gct tta<br>Gly Thr Ala Val Glu Ile Lys Thr Leu Asp Glu Leu Lys Asn Ala Leu<br>           420                    425                   430 | 1296 | |
| aaa taa<br>Lys  * | 1302 | |

<210> SEQ ID NO 180
<211> LENGTH: 433
<212> TYPE: PRT
<213> ORGANISM: Artificial Sequence
<220> FEATURE:
<223> OTHER INFORMATION: Chimeric protein

<400> SEQUENCE: 180

Met Ala Cys Asn Asn Ser Gly Lys Asp Gly Asn Thr Ser Ala Asn Ser
1               5                   10                  15

-continued

Ala Asp Glu Ser Val Lys Gly Pro Asn Leu Thr Glu Ile Ser Lys Lys
        20                  25                  30

Ile Thr Asp Ser Asn Ala Val Leu Leu Ala Val Lys Glu Val Glu Ala
            35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Val Ser
            180                 185                 190

Val Asp Leu Pro Gly Glu Met Lys Val Leu Val Ser Lys Glu Lys Asn
        195                 200                 205

Lys Asp Gly Lys Tyr Asp Leu Ile Ala Thr Val Asp Lys Leu Glu Leu
    210                 215                 220

Lys Gly Thr Ser Asp Lys Asn Asn Gly Ser Gly Val Leu Glu Gly Val
225                 230                 235                 240

Lys Ala Asp Lys Ser Lys Val Lys Leu Thr Ile Ser Asp Asp Leu Gly
                245                 250                 255

Gln Thr Thr Leu Glu Val Phe Lys Glu Asp Gly Lys Thr Leu Val Ser
            260                 265                 270

Lys Lys Val Thr Ser Lys Asp Lys Ser Ser Thr Glu Glu Lys Phe Asn
        275                 280                 285

Glu Lys Gly Glu Val Ser Glu Lys Ile Ile Thr Arg Ala Asp Gly Thr
    290                 295                 300

Arg Leu Glu Tyr Thr Gly Ile Lys Ser Asp Gly Ser Gly Lys Ala Lys
305                 310                 315                 320

Glu Val Leu Lys Gly Phe Thr Leu Glu Gly Lys Val Ala Asn Asp Lys
                325                 330                 335

Val Thr Leu Glu Val Lys Glu Gly Thr Val Thr Leu Ser Lys Ile Ser
            340                 345                 350

Lys Ser Gly Glu Val Ser Val Glu Leu Asn Asp Thr Asp Ser Ser Ala
        355                 360                 365

Ala Thr Lys Lys Thr Ala Ala Trp Asn Ser Lys Thr Ser Thr Leu Thr
    370                 375                 380

Ile Ser Val Asn Ser Lys Thr Thr Gln Leu Val Phe Thr Lys Gln
385                 390                 395                 400

Asp Thr Ile Thr Val Gln Lys Tyr Asp Ser Ala Gly Thr Asn Leu Glu
                405                 410                 415

Gly Thr Ala Val Glu Ile Lys Thr Leu Asp Glu Leu Lys Asn Ala Leu
            420                 425                 430

Lys

<210> SEQ ID NO 181
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 181
gtcatatggc ttgtaataat tcagggaaag a                              31

<210> SEQ ID NO 182
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 182
tttccatgga aggttttttt ggactttctg                                30

<210> SEQ ID NO 183
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 183
tttccatggc caagcaaaat gttagcagcc                                30

<210> SEQ ID NO 184
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 184
taaggatcct tattttaaag cgttttt                                   27

<210> SEQ ID NO 185
<211> LENGTH: 819
<212> TYPE: DNA
<213> ORGANISM: Borrelia burgdorferi
<220> FEATURE:
<221> NAME/KEY: CDS
<222> LOCATION: (1)...(819)

<400> SEQUENCE: 185

```
atg aaa aaa tat tta ttg gga ata ggt cta ata tta gcc tta ata gca     48
Met Lys Lys Tyr Leu Leu Gly Ile Gly Leu Ile Leu Ala Leu Ile Ala
 1               5                  10                  15 tgt aag caa aat gtt agc agc ctt gac gag aaa aac agc gtt tca gta     96
Cys Lys Gln Asn Val Ser Ser Leu Asp Glu Lys Asn Ser Val Ser Val
                20                  25                  30 gat ttg cct ggt gaa atg aaa gtt ctt gta agc aaa gaa aaa aac aaa    144
Asp Leu Pro Gly Glu Met Lys Val Leu Val Ser Lys Glu Lys Asn Lys
            35                  40                  45 gac ggc aag tac gat cta att gca aca gta gac aag ctt gag ctt aaa    192
Asp Gly Lys Tyr Asp Leu Ile Ala Thr Val Asp Lys Leu Glu Leu Lys
        50                  55                  60 gga act tct gat aaa aac aat gga tct gga gta ctt gaa ggc gta aaa    240
Gly Thr Ser Asp Lys Asn Asn Gly Ser Gly Val Leu Glu Gly Val Lys
    65                  70                  75                  80
```

```
gct gac aaa agt aaa gta aaa tta aca att tct gac gat cta ggt caa      288
Ala Asp Lys Ser Lys Val Lys Leu Thr Ile Ser Asp Asp Leu Gly Gln
             85                  90                  95 acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
        100                 105                 110 aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
            115                 120                 125 aaa ggt gaa gta tct gaa aaa ata ata aca aga gca gac gga acc aga      432
Lys Gly Glu Val Ser Glu Lys Ile Ile Thr Arg Ala Asp Gly Thr Arg
130                 135                 140 ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160 gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175 aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190 aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205 gct act aaa aaa act gca gct tgg aat gca ggc act tca act tta aca      672
Ala Thr Lys Lys Thr Ala Ala Trp Asn Ala Gly Thr Ser Thr Leu Thr
    210                 215                 220 att act gta aac aac aaa aaa act aaa gcc ctt gta ttt aca aaa caa      720
Ile Thr Val Asn Asn Lys Lys Thr Lys Ala Leu Val Phe Thr Lys Gln
225                 230                 235                 240 gac aca att aca tca caa aaa tac gac tca gca gga acc aac ttg gaa      768
Asp Thr Ile Thr Ser Gln Lys Tyr Asp Ser Ala Gly Thr Asn Leu Glu
                245                 250                 255 ggc aca gca gtc gaa att aaa aca ctt gat gaa ctt aaa aac gct tta      816
Gly Thr Ala Val Glu Ile Lys Thr Leu Asp Glu Leu Lys Asn Ala Leu
            260                 265                 270 aga                                                                  819
Arg

<210> SEQ ID NO 186
<211> LENGTH: 273
<212> TYPE: PRT
<213> ORGANISM: Borrelia burgdorferi

<400> SEQUENCE: 186

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
```

-continued

```
                100                 105                 110
Lys Val Thr Ser Lys Asp Lys Ser Thr Glu Glu Lys Phe Asn Glu
            115                 120                 125
Lys Gly Glu Val Ser Glu Lys Ile Ile Thr Arg Ala Asp Gly Thr Arg
    130                 135                 140
Leu Glu Tyr Thr Gly Ile Lys Ser Asp Gly Ser Gly Lys Ala Lys Glu
145                 150                 155                 160
Val Leu Lys Gly Tyr Val Leu Glu Gly Thr Leu Thr Ala Glu Lys Thr
                165                 170                 175
Thr Leu Val Val Lys Glu Gly Thr Val Thr Leu Ser Lys Asn Ile Ser
            180                 185                 190
Lys Ser Gly Glu Val Ser Val Glu Leu Asn Asp Thr Asp Ser Ser Ala
    195                 200                 205
Ala Thr Lys Lys Thr Ala Ala Trp Asn Ala Gly Thr Ser Thr Leu Thr
        210                 215                 220
Ile Thr Val Asn Asn Lys Thr Lys Ala Leu Val Phe Thr Lys Gln
225                 230                 235                 240
Asp Thr Ile Thr Ser Gln Lys Tyr Asp Ser Ala Gly Thr Asn Leu Glu
                245                 250                 255
Gly Thr Ala Val Glu Ile Lys Thr Leu Asp Glu Leu Lys Asn Ala Leu
            260                 265                 270
Arg

<210> SEQ ID NO 187
<211> LENGTH: 8
<212> TYPE: PRT
<213> ORGANISM: Borrelia burgdorferi sensu lato

<400> SEQUENCE: 187

Leu Pro Gly Glu Met Lys Val Leu
1               5

<210> SEQ ID NO 188
<211> LENGTH: 8
<212> TYPE: PRT
<213> ORGANISM: Borrelia burgdorferi sensu lato

<400> SEQUENCE: 188

Leu Pro Gly Gly Met Thr Val Leu
1               5

<210> SEQ ID NO 189
<211> LENGTH: 8
<212> TYPE: PRT
<213> ORGANISM: Borrelia burgdorferi sensu lato

<400> SEQUENCE: 189

Leu Pro Gly Glu Ile Lys Val Leu
1               5

<210> SEQ ID NO 190
<211> LENGTH: 8
<212> TYPE: PRT
<213> ORGANISM: Borrelia burgdorferi sensu lato

<400> SEQUENCE: 190

Leu Pro Gly Gly Met Gly Val Leu
1               5
```

```
<210> SEQ ID NO 191
<211> LENGTH: 11
<212> TYPE: PRT
<213> ORGANISM: Borrelia burgdorferi sensu lato

<400> SEQUENCE: 191

Gly Thr Ser Asp Lys Asn Asn Gly Ser Gly Val
1               5                   10

<210> SEQ ID NO 192
<211> LENGTH: 11
<212> TYPE: PRT
<213> ORGANISM: Borrelia burgdorferi sensu lato

<400> SEQUENCE: 192

Gly Thr Ser Asp Lys Ser Asn Gly Ser Gly Thr
1               5                   10

<210> SEQ ID NO 193
<211> LENGTH: 11
<212> TYPE: PRT
<213> ORGANISM: Borrelia burgdorferi sensu lato

<400> SEQUENCE: 193

Gly Thr Ser Asp Lys Asn Asn Gly Ser Gly Thr
1               5                   10

<210> SEQ ID NO 194
<211> LENGTH: 11
<212> TYPE: PRT
<213> ORGANISM: Borrelia burgdorferi sensu lato

<400> SEQUENCE: 194

Gly Thr Ser Asp Lys Asp Asn Gly Ser Gly Thr
1               5                   10

<210> SEQ ID NO 195
<211> LENGTH: 11
<212> TYPE: PRT
<213> ORGANISM: Borrelia burgdorferi sensu lato

<400> SEQUENCE: 195

Gly Thr Ser Asp Lys Asp Asn Gly Ser Gly Val
1               5                   10

<210> SEQ ID NO 196
<211> LENGTH: 31
<212> TYPE: PRT
<213> ORGANISM: Borrelia burgdorferi sensu lato

<400> SEQUENCE: 196

Asn Ile Ser Lys Ser Gly Glu Val Ser Val Glu Leu Asn Asp Thr Asp
1               5                   10                  15

Ser Ser Ala Ala Thr Lys Lys Thr Ala Ala Trp Asn Ser Gly Thr
            20                  25                  30

<210> SEQ ID NO 197
<211> LENGTH: 31
<212> TYPE: PRT
<213> ORGANISM: Borrelia burgdorferi sensu lato

<400> SEQUENCE: 197

His Ile Pro Asn Ser Gly Glu Ile Thr Val Glu Leu Asn Asp Ser Asn
1               5                   10                  15
```

-continued

Ser Thr Gln Ala Thr Lys Lys Thr Gly Lys Trp Asp Ser Asn Thr
            20                  25                  30

<210> SEQ ID NO 198
<211> LENGTH: 31
<212> TYPE: PRT
<213> ORGANISM: Borrelia burgdorferi sensu lato

<400> SEQUENCE: 198

Asn Ile Leu Lys Ser Gly Glu Ile Thr Val Ala Leu Asp Asp Ser Asp
1               5                   10                  15

Thr Thr Gln Ala Thr Lys Lys Thr Gly Lys Trp Asp Ser Lys Thr
            20                  25                  30

<210> SEQ ID NO 199
<211> LENGTH: 31
<212> TYPE: PRT
<213> ORGANISM: Borrelia burgdorferi sensu lato

<400> SEQUENCE: 199

Asn Ile Leu Lys Ser Gly Glu Ile Thr Ala Ala Leu Asp Asp Ser Asp
1               5                   10                  15

Thr Thr Arg Ala Thr Lys Lys Thr Gly Lys Trp Asp Ser Lys Thr
            20                  25                  30

<210> SEQ ID NO 200
<211> LENGTH: 31
<212> TYPE: PRT
<213> ORGANISM: Borrelia burgdorferi sensu lato

<400> SEQUENCE: 200

Glu Ile Ala Lys Ser Gly Glu Val Thr Val Ala Leu Asn Asp Thr Asn
1               5                   10                  15

Thr Thr Gln Ala Thr Lys Lys Thr Gly Ala Trp Asp Ser Lys Thr
            20                  25                  30

<210> SEQ ID NO 201
<211> LENGTH: 31
<212> TYPE: PRT
<213> ORGANISM: Borrelia burgdorferi sensu lato

<400> SEQUENCE: 201

His Ile Ser Asn Ser Gly Glu Ile Thr Val Glu Leu Asn Asp Ser Asp
1               5                   10                  15

Thr Thr Gln Ala Thr Lys Lys Thr Gly Thr Trp Asp Ser Lys Thr
            20                  25                  30

<210> SEQ ID NO 202
<211> LENGTH: 31
<212> TYPE: PRT
<213> ORGANISM: Borrelia burgdorferi sensu lato

<400> SEQUENCE: 202

His Ile Ser Lys Ser Gly Glu Val Thr Ala Glu Leu Asn Asp Thr Asp
1               5                   10                  15

Ser Thr Gln Ala Thr Lys Lys Thr Gly Lys Trp Asp Ala Gly Thr
            20                  25                  30

<210> SEQ ID NO 203
<211> LENGTH: 21
<212> TYPE: PRT
<213> ORGANISM: Borrelia burgdorferi sensu lato

<400> SEQUENCE: 203

Ser Asn Gly Thr Lys Leu Glu Gly Ser Ala Val Glu Ile Thr Lys Leu
1               5                   10                  15

Asp Glu Ile Lys Asn
            20

<210> SEQ ID NO 204
<211> LENGTH: 21
<212> TYPE: PRT
<213> ORGANISM: Borrelia burgdorferi sensu lato

<400> SEQUENCE: 204

Ser Ala Gly Thr Asn Leu Glu Gly Asn Ala Val Glu Ile Lys Thr Leu
1               5                   10                  15

Asp Glu Leu Lys Asn
            20

<210> SEQ ID NO 205
<211> LENGTH: 21
<212> TYPE: PRT
<213> ORGANISM: Borrelia burgdorferi sensu lato

<400> SEQUENCE: 205

Ser Ala Gly Thr Asn Leu Glu Gly Lys Ala Val Glu Ile Thr Thr Leu
1               5                   10                  15

Lys Glu Leu Lys Asn
            20

<210> SEQ ID NO 206
<211> LENGTH: 21
<212> TYPE: PRT
<213> ORGANISM: Borrelia burgdorferi sensu lato

<400> SEQUENCE: 206

Ser Ala Gly Thr Asn Leu Glu Gly Thr Ala Val Glu Ile Lys Thr Leu
1               5                   10                  15

Asp Glu Leu Lys Asn
            20

<210> SEQ ID NO 207
<211> LENGTH: 21
<212> TYPE: PRT
<213> ORGANISM: Borrelia burgdorferi sensu lato

<400> SEQUENCE: 207

Glu Leu Asn Asp Thr Asp Ser Ser Ala Ala Thr Lys Lys Thr Ala Ala
1               5                   10                  15

Trp Asn Ser Gly Thr
            20

<210> SEQ ID NO 208
<211> LENGTH: 21
<212> TYPE: PRT
<213> ORGANISM: Borrelia burgdorferi sensu lato

<400> SEQUENCE: 208

Ala Leu Asp Asp Ser Asp Thr Thr Gln Ala Thr Lys Lys Thr Gly Lys
1               5                   10                  15

Trp Asp Ser Lys Thr
            20

```
<210> SEQ ID NO 209
<211> LENGTH: 21
<212> TYPE: PRT
<213> ORGANISM: Borrelia burgdorferi sensu lato

<400> SEQUENCE: 209

Glu Leu Asn Asp Ser Asp Thr Ser Ala Ala Thr Lys Lys Thr Ala Ala
 1               5                  10                  15

Trp Asn Ser Gly Thr
            20

<210> SEQ ID NO 210
<211> LENGTH: 21
<212> TYPE: PRT
<213> ORGANISM: Borrelia burgdorferi sensu lato

<400> SEQUENCE: 210

Glu Leu Asn Asp Thr Asp Ser Ser Ala Ala Thr Lys Lys Thr Gly Lys
 1               5                  10                  15

Trp Asn Ser Gly Thr
            20

<210> SEQ ID NO 211
<211> LENGTH: 21
<212> TYPE: PRT
<213> ORGANISM: Borrelia burgdorferi sensu lato

<400> SEQUENCE: 211

Glu Leu Asn Asp Thr Asp Ser Ser Ala Ala Thr Lys Lys Thr Ala Ala
 1               5                  10                  15

Trp Asp Ser Lys Thr
            20

<210> SEQ ID NO 212
<211> LENGTH: 21
<212> TYPE: PRT
<213> ORGANISM: Borrelia burgdorferi sensu lato

<400> SEQUENCE: 212

Glu Leu Asn Asp Ser Asp Thr Ser Ala Ala Thr Lys Lys Thr Gly Lys
 1               5                  10                  15

Trp Asn Ser Gly Thr
            20

<210> SEQ ID NO 213
<211> LENGTH: 21
<212> TYPE: PRT
<213> ORGANISM: Borrelia burgdorferi sensu lato

<400> SEQUENCE: 213

Glu Leu Asn Asp Ser Asp Thr Ser Ala Ala Thr Lys Lys Thr Ala Ala
 1               5                  10                  15

Trp Asp Ser Lys Thr
            20
```

RECOMBINANT CONSTRUCTS OF *BORRELIA BURGDORFERI*

RELATED APPLICATIONS

This application is a continuation of International Application No. PCT/US01/24736, filed Aug. 7, 2001, published in English, which claims the benefit of U.S. Provisional Application No. 60/226,484, filed Aug. 18, 2000, said International Application No. PCT/US01/24736 also being a continuation-in-part of U.S. Ser. No. 09/666,017, filed Sep. 19, 2000 (abandoned), which is itself a continuation-in-part of U.S. Ser. No. 08/235,836 (now U.S. Pat. No. 6,248,562), filed Apr. 29, 1994, which is itself a continuation-in-part of U.S. Ser. No. 08/148,191, filed Nov. 1, 1993 (abandoned). The teachings of all of these applications are incorporated herein by reference in their entirety.

GOVERNMENT SUPPORT

The invention was supported, in whole or in part, by Grant 2R01AI37256-05A1 from the National Institute of Allergy and Infectious Diseases. The Government has certain rights in the invention.

BACKGROUND OF THE INVENTION

Lyme disease (Lyme borreliosis) is the most common tick-borne infectious disease in North America and Europe, and has been found in Russia, Japan, China and Australia. Lyme disease begins at the site of a tick bite, producing a primary infection with spread of the organism to secondary sites occurring during the course of infection. The causative bacterial agent of this disease is the spirochete *Borrelia burgdorferi*, which was first isolated and cultivated in 1982 (Burgdorferi, W. A. et al., *Science* 216: 1317–1319 (1982); Steere, A. R. et al., *N. Engl. J. Med.* 308: 733–740 (1983)). With that discovery, a wide array of clinical syndromes, described in both the European and American literature since the early 20th century, could be attributed to infection by *B. burgdorferi* (Afzelius, A., *Acta Derm. Venereol.* 2: 120–125 (1921); Bannwarth, A., *Arch. Psychiatr. Nervenkrankh.* 117: 161–185 (1944); Garin, C. and A. Bujadouz, *J. Med. Lyon* 71: 765–767 (1922); Herxheimer, K. and K. Hartmann, *Arch. Dermatol. Syphilol.* 61: 57–76, 255–300 (1902)).

Three pathogenic genospecies of *Borrelia, B. burgdorferi* sensu stricto (*B. burgdorferi* or *B.b.s.s.*), *B. afzelii* and *B. garinii* have been described (Baranton, G., et al., *Int. J. Syst. Bacteriol.* 42:378–383 (1992)). These are members of a species complex, *B. burgdorferi* sensu lato, which consists of at least 10 different genospecies (Piken, R. N., et al., *J. Invest. Dermatol.,* 110:211–214 (1998); Postic, D., et al., *Int. J. Syst. Bacteriol.* 44:743–752 (1994); Valsangiacomo, C. T., et al., *Int. J. Syst. Bacteriol.* 47:1–10 (1997)). The three genospecies, *B. burgdorferi* sensu stricto, *B. afzelii* and *B. garinii*, all are thought to be pathogenic and all are found in Europe. However, in North America, *B. burgdorferi* sensu stricto is the only identified pathogenic genospecies. Each of these three genospecies is associated with distinct clinical manifestations (Van Dam, A. P. et al., *Clin. Infect. Dis.* 17:708–717 (1993)). This implies that differences in genospecies may play an important role in the wide array of clinical manifestations observed in Lyme Disease.

OspA is a basic lipoprotein of approximately 31 kd, which is encoded on a large linear plasmid along with OspB, a basic lipoprotein of approximately 34 kd (Szczepanski, A., and J. L. Benach, *Microbiol. Rev.* 55:21 (1991)). Analysis of isolates of *B. burgdorferi* obtained from North America and Europe has demonstrated that OspA has antigenic variability, and that several distinct groups can be serologically and genotypically defined (Wilske, B., et al., *World J. Microbiol.* 7: 130 (1991)). Other *Borrelia* proteins demonstrate similar antigenic variability. Surprisingly, the immune response to these outer surface proteins tends to occur late in the disease, if at all (Craft, J. E. et al., *J. Clin Invest.* 78: 934–939 (1986); Dattwyler, R. J. and B. J. Luft, *Rheum. Clin. North Am.* 15: 727–734 (1989)). Furthermore, patients acutely and chronically infected with *B. burgdorferi* respond variably to the different antigens, including OspA, OspB, OspC, OspD, p39, p41 and p93.

As an infected tick begins to feed on a mammal, the synthesis of another outer surface protein, outer surface protein C or OspC, is induced (Schwan, T. G., et al, *Proc. Natl. Acad. Sci.* 2:2909–2913 (1995)). Thus, in early infection, OspC is the major outer membrane protein expressed by the spirochete (Fung, B. P., et al., *Infect. Immun.* 62:3213–3221 (1994); Padula, S. J., et al., *J. Clin. Microbiol.,* 32:1733–1738 (1994)). Even through OspC has been demonstrated to have limited surface exposure (Cox, D. L., et al., *Proc. Natl. Acad. Sci.,* 93:7973–7978 (1996); Mathiesen, M. M., et al., *Infect. Immun.* 66:4073–4079 (1998)), OspC is a potent immunogen. Immunization with OspC is protective against tick-transmitted *Borrelia* infection (Gilmore Jr., R. D., *Infect. Immun.* 64:2234–2239 (1999)). However, because OspC is highly variable in its sequence, the protection is limited to the *Borrelia burgdorferi* strain expressing the same allele of OspC. Challenge with heterologous isolates, expressing other ospC alleles results in infection (Probert, W. S., et al., *J. Infect. D.,* 175:400–405 (1997)). OspC is a very diverse genetic locus (Jauris-Heipke, S., et al., *Med. Microbiol. Immunol.* 182:37–50 (1993)) as evidenced by the fact that Livey et al. found thirty-four alleles of OspC in seventy-six *B. burgdorferi* sensu lato isolates (Livey, I., et al., *Mol. Microbiol.* 18:257–269 (1995)).

Currently, Lyme Disease is treated with a range of antibiotics, e.g., tetracyclines, penicillin and cephalosporins. However, such treatment is not always successful in clearing the infection. Treatment is often delayed due to improper diagnosis with the deleterious effect that the infection proceeds to a chronic condition, where treatment with antibiotics is often not useful. One of the factors contributing to delayed treatment is the lack of effective diagnostic tools.

Vaccines against Lyme borreliosis have been attempted. Mice immunized with a recombinant form of OspA are protected from challenge with the same strain of *B. burgdorferi* from which the protein was obtained (Fikrig, E., et al., *Science* 250: 553–556 (1990)). Furthermore, passively transferred anti-OspA monoclonal antibodies (MAbs) have been shown to be protective in mice, and vaccination with a recombinant protein induced protective immunity against subsequent infection with the homologous strain of *B. burgdorferi* (Simon, M. M., et al., *J. Infect. Dis.* 164: 123 (1991)). In addition, there have been two independent trials of first generation vaccines for the prevention of Lyme disease that have studied the efficacy and safety of a vaccine based on recombinant outer surface protein A (OspA) (Sigal, L. H. et al., *N. Engl. J. Med* 339:216–222, 1998; Steere, A. C. et al., *N. Engl. J. Med.* 339:209–215, (1998)). However, a vaccine that consists of recombinant OspA may require frequent booster immunizations. An additional concern of OspA-based vaccines is the recent identification of a putative autoreactive OspA domain with a high degree of similarity to a region of human leukocyte function-associated antigen-1 (hLFA-1) (Gross, D. M. et al., *Science*, 281: 703–706 (1998)).

It has been noted that immunization with a single protein from a particular strain of *Borrelia* often does not confer resistance to that strain in all individuals (Fikrig, E. et al., *J. Immunol.* 7: 2256–1160 (1992)). There is considerable variation displayed in OspA, OspB and OspC, as well as p93, including the regions conferring antigenicity. Therefore, the degree and frequency of protection from vaccination with a protein from a single strain depend upon the response of the immune system to the particular variation, as well as the frequency of genetic variation in *B. burgdorferi*. In the case of vaccines directed against OspA, the vaccine is typically only effective against strains of *Borrelia* that express OspA that is homologous to OspA from which the vaccine was derived.

Another limitation of current OspA Lyme Disease vaccines is that they are directed against an antigen that is expressed predominantly in the tick vector. Indeed, recent reports have indicated that *Borrelia burgdorferi* in infected ticks alter their surface expression by increasing expression of OspC during ingestion of a blood meal (Schwan, T. G. et al., *Proc. Natl. Acad. Sci. USA*, 92: 2909–2913 (1995)). Thus, it seems that natural infection with *B. burgdorferi* does not elicit an antibody response to OspA, as it does against OspC.

Given the heterogeneity of antigenic determinants present in *Borrelia* proteins, a need exists for a vaccine and diagnostic tool which can provide immunogenicity to various strains and/or genospecies of *Borrelia burgdorferi*, as well as to more epitopes within a strain or genospecies. There is also a need for vaccines and diagnostic tools which detect antibody responses against immunoprotective targets that are expressed at different stages of the life cycle of *Borrelia burgdorferi*. This would allow for diagnosis and/or vaccination against all, or most forms, of *Borrelia* that cause systemic disease.

SUMMARY OF THE INVENTION

The current invention pertains to chimeric *Borrelia* proteins which include two or more antigenic *Borrelia* polypeptides which do not occur naturally (in nature) in the same protein in *Borrelia*, as well as the nucleic acids encoding such chimeric proteins. The proteins from which the antigenic polypeptides are derived can be from the same strain or genospecies of *Borrelia*, from different strains or genospecies, or from combinations of proteins from the same and from different strains or genospecies. Particular chimeric proteins, and the nucleotide sequences encoding them, are set forth in FIGS. 30–37 and 55–72.

The chimeric proteins of the current invention provide antigenic polypeptides of a variety of *Borrelia* strains and/or proteins within a single protein. Such proteins are particularly useful in immunodiagnostic assays to detect the presence of antibodies to native *Borrelia* in potentially infected individuals as well as to measure T-cell reactivity, and can therefore be used as immunodiagnostic reagents. These chimeric proteins are also useful in the generation of immune responses (such as antibody production) against proteins expressed by *Borrelia burgdorferi*. The chimeric proteins of the current invention are additionally useful as vaccine immunogens against *Borrelia* infection.

In one embodiment of the present invention, the chimeric proteins are made up of polypeptide fragments from Lyme Disease-causing strains of *Borrelia*. In another embodiment, the polypeptide fragments that make up the chimeric protein are from outer surface protein A (OspA) and outer surface protein C (OspC), which have the general structure of OspC linked via a peptide bond to the N-terminus of OspA. The present invention encompasses both lipidated and unlipidated chimeric proteins. In one embodiment, the OspA and OspC portions of the chimeric protein possess a lipidation signal. In other embodiments, either the OspA polypeptide portion, the OspC polypeptide portion, or both, do not include a lipidation signal.

The OspA portion of the chimeric polypeptide can itself comprise OspA portions from two or more strains of Lyme Disease-causing *Borrelia* as described herein and provided, for example, in FIGS. 23–29 and 43–46. In another embodiment, the OspA polypeptide comprises OspA portions from two or more genospecies of Lyme Disease-causing *Borrelia*, for example, wherein the genospecies are defined as *Borrelia burgdorferi* sensu stricto, *Borrelia afzelii* and *Borrelia garinii*. In this manner, the OspC and OspA polypeptide fragments that make up the chimeric protein can be from the same strain or genospecies of *Borrelia*, from different strains or genospecies of *Borrelia*, or from combinations of proteins from the same and from different strains or genospecies of *Borrelia*.

The present invention is also drawn to nucleic acids which encode a *Borrelia* chimeric protein. In a particular embodiment, the composition comprises a nucleic acid that encodes a chimeric protein of at least two polypeptides, wherein the first polypeptide comprises *Borrelia burgdorferi* OspC, and the second polypeptide comprises *Borrelia burgdorferi* OspA, such that OspC is upstream of OspA. The OspC and OspA nucleic acid fragments that make up the chimeric protein can be from the same strain or genospecies of *Borrelia*, from different strains or genospecies of *Borrelia*, or from combinations of proteins that are from the same and/or different strains or genospecies of *Borrelia*.

The present invention is also drawn to expression vectors which comprise an isolated DNA encoding a *Borrelia* chimeric protein. In one embodiment, the composition includes an expression vector comprising an isolated DNA which encodes an OspC/OspA chimeric protein as described herein. The present invention also encompasses host cells which comprise a recombinant nucleic acid encoding an OspC/OspA chimeric protein as described herein.

The present invention is also drawn to methods of making the *Borrelia* chimeric polypeptides described herein. In one embodiment, the method of making a chimeric *Borrelia* protein comprises selecting a polynucleotide sequence encoding OspC, or an antigenic portion thereof, selecting a polynucleotide sequence encoding OspA, or an antigenic portion thereof, and ligating these polynucleotide sequences together.

The present invention is also drawn to methods of delivering the *Borrelia* chimeric polypeptides described herein. In one embodiment, the method comprises administering the chimeric protein in a physiologically-acceptable carrier to an individual. As a result of the administration of the chimeric protein, the individual develops at least some immune response to the chimeric protein, e.g., the individual generates a humoral immune response, wherein antibodies are produced by the individual that recognize at least a portion of said chimeric polypeptide.

The present invention is also drawn to methods of delivering nucleic acids which encode the chimeric polypeptides described herein. In one embodiment, the method comprises administering the nucleic acid in a physiologically-acceptable carrier to an individual. As a result of the administration of the nucleic acid, the individual expresses the chimeric protein at least transiently and develops at least some immune response to the chimeric protein encoded by the nucleic acid, e.g., the individual generates a humoral immune response, wherein antibodies that recognize at least a portion of the chimeric polypeptide produced from the nucleic acid, are produced by the individual.

The invention also encompasses methods of using the chimeric proteins described herein in a diagnostic assay. As described herein, the method can be used to detect the presence of OspA- and/or OspC-specific antibodies in a sample, e.g., a host sample of interest. The method comprises contacting a sample, e.g., a host sample of interest, with the chimeric protein, under conditions, wherein antibodies, if present in the host sample, bind to the chimeric protein thereby forming antigen-antibody complexes. The antigen-antibody complexes are then detected. In this manner, the chimeric proteins of the present invention can be used to detect an immune response to Lyme Disease causing *Borrelia*.

The present invention is also drawn to diagnostic kits which comprise the chimeric polypeptides described herein. In one embodiment, the kit comprises a *Borrelia burgdorferi* OspC/OspA chimeric protein. The kit also includes reagents for detecting antibody-antigen complexes that are formed between the OspC/OspA chimeric protein and antibodies that are present in a sample, e.g., a user-supplied host sample.

The present invention is also drawn to pharmaceutical compositions which can be used to vaccinate and/or treat *Borrelia* infection in an animal or human. The pharmaceutical composition can be administered together with a physiologically-acceptable carrier and/or with suitable excipients and/or adjuvants.

The present invention is also drawn to methods of immunizing an animal or human against Lyme disease. In a particular embodiment, the method comprises administering a *Borrelia* chimeric OspC/OspA protein. The chimeric protein can be administered together with a physiologically-acceptable carrier, a suitable excipient and/or a suitable adjuvant, to an animal or human such that the animal or human develops an immune response to at least one of the OspC and/or OspA polypeptides of the composition.

By incorporating polypeptide fragments from multiple *Borrelia burgdorferi* proteins, the present invention provides a composition that has great utility for vaccines and diagnostic kits. As a result of the present invention, there exist diagnostic tools and vaccines that comprise both OspA and OspC antigens from various *Borrelia burgdorferi* strains and/or genospecies in a single protein. Since OspA is primarily expressed in the tick vector, and OspC is upregulated in response to the feeding of an infected tick on a mammal, this allows for a diagnostic tool or vaccine that can recognize antigens that are expressed at different stages of the life cycle of *Borrelia burgdorferi*. Thus, the chimeric proteins of the present invention can act at the level of the tick as well as the level of the host, in preventing infection and/or disease caused by *Borrelia*. Moreover, by incorporating unique polypeptide fragments from pathogenic families of *Borrelia*, such as *Borrelia burgdorferi* sensu stricto, *Borrelia afzelii* and *Borrelia garinii*, an improved diagnostic tool or vaccine is produced which can detect clinically important exposure to a wider variety of pathogenic *Borrelia*, while overlooking the remainder of non-pathogenic families of *Borrelia*. Furthermore, OspC polypeptides can be selected from strains of *Borrelia* that are associated with disseminated disease, as described in WO 00/78966, the teachings of which are incorporated herein in their entirety.

The present invention also provides a combination of *Borrelia* antigens in a single polypeptide that, when used as a vaccine, are expected to prevent Lyme disease from becoming systemic. The chimeric proteins of the present invention can be effective in preventing Lyme disease, as well as having a therapeutic effect on established infection, for example after the tick bite is noticed by the patient.

The present invention is drawn to both lipidated and unlipidated chimeric proteins. Unlipidated chimeric proteins, such as the OspC/OspA chimeric proteins described herein, have certain advantages over their lipidated counterparts. These advantages include simpler production methods, improved yields of protein and simpler purification methods. While the lack of a lipidation signal provides several advantages, it had been thought that the lipidation signal was required for immunogenicity. However, as described herein, the non-lipidated OspC/OspA chimeric proteins of the present invention elicit an immune response that is at least as broadly reactive as that of lipidated OspA and lipidated OspC control proteins. Moreover, the unlipidated OspC/OspA chimeric proteins of the present invention unexpectedly elicit an immune response to more than one genospecies and/or strain of Lyme disease-causing *Borrelia*, including genospecies and/or strains that were not used to generate the particular chimeric OspC/OspA immunogen.

For a better understanding of the present invention together with other and further objects, reference is made to the following description, taken together with the accompanying drawings.

BRIEF DESCRIPTION OF THE DRAWINGS

FIG. 2 is a comparison of the antigenic domains depicted in FIG. 1, for OspA in nine strains of *B. burgdorferi*. In Domain 1, A-B31 is SEQ ID NO: 187, A-TRo is SEQ ID NO: 187; A-K48 is SEQ ID NO: 188; A-DK29 is SEQ ID NO: 188; A-P/Gau is SEQ ID NO: 187; A-PKo is SEQ ID NO: 187; A-IP3 is SEQ ID NO: 189; A-IP90 is SEQ ID NO: 194; and A-25015 is SEQ ID NO: 187. In Domain 2, A-B31 is SEQ ID NO: 191, A-TRo is SEQ ID NO: 192; A-K48 is SEQ ID NO: 193; A-DK29 is SEQ ID NO: 193; A-P/Gau is SEQ ID NO: 194; A-PKo is SEQ ID NO: 194; A-IP3 is SEQ ID NO: 195; A-IP90 is SEQ ID NO: 192; and A-25015 is SEQ ID NO: 191. In Domain 3, A-B31 is SEQ ID NO: 196, A-TRo is SEQ ID NO: 197; A-K48 is SEQ ID NO: 198; A-DK29 is SEQ ID NO: 199; A-P/Gau is SEQ ID NO: 200; A-PKo is SEQ ID NO: 200; A-IP3 is SEQ ID NO: 200; A-IP90 is SEQ ID NO: 201; and A-25015 is SEQ ID NO: 202. In Domain 4, A-B31 is SEQ ID NO: 203, A-TRo is SEQ ID NO: 294; A-K48 is SEQ ID NO: 205; A-DK29 is SEQ ID NO: 205; A-P/Gau is SEQ ID NO: 206; A-PKo is SEQ ID NO: 206; A-IP3 is SEQ ID NO: 206; A-IP90 is SEQ ID NO: 205; and A-25015 is SEQ ID NO: 206.

FIG. 4 depicts the amino acid alignment of residues 200 through 220 for OspAs from strains B31 (SEQ ID NO: 207) and K48 (SEQ ID NO: 208) as well as for the site-directed mutants 613 (SEQ ID NO: 209), 625 (SEQ ID NO: 210), 640 (SEQ ID NO: 211) 613/625 (SEQ ID NO: 212), and 613/640 (SEQ ID NO: 213), The arrow indicates Trp216. Amino acid changes are underlined.

FIGS. 7A and 7B depict the nucleic acid sequence of OspA-B31 (SEQ ID NO. 6), and the encoded protein sequence (SEQ ID NO. 7).

FIGS. 8A, 8B and 8C depict the nucleic acid sequence of OspA-K48 (SEQ ID NO. 8), and the encoded protein sequence (SEQ ID NO. 9).

FIGS. 9A, 9B and 9C depict the nucleic acid sequence of OspA-PGau (SEQ ID NO. 10), and the encoded protein sequence (SEQ ID NO. 11).

FIGS. 10A and 10B depict the nucleic acid sequence of a portion of an OspA gene (SEQ ID NO. 185) and its encoded protein sequence (SEQ ID NO. 186).

FIGS. 11A, 11B and 11C depict the nucleic acid sequence of OspB-B31 (SEQ ID NO. 21), and the encoded protein sequence (SEQ ID NO. 22).

FIGS. 12A and 12B depict the nucleic acid sequence of OspC-B31 (SEQ ID NO. 29), and the encoded protein sequence (SEQ ID NO. 30).

FIGS. 13A and 13B depict the nucleic acid sequence of OspC-K48 (SEQ ID NO. 31), and the encoded protein sequence (SEQ ID NO. 32).

FIGS. 14A and 14B depict the nucleic acid sequence of OspC-PKo (SEQ ID NO. 33), and the encoded protein sequence (SEQ ID NO. 34).

FIGS. 15A and 15B depict the nucleic acid sequence of OspC-PTrob (SEQ ID NO. 35) and the encoded protein sequence (SEQ ID NO. 36).

FIGS. 16A, 16B, 16C, 16D and 16E depict the nucleic acid sequence of p93-B31 (SEQ ID NO. 65) and the encoded protein sequence (SEQ ID NO. 66).

FIG. 17 depicts the nucleic acid sequence of p93-K48 (SEQ ID NO. 67).

FIG. 18 depicts the nucleic acid sequence of p93-PBo (SEQ ID NO. 69).

FIG. 19 depicts the nucleic acid sequence of p93-PTrob (SEQ ID NO. 71).

FIG. 20 depicts the nucleic acid sequence of p93-PGAU (SEQ ID NO. 73).

FIG. 21 depicts the nucleic acid sequence of p93-25015 (SEQ ID NO. 77).

FIG. 22 depicts the nucleic acid sequence of p93-PKo (SEQ ID NO. 75).

FIGS. 23A, 23B and 23C depict the nucleic acid sequence of the OspA-K48/OspA-PGAU chimer (SEQ ID NO. 85) and the encoded chimeric protein sequence (SEQ ID NO. 86).

FIGS. 24A, 24B and 24C depict the nucleic acid sequence of the OspA-B31/OspA-PGAU chimer (SEQ ID NO. 88) and the encoded chimeric protein sequence (SEQ ID NO. 89).

FIGS. 25A and 25B depict the nucleic acid sequence of the OspA-B31/OspA-K48 chimer (SEQ ID NO. 91) and the encoded chimeric protein sequence (SEQ ID NO. 92).

FIGS. 26A, 26B and 26C depict the nucleic acid sequence of the OspA-B31/OspA-25015 chimer (SEQ ID NO. 94) and the encoded chimeric protein sequence (SEQ ID NO. 95).

FIGS. 27A, 27B and 27C depict the nucleic acid sequence of the OspA-K48/OspA-B31/OspA-K48 chimer (SEQ ID NO. 97) and the encoded chimeric protein sequence (SEQ ID NO. 98).

FIGS. 28A, 28B and 28C depict the nucleic acid sequence of the OspA-B31/OspA-K48/OspA-B31/OspA-K48 chimer (SEQ ID NO. 100) and the encoded chimeric protein sequence (SEQ ID NO. 101).

FIGS. 29A, 29B and 29C depict the nucleic acid sequence of the OspA-B31/OspB-B31 chimer (SEQ ID NO. 103) and the encoded chimeric protein sequence (SEQ ID NO. 104).

FIGS. 30A, 30B, 30C and 30D depict the nucleic acid sequence of the OspA-B31/OspB-B31/OspC-B31 chimer (SEQ ID NO. 106) and the encoded chimeric protein sequence (SEQ ID NO. 107).

FIGS. 31A, 31B, 31C and 31D depict the nucleic acid sequence of the OspC-B31/OspA-B31/OspB-B31 chimer (SEQ ID NO. 109) and the encoded chimeric protein sequence (SEQ ID NO. 110).

FIGS. 32A, 32B, 32C, 32D and 32E depict the nucleic acid sequence of the OspA-B31/p93-B31 chimer (SEQ ID NO. 111) and the encoded chimeric protein sequence (SEQ ID NO. 112).

FIGS. 33A, 33B, 33C and 33D depict the nucleic acid sequence of the OspB-B31/p41-B31 (122–234) chimer (SEQ ID NO. 113) and the encoded chimeric protein sequence (SEQ ID NO. 114).

FIGS. 34A, 34B, 34C and 34D depict the nucleic acid sequence of the OspB-B31/p41-B31 (122–295) chimer (SEQ ID NO. 115) and the encoded chimeric protein sequence (SEQ ID NO. 116).

FIGS. 35A, 35B and 35C depict the nucleic acid sequence of the OspB-B31/p41-B31 (140–234) chimer (SEQ ID NO. 117) and the encoded chimeric protein sequence (SEQ ID NO. 118).

FIGS. 36A, 36B, 36C and 36D depict the nucleic acid sequence of the OspB-B31/p41-B31 (140–295) chimer (SEQ ID NO. 119) and the encoded chimeric protein sequence (SEQ ID NO. 120).

FIGS. 37A, 37B, 37C, 37D and 37E depict the nucleic acid sequence of the OspB-B31/p41-B31 (122–234)/OspC-B31 chimer (SEQ ID NO. 121) and the encoded chimeric protein sequence (SEQ ID NO. 122).

FIGS. 38A, 38B, 38C and 38D depict an alignment of the nucleic acid sequences for OspC-B31 (SEQ ID NO. 29), OspC-PKo (SEQ ID NO. 33), OspC-PTrob (SEQ ID NO. 35), and OspC-K48 (SEQ ID NO. 31). Nucleic acids which are identical to those in the lead nucleic acid sequence (here, OspC-B31) are represented by a period (.); differing nucleic acids are shown in lower case letters.

FIGS. 39A, 39B, 39C and 39D depict an alignment of the nucleic acid sequences for OspD-PBo (SEQ ID NO. 123), OspD-PGAU (SEQ ID NO. 124), OspD-DK29 (SEQ ID NO. 125), and OspD-K48 (SEQ ID NO. 126). Nucleic acids which are identical to those in the lead nucleic acid sequence (here, OspD-PBo) are represented by a period (.); differing nucleic acids are shown in lower case letters.

FIGS. 40A, 40B and 40C depict the nucleic acid sequence of p41-B31 (SEQ ID NO. 127) and then encoded protein sequence (SEQ ID NO. 128).

FIGS. 41A, 41B, 41C, 41D, 41E, 41F, 41G and 41H depict an alignment of the nucleic acid sequences for p41-B31 (SEQ ID NO. 127), p41-PKa1 (SEQ ID NO. 129), p41-PGAU (SEQ ID NO. 51), p41-PBo (SEQ ID NO. 130), p41-DK29 (SEQ ID NO. 53), and p41-PKo (SEQ ID NO. 131). Nucleic acids which are identical to those in the lead nucleic acid sequence (here, p41-B31) are represented by a period (.); differing nucleic acids are shown in lower case letters.

FIGS. 42A, 42B, 42C, 42D, 42E, 42F, 42G, 42H, 42I, 42J, 42K, 42L, 42M, 42N, 42O and 42P depict an alignment of the nucleic acid sequences for OspA-B31 (SEQ ID NO. 6), OspA-PKa1 (SEQ ID NO. 132), OspA-N40 (SEQ ID NO. 133), OspA-ZS7 (SEQ ID NO. 134), OspA-25015 (SEQ ID NO. 12), OspA-PTrob (SEQ ID NO. 135), OspA-K48 (SEQ ID NO. 8), OspA-Hei (SEQ ID NO. 136), OspA-DK29 (SEQ ID NO. 49), OspA-Ip90 (SEQ ID NO. 50), OspA-PBo (Seq ID NO. 55), OspA-Ip3 (SEQ ID NO. 56), OspA-PKo (SEQ ID NO. 57), OspA-ACAI (SEQ ID NO. 58), and OspA-PGAU (SEQ ID NO. 10). Nucleic acids which are identical to those in the lead nucleic acid sequence (here, OspA-B31) are represented by a period (.); differing nucleic acids are shown in lower case letters.

FIGS. 43A and 43B depict the nucleic acid sequence of the OspA-Tro/OspA-Bo chimer (SEQ ID NO. 137) which encodes the chimeric protein sequence SEQ ID NO. 138.

FIGS. 44A and 44B depict the nucleic acid sequence of the OspA-PGAU/OspA-Bo chimer (SEQ ID NO. 139) which encodes the chimeric protein sequence SEQ ID NO. 140.

FIGS. 45A and 45B depict the nucleic acid sequence of the OspA-B31/OspA-PGAU/OspA-B31/OspA-K48 chimer (SEQ ID NO. 143) which encodes the chimeric protein sequence SEQ ID NO. 144.

FIGS. 46A and 46B depict the nucleic acid sequence of the OspA-PGAU/OspA-B31/OspA-K48 chimer (SEQ ID NO. 141) which encodes the chimeric protein sequence SEQ ID NO. 142.

FIGS. 55A, 55B and 55C depict the nucleic acid sequence of the OspC-B31 (bp 55–633)/OspA-B31 (bp 52–822) chimer (SEQ ID NO. 145) and the encoded chimeric protein sequence (SEQ ID NO. 146).

FIGS. 56A, 56B and 56C depict the nucleic acid sequence of the OspC-B31 (bp 55–624)/OspA-B31 (bp 52–822) chimer (SEQ ID NO. 147) and the encoded chimeric protein sequence (SEQ ID NO. 148).

FIGS. 57A, 57B and 57C depict the nucleic acid sequence of the OspC-C2 (bp 55–612)/OspA-B31 (bp 52–822) chimer (SEQ ID NO. 149) and the encoded chimeric protein sequence (SEQ ID NO. 150).

FIGS. 58A, 58B and 58C depict the nucleic acid sequence of the OspC-B31 (bp 55–633)/OspA-B31 (bp 52–651)/OspA-K48 (bp 652–820) chimer (SEQ ID NO. 151) and the encoded chimeric protein sequence (SEQ ID NO. 152).

Figure 59A:
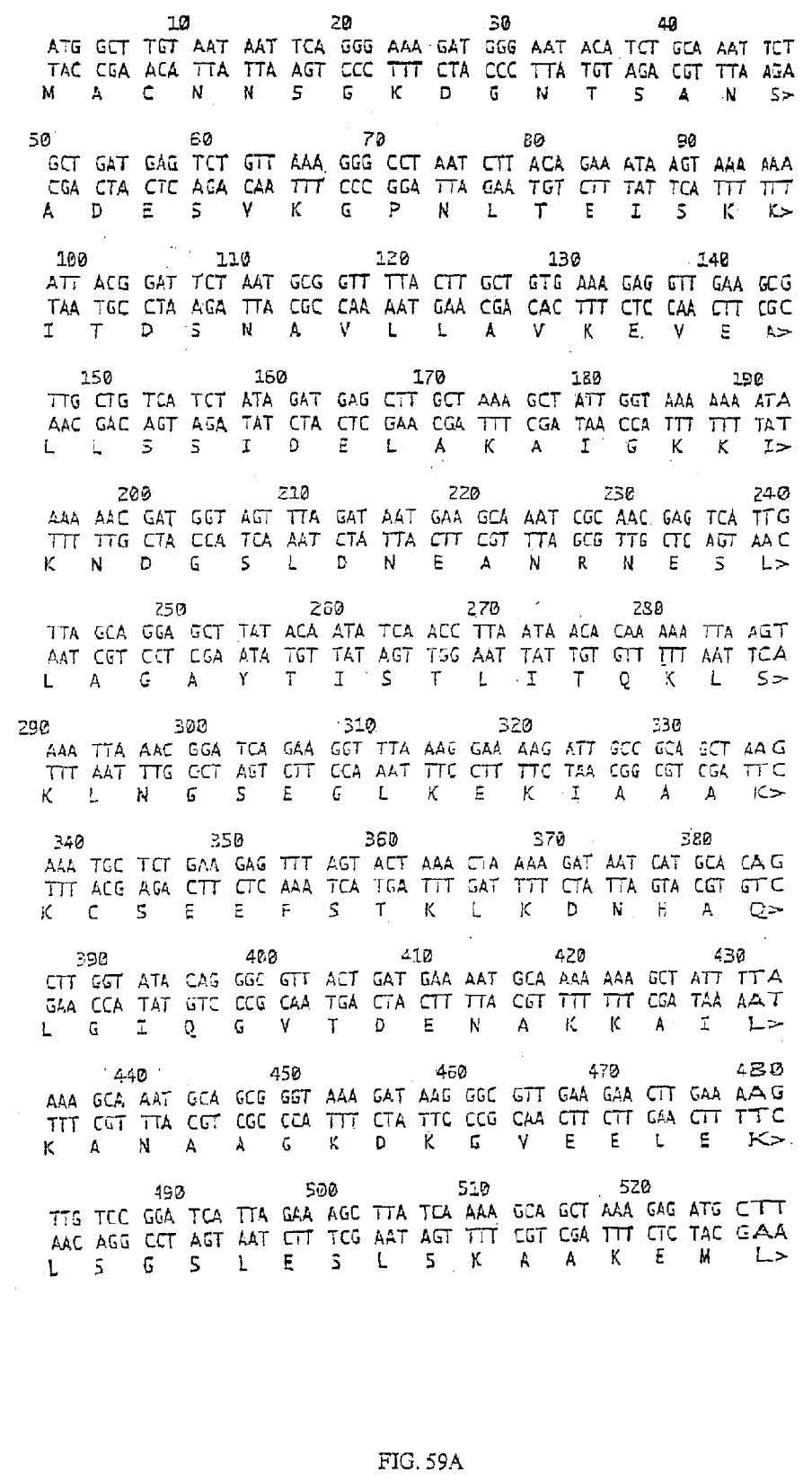

FIGS. 59A, 59B and 59C depict the nucleic acid sequence of the OspC-C2 (bp 55–612)/OspA-B31 (bp 52–651)/OspA-K48 (bp 652–820) chimer (SEQ ID NO. 153) and the encoded chimeric protein sequence (SEQ ID NO. 154).

FIGS. 60A, 60B and 60C depict the nucleic acid sequence of the OspC-B31 (bp 55–633)/OspA-B31 (bp 52–651)/OspA-PKo (bp 652–820) chimer (SEQ ID NO. 155) and the encoded chimeric protein sequence (SEQ ID NO. 156).

FIGS. 61A, 61B and 61C depict the nucleic acid sequence of the OspC-C2 (bp 55–612)/OspA-B31 (bp 52–651)/OspA-PKo (bp 652–820) chimer (SEQ ID NO. 157) and the encoded chimeric protein sequence (SEQ ID NO. 158).

Figure 62B:
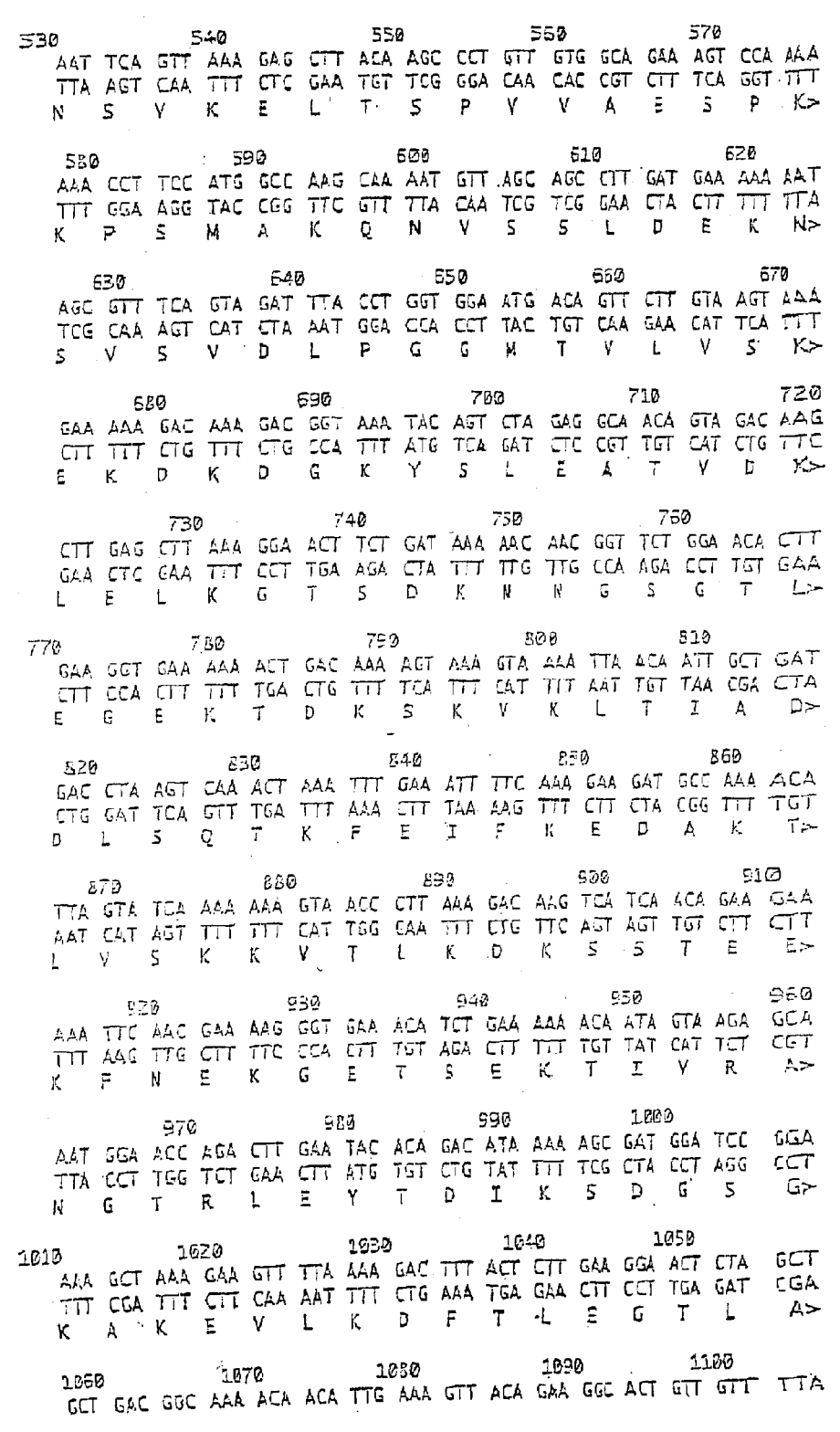

FIGS. 62A, 62B and 62C depict the nucleic acid sequence of the OspC-B31 (bp 55–633)/OspA-K48 (bp 52–654)/

Figure 1:
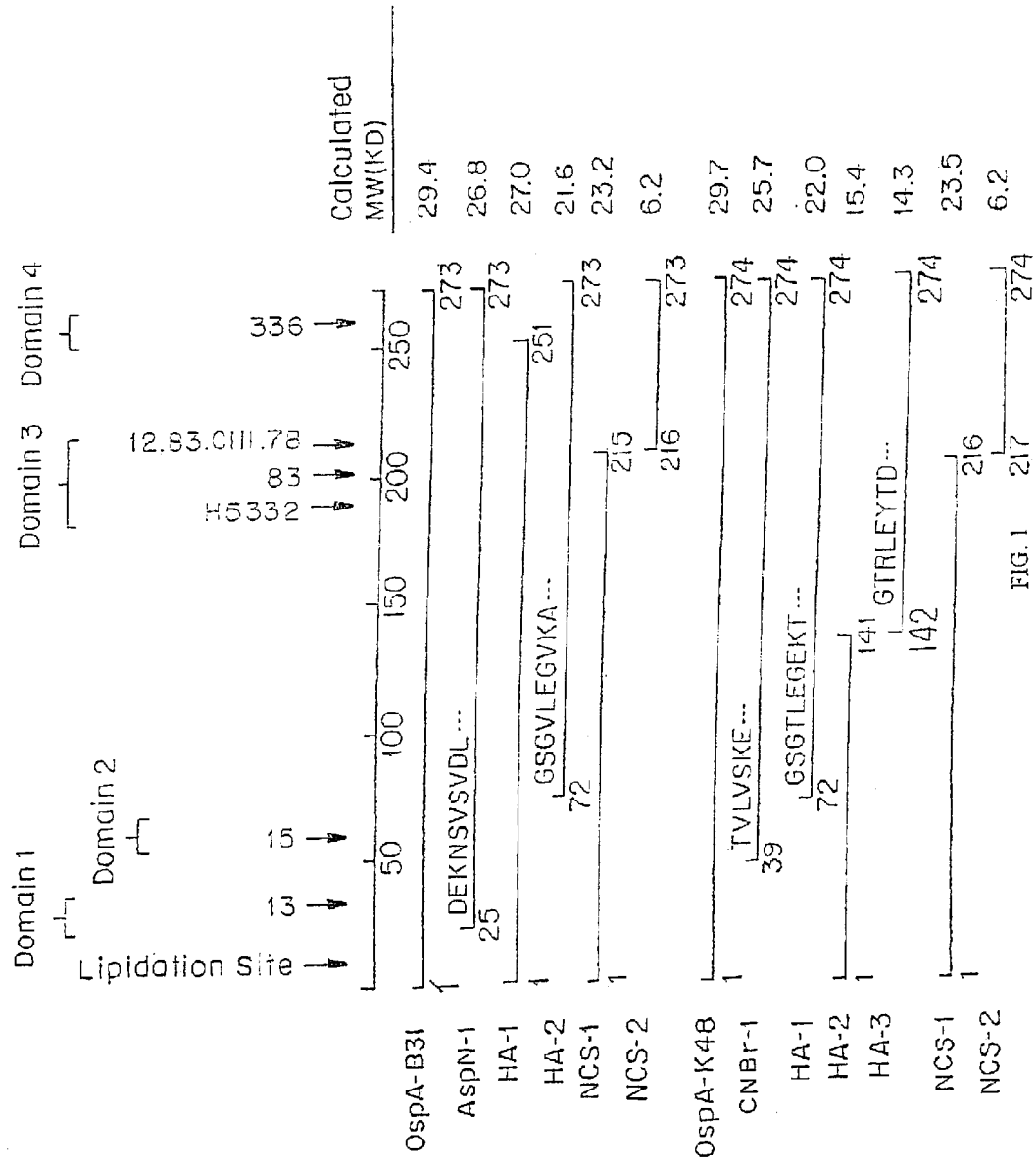
FIG. 1 summarizes peptides and antigenic domains localized by proteolytic and chemical fragmentation of OspA.

OspA-Tro (bp 655–819) chimer (SEQ ID NO. 159) and the encoded chimeric protein sequence (SEQ ID NO. 160).

FIGS. 63A, 63B and 63C depict the nucleic acid sequence of the OspC-C2 (bp 55–612)/OspA-K48 (bp 52–654)/OspA-Tro (bp 655–819) chimer (SEQ ID NO. 161) and the encoded chimeric protein sequence (SEQ ID NO. 162).

FIGS. 64A, 64B and 64C depict the nucleic acid sequence of the OspC-C12 (bp 55–612)/OspA-B31 (bp 88–492)/OspA-PKo (bp 493–537)/OspA-B31 (bp 538–822) chimer (SEQ ID NO. 163) and the encoded chimeric protein sequence (SEQ ID NO. 164).

FIGS. 65A, 65B and 65C depict the nucleic acid sequence of the OspC-PKo (bp 55–639)/OspA-B31 (bp 88–492)/OspA-PKo (bp 493–537)/OspA-B31 (bp 538–651)/OspA-K48 (bp 652–825) chimer (SEQ ID NO. 165) and the encoded chimeric protein sequence (SEQ ID NO. 166).

FIGS. 66A, 66B and 66C depict the nucleic acid sequence of the OspC-Tro (bp 55–624)/OspA-B31 (bp 88–492)/OspA-PKo (bp 493–537)/OspA-B31 (bp 538–651)/OspA-PKo (bp 652–822) chimer (SEQ ID NO. 167) and the encoded chimeric protein sequence (SEQ ID NO. 168).

FIGS. 67A and 67B depict the nucleic acid sequence of the OspC-B31 (bp 55–633)/OspA-B31 (bp 394–820) chimer (SEQ ID NO. 169) and the encoded chimeric protein sequence (SEQ ID NO. 170).

FIGS. 68A and 68B depict the nucleic acid sequence of the OspC-B31 (bp 55–631)/OspA-B31 (bp 394–651)/OspA-K48 (bp 652–820) chimer (SEQ ID NO. 171) and the encoded chimeric protein sequence (SEQ ID NO. 172).

FIGS. 69A and 69B depict the nucleic acid sequence of the OspC-B31 (bp 55–633)/OspA-B31 (bp 394–651)/OspA-PKo (bp 652–820) chimer (SEQ ID NO. 173) and the encoded chimeric protein sequence (SEQ ID NO. 174).

FIGS. 70A and 70B depict the nucleic acid sequence of the OspC-B31 (bp 55–633)/OspA-K48 (bp 394–654)/OspA-Tro (bp 655–819) chimer (SEQ ID NO. 175) and the encoded chimeric protein sequence (SEQ ID NO. 176).

FIGS. 71A, 71B and 71C depict the nucleic acid sequence of the OspC-B31 (bp 55–633)/OspA-B31 (bp 88–492)/OspA-PKo (bp 493–537)/OspA-B31 (bp 541–651)/OspA-PKo (bp 652–822) chimer (SEQ ID NO. 177) and the encoded chimeric protein sequence (SEQ ID NO. 178); a variant of this sequence was also generated, where the N at position 190 of B31 OspA was deleted.

FIGS. 72A, 72B and 72C depict the nucleic acid sequence of the OspC-C2 (bp 55–612)/OspA-B31 (bp 88–492)/OspA-PKo (bp 493–537)/OspA-B31 (bp 541–651)/OspA-PKo (bp 652–822) chimer (SEQ ID NO. 179) and the encoded chimeric protein sequence (SEQ ID NO. 180); a variant of this sequence was also generated, where the N at position 190 of B31 OspA was deleted.

DETAILED DESCRIPTION OF THE INVENTION

The present invention pertains to chimeric proteins comprising various antigenic *Borrelia* polypeptides. In a preferred embodiment, the chimeric protein comprises *Borrelia* outer surface protein C (OspC) and outer surface protein A (OspA). These chimeric proteins have the general structure of OspC linked to OspA via a peptide bond. Each of the OspA and OspC portions of the chimeric OspC/OspA protein can be lipidated or unlipidated. In a preferred embodiment, the OspC/OspA chimer comprises OspC and OspA polypeptide fragments that do not possess their lipidation signals.

The chimeric forms of the OspA and OspC proteins described herein were bioengineered such that the resultant chimeric protein maintained at least some antigenicity of one or both of the parent molecules. As described herein, antigenic refers to the ability of a compound to bind products of an immune response, such as antibodies, T-cell receptors or both. Such responses can be measured using standard antibody detection assays, such as ELISA or standard T-cell activation assays. In a particular embodiment, the chimeric OspC/OspA proteins comprise OspA polypeptides which lack the putative autoreactive domain that has similarity to a region of human leukocyte function-associated antigen-1 (hLFA-1) (Gross, D. M. et al., *Science,* 281: 703–706 (1998)).

The current invention pertains to chimeric proteins comprising antigenic *Borrelia* polypeptides which do not occur in nature in the same *Borrelia* protein. The chimeric proteins are a combination of two or more antigenic polypeptides derived from *Borrelia* proteins. The antigenic polypeptides can be derived from different proteins from the same species of *Borrelia*, or different proteins from different *Borrelia* species, as well as from corresponding proteins from different species. As used herein, the term "chimeric protein" describes a protein comprising two or more polypeptides which are derived from corresponding and/or non-corresponding native *Borrelia* protein. A polypeptide "derived from" a native *Borrelia* protein is a polypeptide which has an amino acid sequence the same as an amino acid sequence present in a *Borrelia* protein, an amino acid sequence equivalent to the amino acid sequence of a naturally occurring *Borrelia* protein, or an amino acid sequence substantially similar to the amino acid sequence of a naturally occurring *Borrelia* protein (e.g., differing by a few amino acids), such as when a nucleic acid encoding a protein is subjected to site-directed mutagenesis. "Corresponding" proteins are equivalent proteins from different species or strains of *Borrelia*, such as outer surface protein A (OspA) from strain B31 and OspA from strain K48. The invention additionally pertains to nucleic acids encoding these chimeric proteins.

In one embodiment, the present invention is drawn to chimeric proteins comprising antigenic polypeptides from Lyme Disease-causing strains of *Borrelia*. In another embodiment, the chimeric proteins described herein comprise antigenic polypeptides from different pathogenic genospecies of *Borrelia*, such as *Borrelia burgdorferi* sensu stricto, *Borrelia afzelii* and *Borrelia garinii*. In a preferred embodiment, the chimeric proteins comprise antigenic polypeptides from each of the pathogenic genospecies of *Borrelia*, including *Borrelia burgdorferi* sensu stricto, *Borrelia afzelii* and *Borrelia garinii*.

The OspA portion of the chimeric molecules of the present invention can themselves be chimeric combinations of more than one OspA polypeptide. Similarly, the OspC portion of the chimeric molecules of the present invention can themselves be chimeric combinations of more than one OspC polypeptide. As described below, Applicants have identified two separate antigenic domains of OspA and OspB which flank the sole conserved tryptophan present in OspA and in OspB. These domains share cross-reactivity with different genospecies of *Borrelia*. The precise amino acids responsible for antigenic variability were determined through site-directed mutagenesis, so that proteins with specific amino acid substitutions are available for the development of chimeric versions of OspA which can be included in the OspC/OspA chimeric proteins of the present invention. Furthermore, Applicants have identified immunologically important hypervariable domains in OspA proteins, as described below in Example 2. The first hypervariable domain of interest for chimeric proteins, Domain A, includes amino acid residues 120–140 of OspA, the second hypervariable domain, Domain B, includes residues 150–180 and the third hypervariable domain, Domain C, includes residues 200–216 or 217 (depending on the position of the sole conserved tryptophan residue in the OspA of that particular species of *Borrelia*) (see FIG. 3). In addition, Applicants have sequenced the genes for several *Borrelia* proteins.

These discoveries have aided in the development of novel recombinant *Borrelia* proteins which include two or more amino acid regions or sequences which do not occur in the same *Borrelia* protein in nature. The recombinant proteins comprise polypeptides from a variety of *Borrelia* proteins, including, but not limited to, OspA, OspB, OspC, OspD, p12, p39, p41, p66, and p93. Preferred combinations include all or a portion of OspC linked to all or a portion of OspA. Antigenically relevant polypeptides from each of a number of proteins are combined into a single chimeric protein.

In one embodiment of the current invention, chimeras are now available which include antigenic OspA polypeptides flanking a tryptophan residue. OspB has a similar primary structure as OspA and is included in the following discussion. The antigenic polypeptides are derived from either the proximal portion from the tryptophan (the portion of the OspA protein present between the amino terminus and the conserved tryptophan of the protein), or the distal portion from the tryptophan (the portion of the OspA protein present between the conserved tryptophan of the protein and the carboxy terminus) in OspA. The resultant chimeras can be OspA-OspA chimeras (e.g., chimeras incorporating polypeptides derived from OspA from different strains of *Borrelia*), OspA-OspB chimeras, or OspB-OspB chimeras, and are constructed such that amino acid residues amino-proximal to an invariant tryptophan are from one protein and residues carboxy-proximal to the invariant tryptophan are from the other protein. For example, one available chimer consists of a polypeptide derived from the amino-proximal region of OspA from strain B31, followed by the tryptophan residue, followed by a polypeptide derived from the carboxy-proximal region of OspA from strain K48 (SEQ ID NO. 92). Another available chimer includes a polypeptide derived from the amino-proximal region of OspA from strain B31, and a polypeptide derived from the carboxy-proximal region of OspB from strain B31 (SEQ ID NO. 104). If the polypeptide proximal to the tryptophan of these chimeric proteins is derived from OspA, the proximal polypeptide can be further subdivided into the three hypervariable domains (Domains A, B, and C), each of which can be derived from OspA from a different strain of *Borrelia*. These chimeric proteins can further comprise antigenic polypeptides from another protein, e.g., OspC, in addition to the antigenic polypeptides flanking the tryptophan residue.

In one embodiment, the chimeric OspC/OspA proteins of the present invention comprise at least a first and a second polypeptide, wherein the first polypeptide comprises *Borrelia burgdorferi* OspC and wherein the second polypeptide comprises *Borrelia burgdorferi* OspA, such that OspC comprises the N-terminus of the protein.

In a particular embodiment, the first polypeptide comprises a *Borrelia burgdorferi* OspC polypeptide from about amino acid residue 19 to about amino acid residue 213, and the second polypeptide comprises a *Borrelia burgdorferi* OspA polypeptide. In another embodiment, the first polypeptide comprises a *Borrelia burgdorferi* OspC polypeptide from about amino acid residue 19 to about amino acid residue 211. In another embodiment, the first polypeptide comprises a *Borrelia burgdorferi* OspC polypeptide from about amino acid residue 19 to about amino acid residue 208. In another embodiment, the first polypeptide comprises a *Borrelia burgdorferi* OspC polypeptide from about amino acid residue 19 to about amino acid residue 204. The numbering of the OspC residues is according to the numbering of SEQ ID NO: 30 (FIGS. 12A and 12B). It is evident that the person of skill in the art recognizes that OspC genes from different strains and/or genospecies may differ in their primary sequence and that based on homology, similar regions of such OspC proteins could be identified and used in the present invention with no or only routine experimentation.

In one embodiment, the invention is drawn to chimeric OspC/OspA proteins wherein the first polypeptide comprises a *Borrelia burgdorferi* OspC polypeptide and the second polypeptide comprises a *Borrelia burgdorferi* OspA polypeptide from about amino acid residue 18 to about amino acid residue 273. In other embodiments, the chimeric OspC/OspA protein comprises a first polypeptide which is a *Borrelia burgdorferi* OspC polypeptide and a second polypeptide which is a *Borrelia burgdorferi* OspA polypeptide selected from the group consisting of an OspA polypeptide from about amino acid residue 132 to about amino acid residue 216, an OspA polypeptide from about amino acid residue 218 to about amino acid residue 273, an OspA polypeptide from about amino acid residue 18 to about amino acid residue 216 and an OspA polypeptide from about 132 to about amino acid residue 273. The numbering of the OspA residues is according to the numbering of SEQ ID NO: 7 (FIGS. 7A and 7B). It is evident that the person of skill in the art recognizes that OspA genes from different strains and/or genospecies may differ in their primary sequence and that based on homology, similar regions of such OspA proteins could be identified and used in the present invention with no or only routine experimentation.

The present invention is also drawn to OspC/OspA chimeric proteins wherein the first polypeptide comprises a *Borrelia burgdorferi* OspC polypeptide and the second polypeptide comprises a *Borrelia burgdorferi* OspA polypeptide, wherein the OspA polypeptide comprises two or more OspA polypeptide fragments as described above. In a preferred embodiment, the OspA polypeptide comprises portions of OspA from two or more strains of *Borrelia*. In another preferred embodiment, the OspA polypeptide comprises portions of OspA from two or more Lyme Disease-causing genospecies of *Borrelia*, e.g., wherein the genospecies are *Borrelia burgdorferi* sensu stricto, *Borrelia afzelii* and/or *Borrelia garinii*. In still another preferred embodiment, the OspC/OspA chimeric protein comprises one or more polypeptides from each of the pathogenic genospecies, *Borrelia burgdorferi* sensu stricto, *Borrelia afzelii* and *Borrelia garinii*.

The chimeras described herein can be produced so that they are highly soluble, hyper-produced in *E. coli*, and non-lipidated. Lipidated chimeric proteins can also be produced. In addition, the chimeric proteins can be designed to end in an affinity tag (His-tag) to facilitate purification. The recombinant proteins described herein have been constructed to maintain antigenicity of at least one of the parent polypeptides. In addition, recombinant proteins specific for the various genospecies of *Borrelia* that cause Lyme disease are now available, because the genes from each of the major genospecies have been sequenced. These recombinant proteins with their novel biophysical and antigenic properties will be important diagnostic reagent and vaccine candidates.

The chimeric proteins of the current invention are advantageous in that they retain at least some specific reactivity to monoclonal or polyclonal antibodies that recognize wild-type Borrelia proteins. The proteins are immunogenic, and elicit antibodies that inhibit growth and/or induce lysis of Borrelia in vitro. Furthermore, in some embodiments, the proteins provide antigenic domains of two or more Borrelia strains and/or proteins within a single protein. Such proteins are particularly useful in immunodiagostic assays. For example, proteins of the present invention can be used as reagents in assays to detect the presence of antibodies to native Borrelia in potentially infected individuals. These proteins can also be used as immunodiagnostic reagents, such as in dot blots, Western blots, enzyme-linked immunosorbent assays (ELISA), or agglutination assays. The chimeric proteins of the present invention can be produced by known techniques, such as by recombinant methodology, polymerase chain reaction, or mutagenesis.

Furthermore, the proteins of the current invention are useful as vaccine immunogens against Borrelia infection. Because Borrelia has been shown to be clonal, a protein comprising antigenic polypeptides from a variety of Borrelia proteins and/or species, will provide immunoprotection for a considerable time when used in a vaccine. The lack of significant intragenic recombination, a process which might rapidly generate novel epitopes with changed antigenic properties, ensures that Borrelia can only change antigenic type by accumulating mutational change, which is slow when compared with recombination in generating different antigenic types. The chimeric protein can be combined with a physiologically-acceptable carrier and administered to a vertebrate animal through standard methods (e.g., intravenously or intramuscularly, for example).

In addition to the chimeric proteins described herein, the present invention is also drawn to nucleic acids which encode the Borrelia chimeric protein described herein. In one embodiment of the present invention, the composition comprises a nucleic acid that encodes a chimeric protein of at least two polypeptides, wherein the first polypeptide comprises Borrelia burgdorferi OspC, and the second polypeptide comprises Borrelia burgdorferi OspA, such that OspC is upstream of OspA. The OspC and OspA nucleic acid fragments that make up the chimeric protein can be from the same strain or genospecies of Borrelia, from different strains or genospecies of Borrelia, or from combinations of nucleic acids that are from the same and/or different strains or genospecies of Borrelia.

It is understood that the nucleic acids that encode the polypeptides that comprise the chimeric protein can include extra nucleotides or fewer nucleotides in order to simplify the construction of the gene encoding the chimeric polypeptide, e.g., to allow for the use of convenient restriction endonuclease sites or to allow the ligation of the gene fragments such that a contiguous coding region is created. Based on the guidance provided herein, one of ordinary skill in the art would readily be able to add or remove nucleotides from the termini of the gene fragments encoding the polypeptides of the chimeric OspC/OspA protein in order to generate the chimeric proteins of the present invention with no or only routine experimentation. Furthermore, there can be an extra about 1 to about 10 amino acids on the N- and/or C-terminus of the polypeptides and chimeric proteins of the present invention and still retain the properties of the present invention. It is also understood that those of skill in the art, using art-known methods and/or the methods described herein, could generate additional OspC-OspA chimeric proteins, and that these chimeric proteins are encompassed by the invention.

The present invention is also drawn to expression vectors which comprise an isolated DNA encoding the Borrelia chimeric protein described herein. In one embodiment, the composition includes an expression vector comprising an isolated DNA which encodes an OspC/OspA chimeric protein, wherein the OspC portion of the protein is upstream of the OspA portion. The present invention also encompasses host cells which comprise a recombinant nucleic acid that encodes an OspC/OspA chimeric protein, as described herein.

The present invention is also drawn to methods of making the Borrelia chimeric polypeptides described herein. In one embodiment, the method of making a chimeric Borrelia protein comprises selecting a polynucleotide sequence encoding OspC, or an antigenic portion thereof, selecting a polynucleotide sequence encoding OspA, or an antigenic portion thereof, and ligating these polynucleotide sequences together, such that OspC comprises the N-terminus of the protein. The polypeptides of the present invention can also be recombinantly expressed in suitable microbial hosts, wherein said hosts include, but are not limited to, bacterial hosts, such as E. coli, fungal hosts, such as S. cerevisiae or cell culture hosts, such as those of mammalian cell culture or insect cell culture.

The present invention is also drawn to methods of delivering the Borrelia chimeric polypeptides described herein. In one embodiment, the method comprises administering the chimeric protein in a physiologically-acceptable carrier to an individual. The individual develops at least some immune response to the chimeric protein. As an example, the individual could generate a humoral immune response, wherein antibodies that recognize at least a portion of said chimeric polypeptide are produced by the individual. The antibodies that recognize the chimeric polypeptide can be of any class of immunoglobulin, such as IgM, IgD, IgA and IgG or combinations thereof.

The present invention is also drawn to methods of delivering a nucleic acid which encodes a chimeric polypeptide described herein. In one embodiment, the method comprises administering the nucleic acid in a physiologically-acceptable carrier to an individual using art-accepted methods of DNA delivery, including but not limited to, biolistic delivery and lipid encapsulation. The chimeric polypeptide is at least transiently expressed and the individual develops at least some immune response to the chimeric protein encoded by the nucleic acid.

The invention also encompasses methods of using the chimeric proteins described herein in diagnostic assays. In one embodiment, the method can be used to detect the presence of OspA- and/or OspC-specific antibodies in a sample, e.g., a host sample of interest. In one embodiment, the method comprises contacting a host sample of interest with the chimeric OspC/OspA protein, under conditions, wherein antibodies, if present in the host sample, bind to the chimeric protein thereby forming antigen-antibody complexes. The antigen-antibody complexes are then detected. In this manner, an immune response to Lyme-Disease causing Borrelia can be detected.

As described herein, the chimeric proteins of the present invention incorporate antigenic domains from different Borrelia proteins, as well as from different Borrelia strains and/or genospecies. As such, they are useful in the detection or diagnosis of the presence of Lyme disease-causing Borrelia, especially Borrelia from groups capable of causing disseminated symptoms of Lyme disease. Disseminated symptoms refer to infection outside of the erythema migrans skin lesion, e.g., infection in blood, CNS or synovia.

The chimeric polypeptides of the present invention elicit specific immune responses to OspC and OspA. In one embodiment, the chimeric polypeptides elicit immune responses to strains of Lyme disease-causing *Borrelia* of the same genospecies as that represented by the OspC/OspA chimeric protein. In another embodiment, the chimeric polypeptides elicit immune responses to strains of Lyme disease-causing *Borrelia* of different genospecies than that represented by the OspC/OspA chimeric protein, as well as to Lyme disease-causing *Borrelia* of the same genospecies as that represented by the OspC/OspA chimeric protein. The immune response includes, but is not limited to, a humoral response, a secretory response, a cell-mediated response, or any combination thereof.

The immunogenic compositions of the present invention can also be used to immunize animals, e.g., mammals, including humans. Immunization is understood to elicit specific immunogenic responses as described herein. In one embodiment, administration of an immunogenic composition, e.g., an OspC/OspA chimeric protein, an OspC/OspA chimeric nucleic acid, to an animal results in the animal developing immunity to infection by Lyme disease-causing *Borrelia*, e.g., *Borrelia burgdorferi*, *Borrelia afzelii* and/or *Borrelia garinii*.

Immunity, as described herein, is understood to mean the ability of the treated animal to resist infection (e.g., systemic infection), to overcome infection (e.g., systemic infection) or to overcome infection (e.g., systemic infection) more easily and/or more quickly when compared to non-immunized and/or non-treated individuals. Immunity can also include an improved ability of the treated individual to sustain an infection with reduced or no clinical symptoms of systemic infection. The individual may be treated with the chimeric proteins of the present invention either proactively, e.g., once a year or alternatively after sustaining a tick bite.

In one embodiment, the OspC/OspA chimeric protein of the present invention, together with suitable excipients and/or adjuvants, is administered to an animal such that the animal develops an immune response to at least one of the OspC and/or OspA polypeptides of the composition. The pharmaceutical composition can also be administered with other components suitable for in vitro and/or in vivo use. These additional components include buffers, carrier proteins, adjuvants, excipients, preservatives and combinations thereof.

The present invention is also drawn to pharmaceutical compositions which can be used to vaccinate and/or treat *Borrelia* infection in an animal or human. In a particular embodiment, the pharmaceutical composition comprises a *Borrelia burgdorferi* OspC/OspA chimeric protein. The pharmaceutical composition can also be administered together with a physiologically-acceptable carrier, an excipient and/or an adjuvant. Suitable adjuvants are well known in the art (see for example PCT Publication WO 96/40290, the entire teachings of which are incorporated herein by reference), and can be used, for example, to enhance immunogenicity, potency or half-life of the chimeric proteins in the treated animal.

The pharmaceutical compositions used to vaccinate and/or treat *Borrelia* infection can be prepared using methods for preparing vaccines which are well known in the art. For example, the OspC/OspA chimeric proteins described herein can be isolated and/or purified by known techniques, such as by size exclusion chromatography, affinity chromatography, ion exchange chromatography, preparative electrophoresis, selective precipitation or combinations thereof. The prepared chimeric proteins can be mixed with suitable other reagents as described herein, such that the chimeric protein is at a suitable concentration. The dosage of the chimeric protein will vary and depends upon the age, weight and/or physical condition of the animal, e.g., mammal, human, to be treated. The optimal dosage can be determined by routine optimization techniques, using suitable animal models.

Administration of the pharmaceutical composition to be used as a vaccine can be by any suitable technique. Suitable techniques for administration of the pharmaceutical composition include, but are not limited to, injection, e.g., subcutaneous injection, intramuscular injection, intravenous injection, intra peritoneal injection; mucosal administration, e.g., exposing nasal mucosa to nose drops containing the proteins or chimeric proteins of the present invention; oral administration; and DNA immunization.

The incorporation of polypeptide fragments from different strains and/or genospecies of *Borrelia burgdorferi* allows for a greater detection range and a more effective vaccination tool. The present invention provides a chimeric combination of proteins that, when used as a vaccine, can prevent Lyme disease from becoming systemic. The chimeric proteins of the present invention can be effective in preventing Lyme disease, as well as having a therapeutic effect on established infection, for example, after the tick bite is noticed by the patient. Since the chimeric proteins of the present invention comprise both OspC and OspA polypeptides, they are expected to act at the level of the tick as well as the level of the host in preventing both infection and disease due to *Borrelia burgdorferi*, *Borrelia afzelii* and/or *Borrelia garinii*.

The present invention is also drawn to diagnostic kits which comprise the chimeric polypeptides described herein. In one embodiment, the kit comprises a chimeric protein comprising at least a first and a second polypeptide, wherein the first polypeptide comprises *Borrelia burgdorferi* OspC and wherein the second polypeptide comprises *Borrelia burgdorferi* OspA, such that OspC comprises the N-terminus of the protein. The kit also includes reagents for detecting antibody-antigen complexes that are formed between the OspC/OspA chimeric protein and antibodies that are present in a sample, e.g., a user-supplied host sample.

As a result of the present invention, it is now possible to prepare improved diagnostic tools comprising both OspA and OspC antigens from various *Borrelia burgdorferi* strains and/or genospecies. Since OspA is primarily expressed in the tick vector, and OspC is upregulated in response to the feeding of an infected tick on a mammal, the diagnostic compositions of the invention can recognize antigens that are expressed at different stages of the life cycle of *Borrelia burgdorferi*. Moreover, by incorporating unique polypeptide fragments from pathogenic families of *Borrelia*, the present invention allows for improved diagnostic compositions which can detect clinically important exposure to pathogenic *Borrelia* while overlooking the remainder of non-pathogenic families of *Borrelia*.

As described herein, the OspC/OspA chimeric proteins were bioengineered such that the protective domains of each protein were maintained. In experiments described herein, mice were either immunized with OspA, OspC or OspC/OspA chimeric proteins in aluminum hydroxide. Mice were then bled and tested for antibody responses against OspC and OspA derived from various strains of *Borrelia*. In additional experiments, these immunized mice were challenged with ticks infected with *Borrelia burgdorferi* and transmission of infection was assessed.

Figure 47:
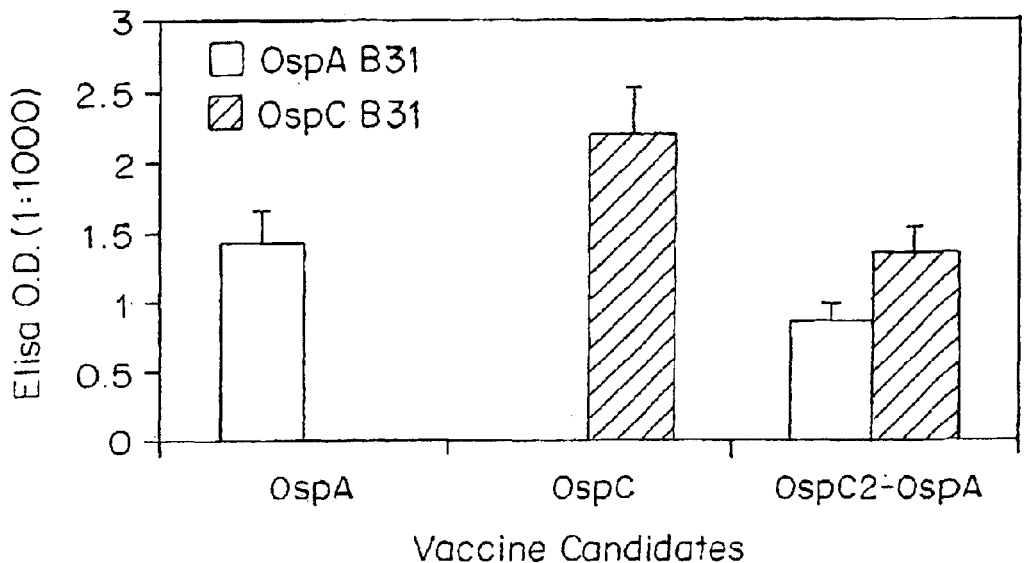
FIG. 47 is a bar graph showing the reactivity (as measured by ELISA) of sera from mice immunized with the indicated Borrelia protein (OspA or OspC) or recombinant chimeric protein (OspC2-OspA) (X-axis) against OspA B31 or OspC B31 antigens (legend).
Figure 48:
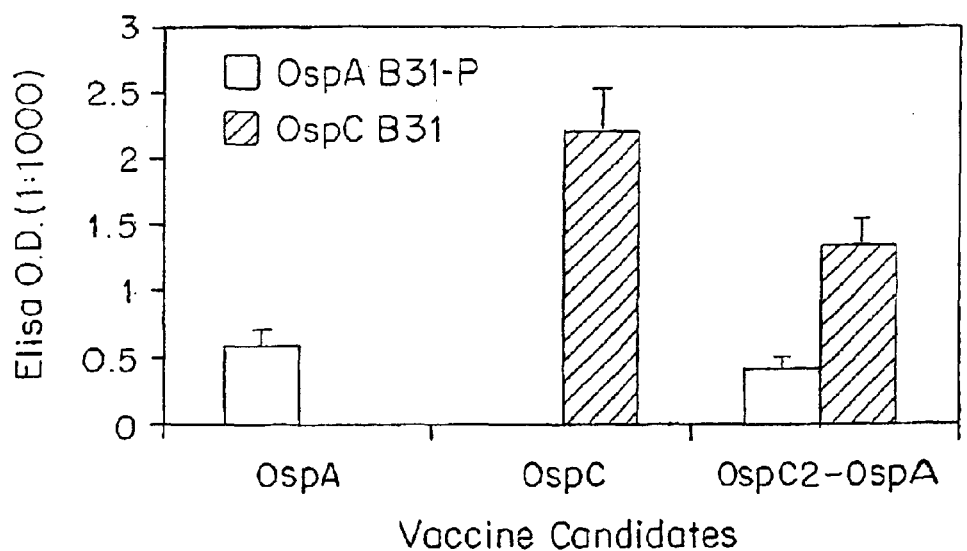
FIG. 48 is a bar graph showing the reactivity (as measured by ELISA) of sera from mice immunized with the indicated Borrelia protein (OspA or OspC) or recombinant chimeric protein (OspC2-OspA) (X-axis) against OspA B31 or OspC B31 antigens (legend). For the ELISA results to the B31 OspA antigen, a purified fragment of B31 OspA (amino acids 18–139) was added in excess to the sera so that the detected immune response was specific for the C-terminal region of OspA.

Mice immunized with the OspC/OspA chimeric protein gave a remarkable and equivalent antibody response to both OspA and OspC, as compared to mice immunized with OspA and OspC control proteins (FIGS. 47 and 48). In addition, antibodies in the sera of mice immunized with the OspC/OspA chimeric protein were also reactive against antigens derived from different strains of *Borrelia burgdorferi* (FIGS. 49–50 and 52–54). Chimer-immunized mice were fully protected against challenge with ticks infected with *Borrelia burgdorferi*, as compared to sham-vaccinated controls (infection rates of 100%) (Table VI).

Figure 49:
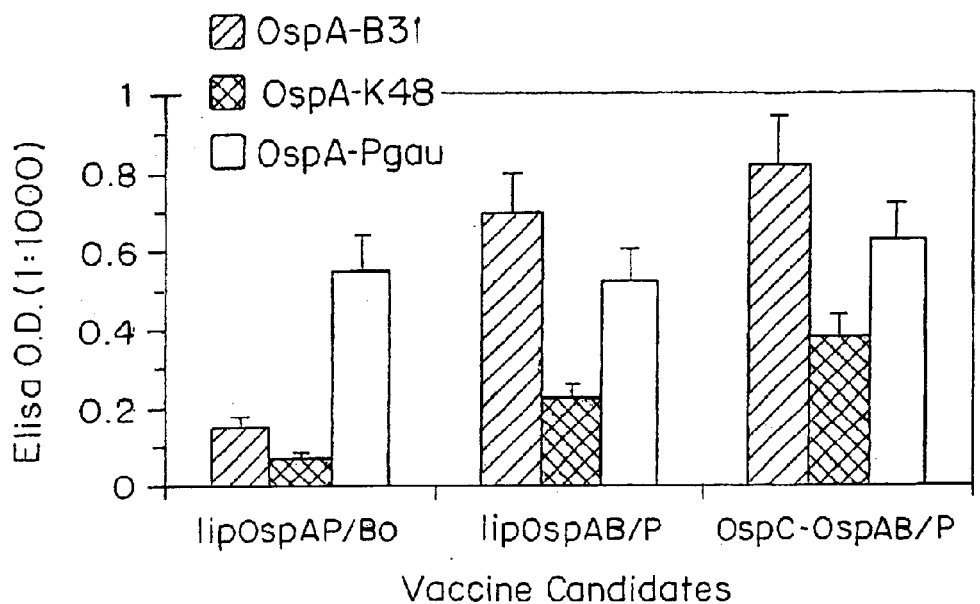
FIG. 49 is a bar graph showing the reactivity of sera from mice immunized with the indicated Borrelia chimeric protein (lipOspA/Bo, lipOspAB/P or OspC-OspAB/P) (X-axis) against the indicated OspA antigens (legend) from strains B31 (*Borrelia burgdorferi* sensu stricto), K48 (*Borrelia garinii*) and PGau (*Borrelia afzelli*).
Figure 50:
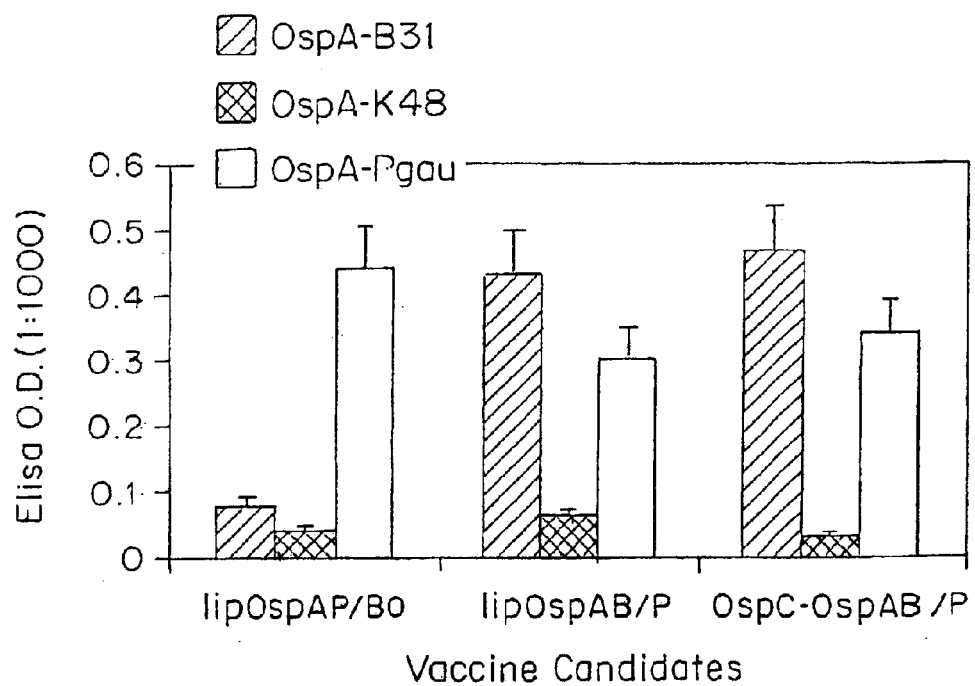
FIG. 50 is a bar graph showing the reactivity of sera from mice immunized with the indicated Borrelia chimeric protein (lipOspAP/Bo, lipOspAB/P) or OspC-OspAB/P) (X-axis) against the indicated OspA (legend) from strains B31 (*Borrelia burgdorferi* sensu stricto), K48 (*Borrelia garinii*) and PGau (*Borrelia afzelli*). In all cases, a purified fragment of B31 OspA (amino acids 18–139) was added in excess to the sera so that the detected immune response is specific for the C-terminal region of OspA.
Figure 51:
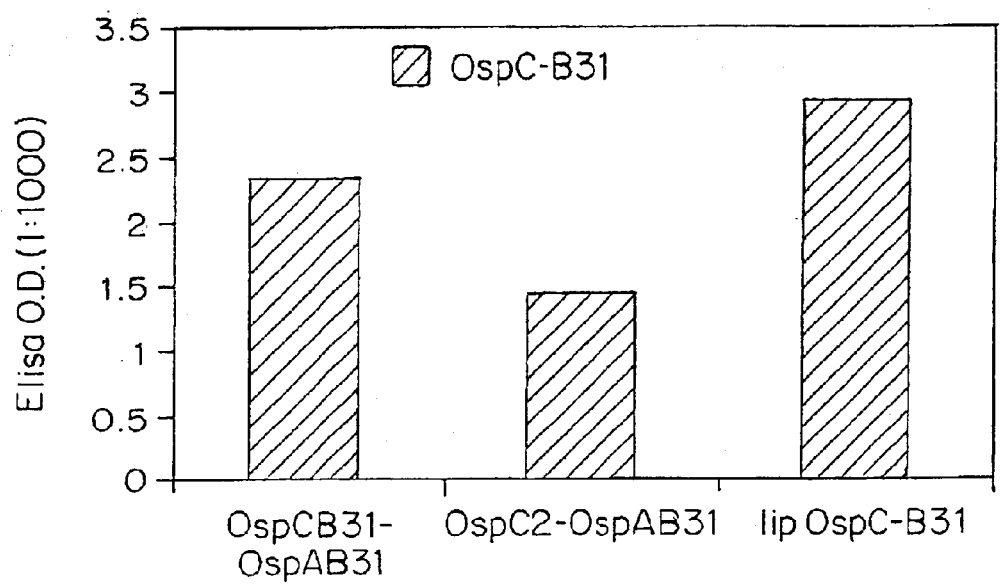
FIG. 51 is a bar graph showing the reactivity of sera from mice immunized with the indicated Borrelia chimeric protein (OspCB31-OspAB31, OspC2-OspAB31 or lip OspC-B31) (X-axis) against the indicated OspC antigen (legend) from the strain B31 (*Borrelia burgdorferi* sensu stricto).

In other experiments described herein, mice were either immunized with a lipidated OspA chimeric protein, a lipidated OspC chimeric protein, or a non-lipidated OspC/OspA chimeric protein, once again in the presence of aluminum hydroxide. Mice were then bled and tested for antibody responses against OspA and OspC derived from various strains of *Borrelia*. Surprisingly, the results of these studies indicate that mice immunized with the non-lipidated OspC/OspA chimeric protein have antibody responses to OspA and OspC that are equivalent or greater than those generated by mice immunized with the corresponding lipidated OspA or lipidated OspC chimeric proteins (FIGS. 49–51).

The results of the studies presented herein indicate that mice immunized with OspC-OspA chimeric proteins generate a potent antibody response against two immunoprotective targets that are expressed at different stages of the life cycle of *Borrelia burgdorferi*.

The current invention is illustrated by the following Examples, which are not to be construed to be limiting in any way.

EXEMPLIFICATION

Example 1

Purification of *Borrelia burgdorferi* Outer Surface Protein A and Analysis of Antibody Binding Domains This example details a method for the purification of large amounts of native outer surface protein A (OspA) to homogeneity, and describes mapping of the antigenic specificities of several anti-OspA MAbs. OspA was purified to homogeneity by exploiting its resistance to trypsin digestion. Intrinsic labeling with $^{14}$C-palmitic acid confirmed that OspA was lipidated, and partial digestion established lipidation at the amino-terminal cysteine of the molecule.

The reactivity of seven anti-OspA murine monoclonal antibodies to nine different *Borrelia* isolates was ascertained by Western blot analysis. Purified OspA was fragmented by enzymatic or chemical cleavage, and the monoclonal antibodies were able to define four distinct immunogenic domains (see FIG. 1). Domain 3, which included residues 190–220 of OspA, was reactive with protective antibodies known to agglutinate the organism in vitro, and included distinct specificities, some of which were not restricted to a genotype of *B. burgdorferi*.

A. Purification of Native OspA

Detergent solubilization of *B. burgdorferi* strips the outer surface proteins and yields partially-purified preparations containing both OspA and outer surface protein B (OspB) (Barbour, A. G. et al., *Infect. Immun.* 52 (5): 549–554 (1986); Coleman, J. L. and J. L. Benach, *J Infect. Dis.* 155 (4): 756–765 (1987); Cunningham, T. M. et al., *Ann. NY Acad. Sci.* 539: 376–378 (1988); Brandt, M. E. et al., *Infect. Immun.* 58: 983–991 (1990); Sambri, V. and R. Cevenini, *Microbiol.* 14: 307–314 (1991)). Although both OspA and OspB are sensitive to proteinase K digestion, in contrast to OspB, OspA is resistant to cleavage by trypsin (Dunn, J. et al., *Prot. Exp. Purif.* 1: 159–168 (1990); Barbour, A. G. et al., *Infect. Immun.* 45: 94–100 (1984)). The relative insensitivity to trypsin is surprising in view of the fact that OspB A has a high (16% for B31) lysine content, and may relate to the relative configuration of OspB A and B in the outer membrane.

Intrinsic Radiolabeling of *Borrelia*

Labeling for lipoproteins was performed as described by Brandt et al. (Brandt et al., *Infect. Immun.* 58: 983–991 (1990)). $^{14}$C-palmitic acid (ICN, Irvine, Calif.) was added to the BSK II media to a final concentration of 0.5 μCi per milliliter (ml). Organisms were cultured at 34° C. in this medium until a density of $10^8$ cells per ml was achieved.

Purification of OspA Protein from *Borrelia* Strain B31

*Borrelia burgdorferi*, either $^{14}$C-palmitic acid-labeled or unlabeled, were harvested and washed as described (Brandt, M. E. et al., *Infect. Immun.* 58: 983–991 (1990)). Whole organisms were trypsinized according to the protocol of Barbour et al. (*Infect. Immun.* 45: 94–100 (1984)) with some modifications. The pellet was suspended in phosphate buffered saline (PBS, 10 mM, pH 7.2), containing 0.8% tosyl-L-phenylalanine chloromethyl ketone (TPCK)-treated trypsin (Sigma, St. Louis, Mo.), the latter at a ratio of 1 μg per $10^8$ cells. Reaction was carried out at 25° C. for 1 hour, following which the cells were centrifuged. The pellet was washed in PBS with 100 μg/ml phenylmethylsulfonyl fluoride (PMSF). Triton X-114 partitioning of the pellet was carried out as described by Brandt et al. (Brandt et al., *Infect. Immun.* 58: 983–991 (1990)). Following trypsin treatment, cells were resuspended in ice-cold 2% (v/v) Triton X-114 in PBS at $10^9$ cells per ml. The suspension was rotated overnight at 4° C., and the insoluble fraction removed as a pellet after centrifugation at 10,000×g for 15 minutes at 4° C. The supernatant (soluble fraction) was incubated at 37° C. for 15 minutes and centrifuged at room temperature at 1000×g for 15 minutes to separate the aqueous and detergent phases. The aqueous phase was decanted, and ice cold PBS added to the lower Triton phase, mixed, warmed to 37° C., and again centrifuged at 1000×g for 15 minutes. Washing was repeated twice more. Finally, detergent was removed from the preparation using a spin column of Bio-beads SM2 (BioRad, Melville, N.Y.) as described (Holloway, P. W., *Anal. Biochem.* 53: 304–308 (1973)).

Ion exchange chromatography was carried out as described by Dunn et al. (Dunn et al., *Prot. Exp. Purif.* 1: 159–168 (1990)) with minor modifications. Crude OspA was dissolved in buffer A (1% Triton X-100, 10 mM phosphate buffer (pH 5.0)) and loaded onto a SP Sepharose resin (Pharmacia, Piscataway, N.J.), pre-equilibrated with buffer A at 25° C. After washing the column with 10 bed-volumes of buffer A, the bound OspA was eluted with buffer B (1% Triton X-100, 10 mM phosphate buffer (pH 8.0)). OspA fractions were detected by protein assay using the BCA method (Pierce, Rockford, Ill.), or as radioactivity when intrinsically labeled material was fractionated. Triton X-100 was removed using a spin column of Bio-beads SM2.

This method purifies OspA from an outer surface membrane preparation. In the absence of trypsin-treatment, OspA and B were the major components of the soluble fraction obtained after Triton partitioning of strain B31. In contrast, when Triton extraction was carried out after trypsin-treatment, the OspB band is not seen. Further purification of OspA-B31 on a SP Sepharose column resulted in a single band by SDS-PAGE. The yield following removal of detergent was approximately 2 mg per liter of culture. This method of purification of OspA, as described herein for strain B31, can be used for other isolates of *Borrelia* as well. For strains such as strain K48, which lack OspB, trypsin treatment can be omitted.

Lipidation Site of OspA-B31

$^{14}$C-palmitic acid labeled OspA from strain B31 was purified as described above and partially digested with endoproteinase Asp-N (data not shown). Following digestion, a new band of lower molecular weight was apparent by SDS-PAGE, found by direct amino-terminal sequencing to begin at $Asp_{25}$. This band had no trace of radioactivity by autoradiography (data not shown). OspA and B contain a signal sequence (L-X-Y-C) similar to the consensus described for lipoproteins of *E. coli*, and it has been predicted that the lipidation site of OspA and B should be the amino-terminal cysteine (Brandt, M. E. et al., *Infect. Immun* 58: 983–991 (1990)). The results presented herein support this prediction.

B. Comparison of OspA Antibody Binding Regions in Nine Strains of *Borrelia burgdorferi*

The availability of the amino acid sequenced for OspA from a number of different isolates, combined with peptide mapping and Western blot analysis, permitted the identification of the antigenic domains recognized by monoclonal antibodies (MAbs) and allowed inference of the key amino acid residues responsible for specific antibody reactivity.

Strains of *Borrelia burgdorferi*

Nine strains of *Borrelia*, including seven European strains and two North American strains, were used in this study of antibody binding domains of several proteins. Information concerning the strains is summarized in Table I, below.

TABLE I

Representative *Borrelia* Strains

| Strain | Location and Source | Reference for Strain |
|---|---|---|
| K48 | Czechoslovakia, *Ixodes ricinus* | none |
| PGAU | Germany, human ACA | Wilske, B. et al., J. Clin. Microbiol. 32: 340–350 (1993) |
| DK29 | Denmark, human EM | Wilske, B. et al. |
| PKo | Germany, human EM | Wilske, B. et al. |
| PTrob | Germany, human skin | Wilske, B. et al. |
| Ip3 | Khabarovsk, Russia, *I. persulcatus* | Asbrink, E. et al., Acta Derm. Venereol. 64: 506–512 (1984) |
| Ip90 | Khabarovsk, Russia, *I. persulcatus* | Asbrink, E. et al. |
| 25015 | Millbrook, NY, *I. persulcatus* | Barbour, A. G. et al., Curr. Microbiol. 8: 123–126 (1983) |
| B31 | Shelter Island, NY, *I. scapularis* | Luft, B. J. et al., Infect. Immun. 60: 4309–4321 (1992); ATCC 35210 |
| PKa1 | Germany, human CSF | Wilske, B. et al. |
| ZS7 | Freiburg, Germany, *I. ricinus* | Wallich, R. et al., Nucl. Acids Res. 17: 8864 (1989) |
| N40 | Westchester Co., NY | Fikrig, E. et al., Science 250: 553–556 (1990) |
| PHei | Germany, human CSF | Wilske, B. et al. |
| ACAI | Sweden, human ACA | Luft, B. J. et al., FEMS Microbiol. Lett. 93: 73–68 (1992) |
| PBo | Germany, human CSF | Wilske, B. et al. |

ACA = patient with acrodermatitis chronica atrophicans;
EM = patient with erythema migrans;
CSF = cerebrospinal fluid of patient with Lyme disease Strains K48, PGAU and DK29 were supplied by R. Johnson, University of Minnesota; PKo and PTrob were provided by B. Wilske and V. Preac-Mursic of the Pettenkhofer Institute, Munich, Germany; and Ip3 and Ip90 were supplied by L. Mayer of the Center for Disease Control, Atlanta, Ga. The North American strains included strain 25015, provided by J. Anderson of the Connecticut Department of Agriculture; and strain B31 (ATCC 35210).

Monoclonal Antibodies

Seven monoclonal antibodies (MAbs) were utilized in this study. Five of the MAbs (12, 13, 15, 83 and 336) were produced from hybridomas cloned and subcloned as previously described (Schubach, W. H., et al, *Infect. Immun.* 59(6):1911–1915 (1991)). MAb H5332 (Barbour, A. G. et al., *Infect. Immun.* 41: 795–804 (1983)) was a gift from Drs. Alan Barbour, University of Texas, and MAb CIII.78 (Sears, J. E. et al., *J. Immunol.* 147(6):1995–2000 (1991)) was a gift from Richard A. Flavell, Yale University. MAbs 12 and 15 were raised against whole sonicated B3; MAb 336 was produced against whole PGAU; and MAbs 13 and 83 were raised to a truncated form of OspA cloned from the K48 strain and expressed in *E. coli* using the T7 RNA polymerase system (McGrath, B. C. et al., *Vaccines*, Cold Spring Harbor Laboratory Press, Plainview, N.Y., pp. 365–370 (1993)). All MAbs were typed as being Immunoglobulin G (IgG).

Methods of Protein Cleavage, Western Blotting and Amino-Terminal Sequencing

Prediction of the various cleavage sites was achieved by knowledge of the primary amino acid sequence derived from the full nucleotide sequences of OspA, many of which are currently available (see Table II, below). Cleavage sites can also be predicted based on the peptide sequence of OspA, which can be determined by standard techniques after isolation and purification of OspA by the method described above. Cleavage of several OspA isolates was conducted to determine the localization of monoclonal antibody binding of the proteins.

Hydroxylamine-HCl (HA), N-chlorosuccinimide (NCS), and cyanogen bromide cleavage of OspA followed the methods described by Bornstein (*Biochem.* 9 (12) :2408–2421 (1970)), Shechter et al., (*Biochem.* 15 (23) :5071–5075 (1976)), and Gross (in Hirs, C. H. W. (ed): *Methods in Enzymology*, (N.Y. Acad. Press), 11:238–255 (1967)) respectively. Protease cleavage by endoproteinase, Asp-N (Boehringer Mannheim, Indianapolis, Ind.), was performed as described by Cleveland D. W. et al., (*J. Biol. Chem.* 252: 1102–1106 (1977)). Ten micrograms of OspA were used for each reaction. The ratio of enzyme to OspA was approximately 1 to 10 (w/w).

Proteins and peptides generated by cleavage were separated by SDS-polyacrylamide gel electrophoresis (SDS-PAGE) (Laemmli, U. K., *Nature* (*London*) 227:680–685 (1970)), and electroblotted onto immobilon Polyvinylidine Difluoride (PVDF) membranes (Ploskal, M. G. et al., *Biotechniques* 4: 272–283 (1986)). They were detected by amido black staining or by immunostaining with murine MAbs, followed by alkaline phosphatase-conjugated goat antimouse IgG. Specific binding was detected using a 5-bromo-4-chloro-3-indolylphosphate (BCIP)/nitroblue tetrazolium (NBT) developer system (KPL Inc., Gathersburg, Md.).

In addition, amino-terminal amino acid sequence analysis was carried out on several cleavage products, as described by Luft et al. (*Infect. Immun.* 57: 3637–3645 (1989)). Amido black stained bands were excised from PVDF blots and sequenced by Edman degradation using a Biosystems model 475A sequenator with model 120A PTH analyzer and model 900A control/data analyzer.

Cleavage Products of Outer Surface Protein a Isolates

Purified OspA-B31, labeled with $^{14}$C-palmitic acid, was fragmented with hydroxylamine-HCl (HA) into two peptides, designated HA1 and HA2 (data not shown). The HA1 band migrated at 27 KD and retained its radioactivity, indicating that the peptide included the lipidation site at the N-terminus of the molecule (data not shown). From the predicted cleavage point, HA1 should correspond to residues 1 to 251 of OspA-B31. HA2 had a MW of 21.6 KD by SDS-PAGE, with amino-terminal sequence analysis showing it to begin at Gly72, i.e. residues 72 to 273 of OspA-B31. By contrast, HA cleaved OspA-K48 into three peptides, designated HA1, HA2, and HA3 with apparent MWs of 22 KD, 16 KD and 12 KD, respectively. Amino-terminal sequencing showed HA1 to start at Gly72, and HA3 at Gly142. HA2 was found to have a blocked amino-terminus, as was observed for the full-length OspA protein. HA1, 2 and 3 of OspA-K48 were predicted to be residues 72–274, 1 to 141 and 142 to 274, respectively.

N-Chlorosuccinimide (NCS) cleaves tryptophan (W), which is at residue 216 of OspA-B31 or residue 217 of OspA-K48 (data not shown). NCS cleaved OspA-B31 into 2 fragments, NCS1, with MW of 23 KD, residues 1–216 of the protein, and NCS2 with a MW of 6.2 KD, residues 217 to 273 (data not shown). Similarly, K48 OspA was divided into 2 pieces, NCS1 residues 1–217, and NCS2 residues 218 to 274 (data not shown).

Cleavage of OspA by cyanogen bromide (CNBr) occurs at the carboxy side of methionine, residue 39. The major fragment, CNBr1, has a MW of 25.7 KD, residues 39–274 by amino-terminal amino acid sequence analysis (data not shown). CNBr2 (about 4 KD) could not be visualized by amido black staining; instead, lightly stained bands of about 20 KD MW were seen. These bands reacted with anti-OspA MAbs, and most likely were degradation products due to cleavage by formic acid.

Determination of Antibody Binding Domains for Anti-OspA Monoclonal Antibodies

The cleavage products of OspA-B31 and OspA-K48 were analyzed by Western blot to assess their ability to bind to the six different MAbs. Preliminary Western blot analysis of the cleavage products demonstrated that strains K48 and DK29 have similar patterns of reactivity, as do Ip3, PGAU and PKo. The OspA of strain PTrob was immunologically distinct from the others, being recognized only by MAb 336. MAb 12 recognized only the two North American strains, B31 and 25015. When the isolates were separated into genogroups, it was remarkable that all the MAbs, except MAb 12, crossed over to react with multiple genogroups.

MAb 12, specific for OspA-B31, bound to both HA1 and HA2 of OspA-B31. However, cleavage of OspA-B31 by NCS at residue Trp216 created fragments which did not react with MAb12, suggesting that the relevant domain is near or is structurally dependent upon the integrity of this residue (data not shown). MAb 13 bound only to OspA-K48, and to peptides containing the amino-terminus of that molecule (e.g. HA2; NCS1). It did not bind to CNBr1 residues 39 to 274. Thus the domain recognized by MAb13 is in the amino-terminal end of OspA-K48, near Met38.

MAb15 reacts with the OspA of both the B31 and K48 strains, and to peptides containing the N-terminus of OspA, such as HA1 of OspA-B31 and NCS1, but not to peptides HA2 of OspA-B31 and HA1 of OspA-K48 (data not shown). Both peptides include residue 72 to the C-terminus of the molecules. MAb 15 bound to CNBr1 of OspA-K48, indicating the domain for this antibody to be residues 39 to 72, specifically near Gly72 (data not shown).

MAb83 binds to OspA-K48, and to peptides containing the C-terminal portion of the molecule, such as HA1. They do not bind to HA2 of OspA-K48, most likely because the C-terminus of HA2 of OspA-K48 ends at 141. Similar to MAb12 and OspA-B31, binding of MAbs 83 and CIII.78 is eliminated by cleavage of OspA at the tryptophan residue. Thus binding of MAbs 12, 83 and CIII.78 to OspA depends on the structural integrity of the $Trp_{216}$ residue, which appears to be critical for antigenicity. Also apparent is that, although these MAbs bind to a common antigenic domain, the precise epitopes which they recognize are distinct from one another given the varying degrees of cross-reactivity to these MAbs among strains.

Although there is similar loss of binding activity of MAb336 with cleavage at $Trp_{216}$, this MAb does not bind to HA1 of OspA-B31, suggesting the domain for this antibody includes the carboxy-terminal end of the molecule, inclusive of residues 251 to 273. Low MW peptides, such as HA3 (10 KD) and NCS2 (6 KD), of OspA-K48 do not bind this MAb on Western blots. In order to confirm this observation, we tested binding of the 6 MAbs with a recombinant fusion construct p3A/EC that contains a trpE leader protein fused with residues 217 to 273 of OspA-B31 (Schubach, W. H. et al., *Infect. Immun.* 59(6): 1911–1915 (1991)). Only MAb336 reacted with this construct (data not shown). Peptides and antigenic domains localized by fragmentation of OspA are summarized in FIG. 1.

Mapping of Domains to Define the Molecular Basis for the Serotype Analysis

To define the molecular basis for the serotype analysis of OspA, we compared the derived amino acid sequences of OspA for the nine isolates (FIG. 2). At the amino terminus of the protein, these predictions can be more precise given the relatively small number of amino acid substitutions in this region compared to the carboxy terminus. Domain 1, which is recognized by MAb13, includes residues Leu34 to Leu41. MAb13 only binds to the OspA of species K48, DK29 and IP90. Within this region, residue 37 is variable, however Gly37 is conserved amongst the three reactive strains. When Gly37 is changed to Glu37, as it is in OspA of strains B31, PTrob, PGAU, and PKo, MAb 13 does not recognize the protein (data not shown). By similar analysis, it can be seen that Asp70 is a crucial residue for Domain 2, which includes residues 65 to 75 and is recognized by MAb15. Domain 3 is reactive with MAbs H5332, 12 and 83, and includes residues 190–220. It is clear that significant heterogeneity exists between MAbs reactive with this domain, and that more than one conformational epitope must be contained within the sequence. Domain 4 binds MAb336, and includes residues 250 to 270. In this region, residue 266 is variable and therefore may be an important determinant. It is apparent, however, that other determinants of the reactivity of this monoclonal antibody reside in the region comprising amino acids 217–250. Furthermore, the structural integrity of Trp216 is essential for antibody reactivity in the intact protein. Finally, it is important to stress that FIG. 2 indicates only the locations of the domains, and does not necessarily encompass the entire domain. Exact epitopes are being analyzed by site-directed mutagenesis of specific residues.

Overall, evidence suggests that the N-terminal portion is not the immunodominant domain of OspA, possibly by virtue of its lipidation, and the putative function of the lipid moiety in anchoring the protein to the outer envelope. The C-terminal end is immunodominant and includes domains that account in part for structural heterogeneity (Wilske, B. et al., *Med. Microbiol. Immunol.* 181: 191–207 (1992)), and may provide epitopes for antibody neutralization (Sears, J. E. et al., *J. Immunol.* 147(6): 1995–2000 (1991)), and relate to other activities, such as the induction of T-cell proliferation (Shanafel, M. M., et al., *J. Immunol.* 148: 218–224 (1992)). There are common epitopes in the carboxy-end of the protein that are shared among genospecies which may have immunoprotective potential (Wilske, B., et al., *Med. Microbiol. Immunol.* 181: 191–207 (1992)).

Prediction of secondary structure on the basis of hydropathy analysis and circular dichroism and fluorescence spectroscopy measurements (McGrath, B. C., et al., *Vaccines*, Cold Spring Harbor Laboratory Press, Plainview, N.Y.; pp. 365–370 (1993)) suggest domains 3 and 4 to be in a region of the molecule with a propensity to form alpha-helix, whereas domains 1 and 2 occur in regions predicted to be beta-sheets (see FIG. 1). These differences may distinguish domains in accessibility to antibody or to reactive T-cells (Shanafel, M. M. et al., *J. Immunol.* 148: 218–224 (1992)). Site-directed mutagenesis of specific epitopes, as described below in Example 2, aids in identifying exact epitopes.

Example 2

Identification of an Immunologically Important Hypervariable Domain of the Major Outer Surface Protein A of *Borrelia*

This Example describes epitope mapping studies using chemically cleaved OspA and TrpE-OspA fusion proteins. The studies indicate a hypervariable region surrounding the single conserved tryptophan residue of OspA (at residue 216, or in some cases 217), as determined by a moving window population analysis of OspA from fifteen European and North American isolates of *Borrelia*. The hypervariable region is important for immune recognition.

Site-directed mutagenesis was also conducted to examine the hypervariable regions more closely. Fluorescence and circular dichroism spectroscopy have indicated that the conserved tryptophan is part of an alpha-helical region in which the tryptophan is buried in a hydrophobic environment (McGrath, B. C., et al., *Vaccines*, Cold Spring Harbor Laboratory Press, Plainview, N.Y.; pp. 365–370 (1993)). More polar amino acid side-chains flanking the tryptophan are likely to be exposed to the hydrophilic solvent. The hypervariability of these solvent-exposed residues among the various strains of *Borrelia* suggested that these amino acid residues may contribute to the antigenic variation in OspA. Therefore, site-directed mutagenesis was performed to replace some of the potentially exposed amino acid side chains in the protein from one strain with the analogous residues of a second strain. The altered proteins were then analyzed by Western Blot using monoclonal antibodies which bind OspA on the surface of the intact, non-mutated spirochete. The results indicated that certain specific amino acid changes near the tryptophan can abolish reactivity of OspA to these monoclonal antibodies.

A. Verification of Clustered Polymorphisms in Outer Surface Protein A Sequences

Cloning and sequencing of the OspA protein from fifteen European and North American isolates (described above in Table I) demonstrated that amino acid polymorphism is not randomly distributed throughout the protein; rather, polymorphism tended to be clustered in three regions of OspA. The analysis was carried out by plotting the moving, weighted average polymorphism of a window (a fixed length subsection of the total sequence) as it is slid along the sequence. The window size in this analysis was thirteen amino acids, based upon the determination of the largest number of significantly deviating points as established by the method of Tajima (*J. Mol. Evol.* 33: 470–473 (1991)). The average weighted polymorphism was calculated by summing the number of variant alleles for each site. Polymorphism calculations were weighted by the severity of amino acid replacement (Dayhoff, M. O. et al., in: Dayhoff, M. O. (ed.) *Atlas of Protein Sequence and Structure NBRF*, Washington, Vol. 5, Suppl. 3: 345 (1978)). The sum was normalized by the window size and plotted. The amino acid sequence position corresponds to a window that encompasses amino acids 1 through 13. Bootstrap resampling was used to generate 95% confidence intervals on the sliding window analysis. Since *Borrelia* has been shown to be clonal, the bootstrap analysis should give a reliable estimate of the expected variance from polymorphism calculations. The bootstrap was iterated five hundred times at each position, and the mean was calculated from the sum of all positions. The clonal nature of *Borrelia* ensures that the stochastic variance that results from differing genealogical histories of the sequence positions (as would be expected if recombination were prevalent) will be minimized.

Figure 3:
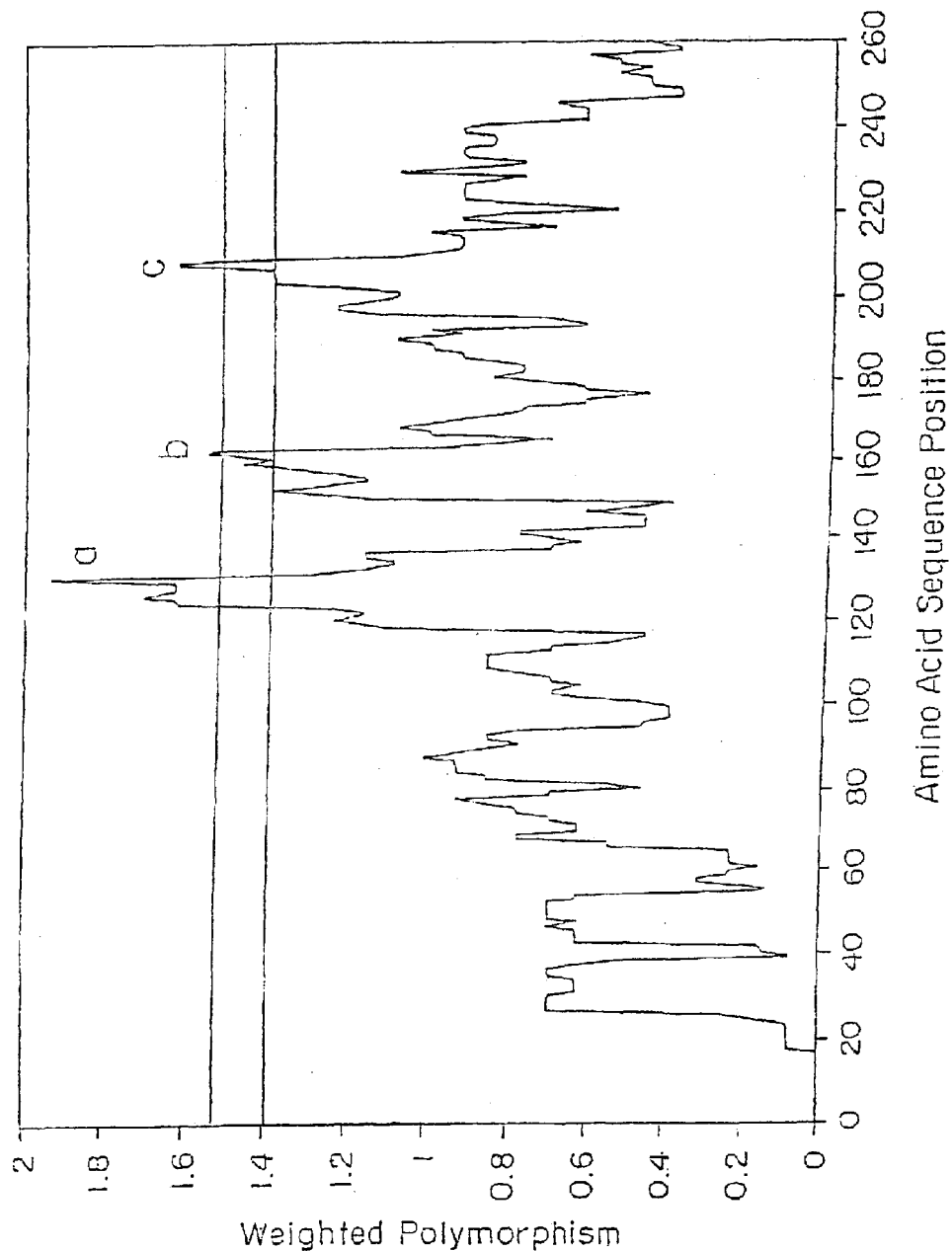
FIG. 3 is a graph depicting a plot of weighted polymorphism versus amino acid position among 14 OspA variants. The marked peaks are: a) amino acids 132–145; b) amino acids 163–177; c) amino acids 208–221. The lower line at polymorphism value 1.395 demarcates statistically significant excesses of polymorphism at p=0.05. The upper line at polymorphism value 1.520 is the same, except that the first 29 amino acids at the monomorphic N-terminus have been removed from the original analysis.
Figure 5:
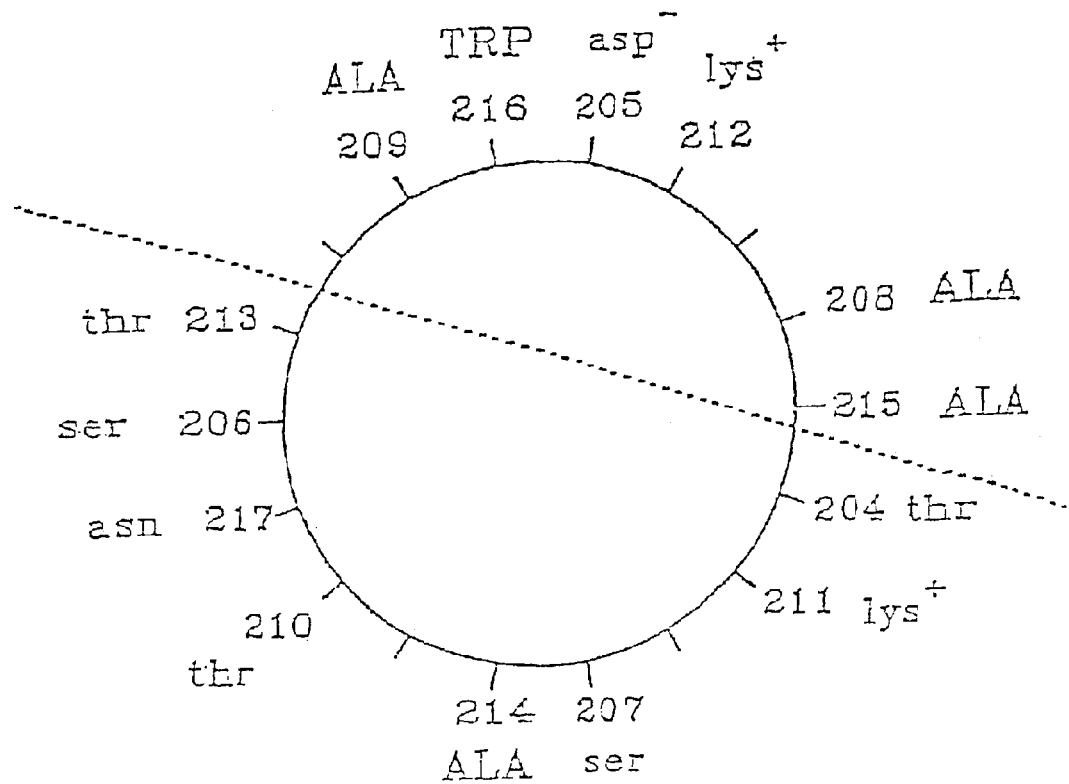
FIG. 5 is a helical wheel projection of residues 204–217 of B31 OspA. Capital letters indicate hydrophobic residues; lower case letters indicate hydrophilic residues; + and − indicate positively and negatively charged residues, respectively. The dashed line indicates division of the alpha-helix into a hydrophobic arc (above the line) and a polar arc (below the line). Adapted from France et al. (*Biochem. Biophys. Acta* 1120: 59 (1992)).
Figure 6:
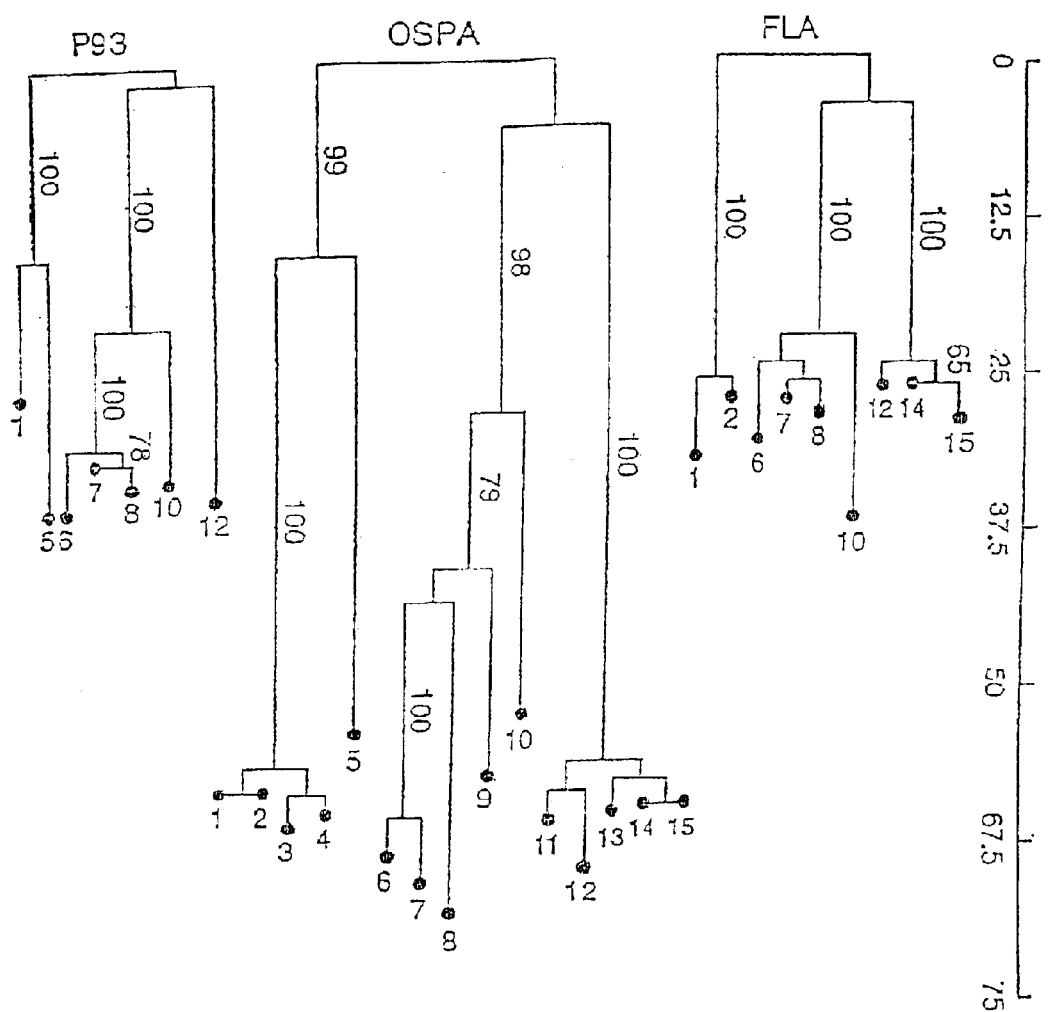
FIG. 6 depicts a phylogenic tree for strains of *Borrelia* described in Table I. The strains are as follows: 1=B31; 2=PKa1; 3=ZS7; 4=N40; 5=25015; 6=K48; 7=DK29; 8=PHei; 9=Ip90; 10=PTrob; 11=ACAI; 12=PGau; 13=Ip3; 14=PBo; 15=PKo.

This test verified that the three regions around the observed peaks all have significant excesses of polymorphism. Excesses of polymorphism were observed in the regions including amino acid residues 132–145, residues 163–177, and residues 208–221 (FIG. 3). An amino acid alignment between residues 200 and 220 for B31, K48 and the four site-directed mutants is shown in FIG. 4. The amino acid 208–221 region includes the region of OspA which has been modeled as an oriented alpha-helix in which the single tryptophan residue at amino acid 216 is buried in a hydrophobic pocket, thereby exposing more polar amino acids to the solvent (FIG. 5) (France, L. L., et al., *Biochem. Biophys. Acta* 1120: 59 (1992)). These potentially solvent-exposed residues showed considerable variability among the OspAs from various strains and may be an important component of OspA antigenic variation. For the purposes of generating chimeric proteins, the hypervariable domains of interest are Domain A, which includes amino acid residues 120–140 of OspA; Domain B, which includes residues 150–180; and Domain C, which includes residues 200–216 or 217.

B. Site-Directed Mutagenesis of the Hypervariable Region

Site-directed mutagenesis was performed to convert residues within the 204–219 domain of the recombinant B31 OspA to the analogous residues of a European OspA variant, K48. In the region of OspA between residues 204 and 219, which includes the helical domain (amino acids 204–217), there are seven amino acid differences between OspA-B31 and OspA-K48. Three oligonucleotides were generated, each containing nucleotide changes which would incorporate K48 amino acids at their analogous positions in the B31 OspA protein. The oligos used to create the site-directed mutants were:

5'-CTTAATGACTCTGACACTAGTGC-3' (#613, which converts serine at position 204 to threonine, and serine at 206 to threonine (Ser204-Thr, Ser206-Thr)) (SEQ ID NO. 1);

5'-GCTACTAAAAAAACCGGGAAATGGAATTCA-3' (#625, which converts alanine at 214 to glycine, and alanine at 215 to lysine (Ala214-Gly, Ala215-Lys)) (SEQ ID NO. 2); and 5'-GCAGCTTGGGATTCAAAAACATCCACTTTAACA-3' (#640, which converts asparagine at 217 to aspartate, and glycine at 219 to lysine (Asn217-Asp, Gly219-Lys)) (SEQ ID NO. 3).

Site-directed mutagenesis was carried out by performing mutagenesis with pairs of the above oligos. Three site-directed mutants were created, each with two changes: OspA 613 (Ser204-Thr, Ser206-Thr), OspA 625 (Ala214-Gly, Ala215-Lys), and 640 (Asn217-Asp, Gly219-Lys). There were also two proteins with four changes: OspA 613/625

(Ser204-Thr, Ser206-Thr, Ala214-Gly, Ala215-Lys) and OspA 613/640 (Ser204-Thr, Ser206-Thr, Asn217-Asp, Gly219-Lys).

Specificity of Antibody Binding to Epitopes of the Non-Mutated Hypervariable Region Monoclonal antibodies that agglutinate spirochetes, including several which are neutralizing in vitro, recognize epitopes that map to the hypervariable region around Trp216 (Barbour, A. G. et al., *Infect. and Immun.* 41: 759 (1983); Schubach, W. H. et al., *Infect. and Immun.* 59: 1911 (1991)). Western Blot analysis demonstrated that chemical cleavage of OspA from the B31 strain at Trp 216 abolishes reactivity of the protein with the agglutinating MAb 105, a monoclonal raised against B31 spirochetes (data not shown). The reagent, n-chlorosuccinimide (NCS), cleaves OspA at the Trp 216, forming a 23.2 kd fragment and a 6.2 kd peptide which is not retained on the Imobilon-P membrane after transfer. The uncleaved material binds MAb 105; however, the 23.2 kd fragment is unreactive. Similar Western blots with a TrpE-OspA fusion protein containing the carboxy-terminal portion of the OspA protein demonstrated that the small 6.2 kd piece also fails to bind MAb 105 (Schubach, W. H. et al., *Infect. and Immun.* 59: 1911 (1991)).

Monoclonal antibodies H5332 and H3TS (Barbour, A. G. et al, *Infect. and Immun.* 41: 759 (1983)) have been shown by immunofluorescence to decorate the surface of fixed spirochetes (Wilske, B. et al., *World J. Microbiol.* 7: 130 (1991)). These monoclonals also inhibit the growth of the organism in culture. Epitope mapping with fusion proteins has confirmed that the epitopes which bind these MAbs are conformationally determined and reside in the carboxy half of the protein. MAb H5332 is cross-reactive among all of the known phylogenetic groups, whereas MAb H3TS and MAb 105 seem to be specific to the B31 strain to which they were raised. Like MAb 105, the reactivities of H5332 and H3TS to OspA are abrogated by fragmentation of the protein at Trp216 (data not shown). MAb 336 was raised to whole spirochetes of the strain PGau. It cross-reacts to OspA from group 1 (the group to which B31 belongs) but not to group 2 (of which K48 is a member). Previous studies using fusion proteins and chemical cleavage have indicated that this antibody recognizes a domain of OspA in the region between residues 217 and 273 (data not shown). All of these MAbs will agglutinate the B31 spirochete.

Western Blot Analysis of Antibody Binding to Mutated Hypervariable Regions

MAbs were used for Western Blot analysis of the site-directed OspA mutants induced in *E. coli* using the T7 expression system (Dunn, J. J. et al., *Protein Expression and Purification* 1: 159 (1990)). *E. coli* cells carrying pET9c plasmids having a site-directed OspA mutant insert were induced at mid-log phase growth with IPTG for four hours at 37° C. Cell lysates were made by boiling an aliquot of the induced cultures in SDS gel loading dye, and this material was then loaded onto a 12% SDS gel (BioRad mini-Protean II), and electrophoresed. The proteins were then transferred to Imobilon-P membranes (Millipore) 70V, 2 hour at 4° C. using the BioRad mini transfer system. Western analysis was carried out as described by Schubach et al. (*Infect. Immun.* 59: 1911 (1991)).

Western Blot analysis indicated that only the 625 mutant (Ala214-Gly and Ala215-Lys) retained binding to the agglutinating monoclonal H3TS antibody (data not shown). However, the 613/625 mutant which has additional alterations to the amino terminus of Trp216 (Ser204-Thr and Ser206-Thr) did not bind this monoclonal antibody. Both 640 and 613/640 OspAs which have the Asn217-Asp and Gly219-Lys changes on the carboxy-terminal side of Trp216 also failed to bind MAb H3TS. This indicated that the epitope of the B31 OspA which binds MAb H3TS is comprised of amino acid side-chains on both sides of Trp216.

The 613/625 mutant failed to bind MAbs 105 and H5332, while the other mutants retained their ability to bind these MAbs. This is important in light of the data using fusion proteins that indicate that MAb 105 behaves more like MAb H3TS in terms of its serotype specificity and binding to OspA (Wilske, B. et al., *Med. Microbiol. Immunol.* 181: 191 (1992)). The 613/625 protein has, in addition to the differences at residues Ser204 and Ser206, changes immediately amino-terminal to Trp216 (Ala214-Gly and Ala215-Lys). The abrogation of reactivity of MAbs 105 and H5332 to this protein indicated that the epitopes of OspA which bind these monoclonals are comprised of residues on the amino-terminal side of Trp216.

The two proteins carrying the Asn217-Asp and Gly219-Lys replacements on the carboxy-terminal side of Trp216 (OspAs 640 and 613/640) retained binding to MAbs 105 and H5332; however, they failed to react with MAb 336, a monoclonal which has been mapped with TrpE-OspA fusion proteins and by chemical cleavage to a more carboxy-terminal domain. This result may explain why MAb 336 failed to recognize the K48-type of OspA (Group 2).

It is clear that amino acids Ser204 and Ser206 play an important part in the agglutinating epitopes in the region of the B31 OspA flanking Trp216. Replacement of these two residues altered the epitopes of OspA that bind MAbs 105, H3TS and H5332. The ability of the 640 changes alone to abolish reactivity of MAb 336 indicated that Ser204 and Ser206 are not involved in direct interaction with MAb 336.

The results indicated that the epitopes of OspA which are available to MAbs that agglutinate spirochetes are comprised at least in part by amino acids in the immediate vicinity of Trp216. Since recent circular dichroism analysis indicated that the structures of B31 and K48 OspA differ very little within this domain, it is unlikely that the changes made by mutation have radically altered the overall structure of the OspA protein (France, L. L. et al., *Biochem. Biophys. Acta* 1120: 59 (1992); and France et al., *Biochem. Biophys. Acta*, submitted (1993)). This hypothesis is supported by the finding that the recombinant, mutant OspAs exhibit the same high solubility and purification properties as the parent B31 protein (data not shown).

In summary, amino acid side-chains at Ser204 and Ser206 are important for many of the agglutinating epitopes. However, a limited set of conservative changes at these sites were not sufficient to abolish binding of all of the agglutinating MAbs. These results suggested that the agglutinating epitopes of OspA are distinct, yet may have some overlap. The results also supported the hypothesis that the surface-exposed epitope around Trp216 which is thought to be important for immune recognition and neutralization is a conformationally-determined and complex domain of OspA.

Example 3

*Borrelia* Strains and Proteins

Proteins and genes from any strain of *Borrelia* can be utilized in the current invention. Representative strains are summarized in Table I, above.

A. Genes Encoding *Borrelia* Proteins

The chimeric peptides of the current invention can comprise peptides derived from any *Borrelia* proteins. Representative proteins include OspA, OspB, OspC, OspD, p12, p39, p41 (fla), p66, and p93. Nucleic acid sequences encoding several *Borrelia* proteins are presently available (see Table II, below); alternatively, nucleic acid sequences encoding *Borrelia* proteins can be isolated and characterized using methods such as those described below.

mM TRIS-HCl (pH 8,3), 1.5 mM $MgCl_2$, 200 $\mu$M each NTP, 2.5 units of TaqI DNA polymerase (Amplitaq, Perkin-Elmer/Cetus) and 100 pmol each of the 5' and 3' primers (described below) were used. Amplification was performed in a Perkin-Elmer/Cetus thermal cycler as described (Schubach, W. H. et al., *Infect. Immun.* 59: 1811–1915 (1991)). The amplicon

TABLE II

References for Nucleic Acid Sequences for Several Proteins of Various *Borrelia* Strains

| Strain | p93 | OspA | p41 (fla) |
|---|---|---|---|
| K48 | X69602 (SID 67) | X62624 (SID 8) | X69610 |
| PGau | SID 73 | X62387 (SID 10) | X69612 (SID 51) |
| DK29 | ND | X63412 (SID 49) | X69608 (SID 53) |
| PKo | X69803 (SID 77) | X65599 (SID 57) | X69613 (SID 131) |
| PTrob | X69604 (SID 71) | X65598 (SID 135) | X69614 |
| Ip3 | ND | X70365 (SID 56) | ND |
| Ip90 | ND | Kryuchechnikov, V. N. et al., J. Microbiol. Epid. Immunobiol. 12: 41–44 (1988) (SID 50) | ND |
| 25015 | X70365 (SID 75) | Fikrig, E. S. et al., J. Immunol. 7: 2256–2260 (1992) (SID 12) | ND |
| B31 | Perng, G. C. et al., Infect. Immun. 59: 2070–74 (1992); Luft, B. J. et al., Infect. Immun. 60: 4309–4321 (1992) (SID 65) | Bergstrom, S. et al., Mol. Microbiol. 3: 479–486 (1989) (SID 6) | Gassmann, G. S. et al., Nucl. Acids Res. 17: 3590 (1989) (SID 127) |
| PKa1 | ND | X69606 (SID 132) | X69611 (SID 129) |
| ZS7 | ND | Jonsson, M. et al., Infect. Immun. 60: 1845–1853 (1992) (SID 134) | ND |
| N40 | ND | Kryuchechnikov, V. N. et al. (SID 133) | ND |
| PHei | ND | X65600 (SID 136) | ND |
| ACAI | ND | Kryuchechnikov, V. N. et al. (SID 58) | ND |
| PBo | X69601 (SID 69) | X65605 (SID 55) | X69610 (SID 130) |

Numbers with an "X" prefix are GenBank data base accession numbers.
SID = SEQ ID NO.

B. Isolation of *Borrelia* Genes

Nucleic acid sequences encoding full length, lipidated proteins from known *Borrelia* strains were isolated using the polymerase chain reaction (PCR) as described below. In addition, nucleic acid sequences were generated which encoded truncated proteins (proteins in which the lipidation signal has been removed, such as by eliminating the nucleic acid sequence encoding the first 18 amino acids, resulting in non-lipidated proteins). Other proteins were generated which encoded polypeptides of a particular gene (i.e., encoding a segment of the protein which has a different number of amino acids than the protein does in nature). Using similar methods as those described below, primers can be generated from known nucleic acid sequences encoding *Borrelia* proteins and used to isolate other genes encoding *Borrelia* proteins. Primers can be designed to amplify all of a gene, as well as to amplify a nucleic acid sequence encoding truncated protein sequences, such as described below for OspC, or nucleic acid sequences encoding a polypeptide derived from a *Borrelia* protein. Primers can also be designed to incorporate unique restriction enzyme cleavage sites into the amplified nucleic acid sequences. Sequence analysis of the amplified nucleic acid sequences can then be performed using standard techniques.

Cloning and Sequencing of OspA Genes and Relevant Nucleic Acid Sequences

*Borrelia* OspA sequences were isolated in the following manner: 100 $\mu$l reaction mixtures containing 50 mM KCl, 10 was visualized on an agarose gel by ethidium bromide staining. Twenty nanograms of the chloroform-extracted PCR product were cloned directly into the PC-TA vector (Invitrogen) by following the manufacturer's instructions. Recombinant colonies containing the amplified fragment were selected, the plasmids were prepared, and the nucleic acid sequence of each OspA was determined by the dideoxy chain-termination technique using the Sequenase kit (United States Biochemical). Directed sequencing was performed with M13 primers followed by OspA-specific primers derived from sequences, previously obtained with M13 primers.

Because the 5' and 3' ends of the OspA gene are highly conserved (Fikrig, E. S. et al., *J. Immunol.* 7: 2256–2260 (1992); Bergstrom, S. et al., *Mol. Microbiol.* 3: 479–486 (1989); Zumstein, G. et al., *Med. Microbiol. Immunol.* 181: 57–70 (1992)), the 5' and 3' primers for cloning can be based upon any known OspA sequences. For example, the following primers based upon the OspA nucleic acid sequence from strain B31 were used:

```
                                        (SEQ ID NO. 4)
5'-GGAGAATATATTATGAAA-3'        (-12 to +6); and (SEQ ID NO. 5)
5'-CTCCTTATTTTAAAGCG-3'         (+826 to +809).
```

-continued
(Schubach, W. H. et al.,
Infect. Immun 59:
1811–1915 (1991)).

OspA genes isolated in this manner include those for strains B31, K48, PGau, and 25015; the nucleic acid sequences are depicted in the sequence listing as SEQ ID NO. 6 (OspA-B31), SEQ ID NO. 8 (OspA-K48), SEQ ID NO. 10 (OspA-PGau), and SEQ ID NO. 12 (OspA-25015). An alignment of these and other OspA nucleic acid sequences is shown in FIG. 42. The amino acid sequences of the proteins encoded by these nucleic acid sequences are represented as SEQ ID NO. 7 (OspA-B31), SEQ ID NO. 9 (OspA-K48), SEQ ID NO. 11 (OspA-PGau), and SEQ ID NO. 13 (OspA-25015).

The following primers were used to generate specific nucleic acid sequences of the OspA gene, to be used to generate chimeric nucleic acid sequences (as described in Example 4):

5'-GTCGGCGGATCCTTAAGGTTTTTTTGGACTTTC TGC-3' (minus strand primer having BamH1 site followed by stop codon) (SEQ ID NO. 28).

The nucleic acid sequences of the OspC genes were then determined by the dideoxy chain-termination technique using the Sequenase kit (United States Biochemical). OspC genes isolated and sequenced in this manner include those for strains B31, K48, PKo, and Tro; the nucleic acid sequences are depicted in the sequence listing as SEQ ID NO. 29 (OspC-B31), SEQ ID NO. 31 (OspC-K48), SEQ ID NO. 33 (OspC-PKo), and SEQ ID NO. 35 (OspC-Tro). An alignment of these sequences is shown in FIG. 38. The amino acid sequences of the proteins encoded by these nucleic acid sequences are represented as SEQ ID NO. 30 (OspC-B31), SEQ ID NO. 32 (PspC-K48), SEQ ID NO. 34 (OspC-PKo), and SEQ ID NO. 36 (OspC-Tro).

Truncated OspC genes were generated using other primers. These primers were designed to amplify nucleic acid

| | | |
|---|---|---|
| 5'-GTCTGCAAAAACCATGACAAG-3' | (plus strand primer #369); | (SEQ ID NO. 14) |
| 5'-GTCATCAACAGAAGAAAAATTC-3' | (plus strand primer #357); | (SEQ ID NO 15) |
| 5'-CCGGATCCATATGAAAAAATATTTATTGGG-3' | (plus strand primer #607); | (SEQ ID NO. 16) |
| 5'-CCGGGATCCATATGGCTAAGCAAAATGTTAGC-3' | (plus strand primer #584); | (SEQ ID NO. 17) |
| 5'-GCGTTCAAGTACTCCAGA-3' | (minus strand primer #200); | (SEQ ID NO. 18) |
| 5'-GATATCTAGATCTTATTTTAAAGCGTT-3' | (minus strand primer #586); and | (SEQ ID NO. 19) |
| 5'-GGATCCGGTGACCTTTTAAAGCGTTTTTAAT-3' | (minus strand primer #1169). | (SEQ ID NO. 20) |

(SEQ ID NO. 20).

Cloning and Sequencing of OspB

Similar methods were also used to isolate OspB genes. One OspB genes isolated is represented as SEQ ID NO. 21 (OspB-B31); its encoded amino acid sequence is SEQ ID NO. 22.

The following primers were used to generate specific nucleic acid sequences of the OspB gene, to be used in generation of chimeric nucleic acid sequences (see Example 4):

sequences, derived from the OspC gene, that lacked the nucleic acids encoding the signal peptidase sequence of the full-length protein. The primers corresponded to bp 58–75 of the natural protein, with codons for Met-Ala attached ahead. For strain B31, the following primer was used:

5'-GTGCGCGACCATATGGCTAATAATTCAGGGAAA GAT-3' (SEQ ID NO. 37).

For strain PKo,
5'-GTGCGCGACCATATGGCTAGTAATTCAGGGAAA GGT-3' (SEQ ID NO. 38) was used.

| | | |
|---|---|---|
| 5'-GGTACAATTACAGTACAA-3' | (plus strand primer #721); | (SEQ ID NO. 23) |
| 5'-CCGAGAATCTCATATGGCACAAAAAGGTGCTGAGTCAATTGG-3' | (plus strand primer #1105); | (SEQ ID NO. 24) |
| 5'-CCGATATCGGATCCTATTTTAAAGCGTTTTTAAGC-3' | (minus strand primer #1106); and | (SEQ ID NO. 25) |
| 5'-GGATCCGGTGACCTTTTAAAGCGTTTTTAAG-3' | (minus strand primer #1170). | (SEQ ID NO. 26) |

Cloning and Sequencing of OspC

Similar methods were also used to isolate OspC genes. The following primers were used to isolate entire OspC genes from *Borrelia* strains B31, K48, PKo, and PTrob:
5'-GTGCGCGACCATATGAAAAAGAATACATTAAGT GCG-3' (plus strand primer having Nde1 site combined with start codon) (SEQ ID NO. 27), and For strains PTrob and K48, 5'-GTGCGCGACCATATG GCTAATAATTCAGGTGGG GAT-3' (SEQ ID NO. 39) was used.

Additional primers were also designed to amplify nucleic acids encoding particular polypeptides, for use in creation of chimeric nucleic acid sequences (see Example 4). These primers included:

| | | |
|---|---|---|
| 5'-CTTGGAAAATTATTTGAA-3' | (plus strand primer #520); | (SEQ ID NO. 40) |
| 5'-CACGGTCACCCCATGGGAAATAATTCAGGGAAAGG-3' | (plus strand primer #58); | (SEQ ID NO. 41) |

```
5'-TATAGATGACAGCAACGC-3'                              (minus strand primer #207); and  (SEQ ID NO. 42)

5'-CCGGTGACCCCATGGTACCAGGTTTTTTTGGACTTTCTGC-3'   (minus strand primer #636).       (SEQ ID NO. 43)
```

Cloning and Sequencing of OspD

Similar methods can be used to isolate OspD genes. An alignment of four OspD nucleic acid sequences (from strains PBo, PGau, DK29, and K48) is shown in FIG. 39.

Cloning and Sequencing of p12

The p12 gene was similarly identified. Primers used to clone the entire p12 gene included: 5'-CCGGATCCA TATGGTTAAAAAAATAATATTTATTTC-3' (forward primer #757) (SEQ ID NO. 44); and 5'-GATATCTAG ATCTTTAATTGCTCTGCTCACTCTCTTC-3' (reverse primer #758) (SEQ ID NO. 45).

To amplify a truncated p12 gene (one in which the transcribed protein is non-lipidated, and begins at amino acid 18 of the native sequence), the following primers were used:
5'-CCGGGATCCATATGGCTAGTGCAATTGGTCGTGG-3' (forward primer #759) (SEQ ID NO. 46); and primer #758 (SEQ ID NO. 45).

Cloning and Sequencing of p41 (fla)

A similar approach was used to clone and sequence genes encoding the p41 (fla) protein. The p41 sequences listed in Table II with GenBank accession numbers were isolated using the following primers from strain B31:
5'-ATGATTATCAATCATAAT-3' (+1 to +18) (SEQ ID NO. 47); and 5'-TCTGAACAATGACAAAAC-3' (+1008 to +991) (SEQ ID NO. 48). The nucleic acid sequences of p41 isolated in this manner are depicted in the sequence listing as SEQ ID NO. 51 (p41-PGau), and SEQ ID NO. 53 (p41-DK29). An alignment of several p41 nucleic acid sequences, including those for strains B31, PKa1, PGau, PBo, DK29, and PKo, is shown in FIG. 41. The amino acid sequences of the proteins encoded by these nucleic acid sequences are represented as SEQ ID NO. 52 (p41-PGau) and SEQ ID NO. 54 (p41-DK29).

Other primers were designed to amplify nucleic acid sequences encoding polypeptides of p41, to be used in chimeric nucleic acid sequences. These primers included:

Cloning and Sequencing of p93

The same approach was also used to clone and sequence p93 proteins. Genes encoding p93, as listed in Table II with GenBank accession numbers, were isolated by this method with the following primers from strain B31:

```
                                                 (SEQ ID NO. 63)
5'-GGTGAATTTAGTTGGTAAGG-3'       (-54 to -35); and (SEQ ID NO. 64)
5'-CACCAGTTTCTTTAAGCTGCTCCTGC-3'  (+1117 to +1092).
```

The nucleic acid sequences of p93 isolated in this manner are depicted in the sequence listing as SEQ ID NO. 65 (p93-B31), SEQ ID NO. 67 (p93-K48) SEQ ID NO. 69 (p93-PBo), SEQ ID NO. 71 (p93-PTrob), SEQ ID NO. 73 (p93-PGau), SEQ ID NO. 77 (p93-25015), and SEQ ID NO. 75 (p93-PKo). The amino acid sequences of the proteins encoded by these nucleic acid sequences are represented as SEQ ID NO. 66 (p93-B31), SEQ ID NO. 68 (p93-K48) SEQ ID NO. 70 (p93-PBo), SEQ ID NO. 72 (p93-PTrob), SEQ ID NO. 74 (p93-PGau), SEQ ID NO. 78 (p93-25015), and SEQ ID NO. 76 (p93-PKo).

Other primers were used to amplify nucleic acid sequences encoding polypeptides of p93 to be used in generating chimeric nucleic acid sequences. These primers included:

```
5'-CCGGTCACCCCATGGCTGCTTTAAAGTCTTTA-3'        (plus strand primer #475);          (SEQ ID NO. 79)

5'-CCGGTCACCCCATGAATCTTGATAAAGCTCAG-3'        (plus strand primer #900);          (SEQ ID NO. 80)

5'-CCGGTCACCCCATGGATGAAAAGCTTTTAAAAAGT-3'     (plus strand primer #1168);         (SEQ ID NO. 81)

5'-CCGGTCACCCCATGGTTGAGAAATTAGATAAG-3'        (plus strand primer #1423); and     (SEQ ID NO. 82)

5'-TTGGATCCGGTGACCCTTAACTTTTTTTAAAG-3'        (minus strand primer #2100).        (SEQ ID NO. 83)
```

C. Expression of Proteins from Borrelia Genes

The nucleic acid sequences described above can be incorporated into expression plasmids, using standard techniques, and transfected into compatible host cells in order to express the proteins encoded by the nucleic acid sequences. As an example, the expression of the p12 gene and the isolation of p12 protein is set forth.

Amplification of the p12 nucleic acid sequence was conducted with primers that included a NdeI restriction site into the nucleic acid sequence. The PCR product was extracted with phenol/chloroform and precipitated with ethanol. The precipitated product was digested and ligated into an expression plasmid as follows: 15 µl (approximately

```
5'-TTGGATCCGGTCACCCCATGGCTCAATATAACCAATG-3'   (minus strand primer #122);        (SEQ ID NO. 59)

5'-TTGGATCCGGTCACCCCATGGCTTCTCAAAATGTAAG-3'   (plus strand primer #140);         (SEQ ID NO. 60)

5'-TTGGATCCGGTGACCAACTCCGCCTTGAGAAGG-3'       (minus strand primer #234); and    (SEQ ID NO. 61)

5'-TTGGATCCGGTGACCTATTTGAGCATAAGATGC-3'       (minus strand primer #141).        (SEQ ID NO. 62)
```

1 µg) of PCR DNA was combined with 2 µl 10× restriction buffer for NdeI (Gibco/BRL), 1 µl NdeI (Gibco/BRL), and 2 µl distilled water, and incubated overnight at 37° C. This mixture was subsequently combined with 3 µl 10× buffer (buffer 3, New England BioLabs), 1 µl BamHI (NEB), and 6 µl distilled water, and incubated at 37° for two hours. The resultant material was purified by preparative gel electrophoresis using low melting point agarose, and the band was visualized under long wave ultraviolet light and excised from the gel. The gel slice was treated with Gelase using conditions recommended by the manufacturer (Epicentre Technologies). The resulting DNA pellet was resuspended in 25–50 µl of 10 mM TRIS-CL (pH 8.0) and 1 mM EDTA (TE). An aliquot of this material was ligated into the pET9c expression vector (Dunn, J. J. et al., *Protein Expression and Purification* 1: 159 (1990)).

To ligate the material into the pET9c expression vector, 20–50 ng of p12 nucleic acid sequences cut and purified as described above was combined with 5 µl 10 One-Phor-All (OPA) buffer (Pharmacia), 30–60 ng pET9c cut with NdeI and BamHI, 2.5 µl 20 mM ATP, 2 µl T4 DNA ligase (Pharmacia) diluted 1:5 in 1×OPA buffer, and sufficient distilled water to bring the final volume to 50 µl. The mixture was incubated at 12° C. overnight.

The resultant ligations were transformed into competent DH5-alpha cells and plated on nutrient agar plates containing 50 µg/ml kanamycin and incubated overnight at 37° C. DH5-alpha is used as a "storage strain" for T7 expression clones, because it is RecA deficient, so that recombination and concatenation are not problematic, and because it lacks the T7 RNA polymerase gene necessary to express the cloned gene. The use of this strain allows for cloning of potentially toxic gene products while minimizing the chance of deletion and/or rearrangement of the desired genes. Other cell lines having similar properties may also be used.

Kanamycin resistant colonies were single-colony purified on nutrient agar plates supplemented with kanamycin at 50 µg/ml. A colony from each isolate was inoculated into 3–5 ml of liquid medium containing 50 µg/ml kanamycin, and incubated at 37° C. without agitation. Plasmid DNA was obtained from 1 ml of each isolate using a hot alkaline lysis procedure (Mantiatis, T. et al., *Molecular Cloning: A Laboratory Manual*, Cold Spring Harbor Laboratory, Cold Spring Harbor, N.Y. (1982)).

Plasmid DNA was digested with EcoRI and BglII in the following manner: 15 µl plasmid DNA was combined with 2 µl 10× buffer 3 (NEB), 1 µl EcoRI (NEB), 1 µl BglII (NEB) and 1 µl distilled water, and incubated for two hours at 37° C. The entire reaction mixture was electrophoresed on an analytical agarose gel. Plasmids carrying the p12 insert were identified by the presence of a band corresponding to 925 base-pairs (full length p12) or 875 base-pairs (nonlipidated p12). One or two plasmid DNAs from the full length and nonlipidated p12 clones in pET9c were used to transform BL21 DE3 pLysS to kanamycin resistance as described by Studier et al. (*Methods in Enzymology*, Goeddel, D. (Ed.), Academic Press, 185: 60–89 (1990)). One or two transformants of the full length and nonlipidated clones were single-colony purified on nutrient plates containing 25 µg/ml chloramphenicol (to maintain pLysS) and 50 µg/ml kanamycin at 37° C. One colony of each isolate was inoculated into liquid medium supplemented with chloramphenicol and kanamycin and incubated overnight at 37° C. The overnight culture was subcultured the following morning into 500 ml of liquid broth with chloramphenicol (25 µg/ml) and kanamycin (50 µg/ml) and grown with aeration at 37° C. in an orbital air-shaker until the absorbance at 600 nm reached 0.4–0.7. Isopropyl-thio-galactoside (IPTG) was added to a final concentration of 0.5 mM, for induction, and the culture was incubated for 3–4 hours at 37° C. as before. The induced cells were pelleted by centrifugation and resuspended in 25 ml of 20 mM NaPO$_4$ (pH 7.7). A small aliquot was removed for analysis by gel electrophoresis. Expressing clones produced proteins which migrated at the 12 kDa position.

A crude cell lysate was prepared from the culture as described for recombinant OspA by Dunn, J. J. et al., (*Protein Expression and Purification* 1: 159 (1990)). The crude lysate was first passed over a Q-sepharose column (Pharmacia) which had been pre-equilibrated in Buffer A: 10 mM NaPO$_4$ (pH 7.7), 10 mM NaCl, 0.5 mM PMSF. The column was washed with 10 mM NaPO$_4$, 50 mM NaCl and 0.5 mM PMSF and then p12 was eluted in 10 mM NaPO$_4$, 0.5 mM PMSF with a NaCl gradient from 50–400 mM. p12 eluted approximately halfway through the gradient between 100 and 200 mM NaCl. The peak fractions were pooled and dialyzed against 10 mM NaPO$_4$ (pH 7.7), 10 mM NaCl, 0.5 mM PMSF. The protein was then concentrated and applied to a Sephadex G50 gel filtration column of approximately 50 ml bed volume (Pharmacia), in 10 mM NaPO$_4$, 200 mM NaCl, 0.5 mM PMSF. p12 would typically elute shortly after the excluded volume marker. Peak fractions were determined by running small aliquots of all fractions on an SDS gel. The p12 peak was pooled and stored in small aliquots at −20° C.

Example 4

Generation of Chimeric Nucleic Acid Sequences and Chimeric Proteins

A. General Protocol for Creation of Chimeric Nucleic Acid Sequences

The megaprimer method of site directed mutagenesis and its modification were used to generate chimeric nucleic acid sequences (Sarkar and Sommer, *Biotechniques* 8(4): 404–407 (1990); Aiyar, A. and J. Leis, *Biotechniques* 14(3): 366–369 (1993)). A 5' primer for the first genomic template and a 3' fusion oligo are used to amplify the desired region. The fusion primer consists of a 3' end of the first template (DNA that encodes the amino-proximal polypeptide of the fusion protein), coupled to a 5' end of the second template (DNA that encodes the carboxy-proximal polypeptide of the fusion protein).

The PCR amplifications are performed using Taq DNA polymerase, 10× PCR buffer, and MgCl$_2$ (Promega Corp., Madison, Wis.), and Ultrapure dNTPs (Pharmacia, Piscataway, N.J.). One µg of genomic template 1, 5 µl, of 10 µM 5' oligo and 5 µl of 10 µM fusion oligo are combined with the following reagents at indicated final concentrations: 10× Buffer-Mg FREE (1×), MgCl$_2$ (2 mM), dNTP mix (200 µM each dNTP), Taq DNA polymerase (2.5 units), water to bring final volume to 100 µl. A Thermal Cycler (Perkin Elmer Cetus, Norwalk, Conn.) is used to amplify under the following conditions: 35 cycles at 95° C. for one minute, 55° C. for two minutes, and 72° for three minutes. This procedure results in a "megaprimer".

The resulting megaprimer is run on a 1× TAE, 4% low-melt agarose gel. The megaprimer band is cut from the gel and purified using the Promega Magic PCR Preps DNA purification system. Purified megaprimer is then used in a second PCR step. One µg of genomic template 2, approximately 0.5 µg of the megaprimer, and 5 µl of 10 µM 3' oligo are added to a cocktail of 10× buffer, MgCl$_2$, dNTPs and Taq at the same final concentrations as noted above, and brought to 100 µl with water. PCR conditions are the same as above.

The fusion product resulting from this amplification is also purified using the Promega Magic PCR Preps DNA purification system.

The fusion product is then ligated into TA vector and transformed into *E. coli* using the Invitrogen (San Diego, Calif.) TA Cloning Kit. Approximately 50 ng of PCR fusion product is ligated to 50 ng of pCRII vector with 1× Ligation Buffer, 4 units of T4 ligase, and brought to 10 µl with water. This ligated product mixture is incubated at 12° C. overnight (approximately 14 hours). Two µl of the ligation product mixture is added to 50 µl competent INC F' cells and 2 µl beta mercaptoethanol. The cells are then incubated for 30 minutes, followed by heat shock treatment at 42° C. for 60 seconds, and an ice quenching for two minutes. 450 µl of warmed SOC media is then added to the cells, resulting in a transformed cell culture which is incubated at 37° C. for one hour with slight shaking. 50 µl of the transformed cell culture is plated on LB+50 µg/µl ampicillin plates and incubated overnight at 37° C. Single white colonies are picked and added to individual overnight cultures containing 3 ml LB with ampicillin (50 µg/µl).

The individual overnight cultures are prepared using Promega's Magic Miniprep DNA purification system. A small amount of the resulting DNA is cut using a restriction digest as a check. DNA sequencing is then performed to check the sequence of the fusion nucleic acid sequence, using the United States Biochemical (Cleveland, Ohio) Sequenase Version 2.0 DNA sequencing kit. Three to five µg of plasmid DNA is used per reaction. 2 µl 2M NaOH/2 mM EDTA are added to the DNA, and the volume is brought to 20 µl with water. The mixture is then incubated at room temperature for five minutes. 7 µl water, 3 µl 3M NaAc, 75 µl EtOH are added. The resultant mixture is mixed by vortex and incubated for ten minutes at −70° C., and then subjected to microcentrifugation. After microcentrifugation for ten minutes, the supernatant is aspirated off, and the pellet is dried in the speed vac for 30 second. 6 µl water, 2 µl annealing buffer, and 2 µl of 10 µM of the appropriate oligo is then added. This mixture is incubated for 10 minutes at 37° C. and then allowed to stand at room temperature for 10 minutes. Subsequently, 5.5 µl of label cocktail (described above) is added to each sample of the mixture, which are incubated at room temperature for an additional five minutes. 3.5 µl labeled DNA is then added to each sample which is then incubated for five minutes at 37° C. 4 µl stop solution is added to each well. The DNA is denatured at 95° for two minutes, and then placed on ice.

Clones with the desired fusion nucleic acid sequences are then reckoned in frame in the pET expression system in the lipidated (full length) and non-lipidated (truncated, i.e., without first 17 amino acids) forms. The product is amplified using restriction sites contained in the PCR primers. The vector and product are cut with the same enzymes and ligated together with T4 ligase. The resultant plasmid is transformed into competent *E. coli* using standard transformation techniques. Colonies are screened as described earlier and positive clones are transformed into expression cells, such as *E. coli* BL21, for protein expression with IPTG for induction. The expressed protein in its bacterial culture lysate form and/or purified form is then injected in mice for antibody production. The mice are bled, and the sera collected for agglutination, in vitro growth inhibition, and complement-dependent and -independent lysis tests.

B. Specific Chimeric Nucleic Acid Sequences

Various chimeric nucleic acid sequences were generated. The nucleic acid sequences are described as encoding polypeptides from *Borrelia* proteins. The chimeric nucleic acid sequences are produced such that the nucleic acid sequence encoding one polypeptide is in the same reading frame as the nucleic acid sequence encoding the next polypeptide in the chimeric protein sequence encoded by the chimeric nucleic acid sequence. The proteins are listed sequentially (in order of presence of the encoding sequence) in the description of the chimeric nucleic acid sequence. For example, if a chimeric nucleic acid sequence consists of bp 1–650 from OspA-1 and bp 651–820 from OspA-2 were sequenced, the sequence of the chimer would include the first 650 base pairs from OspA-1 followed immediately by base pairs 651–820 of OspA-2.

OspA-K48/OspA-PGau

A chimer of OspA from strain K48 (OspA-K48) and OspA from strain PGau (OspA-PGau) was generated using the method described above. This chimeric nucleic acid sequence included bp 1–654 from OspA-K48, followed by bp 655–820 from OspA-PGau. Primers used included: the amino-terminal sequence of OspA primer #607 (SEQ ID NO. 16); the fusion primer, 5'-AAAGTAGAAGTTTTTGAATCCCATTTTCCAGTTTT TTT-3' (minus strand primer #668–654) (SEQ ID NO. 84); the carboxy-terminal sequence of OspA primer #586 (SEQ ID NO. 19); and the sequence primers #369 (SEQ ID NO. 14) and #357 (SEQ ID NO. 15). The chimeric nucleic acid sequence is presented as SEQ ID NO. 85; the chimeric protein encoded by this chimeric nucleic acid sequence is presented as SEQ ID NO. 86.

OspA-B31/OspA-PGau

A chimer of OspA from strain B31 (OspA-B31) and OspA from strain PGau (OspA-PGau) was generated using the method described above. This chimeric nucleic acid sequence included bp 1–651 from OspA-B31, followed by bp 652–820 from OspA-PGau. Primers used included: the fusion primer, 5'-AAAGTAGAAGTTTTTGAATTCCAAGCTGCAGT TTT-3' (minus strand primer #668–651) (SEQ ID NO. 87); and the sequence primer, #369 (SEQ ID NO. 14). The chimeric nucleic acid sequence is presented as SEQ ID NO. 88; the chimeric protein encoded by this chimeric nucleic acid sequence is presented as SEQ ID NO. 89.

OspA-B31/OspA-K48

A chimer of OspA from strain B31 (OspA-B31) and OspA from strain K48 (OspA-K48) was generated using the method described above. This chimeric nucleic acid sequence included bp 1–651 from OspA-B31, followed by bp 652–820 from OspA-K48. Primers used included: the fusion primer, 5'-AAAGTGGAAGTTTTTGAATTCCAAGCTGCAGT TTTTT-3' (minus strand primer #671–651) (SEQ ID NO. 90); and the sequence primer, #369 (SEQ ID NO. 14). The chimeric nucleic acid sequence is presented as SEQ ID NO. 91; the chimeric protein encoded by this chimeric nucleic acid sequence is presented as SEQ ID NO. 92.

OspA-B31/OspA-25015

A chimer of OspA from strain B31 (OspA-B31) and OspA from strain 25015 (OspA-25015) was generated using the method described above. This chimeric nucleic acid sequence included bp 1–651 from OspA-B31, followed by bp 652–820 from OspA-25015. Primers used included: the fusion primer, 5'-TAAAGTTGAAGTGCCTGCATT CCAAGCTGCAGTTT-3' (SEQ ID NO. 93). The chimeric nucleic acid sequence is presented as SEQ ID NO. 94; the chimeric protein encoded by this chimeric nucleic acid sequence is presented as SEQ ID NO. 95.

OspA-K48/OspA-B31/OspA-K48

A chimer of OspA from strain B31 (OspA-B31) and OspA from strain K48 (OspA-K48) was generated using the method described above. This chimeric nucleic acid sequence included bp 1–570 from OspA-K48, followed by bp 570–651 from OspA-B31, followed by bp 650–820 from OspA-K48. Primers used included: the fusion primer, 5'-CCCCAGATTTTGAAATCTTGCTTAAAACAAC-3' (SEQ ID NO. 96); and the sequence primer, #357 (SEQ ID NO. 15). The chimeric nucleic acid sequence is presented as SEQ ID NO. 97; the chimeric protein encoded by this chimeric nucleic acid sequence is presented as SEQ ID NO. 98.

OspA-B31/OspA-K48/OspA-B31/OspA-K48

A chimer of OspA from strain B31 (OspA-B31) and OspA from strain K48 (OspA-K48) was generated using the method described above. This chimeric nucleic acid sequence included bp 1–420 from OspA-B31, followed by 420–570 from OspA-K48, followed by bp 570–650 from OspA-B31, followed by bp 651–820 from OspA-K48. Primers used included: the fusion primer, 5'-CAAGTCTGGTTCCAATTTGCTCTTGTTATTAT-3' (minus strand primer #436–420) (SEQ ID NO. 99); and the sequence primer, #357 (SEQ ID NO. 15). The chimeric nucleic acid sequence is presented as SEQ ID NO. 100; the chimeric protein encoded by this chimeric nucleic acid sequence is presented as SEQ ID NO. 101.

OspA-B31/OspB-B31

A chimer of OspA and OspB from strain B31 (OspA-B31, OspB-B31) was generated using the method described above. The chimeric nucleic acid sequence included bp 1–651 from OspA-B31, followed by bp 652–820 from OspB-B31. Primers used included: the fusion primer, 5'-GTTAAAGTGCTAGTACTGTCATTCCAAGCTGCAGTTTTTTT-3' (minus strand primer #740–651) (SEQ ID NO. 102); the carboxy-terminal sequence of OspB primer #1106 (SEQ ID NO. 25); and the sequence primer #357 (SEQ ID NO. 15). The chimeric nucleic acid sequence is presented as SEQ ID NO. 103; the chimeric protein encoded by this chimeric nucleic acid sequence is presented as SEQ ID NO. 104.

OspA-B31/OspB-B31/OspC-B31

A chimer of OspA, OspB and OspC from strain B31 (OspA-B31, OspB-B31, and OspC-B31) was generated using the method described above. The chimeric nucleic acid sequence included bp 1–650 from OspA-B31, followed by bp 652–820 from OspB-B31, followed by bp 74–630 of OspC-B31. Primers used included: the fusion primer, 5'-TGCAGATGTAATCCCATCCGCCATTTTTAAAGCGTTTTT-3' (SEQ ID NO. 105); and the carboxy-terminal sequence of OspC primer (SEQ ID NO. 28). The chimeric nucleic acid sequence is presented as SEQ ID NO. 106; the chimeric protein encoded by this chimeric nucleic acid sequence is presented as SEQ ID NO. 107.

OspC-B31/OspA-B31/OspB-B31

A chimer of OspA, OspB and OspC from strain B31 (OspA-B31, OspB-B31, and OspC-B31) was generated using the method described above. The chimeric nucleic acid sequence included bp 1–630 from OspC-B31, followed by bp 52–650 from OspA-B31, followed by bp 650–820 of OspB-B31. Primers used included: the amino-terminal sequence of OspC primer having SEQ ID NO. 27; the fusion primer, 5'-GCTGCTAACATTTTGCTTAGGTTTTTTTGGACTTTC-3' (minus strand primer #69–630) (SEQ ID NO. 108); and the sequence primers #520 (SEQ ID NO. 40) and #200 (SEQ ID NO. 18). The chimeric nucleic acid sequence is presented as SEQ ID NO. 109; the chimeric protein encoded by this chimeric nucleic acid sequence is presented as SEQ ID NO. 110.

Additional Chimeric Nucleic Acid Sequences

Using the methods described above, other chimeric nucleic acid sequences were produced. These chimeric nucleic acid sequences, and the proteins encoded, are summarized in Table III.

TABLE III

Chimeric Nucleic acid Sequences and the Encoded Proteins

| Chimers Generated (base pairs) | SEQ ID NO. (nt) | SEQ ID NO. (protein) |
|---|---|---|
| OspA (52–882)/p93 (1168–2100) | 111 | 112 |
| OspB (45–891)/p41 (122–234) | 113 | 114 |
| OspB (45–891)/p41 (122–295) | 115 | 116 |
| OspB (45–891)/p41 (140–234) | 117 | 118 |
| OspB (45–891)/p41 (140–295) | 119 | 120 |
| OspB (45–891)/p41 (122–234)/OspC (58–633) | 121 | 122 |
| OspA-Tro/OspA-Bo | 137 | 138 |
| OspA-PGau/OspA-Bo | 139 | 140 |
| OspA-B31/OspA-PGau/OspA-B31/OspA-K48 | 143 | 144 |
| OspA-PGau/OspA-B31/OspA-K48 | 141 | 142 |

C. Purification of Proteins Generated by Chimeric Nucleic Acid Sequences

The chimeric nucleic acid sequences described above, as well as chimeric nucleic acid sequences produced by the methods described above, are used to produce chimeric proteins encoded by the nucleic acid sequences. Standard methods, such as those described above in Example 3, concerning the expression of proteins from *Borrelia* genes, can be used to express the proteins in a compatible host organism. The chimeric proteins can then be isolated and purified using standard techniques.

If the chimeric protein is soluble, it can be purified on a Sepharose column. Insoluble proteins can be solubilized in guanidine and purified on a $Ni^{2+}$ column; alternatively, they can be solubilized in 10 mM $NaPO_4$ with 0.1–1% TRIXON X 114, and subsequently purified over an S column (Pharmacia). Lipidated proteins were generally purified by the latter method. Solubility was determined by separating both soluble and insoluble fractions of cell lysate on a 12% PAGE gel, and checking for the localization of the protein by Coomasie staining, or by Western blotting with monoclonal antibodies directed to an antigenic polypeptide of the chimeric protein.

Example 5

Generation of OspC/OspA Chimeric Nucleic Acids and Chimeric Proteins

A. General Protocol for Creation of Chimeric Nucleic Acid Sequences

A large number of chimeric nucleic acid sequences encoding proteins comprising at least a first and a second polypeptide from *Borrelia burgdorferi* were generated. These chimeric nucleic acid sequences were produced such that the encoded chimeric protein comprised a *Borrelia burgdorferi* OspC polypeptide upstream of (or N-terminal to) a *Borrelia burgdorferi* OspA polypeptide. The chimeric nucleic acid sequences were also produced such that the nucleic acid encoding one polypeptide was in the same reading frame as the nucleic acid sequence encoding the next polypeptide in the chimeric protein.

The general cloning strategy used to construct the chimeric nucleic acid sequences was as follows. The desired fragment of OspC was amplified using a 5' primer containing a restriction site suitable for cloning the resultant product into a vector of interest and a 3' primer containing a restriction site suitable for ligating the OspC fragment to the OspA fragment. The OspC product is cloned into a suitable vector. For the OspA portion of the chimeric nucleic acid, the desired OspA fragment was amplified using a 5' primer containing a restriction site for ligating the resultant OspA fragment to the OspC fragment and a 3' primer containing a restriction site suitable for cloning the resultant OspA product into the vector with the OspC product. The use of a restriction site to allow ligation of the OspC and OspA fragment results in the insertion of 0 to about 3 amino acids between the OspC and OspA fragments.

A specific example of such a construction follows. It is understood that other suitable restriction sites could be used with no more than routine experimentation. The resultant OspC/OspA chimers could have, therefore, the addition of 0 to about 3 amino acids between the OspC and OspA fragments, depending on the restriction site used.

For the OspC portions of the chimeric nucleic acids, desired fragments of OspC genes from various strains or genospecies were PCR amplified using a 5' primer containing an NdeI site and a 3' primer containing a NcoI and a BamHI site. The amplified OspC product was then cloned into the NdeI and BamHI sites of the T7 promoter driven expression vector, pET9c. For the OspA portion of the chimeric nucleic acid, desired fragments of OspA genes a strain of interest or genospecies of interest were PCR amplified using a 5' primer containing an NcoI site and a 3' primer containing a BamHI site. This OspA portion could then be directly cloned into the NcoI and BamHI sites of the pET9c vector containing the desired OspC sequence, thereby producing the desired OspC-OspA construct. By including the sequence for the NcoI restriction site in the primers, a nine nucleotide linker sequence encoding the amino acids Ser-Met-Ala was produced at the junction between the N-terminal OspC sequence and the C-terminal OspA sequence. The use of the NcoI restriction enzyme (CCATGG) in this cloning strategy was a suitable choice as Borrelia DNA is an AT-rich and therefore possesses only a few NcoI sites in its genome.

As an example, OspC-OspA chimeric nucleic acids which contain unlipidated OspC B31 were generated using the following primers:

(5'OspC-NdeI):
(SEQ ID NO:181)
5'-GT CAT ATG GCT TGT AAT AAT TCA GGG AAA GA-3';

and (3'OspC-NcoI):
(SEQ ID NO:182)
5'-T TTC CAT GGA AGG TTT TTT TGG ACT TTC TG-3'.

For OspC-OspA chimeric nucleic acids which contain unlipidated OspA B31, the following primers were used:

(5'OspA-NcoI:)
(SEQ ID NO:183)
5'-TT TCC ATG GCC AAG CAA AAT GTT AGC AGC C-3';

and (3'OspA-BamHI):
(SEQ ID NO:184)
5'-TAA GGA TCC TTA TTA TAA AGC GTT TTT-3'.

Lipidated versions of the OspC/A chimeras can be constructed by cloning an expression vector that contains a leader sequence containing a lipidation site, such that the leader sequence is linked upstream of the OspC portion of the chimera and in frame with the chimera. The leader sequence comprising a lipidation signal can be, for example, from a gene encoding the OspA, B or C polypeptides.

Chimeric nucleic acid sequences, and the proteins that they encode, which were produced are summarized in Table IV. Other additional chimeric nucleic acid sequences, and encoded proteins, are also depicted in Table IV. In further embodiments, chimeric OspC/OspA proteins are constructed wherein a first segment of OspA is from B31 and comprises base pairs from about 88 to about 450, and a second segment of OspA comprises base pairs from about 451 to about 537 of PKo. These chimeras can also comprise additional OspA segments such as the last two segments of SEQ ID NOs 167 or 165 or the last segment of SEQ ID NO: 163.

TABLE IV

Chimeric OspC/OspA Nucleic Acid Sequences and Encoded Proteins

| [1]Chimers Generated | SEQ ID NO. (nt) | SEQ ID NO. (protein) | FIG. NO. |
| --- | --- | --- | --- |
| OspC-B31(bp55-633)/OspA-B31(bp52-822) | 145 | | 55 |
| OspC-B31(aa19-211)/OspA-B31(aa18-273) | | 146 | 55 |
| OspC-B31(bp55-624)/OspA-B31(bp52-822) | 147 | | 56 |
| OspC-B31(aa19-208)/OspA-B31(aa18-273) | | 148 | 56 |
| OspC-C2(bp55-612)/OspA-B31(bp52-822) | 149 | | 57 |
| OspC-C2(aa19-204)/OspA-B31(aa18-273) | | 150 | 57 |
| OspC-B31(bp55-633)/OspA-B31(bp52-651)/OspA-K48(bp652-820) | 151 | | 58 |
| OspC-B31(aa19-211)/OspA-B31(aa18-216)/OspA-K48(aa217-273) | | 152 | 58 |
| OspC-C2(bp55-612)/OspA-B31(bp52-651)/OspA-K48(bp652-820) | 153 | | 59 |
| OspC-C2(aa19-204)/OspA-B31(aa18-216)/OspA-K48(aa217-273) | | 154 | 59 |
| OspC-B31(bp55-633)/OspA-B31(bp52-651)/OspA-PKo(bp652-820) | 155 | | 60 |
| OspC-B31(aa19-211)/OspA-B31(aa18-216)/OspA-PKo(aa217-273) | | 156 | 60 |
| OspC-C2(bp55-612)/OspA-B31(52-651)/OspA-PKo(bp652-820) | 157 | | 61 |
| OspC-C2(aa19-204)/OspA-B31(aa18-216)/OspA-PKo(aa217-273) | | 158 | 61 |

TABLE IV-continued

Chimeric OspC/OspA Nucleic Acid Sequences and Encoded Proteins

| ¹Chimers Generated | SEQ ID NO. (nt) | SEQ ID NO. (protein) | FIG. NO. |
|---|---|---|---|
| OspC-B31(bp55-633)/OspA-K48(bp52-654)/OspA-Tro(bp655-819) | 159 | | 62 |
| OspC-B31(aa19-211)/OspA-K48(aa18-217)/OspA-Tro(aa218-273) | | 160 | 62 |
| OspC-C2(bp55-612)/OspA-K48(bp52-654)/OspA-Tro(bp655-819) | 161 | | 63 |
| OspC-C2(aa19-204)/OspA-K48(aa18-217)/OspA-Tro(aa218-273) | | 162 | 63 |
| OspC-C2(bp55-612)/OspA-B31(bp88-492)/OspA-PKo(bp493-537)/OspA-B31(bp538-822) | 163 | | 64 |
| OspC-C12(aa19-204)/OspA-B31(aa30-164)/OspA-PKo(aa165-179)/OspA-B31(aa180-273) | | 164 | 64 |
| OspC-PKo(bp55-639)/OspA-B31(bp88-492)/OspA-PKo(bp493-537)/OspA-B31(bp538-651)/OspA-K48(bp652-825) | 165 | | 65 |
| OspC-PKo(aa19-213)/OspA-B31(aa30-164)/OspA-PKo(aa165-179)/OspA-B31(aa180-216)/OspA-K48(aa217-274) | | 166 | 65 |
| OspC-Tro(bp55-624)/OspA-B31(bp88-492)/OspA-PKo(bp493-537)/OspA-B31(bp538-651)/OspA-PKo(bp652-822) | 167 | | 66 |
| OspC-Tro(aa19-208)/OspA-B31(aa30-164)/OspA-PKo(aa165-179)/OspA-B31(aa180-216)/OspA-PKo(aa217-273) | | 168 | 66 |
| OspC-B31(bp55-633)/OspA-B31(bp394-820) | 169 | | 67 |
| OspC-B31(aa19-211)/OspA-B31(aa132-273) | | 170 | 67 |
| OspC-B31(bp55-631)/OspA-B31(bp394-651)/OspA-K48(652–820) | 171 | | 68 |
| OspC-B31(aa19-211)/OspA-B31(aa132-216)/OspA-K48(217–273) | | 172 | 68 |
| OspC-B31(bp55-633)/OspA-B31(bp394-651)/OspA-PKo(652–820) | 173 | | 69 |
| OspC-B31(aa19-211)/OspA-B31(aa132-216)/OspA-PKo(217–273) | | 174 | 69 |
| OspC-B31(bp55-633)/OspA-K48(bp394-654)/OspA-Tro(655–819) | 175 | | 70 |
| OspC-B31(aa19-211)/OspA-K48(aa132-217)/OspA-Tro(218–273) | | 176 | 70 |
| OspC-B31(bp55-633)/OspA-B31(bp88-492)/OspA-PKo(bp493-537)/OspA-B31(bp541-651)/OspA-PKo(bp652-822) | 177 | | 71 |
| OspC-B31(aa19-211)/OspA-B31(aa30-164)/OspA-PKo(aa165-179, aa164(K > G))/OspA-B31(aa180-216)(aa190(N-del))/OspA-PKo(aa217-273) | | 178 | 71 |
| OspC-C2(bp55-612)/OspA-B31(bp88-492)/OspA-PKo(bp493-537)/OspA-B31(bp541-651)/OspA-PKo(bp652-822) | 179 | | 72 |
| OspC-C2(aa19-204)/OspA-B31(aa30-164)/OspA-PKo(aa165-179, aa164(K > G))/OspA-B31(aa180-216)(aa190(N-del))/OspA-PKo(aa217-273) | | 180 | 72 |

¹Chimers Generated are listed as follows: Nucleotide or polypeptide fragment –strain (sequence in base pairs for the top listing and amino acids for the bottom listing)

Separate nucleotide or polypeptide fragments in the chimer are separated by a /

B. Protein Expression

As described in the previous two examples, it is possible to express and purify *Borrelia* proteins such as OspA, OspC and chimeric OspC/OspA polypeptides. This is accomplished by incorporating the desired nucleic acid sequence, which encodes the protein of choice, into an expression plasmid, using standard techniques. This expression plasmid can then be transfected into a compatible host cell in order to express the desired protein.

The purified OspA, OspC or OspC/OspA chimeric proteins, that were used to immunize mice and in the ELISA tests described below, were generated and purified by cloning either OspA, OspC or OspC/OspA chimeric nucleic acid sequences, in frame, into the pET expression plasmid. The expression plasmid was then transfected into the compatible expression cell line *Escherichia coli* strain BL21 (DE3)/(pLysS) or strain B834 (DE3). The BL21 or B834 cells were then grown in 10 ml LB media (5 g/l NaCl, 10 g/l tryptone, 5 g/l yeast extract, 25 mg/l chloramphenicol and 50 mg/l ampicillin) at 37° C., with shaking. When the optical density at 600λ reached 0.3–0.4 units, recombinant protein expression was induced by adding IPTG (isopropyl B-D-thiogalactopyranoside) to a final concentration of 0.5 mM and the cells were grown for an additional three hours. The cultures were harvested by centrifugation at 3800×g for five minutes. The cells were resuspended in 20 mM $NaPO_4$, pH 7.7 and stored at −20° C. overnight. Once thawed, the crude extracts were incubated with DNase (2 µg/ml) in the presence of 2.5 mM $MgCl_2$ at room temperature for thirty minutes and then spun at 14,000 rpm (Eppendorf 5417C) for five minutes.

To purify the OspC proteins described below, the crude extracts from the OspC-expressing cells were loaded onto an anion exchange column (Q Sepharose Fast Flow, 2.2×10 cm, Pharmacia) which had been pre-equilibrated with 20 mM Tris-Cl, pH 9.3. The column was washed in the same buffer (20 mM Tris-Cl, pH 9.3) which eluted the OspC protein. The wash fractions that contained OspC were concentrated using Amicon 10K and then were dialyzed with a solution containing 20 mM NaPO$_4$ pH 8.0 and 250 mM NaCl. The partially purified OspC was then passed over a Ni$^{2+}$ metal affinity column (Chelating Sepharose Fast Flow 2.2×10 cm, Pharmacia) equilibrated with 20 mM NaPO$_4$ pH 8.0 and 250 mM NaCl. The column was washed using a decreasing pH gradient of 20 mM sodium acetic acid and 250 mM NaCl and the bound OspC eluted around pH 5.7. The OspC fractions were then concentrated by ultrafiltration and stored at −70° C.

For purification of OspA proteins, the same procedure was followed, except that the dialysis step, after the Amicon 10K cutoff, was done in 20 nM NaPO$_4$, pH 6.0. The partially purified OspA was then applied to a cation exchange column (S Sepharose Fast Flow 2.2×10 cm, Pharmacia) equilibrated with 20 nM NaPO$_4$, pH 6.0. The column was washed using an increasing NaCl gradient from 0 to 100 mM. The OspA-containing fractions were concentrated by ultrafiltration and stored at −70° C.

As previously indicated, both lipidated and non-lipidated (truncated, i.e., without the first 17 amino acids) forms of OspC, OspA and OspC/OspA chimeric proteins were generated.

C. Immunization of Mice and Serologic Characterization Using ELISA (Enzyme-Linked Immunosorbent Assay)

Immunization of Mice

Mice, either C3H-J or ICR, were immunized with 3 ug of lipidated OspC/OspA chimeric protein or 6 ug of non-lipidated OspC/OspA chimers in 100 ul of aluminum hydroxide adjuvant (concentration of 1.8 mg/ml) by (SC) subcutaneous injection. As a negative control, mice were immunized with 100 ul of aluminum hydroxide adjuvant only. All mice received a total of three injections which were given at two week intervals. One week after the final immunization, blood was drawn from each mouse (including negative controls) and the serum was tested for IgG reactivity using the ELISA method described below, for the presence of anti-OspA antibodies to three different purified OspA proteins (*Borrelia burgdorferi sensu stricto* (B31), *Borrelia garinii* (K48) and *Borrelia afzelli* (PGau). The sera was tested at a dilution of 1:1000.

Mice were immunized with the chimeric proteins described in Table V.

TABLE V

Chimeric Proteins Used to Immunize Mice

| Name | Description (amino acid) | SEQ ID NO.: (nucleic acid) | SEQ ID NO.: (polypeptide) | FIG. No: |
|---|---|---|---|---|
| OspA | OspA-B31(18–273) | 6 | 7 | 47, 48 |
| OspC | OspC-B31(19–211) | 29 | 30 | 47, 48 |
| OspC2-OspA | OspC-C2(19–204)/OspA-B31(18–273) | 149 | 150 | 47, 48 |
| ¹lipOspAP/Bo | OspA-PGau(1–217)/OspA-Bo(218–273) | 139 | 140 | 49, 50 |
| ¹lipOspAB/P | OspA-B31(1–216)/OspA-PKo(217–273) | * | * | 49, 50 |
| OspC-OspAB/P | OspC-B31(19–211)/OspA-B31(18–216)/OspA-PKo(217–273) | 155 | 156 | 49, 50, 52 53, 54 |
| OspCB31-OspAB31 | OspC-B31(19–211)/OspA-B31(18–273) | 145 | 146 | 51, 52, 53, 54 |
| OspC2-OspAB31 | OspC-C2(19–204)/OspA-B31(18–273) | 149 | 150 | 51, 52 |
| ¹lip OspA K/T | OspA-K48(1–217)/OspA-Tro(218–273) | * | * | 52 |
| ¹lip OspC-B31 | OspC-B31(1–211) | 29 | 30 | 51 |
| OspCB31-OspABPBP | OspC-B31(19–211)/OspA-B31(30–150)/OspA-PKo(151–179)/OspA-B31(180–216) (190 N deletion)/OspA-PKo(217–273) B31/B31/PKo | 177 | 178 | 53, 54 |

¹"lip" means the chimeric protein contains its native N-terminal lipidation signal Serologic Characterization Using ELISA (Enzyme-Linked Immunosorbent Assay)

Immobilization of antigen onto ELISA Plates

A solution of purified recombinant OspC or OspA protein from each of the *Borrelia burgdorferi* strains B31 (*Borrelia burgdorferi sensu stricto*), K48 (*Borrelia garinii*) and PGau (*Borrelia afzelli*) was added to sodium phosphate buffer, pH 9.0, and was used to coat a commercial microwell plate (MaxiSorp®, Nunc). The coating procedure was as follows: 100 μl of a solution containing the appropriate OspA or OspC protein (made up at a concentration of 250 ng/ml in the following coating buffer: 100 mM Bis-Tris propane, pH 9.7) was added to each well of a microtiter plate which was incubated for one hour at 37° C. The antigen solution was removed from the wells, the plate was washed three times with phosphate buffered saline (PBS) pH 9.0, and 300 μl of blocking buffer solution was added (3% dry milk, 0.1% polyoxyethylenesorbitan (referred to herein as Tween 20™), 0.02% NaN$_3$ in 100 nM Bis-Tris propane, pH 9.7). Following a one hour incubation at 37° C., the plates were washed four times with TBS-Tween 20™ wash buffer (20 mM Tris-Cl, pH 7.5, 136 mM NaCl, 0.1% Tween 20™ and 0.02% NaN₃) and then were allowed to dry. The plates were then wrapped in plastic and stored at 4° C. until they were used.

ELISA (Enzyme-Linked Immunosorbent Assay) Tests

The standard procedure for the ELISA tests was as follows: mouse serum was diluted 1:1000 in sample dilution buffer (1% dry milk, 136 mM NaCl, 0.1% Tween 20™, 0.02% NaN₃ in 20 mM Tris-Cl, pH 7.5) and 100 µl of the diluted serum was added to the ELISA microtiter plate wells that had been coated with antigen as described above. Following incubation for 1 hour at 37° C., the samples were removed and the plates were washed four times in TBS-Tween™ (20 mM Tris-Cl, pH 7.5; 136 mM NaCl; 0.1% Tween 20™ and 0.02% NaN₃). For the secondary antibody, goat anti-mouse antisera conjugated to alkaline phosphatase-specific for either IgM (Fc) or IgG (Fab), (Jackson Immuno Research Laboratories) was diluted 1:750 in sample dilution buffer (1% dry milk, 136 mM NaCl, 0.1% Tween 20™, 0.02% NaN₃ in 20 mM Tris-Cl, pH 7.5) and 100 µl of the diluted secondary antibody was added to each well. Following incubation for thirty minutes at 37° C., the plates were washed three times with TBS-Tween™ (20 mM Tris-Cl, pH 7.5; 136 mM NaCl; 0.1% Tween 20™ and 0.02% NaN₃) and 100 µl of Phosphatase Substrate solution (5 mg of p-nitrophenylphosphate tablets dissolved in 1× diethanolamine substrate buffer to yield a 2 mg/ml solution—Kirkegaard Perry Laboratory) was added to each well. The plates were incubated for thirty minutes at 37° C. and 100 µl of stop solution (5% EDTA) was added to each well. The absorbance at 405 nm was read on a microplate reader (Dynatech). A sample was considered positive if it produced an average absorbance greater than the mean of the negative controls plus three standard deviations.

Previous work has demonstrated that it is the carboxy-terminal region of OspA that contains the antigenic sites that provide the immunoprotective response. Thus, in addition to the ELISA test described above, a modified ELISA was performed (herein referred to as the Protective ELISA Test), wherein the purified N-terminal region of B31 OspA (amino acids 18–139) was used to block any antibodies present in the mouse serum that had specificity to this N-terminal OspA region. These protective ELISA tests were performed as above, except that 80 µg/ml of a purified B31 OspA fragment (amino acids 18–139) was added to the diluted mouse serum prior to adding the sera to the antigen-coated ELISA microtiter plate wells.

Results of ELISA Tests

Using the above-described ELISA tests, it was demonstrated that mice immunized with a non-lipidated OspC/OspA chimeric protein (OspC2-OspA—composed of OspC (a.a. 19–204 from strain C2)/OspA (a.a. 18–273 from strain B31) (SEQ ID NO. 150) produced an immune response both to OspA and OspC that was comparable to the immune response generated to non-lipidated OspA (OspA—a.a. 18–273 from strain B31) and non-lipidated OspC (OspC—a.a. 19–211 from strain B31) control proteins (FIG. 47). As indicated in FIG. 47 and described above, mice were immunized with OspA, OspC or OspC2-OspA proteins and immune responses of the sera were measured against B31 OspA antigen (stippled bars) and B31 OspC antigen (solid bars).

Using the above-described Protective ELISA Test, it was also shown that mice immunized with the same non-lipidated OspC/OspA chimeric protein (OspC2-OspA—composed of OspC (a.a. 19–204 from strain C2)/OspA (a.a. 18–273 from strain B31) (SEQ ID NO. 150) produced an immune response to the C-terminal portion of OspA that was comparable to the immune response generated to the C-terminal portion of a non-lipidated OspA (OspA—a.a. 18–273 from strain B31) control protein (FIG. 48). As indicated in FIG. 48, mice were immunized with OspA, OspC or OspC2-OspA proteins and immune responses of the sera were measured against B31 OspA antigen. The protective antibody response to B31 OspA antigen is indicated in the stippled bars.

Thus, these results clearly demonstrate that non-lipidated chimeric OspC/OspA proteins are able to induce immune responses in mice that are comparable to the immune response generated against non-lipidated OspC and OspA control proteins.

It had been previously thought that the lipidation signals that are present on *Borrelia burgdorferi* outer surface proteins were required for immunogenicity and that OspC and OspA proteins that lacked this lipidation signal would be less or non-immunogenic. To test this idea, mice were immunized with a non-lipidated OspC/OspA chimeric protein (OspC-OspAB/P—composed of OspC (a.a. 19–211 from strain B31)/OspA (a.a. 18–216 from strain B31)/OspA (a.a. 217–273 from strain PKo)(SEQ ID NO:156) as well as two lipidated OspA proteins, lipOspAP/Bo (composed of OspA (a.a. 1–217 from strain PGau)/OspA (a.a. 218–273 from strain Bo)) and lipOspAB/P (composed of OspA (a.a. 1–216 from strain B31)/OspA (a.a. 217–273 from strain PKo)) and were subjected ELISA tests. Mice immunized with the non-lipidated OspC/OspA chimeric protein (OspC-OspAB/P) produced an immune response to OspA from each of the *Borrelia burgdorferi* strains B31 (*Borrelia burgdorferi sensu stricto*), K48 (*Borrelia garinii*) and PGau (*Borrelia afzelli*), that was equivalent or greater than the immune response generated to the two lipidated OspA control proteins (lipOspAP/Bo and lipOspAb/P) (FIG. 49).

Similar results to these were obtained using the Protective ELISA Test described above. Mice immunized with the non-lipidated OspC/OspA chimeric protein (OspC-OspAB/P) produced an immune response to the C-terminal region of OspA from each of the *Borrelia burgdorferi* strains B31 (*Borrelia burgdorferi sensu stricto*), K48 (*Borrelia garinii*) and PGau (*Borrelia afzelli*), that was equivalent or greater than the immune response generated to the C-terminal region of OspA from the two lipidated OspA control proteins (lipOspAP/Bo and lipOspAb/P) (FIG. 50).

In addition to the comparisons between non-lipidated OspC/OspA chimeric proteins and lipidated OspA control proteins, experiments were also performed to compare non-lipidated OspC/OspA chimeric proteins with a lipidated OspC control protein (FIG. 51). Mice that were immunized with either the non-lipidated OspC/OspA chimeric protein OspCB31-OspAB31 (composed of OspC (a.a. 19–211 from strain B31)/OspA (a.a. 18–273 from strain B31) (SEQ ID NO:146) or the non-lipidated OspC/OspA chimeric protein OspC2-OspAB31 (composed of OspC (a.a. 19–204 from strain C2)/OspA (a.a. 18–273 from strain B31) (SEQ ID NO:150) produced an immune response to OspC derived from the *Borrelia burgdorferi* strain B31 that was comparable to the immune response produced by a lipidated OspC control protein (lip OspC-B31—composed of OspC (a.a. 1–211 from strain B31)) (FIG. 51).

Thus, these results clearly demonstrate that non-lipidated chimeric OspC/OspA proteins are able to induce immune responses against OspA and OspC that are comparable to the immune response generated against OspA and OspC using lipidated OspA or OspC control proteins. The use of unlipidated forms of these proteins as vaccine immunogens or diagnostic antigens is highly desirable because the product yield is much greater and the proteins are much easier to purify. For these reasons, the production of these proteins less expensive.

Figure 52:
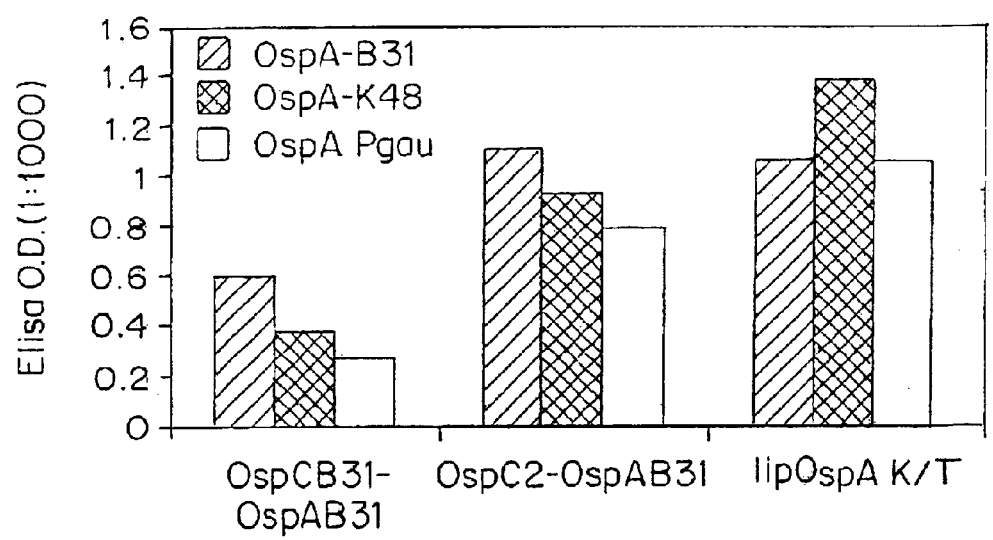
FIG. 52 is a bar graph showing the reactivity of sera from mice immunized with the indicated Borrelia chimeric protein (OspCB31-OspAB31, OspC2-OspAB31 or Lip OspA K/T) (X-axis) against the indicated OspA antigens (legend) from strains B31 (*Borrelia burgdorferi* sensu stricto), K48 (*Borrelia garinii*) and PGau (*Borrelia afzelli*).

The OspC/OspA chimeric proteins of the present invention are also able to generate immune responses against OspA proteins that are derived from strains that are not represented in the chimeric protein. Mice immunized with the OspC/OspA chimeric proteins, OspCB31-OspAB31 (SEQ ID NO:146) and OspC2-OspAB31 (SEQ ID NO:150), are not only able to generate immune responses that recognize OspA derived from strain B31 (*Borrelia burgdorferi* sensu stricto), but also recognize OspA derived from strain K48 (*Borrelia garinii*) and strain PGau (*Borrelia afzelii*) (FIG. 52). For comparison, mice were also immunized with the lipidated OspA chimeric protein, Lip OspA K/T (composed of OspA (a.a. 1–217 from strain K48)/OspA (a.a. 218–273 from strain Tro)) (FIG. 52).

Figure 53:
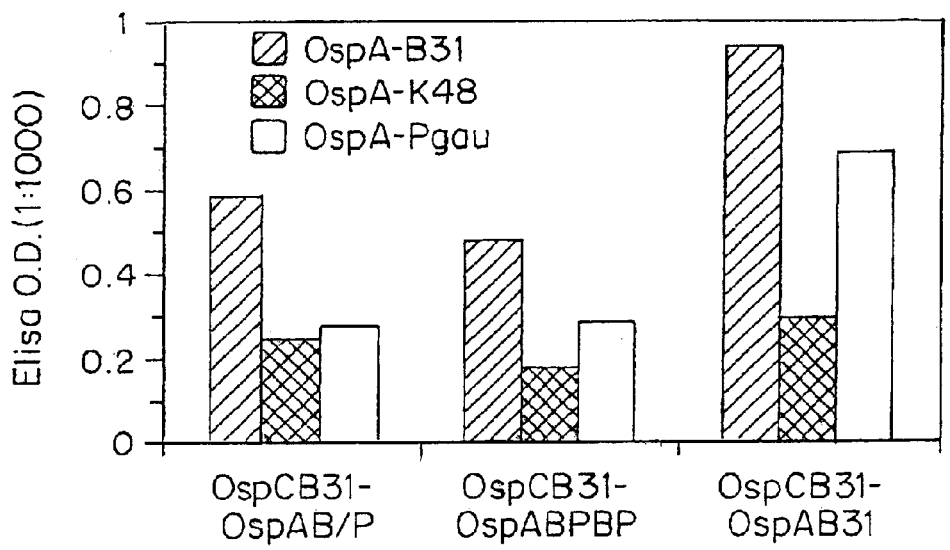
FIG. 53 is a bar graph showing the reactivity of sera from mice immunized with the indicated Borrelia chimeric protein (OspCB31-OspAB/P, OspCB31-OspABPBP or OspCB31-OspAB31) (X-axis) against the indicated OspA antigens (legend) from strains B31 (*Borrelia burgdorferi* sensu stricto), K48 (*Borrelia garinii*) and PGau (*Borrelia afzelli*).
Figure 54:
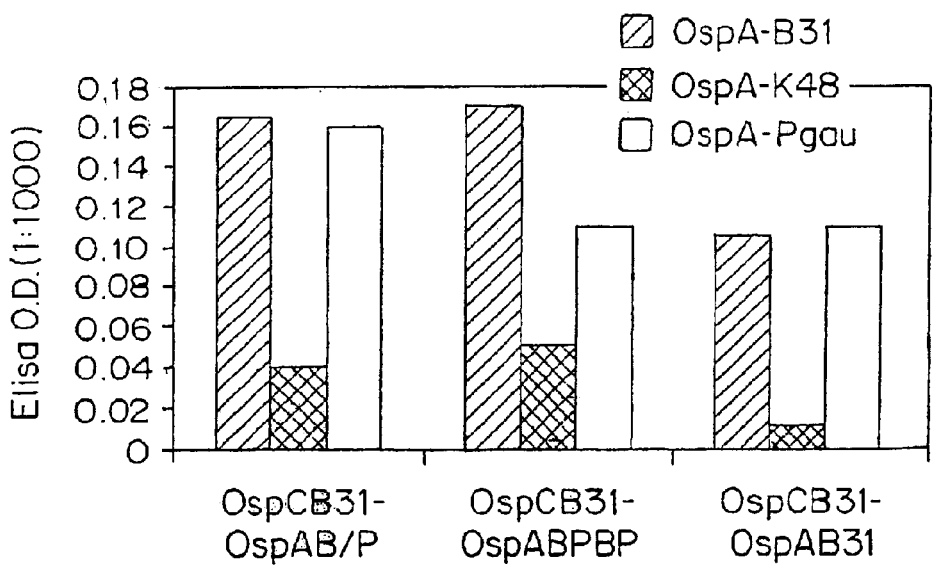
FIG. 54 is a bar graph showing the reactivity of sera from mice immunized with the indicated Borrelia chimeric protein (OspCB31-OspAB/P, OspCB31-OspABPBP or OspCB31-OspAB31) (X-axis) against the indicated OspA (legend) from strains B31 (*Borrelia burgdorferi* sensu stricto), K48 (*Borrelia garinii*) and PGau (*Borrelia afzelli*). In all cases, a purified fragment of B31 OspA (amino acids 18–139) was added in excess to the sera so that the detected immune response is specific for the C-terminal region of OspA.

Additional antibody responses to OspA derived from strain B31 (*Borrelia burgdorferi* sensu stricto), strain K48 (*Borrelia garinii*) and strain PGau (*Borrelia afzelii*) are also presented for sera from mice immunized with other OspC/OspA chimeric proteins. Thus, FIG. 53 presents the ELISA results from mice immunized with either OspCB31-OspAB/P (SEQ ID NO:156), OspCB31-OspABPBP (SEQ ID NO:178) or OspCB31-OspAB31 (SEQ ID NO:146). In each case, sera from the immunized mice was tested against OspA derived from each of strain B31 (*Borrelia burgdorferi* sensu stricto), K48 (*Borrelia garinii*) and PGau (*Borrelia afzelli*). In all cases, a strong immune response was generated (FIG. 53). As with the previously described OspC/OspA chimeric proteins, the three OspC/OspA chimeric proteins used to immunize the mice in FIG. 52 also elicited a strong immune response to the C-terminal region of OspA when examined using the Protective ELISA Test described above (FIG. 54).

Tick Challege of Immunized Mice

Mice, either C3H-J or JCR, that had been immunized as described above, were also challenged with either laboratory-infected nympha or field nympha. The immunized mice were placed in isolation cages and each mouse received 5–10 nymphs. All of the nymphs were collected and counted after 6 days. Four weeks after challenge, the mice were bled and sera was tested using commercially-available Western blot strips to *Borrelia burgdorferi* sensu stricto strain B31 (MarDx strips) and/or *Borrelia garinii* (MRL strips). Eight weeks after challenge, the mice were bled, sera was tested again by Western blot and ear punch and bladder samples were cultured. As a positive control, mice which had been immunized with only aluminum hydroxide adjuvant, as described above, were subjected to the same challenge.

The results of the tick challenge studies (Table VI) demonstrate that while immunization with lipidated OspC protein was unable to protect the mice, as evidenced by a positive Western blot signal (in 4 out of 5 mice), immunization with two different OspC/OspA chimeric proteins (SEQ ID NO.146 and SEQ ID NO.150) did provide protection, as indicated by the absence of Western blot signal (in 0 out of 8 mice and 0 out of 3 mice) (Table VI). The sham positive control showed that the challenge by the ticks was successful in all cases, as evidenced by 100% positive signal in Western blots (Table VI).

TABLE VI

Effect of Vaccination on Transmission of *Borrelia* from Ticks

| Vaccine Candidate | Mouse | Tick-nymph | Seroconversion (Western Blots) Vaccinated | Seroconversion (Western Blots) Sham |
|---|---|---|---|---|
| OspC1-OspAB31 | C3H-J | Long Island | 0 +/ 8 | 8 +/ 8 |
| OspC2-OspAB31 | C3H-J | Long Island | 0 +/ 3 | 4 +/ 4 |
| Lip OspC12 | ICR | Long Island | 4 +/ 5 | 5 +/ 5 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A chimeric protein comprising a first and a second polypeptide, wherein the first polypeptide comprises OspC from *Borrelia burgdorferi* sensu lato and wherein the second polypeptide comprises OspA from *Borrelia burgdorferi* sensu lato, such that the OspC polypeptide is linked to the N-terminus of the OspA polypeptide.

2. The chimeric protein of claim 1, wherein the OspC polypeptide is present in unlipidated form.

3. The chimeric protein of claim 1, wherein the OspA polypeptide is present in unlipidated form.

4. The chimeric protein of claim 1, wherein the OspA and OspC polypeptides are from the same strain of *Borrelia burgdorferi* sensu lato.

5. The chimeric protein of claim 1, wherein the OspA and OspC polypeptides are from the same genospecies of *Borrelia burgdorferi* sensu lato.

6. The chimeric protein of claim 1, wherein the OspA and OspC polypeptides are from different strains of *Borrelia burgdorferi* sensu lato.

7. The chimeric protein of claim 1, wherein the OspA and OspC polypeptides are from different genospecies of *Borrelia burgdorferi* sensu lato.

8. The chimeric protein of claim 1, wherein the OspA polypeptide comprises at least a first OspA amino acid sequence from a first strain of *Borrelia burgdorferi* sensu lato and a second OspA amino acid sequence from a second strain of *Borrelia burgdorferi* sensu lato.

9. The chimeric protein of claim 8, wherein the first strain is from a first genospecies of *Borrelia burgdorferi* sensu lato and wherein the second strain of *Borrelia burgdorferi* is from a second genospecies of *Borrelia burgdorferi* senso lato.

10. The chimeric protein of claim 8, wherein the first OspA polypeptide fragment comprises a *Borrelia burgdorferi* sensu lato OspA polypeptide from about amino acid residue 18 to about amino acid residue 216, and wherein the second OspA polypeptide fragment comprises a *Borrelia burgdorferi* sensu lato OspA polypeptide from about amino acid residue 217 to about amino acid residue 273, wherein amino acid numbering is based on OspA polypeptide numbering of SEQ ID NO: 7.

11. The chimeric protein of claim 8, wherein the first OspA polypeptide fragment comprises a *Borrelia burgdorferi* sensu lato OspA polypeptide from about amino acid residue 132 to about amino acid residue 217, and wherein the second OspA polypeptide fragment comprises a *Borrelia burgdorferi* sensu lato OspA polypeptide from about amino acid residue 218 to about amino acid residue 273, wherein amino acid numbering is based on OspA polypeptide numbering of SEQ ID NO: 7.

12. The chimeric protein of claim 8, wherein the OspA polypeptide comprises at least four separate OspA polypeptide fragments.

13. The chimeric protein of claim 12, wherein the first OspA polypeptide fragment comprises a *Borrelia burgdorferi* sensu lato OspA polypeptide from about amino acid residue 30 to about amino acid residue 150, wherein the second OspA polypeptide fragment comprises a *Borrelia burgdorferi* sensu lato OspA polypeptide from about amino acid residue 151 to about amino acid residue 179, wherein the third OspA polypeptide fragment comprises a *Borrelia burgdorferi* sensu lato OspA polypeptide from about amino acid residue 180 to about amino acid residue 216, and wherein the fourth OspA polypeptide fragment comprises a *Borrelia burgdorferi* sensu lato OspA polypeptide from about amino acid residue 217 to about amino acid residue 273, wherein amino acid numbering is based on OspA polypeptide numbering of SEQ ID NO: 7.

14. The chimeric protein of claim 1, wherein the first polypeptide comprises a *Borrelia burgdorferi* sensu lato OspC polypeptide from about amino acid residue 19 to about amino acid residue 213, wherein amino acid numbering is based on OspC polypeptide numbering of SEQ ID NO: 30.

15. The chimeric protein of claim 1, wherein the first polypeptide comprises a *Borrelia burgdorferi* sensu lato OspC polypeptide from about amino acid residue 19 to about amino acid residue 211, wherein amino acid numbering is based on OspC polypeptide numbering of SEQ ID NO: 30.

16. The chimeric protein of claim 1, wherein the first polypeptide comprises a *Borrelia burgdorferi* sensu lato OspC polypeptide from about amino acid residue 19 to about amino acid residue 204, wherein amino acid numbering is based on OspC polypeptide numbering of SEQ ID NO: 30.

17. The chimeric protein of claim 1, wherein the second polypeptide comprises a *Borrelia burgdorferi* sensu lato OspA polypeptide from about amino acid 18 to about amino acid 273, wherein amino acid numbering is based on OspA polypeptide numbering of SEQ ID NO: 7.

18. The chimeric protein of claim 1, wherein the second polypeptide comprises a *Borrelia burgdorferi* sensu lato OspA polypeptide from about amino acid 132 to about amino acid 216, wherein amino acid numbering is based on OspA polypeptide numbering of SEQ ID NO: 7.

19. A chimeric protein comprising an amino acid sequence selected from the group consisting of: SEQ ID NOs: 146, 148, 150, 152, 154, 156, 158, 160, 162, 164, 166, 168, 170, 172, 174, 176, 178 and 180.

20. A physiological composition to vaccinate against and treat *Borrelia* infection in animals or humans, the composition comprising;

a) a chimeric protein comprising at least a first and a second polypeptide, wherein the first polypeptide comprises *Borrelia burgdorferi* sensu lato OspC and wherein the second polypeptide comprises *Borrelia burgdorferi* sensu lato OspA, such that OspC is linked to the N-terminus of OspA, the amount being effective to ellicit an immune response to *Borrelia burgdorferi;* b) a physiologically-acceptable carrier or vehicle; and c) an adjuvant.

21. The composition of claim 20, wherein the chimeric protein is selected from the group consisting of: SEQ ID NOs: 146, 148, 150, 152, 154, 156, 158, 160, 162, 164, 166, 168, 170, 172, 174, 176, 178 and 180.

* * * * *

UNITED STATES PATENT AND TRADEMARK OFFICE
CERTIFICATE OF CORRECTION

PATENT NO. : 7,008,625 B2
APPLICATION NO. : 10/369100
DATED : March 7, 2006
INVENTOR(S) : Raymond J. Dattwyler et al.

It is certified that error appears in the above-identified patent and that said Letters Patent is hereby corrected as shown below:

Title Page
Add additional Assignee to Column 1, Section (73) -- Brookhaven Sciences Associates, LLC, Upton, NY --

Signed and Sealed this

Twenty-seventh Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,008,625 B2
APPLICATION NO. : 10/369100
DATED : March 7, 2006
INVENTOR(S) : Raymond J. Dattwyler et al.

It is certified that error appears in the above-identified patent and that said Letters Patent is hereby corrected as shown below:

Column 1, line 22, after "Infectious Diseases" add "and with Government support under contract number DE-AC02-98CH10886, awarded by the U.S. Department of Energy"

Signed and Sealed this
Twenty-third Day of August, 2011

David J. Kappos
*Director of the United States Patent and Trademark Office*